US012612399B2

(12) United States Patent
Patel et al.

(10) Patent No.: US 12,612,399 B2
(45) Date of Patent: Apr. 28, 2026

(54) SUBSTITUTED 4-([1,2,4]TRIAZOLO[1,5-A]PYRIDIN-6-YL) THIOPHENE-2-CARBOXAMIDE DERIVATIVES AND USE THEREOF

(71) Applicant: The Johns Hopkins University, Baltimore, MD (US)

(72) Inventors: Amit Patel, Baltimore, MD (US); Donald Zack, Baltimore, MD (US); Derek Welsbie, Rancho Sante Fe, CA (US); Cynthia Berlinicke, Baltimore, MD (US); Brendan N. Lilley, Baltimore, MD (US); Byung-Jin Kim, Baltimore, MD (US); Hartmut Schirok, Langenfeld (DE); William Schubert, Wuppertal (DE); Michael Koch, Berlin (DE); Lionel Nicolas, Berlin (DE); Carsten Terjung, Berlin (DE); Mario Lobell, Berlin (DE); Simon Holton, Berlin (DE); Natalia Jungmann, Berlin (DE)

(73) Assignee: The Johns Hopkins University, Baltimore, MD (US)

( * ) Notice: Subject to any disclaimer, the term of this patent is extended or adjusted under 35 U.S.C. 154(b) by 302 days.

(21) Appl. No.: 18/031,045

(22) PCT Filed: Oct. 12, 2021

(86) PCT No.: PCT/US2021/054493

§ 371 (c)(1),
(2) Date: Apr. 10, 2023

(87) PCT Pub. No.: WO2022/081522

PCT Pub. Date: Apr. 21, 2022

(65) Prior Publication Data

US 2023/0382904 A1 Nov. 30, 2023

Related U.S. Application Data

(60) Provisional application No. 63/091,039, filed on Oct. 13, 2020.

(51) Int. Cl.
*C07D 471/04* (2006.01)
*A61P 27/02* (2006.01)

(52) U.S. Cl.
CPC ............ *C07D 471/04* (2013.01); *A61P 27/02* (2018.01)

(58) Field of Classification Search
CPC ............................... C07D 471/04; A61P 27/02
See application file for complete search history.

(56) References Cited

U.S. PATENT DOCUMENTS

2023/0086702 A1 3/2023 Schirok et al.

FOREIGN PATENT DOCUMENTS

| | | |
|---|---|---|
| WO | WO 2004072033 | 8/2004 |
| WO | WO 2005044195 | 5/2005 |
| WO | WO 2008025821 | 3/2008 |
| WO | WO 2009017954 | 2/2009 |
| WO | WO 2009027283 | 3/2009 |
| WO | WO 2009064835 | 5/2009 |
| WO | WO 2009068482 | 6/2009 |
| WO | WO 2009155565 | 12/2009 |
| WO | WO 2010007100 | 1/2010 |
| WO | WO 2010020363 | 2/2010 |
| WO | WO 2010057877 | 5/2010 |
| WO | WO 2010141796 | 12/2010 |
| WO | WO 2011064328 | 6/2011 |
| WO | WO 2011092272 | 8/2011 |
| WO | WO 2011100502 | 8/2011 |
| WO | WO 2011154677 | 12/2011 |
| WO | WO 2011157688 | 12/2011 |
| WO | WO 2012143329 | 10/2012 |
| WO | WO 2012175522 | 12/2012 |
| WO | WO 2013031671 | 3/2013 |
| WO | WO 2014109414 | 7/2014 |
| WO | WO 2014111496 | 7/2014 |
| WO | WO 2014141187 | 9/2014 |
| WO | WO 2014195276 | 12/2014 |
| WO | WO 2015013715 | 1/2015 |
| WO | WO 2015161011 | 10/2015 |
| WO | WO 2015188681 | 12/2015 |
| WO | WO 2016000615 | 1/2016 |
| WO | WO 2016057522 | 4/2016 |
| WO | WO 2017037573 | 3/2017 |
| WO | WO 2017042114 | 3/2017 |
| WO | WO 2017102091 | 6/2017 |
| WO | WO 2017215506 | 12/2017 |
| WO | WO 2018017633 | 1/2018 |
| WO | WO 2018044808 | 3/2018 |
| WO | WO 2019089442 | 5/2019 |
| WO | WO 2016161160 | 10/2020 |

OTHER PUBLICATIONS

Adib et al., "An axonal stress response pathway: degenerative and regenerative signaling by DLK," Curr. Opin. Neurobiol., 2018, 53:110-119.
Andersen et al., "Direct Access to a,a-Difluoroacylated Arenes by Palladium-Catalyzed Carbonylation of (Hetero)Aryl Boronic Acid Derivatives," Angew. Chem. Int. Ed. 2016, 55, 10396-10400.
Ando et al., "Facile One-Pot Synthesis of N-Difluoromethyl-2-pyridone Derivatives," Org. Lett., 2006, 8:3805-3808.

(Continued)

*Primary Examiner* — Paul V Ward
(74) *Attorney, Agent, or Firm* — Fish & Richardson P.C.

(57) ABSTRACT

Provided herein are 4-([1,2,4]triazolo[1,5-a]pyridin-6-yl) thiophene-2-carboxamide and 4-([1,2,4]triazolo[1,5-a]pyridin-7-yl)thiophene-2-carboxamide derivatives. Such compounds are useful, for example, for the treatment and/or prevention of neurodegenerative diseases or disorders such as ophthalmological neurodegenerative disorders. This disclosure also features compositions containing the same as well as methods of using and making the same.

29 Claims, 6 Drawing Sheets

(56) References Cited

OTHER PUBLICATIONS

Augustine et al., "Propylphosphonic anhydride (T3P®): an efficient reagent for the one-pot synthesis of 1,2,4-oxadiazoles, 1,3,4-oxadiazoles, and 1,3,4-thiadiazoles," Tetrahedron, 2009, 65:9989-9996.
Avitia et al., "Single-flask preparation of polyazatriaryl ligands by sequential borylation/Suzuki-Miyaura coupling," Tetrahedron Lett. 2011, 52:1631-1634.
Bertens et al., "Design of the ocular coil, a new device for non-invasive drug delivery," Eur J Pharm Biopharm. Mar. 12, 2020. pii: S0939-6411(20):30074-6.
Billingsley et al., "Palladium-Catalyzed Borylation of Aryl Chlorides: Scope, Applications, and Computational Studies," Angewandte, 2007, 46, 5359-5363.
Blomberg et al., "Synthesis of a β-strand mimetic based on a pyridine scaffold," Tetrahedron, 2006, 62:10937-10944.
Börchers et al., "TNFα-induced DLK activation contributes to apoptosis in the beta-cell line HIT," Naunyn-Schmideberg's Arch. Pharmacol. 2017, 390:813-825.
Boschelli et al., "Synthesis and Tyrosine Kinase Inhibitory Activity of a Series of 2-Amino-8H-pyrido[2,3-d]pyrimidines: Identification of Potent, Selective Platelet-Derived Growth Factor Receptor Tyrosine Kinase Inhibitors," J. Med. Chem., 1998, 41:4365-4377.
Bouillon et al., "Synthesis of novel halopyridinylboronic acids and esters. Part 3: 2, or 3-Halopyridin-4-yl-boronic acids and esters," Tetrahedron, 2002, 58:4369-4373.
Cao et al., "Syntheses, Antifeedant Activity, and QSAR Analysis of New Oxa(thia)diazolyl 3(2H)-Pyridazinones," J. Agric. Food Chem., 2005, 53:3120-3125.
CAS No. 36953-37-4, dated Nov. 16, 1984; CAS No. 74427-22-8, dated Nov. 16, 1984; CAS No. 1029715-63-6, dated Jun. 22, 2008; CAS No. 1040377-03-4, dated Aug. 12, 2009; CAS No. 1040377-08-9, dated Aug. 12, 2008; CAS No. 10465-78-8, dated Nov. 16, 1984; CAS No. 1049730-40-6, dated Sep. 17, 2008; CAS No. 1049730-42-8, dated Sep. 17, 2008; CAS No. 107496-54-8, dated Apr. 11, 1987; CAS No. 108338-20-1, dated May 30, 1987; CAS No. 1114563-10-8, dated Mar. 2, 2009; CAS No. 1122-58-3, dated Nov. 16, 1984; CAS No. 113118-82-4, dated Feb. 27, 1988; CAS No. 1233526-60-7, dated Jul. 22, 2010,;CAS No. 1256810-49- 7, dated Dec. 16, 2010; CAS No. 125700-67-6, dated Mar. 2, 1990; CAS No. 1310584-14-5, dated Jun. 28, 2011; CAS No. 13466-38-1, dated Nov. 16, 1984; CAS No. 1361849-85-5, dated Mar. 23, 2012; CAS No. 137081-41-5, dated Nov. 1, 1991; CAS No. 139484-32-5, dated Mar. 6, 1992; CAS No. 13965-03-2, dated Nov. 16, 1984; CAS No. 141699-55-0, dated Jun. 5, 1992; CAS No. 148893-10-1, dated Jul. 23, 1993; CAS No. 153077-87-3, dated Feb. 17, 1994; CAS No. 157141- 27-0, dated Aug. 19, 1994; CAS No. 175204-90-7, dated Apr. 17, 1996; CAS No. 1766-28-5, dated Nov. 16, 1984; CAS No. 1883816-46-3, dated Mar. 21, 2016; CAS No. 19172-47-5, dated Nov. 16, 1984; CAS No. 194151-99-0, dated Sep. 18, 1997; CAS No.1956306-65-2, dated Jul. 20, 2016; CAS No. 2101930-90- 7, dated Jul. 13, 2017; CAS No. 223463-13-6, dated May 21, 1999; CAS No. 2340-22-9, dated Nov. 16, 1984; CAS No. 2446-83-5, dated Nov. 16, 1984; CAS No. 26386-88-9, dated Nov. 16, 1984; CAS No. 26543-06-6, dated Nov. 16, 1984; CAS No. 293294-72-1, dated Oct. 6, 2000; CAS No. 2942-58-7, dated Nov. 16, 1984, CAS No. 31181-88-1, dated Nov. 16, 1984; CAS No. 374063-92-0, dated Dec. 6, 2001; CAS No. 38185-55-6, dated Nov. 16; 1984; CAS No. 386704- 12-7, dated Jan. 25; 2002; CAS No. 4397-00-6, dated Nov. 16; 1984; CAS No.4652-27-1, dated Nov. 16, 1984; CAS No. 50675-18-8, dated Nov. 16, 1984; CAS No. 611-69-8, dated Nov. 16, 1984; CAS No. 6246-06-6, dated Nov. 16, 1984; CAS No. 6638-79-5, dated Nov. 16, 1984; CAS No. 6674-22- 2, dated Nov. 16, 1984; CAS No. 68957-94-8, dated Nov. 16, 1984; CAS No. 6914-76-7, dated Nov. 16, 1984; CAS No. 7283-96-7, dated Nov. 16, 1984; CAS No. 73183-34-3, dated Nov. 16, 1984; CAS No. 7789-59-5, dated Nov. 16, 1984; CAS No. 845827-13-6, dated Mar. 17, 2005; CAS No. 870-50-8, dated Nov. 16; 1984; CAS No. 877399-74-1, dated Mar. 21, 2006; CAS No. 887583- 90-6, dated Jun. 13; 2006; CAS No. 921602-78-0, dated Feb. 16, 2007; CAS No. 946578-32-1, dated Sep. 11, 2007; CAS No. 95464-05-4, dated Mar. 23, 1985; CAS No. 97112-03-3, dated Jul. 6, 1985, 50 pages.
Chen et al., "Intramolecular Reactivity of trans [4+4] Photodimers of 2-Pyridones," Synthesis, 2007, 2351-2359.
Chen et al., "Leucine Zipper-Bearing Kinase is a Critical Regulator of Astrocyte Reactivity in the Adult Mammalian CNS," Cell Reports, 2018, 22:3587-3597.
Chen et al., "Leucine Zipper-bearing Kinase promotes axon growth in mammalian central nervous system neurons," Scientific Rep., 2016, 6:31482.
Chowdhury et al., "Synthesis of 1-(methanesulfonyl- and aminosulfonylphenyl)acetylenes that possess a 2-(N-difluoromethyl-1,2-dihydropyridin-2-one) pharmacophore: Evaluation as dual inhibitors of cyclooxygenases and 5-lipoxygenase with anti-inflammatory activity," Bioorg. Med. Chem. Lett., 2009, 19:584-588.
Cook et al., "Efficient and chromatography-free methodology for the modular synthesis of oligo-(1H-pyrazol-4-yl)-arenes with controllable size, shape and steric bulk," Tetrahedron Lett., 2016, 57:895-898.
Cornejo et al., "The First Immobilization of Pyridine-bis(oxazoline) Chiral Ligands," Org. Lett. 2002, 4:3927-3930.
De et al., "Synthesis and Rearrangement of Quinone-Embedded Epoxycyclopentenones: A New Avenue to Pyranonaphthoquinones and Indenopyranones," J. Org. Chem. 2009, 74:1598-1604.
Diemer et al., "Synthesis of 4-[N-methyl-4-pyridinio]-phenolate (POMP) and negative solvatochromism of this model molecule in view of nonlinear optical applications," Tetrahedron Lett. 2005, 46:4737-4740.
Dubald et al., "Ophthalmic Drug Delivery Systems for Antibiotherapy—A Review," Pharmaceutics, 2018, 10(1):10.
East et al., "DNA gyrase (GyrB)/topoisomerase IV (ParE) inhibitors: Synthesis and antibacterial activity," Bioorg. Med. Chem. Lett., 2009, 19: 894-899.
Edmondson et al., "(2S,3S)-3-Amino-4-(3,3-difluoropyrrolidin-1-yl)-N,N-dimethyl-4-oxo-2-(4-[1,2,4]triazolo[1,5-a]-pyridin-6-ylphenyl)butanamide: A Selective α-Amino Amide Dipeptidyl Peptidase IV Inhibitor for the Treatment of Type 2 Diabetes," J. Med. Chem., 2006, 49:3614-3627.
Extended European Search Report in European Application No. 20792265.9, dated Dec. 19, 2022, 9 pages.
Fernandes et al., "DLK-dependent signaling is important for somal but not axonal degeneration of retinal ganglion cells following axonal injury," Neurobiol. Dis., 2014, 69:108-116.
Ferraris et al., "Dual leucine zipper kinase as a therapeutic target for neurodegenerative conditions," Future Med. Chem., 2013, 5:1923-1934.
Furet et al., "Discovery of NVP-BYL719 a potent and selective phosphatidylinositol-3 kinase alpha inhibitor selected for clinical evaluation," Bioorg. Med. Chem. Lett. 2013, 23:3741-3748.
Gerlach et al., "Discovery of tetrahydroindazoles as a novel class of potent and in vivo efficacious gamma secretase modulators," Bioorg. Med. Chem. 2018, 26, 3227-3241.
Ghosh et al., "DLK induces developmental neuronal degeneration via selective regulation of proapoptotic JNK activity," J. Cell. Biol. 2011, 194:751-764.
Han et al., "A practical and expedient synthesis of 2-heterocycle (C—N bond) substituted 4-oxo-4-arylbutanoates," Tetrahedron Lett, 2007, 48:2845-2849.
Hao et al., "An evolutionarily conserved mechanism for cAMP elicited axonal regeneration involves direct activation of the dual leucine zipper kinase DLK," 2016, 5:e14048.
Holland et al., "Palmitoylation controls DLK localization, interactions and activity to ensure effective axonal injury signaling," PNAS 2016, 113:763-768.
Holland et al., "Roles of Palmitoylation in Axon Growth, Degeneration and Regeneration," J. Neuroscience Res., 2017, 95:1528-1539.
Huntwork-Rodriguez et al., "JNK-mediated phosphorylation of DLK suppresses its ubiquitination to promote neuronal apoptosi,". J. Cell Biol.,2013, 202:747-763.
International Preliminary Report on Patentability in Application No. PCT/US2021/054493, dated Apr. 27, 2023, 7 pages.

(56) References Cited

OTHER PUBLICATIONS

International Preliminary Report on Patentability in Appln. No. PCT/US2020/029021, Sep. 28, 2021, 7 pages.
International Search Report and Written Opinion in Application No. PCT/US2021/054493, dated Jan. 20, 2022, 10 pages.
International Search Report and Written Opinion in Appln. No. PCT/US2020/029021, dated Jun. 11, 2020, 10 pages.
Itoh et al., "ZPK/DLK, a mitogen-activated protein kinase kinase kinase, is a critical mediator of programmed cell death of motoneurons," J. Neurosci, 2011, 31:7223-7228.
Jacksonimmuno.com [online], "Goat Anti-Mouse IgM, μ Chain Specific, Catalog No. 115-001-020," available on and before Jun. 16, 2022, retrieved on Jun. 16, 2022, retrieved from URL<https://www.jacksonimmuno.com/catalog/products/115-001-020>, 3 pages.
Jervis, "A Summary of Recent Advances in Ocular Inserts and Implants," J. of Bioequiv. Availab., 2017, 9:1.
Joost, "The role of dual leucine zipper kinase (DLK) in β-cell apoptosis: a potential target for the prevention and treatment of type 2 diabetes?:Commentary to: Börchers et al., TNF-α induced DLK activation contributes to apoptosis in the β-cell line HIT," Naunyn-Schmiedeberg's Arch. Pharmacol., 2017, 390:767-768.
Kamatsuka et al., "Design and Synthesis of Tunable Ligands with 4,4'-Bipyridyl as an Electron-Accepting Unit and Their Rhenium Complexes," Organometallics 2017, 36:3429-3434.
Kuo et al., "Synthesis and Identification of [1,3,5]Triazine-pyridine Biheteroaryl as a Novel Series of Potent Cyclin-Dependent Kinase Inhibitors," J. Med. Chem, 2005, 48:4535-4546.
Larhammar et al., "Dual leucine zipper kinase-dependent PERK activation contributes to neuronal degeneration following insult," eLife 2017, 6:e20725.
Larhammar et al., "The Ste20 Family Kinases MAP4K4, MINK1, and TNIK Converge to Regulate Stress-Induced JNK Signaling in Neurons," J. Neuroscience, 2017, 37:11074-11084.
Le Pichon et al., "Loss of dual leucine zipper kinase signaling is protective in animal models of neurodegenerative disease," Sci. Transl. Med., 2017, 9:403:eaag0394.
Levy et al., "An Improved Synthesis of the Free Base and Diglycolate Salt of CEP-33779; A Janus Kinase 2 Inhibitor," Org. Process. Res. Dev., 2016, 20:2085-2091.
Li et al., "An Improved Protocol for the Preparation of 3-Pyridyl- and Some Arylboronic Acids," J. Org. Chem., 2002, 67:5394-5397.
Lindsay-Scott et al., "A Flexible Strategy for the Regiocontrolled Synthesis of Pyrazolo[1,5-a]pyrazines," J. Org. Chem., 2017, 82:11295-11303.
Liu et al., "Syntheses, crystal structure and photophysical property of iridium complexes with 1,3,4-oxadiazole and 1,3,4-thiadiazole derivatives as ancillary ligands," J. Organomet. Chem., 2015, 785:11-18.
Lu et al., "Preparation and applications of a polymer-supported phosphoryl azide," Tetrahedron Lett. 2003, 44:9267-9269.
Maharvi et al., "Synthesis of a DOTA (Gd3+)-conjugate of proton-pump inhibitor pantoprazole for gastric wall imaging studies," Bioorg. Med. Chem. Lett., 2013, 23:2808-2811.
Mata et al., "Characterization of dual leucine zipper-bearing kinase, a mixed lineage kinase present in synaptic terminals whose phosphorylation state is regulated by membrane depolarization via calcineurin," J. Biol. Chem. Jul. 12, 1996, 271(28):16888-16896.
Menet et al., "Triazolopyridines as Selective JAK1 Inhibitors: From Hit Identification to GLPG0634," J. Med. Chem., 2014, 57:9323-9342.
Mullens et al., "An improved synthesis of 1-methyl-1H-pyrazole-4-boronic acid pinacol ester and its corresponding lithium hydroxy ate complex: application in Suzuki couplings," Tetrahedron Lett. 2009, 50, 6783-6786.
Oetjen et al., "Dual leucine zipper kinase (MAP3K12) modulators: a patent review (2010-2015)," Expert Opin. Ther. Patents 2016, 26:607-616.
Patel et al., "Discovery of Dual Leucine Zipper Kinase (DLK, MAP3K12) Inhibitors with Activity in Neurodegeneration Models," J. Med. Chem. 2015, 58:401-418.
Patel et al., "Ocular drug delivery systems: An overview," World J Pharmacol., 2013, 2(2): 47-64.
Patel et al., "Scaffold-Hopping and Structure-Based Discovery of Potent, Selective, and Brain Penetrant N-(1H-Pyrazol-3-yl)pyridin-2-amine Inhibitors of Dual Leucine Zipper Kinase (DLK, MAP3K12)," J. Med. Chem., 2015, 58, 8182-8199.
Patel et al., "Selective Inhibitors of Dual Leucine Zipper Kinase (DLK, MAP3K12) with Activity in a Model of Alzheimer's Disease," J. Med. Chem., 2017, 60:8083-8102.
Pozniak et al., "Dual leucine zipper kinase is required for excitotoxicity-induced neuronal degeneration," J. Exp. Med., 2013, 210:2553-2567.
Ruchelman et al., "Nitro and amino substitution within the A-ring of 5H-8,9-dimethoxy-5-(2-N,N-dimethylaminoethyl)dibenzo[c,h][1,6]naphthyridin-6-ones: influence on topoisomerase I-targeting activity and cytotoxicity," Bioorg. Med. Chem. 2004, 12, 3731-3742.
Sajitha et al., "Novel Burgess reagent mediated C-to-N aryl migration reaction in nitrones," RSC Adv., 2014, 4:44689-44691.
Sato et al., "CsF in Organic Synthesis. Tuning of N- or O-Alkylation of 2-Pyridone," Synlett, 1995, 1995(8):845-846.
Shin et al., "Dual Leucine Zipper Kinase is Required for Retrograde Injury Signaling and Axonal Regeneration," Neuron, 2012, 74:1015-1022.
Simard-Bisson et al., "A Role for DLK in Microtubule Rorganization to the Cell Periphery and in the Maintenance of Desmosomal and Tight Junction Integrity," J. Invest. Dermatol., 2017, 137:132-141.
Singh et al., "Promising therapeutic drug delivery systems for glaucoma: a comprehensive review," Ther Adv Ophthalmol., 2020, 12:1-17.
Sirakanyan et al., "New heterocyclic systems derived from pyridine: new substrates for the investigation of the azide/tetrazole equilibrium," Tetrahedron 2014, 70:8648-8656.
Siu et al., "Dual Leucine Zipper Kinase Inhibitors for the Treatment of Neurodegeneration," J. Med. Chem., 2018, 61:8078-8087.
Sivasubramanian et al., "Value of zeolites in asymmetric induction during photocyclization of pyridones, cyclohexadienones and naphthalenones," Org. Biomol. Chem., 2007, 5:1569-1576.
Spencer et al., "Breaking Barriers: Bioinspired Strategies for Targeted Neuronal Delivery to the Central Nervous System," Pharmaceutics, 2020, 12(2): 192.
Stewart et al., "Process Development and Large-Scale Synthesis of a c-Met Kinase Inhibitor," Org. Proc. Res. Dev. 2010, 14:849-858.
Tedeschi et al., "The DLK signalling pathway—a double-edged sword in neural development and regeneration," EMBO reports, 2013, 14:605-614.
Valakh et al., "Cytoskeletal disruption activates the DLK/JNK pathway, which promotes axonal regeneration and mimics a preconditioning injury," Neurobiol. Dis. 2015, 77:13-25.
Verheij et al., "Design, Synthesis, and Structure-Activity Relationships of Highly Potent 5-HT3 Receptor Ligands," J. Med. Chem., 2012, 55:8603-8614.
Wallbach et al., "Distinct functions of the dual leucine zipper kinase depending on its subcellular localization," Cell. Signal, 2016, 28:272-283.
Watkins et al., "DLK initiates a transcriptional program that couples apoptotic and regenerative responses to axonal injury," Proc. Natl. Acad. Sci., 2013, 110:4039-4044.
Welsbie et al., "Enhanced Functional Genomic Screening Identifies Novel Mediators of Dual Leucine Zipper Kinase-Dependent Injury Signaling in Neurons," Neuron, 2017, 94:1142-1154.
Welsbie et al., "Functional genomic screening identifies dual leucine zipper kinase as a key mediator of retinal ganglion cell death," PNAS 2013, 110, 4045-4050.
Welsbie et al., "Identification of a retinal neuroprotective kinase inhibitor with preferential activity against DLK compared to LZK," Investigative Ophthalmology & Visual Science, Jul. 2018, 59:2493.
Westaway et al., "Cell Penetrant Inhibitors of the KDM4 and KDM5 Families of Histone Lysine Demethylases. 2. Pyrido[3,4-d]pyrimidin-4(3H)-one Derivatives," J. Med. Chem. 2016, 59:1370-1387.

(56) References Cited

OTHER PUBLICATIONS

Wlaschin et al., “Dual leucine zipper kinase is required for mechanical allodynia and microgliosis after nerve injury.,” eLife, 2018, 7: e33910.
Xi et al., “Structure-based design and synthesis of imidazo[1,2-a]pyridine derivatives as novel and potent Nek2 inhibitors with in vitro and in vivo antitumor activities,” J. Med. Chem., 2017, 126:1083-1106.
Xu et al., “Design, synthesis, and evaluation of novel porcupine inhibitors featuring a fused 3-ring system based on the ‘reversed’ amide scaffold,” Bioorg. Med. Chem. 2016, 24, 5861-5872.
Yin et al., “DLK silencing attenuated neuron apoptosis through JIP3/MA2K7/JNK pathway in early brain injury after SAH in rats,” Neurobiol. Disease, 2017, 103:133-143.
Yin et al., “Tozasertib attenuates neuronal apoptosis via DLK/JIP3/MA2K7/JNK pathway in early brain injury after SAH in rats,” Neuropharmacol., 2016, 108:316-323.
Zhang et al., “Synthesis and biological evaluation of 2-amino-5-aryl-3-benzylthiopyridine scaffold based potent c-Met inhibitors,” Bioorg. Med. Chem. 2013, 21:6804-6820.
Extended European Search Report in European Application No. 21880875.6, dated Apr. 17, 2024, 7 pages.

| Compound | 4 | 19 | 94 | 112 |
|---|---|---|---|---|
| DLK / LZK $IC_{50}$ | 35 nM / 88 nM | 8.7 nM / 109 nM | 4.8 nM / 34 nM | 3.2 nM / 29 nM |
| RGC $EC_{50}$ | 477 nM | 266 nM | 42 nM | 17 nM |
| Caco2 $P_{app}$ A-B / efflux | 370 nm/s / 2.2 | 225 nm/s / 2.6 | 172 nm/s / 2.8 | 187 nm/s / 2.3 |
| Rat Hep CL / $F_{max}$ | 2.9 L/h/kg / 30% | 2.1 L/h/kg / 50% | 2.5 L/h/kg / 40% | 2.2 L/h/kg / 47% |
| Rat *in vivo* $CL_{bl}$ / MRT | 4.1 L/h/kg / 0.42 h | 3.4 L/h/kg / 0.28 h | | 1.90 L/h/kg / 0.28 h |

FIG. 1

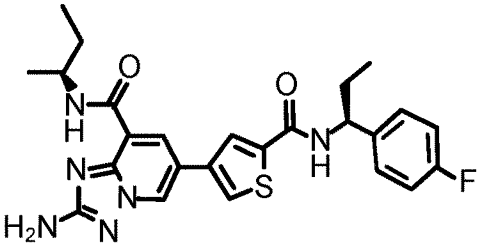

DLK $IC_{50}$ = 3.2 Nm
LZK $EC_{50}$ = 17 Nm
RGC $EC_{50}$ = 17 Nm

● *In silico* ADMET

| | | | | | | |
|---|---|---|---|---|---|---|
| oral PhysChem Score | 3 | | | | | |
| Solubility TL | 2 | | | | | |
| Caco2 Permeation TL | 0 | | | | | |
| Caco2 Effux TL | 1 | | | | | |
| CYP isoform TLs 1A2/2C8/2C9/2D6/3A4/3Apre | 0 | 2 | 2 | 0 | 0 | 2 |
| hERG TL | 0 | | | | | |
| Microsomal CL TL rat/human (mic) | 2 | 2 | | | | |
| $F_u$ (from calc HSA) [%] | 1.1 | | | | | |

● Molecular Properties (calc.)

| | |
|---|---|
| MW [g/mol] | 495 |
| MWcorr [g/mol] | 481 |
| clogD 7.5 | 3.0 |
| TPSA[$A^2$] | 114 |
| Rotatable bonds | 8 |

● Safety

| | |
|---|---|
| hERG $IC_{50}$[mM] | >10 |

● PhyChem (experimentally

| | |
|---|---|
| Sol buffer pH 6.5 [mg/L] | 0.34 / 0.81 |
| pKa base | |
| Exp. logD (pH 7.5) | 3.2 |
| Stability (90°C, 7d, solid) | stable |
| Stability (plasma, r / h) | stable |
| Stability (pH 1,7,10) | stable |
| Confirmed structure | yes |
| Purity [%] | 100 |

● *In vitro* PK properties

| | | | | | | | |
|---|---|---|---|---|---|---|---|
| | | LMF$_{max}$ [%] | | | HEP F$_{max}$ [%] | | |
| Metabolic Stability | Mouse | 11 | | | - | | |
| | Rat | 34 | | | 47 | | |
| | Man | 11 | | | 19 | | |
| Caco2 | | A-B [nm/s] | B-A [nm/s] | Ratio | | | |
| | | 187 | 433 | 2.3 | | | |
| CYP Inh [μM] | | 1A2 | 2C8 | 2C9 | 2D6 | 3A4 | 3A4 preinc |
| | | >20 | 0.9 | 0.9 | 3.8 | 2.5 | 3.0 |
| PXR Assay | | no PXR transactivation up to 2 μM assessment hampered by loss of cell viability | | | | | |
| CYP Induction | | CYP3A4NOEL 1111μg/L CYP1A2NOEL 123μg/L assessment hampered by loss of cell viability | | | | | |
| $F_u$ (unbound fraction) [%] | | 0.87 (m), 1.5 (r), 1.0 (h) | | | | | |

FIG. 2

| | | | |
|---|---|---|---|
| DLK | LZK | 3.2 nM | 20 nM |
| RGC | | 36 nM murine | 49 nM human |
| CYP1A1 vs. 3A4 | | Strong CYP1A1/3A4 metab. | |
| Dose<br>Admin route | | 1 mg/kg<br>*iv* infusion | 1 mg/kg<br>*po* |
| $AUC_{norm}$ | [kg-h/L] | 0.22 | |
| $C_{max,norm}$ | [kg/L] | | < 0.001 |
| $CL_{plasma}$ | [L/h/kg] | 4.5 | |
| $CL_{blood}$ | [L/h/kg] | 1.9 | |
| $V_{ss}$ | [L/kg] | 1.3 | |
| MRT | [h] | 0.28 | |
| $t_{1/2}$ | [h] | 0.46 | |
| F | [%] | | < 2 |
| $f_u$ | [%] | 1.5 | |

FIG. 6

SUBSTITUTED 4-([1,2,4]TRIAZOLO[1,5-A]PYRIDIN-6-YL) THIOPHENE-2-CARBOXAMIDE DERIVATIVES AND USE THEREOF

CROSS-REFERENCE TO RELATED APPLICATION

This application is a National Stage application under 35 U.S.C. § 371 of International Application No. PCT/US2021/054493 having an International Filing Date of Oct. 12, 2021, which claims priority to U.S. Provisional Application No. 63/091,039, filed on Oct. 13, 2020, which is incorporated by reference herein in its entirety.

TECHNICAL FIELD

The present application relates to 4-([1,2,4]triazolo[1,5-a]pyridin-6-yl)thiophene-2-carboxamide derivatives, to processes for preparation thereof, to the use thereof alone or in combination for treatment and/or prevention of diseases and to the use thereof for production of medicaments for treatment and/or prevention of neurodegenerative diseases such as ophthalmological neurodegenerative disorders. Such treatments can be effected as monotherapy or else in combination with other medicaments or further therapeutic measures.

BACKGROUND

Neuronal cell death in response to axon injury is a key feature of many neurodegenerative diseases. As one example, the atrophic (dry) form of age-related macular degeneration (AMD) is a potentially blinding form of neurodegeneration which affects millions of people world-wide, and from which there are no proven or licensed treatments available. As another example, glaucoma, a neurodegenerative disease that affects millions and that results in damage to the optic nerve, is a major cause of vision loss and blindness, worldwide. While an important risk factor for glaucomatous injury of retinal ganglion cells (RGCs) and optic nerve damage is elevated intraocular pressure, lowering pressure can be challenging in some patients, and in others, RGC damage continues despite pressure lowering. Thus, the development of effective neuroprotective strategies could complement pressure lowering by mitigating RGC injury, damage, and cell loss. As an additional example of ocular neurodegenerative disease, retinitis pigmentosa (RP) and associated retinal degenerations constitute a group of diseases in which there is degeneration of photoreceptor and retinal pigment epithelial (RPE) cells. Since vision loss from AMD, glaucoma, and the RIP-like group of diseases, cannot be reversed once it occurs, it is essential to develop better treatments for these diseases to prevent vision loss before it occurs. There is similarly a need to develop better, and safer, treatments for the many other forms of neurodegenerative diseases for which no or inadequate therapies are currently available.

SUMMARY

In one aspect, herein is disclosed a compound of formula (Z)

(Z)

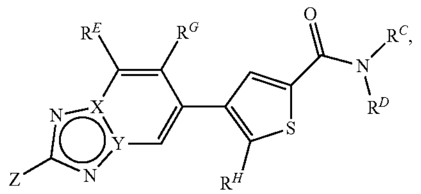

wherein $R^C$, $R^D$, $R^E$, $R^G$, $R^H$, Z, X, and Y are as defined anywhere herein.

Also provided herein are pharmaceutical compositions comprising a compound as described herein, or a pharmaceutically acceptable salt thereof, and a pharmaceutically acceptable excipient.

Also provided herein are methods for treating a neurodegenerative disease in a subject, the method comprising administering to the subject an effective amount of a compound as described herein, or a pharmaceutical composition as described herein.

Also provided herein are method for treating an optic neuropathy in a subject, the method comprising administering to the subject an effective amount of a compound as described herein, or a pharmaceutical composition as described herein.

Also provided herein are methods of inhibiting DLK and/or LZK activity in a mammalian cell, the method comprising contacting the mammalian cell with a compound as described herein, or a pharmaceutically acceptable salt thereof.

The details of one or more embodiments of the disclosure are set forth in the accompanying drawings and the description below. Other features, objects, and advantages of the disclosure will be apparent from the description and drawings, and from the claims.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 1 depicts DLK, LZK, retinal ganglion cell viability assay, and PK data for compounds 4, 19, 94, and 112.

FIG. 2 depicts in silico ADMET, molecular properties, in vitro PhysChem properties, safety data, and in vitro PK of compound 112.

FIG. 6 depicts in vivo PK data of compound 112 in male Wistar rats.

DETAILED DESCRIPTION

Figure 3:
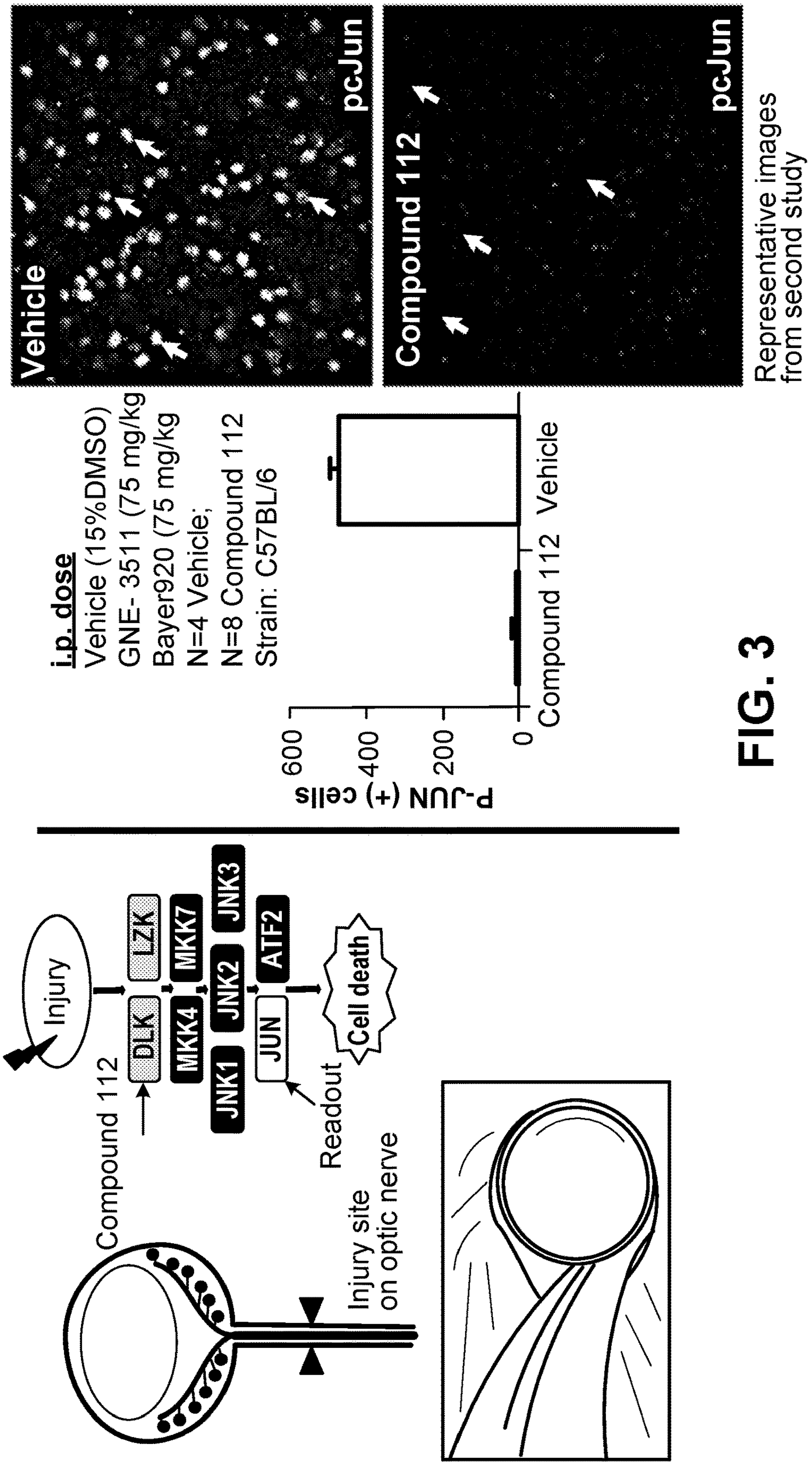
FIG. 3 depicts graphics illustrating aspects of a mouse optic nerve crush experiment, a bar graph showing p-JUN cell population, and confocal microscopy images showing RGCs after injection of a vehicle and compound 112.

Dual leucine zipper kinase (DLK, MAP3K12) is a key component of the neuronal stress response that regulates neurodegeneration in models of acute neuronal injury and chronic neurodegenerative diseases such as Alzheimer's, Parkinson's, and amyotrophic lateral sclerosis (ALS). The neuronally enriched kinase DLK (dual leucine zipper kinase, also known as mitogen activated protein 3 kinase 12, MAP3K12) represents a putative druggable component of this conserved neuronal degeneration pathway. Pharmacological inhibition or genetic deletion of DLK is sufficient to reduce the neuronal injury response and results in the protection of various neuronal populations from degeneration in response to a wide range of neuronal insults, suggesting that the inhibition of DLK might represent an attractive and potent therapeutic strategy. (Mata, M. et al., *J. Biol Chem.* 1996, 271, 16888-16896; Watkins, T. A. et al., *Proc. Natl. Acad Sci.,* 2013, 110, 4039-4044)).

Leucine Zipper-bearing Kinase (LZK/MAP3K13) is a member of the mixed lineage kinase family with high sequence identity to Dual Leucine Zipper Kinase (DLK/MAP3K12) and has been shown to also play a role in neuronal survival. In RGC cell death signaling DLK and LZK appear to be able to compensate for each other, at least partially, likely reflecting their participation in common biochemical complexes. (Welsbie, D. S. et al., *Neuron,* 2017, 94, 1142-1154). Combined inhibition of DLK and LZK is more effective in preventing neuronal cell death than inhibition of either one alone.

Provided herein are compounds of low molecular weight that can inhibit both DLK and LZK. Such compounds can be suitable for treatment and/or prevention of neurodegenerative disorders, such as ophthalmological neurodegenerative disorders.

Compounds of Formula (Z)

The present disclosure provides compounds of Formula (Z)

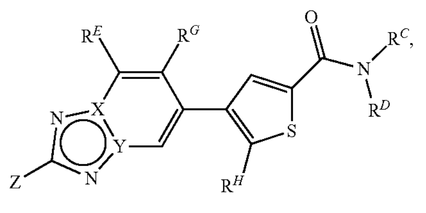

(Z)

wherein

X is nitrogen and Y is carbon, or

X is carbon and Y is nitrogen, $R^E$ is hydrogen, —C(O)—$NR^AR^B$, $C(O)OR^6$, —$S(O)_2NH$ $(C_1$-$C_6)$-alkyl, $(C_1$-$C_6)$-alkyl, halo, $(C_6$-$C_{10})$-aryl, or heteroaryl, wherein the $(C_1$-$C_6)$-alkyl, $(C_6$-$C_{10})$-aryl, and heteroaryl can be substituted by one or more independently selected $(C_1$-$C_4)$-alkyl, $(C_3$-$C_7)$ cycloalkyl, $(C_3$-$C_7)$-cycloalkyl-$(C_1$-$C_3)$-alkyl, 4- to 7-membered heterocyclyl, $(C_1$-$C_4)$-alkoxy, $(C_3$-$C_7)$-cycloalkoxy, —$SO_2R^4$, —$NR^4R^5$, cyano, hydroxyl, or halo, wherein the $(C_1$-$C_4)$-alkyl, $(C_3$-$C_7)$-cycloalkyl, $(C_1$-$C_4)$-alkoxy, $(C_3$-$C_7)$-cycloalkyl-$(C_1$-$C_3)$-alkyl, and $(C_3$-$C_7)$-cycloalkoxy can be substituted by one or more independently selected hydroxyl, cyano, or halo, $R^A$ is hydrogen or —$CR^1R^2R^3$, $R^B$ is hydrogen or $(C_1$-$C_6)$-alkyl, $R^1$ and $R^2$ are each independently hydrogen or $(C_1$-$C_3)$-alkyl, wherein the $(C_1$-$C_3)$-alkyl can be substituted by one or more independently selected halo, $R^3$ is hydrogen, $(C_1$-$C_6)$-alkyl, $(C_3$-$C_7)$cycloalkyl, or $(C_3$-$C_7)$-cycloalkyl-$(C_1$-$C_3)$-alkyl, wherein the $(C_1$-$C_6)$-alkyl, $(C_3$-$C_7)$-cycloalkyl, or $(C_3$-$C_7)$-cycloalkyl-$(C_1$-$C_3)$-alkyl can be substituted by one or more independently selected hydroxyl, $(C_1$-$C_4)$-alkoxy, oxo, cyano, or halo, and wherein the $(C_1$-$C_4)$-alkoxy can be substituted by one or more independently selected halo, or $R^1$ is hydrogen and $R^2$ and $R^3$ are joined to one another and, taken together with the carbon atom to which they are attached, form a 3- to 7-membered ring containing up to two heteroatoms selected from the group consisting of O or N, wherein the ring can be substituted by one or more independently selected hydroxyl, $(C_1$-$C_4)$-alkoxy, $(C_1$-$C_4)$-alkyl, oxo, cyano, or halo, and wherein the $(C_1$-$C_4)$-alkoxy and $(C_1$-$C_4)$-alkyl can be substituted by one or more independently selected hydroxyl or halo, $R^C$ is hydrogen, $(C_6$-$C_{10})$-aryl, or $CR^4R^5R^7$, wherein the $(C_6$-$C_{10})$-aryl is optionally substituted by one or more independently selected $(C_1$-$C_4)$-alkyl, $(C_1$-$C_4)$-alkoxy, or halo, and wherein the $(C_1$-$C_4)$-alkyl and $(C_1$-$C_4)$-alkoxy can be substituted by one or more independently selected hydroxyl or halo, $R^4$ is hydrogen, $(C_1$-$C_6)$alkyl, $(C_3$-$C_7)$-cycloalkyl, or 4- to 7-membered heterocyclyl, wherein the $(C_1$-$C_6)$-alkyl, $(C_1$-$C_7)$-cycloalkyl, or 4- to 7-membered heterocyclyl can be substituted by one or more independently selected $(C_1$-$C_4)$-alkyl, $(C_1$-$C_4)$-alkoxy, hydroxyl, oxo, cyano, or halo, wherein the $(C_1$-$C_4)$-alkoxy and $(C_1$-$C_4)$-alkyl can be substituted by one or more independently selected halo, and any nitrogen of the 4- to 7-membered heterocyclyl can be substituted by C(O) $OR^6$ or $C(O)R^6$, $R^5$ is $(C_1$-$C_6)$-alkyl, $(C_3$-$C_7)$-cycloalkyl, cyanomethyl, $(C_6$-$C_{10})$-aryl, $(C_6$-$C_{10})$-aryl-$(C_1$-$C_4)$-alkyl, heteroaryl, or 4- to 7-membered heterocyclyl wherein:

(i) the $(C_1$-$C_6)$-alkyl, $(C_3$-$C_7)$-cycloalkyl, $(C_6$-$C_{10})$-aryl, $(C_6$-$C_{10})$-aryl-$(C_1$-$C_4)$-alkyl, heteroaryl, or 4- to 7-membered heterocyclyl can be substituted by one or more independently selected $(C_1$-$C_4)$-alkyl, $(C_1$-$C_4)$-alkoxy, $C(O)OR^6$, $(C_3$-$C_7)$-cycloalkoxy, cyano, 4- to 7-membered heterocyclyl, or halo, and wherein the $(C_1$-$C_4)$-alkyl and $(C_1$-$C_4)$-alkoxy can be substituted by one or more independently selected 4- to 7-membered heterocyclyl optionally substituted with oxo or $(C_1$-$C_4)$-alkyl, $(C_1$-$C_4)$-alkoxy, —NR'R", or halo, and (ii) the $(C_3$-$C_7)$-cycloalkyl, $(C_6$-$C_{10})$-aryl, $(C_6$-$C_{10})$-aryl-$(C_1$-$C_4)$-alkyl, heteroaryl, or 4- to 7-membered heterocyclyl can be fused with a 4- to 7-membered heterocyclyl or $(C_3$-$C_7)$-cycloalkyl, or $R^4$ and $R^5$ are joined to one another and, taken together with the carbon atom to which they are attached, form a 3- to 8-membered monocyclic or bridged bicyclic ring containing up to two heteroatoms selected from the group consisting of O or N, wherein:

(i) the ring can be substituted by one or more independently selected ($C_6$-$C_{10}$)-aryl-($C_1$-$C_4$)-alkyl, ($C_6$-$C_{10}$)-aryl, 4- to 7-membered heterocyclyl, ($C_1$-$C_4$)-alkyl, ($C_1$-$C_4$)-alkoxy, oxo, cyano, or halo, wherein the ($C_1$-$C_4$)-alkyl and ($C_6$-$C_{10}$)-aryl can be substituted by one or more independently selected 4- to 7-membered heterocyclyl, ($C_1$-$C_4$)-alkoxy, or halo, and the nitrogen of each of the 4- to 7-membered heterocyclyl can independently be substituted by $C(O)OR^6$ or $C(O)R^6$, and (ii) the ring can be fused with ($C_6$-$C_{10}$)-aryl, heteroaryl, or 4- to 7-membered heterocyclyl, each of which is optionally substituted with one or more independently selected ($C_1$-$C_4$)-alkoxy or halo, or $R^6$ is hydrogen or ($C_1$-$C_4$)-alkyl, $R^7$ is hydrogen, ($C_1$-$C_6$)-alkyl, ($C_3$-$C_7$)cycloalkyl, ($C_6$-$C_{10}$)-aryl, or 4- to 7-membered heterocyclyl, wherein the ($C_1$-$C_6$)-alkyl, ($C_3$-$C_7$)-cycloalkyl, ($C_6$-$C_{10}$)-aryl, or 4- to 7-membered heterocyclyl can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more independently selected halo, and the nitrogen of the 4- to 7-membered heterocyclyl can be substituted by $C(O)OR^6$ or $C(O)R^6$, $R^D$ is hydrogen or ($C_1$-$C_6$)-alkyl, or $R^C$ and $R^D$ are joined to one another and, taken together with the carbon atom to which they are attached, form a 4- to 10-membered monocyclic or bicyclic ring containing up to three heteroatoms selected from the group consisting of O or N, and wherein the 4- to 10-membered monocyclic or bicyclic ring is optionally substituted with one or more independently selected ($C_1$-$C_6$)-alkyl or ($C_1$-$C_4$)-alkoxy, Z is —$NHR^F$ or H, $R^F$ is hydrogen or ($C_1$-$C_6$)-alkyl, wherein the ($C_1$-$C_6$)-alkyl is optionally substituted with one or more independently selected —NR'R", each occurrence of R' and R" is selected from hydrogen and ($C_1$-$C_4$)-alkyl, or R' and R", joined to one another and, taken together with the nitrogen atom to which they are attached, form a 3-6 membered heterocyclyl, $R^G$ is hydrogen or halo, $R^H$ is hydrogen, halo, or ($C_1$-$C_4$)-alkyl, and salts, solvates, and solvates of salts thereof.

The present disclosure provides compounds of Formula (Y)

(Y)

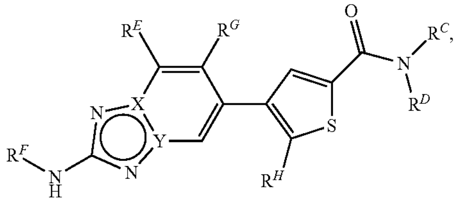

wherein

X is nitrogen and Y is carbon, or

X is carbon and Y is nitrogen, $R^E$ is hydrogen or —C(O)—$NR^AR^B$, $R^A$ is hydrogen or —$CR^1R^2R^3$, $R^B$ is hydrogen or ($C_1$-$C_6$)-alkyl, $R^1$ and $R^2$ are each independently hydrogen or ($C_1$-$C_3$)-alkyl, wherein the ($C_1$-$C_3$)-alkyl can be substituted by one or more independently selected halo, $R^3$ is hydrogen, ($C_1$-$C_6$)-alkyl, ($C_3$-$C_7$)-cycloalkyl or ($C_3$-$C_7$)-cycloalkyl-($C_1$-$C_3$)-alkyl wherein the ($C_1$-$C_6$)-alkyl, ($C_3$-$C_7$)-cycloalkyl, or ($C_3$-$C_7$)-cycloalkyl-($C_1$-$C_3$)-alkyl can be substituted by one or more independently selected hydroxyl, ($C_1$-$C_4$)-alkoxy, oxo, cyano, or halo, and wherein the ($C_1$-$C_4$)-alkoxy can be substituted by one or more independently selected halo, or $R^1$ is hydrogen and $R^2$ and $R^3$ are joined to one another and, taken together with the carbon atom to which they are attached, form a 3- to 7-membered ring containing up to two heteroatoms selected from the group consisting of O or N, wherein the ring can be substituted by one or more independently selected hydroxyl, ($C_1$-$C_4$)-alkoxy, ($C_1$-$C_4$)-alkyl, oxo, cyano, or halo, and wherein the ($C_1$-$C_4$)-alkoxy and ($C_1$-$C_4$)-alkyl can be substituted by one or more independently selected hydroxyl or halo, $R^C$ is hydrogen, ($C_6$-$C_{10}$)-aryl, or $CR^4R^5R^7$, wherein the ($C_6$-$C_{10}$)-aryl is optionally substituted by one or more independently selected ($C_1$-$C_4$)-alkyl, ($C_1$-$C_4$)-alkoxy, halo, and wherein the ($C_1$-$C_4$)-alkyl and ($C_1$-$C_4$)-alkoxy can be substituted by one or more independently selected hydroxyl or halo, $R^4$ is hydrogen, ($C_1$-$C_6$)-alkyl, ($C_3$-$C_7$)-cycloalkyl, or 4- to 7-membered heterocyclyl wherein the ($C_1$-$C_6$)-alkyl, ($C_3$-$C_7$)-cycloalkyl, or 4- to 7-membered heterocyclyl can be substituted by one or more independently selected ($C_1$-$C_4$)-alkyl, ($C_1$-$C_4$)-alkoxy, hydroxyl, oxo, cyano, or halo, wherein the ($C_1$-$C_4$)-alkoxy and ($C_1$-$C_4$)-alkyl can be substituted by one or more independently selected halo, and the nitrogen of the 4- to 7-membered heterocyclyl can be substituted by $C(O)OR^6$ or $C(O)R^6$, $R^5$ is ($C_1$-$C_6$)-alkyl, ($C_3$-$C_7$)-cycloalkyl, cyanomethyl, ($C_6$-$C_{10}$)-aryl, ($C_6$-$C_{10}$)-aryl-($C_1$-$C_4$)-alkyl, heteroaryl, or 4- to 7-membered heterocyclyl wherein:

(i) the ($C_1$-$C_6$)-alkyl, ($C_3$-$C_7$)-cycloalkyl, ($C_6$-$C_{10}$)-aryl, ($C_6$-$C_{10}$)-aryl-($C_1$-$C_4$)-alkyl, heteroaryl, or 4- to 7-membered heterocyclyl can be substituted by one or more independently selected ($C_1$-$C_4$)-alkyl, ($C_1$-$C_4$)-alkoxy, $C(O)OR^6$, ($C_3$-$C_7$ cycloalkoxy, cyano, 4- to 7-membered heterocyclyl, or halo, and wherein the ($C_1$-$C_4$)-alkyl and ($C_1$-$C_4$)-alkoxy can be substituted by one or more independently selected 4- to 7-membered heterocyclyl optionally substituted with oxo or ($C_1$-$C_4$)-alkyl, ($C_1$-$C_4$)-alkoxy, —NR'R", or halo, and (ii) the ($C_3$-$C_7$)cycloalkyl, ($C_6$-$C_{10}$)-aryl, ($C_6$-$C_{10}$)-aryl-($C_1$-$C_4$-alkyl, heteroaryl, or 4- to 7-membered heterocyclyl can be fused with a 4- to 7-membered heterocyclyl or ($C_3$-$C_7$)-cycloalkyl, or $R^4$ and $R^5$ are joined to one another and, taken together with the carbon atom to which they are attached, form a 3- to 8-membered monocyclic or bridged bicyclic ring containing up to two heteroatoms selected from the group consisting of O or N, wherein:

(i) the ring can be substituted by one or more ($C_6$-$C_{10}$)-aryl-($C_1$-$C_4$)-alkyl, ($C_6$-$C_{10}$)-aryl, 4- to 7-membered heterocyclyl, ($C_1$-$C_4$)-alkyl, ($C_1$-$C_4$)-alkoxy, oxo, cyano, or halo, wherein the ($C_1$-$C_4$)-alkyl and ($C_6$-

$C_{10}$)-aryl substituents are optionally substituted by one or more independently selected 4- to 7-membered heterocyclyl, ($C_1$-$C_4$)-alkoxy, or halo, and the nitrogen of each of the 4- to 7-membered heterocyclyl can independently be substituted by $C(O)OR^6$ or $C(O)R^6$, and (ii) the ring can be fused with phenyl, heteroaryl, or 4- to 7-membered heterocyclyl, each of which is optionally substituted with one or more independently selected ($C_1$-$C_4$)-alkoxy or halo, $R^6$ is hydrogen or ($C_1$-$C_4$)-alkyl, $R^7$ is hydrogen, ($C_1$-$C_6$)-alkyl, ($C_3$-$C_7$)-cycloalkyl, ($C_6$-$C_{10}$)-aryl, or 4- to 7-membered heterocyclyl wherein the ($C_1$-$C_6$)-alkyl, ($C_3$-$C_7$)-cycloalkyl, ($C_6$-$C_{10}$)-aryl, or 4- to 7-membered heterocyclyl can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more independently selected halo, and the nitrogen of the 4- to 7-membered heterocyclyl can be substituted by $C(O)OR^6$ or $C(O)R^6$, $R^D$ is hydrogen or ($C_1$-$C_6$)-alkyl, or $R^C$ and $R^D$ are joined to one another and, taken together with the carbon atom to which they are attached, form a 4- to 10-membered monocyclic or bicyclic ring containing up to three heteroatoms selected from the group consisting of O or N, and wherein the 4- to 10-membered monocyclic or bicyclic ring is optionally substituted by one or more independently selected ($C_1$-$C_6$)-alkyl or ($C_1$-$C_4$)-alkoxy, $R^F$ is hydrogen or ($C_1$-$C_6$)-alkyl, wherein the ($C_1$-$C_6$)-alkyl is optionally substituted with one or more independently selected —NR'R", each occurrence of R' and R" is selected from hydrogen and ($C_1$-$C_4$)-alkyl, $R^G$ is hydrogen or halo, $R^H$ is hydrogen, halo, or ($C_1$-$C_4$)-alkyl.

The present disclosure provides compounds of Formula (X)

(X)

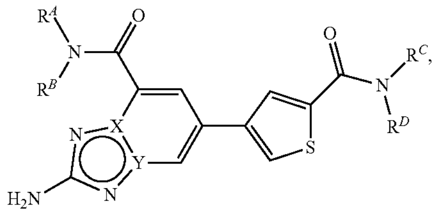

in which

X is nitrogen and Y is carbon, or

X is carbon and Y is nitrogen, $R^A$ is hydrogen or $—CR^1R^2R^3$, $R^B$ is hydrogen or ($C_1$-$C_5$)-alkyl, $R^1$ and $R^2$ are each independently hydrogen or ($C_1$-$C_3$)-alkyl, wherein the ($C_1$-$C_3$)-alkyl can be substituted by one or more independently selected halo, $R^3$ is hydrogen, ($C_1$-$C_6$)-alkyl, ($C_3$-$C_4$)cycloalkyl or ($C_3$-$C_7$)-cycloalkyl($C_1$-$C_3$)-alkyl wherein the ($C_1$-$C_6$)-alkyl, ($C_3$-$C_7$)-cycloalkyl, or ($C_3$-$C_7$)-cycloalkyl-($C_1$-$C_3$)-alkyl can be substituted by one or more independently selected hydroxyl, ($C_1$-$C_4$)-alkoxy, oxo, cyano, or halo, and wherein the ($C_1$-$C_4$)-alkoxy can be substituted by one or more independently selected halo, or $R^1$ is hydrogen and $R^2$ and $R^3$ are joined to one another and, taken together with the carbon atom to which they are attached, form a 3- to 7-membered ring containing up to two heteroatoms selected from the group consisting of O or N, wherein the ring can be substituted by one or more independently selected hydroxyl, ($C_1$-$C_4$)-alkoxy, ($C_1$-$C_4$)-alkyl, oxo, cyano, or halo, and wherein the ($C_1$-$C_4$)-alkoxy and ($C_1$-$C_4$)-alkyl can be substituted by one or more independently selected hydroxyl or halo, $R^C$ is hydrogen or $CR^4R^5R^7$, $R^4$ is hydrogen, ($C_1$-$C_6$)-alkyl, ($C_3$-$C_7$)-cycloalkyl or 4- to 7-membered heterocyclyl wherein the ($C_1$-$C_6$)-alkyl, ($C_3$-$C_7$)-cycloalkyl or 4- to 7-membered heterocyclyl can be substituted by one or more independently selected ($C_1$-$C_4$)-alkyl, ($C_1$-$C_4$)-alkoxy, oxo, cyano, halo, wherein the ($C_1$-$C_4$)-alkoxy and ($C_1$-$C_4$)-alkyl can be substituted by one or more independently selected halo, and the nitrogen of the 4- to 7-membered heterocyclyl can be substituted by $C(O)OR^6$ or $C(O)R^6$, $R^5$ is ($C_3$-$C_7$)-cycloalkyl, cyanomethyl, ($C_6$-$C_{10}$)-aryl, or heteroaryl, wherein the ($C_3$-$C_7$)-cycloalkyl, ($C_6$-$C_{10}$)-aryl or heteroaryl can be substituted by one or more independently selected ($C_1$-$C_4$)-alkyl, ($C_1$-$C_4$)-alkoxy, cyano, 4- to 7-membered heterocyclyl, or halo, and wherein the ($C_1$-$C_4$)-alkyl and ($C_1$-$C_4$)-alkoxy can be substituted by one or more independently selected halo, or $R^4$ and $R^5$ are joined to one another and, taken together with the carbon atom to which they are attached, form a 3- to 8-membered monocyclic or bridged bicyclic ring containing up to two heteroatoms selected from the group consisting of O or N, wherein:

(i) the ring can be substituted by one or more ($C_6$-$C_{10}$)-aryl-($C_1$-$C_4$)-alkyl, ($C_6$-$C_{10}$)-aryl, 4- to 7-membered heterocyclyl, ($C_1$-$C_4$)-alkyl, ($C_1$-$C_4$)-alkoxy, oxo, cyano, or halo, wherein the ($C_1$-$C_4$)-alkyl and ($C_6$-$C_{10}$)-aryl substituents are optionally substituted by one or more independently selected 4- to 7-membered heterocyclyl, or halo, and the nitrogen of each of the 4- to 7-membered heterocyclyl can independently be substituted by $C(O)OR^6$ or $C(O)R^6$, and (ii) the ring can be fused with phenyl or heteroaryl, each of which is optionally substituted with one or more independently selected ($C_1$-$C_4$)-alkoxy or halo, $R^6$ is ($C_1$-$C_4$)-alkyl, $R^7$ is hydrogen, ($C_1$-$C_6$)-alkyl, ($C_3$-$C_7$)-cycloalkyl, ($C_6$-$C_{10}$)-aryl, or 4- to 7-membered heterocyclyl, wherein the ($C_1$-$C_6$)-alkyl, ($C_3$-$C_7$)-cycloalkyl, ($C_6$-$C_{10}$)-aryl, or 4- to 7-membered heterocyclyl can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more independently selected halo, and the nitrogen of the 4- to 7-membered heterocyclyl can be substituted by $C(O)OR^6$ or $C(O)R^6$, $R^D$ is hydrogen or ($C_1$-$C_6$)-alkyl.

The present disclosure provides compounds of Formula (A)

(A)

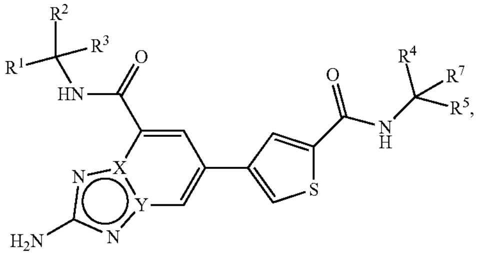

wherein

X is nitrogen and Y is carbon, or

X is carbon and Y is nitrogen, $R^1$ and $R^2$ are each independently hydrogen or ($C_1$-$C_3$)-alkyl optionally substituted by one or more fluoro, $R^3$ is ($C_1$-$C_6$)-alkyl, ($C_3$-$C_7$)-cycloalkyl, or ($C_3$-$C_7$)-cycloalkyl-($C_1$-$C_3$)-alkyl, wherein the ($C_1$-$C_6$)-alkyl, ($C_3$-$C_7$)-cycloalkyl, or ($C_3$-$C_7$)-cycloalkyl-($C_1$-$C_3$)-alkyl can be substituted by one or more independently selected hydroxyl, ($C_1$-$C_4$)-alkoxy, oxo, cyano, or halo, and wherein the ($C_1$-$C_4$)-alkoxy can be substituted by one or more independently selected halo, or $R^1$ is hydrogen and $R^2$ and $R^3$ are joined to one another and, taken together with the carbon atom to which they are attached, form a 4- to 7-membered ring containing up to two heteroatoms selected from the group consisting of O or N, wherein the ring can be substituted by one or more independently selected hydroxyl, ($C_1$-$C_4$)-alkoxy, ($C_1$-$C_4$)-alkyl, oxo, cyano, or halo, and wherein the ($C_1$-$C_4$)-alkoxy and ($C_1$-$C_4$)-alkyl can be substituted by one or more independently selected halo, $R^4$ is hydrogen, ($C_1$-$C_6$)-alkyl, ($C_3$-$C_7$)-cycloalkyl, or 4- to 7-membered heterocyclyl, wherein the ($C_1$-$C_6$)-alkyl, ($C_3$-$C_7$)-cycloalkyl or 4- to 7-membered heterocyclyl can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more independently selected halo, and any nitrogen of the 4- to 7-membered heterocyclyl can be substituted by C(O)OR$^6$ or C(O)R$^6$, $R^5$ is ($C_3$-$C_7$)-cycloalkyl, cyanomethyl, ($C_6$-$C_{10}$)-aryl, or heteroaryl, wherein the ($C_3$-$C_7$)-cycloalkyl, ($C_6$-$C_{10}$)-aryl, or heteroaryl can be substituted by one or more independently selected ($C_1$-$C_4$)-alkyl, ($C_1$-$C_4$)-alkoxy, cyano, 4- to 7-membered heterocyclyl, or halo, and wherein the ($C_1$-$C_4$)-alkyl and ($C_1$-$C_4$)-alkoxy can be substituted by one or more independently selected halo, or $R^4$ and $R^5$ are joined to one another and, taken together with the carbon atom to which they are attached, form a 4- to 7-membered ring containing tip to two heteroatoms selected from the group consisting of O or N, wherein:

(i) the ring can be substituted by one or more independently selected ($C_6$-$C_{10}$)-aryl-($C_1$-$C_4$)-alkyl, 4- to 7-membered heterocyclyl, ($C_1$-$C_4$)-alkyl, ($C_1$-$C_4$)-alkoxy, oxo, cyano, or halo, wherein the ($C_1$-$C_4$)-alkyl is optionally substituted by one or more independently selected 4- to 7-membered heterocyclyl or halo, and any nitrogen of each of the 4- to 7-membered heterocyclyl can independently be substituted by C(O)OR$^6$ or C(O)R$^6$, and (ii) the ring can be fused with ($C_6$-$C_{10}$)-aryl or heteroaryl, $R^6$ is ($C_1$-$C_4$)-alkyl, $R^7$ is hydrogen, ($C_1$-$C_6$)-alkyl, ($C_6$-$C_{10}$)-aryl, ($C_3$-$C_7$)-cycloalkyl, or 4- to 7-membered heterocyclyl, wherein the ($C_1$-$C_6$)-alkyl, ($C_3$-$C_7$)-cycloalkyl, or 4- to 7-membered heterocyclyl can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more independently selected halo, and any nitrogen of the 4- to 7-membered heterocyclyl can be substituted by C(O)OR$^6$ or C(O)R$^6$.

The present disclosure provides compounds of Formula (I)

(I)

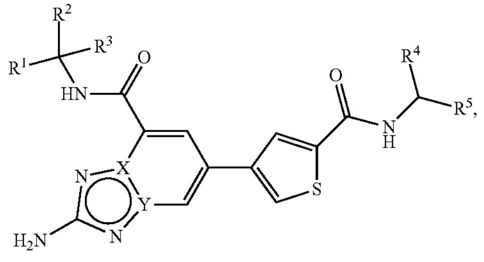

wherein

X is nitrogen and Y is carbon, or

X is carbon and Y is nitrogen, $R^1$ and $R^2$ are each independently hydrogen or ($C_1$-$C_3$)-alkyl optionally substituted by one or more fluoro, $R^3$ is ($C_1$-$C_6$)-alkyl, ($C_3$-$C_7$)-cycloalkyl, or ($C_3$-$C_7$)-cycloalkyl-($C_1$-$C_3$)-alkyl wherein the ($C_1$-$C_6$)-alkyl, ($C_3$-$C_7$)cycloalkyl, or ($C_3$-$C_7$)-cycloalkyl-($C_1$-$C_3$)-alkyl can be substituted by one or more independently selected hydroxyl, ($C_1$-$C_4$)-alkoxy, oxo, cyano, or halo, and wherein the ($C_1$-$C_4$)-alkoxy can be substituted by one or more independently selected halo, or $R^1$ is hydrogen and $R^2$ and $R^3$ are joined to one another and, taken together with the carbon atom to which they are attached, form a 4- to 7-membered ring containing up to two heteroatoms selected from the group consisting of O or N, wherein the ring can be substituted by one or more independently selected hydroxyl, ($C_1$-$C_4$)-alkoxy, ($C_1$-$C_4$)-alkyl, oxo, cyano, or halo, and wherein the ($C_1$-$C_4$)-alkoxy and ($C_1$-$C_4$)-alkyl can be substituted by one or more independently selected halo, $R^4$ is hydrogen, ($C_1$-$C_6$)-alkyl, ($C_3$-$C_7$)-cycloalkyl, or 4- to 7-membered heterocyclyl wherein the ($C_1$-$C_6$)-alkyl, ($C_3$-$C_7$)-cycloalkyl, or 4- to 7-membered heterocyclyl can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more independently selected halo, and any nitrogen of the 4- to 7-membered heterocyclyl can be substituted by C(O)OR$^6$ or C(O)R$^6$, $R^5$ is ($C_3$-$C_7$)-cycloalkyl, ($C_6$-$C_{10}$)-aryl, or heteroaryl, wherein the ($C_3$-$C_7$)-cycloalkyl, ($C_6$-$C_{10}$)-aryl, or heteroaryl can be substituted by one or more independently selected $(C_1-C_4)$-alkyl, $(C_1-C_4)$-alkoxy, cyano, 4- to 7-membered heterocyclyl, or halo, and wherein the $(C_1-C_4)$-alkyl and $(C_1-C_4)$-alkoxy can be substituted by one or more fluoro, or $R^4$ and $R^5$ are joined to one another and, taken together with the carbon atom to which they are attached, form a 4- to 7-membered ring containing up to two heteroatoms selected from the group consisting of O or N, wherein:

(i) the ring can be substituted by one or more independently selected $(C_6-C_{10})$-aryl-$(C_1-C_4)$-alkyl, 4- to 7-membered heterocyclyl, $(C_1-C_4)$-alkyl, $(C_1-C_4)$-alkoxy, oxo, cyano, or halo, wherein the $(C_1-C_4)$-alkyl is optionally substituted by one or more independently selected 4- to 7-membered heterocyclyl or fluoro, and any nitrogen of each of the 4- to 7-membered heterocyclyl can independently be substituted by $C(O)OR^6$ or $C(O)R^6$, and (ii) the ring can be fused with $(C_6-C_{10})$-aryl or heteroaryl, $R^6$ is $(C_1-C_4)$-alkyl.

In some embodiments, $R^1$ and $R^2$ are each independently hydrogen or methyl, $R^3$ is $(C_1-C_6)$-alkyl which can be substituted by one or more independently selected hydroxyl, $(C_1-C_4)$-alkoxy, oxo, cyano, or halo, wherein the $(C_1-C_4)$-alkoxy can be substituted by one or more fluoro, or $R^1$ is hydrogen and $R^2$ and $R^3$ are joined to one another and, taken together with the carbon atom to which they are attached, form a pyrrolidinone, a cyclobutyl, or a tetrahydrofuranyl, $R^4$ is $(C_1-C_6)$-alkyl, $(C_3-C_7)$-cycloalkyl, 4- to 7-membered heterocyclyl wherein the $(C_1-C_6)$-alkyl, $(C_3-C_7)$-cycloalkyl, or 4- to 7-membered heterocyclyl can be substituted by one or more independently selected $(C_1-C_4)$-alkoxy or halo, and any nitrogen of the 4- to 7-membered heterocyclyl can be substituted by $C(O)OR^6$ or $C(O)R^6$, $R^5$ is phenyl or benzoxazolyl, wherein the phenyl or benzoxazolyl can be substituted by one or more independently selected $(C_1-C_4)$-alkyl, $(C_1-C_4)$-alkoxy, cyano, or halo, wherein the $(C_1-C_4)$-alkyl and $(C_1-C_4)$-alkoxy can be substituted by one or more fluoro, $R^6$ is $(C_1-C_4)$-alkyl and salts, solvates, and solvates of salts thereof.

In some embodiments,

X is carbon and Y is nitrogen, $R^1$ is hydrogen, $R^2$ is methyl, $R^3$ is $(C_1-C_4)$-alkyl which can be substituted by one or more independently selected hydroxyl, $(C_1-C_4)$-alkoxy, chloro, or fluoro, wherein the $(C_1-C_4)$-alkoxy can be substituted by one or more fluoro, or $R^1$ is hydrogen and $R^1$ and $R^3$ are joined to one another and, taken together with the carbon atom to which they are attached, form a 4- to 7-membered ring containing up to one O or N atom, wherein the ring can be substituted by one or more independently selected hydroxyl, oxo, $(C_1-C_4)$-alkoxy, or halo, wherein the $(C_1-C_4)$-alkoxy can be substituted by one or more fluoro, $R^4$ is $(C_1-C_6)$-alkyl, $(C_3-C_7)$-cycloalkyl, 4- to 7-membered heterocyclyl wherein the $(C_1-C_6)$-alkyl, $(C_3-C_7)$-cycloalkyl, or 4- to 7-membered heterocyclyl can be substituted by one or more independently selected halo, and any nitrogen of the 4- to 7-membered heterocyclyl can be substituted by $C(O)OR^6$ or $C(O)R^6$, $R^5$ is phenyl or benzoxazolyl wherein the phenyl or benzoxazolyl can be substituted by one or more independently selected $(C_1-C_4)$-alkyl, $(C_1-C_4)$-alkoxy, cyano, or halo, wherein the $(C_1-C_4)$-alkyl and $(C_1-C_4)$-alkoxy can be substituted by one or more fluoro, $R^6$ is $(C_1-C_4)$-alkyl and salts, solvates, and solvates of salts thereof.

In some embodiments, $R^1$ is hydrogen, $R^2$ is methyl, $R^3$ is $(C_1-C_4)$-alkyl which can be substituted by one or more independently selected hydroxyl, $(C_1-C_4)$-alkoxy, chloro, or fluoro, wherein the $(C_1-C_4)$-alkoxy can be substituted by one or more fluoro, or $R^1$ is hydrogen and $R^2$ and $R^3$ are joined tone another and, taken together with the carbon atom to which they are attached, form a pyrrolidinone, a cyclobutyl, or a tetrahydrofuranyl, $R^4$ is $(C_1-C_6)$-alkyl, $(C_3-C_7)$-cycloalkyl, 4- to 7-membered heterocyclyl, wherein the $(C_1-C_6)$-alkyl, $(C_3-C_7)$-cycloalkyl, or 4- to 7-membered heterocyclyl can be substituted by one or more independently selected $(C_1-C_4)$-alkoxy or halo, and any nitrogen of the 4- to 7-membered heterocyclyl can be substituted by $C(O)OR^6$ or $C(O)R^6$, $R^5$ is phenyl or benzoxazolyl, wherein the phenyl or benzoxazolyl can be substituted by one or more independently selected $(C_1-C_4)$-alkyl, $(C_1-C_4)$-alkoxy, cyano, or halo, wherein the $(C_1-C_4)$-alkyl and $(C_1-C_4)$-alkoxy can be substituted by one or more fluoro, $R^6$ is $(C_1-C_4)$-alkyl and salts, solvates, and solvates of salts thereof.

In some embodiments, the compound is a compound of formula (I-A)

(I-A)

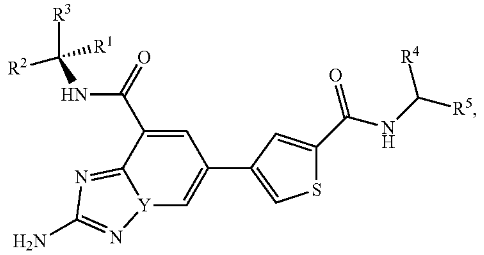

wherein $R^1$ is hydrogen, $R^2$ is methyl optionally substituted by one or more fluoro $R^3$ is $(C_1-C_3)$-alkyl which can be substituted by one or more independently selected hydroxyl, $(C_1-C_4)$-alkoxy, chloro, or fluoro, and wherein the $(C_1-C_4)$-alkoxy can be substituted by one or more fluoro, or $R^2$ and $R^3$ are joined to one another and, taken together with the carbon atom to which they are attached, form a 4- to 7-membered ring containing up to one O or N atom, wherein the ring can be substituted by oxo, $R^4$ is hydrogen, $(C_1-C_6)$-alkyl, $(C_3-C_7)$-cycloalkyl, 4- to 7-membered heterocyclyl, wherein the $(C_1-C_6)$-alkyl, $(C_3-C_7)$-cycloalkyl, or 4- to 7-membered heterocyclyl can be substituted by one or more independently selected ($C_1$-$C_4$)-alkoxy or halo, and any nitrogen of the 4- to 7-membered heterocyclyl can be substituted by C(O)OR$^6$ or C(O)R$^6$, $R^5$ is phenyl or benzoxazolyl, wherein the phenyl or benzoxazolyl can be substituted by one or more independently selected ($C_1$-$C_4$-alkyl, ($C_1$-$C_4$)-alkoxy, cyano, or halo, and wherein the ($C_1$-$C_4$)-alkyl and ($C_1$-$C_4$)-alkoxy can be substituted by one or more fluoro, $R^4$ and $R^5$ are joined to one another and, taken together with the carbon atom to which they are attached, form a 5- to 6-membered ring containing up to one 0 atom, wherein the ring can be fused with phenyl, $R^6$ is ($C_1$-$C_4$)-alkyl.

In some embodiments, the compound is a compound of formula (I-B) wherein (I-B)

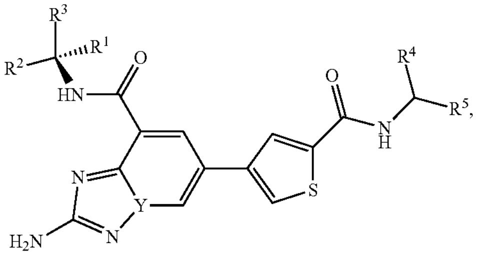

$R^1$ is hydrogen, $R^2$ is methyl optionally substituted by one or more fluoro, $R^3$ is methyl or ethyl which can be substituted by one or more independently selected hydroxyl, ($C_1$-$C_4$)-alkoxy, chloro, or fluoro, wherein the ($C_1$-$C_4$)-alkoxy can be substituted by one or more fluoro, or $R^2$ and $R^3$ are joined to one another and, taken together with the carbon atom to which they are attached, form a pyrrolidinone, a cyclobutyl, or a tetrahydrofuranyl, $R^4$ is hydrogen, ($C_1$-$C_6$)-alkyl, cyclopropyl, cyclobutyl, cyclopentyl, or 4- to 7-membered heterocyclyl, each of which can be substituted by one or more independently selected ($C_1$-$C_4$)-alkoxy or halo, and any nitrogen of the 4- to 7-membered heterocyclyl can be substituted by C(O)OR$^6$ or C(O)R$^6$, $R^5$ is phenyl or benzoxazolyl, each of which can be substituted by one or more independently selected ($C_1$-$C_4$)-alkyl, ($C_1$-$C_4$)-alkoxy, cyano, or balo, wherein the ($C_1$-$C_4$)-alkyl and ($C_1$-$C_4$)-alkoxy can be substituted by one or more fluoro, $R^4$ and $R^5$ are joined to one another and, taken together with the carbon atom to which they are attached, form a 5- to 6-membered ring containing up to one O atom, wherein the ring can be fused with phenyl, $R^6$ is ($C_1$-$C_4$)-alkyl and salts, solvates, and solvates of salts thereof.

In some embodiments, the compound is a compound of formula (I-C)

(I-C)

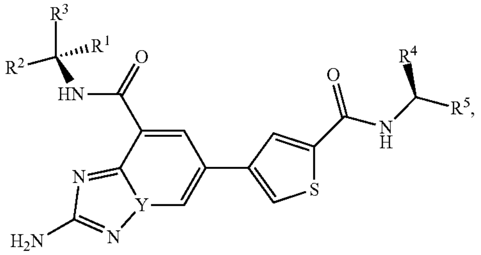

wherein $R^1$ is hydrogen, $R^2$ is methyl optionally substituted by one or more fluoro, $R^3$ is methyl or ethyl which can be substituted by one or more independently selected hydroxyl, ($C_1$-$C_4$)-alkoxy, chloro, or fluoro, wherein the ($C_1$-$C_4$)-alkoxy can be substituted by one or more fluoro, or $R^2$ and $R^3$ are joined to one another and, taken together with the carbon atom to which they are attached, form pyrrolidinone, a cyclobutyl, or a tetrahydrofuranyl, $R^4$ is hydrogen, ($C_1$-$C_6$)-alkyl, cyclopropyl, cyclobutyl, cyclopentyl, or 4- to 7-membered heterocyclyl wherein the ($C_1$-$C_6$)-alkyl, cyclopropyl, cyclobutyl, cyclopentyl, or 4- to 7-membered heterocyclyl can be substituted by one or more independently selected ($C_1$-$C_4$)-alkoxy or halo, and any nitrogen of the 4- to 7-membered heterocyclyl can be substituted by C(O)OR$^6$ or C(O)R$^6$, $R^5$ is phenyl or benzoxazolyl, each of which can be substituted by one or more independently selected ($C_1$-$C_4$)-alkyl, ($C_1$-$C_4$)-alkoxy, cyano, or halo, wherein the ($C_1$-$C_4$)-alkyl and ($C_1$-$C_4$)-alkoxy can be substituted by one or more fluoro, $R^4$ and $R^5$ are joined to one another and, taken together with the carbon atom to which they are attached, form a 5- to 6-membered ring containing up to one O atom, wherein the ring can be fused with phenyl, $R^6$ is ($C_1$-$C_4$)-alkyl.

In some embodiments, the compound is a compound of formula (I-D) wherein (I-D)

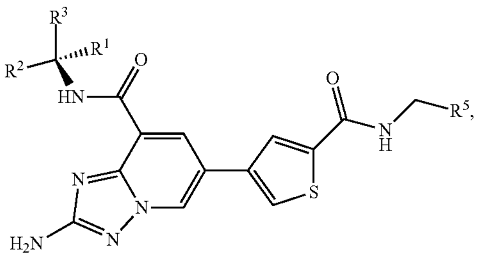

$R^1$ is hydrogen, $R^2$ is methyl, $R^3$ is methyl or ethyl which can be substituted by one or more independently selected hydroxyl, ($C_1$-$C_4$)-alkoxy, chloro, or fluoro, wherein the ($C_1$-$C_4$)-alkoxy can be substituted by one or more fluoro, $R^5$ is phenyl or benzoxazolyl, each of which can be substituted by one or more independently selected $(C_1-C_4)$-alkyl, $(C_1-C_4)$-alkoxy, cyano, or halo, wherein the $(C_1-C_4)$-alkyl and $(C_1-C_4)$-alkoxy can be substituted by one or more fluoro, and salts, solvates, and solvates of salts thereof.

The variables Z and $R^F$

In some embodiments, Z is H.

In some embodiments, Z is —$NHR^F$. In some embodiments, Z is $NH_2$.

In some embodiments, $R^F$ is hydrogen.

In some embodiments, $R^F$ is $(C_1-C_6)$-alkyl, wherein the $(C_1-C_6)$-alkyl is optionally substituted with one or more independently selected —NR'R". In some embodiments, $R^F$ is $(C_1-C_6)$-alkyl, wherein the $(C_1-C_6)$-alkyl is substituted with one or more independently selected —NR'R". In some embodiments, $R^F$ is $(C_1-C_3)$-alkyl, wherein the $(C_1-C_3)$-alkyl is optionally substituted with one or more independently selected —NR'R". In some embodiments, $R^F$ is $(C_1-C_3)$-alkyl, wherein the $(C_1-C_3)$-alkyl is optionally substituted with one or more independently selected —NR'R". In some embodiments, $R^F$ is ethyl or propyl, wherein the ethyl or propyl is optionally substituted with one or more independently selected —NR'R". In some embodiments, R is ethyl, wherein the ethyl is optionally substituted (e.g., substituted) with one or more independently selected —NR'R". In some embodiments, $R^F$ is propyl, wherein the propyl is optionally substituted (e.g., substituted) with one or more independently selected —NR'R". In some embodiments, the R alkyl is unsubstituted.

In some embodiments, —NR'R" is —$N(CH_3)_2$ or —$N(CH_2CH_3)_2$.

In some embodiments, each occurrence of R' and R" is selected from hydrogen and $(C_1-C_4)$-alkyl. In some embodiments, one occurrence of R' and R" is hydrogen and the other occurrence of R' and R" is $(C_1-C_4)$-alkyl. In some embodiments, one occurrence of R' and R" is hydrogen and the other occurrence of R' and R" is methyl, ethyl, or isopropyl (e.g., methyl; e.g., ethyl). In some embodiments, R' and R" are hydrogen. In some embodiments, R' and R" are independently selected $(C_1-C_4)$-alkyl. In some embodiments, R' and R" are methyl.

In some embodiments, R' and R", joined to one another and, taken together with the nitrogen atom to which they are attached, form a 3-6 membered heterocyclyl. In some embodiments, R' and R", joined to one another and, taken together with the nitrogen atom to which they are attached, form a morphlinyl.

The Variables X and Y

In some embodiments, X is carbon and Y is nitrogen. In some embodiments, Y is carbon and X is nitrogen.

The Variable $R^E$

In some embodiments, $R^E$ is hydrogen.

In some embodiments, $R^E$ is —C(O)—$NR^AR^B$.

In some embodiments, $R^E$ is $C(O)OR^6$. In some embodiments, R is C(O)OMe.

In some embodiments, $R^E$ is —$S(O)_2NH(C_1-C_6)$alkyl. In some embodiments, $R^E$ is —$S(O)_2$NHMe.

In some embodiments, $R^E$ is $(C_1-C_6)$-alkyl, wherein the $(C_1-C_6)$-alkyl can be substituted by one or more independently selected $(C_1-C_4)$-alkyl, $(C_3-C_7)$-cycloalkyl, $(C_3-C_7)$-cycloalkyl-$(C_1-C_3)$-alkyl, 4- to 7-membered heterocyclyl, $(C_1-C_4)$alkoxy, $(C_3-C_7)$-cycloalkoxy, —$SO_2R^4$, —$NR^4R_5$, cyano, hydroxyl, or halo, wherein the $(C_1-C_4)$-alkyl, $(C_3-C_7)$cycloalkyl, $(C_1-C_4)$-alkoxy, $(C_3-C_7)$-cycloalkyl-$(C_1-C_3)$-alkyl, and $(C_3-C_7)$-cycloalkoxy can be substituted by one or more independently selected hydroxyl, cyano, or halo. In some embodiments, $R^E$ is $(C_1-C_6)$-alkyl, wherein the $(C_1-C_6)$-alkyl is substituted by one or more independently selected $(C_1-C_4)$-alkyl, $(C_3-C_7)$-cycloalkyl, $(C_3-C_7)$-cycloalkyl-$(C_1-C_3)$-alkyl, 4- to 7-membered heterocyclyl, $(C_1-C_4)$-alkoxy, $(C_3-C_7)$-cycloalkoxy, —$SO_2R^4$, —$NR^4R^5$, cyano, hydroxyl, or halo, wherein the $(C_1-C_4)$-alkyl, $(C_3-C_7)$-cycloalkyl, $(C_1-C_4)$-alkoxy, $(C_3-C_7)$-cycloalkyl-$(C_1-C_3)$-alkyl, and $(C_3-C_7)$-cycloalkoxy can be substituted by one or more independently selected hydroxyl, cyano, or halo. In some embodiments, $R^E$ is methyl, wherein the methyl can be substituted by one or more independently selected $(C_1-C_4)$-alkyl, $(C_3-C_7)$-cycloalkyl, $(C_3-C_7)$-cycloalkyl-$(C_1-C_3)$-alkyl, 4- to 7-membered heterocyclyl, $(C_1-C_4)$-alkoxy, $(C_3-C_7)$-cycloalkoxy, —$SO_2R^4$, —$NR^4R^5$, cyano, hydroxyl, or halo, wherein the $(C_1-C_4)$-alkyl, $(C_3-C_7)$-cycloalkyl, $(C_1-C_4)$-alkoxy, $(C_3-C_7)$-cycloalkyl-$(C_1-C_3)$-alkyl, and $(C_3-C_7)$-cycloalkoxy can be substituted by one or more independently selected hydroxyl, cyano, or halo. In some embodiments, $R^E$ is unsubstituted $(C_1-C_6)$-alkyl. In some embodiments, $R^E$ is unsubstituted methyl.

In some embodiments, $R^E$ is halo (e.g., fluoro).

In some embodiments, $R^E$ is $(C_6-C_{10})$-aryl, wherein the $(C_6-C_{10})$-aryl can be substituted by one or more independently selected $(C_1-C_4)$-alkyl, $(C_3-C_7)$-cycloalkyl, $(C_3-C_7)$-cycloalkyl-$(C_1-C_4)$-alkyl, 4- to 7-membered heterocyclyl, $(C_1-C_4)$-alkoxy, $(C_3-C_7)$-cycloalkoxy, —$SO_2$R, —$NR^4R^5$, cyano, hydroxyl, or halo, wherein the $(C_1-C_4)$-alkyl, $(C_3-C_7)$-cycloalkyl, $(C_1-C_4)$-alkoxy, $(C_3-C_7)$-cycloalkyl-$(C_1-C_3)$-alkyl, and $(C_1-C_4)$-cycloalkoxy can be substituted by one or more independently selected hydroxyl, cyano, or halo. In some embodiments, $R^E$ is $(C_6-C_{10})$-aryl, wherein the $(C_6-C_{10})$-aryl is substituted by one or more independently selected $(C_1-C_4)$-alkyl, $(C_3-C_7)$-cycloalkyl, $(C_3-C_7)$-cycloalkyl-$(C_1-C_3)$-alkyl, 4- to 7-membered heterocyclyl, $(C_1-C_4)$-alkoxy, $(C_3-C_7)$-cycloalkoxy, —$SO_2R^4$, —$NR^4R^5$, cyano, hydroxyl, or halo, wherein the $(C_1-C_4)$-alkyl, $(C_3-C_7)$-cycloalkyl, $(C_1-C_4)$-alkoxy, $(C_3-C_7)$-cycloalkyl-$(C_1-C_3)$-alkyl, and $(C_3-C_7)$-cycloalkoxy can be substituted by one or more independently selected hydroxyl, cyano, or halo. In some embodiments, $R^E$ is phenyl, wherein the phenyl can be substituted by one or more independently selected $(C_1-C_4)$-alkyl, $(C_3-C_7)$-cycloalkyl, $(C_3-C_7)$-cycloalkyl-$(C_1-C_3)$-alkyl, 4- to 7-membered heterocyclyl, $(C_1-C_4)$-alkoxy, $(C_3-C_7)$-cycloalkoxy, —$SO_2$R, —$NR^4R^5$, cyano, hydroxyl, or halo, wherein the $(C_1-C_4)$-alkyl, $(C_3-C_7)$-cycloalkyl, $(C_1-C_4)$-alkoxy, $(C_3-C_4)$-cycloalkyl-$(C_1-C_3)$-alkyl, and $(C_3-C_7)$-cycloalkoxy can be substituted by one or more independently selected hydroxyl, cyano, or halo. In some embodiments, $R^E$ is unsubstituted $(C_6-C_{10})$-aryl. In some embodiments, $R^E$ is unsubstituted phenyl.

In some embodiments, $R^E$ is heteroaryl, wherein the heteroaryl can be substituted by one or more independently selected $(C_1-C_4)$-alkyl, $(C_3-C_7)$-cycloalkyl, $(C_3-C_7)$-cycloalkyl-$(C_1-C_3)$alkyl, 4- to 7-membered heterocyclyl, $(C_1-C_4)$-alkoxy, $(C_3-C_7)$-cycloalkoxy, —$SO_2R^4$, —$NR^4R^5$, cyano, hydroxyl, or halo, wherein the $(C_1-C_4)$-alkyl, $(C_3-C_7)$-cycloalkyl, $(C_1-C_4)$-alkoxy, $(C_3-C_7)$-cycloalkyl-$(C_1-C_3)$-alkyl, and $(C_3-C_7)$-cycloalkoxy can be substituted by one or more independently selected hydroxyl, cyano, or halo. In some embodiments, $R^E$ is heteroaryl, wherein the heteroaryl is substituted by one or more independently selected $(C_1-C_4)$-alkyl, $(C_3-C_7)$-cycloalkyl, $(C_3-C_7)$-cycloalkyl-$(C_1-C_3)$-alkyl, 4- to 7-membered heterocyclyl, $(C_1-C_4)$-alkoxy, $(C_3-C_7)$-cycloalkoxy, —$SO_2$R, —$NR^4R^5$, cyano, hydroxyl, or halo, wherein the $(C_1-C_4)$-alkyl, $(C_3-C_7)$-cycloalkyl, $(C_1-C_4)$-alkoxy, $(C_3-C_7)$-cycloalkyl-$(C_1-C_3)$-alkyl, and $(C_3-C_7)$-cycloalkoxy can be substituted by one or more independently selected hydroxyl, cyano, or halo. In some embodiments, the heteroaryl is thiadiazolyl, oxadiazolyl, or pyrazolyl. In some embodiments, the heteroaryl is thiadiazolyl. In some embodiments, the heteroaryl is oxadiazolyl. In some embodiments, the heteroaryl is pyrazolyl. In some embodiments, the $R^E$ heteroaryl is unsubstituted.

In some embodiments, $R^E$ is —C(O)—$NR^AR^B$, and —C(O)—$NR^AR^B$ is

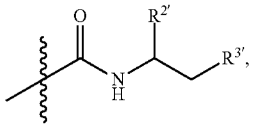

wherein:

- the wavy line indicates the point of attachment to the triazolopyridine core;
- $R^{2'}$ is hydrogen or $(C_1$-$C_3)$-alkyl, wherein the $(C_1$-$C_3)$-alkyl can be substituted by one or more independently selected halo;
- $R^3$ is —$((C_0$-$C_5)$-alkyl)-X, wherein X is hydroxyl, $(C_1$-$C_4)$-alkoxy, oxo, cyano, or halo, and wherein the $(C_1$-$C_4)$-alkoxy can be substituted by one or more independently selected halo.

In some embodiments, X is hydroxyl.

In some embodiments, X is $(C_1$-$C_4)$-alkoxy, wherein the $(C_1$-$C_4)$-alkoxy can be substituted by one or more independently selected halo. For example, X is methoxy.

In some embodiments, X is oxo.

In some embodiments, X is cyano.

In some embodiments, X is halo (e.g., fluoro).

In some embodiments, —C(O)—$NR^AR^B$ is

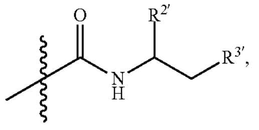

wherein:

- the wavy line indicates the point of attachment to the triazolopyridine core;
- R" is hydrogen, methyl, or trifluoromethyl;
- $R^{3'}$ is hydroxyl, methyl, tluoro, or methoxy.

The Variables $R^A$ and $R^B$

In some embodiments, $R^A$ is hydrogen.

In some embodiments, $R^A$ is —$CR^1R^2R^3$.

In some embodiments, $R^B$ is hydrogen.

In some embodiments, $R^B$ is $(C_1$-$C_6)$-alkyl. In some embodiments, $R^B$ is methyl.

In some embodiments, $R^B$ is ethyl.

In some embodiments, $R^A$ and $R^B$ are hydrogen.

In some embodiments, $R^A$ is hydrogen and $R^B$ is $(C_1$-$C_6)$-alkyl. In some embodiments, $R^A$ is hydrogen and $R^B$ is methyl. In some embodiments, $R^A$ is hydrogen and R is $(C_1$-$C_6)$-alkyl. In some embodiments, $R^A$ is hydrogen and $R^B$ is ethyl. In some embodiments, $R^A$ is —$CR^1R^2R^3$ and $R^B$ is hydrogen.

In some embodiments, $R^A$ is —$CR^1R^2R^3$ and $R^B$ is $(C_1$-$C_6)$-alkyl. In some embodiments, $R^A$ is —$CR^1R^2R^3$ and $R^B$ is methyl. In some embodiments, $R^A$ is —$CR^1R^2R^3$ and $R^B$ is ethyl.

In some embodiments, —C(O)—$NR^AR^B$ is

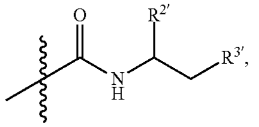

wherein:

- the wavy line indicates the point of attachment to the triazolopyridine core;
- $R^{2'}$ is hydrogen or $(C_1$-$C_3)$-alkyl, wherein the $(C_1$-$C_3)$-alkyl can be substituted by one or more independently selected halo;
- $R^{3'}$ is —$((C_0$-$C_5)$-alkyl)-X, wherein X is hydroxyl, $(C_1$-$C_4)$-alkoxy, oxo, cyano, or halo, and wherein the $(C_1$-$C_4)$-alkoxy can be substituted by one or more independently selected halo.

In some embodiments, X is hydroxyl.

In some embodiments, X is $(C_1$-$C_4)$-alkoxy, wherein the $(C_1$-$C_4)$-alkoxy can be substituted by one or more independently selected halo. For example, X is methoxy.

In some embodiments, X is oxo.

In some embodiments, X is cyano.

In some embodiments, X is halo (e.g., fluoro).

In some embodiments, —C(O)—$NR^AR^B$ is

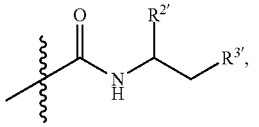

wherein:

- the wavy line indicates the point of attachment to the triazolopyridine core;
- $R^{2'}$ is hydrogen, methyl, or trifluoromethyl;
- $R^{3'}$ is hydroxyl, methyl, fluoro, or methoxy.

The Variable $R^G$

In some embodiments, $R^G$ is hydrogen.

In some embodiments, $R^G$ is halo (e.g., fluoro or chloro; e.g., fluoro; e.g., chloro).

The Variable $R^H$

In some embodiments, $R^H$ is hydrogen.

In some embodiments, $R^H$ is halo (e.g., fluoro or chloro; e.g., fluoro; e.g., chloro).

In some embodiments, $R^H$ is $(C_1$-$C_4)$-alkyl (e.g., methyl).

The Variables $R^1$, $R^2$ and $R^3$

In some embodiments, R' is hydrogen.

In some embodiments, R' is $(C_1$-$C_3)$-alkyl optionally substituted by one or more fluoro. In some embodiments, $R^1$ is $(C_1$-$C_3)$-alkyl substituted by one or more fluoro. In some embodiments, $R^1$ is unsubstituted $(C_1$-$C_3)$-alkyl. In some embodiments, $R^1$ is methyl. In some embodiments, $R^1$ is fluoromethyl. In some embodiments, $R^1$ is difluoromethyl. In some embodiments, $R^1$ is trifluoromethyl.

In some embodiments, $R^2$ is hydrogen.

In some embodiments, $R^2$ is $(C_1$-$C_3)$alkyl optionally substituted by one or more fluoro. In some embodiments, $R^1$ is $(C_1$-$C_3)$-alkyl substituted by one or more fluoro. In some embodiments, $R^1$ is unsubstituted $(C_1$-$C_3)$-alkyl. In some embodiments, $R^2$ is methyl. In some embodiments, $R^1$ is fluoromethyl. In some embodiments, $R^1$ is difluoromethyl. In some embodiments, $R^1$ is trifluoromethyl.

In some embodiments, $R^1$ and $R^2$ are each independently hydrogen, methyl, or trifluoromethyl. In some embodiments, $R^1$ and $R^2$ are each independently hydrogen or methyl. In some embodiments, $R^1$ and $R^2$ are each independently hydrogen or trifluoromethyl.

In some embodiments, $R^3$ is hydrogen.

In some embodiments, $R^3$ is hydrogen, $(C_3-C_7)$-cycloalkyl, or $(C_1-C_6)$-alkyl, wherein the $(C_1-C_6)$-alkyl can be substituted by one or more independently selected hydroxyl, $(C_1-C_4)$-alkoxy, oxo, cyano, or halo, and wherein the $(C_1-C_4)$-alkoxy can be substituted by one or more independently selected halo.

In some embodiments, $R^3$ is hydrogen, $(C_3-C_7)$-cycloalkyl-$(C_1-C_3)$-alkyl, or $(C_1-C_6)$-alkyl, wherein the $(C_1-C_6)$-alkyl can be substituted by one or more independently selected hydroxyl, $(C_1-C_4)$-alkoxy, oxo, cyano, or halo, and wherein the $(C_1-C_{49}$-alkoxy can be substituted by one or more independently selected halo.

In some embodiments, $R^3$ is hydrogen or $(C_1-C_6)$-alkyl, wherein the $(C_1-C_5)$-alkyl can be substituted by one or more independently selected hydroxyl, $(C_1-C_4)$-alkoxy, oxo, cyano, or halo, and wherein the $(C_1-C_4)$-alkoxy can be substituted by one or more independently selected halo.

In some embodiments, $R^3$ is $(C_1-C_6)$-alkyl, wherein the $(C_1-C_6)$-alkyl can be substituted by one or more independently selected hydroxyl, $(C_1-C_4)$-alkoxy, oxo, cyano, or halo, and wherein the $(C_1-C_4)$-alkoxy can be substituted by one or more independently selected halo.

In some embodiments, $R^3$ is $(C_1-C_3)$-alkyl which can be substituted by one or more independently selected hydroxyl, $(C_1-C_4)$-alkoxy, or fluoro, wherein the $(C_1-C_4)$-alkoxy can be substituted by one or more fluoro. In some embodiments, $R^3$ is $(C_1-C_6)$-alkyl, which can be substituted by one or more independently selected hydroxyl, $(C_1-C_4)$-alkoxy, chloro, or fluoro, wherein the $(C_1-C_4)$-alkoxy can be substituted by one or more fluoro. In some embodiments, $R^3$ is $(C_1-C_3)$-alkyl which can be substituted by one or more independently selected hydroxyl, $(C_1-C_4)$-alkoxy, chloro, or fluoro, and wherein the $(C_1-C_4)$-alkoxy can be substituted by one or more fluoro. In some embodiments, $R^3$ is methyl or ethyl, each of which can be substituted by one or more independently selected hydroxyl, $(C_1-C_4)$-alkoxy, chloro, or fluoro, wherein the $(C_1-C_4)$-alkoxy can be substituted by one or more fluoro. In some embodiments, $R^3$ is methyl or ethyl, each of which can be substituted by one or more independently selected $(C_1-C_4)$-alkoxy, chloro, or fluoro, wherein the $(C_1-C_4)$-alkoxy can be substituted by one or more fluoro. In some embodiments, $R^3$ is methyl or ethyl, each of which can be substituted by one or more independently selected $(C_1-C_4)$-alkoxy, or fluoro, wherein the $(C_1-C_4)$-alkoxy can be substituted by one or more fluoro. In some embodiments, $R^3$ is methyl or ethyl, each of which can be substituted by one or more fluoro.

In some embodiments, $R^3$ is methyl which can be substituted by one or more independently selected hydroxyl, $(C_1-C_4)$-alkoxy, chloro, or fluoro, wherein the $(C_1-C_4)$-alkoxy can be substituted by one or more fluoro. In some embodiments, $R^3$ is methyl which can be substituted by one or more independently selected $(C_1-C_4)$-alkoxy, chloro, or fluoro, wherein the $(C_1-C_4)$-alkoxy can be substituted by one or more fluoro. In some embodiments, $R^3$ is methyl which can be substituted by one or more independently selected $(C_1-C_4)$-alkoxy, wherein the $(C_1-C_4)$-alkoxy can be substituted by one or more fluoro. In some embodiments, $R^3$ is methyl which can be substituted by one or more fluoro. In some embodiments, $R^3$ is unsubstituted methyl.

In some embodiments, $R^3$ is ethyl which can be substituted by one or more independently selected hydroxyl, $(C_1-C_4)$-alkoxy, chloro, or fluoro, wherein the $(C_1-C_4)$-alkoxy can be substituted by one or more fluoro. In some embodiments, $R^3$ is ethyl which can be substituted by one or more independently selected $(C_1-C_4)$-alkoxy, chloro, or fluoro, wherein the $(C_1-C_4)$-alkoxy can be substituted by one or more fluoro. In some embodiments, $R^3$ is ethyl which can be substituted by one or more independently selected $(C_1-C_4)$-alkoxy, wherein the $(C_1-C_4)$-alkoxy can be substituted by one or more fluoro. In some embodiments, $R^3$ is ethyl which can be substituted by one or more fluoro.

In some embodiments, $R^3$ is methyl or ethyl, each of which can be substituted by one or more independently selected hydroxyl or fluoro. In some embodiments, $R^3$ is methyl or ethyl, each of which can be substituted by hydroxyl. For example, $R^3$ is hydroxymethyl. For example, $R^3$ is unsubstituted ethyl. For example, $R^3$ is unsubstituted methyl.

In some embodiments, $R^3$ is $(C_3-C_7)$-cycloalkyl wherein the $(C_3-C_7)$-cycoalkyl can be substituted by one or more independently selected hydroxyl, $(C_1-C_4)$-alkoxy, oxo, cyano, or halo, and wherein the $(C_1-C_4)$-alkoxy can be substituted by one or more independently selected halo.

In some embodiments, $R^3$ is $(C_3-C_7)$-cycloalkyl-$(C_1-C_3)$-alkyl wherein the $(C_3-C_7)$-cycloalkyl-$(C_1-C_3)$-alkyl can be substituted by one or more independently selected hydroxyl, $(C_1-C_4)$-alkoxy, oxo, cyano, or halo, and wherein the $(C_1-C_4)$-alkoxy can be substituted by one or more independently selected halo.

In some embodiments, $R^1$ is hydrogen and $R^2$ and $R^3$ are joined to one another and, taken together with the carbon atom to which they are attached, form a 4- to 7-membered ring containing up to two heteroatoms selected from the group consisting of O or N, wherein the ring can be substituted by one or more independently selected hydroxyl, $(C_1-C_4)$-alkoxy, $(C_1-C_4)$-alkyl, oxo, cyano, or halo, and wherein the $(C_1-C_4)$-alkoxy and $(C_1-C_4)$-alkyl can be substituted by one or more independently selected halo. In some embodiments, $R^1$ is hydrogen and $R^2$ and $R^3$ are joined to one another and, taken together with the carbon atom to which they are attached, form a 4- to 7-membered ring containing up to two heteroatoms selected from the group consisting of O or N, wherein the ring is substituted by one or more independently selected hydroxyl, $(C_1-C_4)$-alkoxy, $(C_1-C_4)$-alkyl, oxo, cyano, or halo, and wherein the $(C_1-C_4)$-alkoxy and $(C_1-C_4)$-alkyl can be substituted by one or more independently selected halo. In some embodiments, $R^1$ is hydrogen and $R^2$ and $R^3$ are joined to one another and, taken together with the carbon atom to which they are attached, form a 3- to 7-membered ring containing up to two heteroatoms selected from the group consisting of O or N, wherein the ring can be substituted by one or more independently selected hydroxyl, $(C_1-C_4)$-alkyl, oxo, or halo. In some embodiments, $R^1$ is hydrogen and $R^2$ and $R^3$ are joined to one another and, taken together with the carbon atom to which they are attached, form an unsubstituted 4- to 7-membered ring containing up to two heteroatoms selected from the group consisting of O or N.

In some embodiments, $R^2$ and $R^3$ are joined to one another and, taken together with the carbon atom to which they are attached, form a 4- to 7-membered ring containing up to one O or N atom, wherein the ring can be substituted by oxo. In some embodiments, $R^2$ and $R^3$ are joined to one another and, taken together with the carbon atom to which they are attached, form pyrrolidinone, a cyclobutyl, or a tetrahydrofuranyl. In some embodiments, $R^2$ and $R^3$ are joined to one another and, taken together with the carbon atom to which they are attached, form pyrrolidinone. In some embodiments, $R^2$ and $R^3$ are joined to one another and, taken together with the carbon atom to which they are attached, form cyclobutyl. In some embodiments, $R^2$ and $R^3$ are joined to one another and, taken together with the carbon atom to which they are attached, form tetrahydrofuranyl.

In some embodiments, $R^1$ is hydrogen;

$R^2$ is hydrogen or $(C_1\text{-}C_3)$-alkyl, wherein the $(C_1\text{-}C_3)$-alkyl can be substituted by one or more independently selected halo; and $R^3$ is —$CH_2$—$R^{3'}$ is —$((C_0\text{-}C_5)$-alkyl)-X, wherein X is hydroxyl, $(C_1\text{-}C_4)$-alkoxy, oxo, cyano, or halo, and wherein the $(C_1\text{-}C_4)$-alkoxy can be substituted by one or more independently selected halo.

In some embodiments, X is hydroxyl.

In some embodiments, X is $(C_1\text{-}C_4)$-alkoxy, wherein the $(C_1\text{-}C_4)$-alkoxy can be substituted by one or more independently selected halo. For example, X is methoxy.

In some embodiments, X is oxo.

In some embodiments, X is cyano.

In some embodiments, X is halo (e.g., fluoro).

In some embodiments, $R^1$ is hydrogen;

$R^2$ is hydrogen, methyl, or trifluoromethyl;

$R^3$ is —$CH_2R^{3'}$ is hydroxyl, methyl, fluoro, or methoxy.

In some embodiments, the stereochemical configuration of the atom that $R^1$, $R^2$, and $R^3$ are bonded to is (S). In some embodiments, the stereochemical configuration of the atom that $R^1$, $R^2$, and $R^3$ are bonded to is (R).

The Variables $R^C$ and $R^D$

In some embodiments, $R^C$ is hydrogen.

In some embodiments, $R^C$ is $CR^4R^5R^7$.

In some embodiments, $R^C$ is $(C_6\text{-}C_{10})$-aryl, wherein the $(C_6\text{-}C_{10})$-aryl is optionally substituted by one or more independently selected $(C_1\text{-}C_4)$-alkyl, $(C_1\text{-}C_4)$-alkoxy, or halo, and wherein the $(C_1\text{-}C_4)$-alkyl and $(C_1\text{-}C_4)$-alkoxy can be substituted by one or more independently selected hydroxyl or halo. In some embodiments, $R^C$ is phenyl, wherein the phenyl is optionally substituted by one or more independently selected $(C_1\text{-}C_4)$-alkyl, $(C_1\text{-}C_4)$-alkoxy, or halo, and wherein the $(C_1\text{-}C_4)$-alkyl and $(C_1\text{-}C_4)$-alkoxy can be substituted by one or more independently selected hydroxyl or halo.

In some embodiments, $R^D$ is hydrogen.

In some embodiments, $R^D$ is $(C_1\text{-}C_6)$-alkyl. In some embodiments, $R^D$ is methyl.

In some embodiments, $R^C$ and $R^D$ are joined to one another and, taken together with the carbon atom to which they are attached, form a 4- to IG-membered monocyclic or bicyclic ring containing up to three heteroatoms selected from the group consisting of O or N, and wherein the 4- to 10-membered monocyclic or bicyclic ring is optionally substituted by one or more independently selected $(C_1\text{-}C_6)$-alkyl or $(C_1\text{-}C_4)$-alkoxy.

In some embodiments, $R^C$ and $R^D$ are joined to one another and, taken together with the carbon atom to which they are attached, form a 4- to 10-membered monocyclic or bicyclic ring containing up to three heteroatoms selected from the group consisting of 0 or N, and wherein the 4- to 10-membered monocyclic or bicyclic ring is optionally substituted by one or more independently selected $(C_1\text{-}C_6)$-alkyl or $(C_1\text{-}C_4)$-alkoxy. $R^C$ and $R^D$ are joined to one another and, taken together with the carbon atom to which they are attached, form a 4- to 7-membered monocyclic ring containing up to three heteroatoms selected from the group consisting of O or N, and wherein the 4- to 10-membered monocyclic or bicyclic ring is optionally substituted by one or more independently selected $(C_1\text{-}C_6)$-alkyl or $(C_1\text{-}C_4)$-alkoxy. In some embodiments, $R^C$ and $R^D$ are joined to one another and, taken together with the carbon atom to which they are attached, form a 4- to 6-membered monocyclic or bicyclic ring containing up to two heteroatoms selected from the group consisting of O or N, and wherein the 4- to 10-membered monocyclic or bicyclic ring is optionally substituted by one or more independently selected methyl or methoxy.

In some embodiments, $R^C$ is $CR^4R^5R^7$; and $R^D$ is hydrogen.

In some embodiments, $R^C$ is $CR^4R^5R^7$; and $R^D$ is $(C_1\text{-}C_6)$-alkyl.

In some embodiments, $R^C$ is $(C_6\text{-}C_{10})$-aryl, wherein the $(C_6\text{-}C_{10})$-aryl is optionally substituted by one or more independently selected $(C_1\text{-}C_4)$-alkyl, $(C_1\text{-}C_4)$-alkoxy, or halo, and wherein the $(C_1\text{-}C_4)$-alkyl and $(C_1\text{-}C_4)$-alkoxy can be substituted by one or more independently selected hydroxyl or halo; and $R^D$ is hydrogen.

In some embodiments, $R^C$ is $(C_6\text{-}C_{10})$-aryl, wherein the $(C_6\text{-}C_{10})$-aryl is optionally substituted by one or more independently selected $(C_1\text{-}C_4)$-alkyl, $(C_1\text{-}C_4)$-alkoxy, or halo, and wherein the $(C_1\text{-}C_4)$-alkyl and $(C_1\text{-}C_4)$-alkoxy can be substituted by one or more independently selected hydroxyl or halo; and $R^D$ is $(C_1\text{-}C_6)$-alkyl.

In some embodiments, —$C(O)NR^CR^D$ is

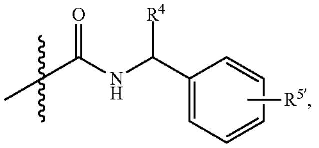

wherein: the wavy line indicates the point of attachment to the thiophene;

$R^4$ is hydrogen, $(C_1\text{-}C_6)$-alkyl, $(C_3\text{-}C_7)$-cycloalkyl, or 4- to 7-membered heterocyclyl, wherein the $(C_1\text{-}C_6)$-alkyl, $(C_3\text{-}C_7)$-cycloalkyl, or 4- to 7-membered heterocyclyl can be substituted by one or more independently selected $(C_1\text{-}C_4)$-alkyl, $(C_1\text{-}C_4)$-alkoxy, hydroxyl, oxo, cyano, or halo, wherein the $(C_1\text{-}C_4)$-alkoxy and $(C_1\text{-}C_4)$-alkyl can be substituted by one or more independently selected halo, and any nitrogen of the 4- to 7-membered heterocyclyl can be substituted by $C(O)OR^6$ or $C(O)R^6$; and $R^5$ is $(C_1\text{-}C_4)$-alkyl, $(C_1\text{-}C_4)$-alkoxy, $C(O)OR^6$, $(C_3\text{-}C_7)$-cycloalkoxy, cyano, 4- to 7-membered heterocyclyl, or halo, and wherein the $(C_1\text{-}C_4)$-alkyl and $(C_1\text{-}C_4)$-alkoxy can be substituted by one or more independently selected 4- to 7-membered heterocyclyl optionally substituted with oxo or $(C_1\text{-}C_4)$-alkyl, $(C_1\text{-}C_4)$-alkoxy, —NR'R", or halo.

In some embodiments, $R^{5'}$ is $(C_1\text{-}C_4)$-alkyl, wherein the $(C_1\text{-}C_4)$-alkyl can be substituted by one or more independently selected 4- to 7-membered heterocyclyl optionally substituted with oxo or $(C_1\text{-}C_4)$-alkyl, $(C_1\text{-}C_4)$-alkoxy, —NR'R", or halo. For example, $R^{5'}$ is methyl or ethyl (e.g., methyl).

In some embodiments, $R^{5'}$ is $(C_1\text{-}C_4)$-alkoxy, wherein the $(C_1\text{-}C_4)$-alkoxy can be substituted by one or more independently selected 4- to 7-membered heterocyclyl optionally substituted with oxo or $(C_1\text{-}C_4)$-alkyl, $(C_1\text{-}C_4)$-alkoxy, —NR'R", or halo. For example, $R^{5'}$ is methoxy.

In some embodiments, $R^{5'}$ is $C(O)OR^6$. For example, $R^{5'}$ is C(O)OMe.

In some embodiments, $R^{5'}$ is $(C_3\text{-}C_7)$-cycloalkoxy. In some embodiments. $R^{5'}$ is $(C_5\text{-}C_6)$-cycloalkoxy.

In some embodiments, $R^{5'}$ is cyano.

In some embodiments, $R^{5'}$ is 4- to 7-membered heterocyclyl.

In some embodiments, $R^{5'}$ is halo (e.g., fluoro).

In some embodiments, —$C(O)NR^cR^D$

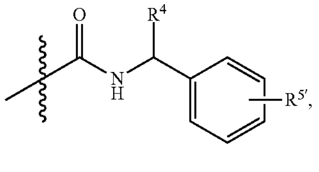

wherein:

the wavy line indicates the point of attachment to the thiophene;

$R^4$ is hydrogen, methyl, or ethyl, wherein the methyl or ethyl can be substituted by one or more independently selected ($C_1$-$C_4$)-alkyl, ($C_1$-$C_4$)-alkoxy, hydroxyl, oxo, cyano, or halo, wherein the ($C_1$-$C_4$)-alkoxy and ($C_1$-$C_4$)-alkyl can be substituted by one or more independently selected halo, and any nitrogen of the 4- to 7-membered heterocyclyl can be substituted by C(O)$OR^6$ or C(O)R; and $R^{5'}$ is methyl, methoxy, or fluoro.

The Variables $R^4$, $R^5$, and $R^7$

In some embodiments, $R^4$ is hydrogen.

In some embodiments, $R^4$ is ($C_1$-$C_6$)-alkyl, wherein the ($C_1$-$C_6$)-alkyl can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more independently selected halo.

In some embodiments, $R^4$ is ($C_3$-$C_7$)-cycloalkyl, wherein the ($C_3$-$C_7$)cycloalkyl can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more independently selected halo.

In some embodiments, $R^4$ is 4- to 7-membered heterocyclyl wherein the 4- to 7-membered heterocyclyl can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more independently selected halo, and any nitrogen of the 4- to 7-membered heterocyclyl can be substituted by C(O)$OR^6$ or C(O)$R^6$.

In some embodiments, $R^4$ is hydrogen, ($C_1$-$C_6$)-alkyl, cyclopropyl, cyclobutyl, or cyclopentyl, wherein the ($C_1$-$C_6$)-alkyl, cyclopropyl, cyclobutyl, cyclopentyl can be substituted by one or more independently selected ($C_1$-$C_4$)-alkoxy or halo. In some embodiments, $R^4$ is ($C_1$-$C_6$)-alkyl, cyclopropyl, cyclobutyl, or cyclopentyl, wherein the ($C_1$-$C_6$)-alkyl, cyclopropyl, cyclobutyl, and cyclopentyl can be substituted by one or more ($C_1$-$C_4$)-alkoxy or fluoro. In some embodiments, $R^4$ is ($C_1$-$C_6$)-alkyl, cyclopropyl, cyclobutyl, or cyclopentyl, wherein the ($C_1$-$C_6$)-alkyl, cyclopropyl, cyclobutyl, and cyclopentyl can be substituted by one fluoro. In some embodiments, $R^4$ is ($C_1$-$C_6$)-alkyl, wherein the ($C_1$-$C_6$)-alkyl can be substituted by one or more independently selected halo. In some embodiments, $R^4$ is ($C_1$-$C_3$)-alkyl, wherein the ($C_1$-$C_3$)-alkyl can be substituted by one or more independently selected halo. In some embodiments, $R^4$ is ($C_1$-$C_3$)-alkyl, wherein the ($C_1$-$C_1$)-alkyl can be substituted by one fluoro. In some embodiments, $R^4$ is methyl or ethyl, wherein the methyl or ethyl can be substituted by one fluoro. In some embodiments, $R^4$ is methyl or ethyl. For example, $R^4$ is methyl. For example, $R^4$ is ethyl.

In some embodiments, $R^4$ is hydrogen, ($C_1$-$C_6$)-alkyl, cyclopropyl, cyclobutyl, or cyclopentyl, wherein the ($C_1$-$C_6$)-alkyl, cyclopropyl, cyclobutyl, and cyclopentyl can be substituted by one or more ($C_1$-$C_4$)-alkoxy or fluoro. In some embodiments, $R^4$ is hydrogen, ($C_1$-$C_6$)-alkyl, cyclopropyl, cyclobutyl, or cyclopentyl, wherein the ($C_1$-$C_6$)-alkyl, cyclopropyl, cyclobutyl, and cyclopentyl can be substituted by one methoxy or one fluoro. In some embodiments, $R^4$ is hydrogen or ($C_1$-$C_6$)-alkyl, wherein the ($C_1$-$C_6$)-alkyl can be substituted by one or more independently selected ($C_1$-$C_4$)-alkoxy or halo. In some embodiments, $R^4$ is hydrogen or ($C_1$-$C_3$)-alkyl, wherein the ($C_1$-$C_3$)-alkyl can be substituted by one or more independently selected halo. In some embodiments, $R^4$ is hydrogen or ($C_1$-$C_3$)-alkyl, wherein the ($C_1$-$C_3$)-alkyl can be substituted by one fluoro. In some embodiments, $R^4$ is hydrogen or ($C_1$-$C_3$)-alkyl. In some embodiments, $R^4$ is hydrogen or methyl. In some embodiments, $R^4$ is hydrogen.

In some embodiments, $R^4$ is hydrogen, ($C_1$-$C_6$)-alkyl, or 4- to 7-membered heterocyclyl, wherein the ($C_1$-$C_6$)-alkyl or 4- to 7-membered heterocyclyl can be substituted by one or more independently selected ($C_1$-$C_4$)-alkoxy or halo, and any nitrogen of the 4- to 7-membered heterocyclyl can be substituted by C(O)$OR^6$ or C(O)$R^6$. In some embodiments, $R^4$ is hydrogen or ($C_1$-$C_6$)-alkyl, wherein the ($C_1$-$C_6$)-alkyl can be substituted by one or more independently selected ($C_1$-$C_4$)-alkoxy or halo.

In some embodiments, $R^4$ is hydrogen, methyl, ethyl, or methoxymethyl.

In some embodiments, $R^4$ is ($C_3$-$C_7$)-cycloalkyl or 4- to 7-membered heterocyclyl, each of which can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more fluoro; and any nitrogen of the 4- to 7-membered heterocyclyl can be substituted by C(O)$OR^6$ or C(O)$R^6$. In some embodiments, $R^4$ is cyclobutyl, cyclopentyl, or 4- to 7-membered heterocyclyl, each of which can be substituted by one or more independently selected or halo; and any nitrogen of the 4- to 7-membered heterocyclyl can be substituted by C(O)$OR^6$ or C(O)$R^6$. In some embodiments, $R^4$ is piperidinyl which can be substituted by one or more independently selected or halo and the nitrogen of the piperidinyl can be substituted by C(O)OR" or C(O)$R^0$.

In some embodiments, $R^6$ is methyl or t-butyl. For example, $R^6$ is methyl. For example, $R^6$ is t-butyl.

In some embodiments, $R^5$ is ($C_1$-$C_6$)-alkyl that can be substituted by one or more independently selected ($C_1$-$C_4$)-alkyl, ($C_1$-$C_4$)-alkoxy, C(O)$OR^6$, ($C_3$-$C_7$)-cycloalkoxy, cyano, 4- to 7-membered heterocyclyl, or halo, and wherein the ($C_1$-$C_4$)-alkyl and ($C_1$-$C_4$)-alkoxy can be substituted by one or more independently selected 4- to 7-membered heterocyclyl optionally substituted with oxo or ($C_1$-$C_4$)-alkyl, ($C_1$-$C_4$)-alkoxy, —NR'R", or halo. In some embodiments, $R^5$ is ($C_1$-$C_3$)-alkyl that can be substituted by one or more independently selected ($C_1$-$C_4$)-alkyl, ($C_1$-$C_4$)-alkoxy, C(O)$OR^6$, ($C_3$-$C_7$)-cycloalkoxy, cyano, 4- to 7-membered heterocyclyl, or halo, and wherein the ($C_1$-$C_4$)-alkyl and ($C_1$-$C_4$)-alkoxy can be substituted by one or more independently selected 4- to 7-membered heterocyclyl optionally substituted with oxo or ($C_1$-$C_4$)-alkyl, ($C_1$-$C_4$)-alkoxy, —NR'R", or halo. In some embodiments, the $R^5$ ($C_1$-$C_6$)-alkyl is methyl, ethyl, or propyl (e.g., isopropyl). In some embodiments, the $R^5$ ($C_1$-$C_6$)-alkyl is methyl.

In some embodiments, $R^5$ is ($C_3$-$C_7$)-cycloalkyl, wherein the ($C_3$-$C_7$)-cycloalkyl can be substituted by one or more independently selected ($C_1$-$C_4$)-alkyl, ($C_1$-$C_4$)-alkoxy, cyano, 4- to 7-membered heterocyclyl, or halo, and wherein the ($C_1$-$C_4$)-alkyl and ($C_1$-$C_4$)-alkoxy can be substituted by one or more fluoro, and wherein the ($C_3$-$C_7$)-cycloalkyl can be fused with a 4- to 7-membered heterocyclyl or ($C_3$-$C_7$)-cycloalkyl. In some embodiments, $R^5$ is ($C_3$-$C_7$)-cycloalkyl, wherein the ($C_3$-$C_7$)-cycloalkyl can be substituted by one or more independently selected ($C_1$-$C_4$)-alkyl, ($C_1$-$C_4$)-alkoxy, cyano, 4- to 7-membered heterocyclyl, or halo, and wherein the ($C_1$-$C_4$)-alkyl and ($C_1$-$C_4$)-alkoxy can be substituted by one or more fluoro. In some embodiments, $R^5$ is ($C_3$-$C_7$)-cycoalkyl, wherein the ($C_3$-$C_7$)-cycloalkyl can be substituted by one or more independently selected ($C_1$-$C_4$)-alkyl, methoxy, 4- to 7-membered heterocyclyl, or halo, and wherein the ($C_1$-$C_4$)-alkyl and ($C_1$-$C_4$)-alkoxy can be substituted by one or more fluoro. In some embodiments, $R^5$ is cyclopropyl, cyclobutyl, cyclopentyl, or cyclohexyl, wherein the cyclopropyl, cyclobutyl, cyclopentyl, or cyclohexyl can be substituted by one or more independently selected ($C_1$-$C_4$)-alkyl, methoxy, 4- to 7-membered heterocyclyl, or halo, and wherein the ($C_1$-$C_4$)-alkyl and ($C_1$-$C_4$)-alkoxy can be substituted by one or more fluoro. In some embodiments, $R^5$ is cyclohexyl, wherein the cyclohexyl can be substituted by one or more independently selected ($C_1$-$C_4$)-alkyl, methoxy, 4- to 7-membered heterocyclyl, or halo, and wherein the ($C_1$-$C_4$)-alkyl and ($C_1$-$C_4$)-alkoxy can be substituted by one or more fluoro. In some embodiments, $R^5$ is unsubstituted ($C_3$-$C_7$)-cycloalkyl. In some embodiments, $R^5$ is unsubstituted cyclohexyl.

In some embodiments, $R^5$ is cyanomethyl.

In some embodiments, $R^5$ is ($C_6$-$C_{10}$)-aryl, wherein the ($C_6$-$C_{10}$)-aryl can be substituted by one or more independently selected ($C_1$-$C_4$)-alkyl, ($C_1$-$C_4$)-alkoxy, cyano, 4- to 7-membered heterocyclyl, or halo, and wherein the ($C_1$-$C_4$)-alkyl and ($C_1$-$C_4$)-alkoxy can be substituted by one or more fluoro, and wherein the ($C_6$-$C_{10}$)-aryl can be fused with a 4- to 7-membered heterocyclyl or ($C_3$-$C_7$)cycloalkyl. In some embodiments, $R^5$ is ($C_6$-$C_{10}$)-aryl, wherein the ($C_6$-$C_{10}$)-aryl can be substituted by one or more independently selected ($C_1$-$C_4$)-alkyl, ($C_1$-$C_4$)-alkoxy, cyano, 4- to 7-membered heterocyclyl, or balo, and wherein the ($C_1$-$C_4$)-alkyl and ($C_1$-$C_4$)-alkoxy can be substituted by one or more fluoro. In some embodiments, $R^5$ is phenyl, wherein the phenyl can be substituted by one or more independently selected ($C_1$-$C_4$)-alkyl, ($C_1$-$C_4$)-alkoxy, cyano, 4- to 7-membered heterocyclyl, or halo, and wherein the ($C_1$-$C_4$)-alkyl and ($C_1$-$C_4$)-alkoxy can be substituted by one or more fluoro. In some embodiments, $R^5$ is phenyl, wherein the phenyl can be substituted by one or more independently selected ($C_1$-$C_4$)-alkyl, ($C_1$-$C_4$)-alkoxy, or halo, and wherein the ($C_1$-$C_4$)-alkyl and ($C_1$-$C_4$)-alkoxy can be substituted by one or more fluoro. In some embodiments, $R^5$ is phenyl, wherein the phenyl can be substituted by one or more independently selected methyl, ethyl, methoxy, or fluoro, and wherein the methyl, ethyl, and methoxy can be substituted by one or more fluoro.

In some embodiments, $R^5$ is ($C_6$-$C_{10}$)-aryl-($C_1$-$C_4$)-alkyl that can be substituted by one or more independently selected ($C_1$-$C_4$)-alkyl, ($C_1$-$C_4$)-alkoxy, C(O)OR$^6$, ($C_3$-$C_7$)-cycloalkoxy, cyano, 4- to 7-membered heterocyclyl, or halo, and wherein the ($C_1$-$C_4$)-alkyl and ($C_1$-$C_4$)-alkoxy can be substituted by one or more independently selected 4- to 7-membered heterocyclyl optionally substituted with oxo or ($C_1$-$C_4$)-alkyl, ($C_1$-$C_4$)-alkoxy, —NR'R", or halo, and wherein the ($C_6$-$C_{10}$)-aryl of the ($C_6$-$C_{10}$)-aryl-($C_1$-$C_4$)-alkyl can be fused with a 4- to 7-membered heterocyclyl or ($C_3$-$C_7$)-cycloalkyl. In some embodiments, $R^5$ is ($C_6$-$C_{10}$)-aryl-($C_1$-$C_4$)-alkyl that can be substituted by one or more independently selected ($C_1$-$C_4$)-alkyl, ($C_1$-$C_4$)-alkoxy, C(O)OR$^6$, ($C_3$-$C_7$)-cycloalkoxy, cyano, 4- to 7-membered heterocyclyl, or halo, and wherein the ($C_1$-$C_4$)-alkyl and ($C_1$-$C_4$)-alkoxy can be substituted by one or more independently selected 4- to 7-membered heterocyclyl optionally substituted with oxo or ($C_1$-$C_4$)-alkyl, ($C_1$-$C_4$)-alkoxy, —NR'R", or halo. In some embodiments, $R^5$ is phenyl-($C_1$-$C_4$)-alkyl that can be substituted by one or more independently selected ($C_1$-$C_4$)-alkyl, ($C_1$-$C_4$)-alkoxy, C(O)OR$^6$, ($C_3$-$C_7$)-cycloalkoxy, cyano, 4- to 7-membered heterocyclyl, or halo, and wherein the ($C_1$-$C_4$)-alkyl and ($C_1$-$C_4$)-alkoxy can be substituted by one or more independently selected 4- to 7-membered heterocyclyl optionally substituted with oxo or ($C_1$-$C_4$)-alkyl, ($C_1$-$C_4$)-alkoxy, —NR'R", or halo. In some embodiments, $R^5$ is phenyl-($C_1$-$C_2$)-alkyl that can be substituted by one or more independently selected ($C_1$-$C_4$)-alkyl, ($C_1$-$C_4$)-alkoxy, C(O)OR$^6$, ($C_3$-$C_7$)-cycloalkoxy, cyano, 4- to 7-membered heterocyclyl, or halo, and wherein the ($C_1$-$C_4$)-alkyl and ($C_1$-$C_4$)-alkoxy can be substituted by one or more independently selected 4- to 7-membered heterocyclyl optionally substituted with oxo or ($C_1$-$C_4$)-alkyl, ($C_1$-$C_4$)-alkoxy, —NR'R", or halo. In some embodiments, $R^5$ is phenyl-($C_1$-$C_2$)-alkyl that can be substituted by one or more independently selected ($C_1$-$C_2$)-alkyl, ($C_1$-$C_2$)-alkoxy, C(O)OR$^6$, ($C_3$-$C_7$)-cycloalkoxy, or fluoro. In some embodiments, $R^5$ is benzyl that can be substituted by one or more independently selected ($C_1$-$C_4$)-alkyl, ($C_1$-$C_4$)-alkoxy, C(O)OR$^6$, ($C_3$-$C_7$)-cycloalkoxy, cyano, 4- to 7-membered heterocyclyl, or halo, and wherein the ($C_1$-$C_4$)-alkyl and ($C_1$-$C_4$)-alkoxy can be substituted by one or more independently selected 4- to 7-membered heterocyclyl optionally substituted with oxo or ($C_1$-$C_4$)-alkyl, ($C_1$-$C_4$)-alkoxy, —NR'R", or halo. In some embodiments, $R^5$ is phenethyl that can be substituted by one or more independently selected ($C_1$-$C_4$)-alkyl, ($C_1$-$C_4$)-alkoxy, C(O)OR$^6$, ($C_3$-$C_7$)-cycloalkoxy, cyano, 4- to 7-membered heterocyclyl, or halo, and wherein the ($C_1$-$C_4$)-alkyl and ($C_1$-$C_4$)-alkoxy can be substituted by one or more independently selected 4- to 7-membered heterocyclyl optionally substituted with oxo or ($C_1$-$C_4$)-alkyl, ($C_1$-$C_4$)-alkoxy, —NR'R", or halo.

In some embodiments, $R^5$ is heteroaryl, wherein the heteroaryl can be substituted by one or more independently selected ($C_1$-$C_4$)-alkyl, ($C_1$-$C_4$)-alkoxy, cyano, 4- to 7-membered heterocyclyl, or halo, and wherein the ($C_1$-$C_4$)-alkyl and ($C_1$-$C_4$)-alkoxy can be substituted by one or more fluoro. In some embodiments, $R^5$ is unsubstituted heteroaryl. In some embodiments, the R heteroaryl is a monocyclic heteroaryl. In some embodiments, the $R^5$ heteroaryl is a bicyclic heteroaryl. In some embodiments, the $R^5$ heteroaryl is thiophene, furan, benzoxazole, pyrazolyl, or imidazolyl. In some embodiments, $R^5$ is benzoxazole, wherein the benzoxazole can be substituted by one or more independently selected ($C_1$-$C_4$)-alkyl, ($C_1$-$C_4$)-alkoxy, cyano, 4- to 7-membered heterocyclyl, or halo, and wherein the ($C_1$-$C_4$)-alkyl and ($C_1$-$C_4$)-alkoxy can be substituted by one or more fluoro. In some embodiments, $R^5$ is unsubstituted benzoxazole.

In some embodiments, R is 4- to 7-membered heterocyclyl that can be substituted by one or more independently selected ($C_1$-$C_4$)-alkyl, ($C_1$-$C_4$)-alkoxy, C(O)OR$^6$, ($C_3$-$C_7$)-cycloalkoxy, cyano, 4- to 7-membered heterocyclyl, or halo, and wherein the ($C_1$-$C_4$)-alkyl and ($C_1$-$C_4$)-alkoxy can be substituted by one or more independently selected 4- to 7-membered heterocyclyl optionally substituted with oxo or $(C_1-C_4)$-alkyl, $(C_1-C_4)$-alkoxy, —NR'R", or halo, and wherein the 4- to 7-membered heterocyclyl can be fused with a 4- to 7-membered heterocyclyl or $(C_3-C_7)$-cycloalkyl. In some embodiments, $R^5$ is 4- to 7-membered heterocyclyl that can be substituted by one or more independently selected $(C_1-C_4)$-alkyl, $(C_1-C_4)$-alkoxy, $C(O)OR^6$, $(C_3-C_7)$-cycloalkoxy, cyano, 4- to 7-membered heterocyclyl, or halo, and wherein the $(C_1-C_4)$-alkyl and $(C_1-C_4)$-alkoxy can be substituted by one or more independently selected 4- to 7-membered heterocyclyl optionally substituted with oxo or $(C_1-C_4)$-alkyl, $(C_1-C_4)$-alkoxy, —NR'R", or halo. In some embodiments, $R^5$ is 4- to 6-membered heterocyclyl that can be substituted by one or more independently selected $(C_1-C_2)$-alkyl, $(C_1-C_2)$-alkoxy, $C(O)OR^6$, $(C_3-C_7)$-cycloalkoxy, cyano, 4- to 7-membered heterocyclyl, or halo, and wherein the $(C_1-C_4)$-alkyl and $(C_1-C_4)$-alkoxy can be substituted by one or more independently selected 4- to 7-membered heterocyclyl optionally substituted with oxo or $(C_1-C_4)$-alkyl, $(C_1-C_4)$-alkoxy, —NR'R", or halo. In some embodiments, the $R^5$ heterocyclyl contains 1 O ring atom. In some embodiments, the $R^5$ heterocyclyl is oxetanyl, tetrahydrofuranyl, or tetrahydropyranyl. In some embodiments, the $R^5$ heterocyclyl contains 1 N ring atom. In some embodiments, the $R^5$ heterocyclyl is piperidinyl. In some embodiments, the $R^5$ heterocyclyl contains 1 O ring atom and 1 N ring atom. In some embodiments, the $R^5$ heterocyclyl is

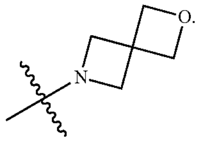 [SMILES: *N1CC2(COC2)C1]

In some embodiments, $R^5$ is unsubstituted 4- to 7-membered heterocyclyl.

In some embodiments, $R^5$ is $(C_3-C_7)$-cycloalkyl, phenyl, or heteroaryl wherein the $(C_3-C_7)$cycloalkyl, phenyl, or heteroaryl can be substituted by one or more independently selected $(C_1-C_4)$-alkyl, $(C_1-C_4)$-alkoxy, cyano, 4- to 7-membered heterocyclyl, or halo, wherein the $(C_1-C_4)$-alkyl and $(C_1-C_4)$-alkoxy can be substituted by one or more fluoro. In some embodiments, $R^5$ is phenyl or heteroaryl wherein the phenyl or heteroaryl can be substituted by one or more independently selected $(C_1-C_4)$-alkyl, $(C_1-C_4)$-alkoxy, cyano, 4- to 7-membered heterocyclyl, or halo, wherein the $(C_1-C_4)$-alkyl and $(C_1-C_4)$-alkoxy can be substituted by one or more fluoro. In some embodiments, $R^5$ is $(C_3-C_7)$-cycloalkyl, phenyl, or heteroaryl wherein the $(C_3-C_7)$-cycloalkyl, phenyl, or heteroaryl can be substituted by one or more independently selected $(C_1-C_4)$-alkyl, $(C_1-C_4)$-alkoxy, 4- to 7-membered heterocyclyl, or fluoro. In some embodiments, $R^5$ is phenyl or heteroaryl wherein the phenyl or heteroaryl can be substituted by one or more independently selected $(C_1-C_4)$-alkyl, $(C_1-C_4)$-alkoxy, 4- to 7-membered heterocyclyl, or fluoro.

In some embodiments, $R^5$ is phenyl or benzoxazolyl, each of which can be substituted by one or more independently selected $(C_1-C_4)$-alkyl, $(C_1-C_4)$-alkoxy, cyano, or halo; wherein the $(C_1-C_4)$-alkyl and $(C_1-C_4)$-alkoxy can be substituted by one or more fluoro. In some embodiments, $R^5$ is phenyl or benzoxazolyl, each of which can be substituted by one or more independently selected $(C_1-C_4)$-alkyl, $(C_1-C_4)$-alkoxy, cyano, chloro, or fluoro; wherein the $(C_1-C_4)$-alkyl and $(C_1-C_4)$-alkoxy can be substituted by one or more fluoro. In some embodiments, $R^5$ is phenyl or benzoxazolyl, each of which can be substituted by one or more independently selected $(C_1-C_4)$-alkyl, $(C_1-C_4)$-alkoxy, cyano, or fluoro. In some embodiments, $R^5$ is phenyl or benzoxazolyl, each of which can be substituted by one or more independently selected $(C_1-C_4)$-alkyl, $(C_1-C_4)$-alkoxy, or fluoro. In some embodiments, $R^5$ is phenyl or benzoxazolyl, each of which can be substituted by one or more fluoro. In some embodiments, $R^5$ is benzoxazolyl, which can be substituted by one or more independently selected $(C_1-C_4)$-alkyl, $(C_1-C_4)$-alkoxy, cyano, or halo, and wherein the $(C_1-C_4)$-alkyl and $(C_1-C_4)$-alkoxy can be substituted by one or more fluoro.

In some embodiments, $R^5$ is phenyl, which can be substituted by one or more independently selected $(C_1-C_4)$-alkyl, $(C_1-C_4)$-alkoxy, cyano, or halo, and wherein the $(C_1-C_4)$-alkyl and $(C_1-C_4)$-alkoxy can be substituted by one or more fluoro. In some embodiments, $R^5$ is phenyl optionally substituted by one or more independently selected $(C_1-C_4)$-alkyl, $(C_1-C_4)$-alkoxy, cyano, 4- to 7-membered heterocyclyl, or halo, wherein the $(C_1-C_4)$-alkyl and $(C_1-C_4)$-alkoxy can be substituted by one or more fluoro. In some embodiments, $R^5$ is phenyl optionally substituted by one or more independently selected $(C_1-C_4)$-alkyl, $(C_1-C_4)$-alkoxy, cyano, or fluoro, wherein the $(C_1-C_4)$-alkyl and $(C_1-C_4)$-alkoxy can be substituted by one or more fluoro. In some embodiments, $R^5$ is phenyl optionally substituted by one or more independently selected $(C_1-C_4)$-alkyl, $(C_1-C_4)$-alkoxy, or fluoro, wherein the $(C_1-C_4)$-alkyl can be substituted by one or more fluoro. In some embodiments, $R^5$ is phenyl optionally substituted by one or more independently selected $(C_1-C_4)$-alkyl, $(C_1-C_4)$-alkoxy, or fluoro, wherein the $(C_1-C_4)$-alkyl can be substituted by one or more fluoro. In some embodiments, $R^5$ is phenyl, which can be substituted by one or more independently selected $(C_1-C_4)$-alkoxy or halo. In some embodiments, $R^5$ is phenyl optionally substituted by one or more independently selected $(C_1-C_4)$-alkoxy or fluoro. In some embodiments, $R^5$ is phenyl which can be substituted by one or more fluoro or methoxy. For example, $R^5$ is phenyl. For example, $R^5$ is fluorophenyl. For example, $R^5$ is methoxyphenyl. For example, $R^5$ is 4-fluorophenyl. For example, $R^5$ is 3-methoxyphenyl.

In some embodiments, $R^5$ is phenyl, 3-pyridinyl, or 4-pyridinyl, each of which can be substituted by one or more independently selected $(C_1-C_4)$-alkyl or $(C_1-C_4)$-alkoxy; wherein the $(C_1-C_4)$-alkyl and $(C_1-C_4)$-alkoxy can be substituted by one or more fluoro.

In some embodiments, $R^4$ and $R^5$ are joined to one another and, taken together with the carbon atom to which they are attached, form a 4- to 7-membered ring containing up to two heteroatoms selected from the group consisting of O or N, wherein:

(i) the ring can be substituted by one or more independently selected $(C_6-C_{10})$-aryl-$(C_1-C_4)$-alkyl, 4- to 7-membered heterocyclyl, $(C_1-C_4)$-alkyl, $(C_1-C_4)$-alkoxy, oxo, cyano, or halo, wherein the $(C_1-C_4)$-alkyl is optionally substituted by one or more independently selected 4- to 7-membered heterocyclyl or fluoro, and any nitrogen of each of the 4- to 7-membered heterocyclyl can independently be substituted by $C(O)OR^6$ or $C(O)R^6$, and (ii) the ring can be fused with $(C_6-C_{10})$-aryl or heteroaryl.

In some embodiments, $R^4$ and $R^5$ are joined to one another and, taken together with the carbon atom to which they are attached, form a 5- to 6-membered ring containing up to two heteroatoms selected from the group consisting of O or N, wherein:

(i) the ring can be substituted by one or more independently selected $(C_6-C_{10})$-aryl-$(C_1-C_4)$-alkyl, 4- to 7-membered heterocyclyl, $(C_1-C_4)$-alkyl, $(C_1-C_4)$-alkoxy, oxo, cyano, or halo, wherein the $(C_1-C_4)$-alkyl is optionally substituted by one or more independently selected 4- to 7-membered heterocyclyl or fluoro, and any nitrogen of each of the 4- to 7-membered heterocyclyl can independently be substituted by $C(O)OR^6$ or $C(O)R^6$, and (ii) the ring can be fused with $(C_6-C_{10})$-aryl or heteroaryl.

In some embodiments, $R^4$ and $R^5$ are joined to one another and, taken together with the carbon atom to which they are attached, form a 5- to 6-membered ring containing up to two heteroatoms selected from the group consisting of O or N, wherein:

(i) the ring can be substituted by one or more independently selected $(C_6-C_{10})$-aryl-$(C_1-C_4)$-alkyl, 4- to 7-membered heterocyclyl, $(C_1-C_4)$-alkyl, $(C_1-C_4)$-alkoxy, oxo, cyano, or halo, wherein the $(C_1-C_4)$-alkyl is optionally substituted by one or more independently selected 4- to 7-membered heterocyclyl or fluoro, and any nitrogen of each of the 4- to 7-membered heterocyclyl can independently be substituted by $C(O)OR^6$ or $C(O)R^6$, and (ii) the ring can be fused with phenyl.

In some embodiments, $R^4$ and $R^5$ are joined to one another and, taken together with the carbon atom to which they are attached, form a 5- to 6-membered ring containing up to one heteroatom selected from the group consisting of O or N, wherein:

(i) the ring can be substituted by one or more independently selected $(C_6-C_{10})$-aryl-$(C_1-C_4)$-alkyl, 4- to 7-membered heterocyclyl, $(C_1-C_4)$-alkyl, $(C_1-C_4)$-alkoxy, oxo, cyano, or fluoro, wherein the $(C_1-C_4)$-alkyl is optionally substituted by one or more independently selected 4- to 7-membered heterocyclyl or fluoro, and any nitrogen of each of the 4- to 7-membered heterocyclyl can independently be substituted by $C(O)OR^6$ or $C(O)R^6$, and (ii) the ring can be fused with phenyl.

In some embodiments, $R^4$ and $R^5$ are joined to one another and, taken together with the carbon atom to which they are attached, form a 5- to 6-membered ring containing up to one heteroatom selected from the group consisting of O or N, wherein:

(i) the ring can be substituted by one or more independently selected $(C_1-C_4)$-alkyl, $(C_1-C_4)$-alkoxy, oxo, cyano, or fluoro, wherein the $(C_1-C_4)$-alkyl is optionally substituted by one or more fluoro, and (ii) the ring can be fused with phenyl.

In some embodiments, $R^4$ and $R^5$ are joined to one another and, taken together with the carbon atom to which they are attached, form a 5- to 6-membered ring containing one heteroatom selected from the group consisting of O or N, wherein:

(i) the ring can be substituted by one or more independently selected $(C_1-C_4)$-alkyl, $(C_1-C_4)$-alkoxy, oxo, cyano, or fluoro, wherein the $(C_1-C_4)$-alkyl is optionally substituted by one or more fluoro, and (ii) the ring can be fused with phenyl.

In some embodiments, $R^4$ and $R^5$ are joined to one another and, taken together with the carbon atom to which they are attached, form a 5- to 6-membered ring containing one heteroatom selected from the group consisting of O or N, wherein:

(i) the ring can be substituted by one or more independently selected $(C_1-C_4)$-alkyl, $(C_1-C_4)$-alkoxy, oxo, cyano, or fluoro, wherein the $(C_1-C_4)$-alkyl is optionally substituted by one or more fluoro, and (ii) the ring can be fused with phenyl; and $R^7$ is selected from hydrogen and $(C_6-C_{10})$-aryl that can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more independently selected halo, and the nitrogen of the 4- to 7-membered heterocyclyl can be substituted by $C(O)OR^6$ or $C(O)R^6$.

In some embodiments, $R^4$ and $R^5$ are joined to one another and, taken together with the carbon atom to which they are attached, form a 5- to 6-membered ring containing no heteroatom ring members, wherein:

(i) the ring can be substituted by one or more independently selected $(C_1-C_4)$-alkyl, $(C_1-C_4)$-alkoxy, oxo, cyano, or fluoro, wherein the $(C_1-C_4)$-alkyl is optionally substituted by one or more fluoro, and (ii) the ring can be fused with phenyl.

In some embodiments, $R^4$ and $R^5$ are joined to one another and, taken together with the carbon atom to which they are attached, form a 5- to 6-membered ring containing up to one O atom, wherein the ring can be fused with phenyl.

In some embodiments, $R^4$ and $R^5$ are joined to one another and, taken together with the carbon atom to which they are attached, form a cyclopentyl.

In some embodiments, $R^4$ and $R^5$ are joined to one another and, taken together with the carbon atom to which they are attached, form a cyclopentyl; and $R^7$ is phenyl that can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more independently selected halo, and the nitrogen of the 4- to 7-membered heterocyclyl can be substituted by $C(O)OR^6$ or $C(O)R^6$.

In some embodiments, $R^4$ and $R^5$ are joined to one another and, taken together with the carbon atom to which they are attached, form a 6-membered ring containing up to one O atom, wherein the ring is fused with phenyl. In some embodiments, $R^4$ and $R^5$ are joined to one another and, taken together with the carbon atom to which they are attached, form 1,2,3,4-tetrahydronaphthalenyl or chromanyl.

In some embodiments, $R^7$ is hydrogen.

In some embodiments, $R^7$ is $(C_1-C_6)$-alkyl, wherein the $(C_1-C_6)$-alkyl can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more independently selected halo. In some embodiments, $R^7$ is $(C_1-C_6)$-alkyl, wherein the $(C_1-C_4)$-alkyl can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more independently selected halo.

In some embodiments, $R^7$ is $(C_3-C_7)$-cycloalkyl, wherein the $(C_3-C_7)$-cycloalkyl can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more independently selected halo.

In some embodiments, $R^7$ is 4- to 7-membered heterocyclyl, wherein the or 4- to 7-membered heterocyclyl can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more independently selected halo, and any nitrogen of the 4- to 7-membered heterocyclyl can be substituted by $C(O)OR^6$ or $C(O)R^6$.

In some embodiments, $R^7$ is $(C_6\text{-}C_{10})$-aryl, wherein the $(C_6\text{-}C_{10})$-aryl can be substituted by one or more independently selected $(C_1\text{-}C_4)$-alkyl, $(C_1\text{-}C_4)$-alkoxy, oxo, cyano, or halo, wherein the $(C_1\text{-}C_4)$-alkoxy and $(C_1\text{-}C_4)$-alkyl can be substituted by one or more independently selected halo.

In some embodiments, $R^7$ is phenyl, wherein the phenyl can be substituted by one or more independently selected $(C_1\text{-}C_4)$-alkyl, $(C_1\text{-}C_4)$-alkoxy, oxo, cyano, or halo, wherein the $(C_1\text{-}C_4)$-alkoxy and $(C_1\text{-}C_4)$-alkyl can be substituted by one or more independently selected halo. In some embodiments, $R^7$ is phenyl, wherein the phenyl can be substituted by one or more independently selected halo. In some embodiments, $R^7$ is $(C_6\text{-}C_{10})$-aryl, wherein the $(C_6\text{-}C_{10})$-aryl can be substituted by one or more independently selected $(C_1\text{-}C_4)$-alkyl, $(C_1\text{-}C_4)$-alkoxy, oxo, cyano, or halo, wherein the $(C_1\text{-}C_4)$-alkoxy and $(C_1\text{-}C_4)$-alkyl can be substituted by one or more independently selected halo, and the nitrogen of the 4- to 7-membered heterocyclyl can be substituted by $C(O)OR^6$ or $C(O)R^6$. In some embodiments, $R^7$ is phenyl, wherein the phenyl can be substituted by one or more independently selected halo. In some embodiments, $R^7$ is phenyl, wherein the phenyl can be substituted by one or more independently selected fluoro. In some embodiments, $R^7$ is 4-fluorophenyl.

In some embodiments, $R^4$ and $R^5$ are joined to one another and, taken together with the carbon atom to which they are attached, form a 5- to 6-membered ring containing one heteroatom selected from the group consisting of O or N, wherein:

(i) the ring can be substituted by one or more independently selected $(C_1\text{-}C_4)$-alkyl, $(C_1\text{-}C_4)$-alkoxy, oxo, cyano, or fluoro, wherein the $(C_1\text{-}C_4)$-alkyl is optionally substituted by one or more fluoro, and (ii) the ring can be fused with phenyl; and $R^7$ is hydrogen.

In some embodiments, $R^4$ and $R^5$ are joined to one another and, taken together with the carbon atom to which they are attached, form a cyclopentyl; and $R^7$ is phenyl, wherein the phenyl can be substituted by one or more independently selected halo.

In some embodiments, $R^6$ is hydrogen.

In some embodiments, $R^6$ is $(C_1\text{-}C_4)$-alkyl. In some embodiments, $R^6$ is methyl, ethyl, isopropyl, or t-butyl. For example, $R^6$ is methyl. For example, $R^6$ is t-butyl.

In some embodiments (e.g., when the compound is a compound of Formula (A)), —$C(O)NHCH(R^4)R^7R^5$ is

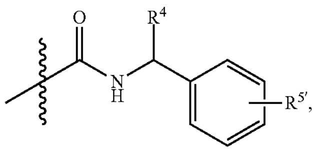

wherein:

the wavy line indicates the point of attachment to the thiophene;

$R^4$ is hydrogen, $(C_1\text{-}C_6)$-alkyl, $(C_3\text{-}C_7)$-cycloalkyl, or 4- to 7-membered heterocyclyl, wherein the $(C_1\text{-}C_6)$-alkyl, $(C_3\text{-}C_7)$-cycloalkyl, or 4- to 7-membered heterocyclyl can be substituted by one or more independently selected $(C_1\text{-}C_1)$-alkyl, $(C_1\text{-}C_4)$-alkoxy, hydroxyl, oxo, cyano, or halo, wherein the $(C_1\text{-}C_4)$-alkoxy and $(C_1\text{-}C_4)$-alkyl can be substituted by one or more independently selected halo, and any nitrogen of the 4- to 7-membered heterocyclyl can be substituted by $C(O)OR^6$ or $C(O)R^6$; and $R^{5'}$ is $(C_1\text{-}C_4)$-alkyl, $(C_1\text{-}C_4)$-alkoxy, $C(O)OR^6$, $(C_3\text{-}C_7)$-cycloalkoxy, cyano, 4- to 7-membered heterocycyl, or halo, and wherein the $(C_1\text{-}C_4)$-alkyl and $(C_1\text{-}C_4)$-alkoxy can be substituted by one or more independently selected 4- to 7-membered heterocyclyl optionally substituted with oxo or $(C_1\text{-}C_4)$-alkyl, $(C_1\text{-}C_4)$-alkoxy, —NR'R", or halo.

In some embodiments, $R^{5'}$ is $(C_1\text{-}C_4)$-alkyl, wherein the $(C_1\text{-}C_4)$-alkyl can be substituted by one or more independently selected 4- to 7-membered heterocyclyl optionally substituted with oxo or $(C_1\text{-}C_4)$-alkyl, $(C_1\text{-}C_4)$-alkoxy, —NR'R", or halo. For example, $R^{5'}$ is methyl or ethyl (e.g., methyl).

In some embodiments, $R^{5'}$ is $(C_1\text{-}C_4)$-alkoxy, wherein the $(C_1\text{-}C_4)$-alkoxy can be substituted by one or more independently selected 4- to 7-membered heterocyclyl optionally substituted with oxo or $(C_1\text{-}C_4)$-alkyl, $(C_1\text{-}C_4)$-alkoxy, —NR'R", or halo. For example, $R^{5'}$ is methoxy.

In some embodiments, $R^{5'}$ is $C(O)OR^6$. For example, $R^5$ is C(O)OMe.

In some embodiments, $R^{5'}$ is $(C_3\text{-}C_7)$-cycloalkoxy. In some embodiments, $R^{5'}$ is $(C_5\text{-}C_6)$-cycloalkoxy.

In some embodiments, $R^{5'}$ is cyano.

In some embodiments, $R^{5'}$ is 4- to 7-membered heterocyclyl.

In some embodiments, $R^{5'}$ is halo (e.g., fluoro).

In some embodiments (e.g., when the compound is a compound of Formula (A)), —$C(O)NHCH(R^4)R^7R^5$ is

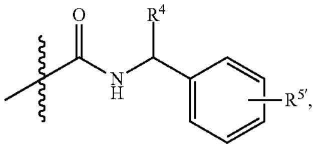

wherein:

the wavy line indicates the point of attachment to the thiophene;

$R^4$ is hydrogen, methyl, or ethyl, wherein the methyl or ethyl can be substituted by one or more independently selected $(C_1\text{-}C_4)$-alkyl, $(C_1\text{-}C_4)$-alkoxy, hydroxyl, oxo, cyano, or halo, wherein the $(C_1\text{-}C_4)$-alkoxy and $(C_1\text{-}C_4)$-alkyl can be substituted by one or more independently selected halo, and any nitrogen of the 4- to 7-membered heterocyclyl can be substituted by $C(O)OR^6$ or $C(O)R^6$; and $R^{5'}$ is methyl, methoxy, or fluoro.

In some embodiments, the stereochemical configuration of the atom that $R^4$ and $R^5$ are bonded to is (S). In some embodiments, the stereochemical configuration of the atom that $R^4$ and $R^5$ are bonded to is (R).

In some embodiments (e.g., when the compound is a compound of Formula (I), (I-A), or (I-B)), —$C(O)NHCH(R^4)R^7R^5$ is

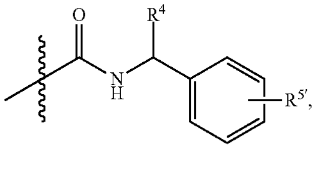

wherein:

the wavy line indicates the point of attachment to the thiophene;

$R^4$ is hydrogen, $(C_1\text{-}C_6)$-alkyl, $(C_3\text{-}C_7)$-cycloalkyl, or 4- to 7-membered heterocyclyl, wherein the $(C_1\text{-}C_6)$-alkyl, $(C_3\text{-}C_7)$cycloalkyl, or 4- to 7-membered heterocyclyl can be substituted by one or more independently selected $(C_1\text{-}C_4)$-alkyl, $(C_1\text{-}C_4)$-alkoxy, hydroxyl, oxo, cyano, or halo, wherein the $(C_1\text{-}C_4)$-alkoxy and $(C_1\text{-}C_4)$-alkyl can be substituted by one or more independently selected halo, and any nitrogen of the 4- to 7-membered heterocyclyl can be substituted by C(O)$OR^6$ or C(O)$R^6$, and $R^{5'}$ is $(C_1\text{-}C_4)$-alkyl, $(C_1\text{-}C_4)$-alkoxy, C(O)$OR^6$, $(C_3\text{-}C_7)$-cycloalkoxy, cyano, 4- to 7-membered heterocyclyl, or halo, and wherein the $(C_1\text{-}C_4)$-alkyl and $(C_1\text{-}C_4)$-alkoxy can be substituted by one or more independently selected 4- to 7-membered heterocyclyl optionally substituted with oxo or $(C_1\text{-}C_4)$-alkyl, $(C_1\text{-}C_4)$-alkoxy, —NR'R", or halo.

In some embodiments, $R^{5'}$ is $(C_1\text{-}C_4)$-alkyl, wherein the $(C_1\text{-}C_4)$-alkyl can be substituted by one or more independently selected 4- to 7-membered heterocyclyl optionally substituted with oxo or $(C_1\text{-}C_4)$-alkyl, $(C_1\text{-}C_4)$-alkoxy, —NR'R", or halo. For example, $R^{5'}$ is methyl or ethyl (e.g., methyl).

In some embodiments, $R^{5'}$ is $(C_1\text{-}C_4)$-alkoxy, wherein the $(C_1\text{-}C_4)$-alkoxy can be substituted by one or more independently selected 4- to 7-membered heterocyclyl optionally substituted with oxo or $(C_1\text{-}C_4)$-alkyl, $(C_1\text{-}C_4)$-alkoxy, —NR'R", or halo. For example, $R^{5'}$ is methoxy.

In some embodiments, $R^{5'}$ is C(O)$OR^6$. For example, $R^{5'}$ is C(O)OMe.

In some embodiments, $R^{5'}$ is $(C_3\text{-}C_7)$-cycloalkoxy. In some embodiments, $R^{5'}$ is $(C_5\text{-}C_6)$-cycloalkoxy.

In some embodiments, $R^{5'}$ is cyano.

In some embodiments, $R^{5'}$ is 4- to 7-membered heterocyclyl.

In some embodiments, $R^{5'}$ is halo (e.g., fluoro).

In some embodiments (e.g., when the compound is a compound of Formula Formula (I), (I-A), or (I-B)), —C(O)NHCH($R^4$)$R^7R^5$ is

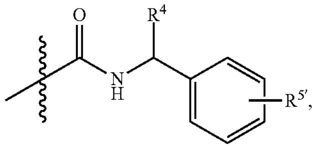

wherein:

the wavy line indicates the point of attachment to the thiophene;

$R^4$ is hydrogen, methyl, or ethyl, wherein the methyl or ethyl can be substituted by one or more independently selected $(C_1\text{-}C_4)$-alkyl, $(C_1\text{-}C_4)$-alkoxy, hydroxyl, oxo, cyano, or halo, wherein the $(C_1\text{-}C_4)$-alkoxy and $(C_1\text{-}C_4)$-alkyl can be substituted by one or more independently selected halo, and any nitrogen of the 4- to 7-membered heterocyclyl can be substituted by C(O)$OR^6$ or C(O)$R^6$; and $R^{5'}$ is methyl, methoxy, or fluoro.

In some embodiments, the stereochemical configuration of the atom that $R^4$ and $R^5$ are bonded to is (S). In some embodiments, the stereochemical configuration of the atom that $R^4$ and $R^5$ are bonded to is (R).

Non-Limiting Combinations

In some embodiments, $R^E$ is —C(O)—$NR^AR^B$, $R^A$ is —$CR^1R^2R^3$, and $R^B$ is hydrogen.

In some embodiments,

Z is $NH_2$, $R^E$ is —C(O)—NR ARP $R^A$ is —$CR^1R^2R^3$ $R^B$ is hydrogen, $R^C$ is $CR^4R^5R^7$, and $R^D$ is hydrogen.

In some embodiments, $R^E$ is —C(O)—$NR^AR^B$, $R^A$ is —$CR^1R^2R^3$, $R^B$ is hydrogen, $R^1$ and $R^2$ are each independently hydrogen or methyl;

$R^3$ is methyl or ethyl, each of which can be substituted by one or more independently selected hydroxyl, $(C_1\text{-}C_4)$-alkoxy, chloro, or fluoro, wherein the $(C_1\text{-}C_4)$-alkoxy can be substituted by one or more fluoro; or $R^1$ is hydrogen and $R^2$ and $R^3$ are joined to one another and, taken together with the carbon atom to which they are attached, form a 3- to 7-membered ring containing up to two heteroatoms selected from the group consisting of O or N, wherein the ring can be substituted by one or more independently selected hydroxyl, $(C_1\text{-}C_4)$-alkyl, oxo, or halo.

In some embodiments, $R^E$ is —C(O)—$NR^AR^B$, $R^A$ is —$CR^1R^2R^3$, $R^B$ is hydrogen, $R^1$ and $R^2$ are each independently hydrogen or methyl; and $R^3$ is methyl or ethyl, each of which can be substituted by one or more independently selected hydroxyl, $(C_1\text{-}C_4)$-alkoxy, chloro, or fluoro, wherein the $(C_1\text{-}C_4)$-alkoxy can be substituted by one or more fluoro.

In some embodiments,

Z is $NH_2$, $R^E$ is —C(O)—$NR^AR^B$, $R^A$ is —$CR^1R^2R^3$, $R^B$ is hydrogen, $R^C$ is $CR^4R^5R^7$, and $R^D$ is hydrogen.

X is carbon and Y is nitrogen;

$R^1$ and $R^2$ are each independently hydrogen or methyl;

$R^3$ is methyl or ethyl, each of which can be substituted by one or more independently selected hydroxyl, $(C_1\text{-}C_4)$-alkoxy, chloro, or fluoro, wherein the $(C_1\text{-}C_4)$-alkoxy can be substituted by one or more fluoro;

$R^4$ is hydrogen, $(C_1\text{-}C_6)$-alkyl, $(C_3\text{-}C_7)$-cycloalkyl, or 4- to 7-membered heterocyclyl, each of which can be substituted by one or more independently selected $(C_1\text{-}C_4)$-alkyl, $(C_1\text{-}C_4)$-alkoxy, oxo, cyano, or halo, wherein the $(C_1\text{-}C_4)$-alkoxy and $(C_1\text{-}C_4)$-alkyl can be substituted by one or more fluoro; and any nitrogen of the 4- to 7-membered heterocyclyl can be substituted by C(O)$OR^6$ or C(O)$R^6$, $R^5$ is $(C_3\text{-}C_7)$-cycloalkyl, phenyl, or heteroaryl wherein the $(C_3\text{-}C_7)$-cycloalkyl, phenyl, or heteroaryl can be substituted by one or more independently selected $(C_1\text{-}C_4)$-alkyl, $(C_1\text{-}C_4)$-alkoxy, cyano, 4- to 7-membered heterocyclyl, or halo, wherein the $(C_1\text{-}C_4)$-alkyl and $(C_1\text{-}C_4)$-alkoxy can be substituted by one or more fluoro; and $R^6$ is methyl or t-butyl.

In some embodiments,

Z is $NH_2$, $R^E$ is —C(O)—$NR^AR^B$, $R^A$ is —$CR^1R^2R^3$, $R^B$ is hydrogen, $R^C$ is $CR^4R^5R^7$, and $R^D$ is hydrogen.

X is nitrogen and Y is carbon;

$R^1$ and $R^2$ are each independently hydrogen or methyl;

$R^3$ is methyl or ethyl, each of which can be substituted by one or more independently selected hydroxyl, ($C_1$-$C_4$)-alkoxy, chloro, or fluoro, wherein the ($C_1$-$C_4$)-alkoxy can be substituted by one or more fluoro;

$R^4$ is hydrogen, ($C_1$-$C_6$)-alkyl, ($C_3$-$C_7$)-cycloalkyl, or 4- to 7-membered heterocyclyl, each of which can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more fluoro; and any nitrogen of the 4- to 7-membered heterocyclyl can be substituted by $C(O)OR^6$ or $C(O)R^6$;

$R^5$ is ($C_3$-$C_7$)-cycloalkyl, phenyl, or heteroaryl wherein the ($C_3$-$C_7$)-cycloalkyl, phenyl, or heteroaryl can be substituted by one or more independently selected ($C_1$-$C_4$)-alkyl, ($C_1$-$C_4$)-alkoxy, cyano, 4- to 7-membered heterocyclyl, or halo, wherein the ($C_1$-$C_4$)-alkyl and ($C_1$-$C_4$)-alkoxy can be substituted by one or more fluoro; and $R^6$ is methyl or t-butyl.

In some embodiments,

Z is —$NHR^F$, wherein $R^F$ is hydrogen or ($C_1$-$C_6$)-alkyl, wherein the ($C_1$-$C_6$)-alkyl is optionally substituted with one or more independently selected —NR'R", $R^E$ is —C(O)—$NR^AR^B$, $R^A$ is —$CR^1R^2R^3$, $R^B$ is hydrogen, $R^C$ is $CR^4R^5R^7$, and $R^D$ is hydrogen.

X is nitrogen and Y is carbon;

$R^1$ and $R^2$ are each independently hydrogen or methyl;

$R^3$ is methyl or ethyl, each of which can be substituted by one or more independently selected hydroxyl, ($C_1$-$C_4$)-alkoxy, chloro, or fluoro, wherein the ($C_1$-$C_4$)-alkoxy can be substituted by one or more fluoro;

$R^4$ is hydrogen, ($C_1$-$C_6$)-alkyl, ($C_3$-$C_7$)-cycloalkyl, or 4- to 7-membered heterocyclyl, each of which can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more fluoro; and any nitrogen of the 4- to 7-membered heterocyclyl can be substituted by $C(O)OR^6$ or $C(O)R^6$;

$R^5$ is ($C_3$-$C_7$)-cycloalkyl, phenyl, or heteroaryl wherein the ($C_3$-$C_7$)-cycloalkyl, phenyl, or heteroaryl can be substituted by one or more independently selected ($C_1$-$C_4$)-alkyl, ($C_1$-$C_4$)-alkoxy, cyano, 4- to 7-membered heterocyclyl, or halo, wherein the ($C_1$-$C_4$)-alkyl and ($C_1$-$C_4$)-alkoxy can be substituted by one or more fluoro; and $R^6$ is methyl or t-butyl.

In some embodiments,

Z is H, $R^E$ is —C(O)—$NR^AR^B$ $R^A$ is —$CR^1R^2R^3$, $R^B$ is hydrogen, $R^C$ is $CR^4R^5R^7$, and $R^D$ is hydrogen.

X is nitrogen and Y is carbon;

$R^1$ and $R^2$ are each independently hydrogen or methyl;

$R^3$ is methyl or ethyl, each of which can be substituted by one or more independently selected hydroxyl, ($C_1$-$C_4$)-alkoxy, chloro, or fluoro, wherein the ($C_1$-$C_4$)-alkoxy can be substituted by one or more fluoro;

$R^4$ is hydrogen, ($C_1$-$C_6$)-alkyl, ($C_3$-$C_7$)-cycloalkyl, or 4- to 7-membered heterocyclyl, each of which can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more fluoro; and any nitrogen of the 4- to 7-membered heterocyclyl can be substituted by $C(O)OR^6$ or $C(O)R^6$;

$R^5$ is ($C_3$-$C_7$)-cycloalkyl, phenyl, or heteroaryl wherein the ($C_3$-$C_7$)-cycloalkyl, phenyl, or heteroaryl can be substituted by one or more independently selected ($C_1$-$C_4$)-alkyl, ($C_1$-$C_4$)-alkoxy, cyano, 4- to 7-membered heterocyclyl, or halo, wherein the ($C_1$-$C_4$)-alkyl and ($C_1$-$C_4$)-alkoxy can be substituted by one or more fluoro; and $R^6$ is methyl or t-butyl.

In some embodiments,

Z is —$NH_2$, $R^E$ is H or halo, $R^C$ is $CR^4R^5R^7$, and $R^D$ is hydrogen.

X is nitrogen and Y is carbon;

$R^4$ is hydrogen, ($C_1$-$C_6$)-alkyl, ($C_3$-$C_7$)-cycloalkyl, or 4- to 7-membered heterocyclyl, each of which can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more fluoro; and any nitrogen of the 4- to 7-membered heterocyclyl can be substituted by $C(O)OR^6$ or $C(O)R^6$;

$R^5$ is ($C_3$-$C_7$)-cycloalkyl, phenyl, or heteroaryl wherein the ($C_3$-$C_7$)-cycloalkyl, phenyl, or heteroaryl can be substituted by one or more independently selected ($C_1$-$C_4$)-alkyl, ($C_1$-$C_4$)-alkoxy, cyano, 4- to 7-membered heterocyclyl, or halo, wherein the ($C_1$-$C_4$)-alkyl and ($C_1$-$C_4$)-alkoxy can be substituted by one or more fluoro; and $R^6$ is methyl or t-butyl.

In some embodiments,

Z is —$NH_2$, $R^E$ is —C(O)—$NR^AR^B$, $C(O)OR^6$, —$S(O)_2NH$($C_1$-$C_6$)-alkyl, ($C_1$-$C_6$)-alkyl, or ($C_6$-$C_{10}$)-aryl, wherein the ($C_1$-$C_6$)-alkyl and ($C_6$-$C_{10}$)-aryl can be substituted by one or more independently selected ($C_1$-$C_4$)-alkyl, ($C_3$-$C_1$)-cycloalkyl, ($C_3$-$C_7$)-cycloalkyl-($C_1$-$C_3$)-alkyl, 4- to 7-membered heterocyclyl, ($C_1$-$C_4$)-alkoxy, ($C_3$-$C_7$)-cycloalkoxy, —$SO_2R^4$, —$NR^4R^5$, cyano, hydroxyl, or halo, wherein the ($C_1$-$C_4$)-alkyl, ($C_3$-$C_7$)-cycloalkyl, ($C_1$-$C_4$)-alkoxy, ($C_3$-$C_7$)-cycloalkyl-($C_1$-$C_3$)-alkyl, and ($C_3$-$C_7$)-cycloalkoxy can be substituted by one or more independently selected hydroxyl, cyano, or halo, $R^A$ is —$CR^1R^2R^3$ $R^B$ is hydrogen, $R^C$ is $CR^4R^5R^7$, and $R^D$ is hydrogen.

X is nitrogen and Y is carbon;

$R^1$ and $R^2$ are each independently hydrogen or methyl;

$R^3$ is methyl or ethyl, each of which can be substituted by one or more independently selected hydroxyl, ($C_1$-$C_4$)-alkoxy, chloro, or fluoro, wherein the ($C_1$-$C_4$)-alkoxy can be substituted by one or more fluoro;

$R^4$ is hydrogen, ($C_1$-$C_6$)-alkyl, ($C_3$-$C_7$)-cycloalkyl, or 4- to 7-membered heterocyclyl, each of which can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more fluoro; and any nitrogen of the 4- to 7-membered heterocyclyl can be substituted by $C(O)OR^6$ or $C(O)R^6$;

$R^5$ is $(C_3-C_7)$-cycloalkyl, phenyl, or heteroaryl wherein the $(C_3-C_7)$-cycloalkyl, phenyl, or heteroaryl can be substituted by one or more independently selected $(C_1-C_4)$-alkyl, $(C_1-C_4)$-alkoxy, cyano, 4- to 7-membered heterocyclyl, or halo, wherein the $(C_1-C_4)$-alkyl and $(C_1-C_4)$-alkoxy can be substituted by one or more fluoro; and $R^6$ is methyl or t-butyl.

In some embodiments,

Z is $NH_2$, $R^E$ is —C(O)—$NR^AR^B$, $R^A$ is —$CR^1R^2R^3$, $R^B$ is hydrogen, $R^C$ is $CR^4R^5R^7$, and $R^D$ is hydrogen.

X is carbon and Y is nitrogen;

$R^1$ and $R^2$ are each independently hydrogen or methyl;

$R^3$ is methyl or ethyl, each of which can be substituted by one or more independently selected hydroxyl, $(C_1-C_4)$-alkoxy, or fluoro, wherein the $(C_1-C_4)$-alkoxy can be substituted by one or more fluoro;

$R^4$ is hydrogen or $(C_1-C_6)$-alkyl, wherein the $(C_1-C_6)$-alkyl can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more fluoro; and $R^5$ is phenyl or heteroaryl wherein the phenyl or heteroaryl can be substituted by one or more independently selected $(C_1-C_4)$-alkyl, $(C_1-C_4)$-alkoxy, cyano, 4- to 7-membered heterocyclyl, or halo, wherein the $(C_1-C_4)$-alkyl and $(C_1-C_4)$-alkoxy can be substituted by one or more fluoro.

In some embodiments,

Z is $NH_2$, $R^E$ is —C(O)—$NR^AR^B$, $R^A$ is —$CR^1R^2R^3$, $R^B$ is hydrogen, $R^C$ is $CR^4R^5R^7$, and $R^D$ is hydrogen X is carbon and Y is nitrogen;

$R^1$ and $R^2$ are each independently hydrogen or methyl that can be substituted by one or more fluoro;

$R^3$ is methyl or ethyl, each of which can be substituted by one or more independently selected hydroxyl or fluoro;

$R^4$ is hydrogen or $(C_1-C_6)$-alkyl, wherein the $(C_1-C_6)$-alkyl can be substituted by one or more fluoro; and $R^5$ is phenyl or heteroaryl, wherein the phenyl or heteroaryl can be substituted by one or more independently selected $(C_1-C_4)$-alkyl, $(C_1-C_4)$-alkoxy, cyano, or fluoro, wherein the $(C_1-C_4)$-alkyl and $(C_1-C_4)$-alkoxy can be substituted by one or more fluoro.

In some embodiments,

Z is $NH_2$, $R^E$ is —C(O)—$NR^AR^B$, $R^A$ is —$CR^1R^2R^3$, $R^B$ is hydrogen, $R^C$ is $CR^4R^5R^7$, and $R^D$ is hydrogen.

X is carbon and Y is nitrogen;

$R^1$ and $R^2$ are each independently hydrogen or methyl that can be substituted by one or more fluoro;

$R^3$ is methyl or ethyl, each of which can be substituted by hydroxyl;

$R^4$ is $(C_1-C_6)$-alkyl, wherein the $(C_1-C_6)$-alkyl can be substituted by one or more fluoro; and $R^5$ is phenyl or heteroaryl wherein the phenyl or heteroaryl can be substituted by one or more independently selected $(C_1-C_4)$-alkyl, $(C_1-C_4)$-alkoxy, cyano, or fluoro, wherein the $(C_1-C_4)$-alkyl and $(C_1-C_4)$-alkoxy can be substituted by one or more fluoro.

In some embodiments.

Z is $NH_2$, $R^E$ is —C(O)—$NR^AR^B$, $R^A$ is —$CR^1R^2R^3$, $R^B$ is hydrogen, $R^C$ is $CR^4R^5R^7$, and $R^D$ is hydrogen.

X is nitrogen and Y is carbon;

$R^1$ and $R^2$ are each independently hydrogen or methyl that can be substituted by one or more fluoro;

$R^3$ is methyl or ethyl, each of which can be substituted by hydroxyl;

$R^4$ is $(C_1-C_6)$-alkyl, wherein the $(C_1-C_6)$-alkyl can be substituted by one or more fluoro; and $R^5$ is phenyl or heteroaryl wherein the phenyl or heteroaryl can be substituted by one or more independently selected $(C_1-C_4)$-alkyl, $(C_1-C_4)$-alkoxy, cyano, or fluoro, wherein the $(C_1-C_4)$-alkyl and $(C_1-C_4)$-alkoxy can be substituted by one or more fluoro.

In some embodiments,

Z is $NH_2$, $R^E$ is —C(O)—$NR^AR^B$, $R^A$ is —$CR^1R^2R^3$, $R^B$ is hydrogen, $R^C$ is $CR^4R^5R^7$, and $R^D$ is hydrogen.

X is carbon and Y is nitrogen;

$R^1$ and $R^2$ are each independently hydrogen or methyl that can be substituted by one or more fluoro;

$R^3$ is methyl or ethyl, each of which can be substituted by hydroxyl;

$R^4$ is $(C_1-C_6)$-alkyl that can be substituted by one or more independently selected $(C_1-C_4)$-alkoxy or halo; and $R^5$ is phenyl, wherein the phenyl can be substituted by one or more fluoro.

In some embodiments,

Z is $NH_2$, $R^E$ is —C(O)—$NR^AR^B$, $R^A$ is —$CR^1R^2R^3$, $R^B$ is hydrogen, $R^C$ is $CR^4R^5R^7$, and $R^D$ is hydrogen.

X is carbon and Y is nitrogen;

$R^1$ and $R^2$ are each independently hydrogen or methyl that can be substituted by one or more fluoro;

$R^3$ is methyl or ethyl, each of which can be substituted by hydroxyl;

$R^4$ is hydrogen; and $R^5$ is phenyl or heteroaryl, wherein the phenyl or heteroaryl can be substituted by one or more independently selected $(C_1-C_4)$-alkyl, $(C_1-C_4)$-alkoxy, cyano, or fluoro, wherein the $(C_1-C_4)$-alkyl and $(C_1-C_4)$-alkoxy can be substituted by one or more fluoro.

In some embodiments,

Z is $NH_2$, $R^E$ is —C(O)—$NR^AR^B$, $R^A$ is —$CR^1R^2R^3$, $R^B$ is hydrogen, $R^C$ is $CR^4R^5R^7$, and $R^D$ is hydrogen.

X is carbon and Y is nitrogen;

$R^1$ and $R^2$ are each independently hydrogen or methyl that can be substituted by one or more fluoro;

$R^3$ is methyl or ethyl, each of which can be substituted by hydroxyl;

$R^4$ is hydrogen; and $R^5$ is phenyl, wherein the phenyl can be substituted by by one or more fluoro.

In some embodiments,

Z is $NH_2$, $R^E$ is —C(O)—$NR^AR^B$, $R^A$ is —$CR^1R^2R^3$, $R^B$ is hydrogen, $R^C$ is $CR^1R^2R^3$, and $R^D$ is hydrogen.

X is carbon and Y is nitrogen;

$R^1$ and $R^2$ are each independently hydrogen or methyl;

$R^3$ is methyl or ethyl, each of which can be substituted by one or more independently selected hydroxyl, $(C_1-C_4)$-alkoxy, chloro, or fluoro, wherein the $(C_1-C_4)$-alkoxy can be substituted by one or more fluoro;

$R^4$ is $(C_3-C_7)$-cycloalkyl or 4- to 7-membered heterocyclyl, each of which can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more fluoro; and any nitrogen of the 4- to 7-membered heterocyclyl can be substituted by $C(O)OR^6$ or $C(O)R^6$;

$R^5$ is $(C_3-C_7)$-cycloalkyl, phenyl, or heteroaryl wherein the $(C_3-C_7)$-cycloalkyl, phenyl, or heteroaryl can be substituted by one or more independently selected $(C_1-C_4)$-alkyl, $(C_1-C_4)$-alkoxy, cyano, 4- to 7-membered heterocyclyl, or halo, wherein the $(C_1-C_4)$-alkyl and $(C_1-C_4)$-alkoxy can be substituted by one or more fluoro; and $R^6$ is methyl or t-butyl.

In some embodiments,

Z is $NH_2$, $R^E$ is —C(O)—NRAR, $R^A$ is —$CR^1R^2R^3$, $R^B$ is hydrogen, $R^C$ is $CR^4R^5R^7$, and $R^D$ is hydrogen.

X is carbon and Y is nitrogen;

$R^1$ and $R^2$ are each independently hydrogen or methyl;

$R^3$ is ethyl which can be substituted by one or more independently selected hydroxyl, $(C_1-C_4)$-alkoxy, chloro, or fluoro;

$R^4$ is $(C_3-C_6)$-cycloalkyl or 4- to 7-membered heterocyclyl, each of which can be substituted by one or more independently selected $(C_1-C_4)$-alkyl, $(C_1-C_4)$-alkoxy, oxo, cyano, or halo; and any nitrogen of the 4- to 7-membered heterocyclyl can be substituted by C(O) $OR^6$ or $C(O)R^6$.

$R^5$ is phenyl or heteroaryl wherein the phenyl, or heteroaryl can be substituted by one or more independently selected $(C_1-C_4)$-alkyl, $(C_1-C_6)$-alkoxy, cyano, 4- to 7-membered heterocyclyl, or fluoro; and $R^6$ is methyl or t-butyl.

In some embodiments,

Z is $NH_2$;

$R^E$ is —C(O)—$NR^AR^B$, $R^A$ is —$CR^1R^2R^3$, $R^B$ is hydrogen,

X is carbon and Y is nitrogen;

$R^4$ is hydrogen, $(C_1-C_6)$-alkyl, $(C_3-C_7)$-cycloalkyl, or 4- to 7-membered heterocyclyl, each of which can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more fluoro; and any nitrogen of the 4- to 7-membered heterocyclyl can be substituted by $C(O)OR^6$ or $C(O)R^6$;

$R^5$ is $(C_3-C_7)$-cycloalkyl, phenyl, or heteroaryl wherein the $(C_3-C_7)$-cycloalkyl, phenyl, or heteroaryl can be substituted by one or more independently selected $(C_1-C_4)$-alkyl, $(C_1-C_4)$-alkoxy, cyano, 4- to 7-membered heterocyclyl, or halo, wherein the $(C_1-C_4)$-alkyl and $(C_1-C_4)$-alkoxy can be substituted by one or more fluoro; and $R^6$ is methyl or t-butyl.

In some embodiments,

Z is $NH_2$;

$R^E$ is H;

$R^C$ is $CR^4R^5R^7$;

$R^D$ is hydrogen;

X is carbon and Y is nitrogen;

$R^4$ is hydrogen, $(C_1-C_6)$-alkyl, $(C_3-C_7)$-cycloalkyl, or 4- to 7-membered heterocyclyl, each of which can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more fluoro; and any nitrogen of the 4- to 7-membered heterocyclyl can be substituted by $C(O)OR^6$ or $C(O)R^6$;

$R^5$ is $(C_3-C_7)$-cycloalkyl, phenyl, or heteroaryl wherein the $(C_3-C_7)$-cycloalkyl, phenyl, or heteroaryl can be substituted by one or more independently selected $(C_1-C_4)$-alkyl, $(C_1-C_4)$-alkoxy, cyano, 4- to 7-membered heterocyclyl, or halo, wherein the $(C_1-C_4)$-alkyl and $(C_1-C_4)$-alkoxy can be substituted by one or more fluoro; and $R^6$ is methyl or t-butyl.

In some embodiments,

Z is NH;

$R^E$ is H;

$R^C$ is $CR^4R^5R^7$;

$R^D$ is hydrogen;

X is carbon and Y is nitrogen;

$R^1$ and $R^2$ are each independently hydrogen or methyl;

$R^3$ is methyl or ethyl, each of which can be substituted by one or more independently selected hydroxyl, $(C_1-C_4)$-alkoxy, chloro, or fluoro, wherein the $(C_1-C_4)$-alkoxy can be substituted by one or more fluoro;

$R^4$ is hydrogen, $(C_1-C_6)$-alkyl, $(C_3-C_7)$-cycloalkyl, or 4- to 7-membered heterocyclyl, each of which can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more fluoro; and any nitrogen of the 4- to 7-membered heterocyclyl can be substituted by $C(O)OR^6$ or $C(O)R^6$;

$R^5$ is $(C_3-C_7)$-cycloalkyl, phenyl, or heteroaryl wherein the $(C_3-C_7)$-cycloalkyl, phenyl, or heteroaryl can be substituted by one or more independently selected $(C_1-C_4)$-alkyl, $(C_1-C_4)$-alkoxy, cyano, 4- to 7-membered heterocyclyl, or halo, wherein the $(C_1-C_4)$-alkyl and $(C_1-C_4)$-alkoxy can be substituted by one or more fluoro; and $R^6$ is methyl or t-butyl.

In some embodiments,

Z is $NH_2$, $R^E$ is H,
$R^C$ is $CR^4R^5R^7$, and
$R^D$ is hydrogen.
X is carbon and Y is nitrogen;
$R^4$ is hydrogen, $(C_1-C_6)$-alkyl, $(C_3-C_7)$-cycloalkyl, or 4- to 7-membered heterocyclyl, each of which can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more fluoro; and any nitrogen of the 4- to 7-membered heterocyclyl can be substituted by $C(O)OR^6$ or $C(O)R^6$;
$R^5$ is $(C_3-C_7)$-cycloalkyl, phenyl, or heteroaryl wherein the $(C_3-C_7)$-cycloalkyl, phenyl, or heteroaryl can be substituted by one or more independently selected $(C_1-C_4)$-alkyl, $(C_1-C_4)$-alkoxy, cyano, 4- to 7-membered heterocyclyl, or halo, wherein the $(C_1-C_4)$-alkyl and $(C_1-C_4)$-alkoxy can be substituted by one or more fluoro; and
$R^6$ is methyl or t-butyl.
In some embodiments,
Z is $NH_2$,
$R^E$ is —C(O)—$NR^AR^B$,
$R^A$ is —$CR^1R^2R^3$,
$R^B$ is hydrogen,
$R^C$ is $CR^4R^5R^7$, and
$R^D$ is hydrogen.
X is carbon and Y is nitrogen;
$R^1$ and $R^2$ are each independently hydrogen or methyl;
$R^3$ is methyl or ethyl, each of which can be substituted by one or more independently selected hydroxyl, $(C_1-C_4)$-alkoxy, chloro, or fluoro, wherein the $(C_1-C_4)$-alkoxy can be substituted by one or more fluoro;
$R^4$ is hydrogen, $(C_1-C_6)$-alkyl, $(C_3-C_7)$-cycloalkyl, or 4- to 7-membered heterocyclyl, each of which can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more fluoro; and any nitrogen of the 4- to 7-membered heterocyclyl can be substituted by $C(O)OR^6$ or $C(O)R^6$;
$R^5$ is $(C_3-C_7)$-cycloalkyl, phenyl, or heteroaryl wherein the $(C_3-C_7)$-cycloalkyl, phenyl, or heteroaryl can be substituted by one or more independently selected $(C_1-C_4)$-alkyl, $(C_1-C_4)$-alkoxy, cyano, 4- to 7-membered heterocyclyl, or halo, wherein the $(C_1-C_{49}$-alkyl and $(C_1-C_4)$-alkoxy can be substituted by one or more fluoro; and
$R^6$ is methyl or t-butyl.
In some embodiments,
Z is $NH_2$,
$R^E$ is H,
$R^C$ is $CR^4R^5R^7$, and
$R^D$ is hydrogen
X is nitrogen and Y is carbon;
$R^4$ is hydrogen, $(C_1-C_6)$-alkyl, $(C_1-C_6)$-cycloalkyl, or 4- to 7-membered heterocyclyl, each of which can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more fluoro; and any nitrogen of the 4- to 7-membered heterocyclyl can be substituted by $C(O)OR^6$ or $C(O)R^6$;
$R^5$ is $(C_3-C_7)$-cycloalkyl, phenyl, or heteroaryl wherein the $(C_3-C_7)$-cycloalkyl, phenyl, or heteroaryl can be substituted by one or more independently selected $(C_1-C_4)$-alkyl, $(C_1-C_4)$-alkoxy, cyano, 4- to 7-membered heterocyclyl, or halo, wherein the $(C_1-C_4)$-alkyl and $(C_1-C_4)$-alkoxy can be substituted by one or more fluoro; and
$R^6$ is methyl or t-butyl.
In some embodiments.
Z is $NH_2$,
R is H,
$R^C$ is $CR^4R^5R^7$, and
$R^D$ is hydrogen.
X is nitrogen and Y is carbon;
$R^4$ is hydrogen, $(C_1-C_6)$-alkyl, $(C_3-C_7)$-cycloalkyl, or 4- to 7-membered heterocyclyl, each of which can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more fluoro; and any nitrogen of the 4- to 7-membered heterocyclyl can be substituted by $C(O)OR^6$ or C(O)R
$R^5$ is $(C_3-C_7)$-cycloalkyl, phenyl, or heteroaryl wherein the $(C_3-C_4)$-cycloalkyl, phenyl, or heteroaryl can be substituted by one or more independently selected $(C_1-C_4)$-alkyl, $(C_1-C_4)$-alkoxy, cyano, 4- to 7-membered heterocyclyl, or halo, wherein the $(C_1-C_4)$-alkyl and $(C_1-C_4)$-alkoxy can be substituted by one or more fluoro; and
$R^6$ is methyl or t-butyl.
In some embodiments,
Z is $NH_2$,
$R^E$ is heteroaryl, wherein the heteroaryl can be substituted by one or more independently selected $(C_1-C_4)$-alkyl, $(C_3-C_7)$-cycloalkyl, $(C_3-C_7)$-cycloalkyl-$(C_1-C_3)$-alkyl, 4- to 7-membered heterocyclyl, $(C_1-C_4)$-alkoxy, $(C_3-C_7)$-cycloalkoxy, —$SO_2R^4$, —$NR^4R^5$ cyano, hydroxyl, or halo, wherein the $(C_1-C_4)$-alkyl, $(C_3-C^7)$-cycloalkyl, $(C_1-C_4)$-alkoxy, $(C_3-C_7)$-cycloalkyl-$(C_1-C_3)$-alkyl, and $(C_3-C_7)$-cycloalkoxy can be substituted by one or more independently selected hydroxyl, cyano, or halo,
$R^C$ is $CR^4R^5R_7$, and
$R^D$ is hydrogen.
X is carbon and Y is nitrogen;
$R^4$ is hydrogen, $(C_1-C_6)$-alkyl, $(C_3-C_7)$-cycloalkyl, or 4- to 7-membered heterocyclyl, each of which can be substituted by one or more independently selected $(C_1-C_4)$-alkyl, $(C_1-C_4)$-alkoxy, oxo, cyano, or halo, wherein the $(C_1-C_4)$-alkoxy and $(C_1-C_4)$-alkyl can be substituted by one or more fluoro; and any nitrogen of the 4- to 7-membered heterocyclyl can be substituted by $C(O)OR^6$ or $C(O)R^6$;
$R^5$ is $(C_3-C_7)$-cycloalkyl, phenyl, or heteroaryl wherein the $(C_3-C_7)$-cycloalkyl, phenyl, or heteroaryl can be substituted by one or more independently selected $(C_1-C_4)$-alkyl, $(C_1-C_4)$-alkoxy, cyano, 4- to 7-membered heterocyclyl, or halo, wherein the $(C_1-C_4)$-alkyl and $(C_1-C_4)$-alkoxy can be substituted by one or more fluoro; and
$R^6$ is methyl or t-butyl.
In some embodiments,
Z is $NH_2$,
$R^E$ is thiadiazolyl or oxadiazolyl, each of which can be substituted by one or more independently selected $(C_1-C_4)$-alkyl, wherein the $(C_1-C_4)$-alkyl, can be substituted by one or more independently selected hydroxyl, cyano, or halo,
$R^C$ is $CR^4R^5R^7$, and
$R^D$ is hydrogen.
X is carbon and Y is nitrogen;

$R^4$ is $(C_1-C_6)$-alkyl, wherein the $(C_1-C_6)$-alkyl can be substituted by one or more fluoro; and $R^5$ is phenyl or heteroaryl wherein the phenyl or heteroaryl can be substituted by one or more independently selected $(C_1-C_4)$-alkyl, $(C_1-C_4)$-alkoxy, cyano, or fluoro, wherein the $(C_1-C_4)$-alkyl and $(C_7-C_4)$-alkoxy can be substituted by one or more fluoro.

In some embodiments, the compound is selected from the group consisting of the compounds disclosed in Table 1A below:

TABLE 1A

| Compound Number | Structure |
|---|---|
| 1 | 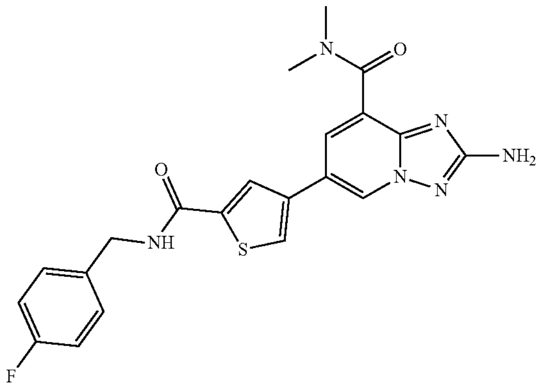 [SMILES: CN(C)C(=O)c1cc(-c2csc(C(=O)NCc3ccc(F)cc3)c2)cn2nc(N)nc12] |
| 2 | 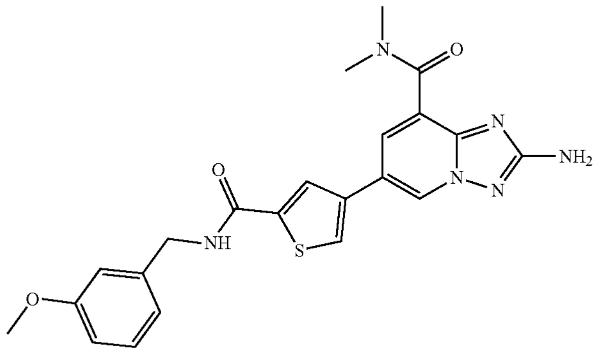 [SMILES: COc1cccc(CNC(=O)c2cc(-c3cc(C(=O)N(C)C)c4nc(N)nn4c3)cs2)c1] |
| 3 | 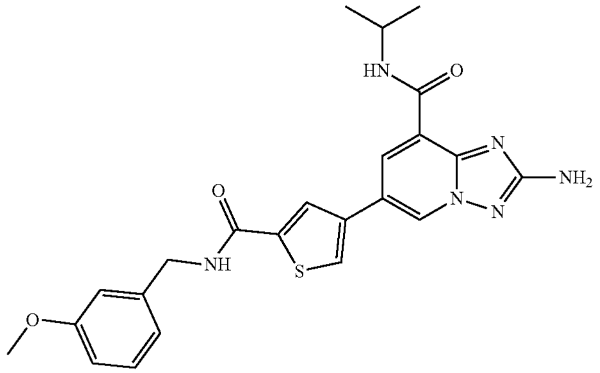 [SMILES: COc1cccc(CNC(=O)c2cc(-c3cc(C(=O)NC(C)C)c4nc(N)nn4c3)cs2)c1] |

TABLE 1A-continued
| Compound Number | Structure |
|---|---|
| 4 | 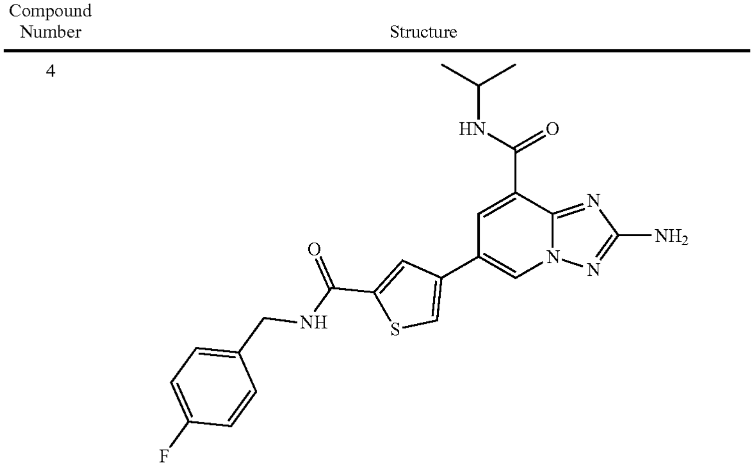 |
| 5 | 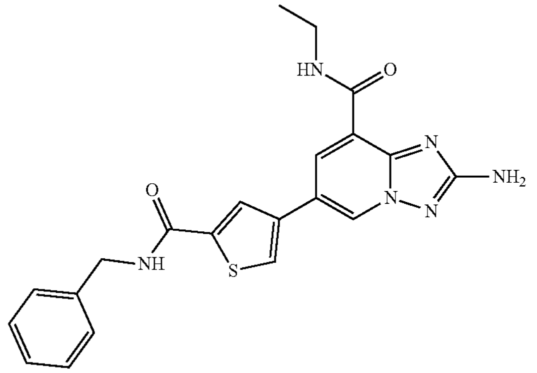 [SMILES: CCNC(=O)c1cc(-c2csc(C(=O)NCc3ccccc3)c2)cn2nc(N)nc12] |
| 6 | 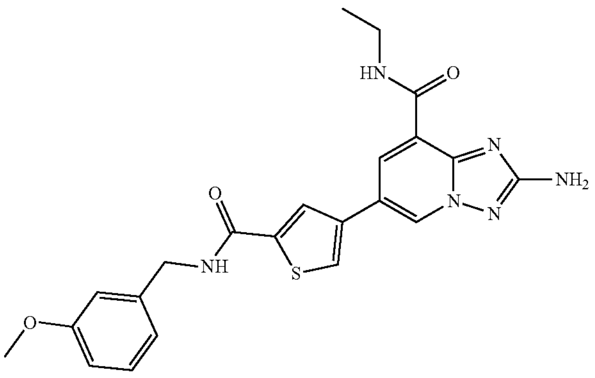 [SMILES: CCNC(=O)c1cc(-c2csc(C(=O)NCc3cccc(OC)c3)c2)cn2nc(N)nc12] |
| 7 | 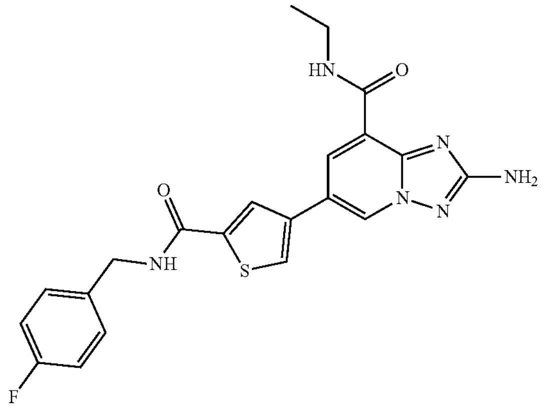 [SMILES: CCNC(=O)c1cc(-c2csc(C(=O)NCc3ccc(F)cc3)c2)cn2nc(N)nc12] |

TABLE 1A-continued
| Compound Number | Structure |
|---|---|
| 8 | 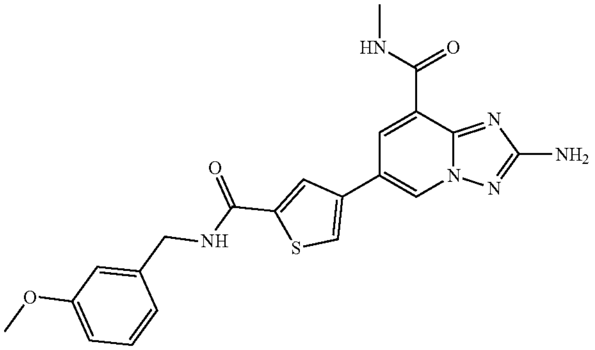 [SMILES: CNC(=O)c1cc(-c2csc(C(=O)NCc3cccc(OC)c3)c2)cn2nc(N)nc12] |
| 9 | 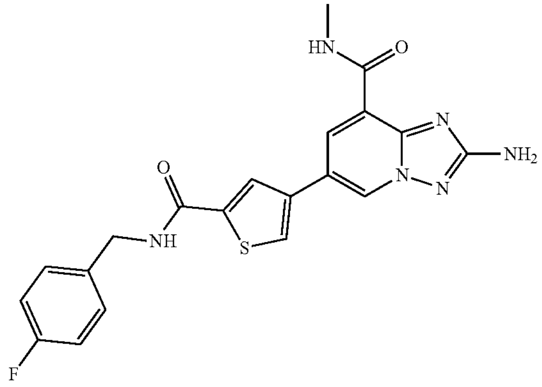 [SMILES: CNC(=O)c1cc(-c2csc(C(=O)NCc3ccc(F)cc3)c2)cn2nc(N)nc12] |
| 10 | 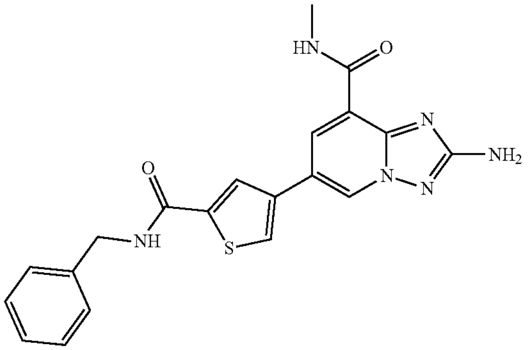 [SMILES: CNC(=O)c1cc(-c2csc(C(=O)NCc3ccccc3)c2)cn2nc(N)nc12] |
| 11 | 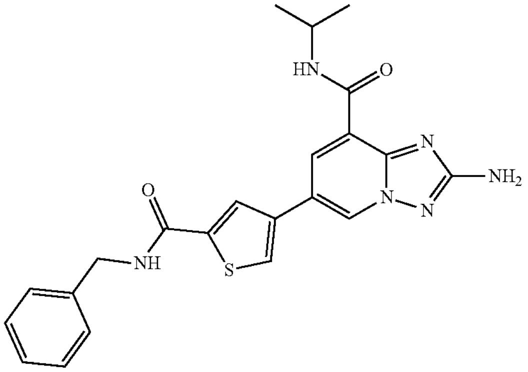 [SMILES: CC(C)NC(=O)c1cc(-c2csc(C(=O)NCc3ccccc3)c2)cn2nc(N)nc12] |

TABLE 1A-continued
| Compound Number | Structure |
| --- | --- |
| 12 | 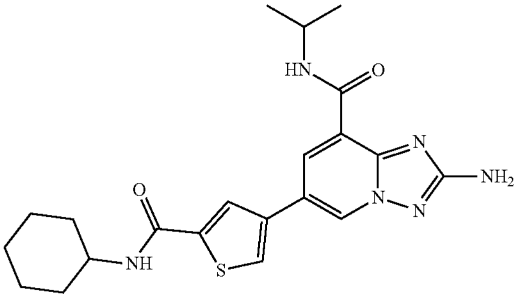 [SMILES: CC(C)NC(=O)c1cc(-c2csc(C(=O)NC3CCCCC3)c2)cn2nc(N)nc12] |
| 13 | 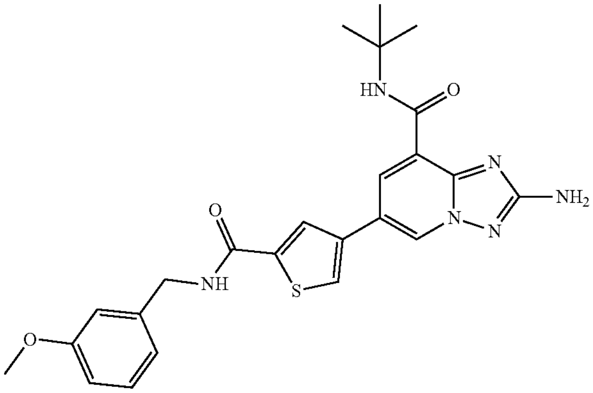 [SMILES: COc1cccc(CNC(=O)c2cc(-c3cc(C(=O)NC(C)(C)C)c4nc(N)nn4c3)cs2)c1] |
| 14 | 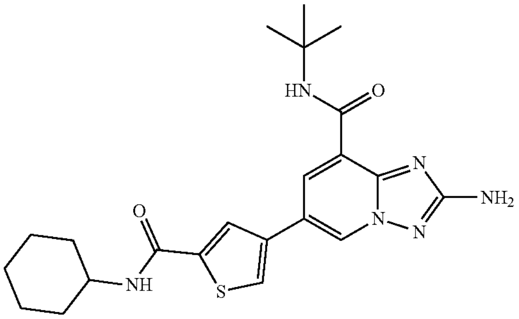 [SMILES: CC(C)(C)NC(=O)c1cc(-c2csc(C(=O)NC3CCCCC3)c2)cn2nc(N)nc12] |
| 15 | 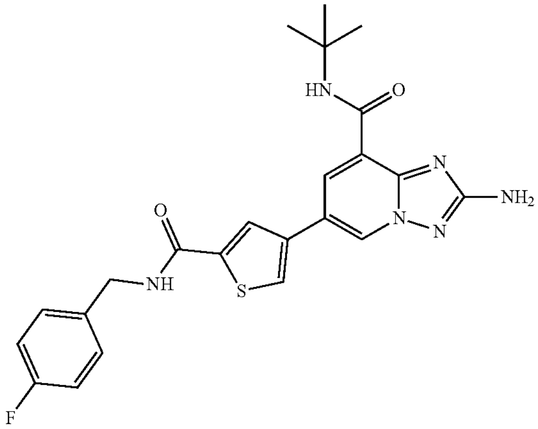 [SMILES: CC(C)(C)NC(=O)c1cc(-c2csc(C(=O)NCc3ccc(F)cc3)c2)cn2nc(N)nc12] |

TABLE 1A-continued
| Compound Number | Structure |
| --- | --- |
| 16 | 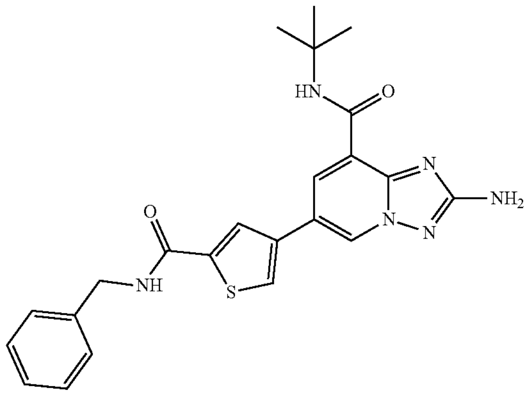 [SMILES: CC(C)(C)NC(=O)c1cc(-c2csc(C(=O)NCc3ccccc3)c2)cn2nc(N)nc12] |
| 17 | 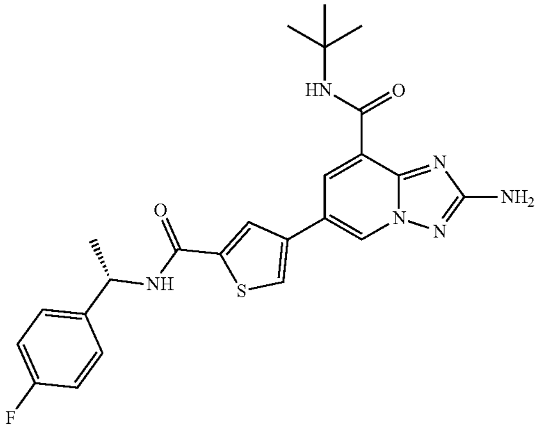 [SMILES: C[C@H](NC(=O)c1cc(-c2cc(C(=O)NC(C)(C)C)c3nc(N)nn3c2)cs1)c1ccc(F)cc1] |
| 18 | 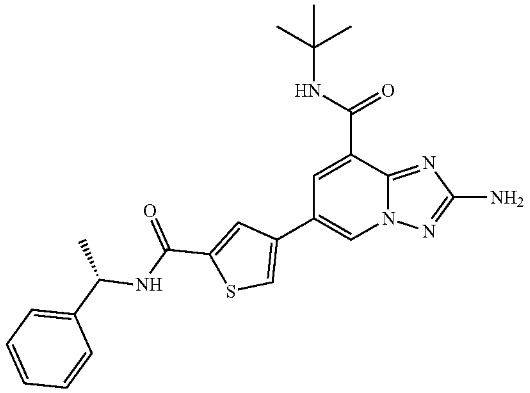 [SMILES: C[C@H](NC(=O)c1cc(-c2cc(C(=O)NC(C)(C)C)c3nc(N)nn3c2)cs1)c1ccccc1] |

TABLE 1A-continued
| Compound Number | Structure |
| --- | --- |
| 19 | 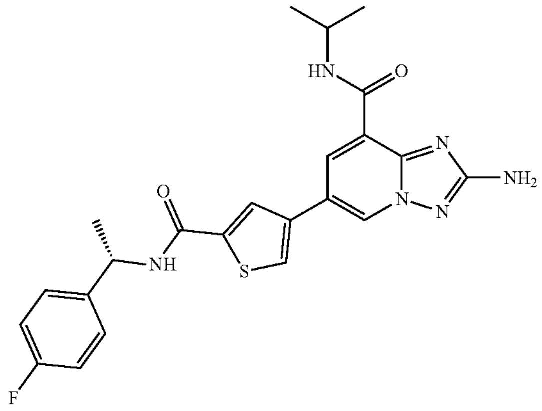 [SMILES: CC(C)NC(=O)c1cc(-c2csc(C(=O)N[C@@H](C)c3ccc(F)cc3)c2)cn2nc(N)nc12] |
| 20 | 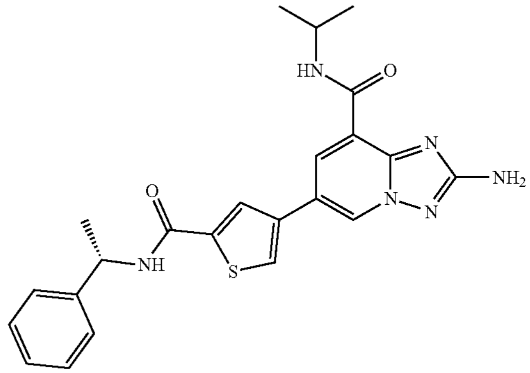 [SMILES: CC(C)NC(=O)c1cc(-c2csc(C(=O)N[C@@H](C)c3ccccc3)c2)cn2nc(N)nc12] |
| 21 | 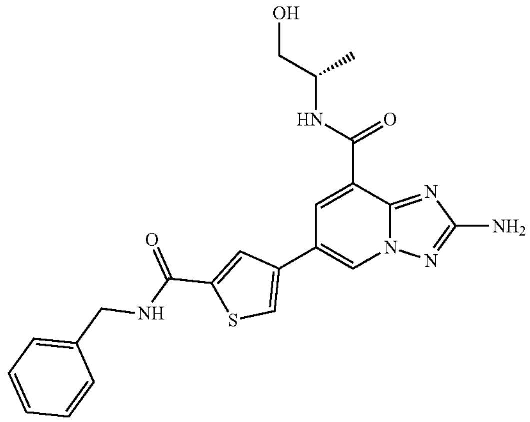 [SMILES: C[C@@H](CO)NC(=O)c1cc(-c2csc(C(=O)NCc3ccccc3)c2)cn2nc(N)nc12] |

TABLE 1A-continued
| Compound Number | Structure |
| --- | --- |
| 22 | 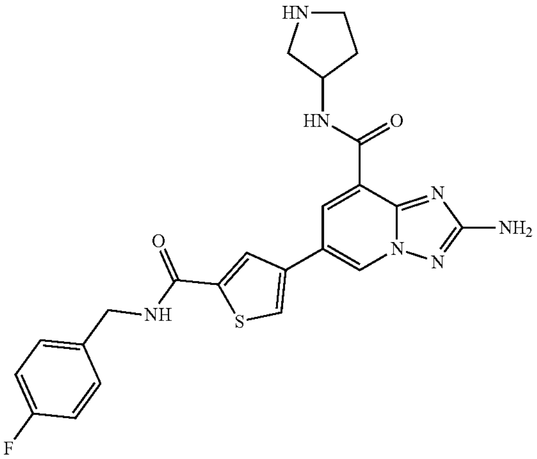 |
| 23 | 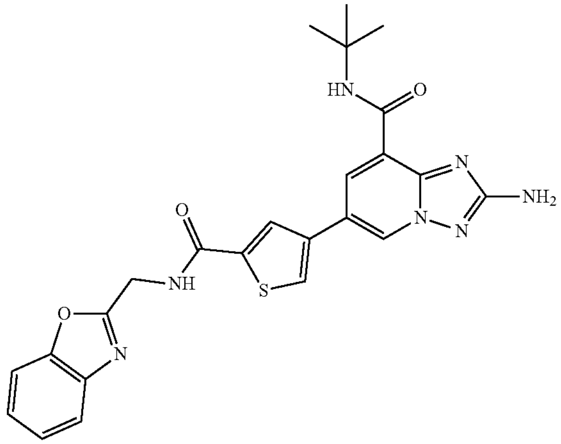 [SMILES: CC(C)(C)NC(=O)c1cc(-c2csc(C(=O)NCc3nc4ccccc4o3)c2)cn2nc(N)nc12] |
| 24 | 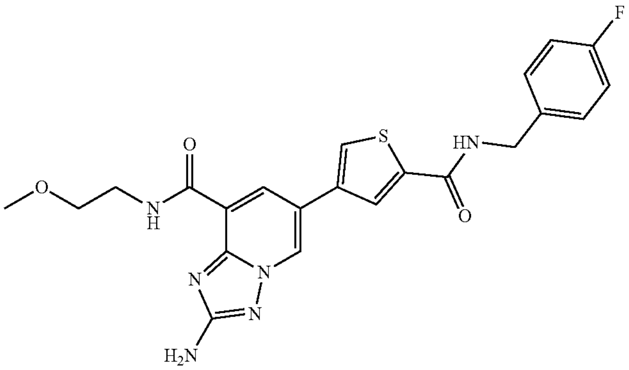 [SMILES: COCCNC(=O)c1cc(-c2csc(C(=O)NCc3ccc(F)cc3)c2)cn2nc(N)nc12] |

TABLE 1A-continued
| Compound Number | Structure |
| --- | --- |
| 25 | 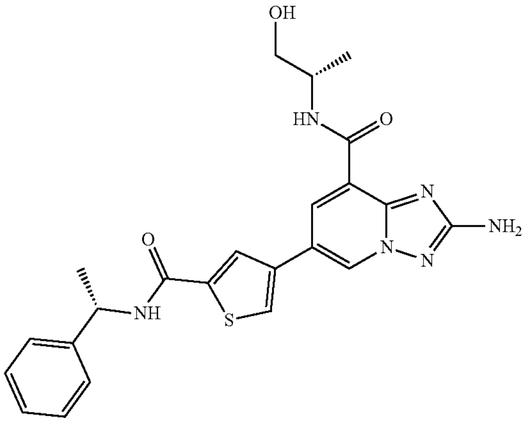 [SMILES: C[C@H](NC(=O)c1cc(-c2cc(C(=O)N[C@@H](C)CO)c3nc(N)nn3c2)cs1)c1ccccc1] |
| 26 | 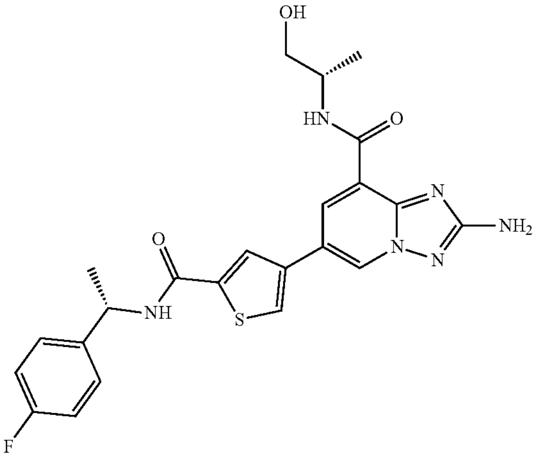 [SMILES: C[C@H](NC(=O)c1cc(-c2cc(C(=O)N[C@@H](C)CO)c3nc(N)nn3c2)cs1)c1ccc(F)cc1] |
| 27 | 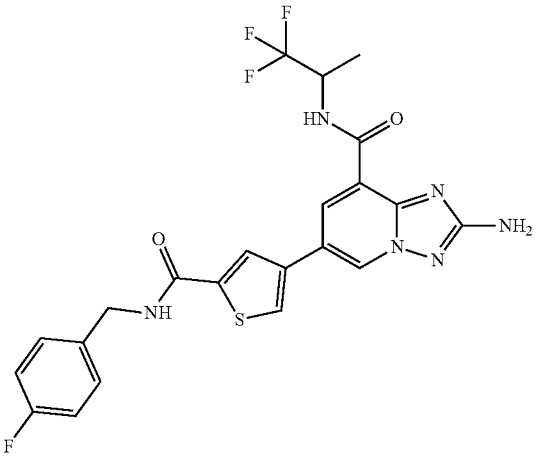 [SMILES: CC(NC(=O)c1cc(-c2csc(C(=O)NCc3ccc(F)cc3)c2)cn2nc(N)nc12)C(F)(F)F] |

TABLE 1A-continued
| Compound Number | Structure |
|---|---|
| 28 | 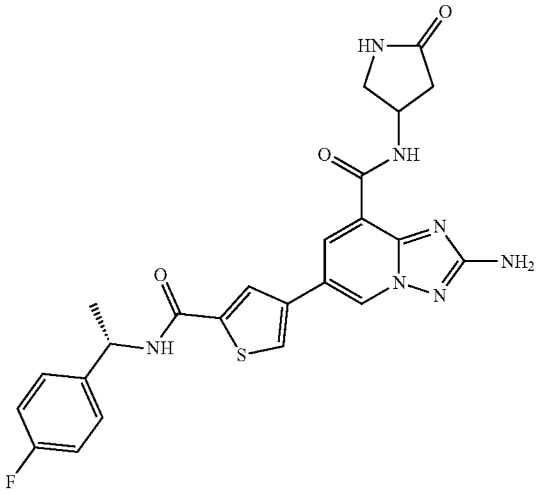 mixture of diastereomers |
| 29 | 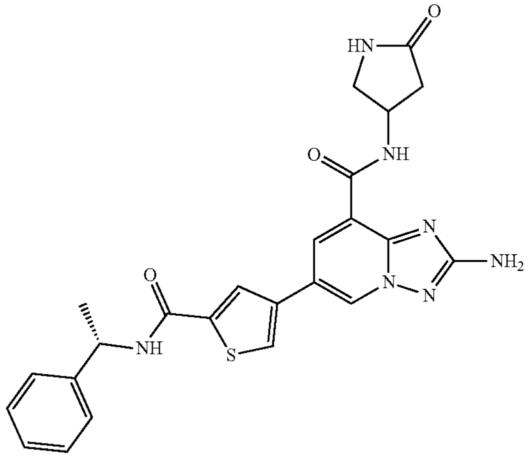 mixture of diastereomers |
| 30 | 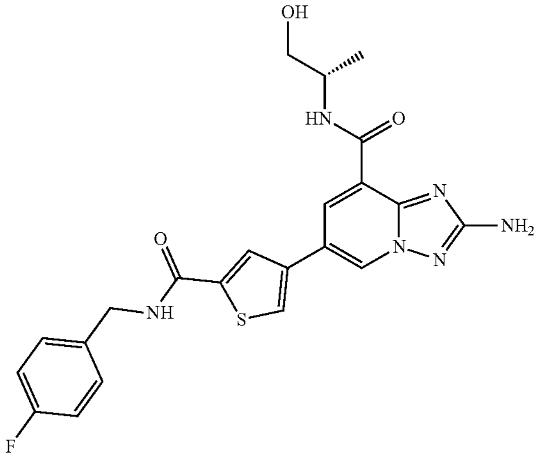 [SMILES: C[C@@H](CO)NC(=O)c1cc(-c2csc(C(=O)NCc3ccc(F)cc3)c2)cn2nc(N)nc12] |

TABLE 1A-continued
| Compound Number | Structure |
|---|---|
| 31 | 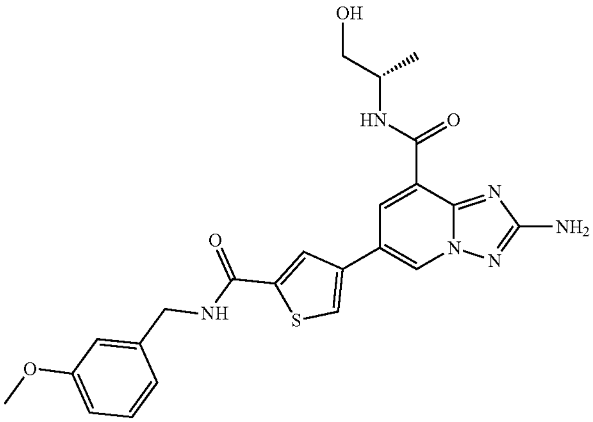 [SMILES: COc1cccc(CNC(=O)c2cc(-c3cc(C(=O)N[C@@H](C)CO)c4nc(N)nn4c3)cs2)c1] |
| 32 | 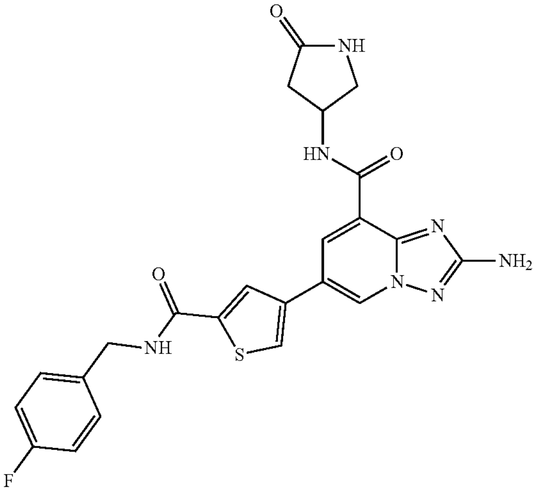 [SMILES: Nc1nc2c(C(=O)NC3CNC(=O)C3)cc(-c3csc(C(=O)NCc4ccc(F)cc4)c3)cn2n1] |
| 33 | 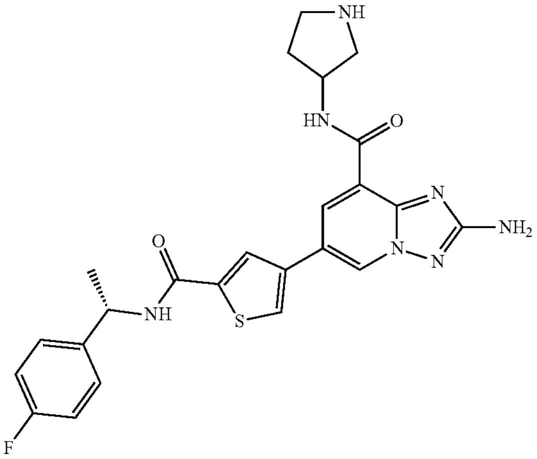 mixture of diastereomers |

TABLE 1A-continued
| Compound Number | Structure |
|---|---|
| 34 | 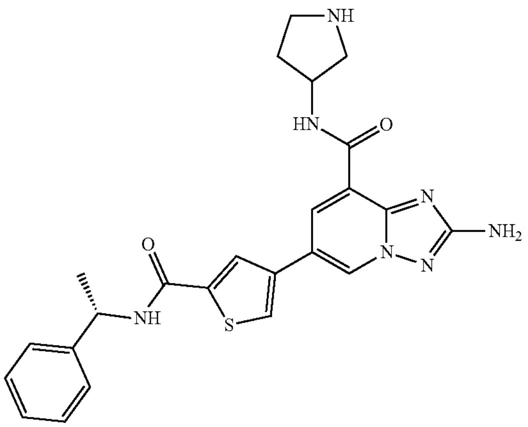 mixture of diastereomers |
| 35 | 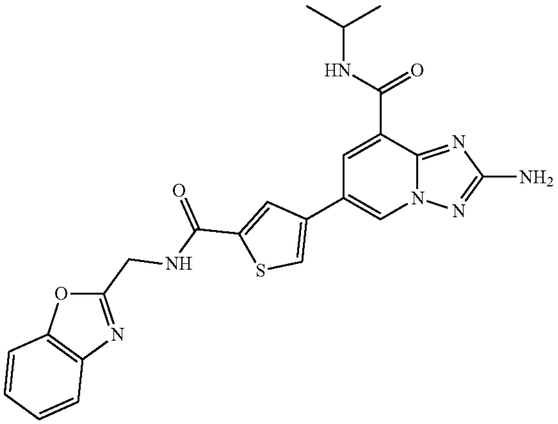 [SMILES: CC(C)NC(=O)c1cc(-c2csc(C(=O)NCc3nc4ccccc4o3)c2)cn2nc(N)nc12] |
| 36 | 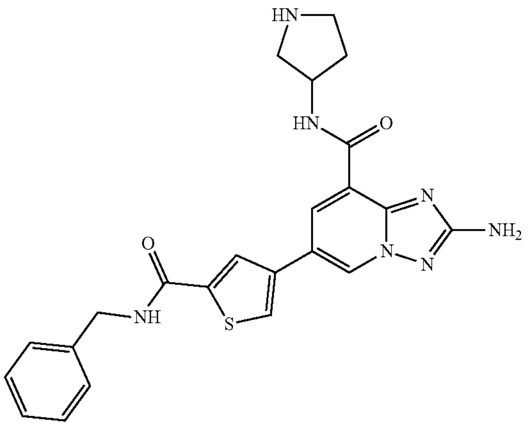 [SMILES: Nc1nc2c(C(=O)NC3CCNC3)cc(-c3csc(C(=O)NCc4ccccc4)c3)cn2n1] |

TABLE 1A-continued
| Compound Number | Structure |
|---|---|
| 37 | 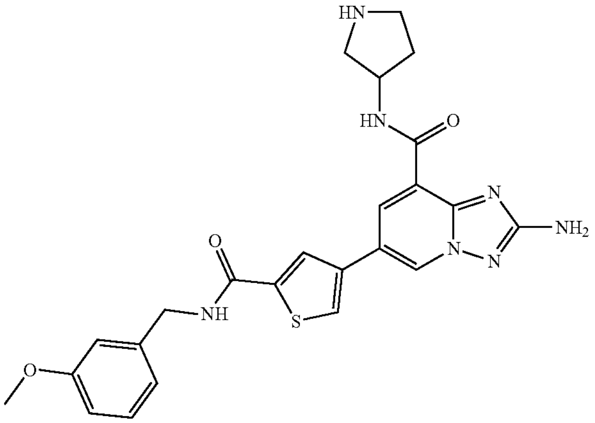 [SMILES: COc1cccc(CNC(=O)c2cc(-c3cc(C(=O)NC4CCNC4)c4nc(N)nn4c3)cs2)c1] |
| 38 | 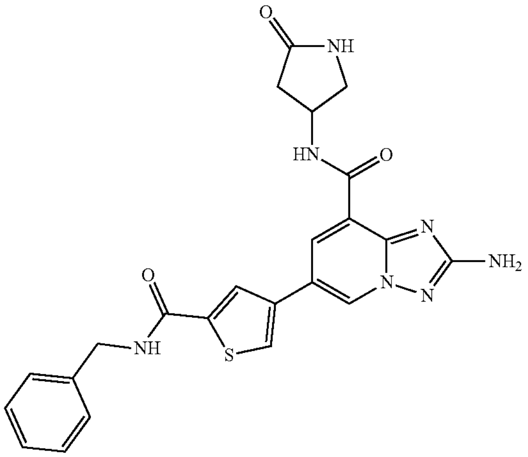 [SMILES: Nc1nc2c(C(=O)NC3CNC(=O)C3)cc(-c3csc(C(=O)NCc4ccccc4)c3)cn2n1] |
| 39 | 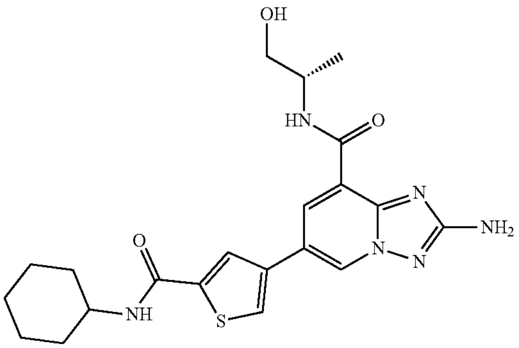 [SMILES: C[C@@H](CO)NC(=O)c1cc(-c2csc(C(=O)NC3CCCCC3)c2)cn2nc(N)nc12] |

TABLE 1A-continued
| Compound Number | Structure |
|---|---|
| 40 | 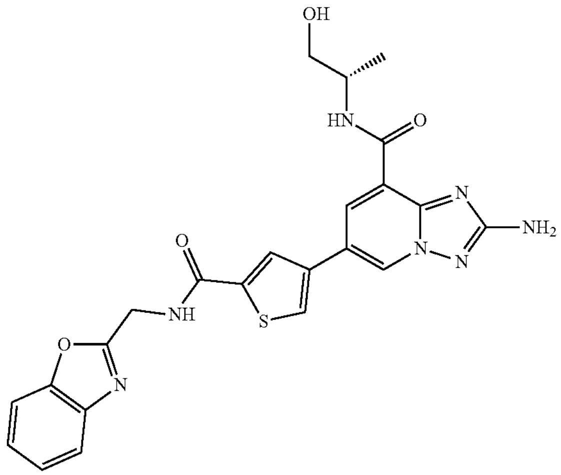 [SMILES: C[C@@H](CO)NC(=O)c1cc(-c2csc(C(=O)NCc3nc4ccccc4o3)c2)cn2nc(N)nc12] |
| 41 | 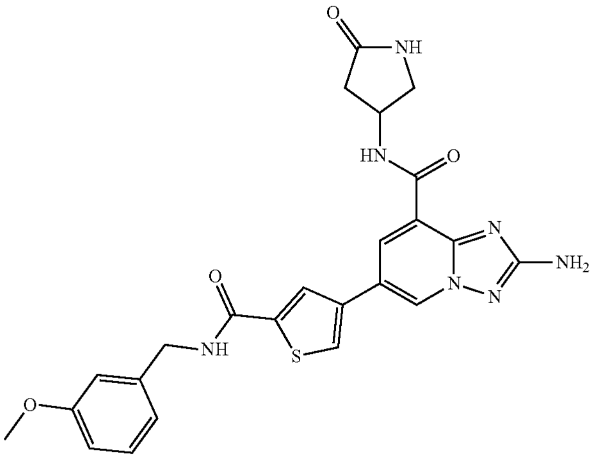 [SMILES: COc1cccc(CNC(=O)c2cc(-c3cc(C(=O)NC4CNC(=O)C4)c4nc(N)nn4c3)cs2)c1] |
| 42 | 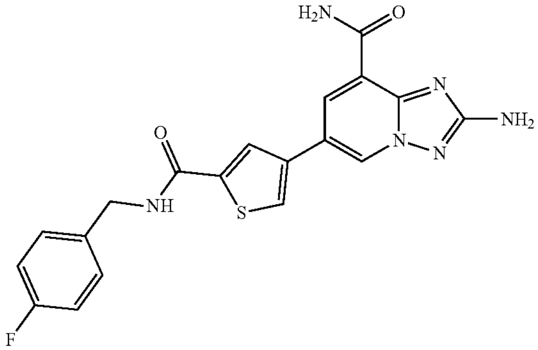 [SMILES: NC(=O)c1cc(-c2csc(C(=O)NCc3ccc(F)cc3)c2)cn2nc(N)nc12] |

TABLE 1A-continued
| Compound Number | Structure |
|---|---|
| 43 | 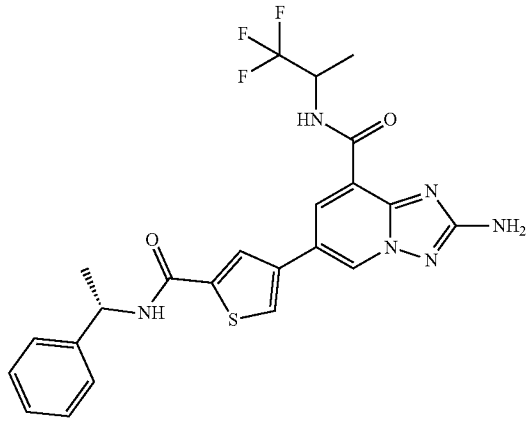 mixture of diastereomers |
| 44 | 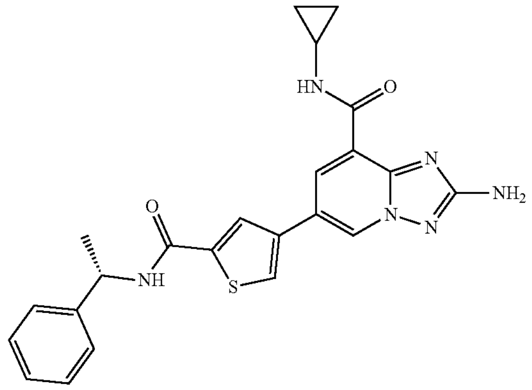 [SMILES: C[C@H](NC(=O)c1cc(-c2cc(C(=O)NC3CC3)c3nc(N)nn3c2)cs1)c1ccccc1] |
| 45 | 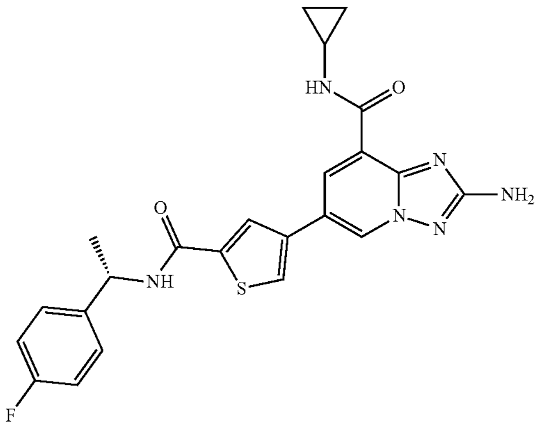 [SMILES: C[C@H](NC(=O)c1cc(-c2cc(C(=O)NC3CC3)c3nc(N)nn3c2)cs1)c1ccc(F)cc1] |

TABLE 1A-continued
| Compound Number | Structure |
|---|---|
| 46 | 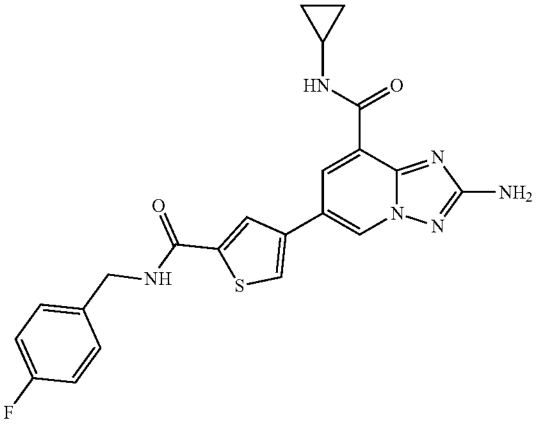 [SMILES: Nc1nc2c(C(=O)NC3CC3)cc(-c3csc(C(=O)NCc4ccc(F)cc4)c3)cn2n1] |
| 47 | 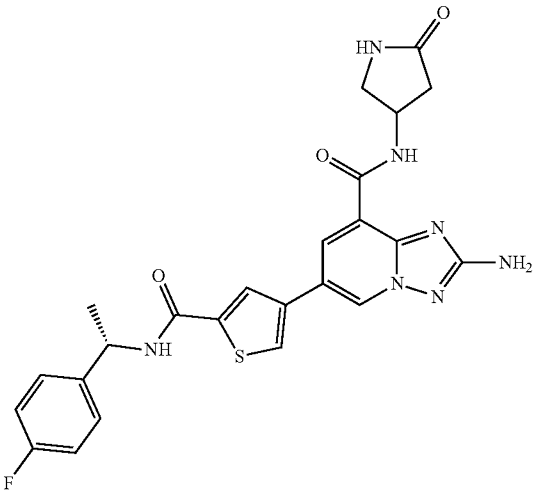 stereoisomer 1 |
| 48 | 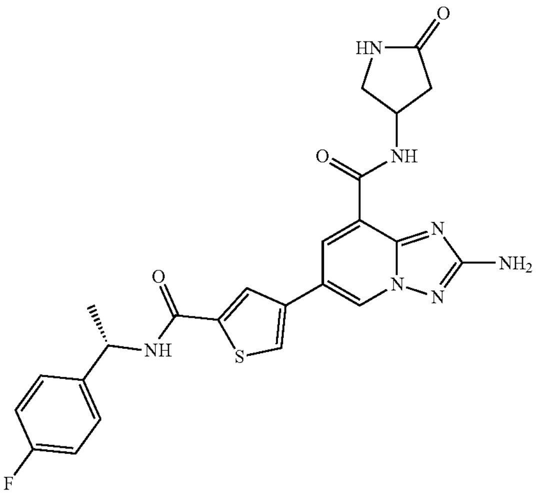 stereoisomer 2 |

TABLE 1A-continued
| Compound Number | Structure |
|---|---|
| 49 | 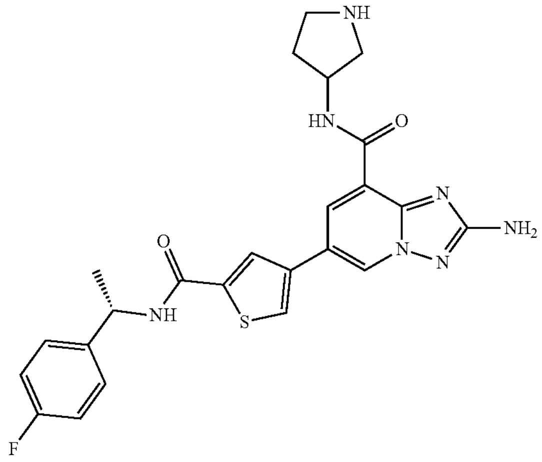 stereoisomer 1 |
| 50 | 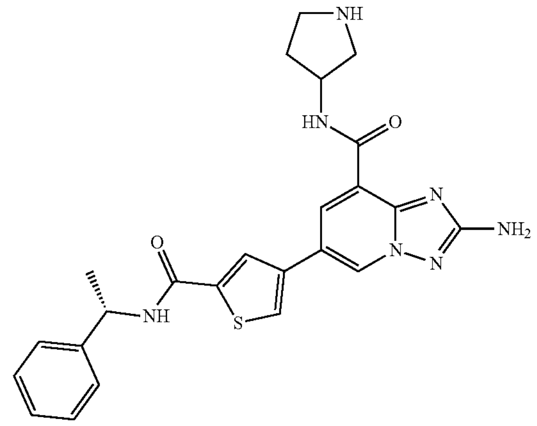 stereoisomer 1 |
| 51 | 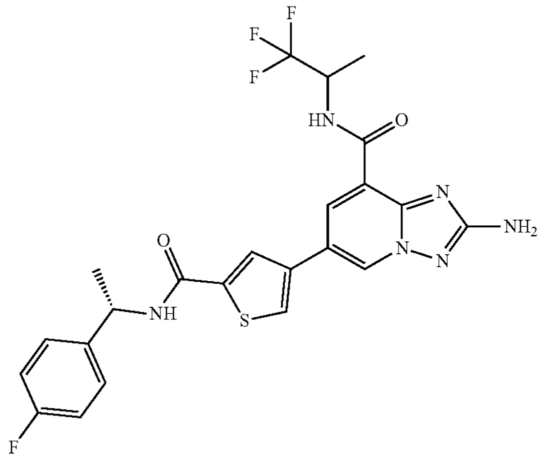 mixture of diastereomers |

TABLE 1A-continued
| Compound Number | Structure |
|---|---|
| 52 | 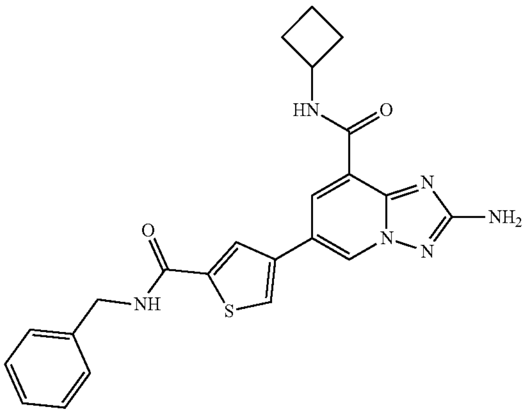 [SMILES: Nc1nc2c(C(=O)NC3CCC3)cc(-c3csc(C(=O)NCc4ccccc4)c3)cn2n1] |
| 53 | 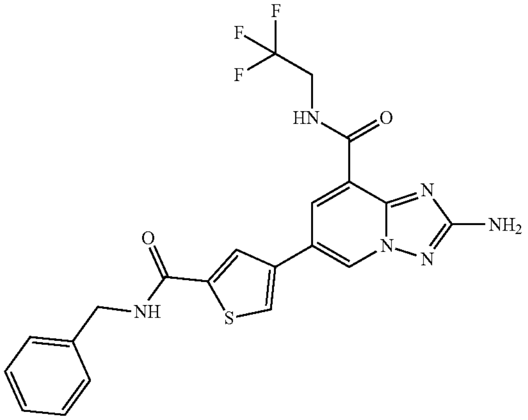 [SMILES: Nc1nc2c(C(=O)NCC(F)(F)F)cc(-c3csc(C(=O)NCc4ccccc4)c3)cn2n1] |
| 54 | 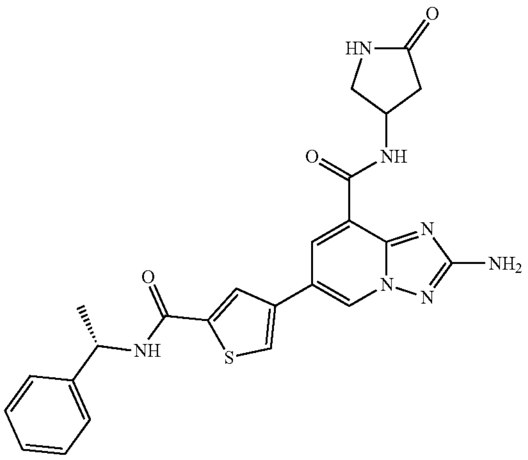 stereoisomer 1 |

TABLE 1A-continued
| Compound Number | Structure |
|---|---|
| 55 | 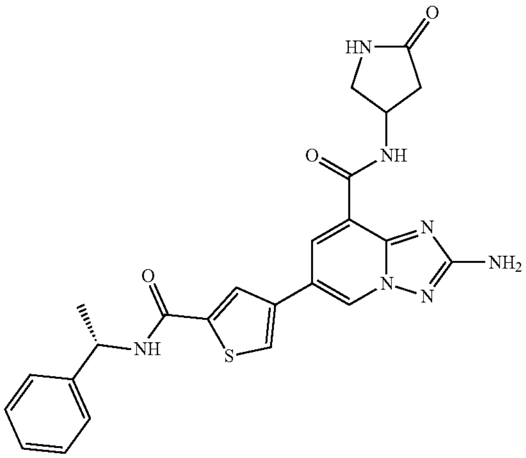 stereoisomer 2 |
| 56 | 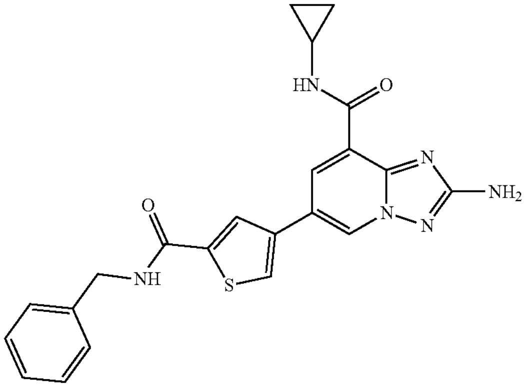 [SMILES: Nc1nc2c(C(=O)NC3CC3)cc(-c3csc(C(=O)NCc4ccccc4)c3)cn2n1] |
| 57 | 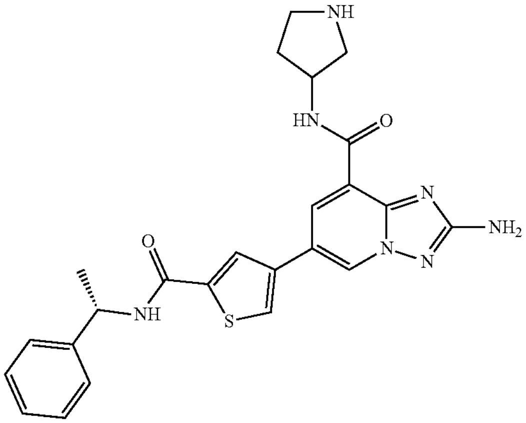 stereoisomer 2 |

TABLE 1A-continued
| Compound Number | Structure |
|---|---|
| 58 | 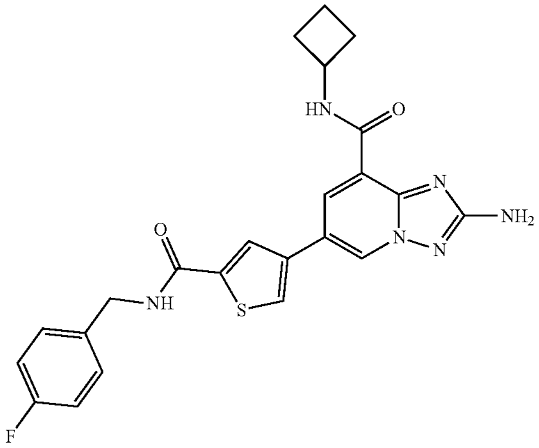 |
| 59 | 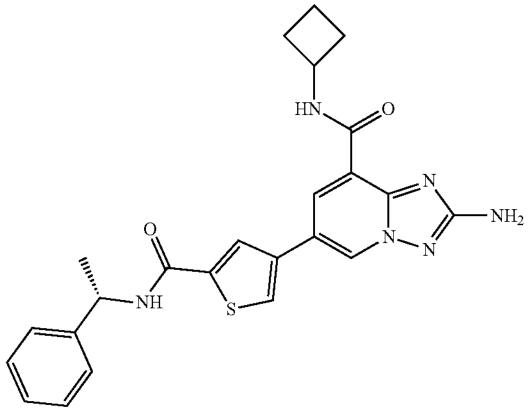 [SMILES: C[C@H](NC(=O)c1cc(-c2cc(C(=O)NC3CCC3)c3nc(N)nn3c2)cs1)c1ccccc1] |
| 60 | 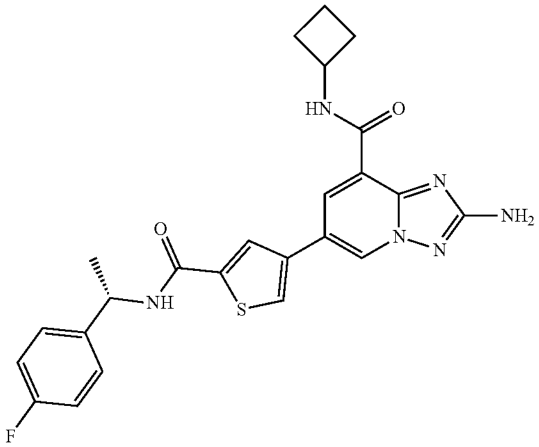 [SMILES: C[C@H](NC(=O)c1cc(-c2cc(C(=O)NC3CCC3)c3nc(N)nn3c2)cs1)c1ccc(F)cc1] |

TABLE 1A-continued
| Compound Number | Structure |
|---|---|
| 61 | 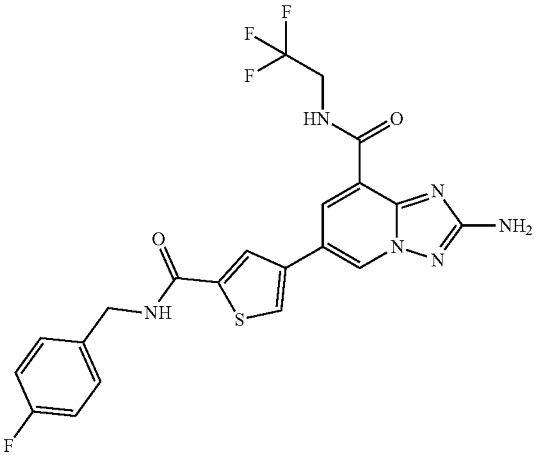 [SMILES: Nc1nc2c(C(=O)NCC(F)(F)F)cc(-c3csc(C(=O)NCc4ccc(F)cc4)c3)cn2n1] |
| 62 | 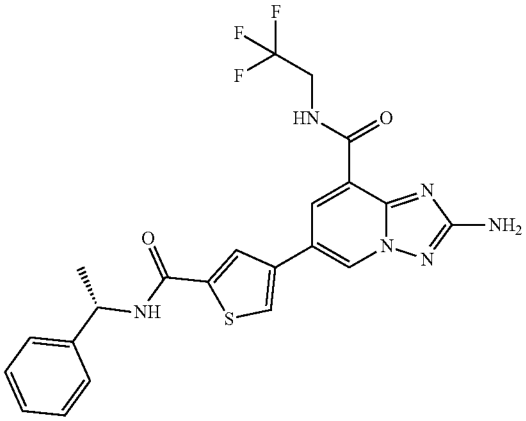 [SMILES: C[C@H](NC(=O)c1cc(-c2cc(C(=O)NCC(F)(F)F)c3nc(N)nn3c2)cs1)c1ccccc1] |
| 63 | 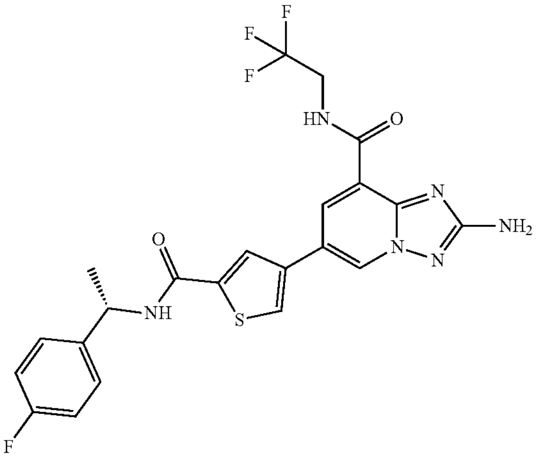 [SMILES: C[C@H](NC(=O)c1cc(-c2cc(C(=O)NCC(F)(F)F)c3nc(N)nn3c2)cs1)c1ccc(F)cc1] |

TABLE 1A-continued
| Compound Number | Structure |
|---|---|
| 64 | 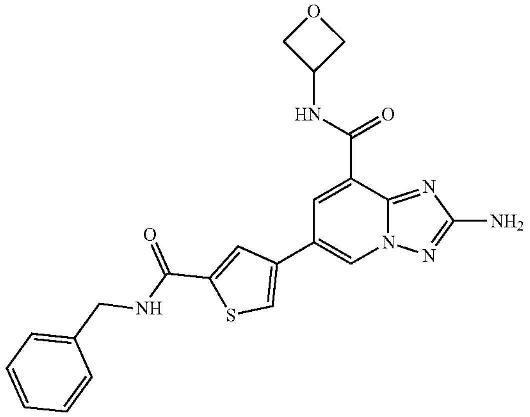 [SMILES: Nc1nc2c(C(=O)NC3COC3)cc(-c3csc(C(=O)NCc4ccccc4)c3)cn2n1] |
| 65 | 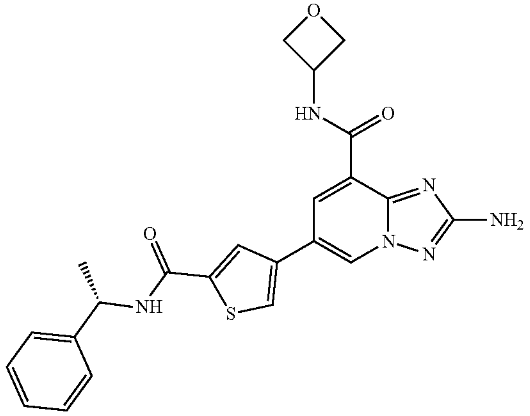 [SMILES: C[C@H](NC(=O)c1cc(-c2cc(C(=O)NC3COC3)c3nc(N)nn3c2)cs1)c1ccccc1] |
| 66 | 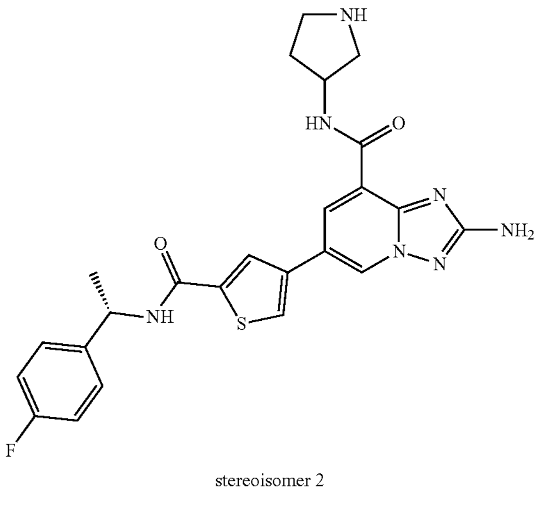 [SMILES: C[C@H](NC(=O)c1cc(-c2cc(C(=O)NC3CCNC3)c3nc(N)nn3c2)cs1)c1ccc(F)cc1] stereoisomer 2 |

TABLE 1A-continued
| Compound Number | Structure |
|---|---|
| 67 | 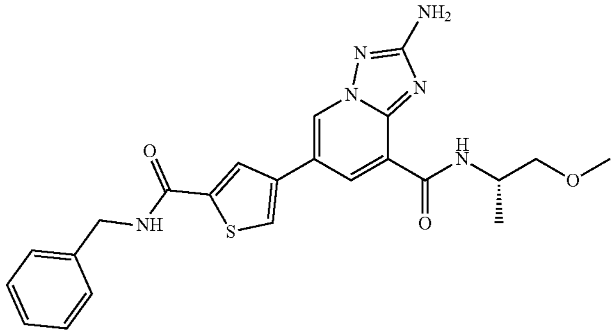 [SMILES: COC[C@H](C)NC(=O)c1cc(-c2csc(C(=O)NCc3ccccc3)c2)cn2nc(N)nc12] |
| 68 | 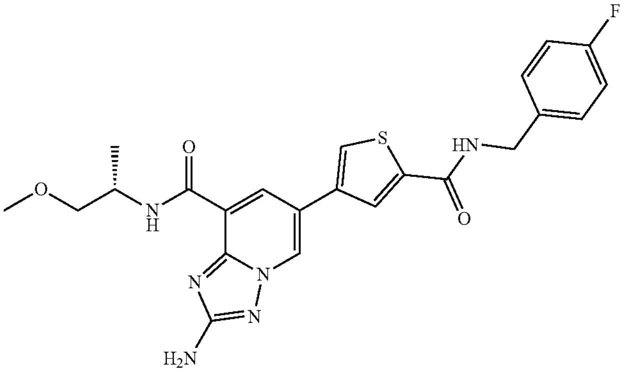 [SMILES: COC[C@H](C)NC(=O)c1cc(-c2csc(C(=O)NCc3ccc(F)cc3)c2)cn2nc(N)nc12] |
| 69 | 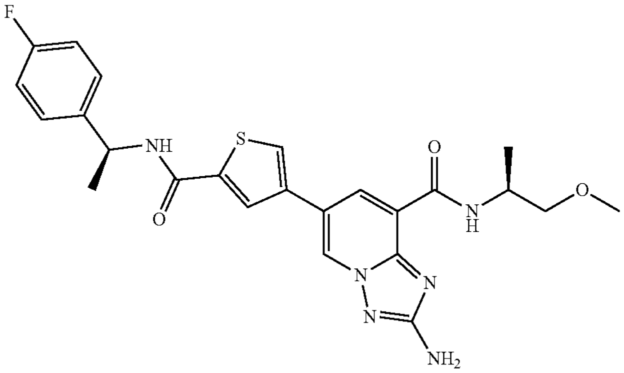 [SMILES: COC[C@H](C)NC(=O)c1cc(-c2csc(C(=O)N[C@@H](C)c3ccc(F)cc3)c2)cn2nc(N)nc12] |
| 70 | 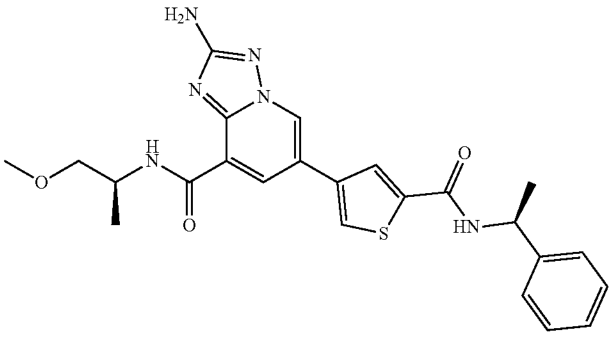 [SMILES: COC[C@H](C)NC(=O)c1cc(-c2csc(C(=O)N[C@@H](C)c3ccccc3)c2)cn2nc(N)nc12] |

TABLE 1A-continued
| Compound Number | Structure |
|---|---|
| 71 | 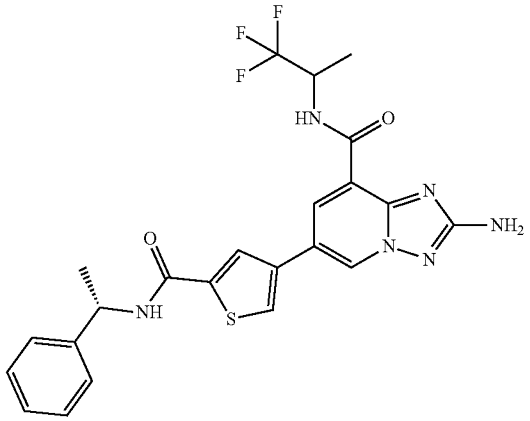 stereoisomer 1 |
| 72 | 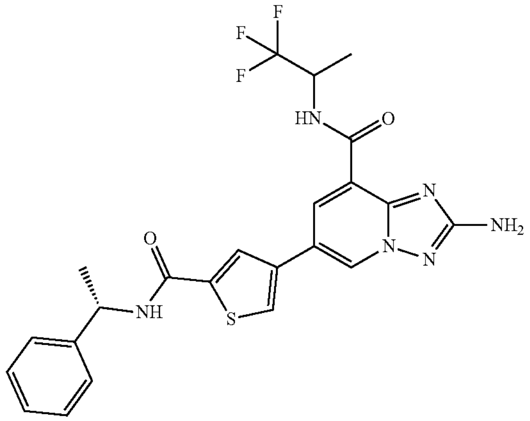 stereoisomer 2 |
| 73 | 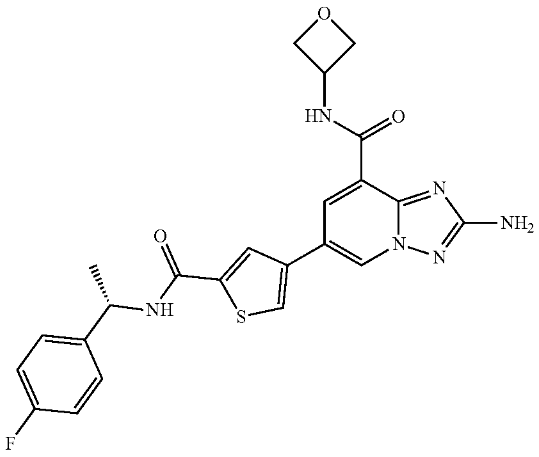 [SMILES: C[C@H](NC(=O)c1cc(-c2cc(C(=O)NC3COC3)c3nc(N)nn3c2)cs1)c1ccc(F)cc1] |

TABLE 1A-continued
| Compound Number | Structure |
|---|---|
| 74 | 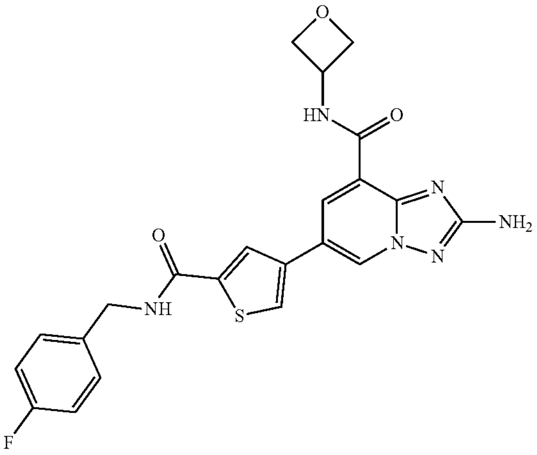 [SMILES: Nc1nc2c(C(=O)NC3COC3)cc(-c3csc(C(=O)NCc4ccc(F)cc4)c3)cn2n1] |
| 75 | 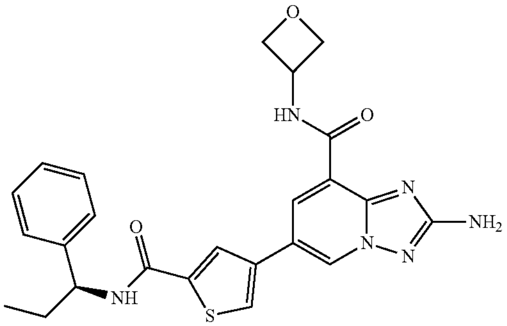 [SMILES: CC[C@H](NC(=O)c1cc(-c2cc(C(=O)NC3COC3)c3nc(N)nn3c2)cs1)c1ccccc1] |
| 76 | 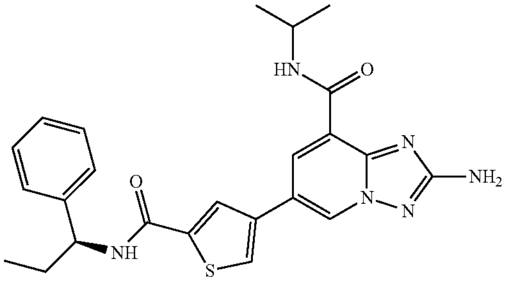 [SMILES: CC[C@H](NC(=O)c1cc(-c2cc(C(=O)NC(C)C)c3nc(N)nn3c2)cs1)c1ccccc1] |
| 77 | 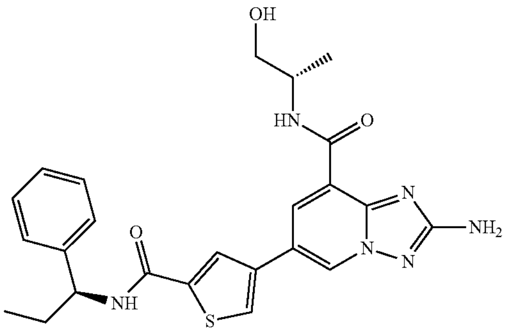 [SMILES: CC[C@H](NC(=O)c1cc(-c2cc(C(=O)N[C@@H](C)CO)c3nc(N)nn3c2)cs1)c1ccccc1] |

TABLE 1A-continued
| Compound Number | Structure |
| --- | --- |
| 78 | 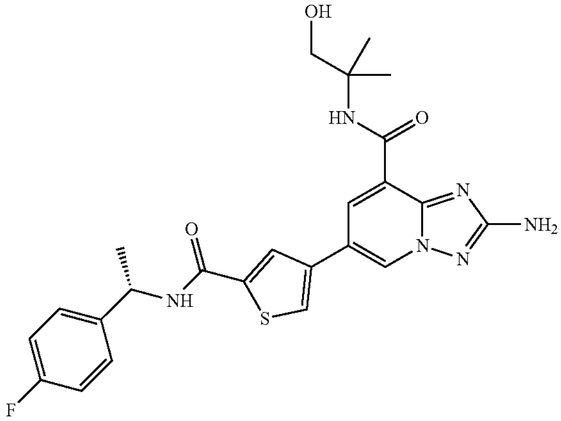 [SMILES: C[C@H](NC(=O)c1cc(-c2cc(C(=O)NC(C)(C)CO)c3nc(N)nn3c2)cs1)c1ccc(F)cc1] |
| 79 | 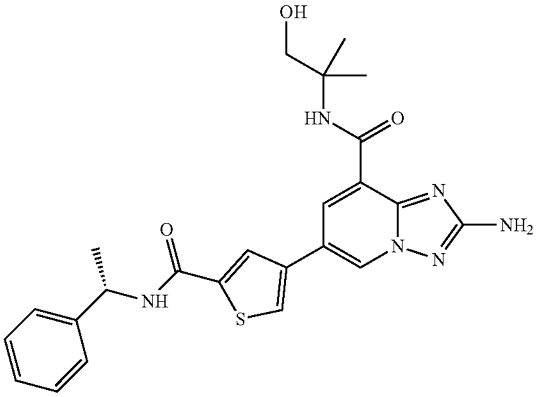 [SMILES: C[C@H](NC(=O)c1cc(-c2cc(C(=O)NC(C)(C)CO)c3nc(N)nn3c2)cs1)c1ccccc1] |
| 80 | 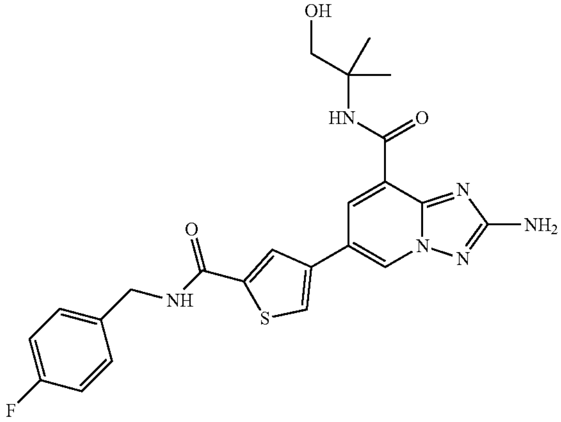 [SMILES: CC(C)(CO)NC(=O)c1cc(-c2csc(C(=O)NCc3ccc(F)cc3)c2)cn2nc(N)nc12] |
| 81 | 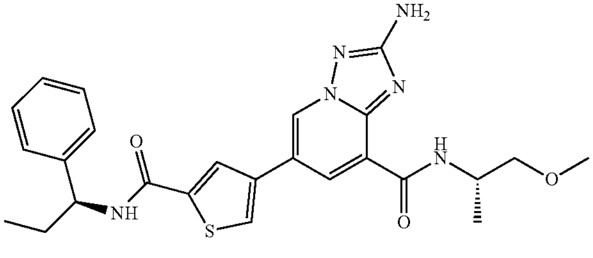 [SMILES: CC[C@H](NC(=O)c1cc(-c2cc(C(=O)N[C@@H](C)COC)c3nc(N)nn3c2)cs1)c1ccccc1] |

TABLE 1A-continued
| Compound Number | Structure |
|---|---|
| 82 | 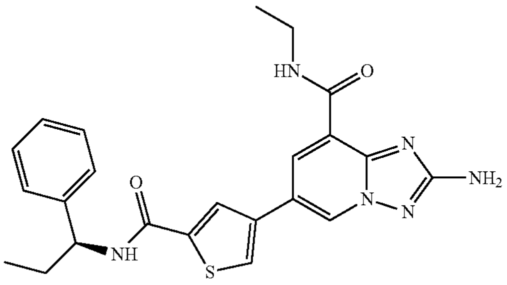 [SMILES: CCNC(=O)c1cc(-c2csc(C(=O)N[C@@H](CC)c3ccccc3)c2)cn2nc(N)nc12] |
| 83 | 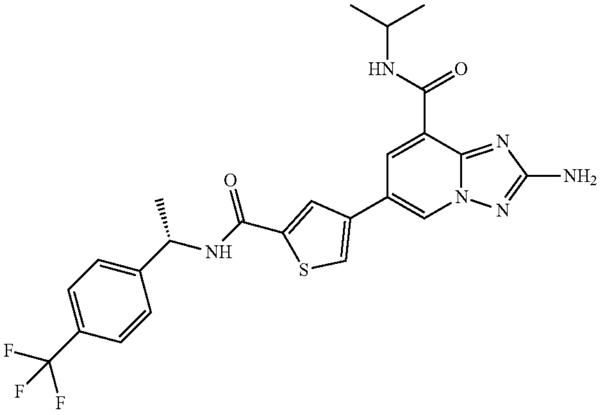 [SMILES: CC(C)NC(=O)c1cc(-c2csc(C(=O)N[C@@H](C)c3ccc(C(F)(F)F)cc3)c2)cn2nc(N)nc12] |
| 84 | 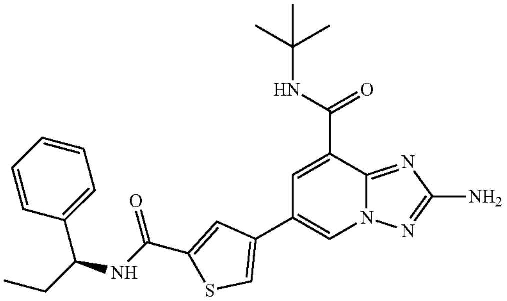 [SMILES: CC[C@H](NC(=O)c1cc(-c2cc(C(=O)NC(C)(C)C)c3nc(N)nn3c2)cs1)c1ccccc1] |
| 85 | 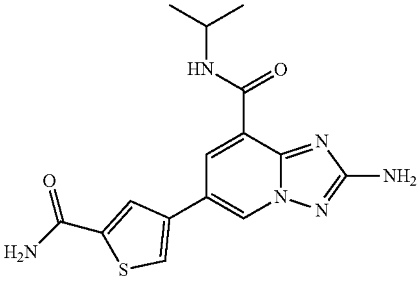 [SMILES: CC(C)NC(=O)c1cc(-c2csc(C(N)=O)c2)cn2nc(N)nc12] |

TABLE 1A-continued
| Compound Number | Structure |
|---|---|
| 86 | 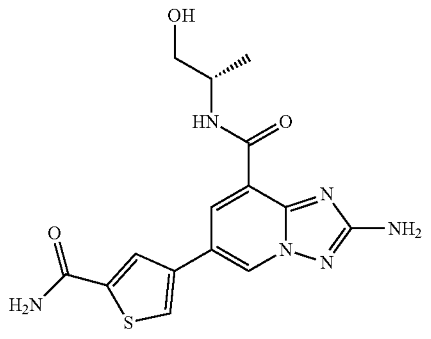 [SMILES: C[C@@H](CO)NC(=O)c1cc(-c2csc(C(N)=O)c2)cn2nc(N)nc12] |
| 87 | 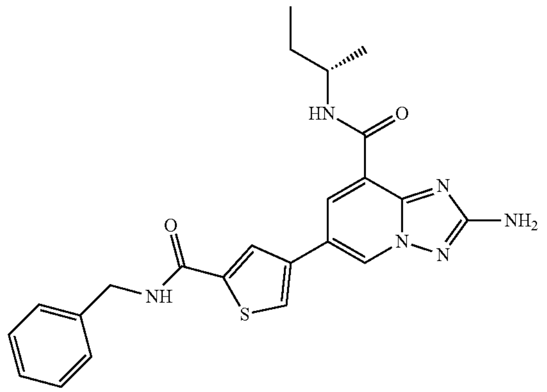 [SMILES: CC[C@H](C)NC(=O)c1cc(-c2csc(C(=O)NCc3ccccc3)c2)cn2nc(N)nc12] |
| 88 | 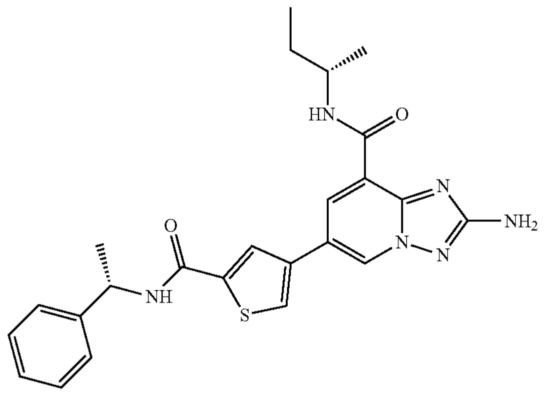 [SMILES: CC[C@H](C)NC(=O)c1cc(-c2csc(C(=O)N[C@@H](C)c3ccccc3)c2)cn2nc(N)nc12] |
| 89 | 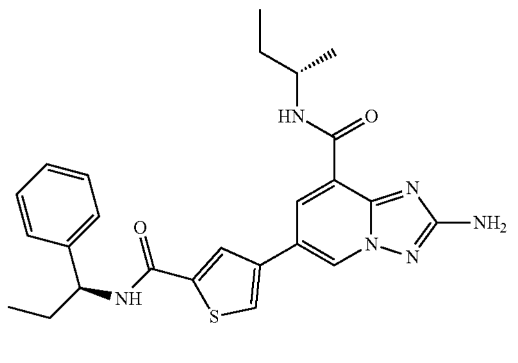 [SMILES: CC[C@H](NC(=O)c1cc(-c2cc(C(=O)N[C@@H](C)CC)c3nc(N)nn3c2)cs1)c1ccccc1] |

TABLE 1A-continued
| Compound Number | Structure |
|---|---|
| 90 | 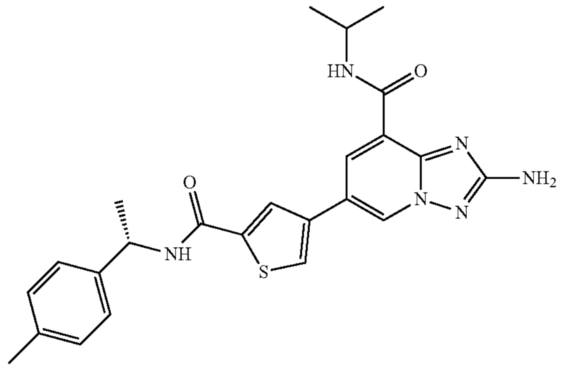 [SMILES: Cc1ccc([C@H](C)NC(=O)c2cc(-c3cc(C(=O)NC(C)C)c4nc(N)nn4c3)cs2)cc1] |
| 91 | 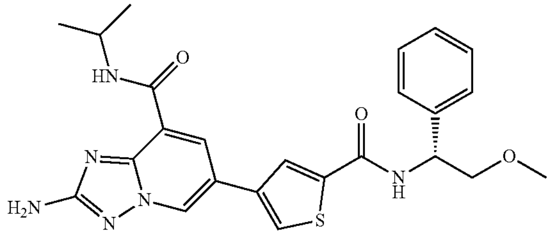 [SMILES: COC[C@H](NC(=O)c1cc(-c2cc(C(=O)NC(C)C)c3nc(N)nn3c2)cs1)c1ccccc1] |
| 92 | 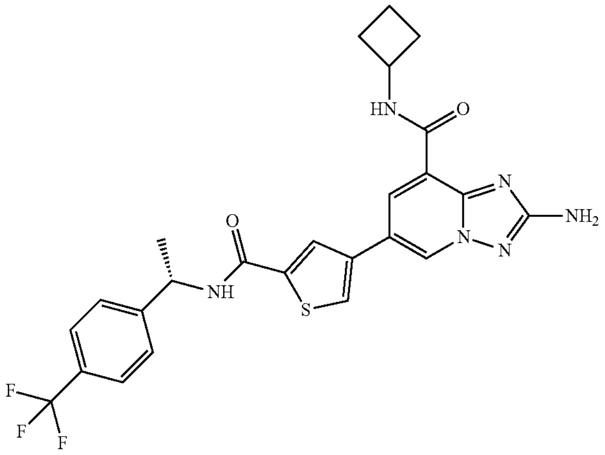 [SMILES: C[C@H](NC(=O)c1cc(-c2cc(C(=O)NC3CCC3)c3nc(N)nn3c2)cs1)c1ccc(C(F)(F)F)cc1] |
| 93 | 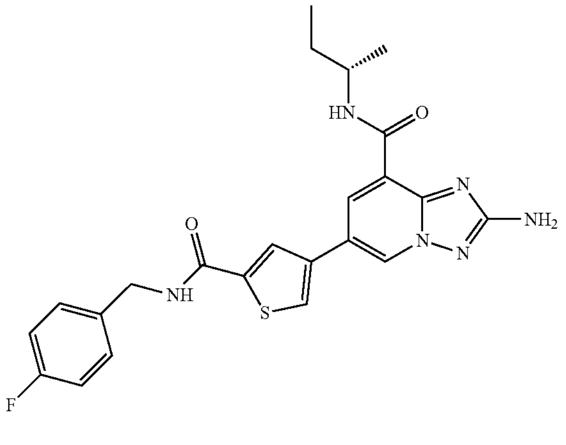 [SMILES: CC[C@H](C)NC(=O)c1cc(-c2csc(C(=O)NCc3ccc(F)cc3)c2)cn2nc(N)nc12] |

TABLE 1A-continued
| Compound Number | Structure |
|---|---|
| 94 | 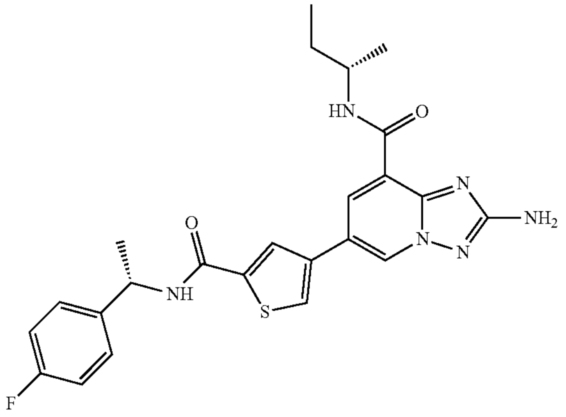 [SMILES: CC[C@H](C)NC(=O)c1cc(-c2csc(C(=O)N[C@@H](C)c3ccc(F)cc3)c2)cn2nc(N)nc12] |
| 95 | 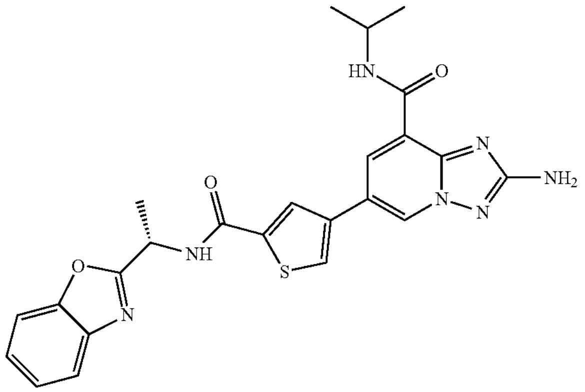 [SMILES: CC(C)NC(=O)c1cc(-c2csc(C(=O)N[C@@H](C)c3nc4ccccc4o3)c2)cn2nc(N)nc12] |
| 96 | 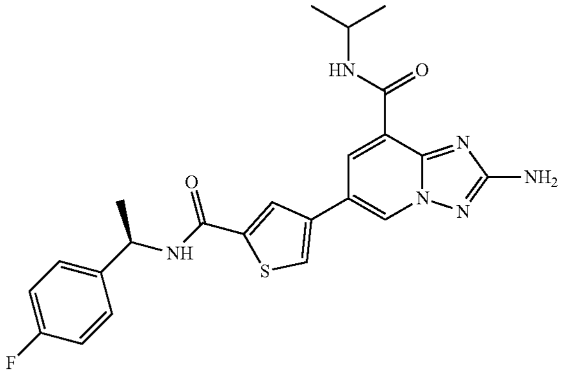 [SMILES: CC(C)NC(=O)c1cc(-c2csc(C(=O)N[C@H](C)c3ccc(F)cc3)c2)cn2nc(N)nc12] |
| 97 | 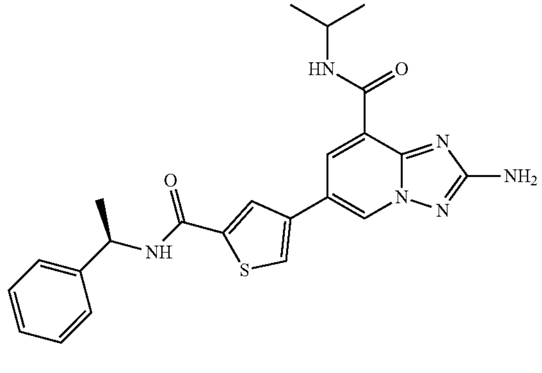 [SMILES: CC(C)NC(=O)c1cc(-c2csc(C(=O)N[C@H](C)c3ccccc3)c2)cn2nc(N)nc12] |

TABLE 1A-continued
| Compound Number | Structure |
|---|---|
| 98 | 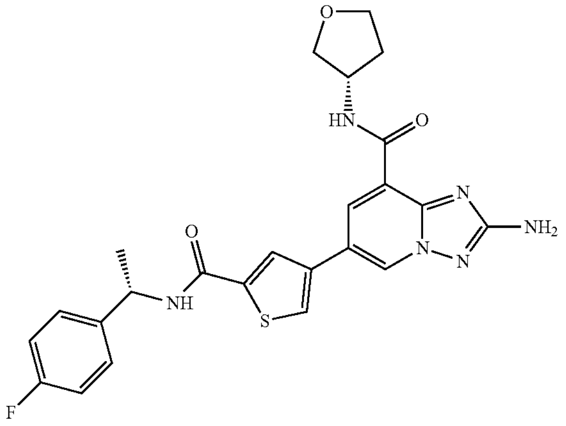 [SMILES: C[C@H](NC(=O)c1cc(-c2cc(C(=O)N[C@H]3CCOC3)c3nc(N)nn3c2)cs1)c1ccc(F)cc1] |
| 99 | 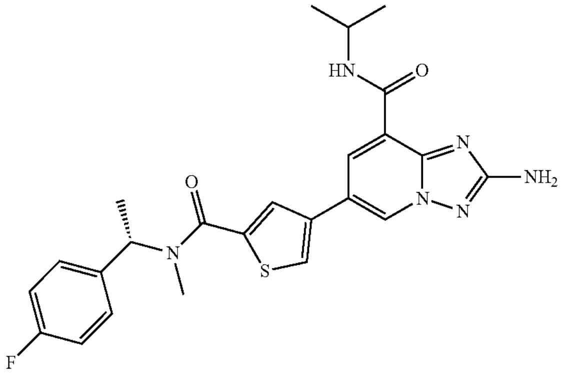 [SMILES: CC(C)NC(=O)c1cc(-c2csc(C(=O)N(C)[C@@H](C)c3ccc(F)cc3)c2)cn2nc(N)nc12] |
| 100 | 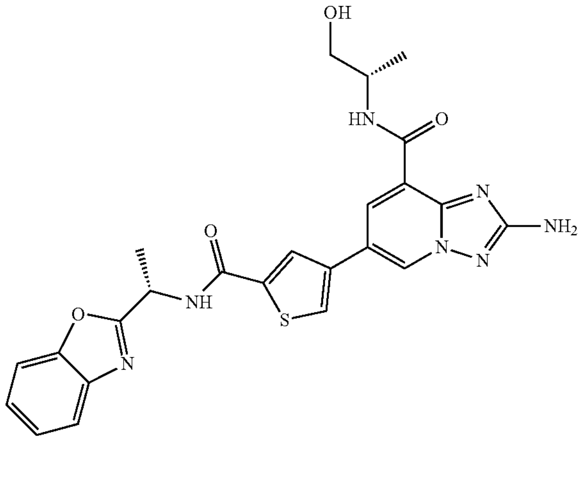 [SMILES: C[C@H](NC(=O)c1cc(-c2cc(C(=O)N[C@@H](C)CO)c3nc(N)nn3c2)cs1)c1nc2ccccc2o1] |

TABLE 1A-continued
| Compound Number | Structure |
| --- | --- |
| 101 | 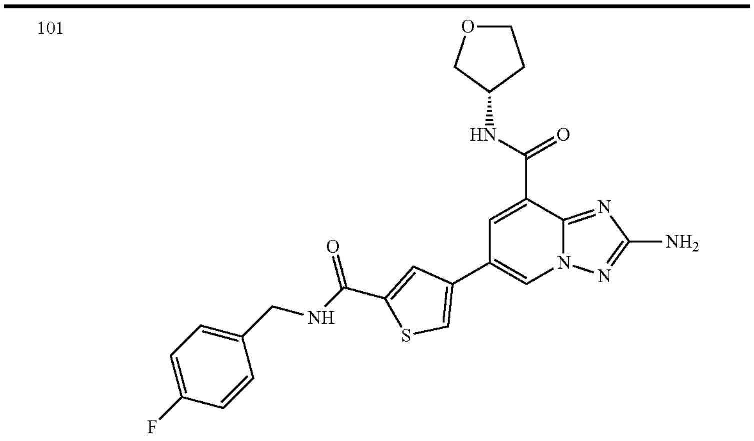 |
| 102 | 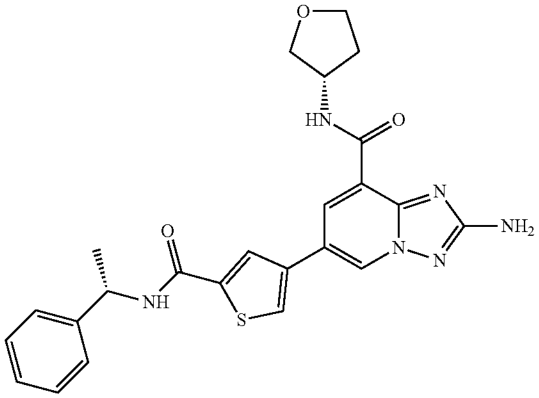 [SMILES: C[C@H](NC(=O)c1cc(-c2cc(C(=O)N[C@H]3CCOC3)c3nc(N)nn3c2)cs1)c1ccccc1] |
| 103 | 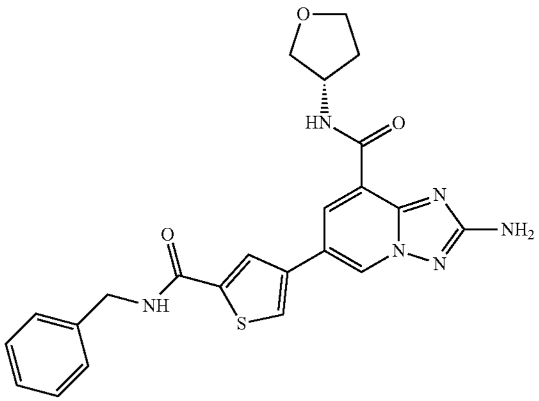 [SMILES: Nc1nc2c(C(=O)N[C@H]3CCOC3)cc(-c3csc(C(=O)NCc4ccccc4)c3)cn2n1] |
| 104 | 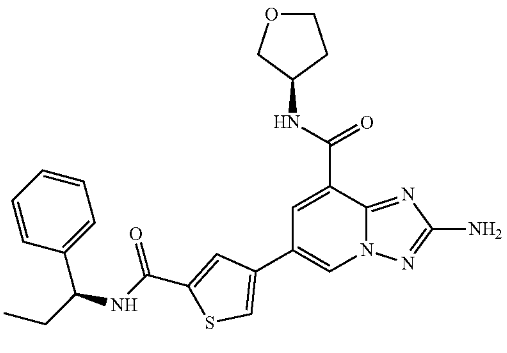 [SMILES: CC[C@H](NC(=O)c1cc(-c2cc(C(=O)N[C@@H]3CCOC3)c3nc(N)nn3c2)cs1)c1ccccc1] |

TABLE 1A-continued
| Compound Number | Structure |
| --- | --- |
| 105 | 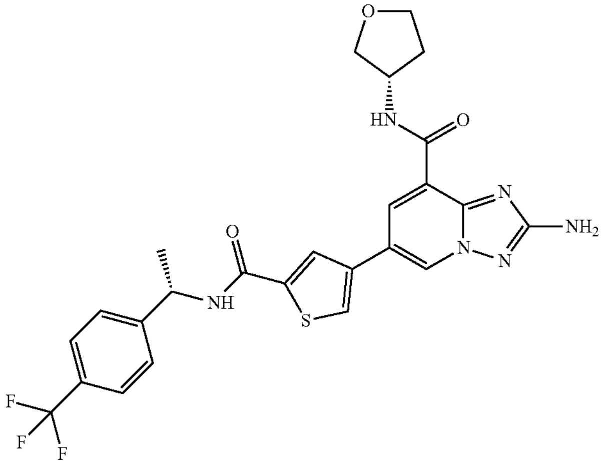 [SMILES: C[C@H](NC(=O)c1cc(-c2cc(C(=O)N[C@H]3CCOC3)c3nc(N)nn3c2)cs1)c1ccc(C(F)(F)F)cc1] |
| 106 | 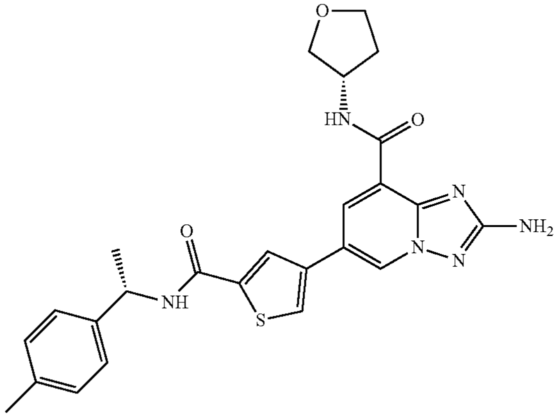 [SMILES: Cc1ccc([C@H](C)NC(=O)c2cc(-c3cc(C(=O)N[C@H]4CCOC4)c4nc(N)nn4c3)cs2)cc1] |
| 107 | 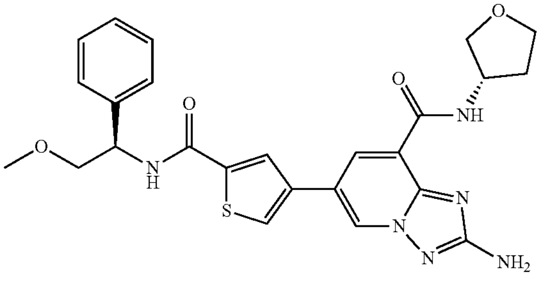 [SMILES: COC[C@H](NC(=O)c1cc(-c2cc(C(=O)N[C@H]3CCOC3)c3nc(N)nn3c2)cs1)c1ccccc1] |
| 108 | 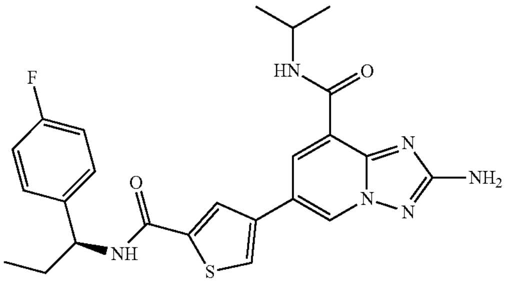 [SMILES: CC[C@H](NC(=O)c1cc(-c2cc(C(=O)NC(C)C)c3nc(N)nn3c2)cs1)c1ccc(F)cc1] |

TABLE 1A-continued
| Compound Number | Structure |
|---|---|
| 109 | 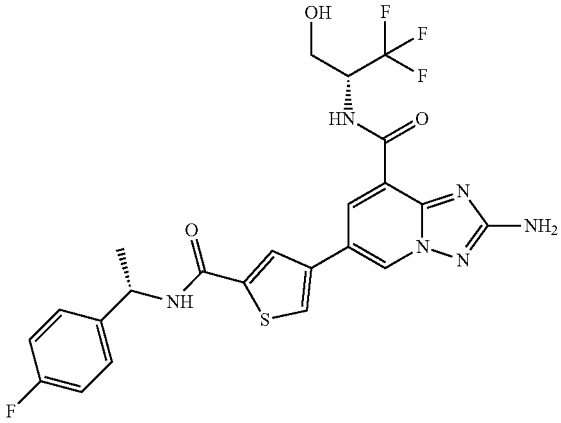 [SMILES: C[C@H](NC(=O)c1cc(-c2cc(C(=O)N[C@H](CO)C(F)(F)F)c3nc(N)nn3c2)cs1)c1ccc(F)cc1] |
| 110 | 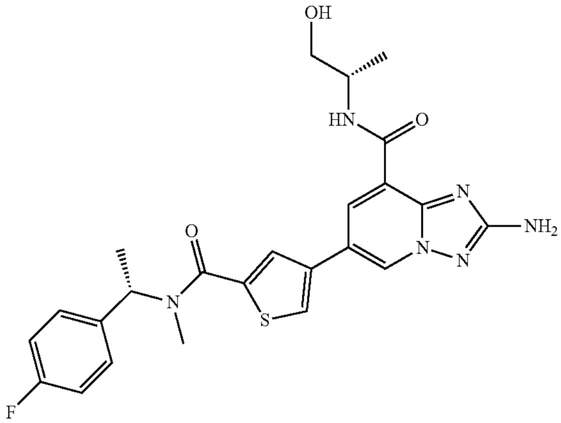 [SMILES: C[C@@H](CO)NC(=O)c1cc(-c2csc(C(=O)N(C)[C@@H](C)c3ccc(F)cc3)c2)cn2nc(N)nc12] |
| 111 | 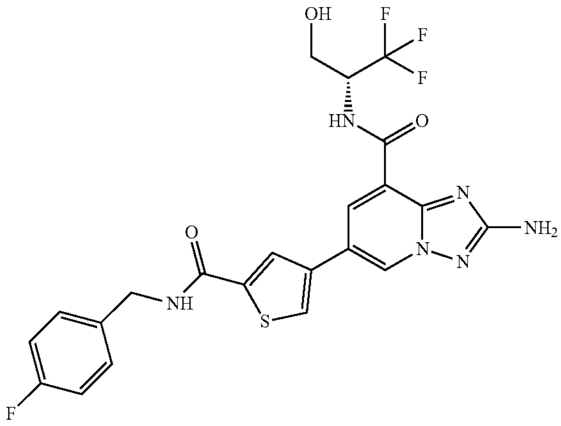 [SMILES: Nc1nc2c(C(=O)N[C@H](CO)C(F)(F)F)cc(-c3csc(C(=O)NCc4ccc(F)cc4)c3)cn2n1] |

TABLE 1A-continued
| Compound Number | Structure |
| --- | --- |
| 112 | 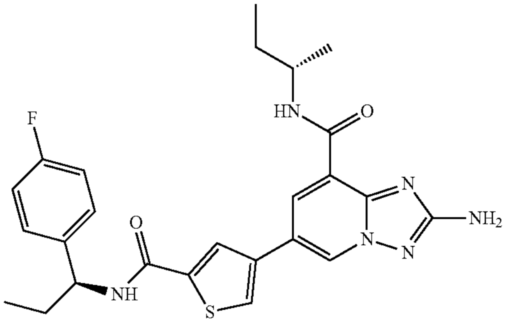 [SMILES: CC[C@H](NC(=O)c1cc(-c2cc(C(=O)N[C@@H](C)CC)c3nc(N)nn3c2)cs1)c1ccc(F)cc1] |
| 113 | 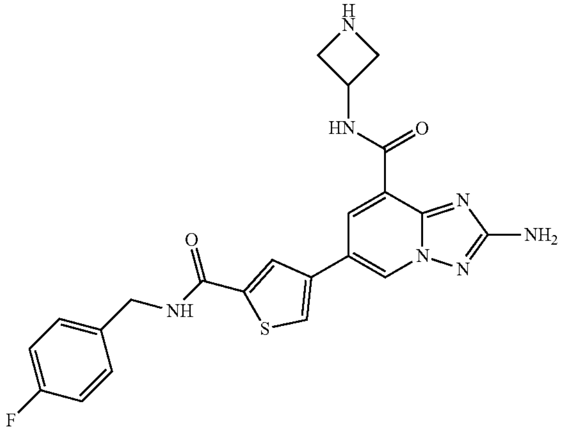 [SMILES: Nc1nc2c(C(=O)NC3CNC3)cc(-c3csc(C(=O)NCc4ccc(F)cc4)c3)cn2n1] |
| 114 | 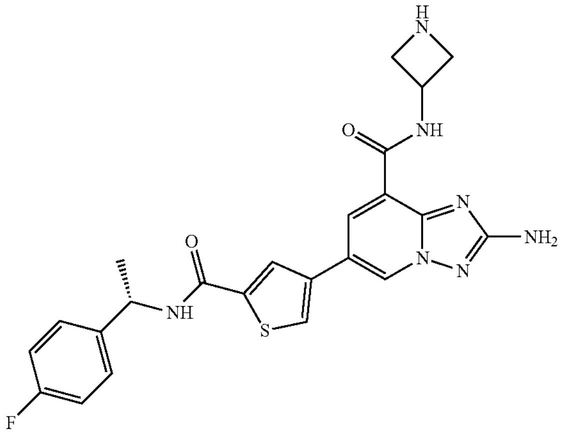 [SMILES: C[C@H](NC(=O)c1cc(-c2cc(C(=O)NC3CNC3)c3nc(N)nn3c2)cs1)c1ccc(F)cc1] |
| 115 | 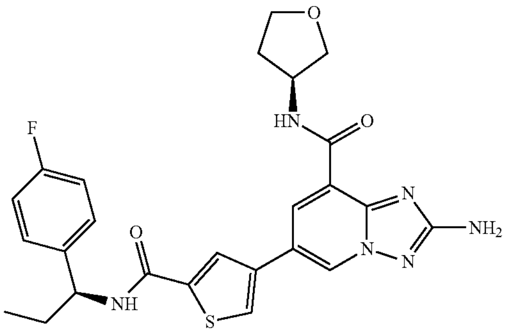 [SMILES: CC[C@H](NC(=O)c1cc(-c2cc(C(=O)N[C@H]3CCOC3)c3nc(N)nn3c2)cs1)c1ccc(F)cc1] |

TABLE 1A-continued
| Compound Number | Structure |
| --- | --- |
| 116 | 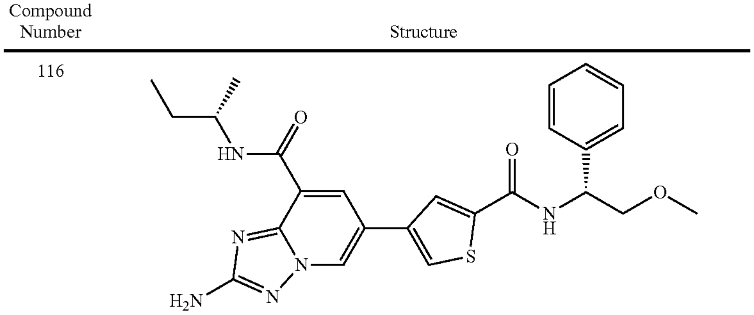 |
| 117 | 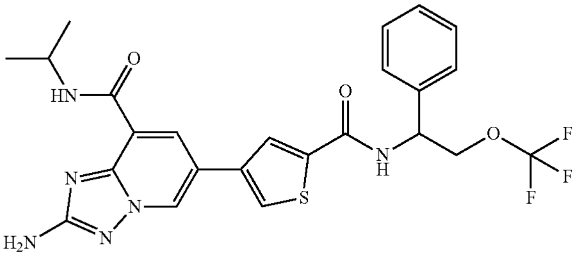 [SMILES: CC(C)NC(=O)c1cc(-c2csc(C(=O)NC(COC(F)(F)F)c3ccccc3)c2)cn2nc(N)nc12] |
| 118 | 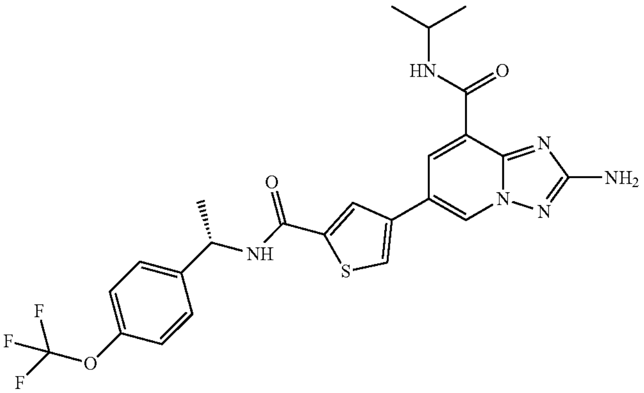 [SMILES: CC(C)NC(=O)c1cc(-c2csc(C(=O)N[C@@H](C)c3ccc(OC(F)(F)F)cc3)c2)cn2nc(N)nc12] |
| 119 | 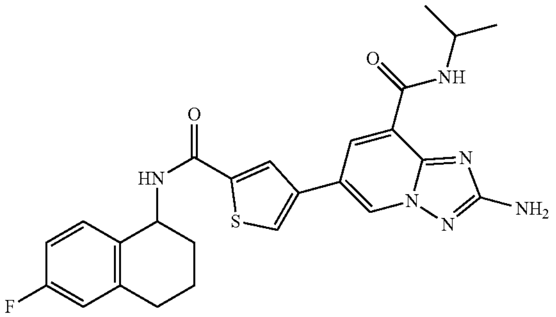 [SMILES: CC(C)NC(=O)c1cc(-c2csc(C(=O)NC3CCCc4cc(F)ccc43)c2)cn2nc(N)nc12] |
| 120 | 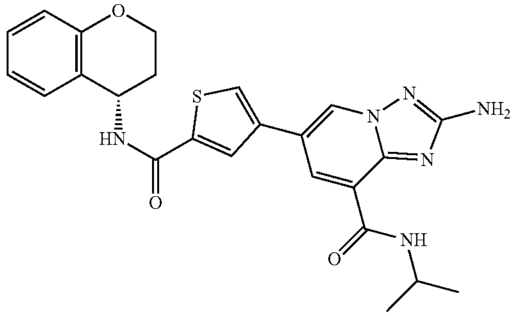 [SMILES: CC(C)NC(=O)c1cc(-c2csc(C(=O)N[C@H]3CCOc4ccccc43)c2)cn2nc(N)nc12] |

TABLE 1A-continued
| Compound Number | Structure |
|---|---|
| 121 | 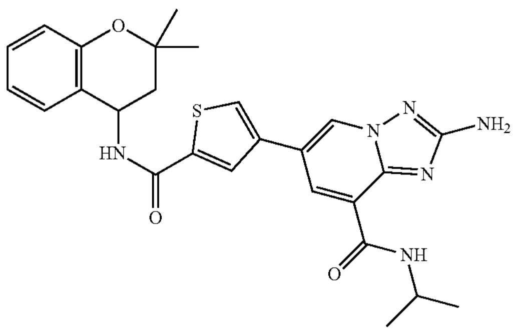 [SMILES: CC(C)NC(=O)c1cc(-c2csc(C(=O)NC3CC(C)(C)Oc4ccccc43)c2)cn2nc(N)nc12] |
| 122 | 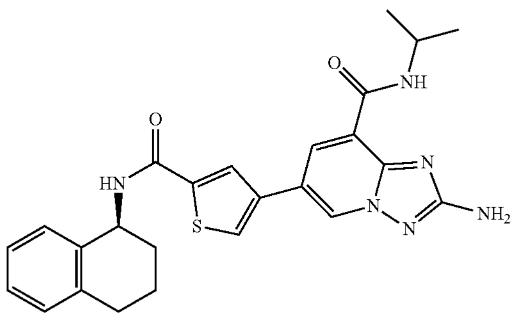 [SMILES: CC(C)NC(=O)c1cc(-c2csc(C(=O)N[C@H]3CCCc4ccccc43)c2)cn2nc(N)nc12] |
| 123 | 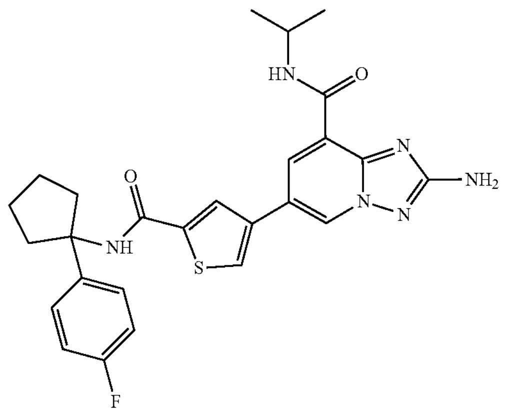 [SMILES: CC(C)NC(=O)c1cc(-c2csc(C(=O)NC3(c4ccc(F)cc4)CCCC3)c2)cn2nc(N)nc12] |
| 124 | 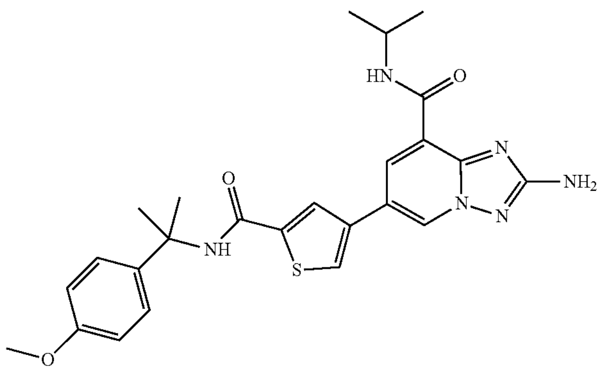 [SMILES: COc1ccc(C(C)(C)NC(=O)c2cc(-c3cc(C(=O)NC(C)C)c4nc(N)nn4c3)cs2)cc1] |

TABLE 1A-continued
| Compound Number | Structure |
| --- | --- |
| 125 | 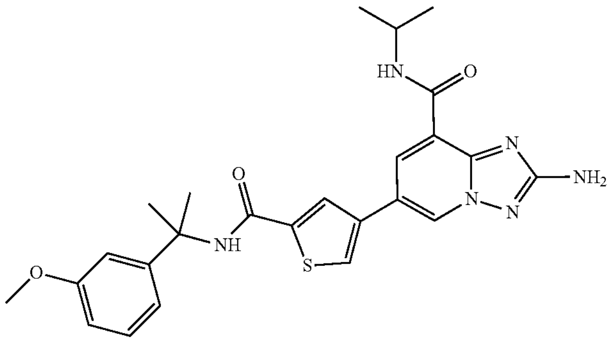 [SMILES: COc1cccc(C(C)(C)NC(=O)c2cc(-c3cc(C(=O)NC(C)C)c4nc(N)nn4c3)cs2)c1] |
| 126 | 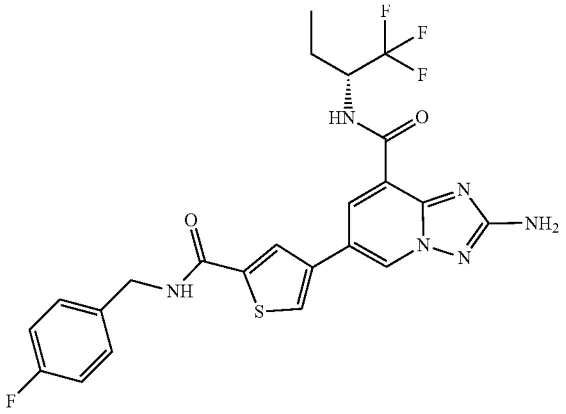 [SMILES: CC[C@@H](NC(=O)c1cc(-c2csc(C(=O)NCc3ccc(F)cc3)c2)cn2nc(N)nc12)C(F)(F)F] |
| 127 | 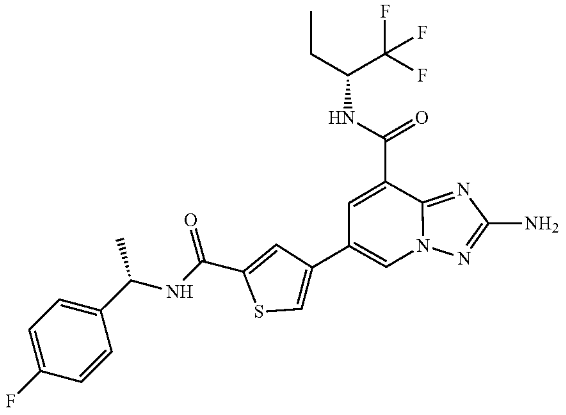 [SMILES: CC[C@@H](NC(=O)c1cc(-c2csc(C(=O)N[C@@H](C)c3ccc(F)cc3)c2)cn2nc(N)nc12)C(F)(F)F] |
| 128 | 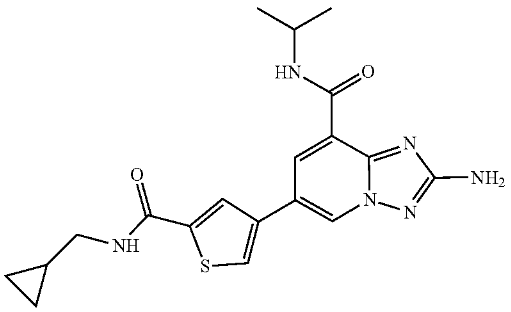 [SMILES: CC(C)NC(=O)c1cc(-c2csc(C(=O)NCC3CC3)c2)cn2nc(N)nc12] |

TABLE 1A-continued
| Compound Number | Structure |
|---|---|
| 129 | 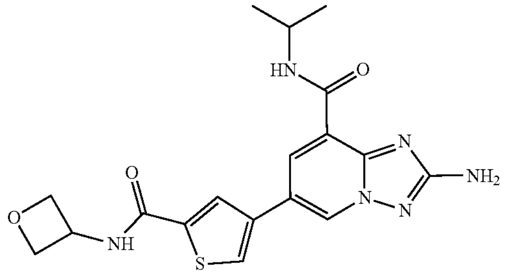 [SMILES: CC(C)NC(=O)c1cc(-c2csc(C(=O)NC3COC3)c2)cn2nc(N)nc12] |
| 130 | 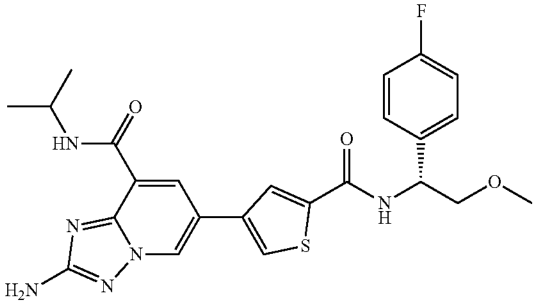 [SMILES: COC[C@H](NC(=O)c1cc(-c2cc(C(=O)NC(C)C)c3nc(N)nn3c2)cs1)c1ccc(F)cc1] |
| 131 | 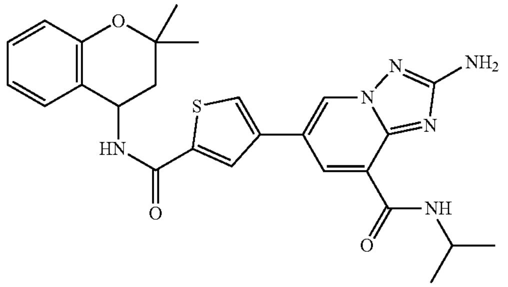 enantiomer 1 |
| 132 | 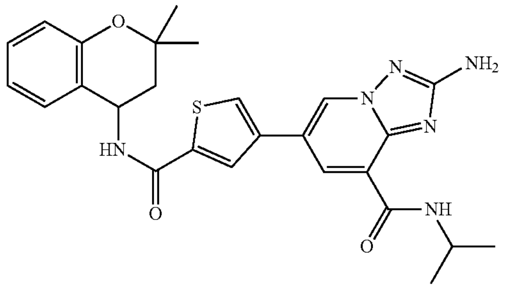 enantiomer 2 |
| 133 | 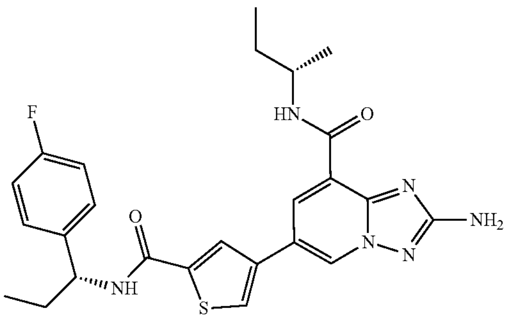 [SMILES: CC[C@H](C)NC(=O)c1cc(-c2csc(C(=O)N[C@H](CC)c3ccc(F)cc3)c2)cn2nc(N)nc12] |

TABLE 1A-continued
| Compound Number | Structure |
|---|---|
| 134 | 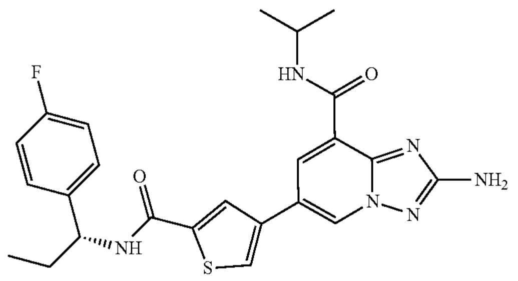 [SMILES: CC[C@@H](NC(=O)c1cc(-c2cc(C(=O)NC(C)C)c3nc(N)nn3c2)cs1)c1ccc(F)cc1] |
| 135 | 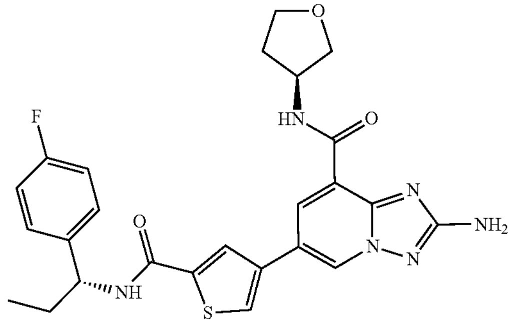 [SMILES: CC[C@@H](NC(=O)c1cc(-c2cc(C(=O)N[C@H]3CCOC3)c3nc(N)nn3c2)cs1)c1ccc(F)cc1] |
| 136 | 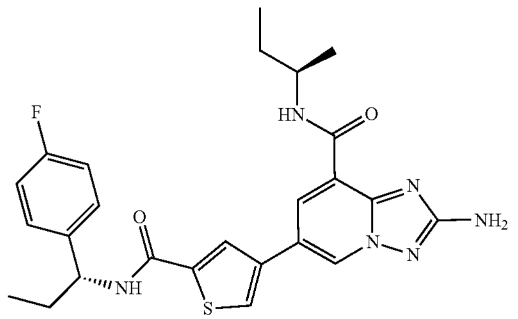 [SMILES: CC[C@@H](C)NC(=O)c1cc(-c2csc(C(=O)N[C@H](CC)c3ccc(F)cc3)c2)cn2nc(N)nc12] |
| 137 | 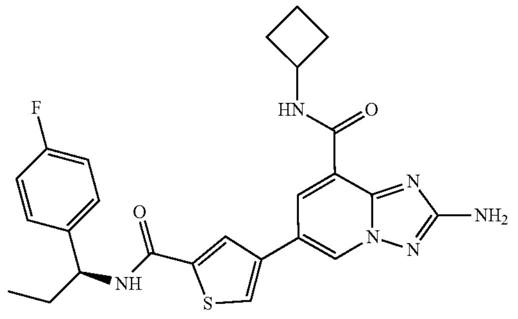 [SMILES: CC[C@H](NC(=O)c1cc(-c2cc(C(=O)NC3CCC3)c3nc(N)nn3c2)cs1)c1ccc(F)cc1] |
| 138 | 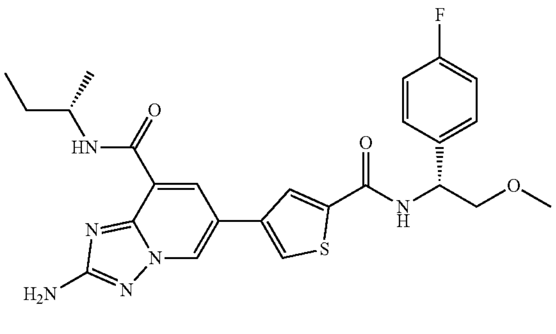 [SMILES: CC[C@H](C)NC(=O)c1cc(-c2csc(C(=O)N[C@@H](COC)c3ccc(F)cc3)c2)cn2nc(N)nc12] |

TABLE 1A-continued
| Compound Number | Structure |
|---|---|
| 139 | 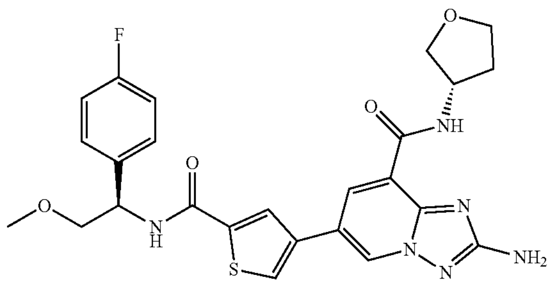 [SMILES: COC[C@H](NC(=O)c1cc(-c2cc(C(=O)N[C@H]3CCOC3)c3nc(N)nn3c2)cs1)c1ccc(F)cc1] |
| 140 | 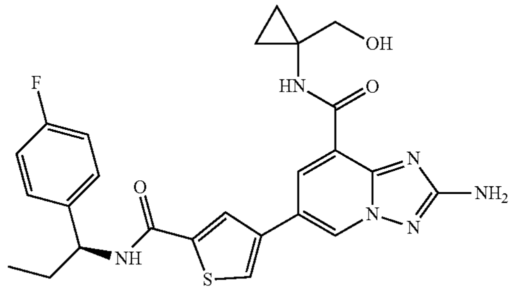 [SMILES: CC[C@H](NC(=O)c1cc(-c2cc(C(=O)NC3(CO)CC3)c3nc(N)nn3c2)cs1)c1ccc(F)cc1] |
| 141 | 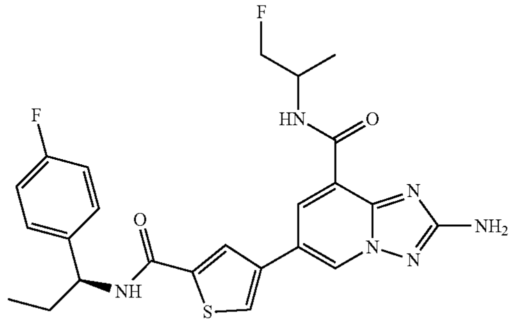<br>mixture of diastereomers |
| 142 | 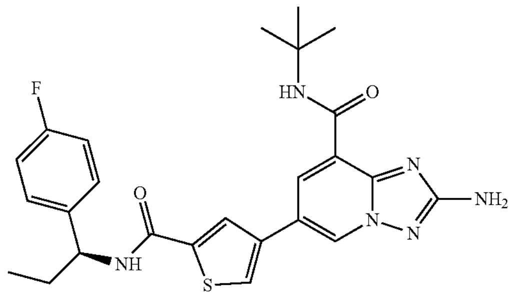 [SMILES: CC[C@H](NC(=O)c1cc(-c2cc(C(=O)NC(C)(C)C)c3nc(N)nn3c2)cs1)c1ccc(F)cc1] |

TABLE 1A-continued
| Compound Number | Structure |
| --- | --- |
| 143 | 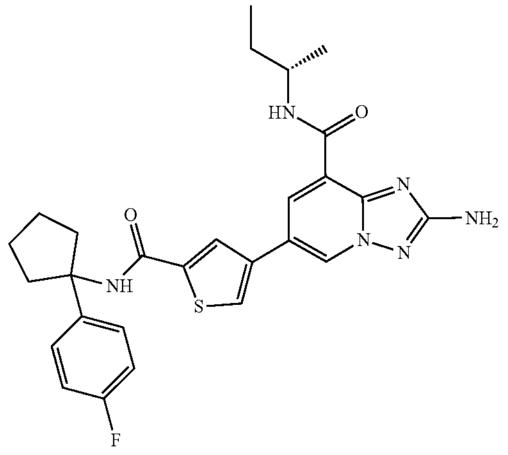 [SMILES: CC[C@H](C)NC(=O)c1cc(-c2csc(C(=O)NC3(c4ccc(F)cc4)CCCC3)c2)cn2nc(N)nc12] |
| 144 | 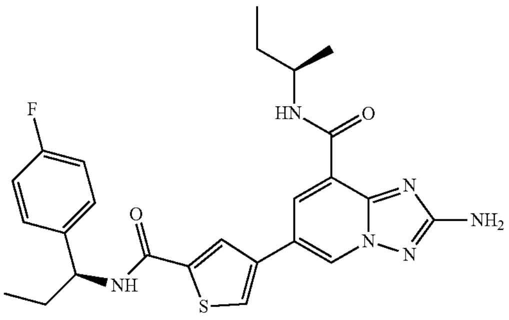 [SMILES: CC[C@@H](C)NC(=O)c1cc(-c2csc(C(=O)N[C@@H](CC)c3ccc(F)cc3)c2)cn2nc(N)nc12] |
| 144-1 | 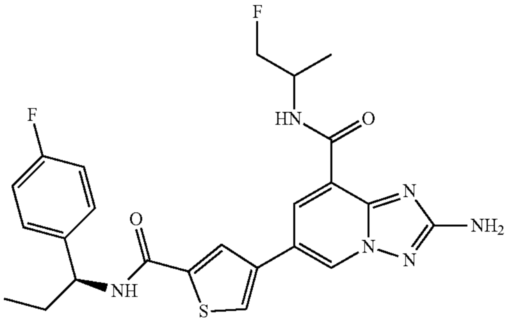 stereoisomer 1 |
| 144-2 | 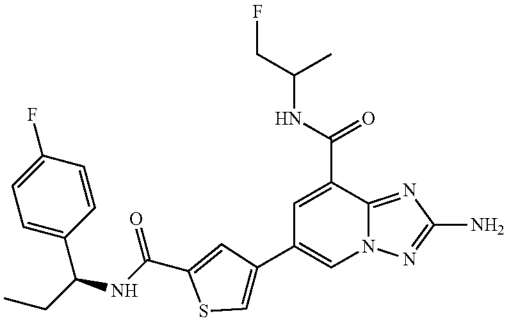 stereoisomer 2 |

TABLE 1A-continued
| Compound Number | Structure |
| --- | --- |
| 144-3 | 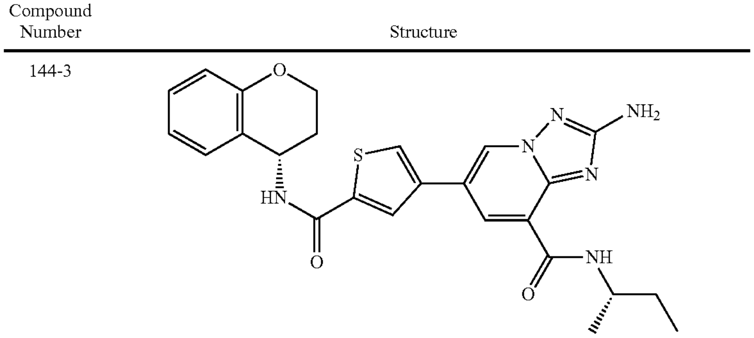 |
| 144-4 | 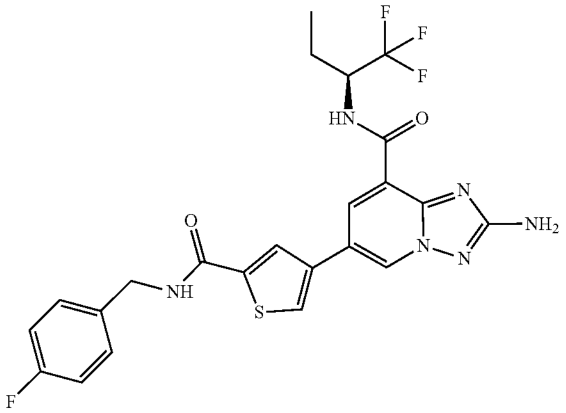 [SMILES: CC[C@H](NC(=O)c1cc(-c2csc(C(=O)NCc3ccc(F)cc3)c2)cn2nc(N)nc12)C(F)(F)F] |
| 144-5 | 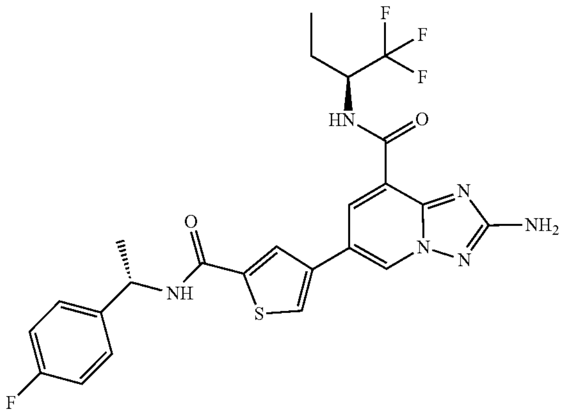 [SMILES: CC[C@H](NC(=O)c1cc(-c2csc(C(=O)N[C@@H](C)c3ccc(F)cc3)c2)cn2nc(N)nc12)C(F)(F)F] |
and pharmaceutically acceptable salts thereof.

In some embodiments, the compound is selected from the group consisting of the compounds disclosed in Table 1B below:
TABLE 1B
| Compound Number | Structure |
| --- | --- |
| 145 | 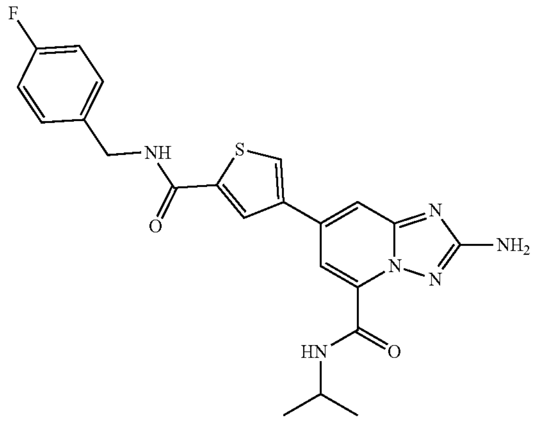 [SMILES: CC(C)NC(=O)c1cc(-c2csc(C(=O)NCc3ccc(F)cc3)c2)cc2nc(N)nn12] |
| 146 | 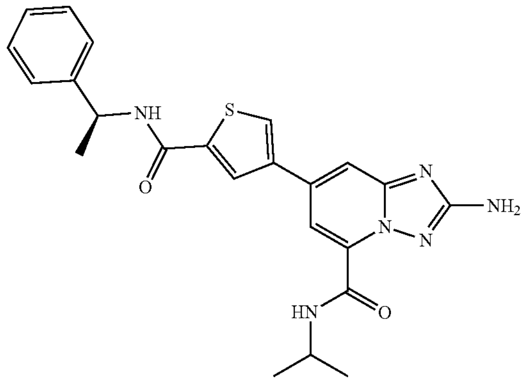 [SMILES: CC(C)NC(=O)c1cc(-c2csc(C(=O)N[C@@H](C)c3ccccc3)c2)cc2nc(N)nn12] |
| 147 | 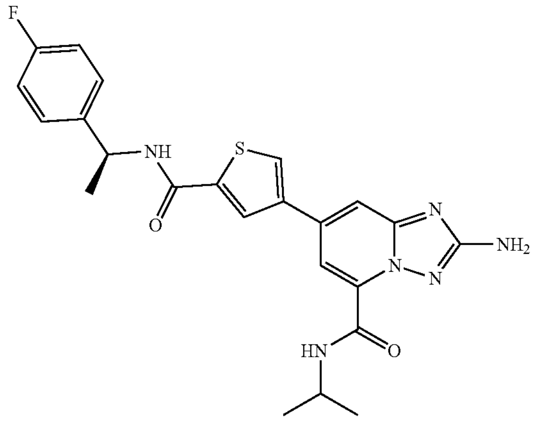 [SMILES: CC(C)NC(=O)c1cc(-c2csc(C(=O)N[C@@H](C)c3ccc(F)cc3)c2)cc2nc(N)nn12] |

TABLE 1B-continued
| Compound Number | Structure |
| --- | --- |
| 148 | 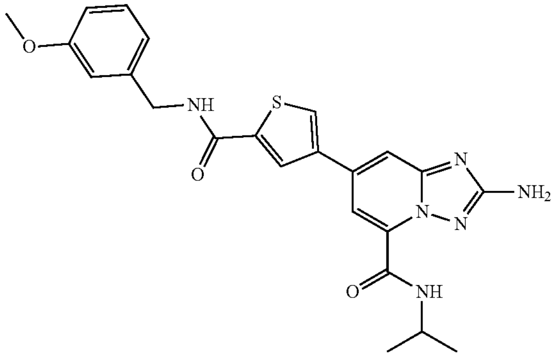 [SMILES: COc1cccc(CNC(=O)c2cc(-c3cc(C(=O)NC(C)C)n4nc(N)nc4c3)cs2)c1] |
| 149 | 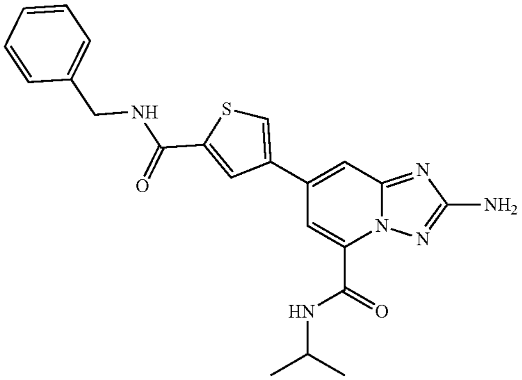 [SMILES: CC(C)NC(=O)c1cc(-c2csc(C(=O)NCc3ccccc3)c2)cc2nc(N)nn12] |
| 150 | 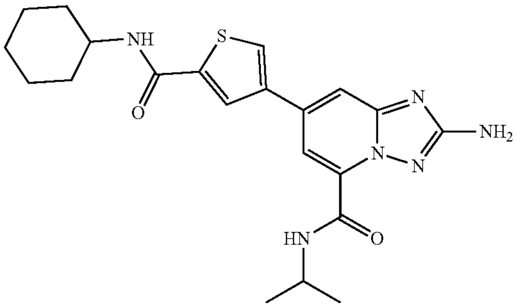 [SMILES: CC(C)NC(=O)c1cc(-c2csc(C(=O)NC3CCCCC3)c2)cc2nc(N)nn12] |
| 151 | 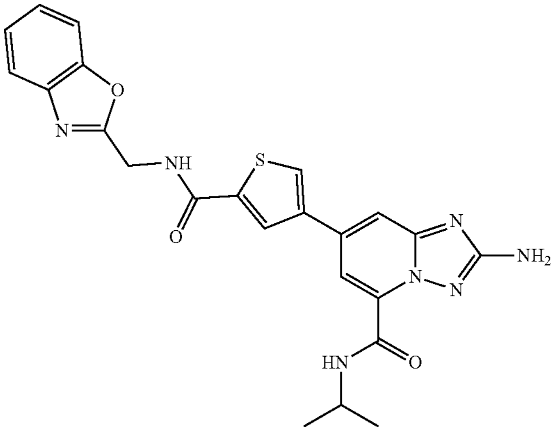 [SMILES: CC(C)NC(=O)c1cc(-c2csc(C(=O)NCc3nc4ccccc4o3)c2)cc2nc(N)nn12] |

TABLE 1B-continued
| Compound Number | Structure |
| --- | --- |
| 152 | 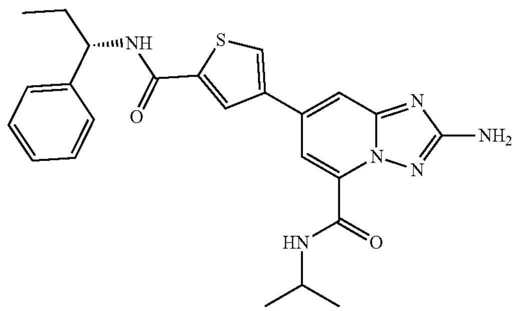 [SMILES: CC[C@H](NC(=O)c1cc(-c2cc(C(=O)NC(C)C)n3nc(N)nc3c2)cs1)c1ccccc1] |
| 153 | 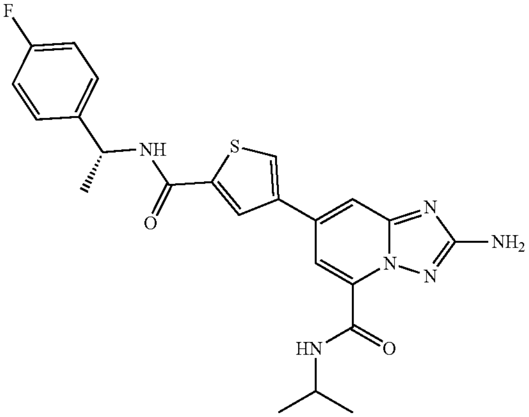 [SMILES: CC(C)NC(=O)c1cc(-c2csc(C(=O)N[C@H](C)c3ccc(F)cc3)c2)cc2nc(N)nn12] |
| 154 | 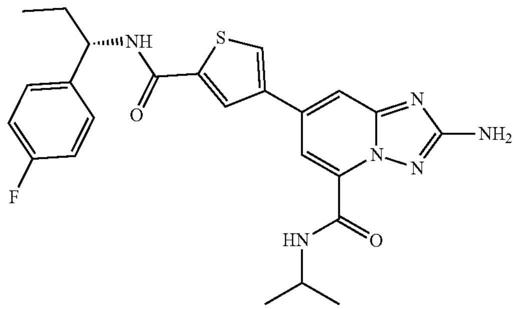 [SMILES: CC[C@H](NC(=O)c1cc(-c2cc(C(=O)NC(C)C)n3nc(N)nc3c2)cs1)c1ccc(F)cc1] |
| 155 | 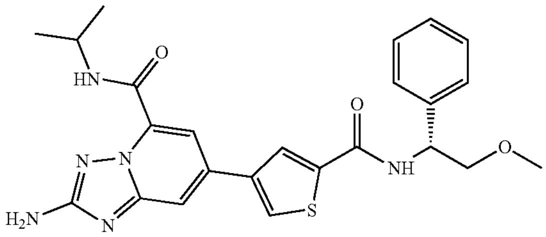 [SMILES: COC[C@H](NC(=O)c1cc(-c2cc(C(=O)NC(C)C)n3nc(N)nc3c2)cs1)c1ccccc1] |

TABLE 1B-continued
| Compound Number | Structure |
|---|---|
| 156 | 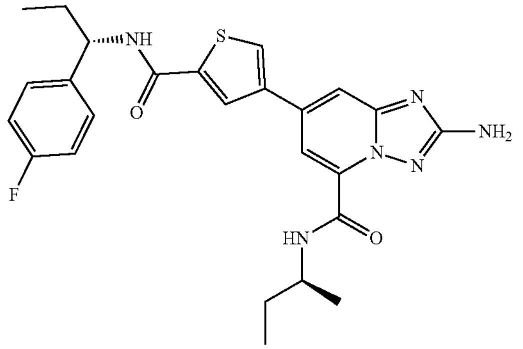 [SMILES: CC[C@H](NC(=O)c1cc(-c2cc(C(=O)N[C@@H](C)CC)n3nc(N)nc3c2)cs1)c1ccc(F)cc1] |
| 157 | 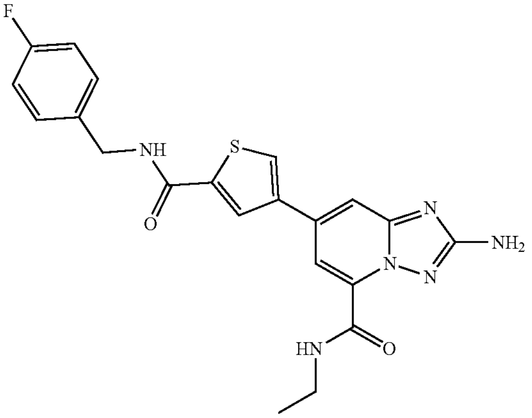 [SMILES: CCNC(=O)c1cc(-c2csc(C(=O)NCc3ccc(F)cc3)c2)cc2nc(N)nn12] |
| 158 | 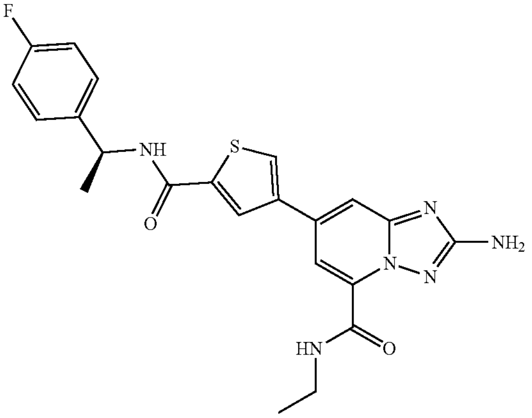 [SMILES: CCNC(=O)c1cc(-c2csc(C(=O)N[C@@H](C)c3ccc(F)cc3)c2)cc2nc(N)nn12] |
| 159 | 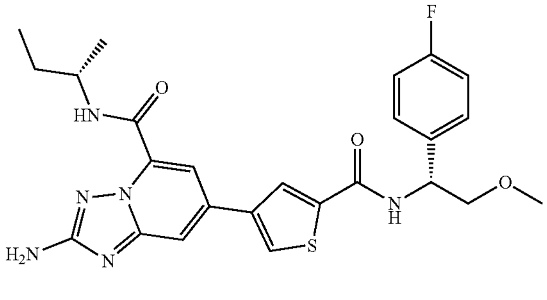 [SMILES: CC[C@H](C)NC(=O)c1cc(-c2csc(C(=O)N[C@@H](COC)c3ccc(F)cc3)c2)cc2nc(N)nn12] |

TABLE 1B-continued
| Compound Number | Structure |
| --- | --- |
| 160 | 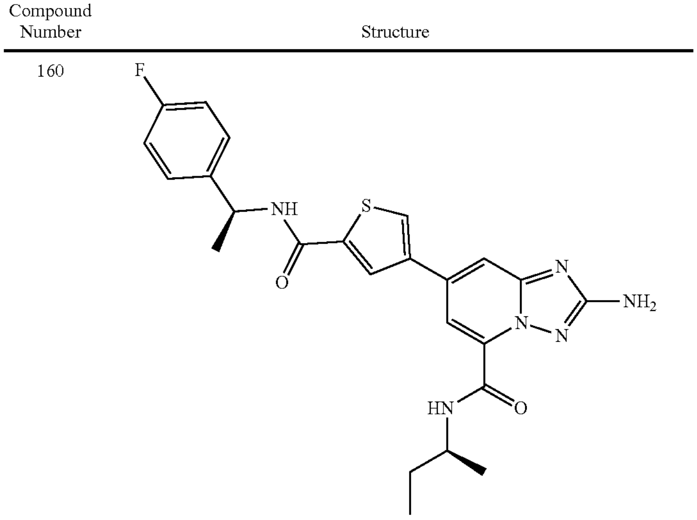 |
| 161 | 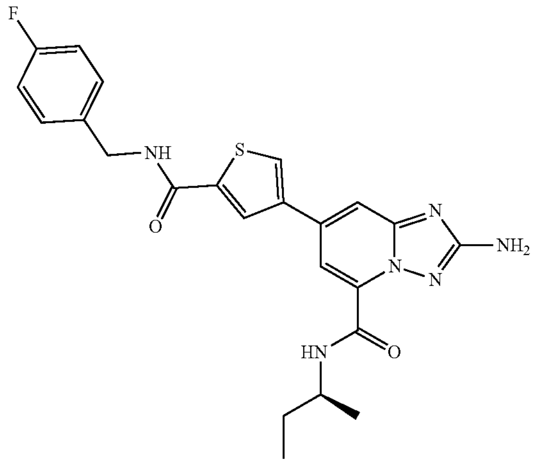 [SMILES: CC[C@H](C)NC(=O)c1cc(-c2csc(C(=O)NCc3ccc(F)cc3)c2)cc2nc(N)nn12] |
| 162 | 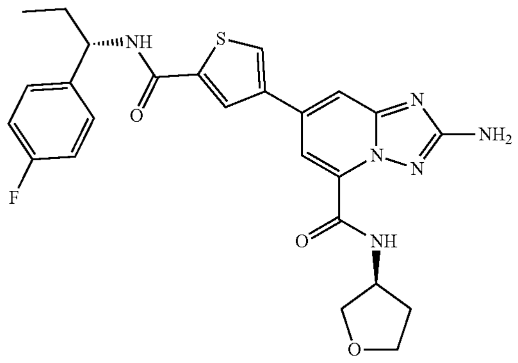 [SMILES: CC[C@H](NC(=O)c1cc(-c2cc(C(=O)N[C@H]3CCOC3)n3nc(N)nc3c2)cs1)c1ccc(F)cc1] |
and pharmaceutically acceptable salts thereof.

In some embodiments, the compound is selected from the group consisting of the compounds disclosed in Table 1C below:
TABLE IC
| Compound Number | Structure |
| --- | --- |
| 163 | 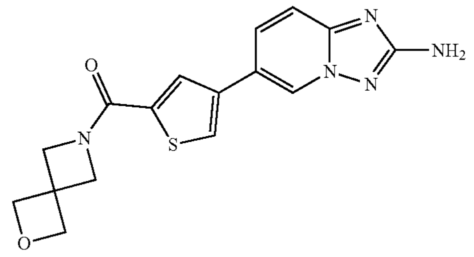 [SMILES: Nc1nc2ccc(-c3csc(C(=O)N4CC5(COC5)C4)c3)cn2n1] |
| 164 | 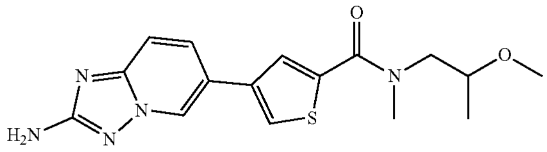 [SMILES: COC(C)CN(C)C(=O)c1cc(-c2ccc3nc(N)nn3c2)cs1] |
| 165 | 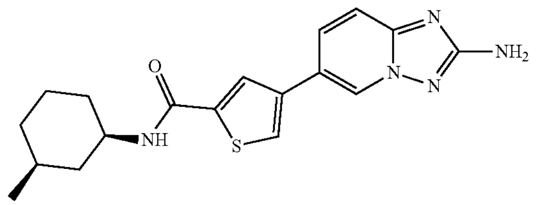 stereoisomer 1 |
| 166 | 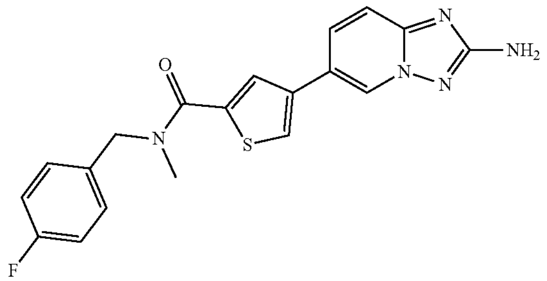 [SMILES: CN(Cc1ccc(F)cc1)C(=O)c1cc(-c2ccc3nc(N)nn3c2)cs1] |
| 167 | 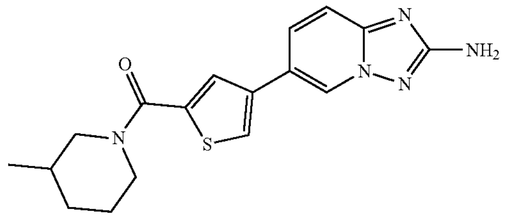 [SMILES: CC1CCCN(C(=O)c2cc(-c3ccc4nc(N)nn4c3)cs2)C1] |
| 168 | 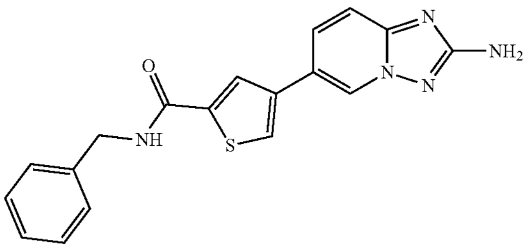 [SMILES: Nc1nc2ccc(-c3csc(C(=O)NCc4ccccc4)c3)cn2n1] |

TABLE IC-continued
| Compound Number | Structure |
|---|---|
| 169 | 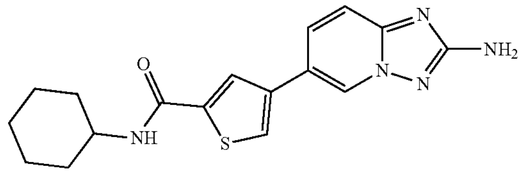 [SMILES: Nc1nc2ccc(-c3csc(C(=O)NC4CCCCC4)c3)cn2n1] |
| 170 | 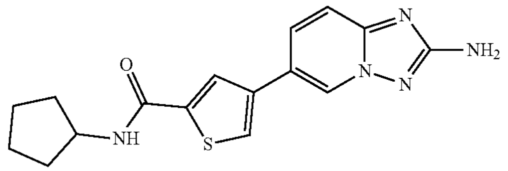 [SMILES: Nc1nc2ccc(-c3csc(C(=O)NC4CCCC4)c3)cn2n1] |
| 171 | 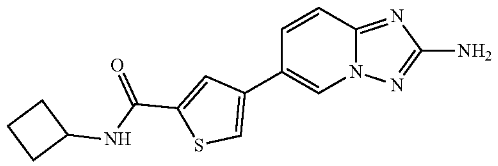 [SMILES: Nc1nc2ccc(-c3csc(C(=O)NC4CCC4)c3)cn2n1] |
| 172 | 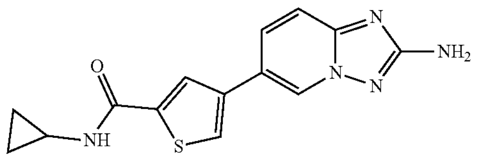 [SMILES: Nc1nc2ccc(-c3csc(C(=O)NC4CC4)c3)cn2n1] |
| 173 | 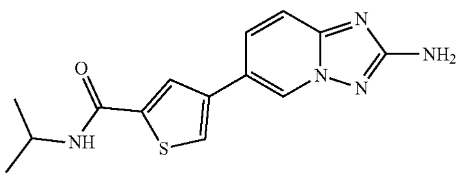 [SMILES: CC(C)NC(=O)c1cc(-c2ccc3nc(N)nn3c2)cs1] |
| 174 | 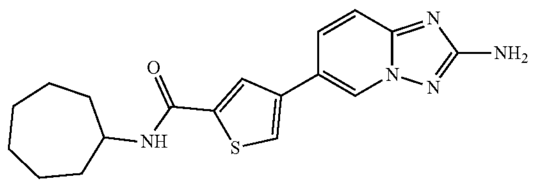 [SMILES: Nc1nc2ccc(-c3csc(C(=O)NC4CCCCCC4)c3)cn2n1] |
| 175 | 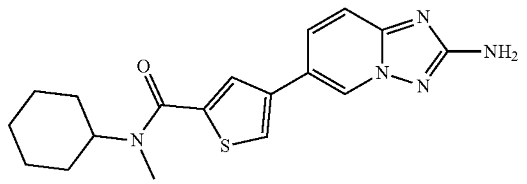 [SMILES: CN(C(=O)c1cc(-c2ccc3nc(N)nn3c2)cs1)C1CCCCC1] |
| 176 | 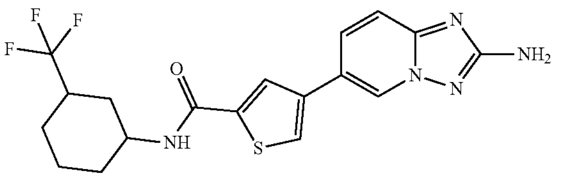 [SMILES: Nc1nc2ccc(-c3csc(C(=O)NC4CCCC(C(F)(F)F)C4)c3)cn2n1] |

TABLE IC-continued
| Compound Number | Structure |
|---|---|
| 177 | 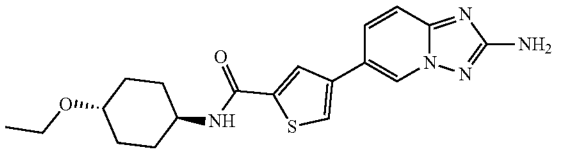 [SMILES: CCO[C@H]1CC[C@H](NC(=O)c2cc(-c3ccc4nc(N)nn4c3)cs2)CC1] |
| 178 | 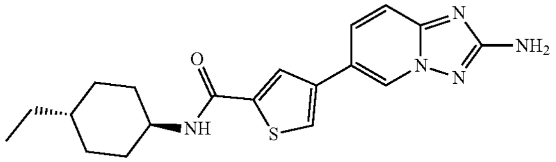 [SMILES: CC[C@H]1CC[C@H](NC(=O)c2cc(-c3ccc4nc(N)nn4c3)cs2)CC1] |
| 179 | 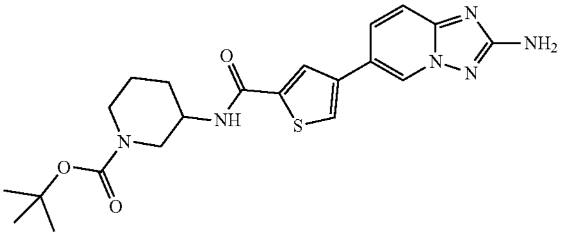 [SMILES: CC(C)(C)OC(=O)N1CCCC(NC(=O)c2cc(-c3ccc4nc(N)nn4c3)cs2)C1] |
| 180 | 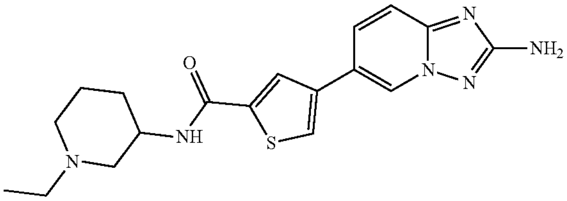 [SMILES: CCN1CCCC(NC(=O)c2cc(-c3ccc4nc(N)nn4c3)cs2)C1] |
| 181 | 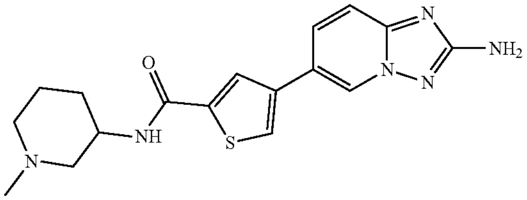 [SMILES: CN1CCCC(NC(=O)c2cc(-c3ccc4nc(N)nn4c3)cs2)C1] |
| 182 | 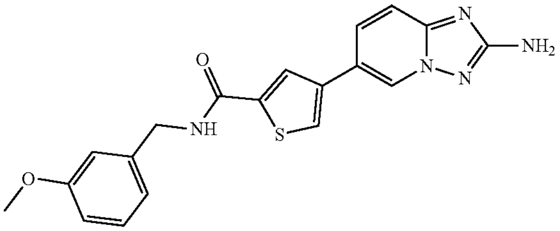 |
| 183 | 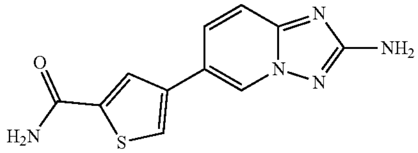 [SMILES: NC(=O)c1cc(-c2ccc3nc(N)nn3c2)cs1] |
| 184 | 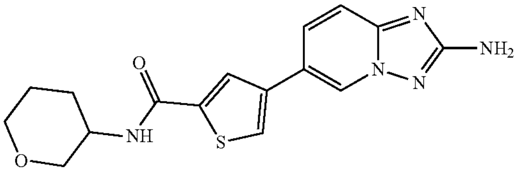 |

TABLE IC-continued
| Compound Number | Structure |
|---|---|
| 185 | 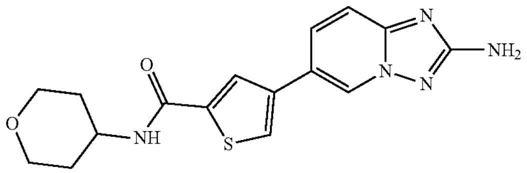 [SMILES: Nc1nc2ccc(-c3csc(C(=O)NC4CCOCC4)c3)cn2n1] |
| 186 | 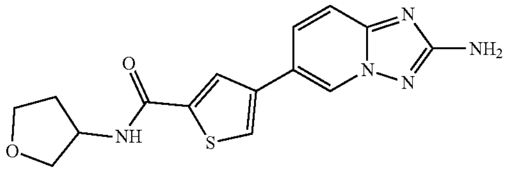 [SMILES: Nc1nc2ccc(-c3csc(C(=O)NC4CCOC4)c3)cn2n1] |
| 187 | 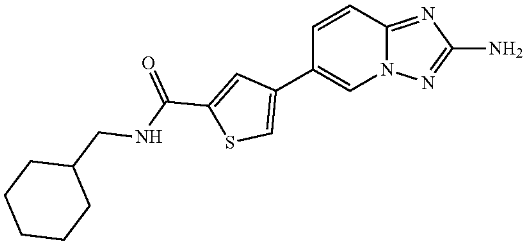 [SMILES: Nc1nc2ccc(-c3csc(C(=O)NCC4CCCCC4)c3)cn2n1] |
| 188 | 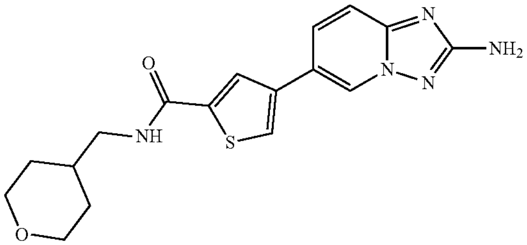 [SMILES: Nc1nc2ccc(-c3csc(C(=O)NCC4CCOCC4)c3)cn2n1] |
| 189 | 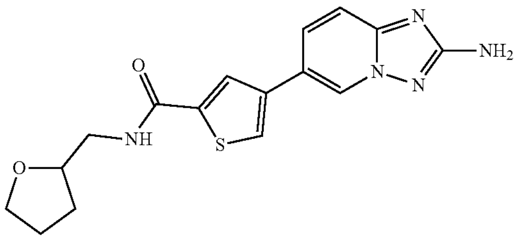 |
| 190 | 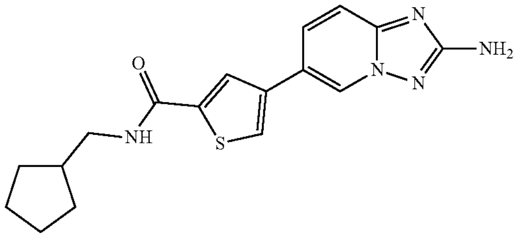 |

TABLE IC-continued
| Compound Number | Structure |
| --- | --- |
| 191 | 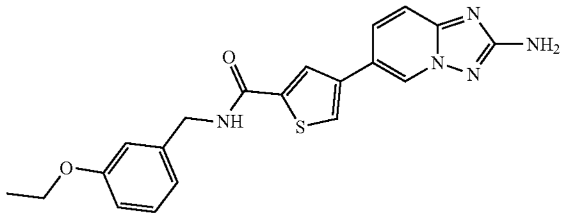 [SMILES: CCOc1cccc(CNC(=O)c2cc(-c3ccc4nc(N)nn4c3)cs2)c1] |
| 192 | 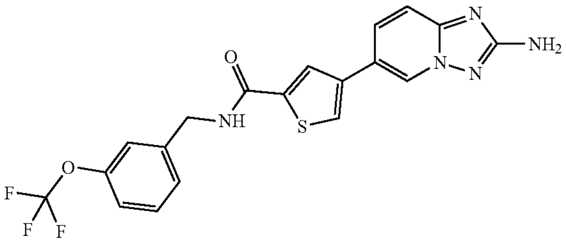 [SMILES: Nc1nc2ccc(-c3csc(C(=O)NCc4cccc(OC(F)(F)F)c4)c3)cn2n1] |
| 193 | 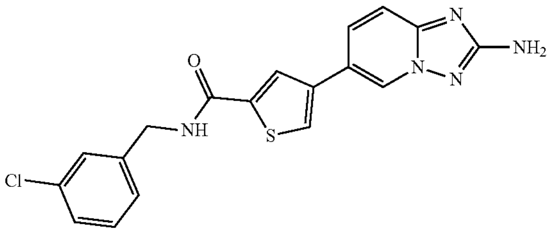 [SMILES: Nc1nc2ccc(-c3csc(C(=O)NCc4cccc(Cl)c4)c3)cn2n1] |
| 194 | 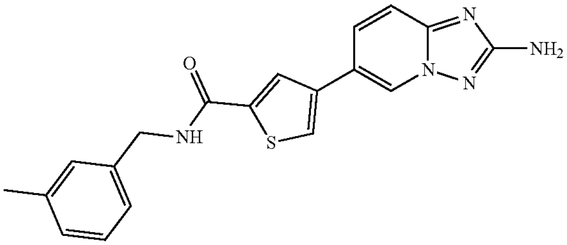 [SMILES: Cc1cccc(CNC(=O)c2cc(-c3ccc4nc(N)nn4c3)cs2)c1] |
| 195 | 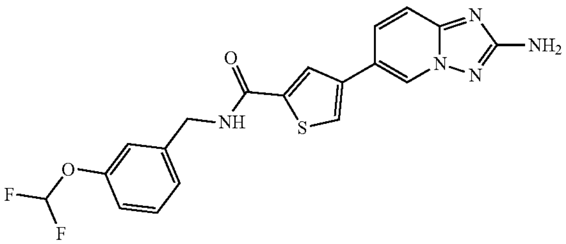 [SMILES: Nc1nc2ccc(-c3csc(C(=O)NCc4cccc(OC(F)F)c4)c3)cn2n1] |
| 196 | 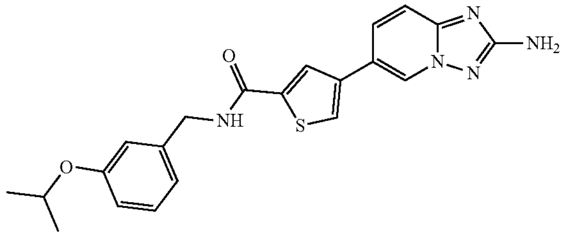 [SMILES: CC(C)Oc1cccc(CNC(=O)c2cc(-c3ccc4nc(N)nn4c3)cs2)c1] |

TABLE IC-continued
| Compound Number | Structure |
|---|---|
| 197 | 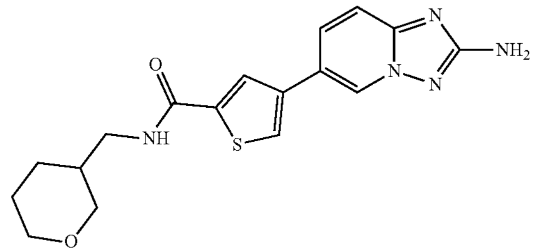 [SMILES: Nc1nc2ccc(-c3csc(C(=O)NCC4CCCOC4)c3)cn2n1] |
| 198 | 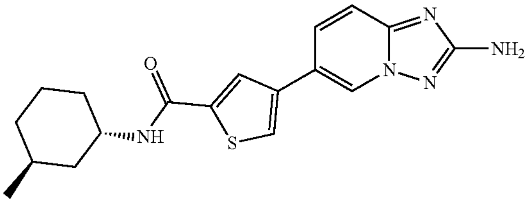<br>stereoisomer 1 |
| 199 | 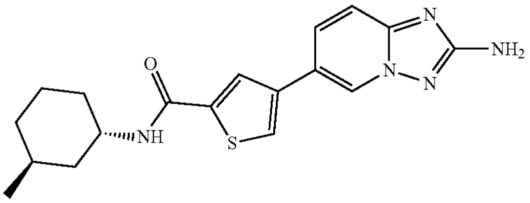<br>stereoisomer 2 |
| 200 | 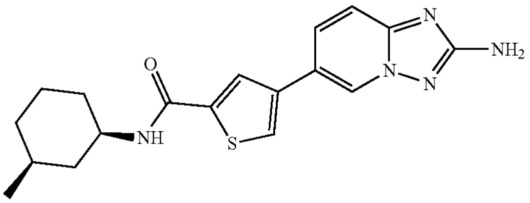<br>stereoisomer 2 |
| 201 | 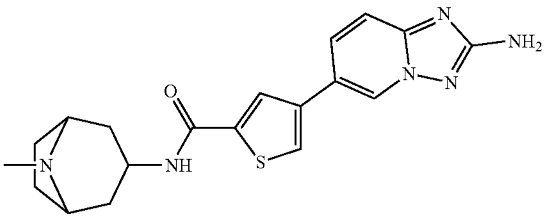 [SMILES: CN1C2CCC1CC(NC(=O)c1cc(-c3ccc4nc(N)nn4c3)cs1)C2] |
| 202 | 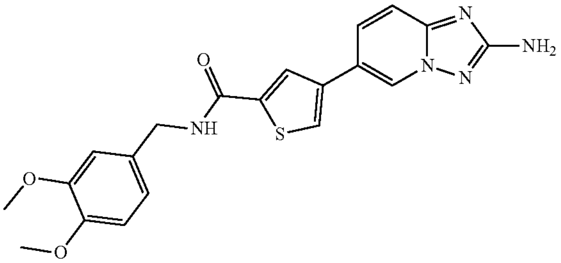 [SMILES: COc1ccc(CNC(=O)c2cc(-c3ccc4nc(N)nn4c3)cs2)cc1OC] |

TABLE IC-continued
| Compound Number | Structure |
|---|---|
| 203 | 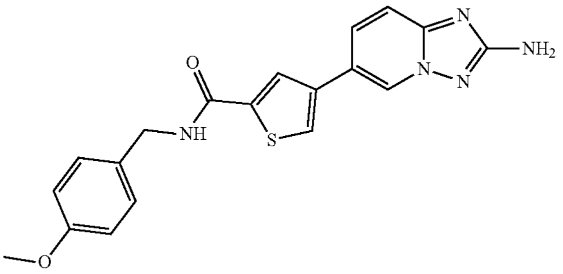 [SMILES: COc1ccc(CNC(=O)c2cc(-c3ccc4nc(N)nn4c3)cs2)cc1] |
| 204 | 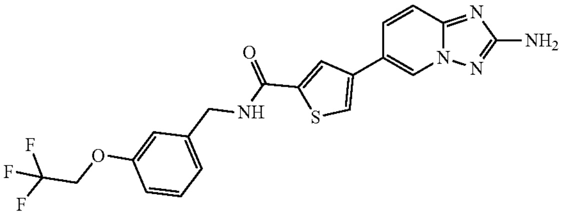 [SMILES: Nc1nc2ccc(-c3csc(C(=O)NCc4cccc(OCC(F)(F)F)c4)c3)cn2n1] |
| 205 | 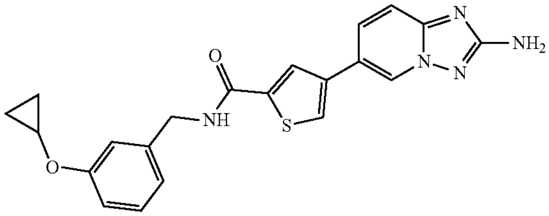 [SMILES: Nc1nc2ccc(-c3csc(C(=O)NCc4cccc(OC5CC5)c4)c3)cn2n1] |
| 206 | 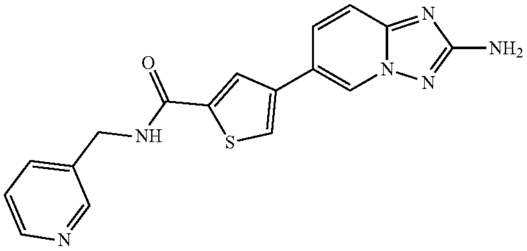 [SMILES: Nc1nc2ccc(-c3csc(C(=O)NCc4cccnc4)c3)cn2n1] |
| 207 | 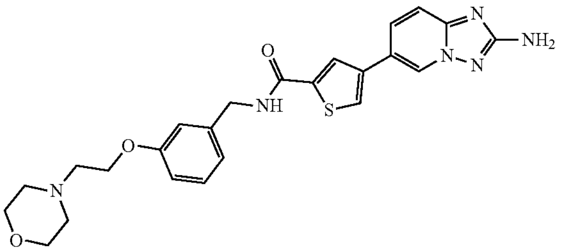 [SMILES: Nc1nc2ccc(-c3csc(C(=O)NCc4cccc(OCCN5CCOCC5)c4)c3)cn2n1] |
| 208 | 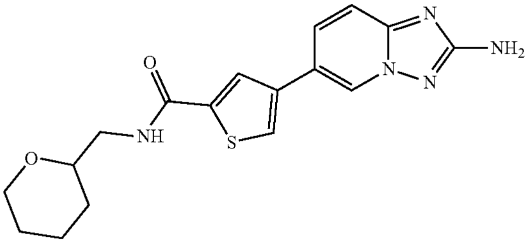 [SMILES: Nc1nc2ccc(-c3csc(C(=O)NCC4CCCCO4)c3)cn2n1] |

TABLE IC-continued
| Compound Number | Structure |
|---|---|
| 209 | 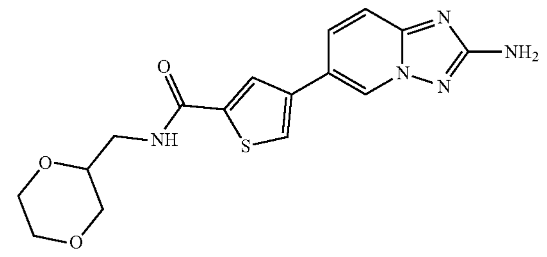 |
| 210 | 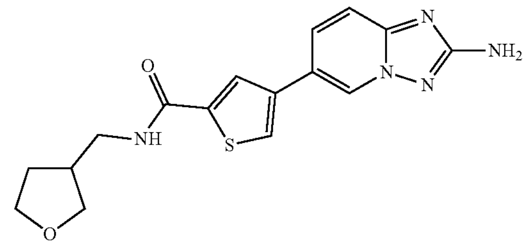 [SMILES: Nc1nc2ccc(-c3csc(C(=O)NCC4CCOC4)c3)cn2n1] |
| 211 | 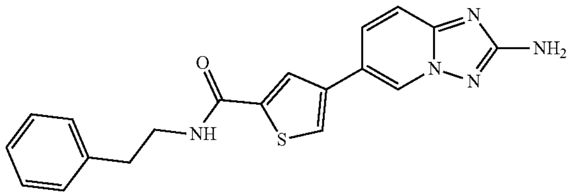 [SMILES: Nc1nc2ccc(-c3csc(C(=O)NCCc4ccccc4)c3)cn2n1] |
| 212 | 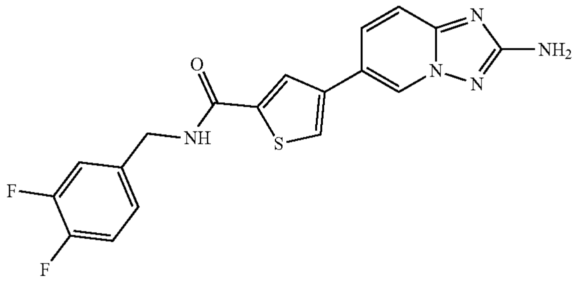 [SMILES: Nc1nc2ccc(-c3csc(C(=O)NCc4ccc(F)c(F)c4)c3)cn2n1] |
| 213 | 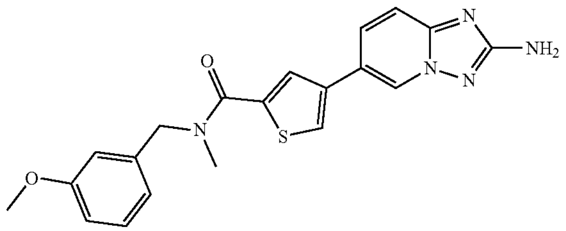 [SMILES: COc1cccc(CN(C)C(=O)c2cc(-c3ccc4nc(N)nn4c3)cs2)c1] |
| 214 | 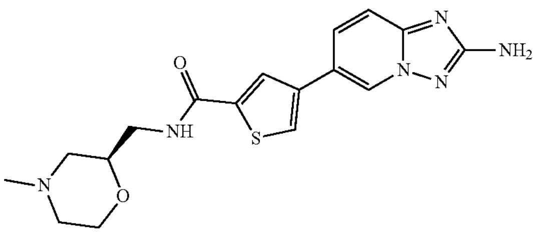 [SMILES: CN1CCO[C@H](CNC(=O)c2cc(-c3ccc4nc(N)nn4c3)cs2)C1] |

TABLE IC-continued
| Compound Number | Structure |
| --- | --- |
| 215 | 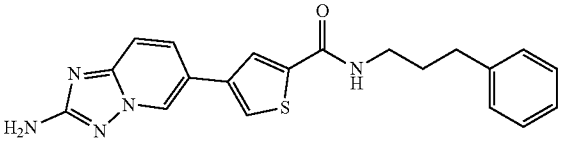 [SMILES: Nc1nc2ccc(-c3csc(C(=O)NCCCc4ccccc4)c3)cn2n1] |
| 216 | 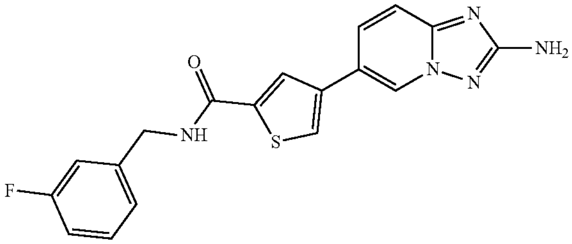 [SMILES: Nc1nc2ccc(-c3csc(C(=O)NCc4cccc(F)c4)c3)cn2n1] |
| 217 | 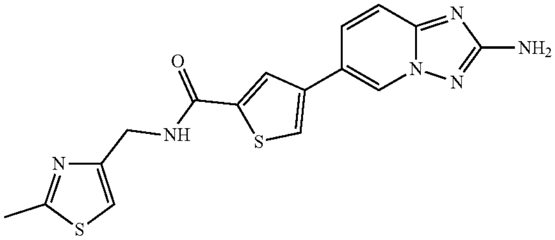 [SMILES: Cc1nc(CNC(=O)c2cc(-c3ccc4nc(N)nn4c3)cs2)cs1] |
| 218 | 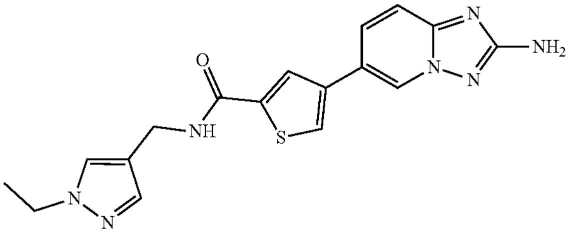 [SMILES: CCn1cc(CNC(=O)c2cc(-c3ccc4nc(N)nn4c3)cs2)cn1] |
| 219 | 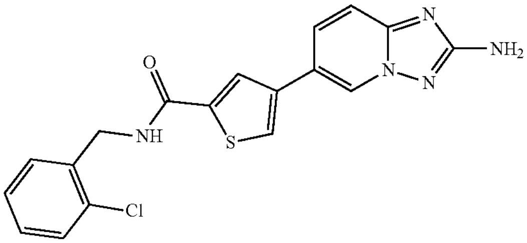 |
| 220 | 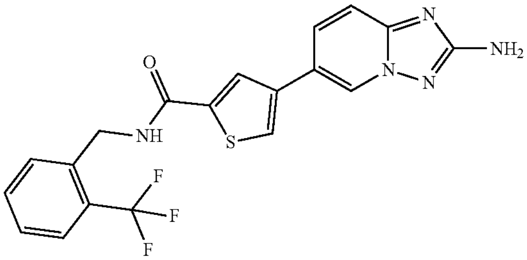 [SMILES: Nc1nc2ccc(-c3csc(C(=O)NCc4ccccc4C(F)(F)F)c3)cn2n1] |

TABLE IC-continued
| Compound Number | Structure |
| --- | --- |
| 221 | 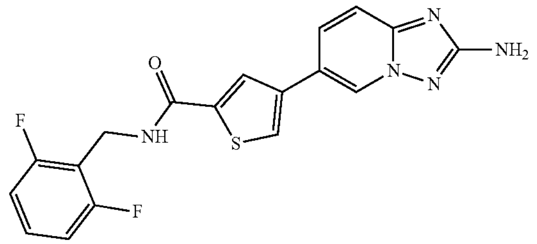 [SMILES: Nc1nc2ccc(-c3csc(C(=O)NCc4c(F)cccc4F)c3)cn2n1] |
| 222 | 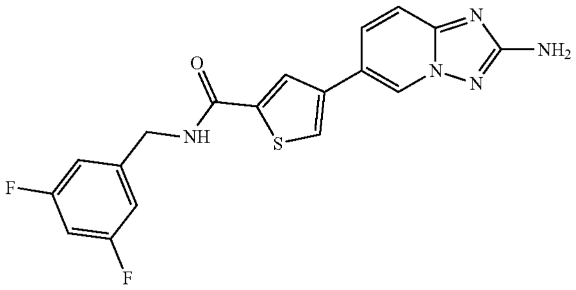 [SMILES: Nc1nc2ccc(-c3csc(C(=O)NCc4cc(F)cc(F)c4)c3)cn2n1] |
| 223 | 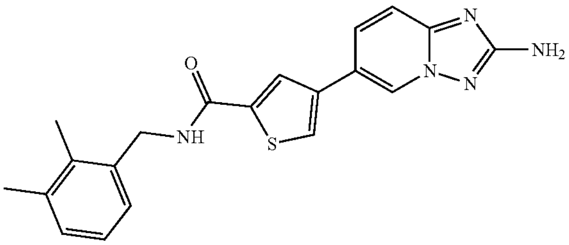 [SMILES: Cc1cccc(CNC(=O)c2cc(-c3ccc4nc(N)nn4c3)cs2)c1C] |
| 224 | 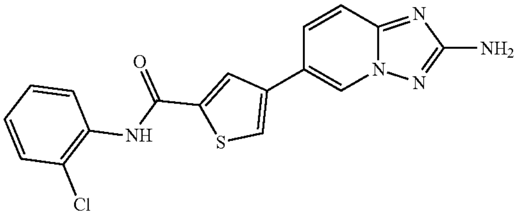 [SMILES: Nc1nc2ccc(-c3csc(C(=O)Nc4ccccc4Cl)c3)cn2n1] |
| 225 | 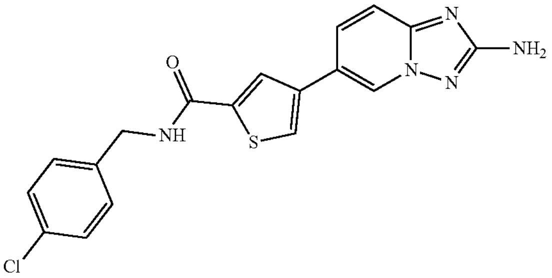 [SMILES: Nc1nc2ccc(-c3csc(C(=O)NCc4ccc(Cl)cc4)c3)cn2n1] |
| 226 | 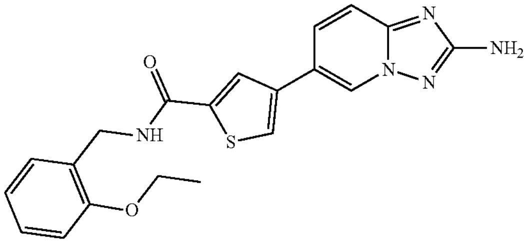 [SMILES: CCOc1ccccc1CNC(=O)c1cc(-c2ccc3nc(N)nn3c2)cs1] |

TABLE IC-continued
| Compound Number | Structure |
|---|---|
| 227 | 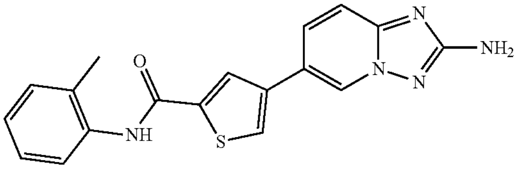 [SMILES: Cc1ccccc1NC(=O)c1cc(-c2ccc3nc(N)nn3c2)cs1] |
| 228 | 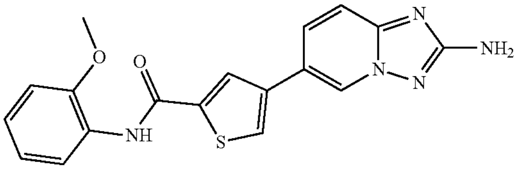 [SMILES: COc1ccccc1NC(=O)c1cc(-c2ccc3nc(N)nn3c2)cs1] |
| 229 | 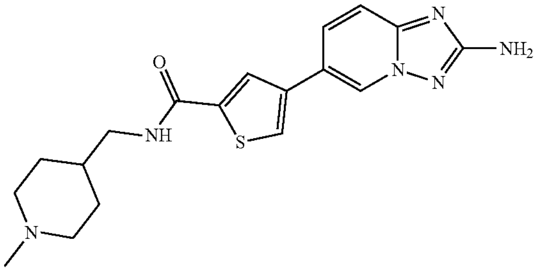 [SMILES: CN1CCC(CNC(=O)c2cc(-c3ccc4nc(N)nn4c3)cs2)CC1] |
| 230 | 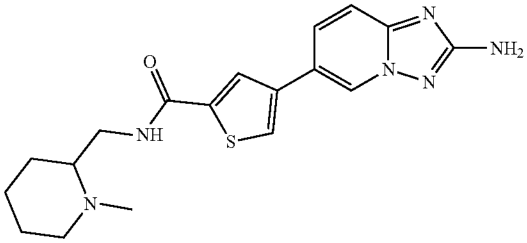 [SMILES: CN1CCCCC1CNC(=O)c1cc(-c2ccc3nc(N)nn3c2)cs1] |
| 231 | 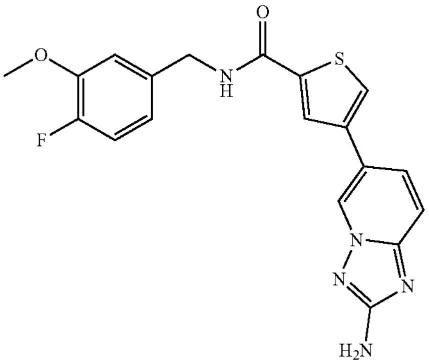 [SMILES: COc1cc(CNC(=O)c2cc(-c3ccc4nc(N)nn4c3)cs2)ccc1F] |
| 232 | 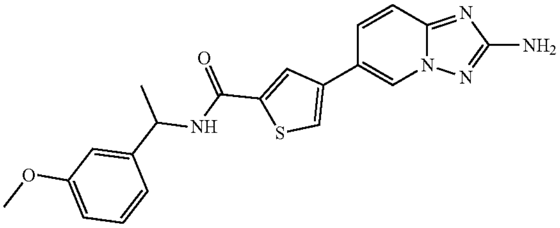 [SMILES: COc1cccc(C(C)NC(=O)c2cc(-c3ccc4nc(N)nn4c3)cs2)c1] |

TABLE IC-continued
| Compound Number | Structure |
| --- | --- |
| 233 | 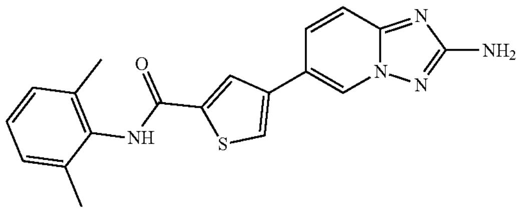 [SMILES: Cc1cccc(C)c1NC(=O)c1cc(-c2ccc3nc(N)nn3c2)cs1] |
| 234 | 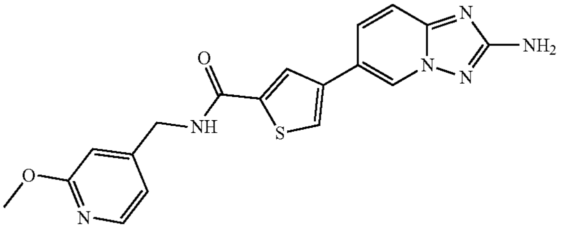 [SMILES: COc1cc(CNC(=O)c2cc(-c3ccc4nc(N)nn4c3)cs2)ccn1] |
| 235 | 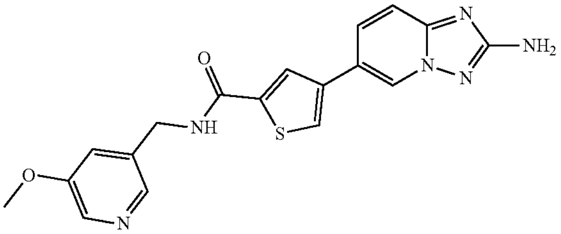 [SMILES: COc1cncc(CNC(=O)c2cc(-c3ccc4nc(N)nn4c3)cs2)c1] |
| 236 | 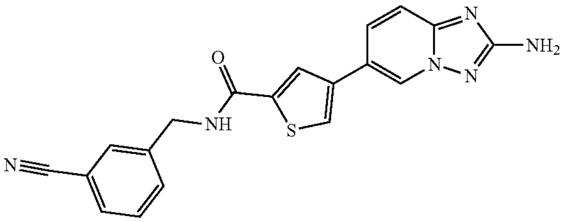 [SMILES: N#Cc1cccc(CNC(=O)c2cc(-c3ccc4nc(N)nn4c3)cs2)c1] |
| 237 | 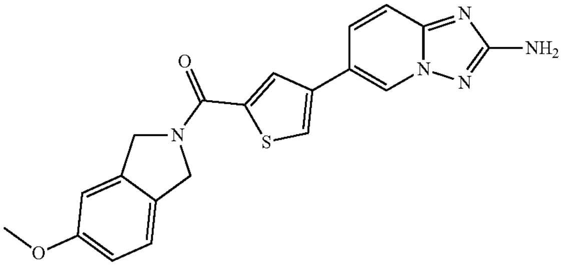 [SMILES: COc1ccc2c(c1)CN(C(=O)c1cc(-c3ccc4nc(N)nn4c3)cs1)C2] |
| 238 | 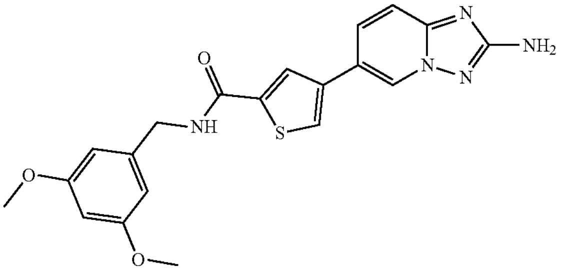 [SMILES: COc1cc(CNC(=O)c2cc(-c3ccc4nc(N)nn4c3)cs2)cc(OC)c1] |

TABLE IC-continued
| Compound Number | Structure |
| --- | --- |
| 239 | 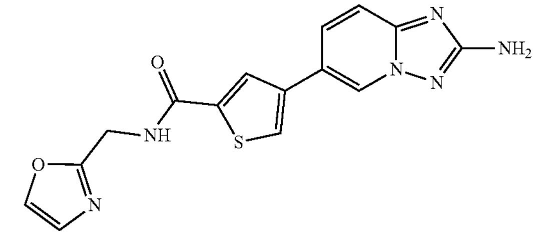 |
| 240 | 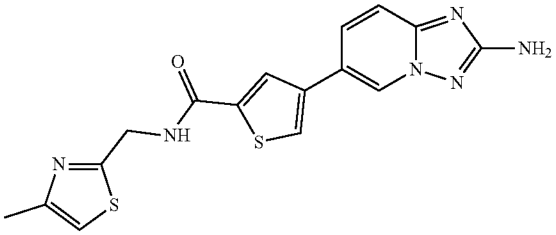 [SMILES: Cc1csc(CNC(=O)c2cc(-c3ccc4nc(N)nn4c3)cs2)n1] |
| 241 | 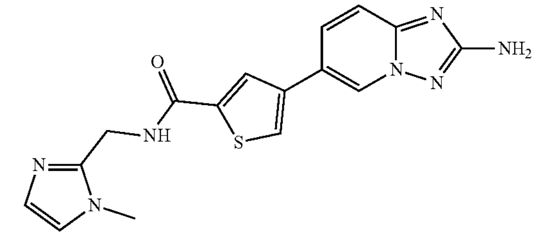 |
| 242 | 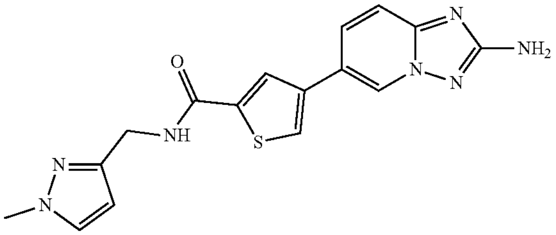 [SMILES: Cn1ccc(CNC(=O)c2cc(-c3ccc4nc(N)nn4c3)cs2)n1] |
| 243 | 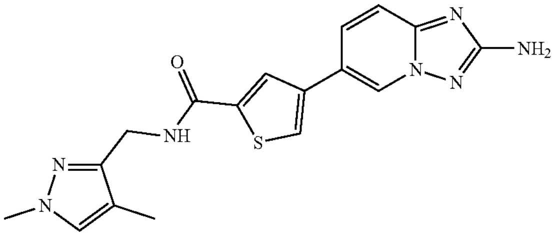 [SMILES: Cc1cn(C)nc1CNC(=O)c1cc(-c2ccc3nc(N)nn3c2)cs1] |
| 244 | 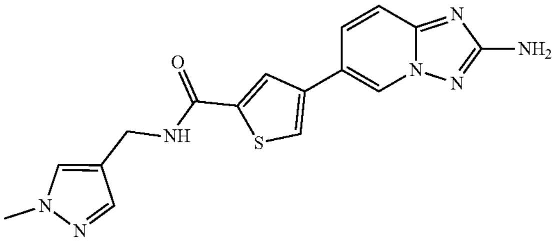 [SMILES: Cn1cc(CNC(=O)c2cc(-c3ccc4nc(N)nn4c3)cs2)cn1] |

TABLE IC-continued
| Compound Number | Structure |
| --- | --- |
| 245 | 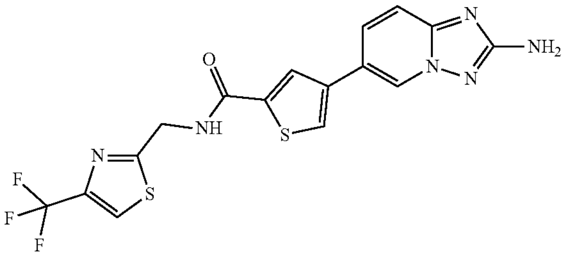 [SMILES: Nc1nc2ccc(-c3csc(C(=O)NCc4nc(C(F)(F)F)cs4)c3)cn2n1] |
| 246 | 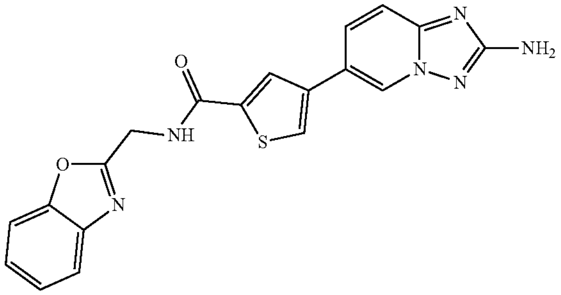 [SMILES: Nc1nc2ccc(-c3csc(C(=O)NCc4nc5ccccc5o4)c3)cn2n1] |
| 247 | 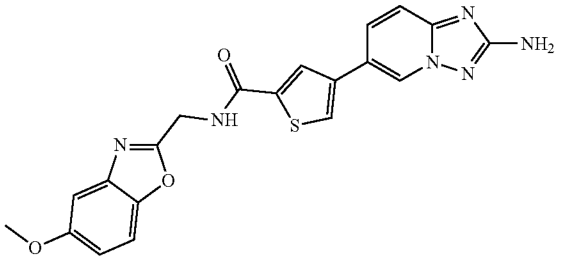 [SMILES: COc1ccc2oc(CNC(=O)c3cc(-c4ccc5nc(N)nn5c4)cs3)nc2c1] |
| 248 | 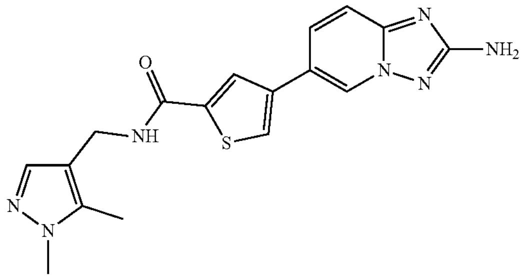 [SMILES: Cc1c(CNC(=O)c2cc(-c3ccc4nc(N)nn4c3)cs2)cnn1C] |
| 249 | 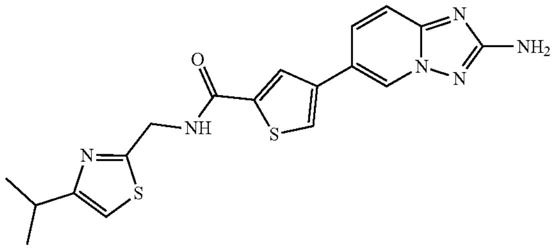 [SMILES: CC(C)c1csc(CNC(=O)c2cc(-c3ccc4nc(N)nn4c3)cs2)n1] |

TABLE IC-continued
| Compound Number | Structure |
| --- | --- |
| 250 | 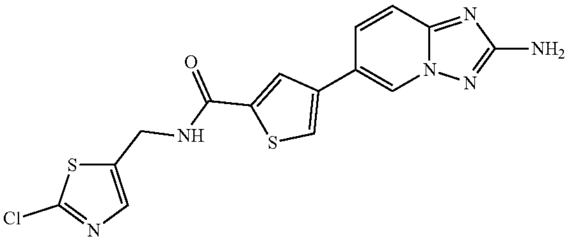 [SMILES: Nc1nc2ccc(-c3csc(C(=O)NCc4cnc(Cl)s4)c3)cn2n1] |
| 251 | 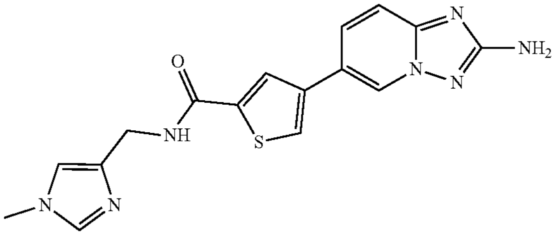 [SMILES: Cn1cnc(CNC(=O)c2cc(-c3ccc4nc(N)nn4c3)cs2)c1] |
| 252 | 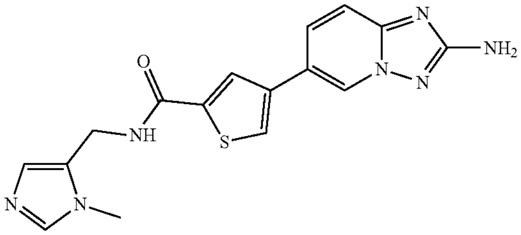 [SMILES: Cn1cncc1CNC(=O)c1cc(-c2ccc3nc(N)nn3c2)cs1] |
| 253 | 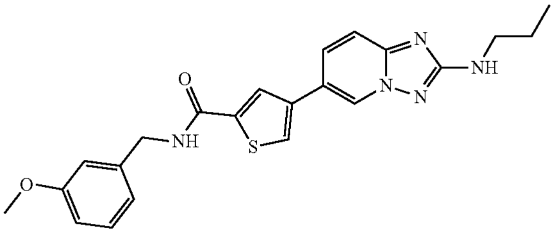 [SMILES: CCCNc1nc2ccc(-c3csc(C(=O)NCc4cccc(OC)c4)c3)cn2n1] |
| 254 | 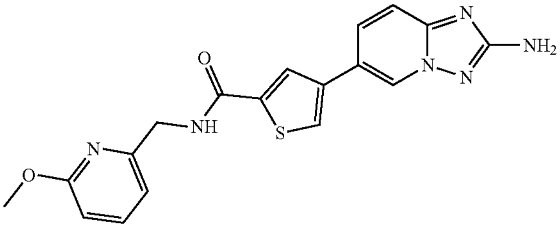 [SMILES: COc1cccc(CNC(=O)c2cc(-c3ccc4nc(N)nn4c3)cs2)n1] |
| 255 | 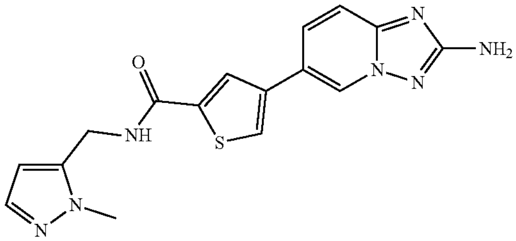 [SMILES: Cn1nccc1CNC(=O)c1cc(-c2ccc3nc(N)nn3c2)cs1] |

TABLE IC-continued
| Compound Number | Structure |
|---|---|
| 256 | 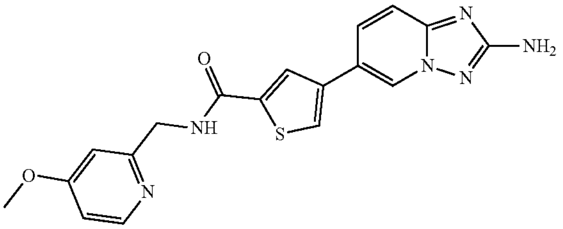 [SMILES: COc1ccnc(CNC(=O)c2cc(-c3ccc4nc(N)nn4c3)cs2)c1] |
| 257 | 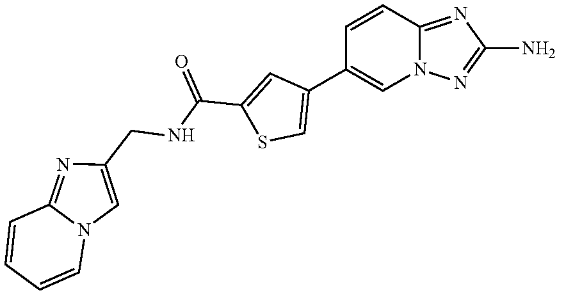 [SMILES: Nc1nc2ccc(-c3csc(C(=O)NCc4cn5ccccc5n4)c3)cn2n1] |
| 258 | 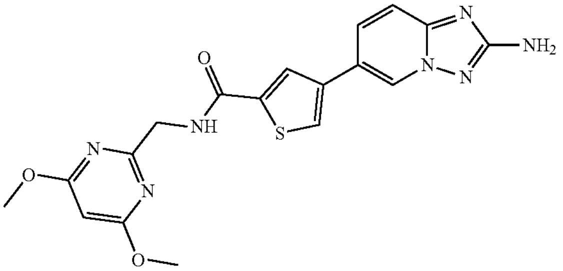 [SMILES: COc1cc(OC)nc(CNC(=O)c2cc(-c3ccc4nc(N)nn4c3)cs2)n1] |
| 259 | 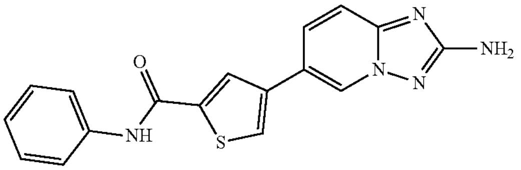 [SMILES: Nc1nc2ccc(-c3csc(C(=O)Nc4ccccc4)c3)cn2n1] |
| 260 | 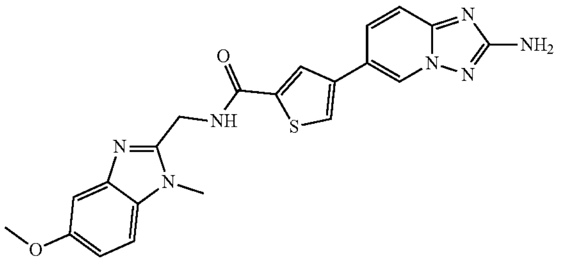 [SMILES: COc1ccc2c(c1)nc(CNC(=O)c1cc(-c3ccc4nc(N)nn4c3)cs1)n2C] |
| 261 | 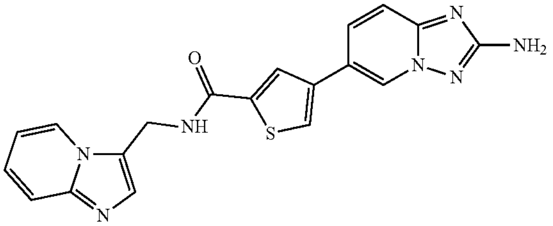 [SMILES: Nc1nc2ccc(-c3csc(C(=O)NCc4cnc5ccccn45)c3)cn2n1] |

TABLE IC-continued
| Compound Number | Structure |
|---|---|
| 262 | 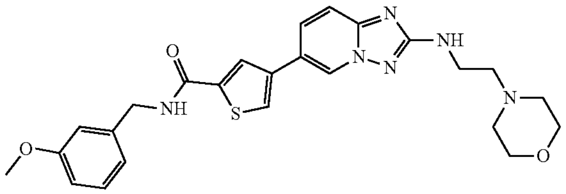 [SMILES: COc1cccc(CNC(=O)c2cc(-c3ccc4nc(NCCN5CCOCC5)nn4c3)cs2)c1] |
| 263 | 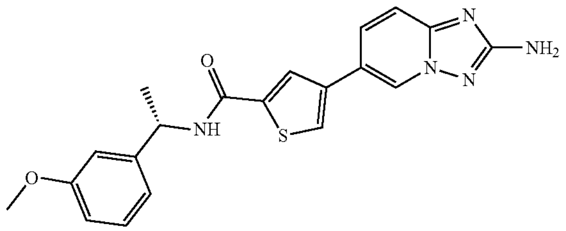 |
| 264 | 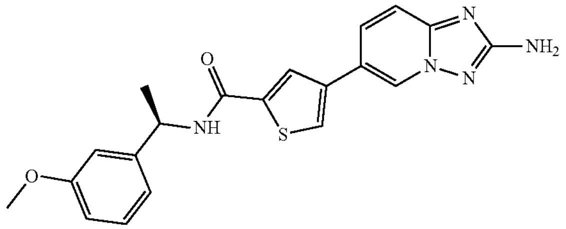 [SMILES: COc1cccc([C@@H](C)NC(=O)c2cc(-c3ccc4nc(N)nn4c3)cs2)c1] |
| 265 | 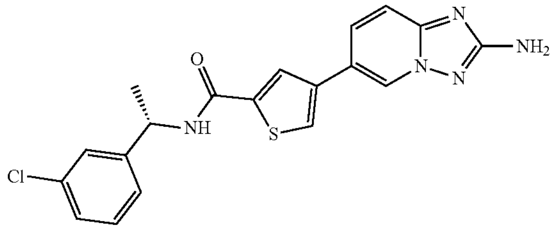 [SMILES: C[C@H](NC(=O)c1cc(-c2ccc3nc(N)nn3c2)cs1)c1cccc(Cl)c1] |
| 266 | 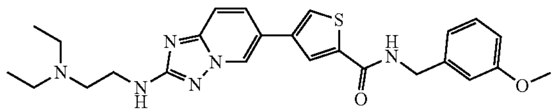 [SMILES: CCN(CC)CCNc1nc2ccc(-c3csc(C(=O)NCc4cccc(OC)c4)c3)cn2n1] |
| 267 | 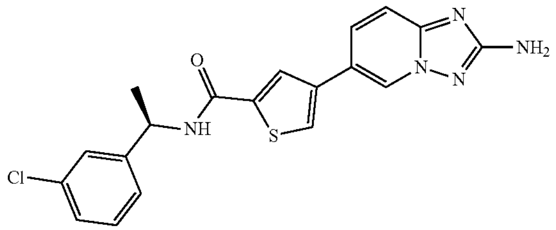 [SMILES: C[C@@H](NC(=O)c1cc(-c2ccc3nc(N)nn3c2)cs1)c1cccc(Cl)c1] |
| 268 | 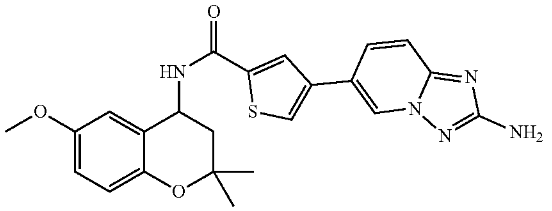 [SMILES: COc1ccc2c(c1)C(NC(=O)c1cc(-c3ccc4nc(N)nn4c3)cs1)CC(C)(C)O2] |

TABLE IC-continued
| Compound Number | Structure |
|---|---|
| 269 | 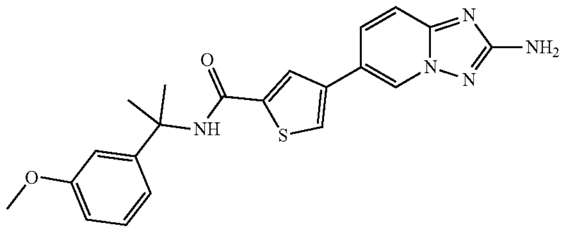 [SMILES: COc1cccc(C(C)(C)NC(=O)c2cc(-c3ccc4nc(N)nn4c3)cs2)c1] |
| 270 | 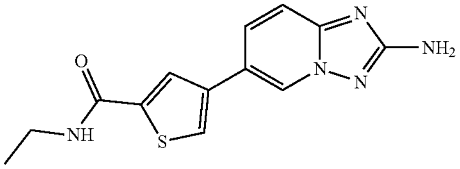 [SMILES: CCNC(=O)c1cc(-c2ccc3nc(N)nn3c2)cs1] |
| 271 | 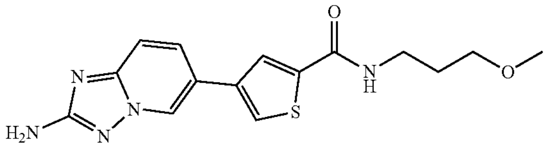 [SMILES: COCCCNC(=O)c1cc(-c2ccc3nc(N)nn3c2)cs1] |
| 272 | 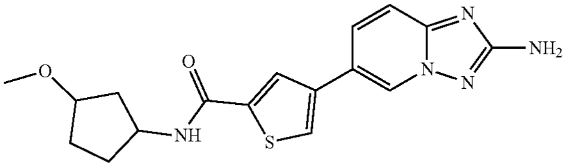 [SMILES: COC1CCC(NC(=O)c2cc(-c3ccc4nc(N)nn4c3)cs2)C1] |
| 273 | 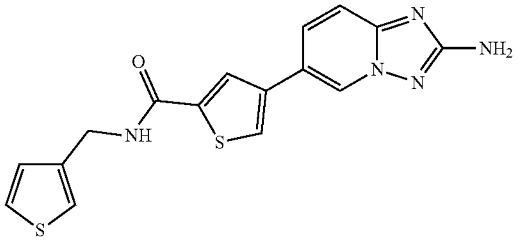 |
| 274 | 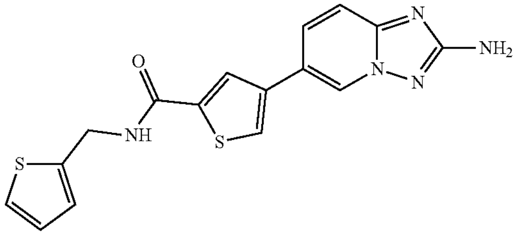 |
| 275 | 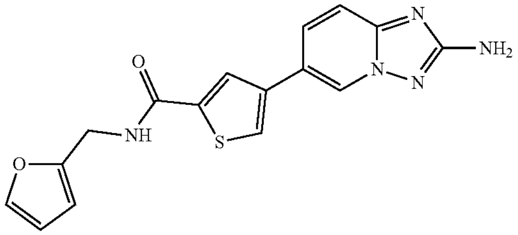 |

TABLE IC-continued
| Compound Number | Structure |
|---|---|
| 276 | 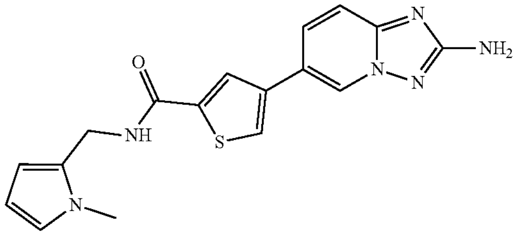 [SMILES: Cn1cccc1CNC(=O)c1cc(-c2ccc3nc(N)nn3c2)cs1] |
| 277 | 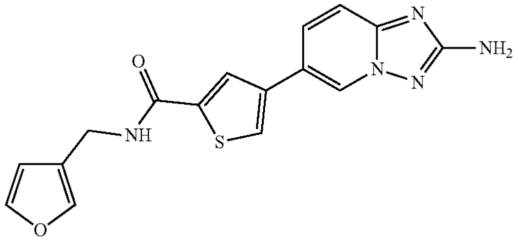 |
| 278 | 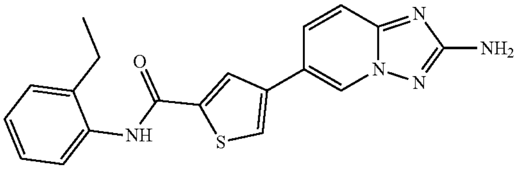 [SMILES: CCc1ccccc1NC(=O)c1cc(-c2ccc3nc(N)nn3c2)cs1] |
| 279 | 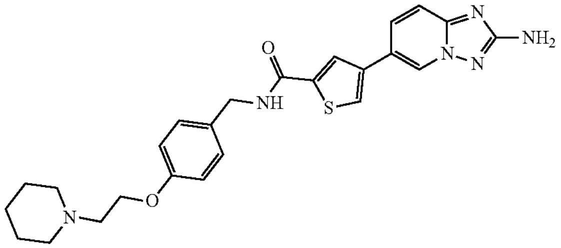 [SMILES: Nc1nc2ccc(-c3csc(C(=O)NCc4ccc(OCCN5CCCCC5)cc4)c3)cn2n1] |
| 280 | 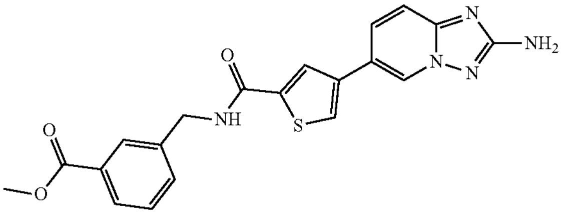 [SMILES: COC(=O)c1cccc(CNC(=O)c2cc(-c3ccc4nc(N)nn4c3)cs2)c1] |
| 281 | 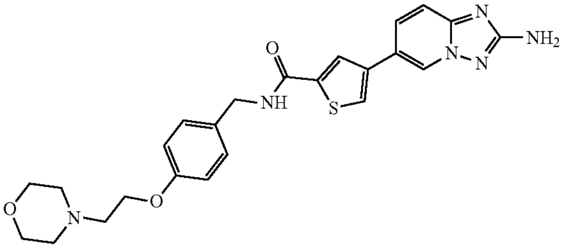 [SMILES: Nc1nc2ccc(-c3csc(C(=O)NCc4ccc(OCCN5CCOCC5)cc4)c3)cn2n1] |

TABLE IC-continued
| Compound Number | Structure |
|---|---|
| 282 | 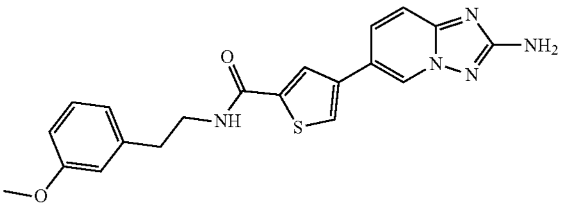 [SMILES: COc1cccc(CCNC(=O)c2cc(-c3ccc4nc(N)nn4c3)cs2)c1] |
| 283 | 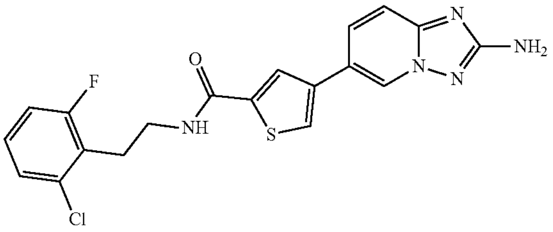 [SMILES: Nc1nc2ccc(-c3csc(C(=O)NCCc4c(F)cccc4Cl)c3)cn2n1] |
| 284 | 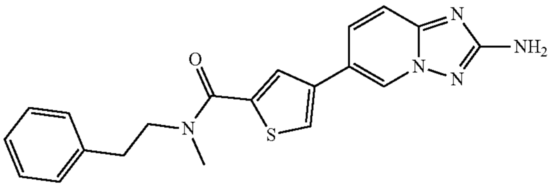 [SMILES: CN(CCc1ccccc1)C(=O)c1cc(-c2ccc3nc(N)nn3c2)cs1] |
| 285 | 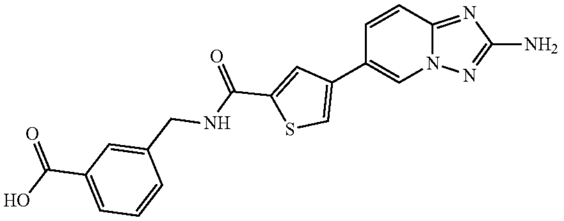 [SMILES: Nc1nc2ccc(-c3csc(C(=O)NCc4cccc(C(=O)O)c4)c3)cn2n1] |
| 286 | 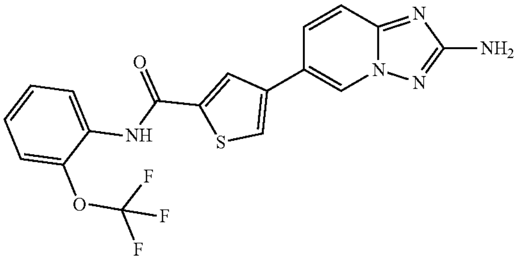 [SMILES: Nc1nc2ccc(-c3csc(C(=O)Nc4ccccc4OC(F)(F)F)c3)cn2n1] |
| 287 | 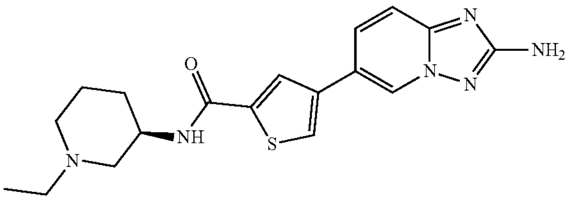 [SMILES: CCN1CCC[C@@H](NC(=O)c2cc(-c3ccc4nc(N)nn4c3)cs2)C1] |

TABLE IC-continued
| Compound Number | Structure |
|---|---|
| 288 | 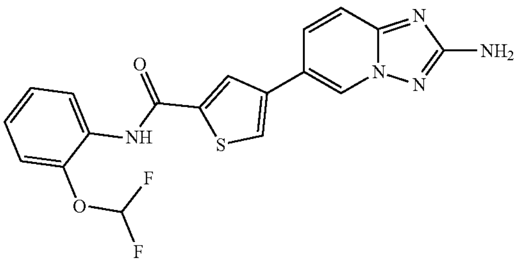 [SMILES: Nc1nc2ccc(-c3csc(C(=O)Nc4ccccc4OC(F)F)c3)cn2n1] |
| 289 | 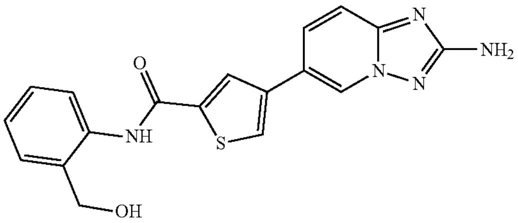 [SMILES: Nc1nc2ccc(-c3csc(C(=O)Nc4ccccc4CO)c3)cn2n1] |
| 290 | 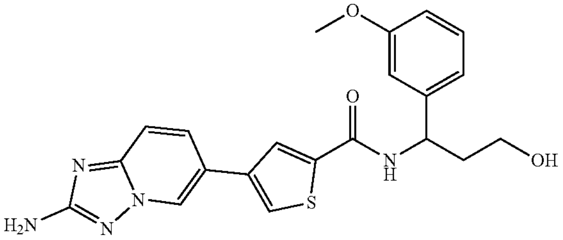 [SMILES: COc1cccc(C(CCO)NC(=O)c2cc(-c3ccc4nc(N)nn4c3)cs2)c1] |
| 291 | 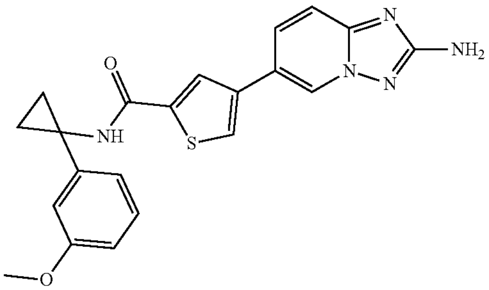 [SMILES: COc1cccc(C2(NC(=O)c3cc(-c4ccc5nc(N)nn5c4)cs3)CC2)c1] |
| 292 | 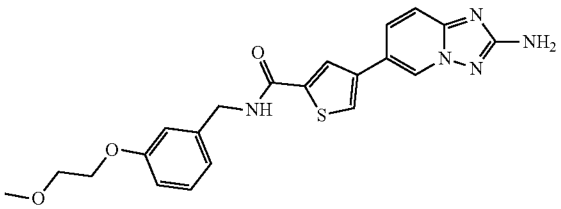 [SMILES: COCCOc1cccc(CNC(=O)c2cc(-c3ccc4nc(N)nn4c3)cs2)c1] |
| 293 | 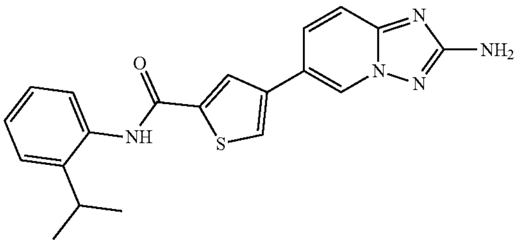 [SMILES: CC(C)c1ccccc1NC(=O)c1cc(-c2ccc3nc(N)nn3c2)cs1] |

TABLE IC-continued
| Compound Number | Structure |
| --- | --- |
| 294 | 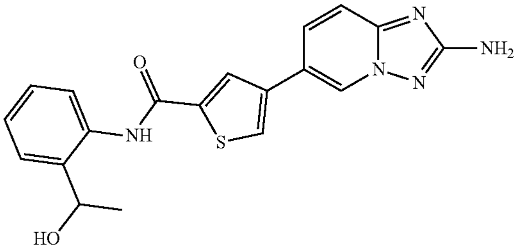 [SMILES: CC(O)c1ccccc1NC(=O)c1cc(-c2ccc3nc(N)nn3c2)cs1] |
| 295 | 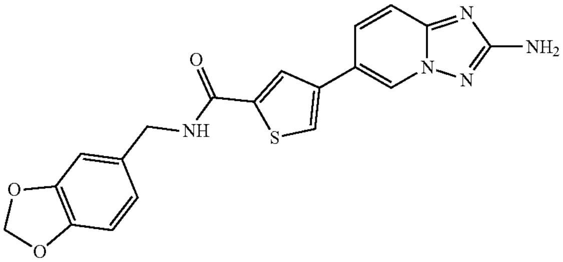 [SMILES: Nc1nc2ccc(-c3csc(C(=O)NCc4ccc5c(c4)OCO5)c3)cn2n1] |
| 296 | 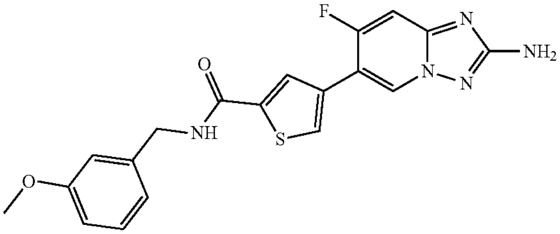 [SMILES: COc1cccc(CNC(=O)c2cc(-c3cn4nc(N)nc4cc3F)cs2)c1] |
| 297 | 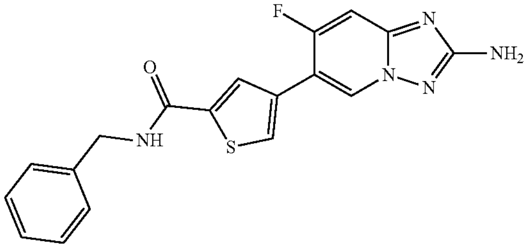 [SMILES: Nc1nc2cc(F)c(-c3csc(C(=O)NCc4ccccc4)c3)cn2n1] |
| 298 | 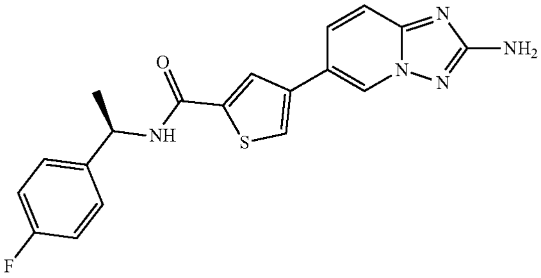 [SMILES: C[C@@H](NC(=O)c1cc(-c2ccc3nc(N)nn3c2)cs1)c1ccc(F)cc1] |

TABLE IC-continued
| Compound Number | Structure |
|---|---|
| 299 | 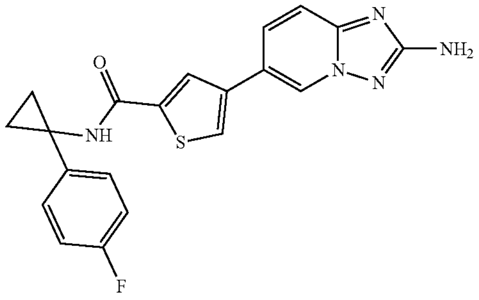 [SMILES: Nc1nc2ccc(-c3csc(C(=O)NC4(c5ccc(F)cc5)CC4)c3)cn2n1] |
| 300 | 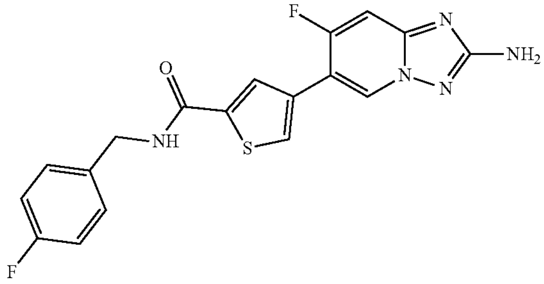 [SMILES: Nc1nc2cc(F)c(-c3csc(C(=O)NCc4ccc(F)cc4)c3)cn2n1] |
| 301 | 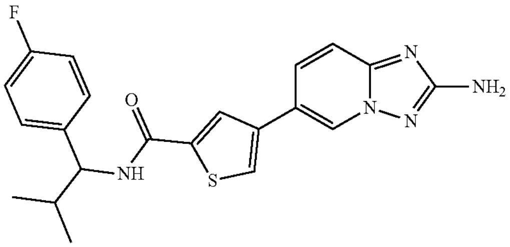 [SMILES: CC(C)C(NC(=O)c1cc(-c2ccc3nc(N)nn3c2)cs1)c1ccc(F)cc1] |
| 302 | 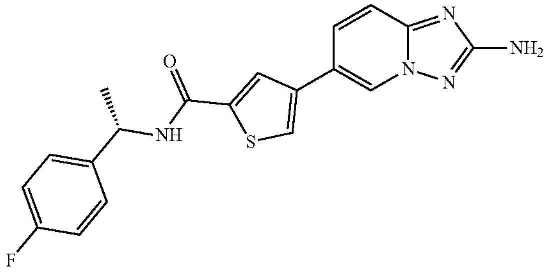 [SMILES: C[C@H](NC(=O)c1cc(-c2ccc3nc(N)nn3c2)cs1)c1ccc(F)cc1] |
| 303 | 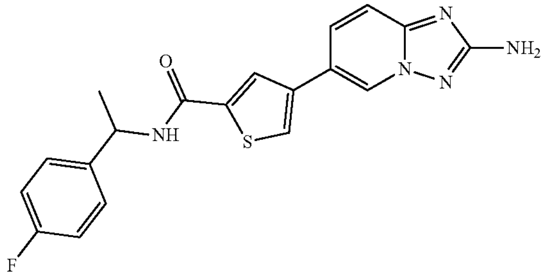 [SMILES: CC(NC(=O)c1cc(-c2ccc3nc(N)nn3c2)cs1)c1ccc(F)cc1] |

TABLE IC-continued
| Compound Number | Structure |
|---|---|
| 304 | 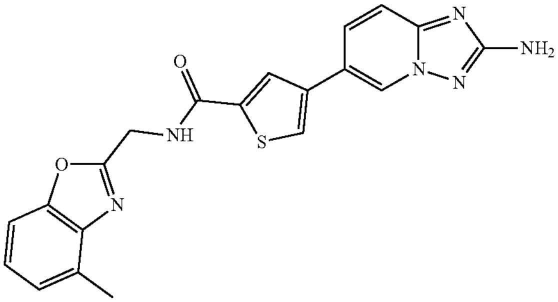 [SMILES: Cc1cccc2oc(CNC(=O)c3cc(-c4ccc5nc(N)nn5c4)cs3)nc12] |
| 305 | 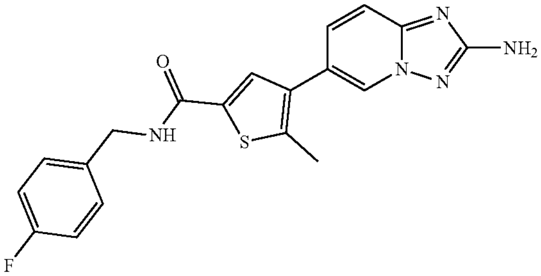 [SMILES: Cc1sc(C(=O)NCc2ccc(F)cc2)cc1-c1ccc2nc(N)nn2c1] |
| 306 | 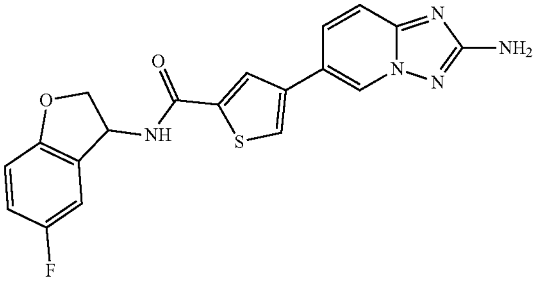 [SMILES: Nc1nc2ccc(-c3csc(C(=O)NC4COc5ccc(F)cc54)c3)cn2n1] |
| 307 | 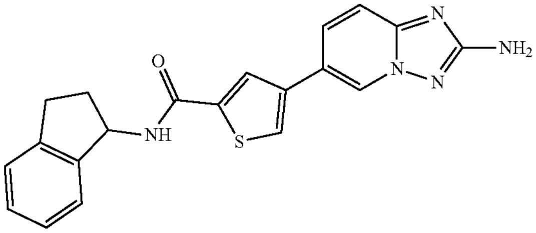 [SMILES: Nc1nc2ccc(-c3csc(C(=O)NC4CCc5ccccc54)c3)cn2n1] |
| 308 | 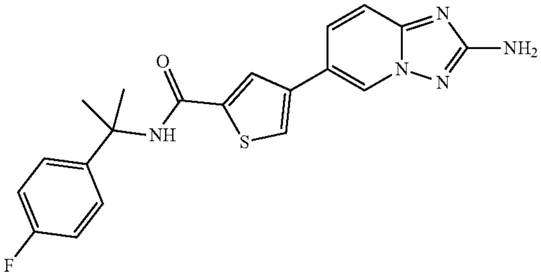 [SMILES: CC(C)(NC(=O)c1cc(-c2ccc3nc(N)nn3c2)cs1)c1ccc(F)cc1] |

TABLE IC-continued
| Compound Number | Structure |
|---|---|
| 309 | 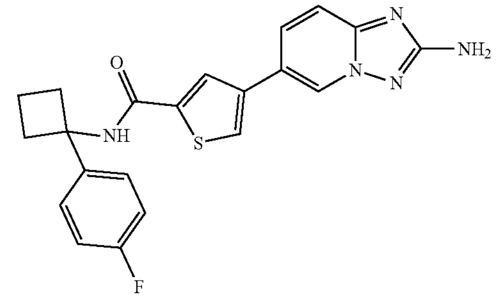 [SMILES: Nc1nc2ccc(-c3csc(C(=O)NC4(c5ccc(F)cc5)CCC4)c3)cn2n1] |
| 310 | 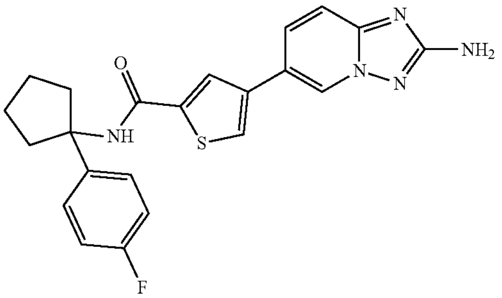 [SMILES: Nc1nc2ccc(-c3csc(C(=O)NC4(c5ccc(F)cc5)CCCC4)c3)cn2n1] |
| 311 | 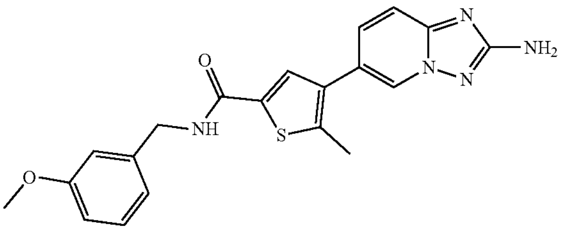 [SMILES: COc1cccc(CNC(=O)c2cc(-c3ccc4nc(N)nn4c3)c(C)s2)c1] |
| 312 | 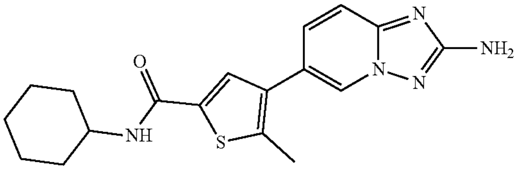 [SMILES: Cc1sc(C(=O)NC2CCCCC2)cc1-c1ccc2nc(N)nn2c1] |
| 313 | 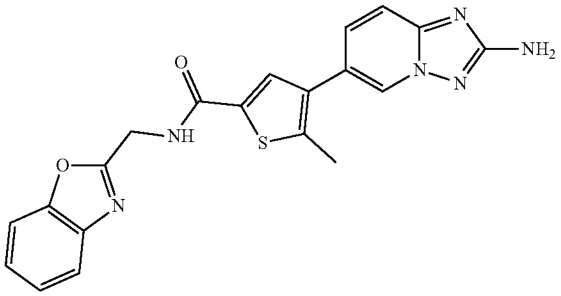 [SMILES: Cc1sc(C(=O)NCc2nc3ccccc3o2)cc1-c1ccc2nc(N)nn2c1] |

TABLE IC-continued
| Compound Number | Structure |
|---|---|
| 314 | 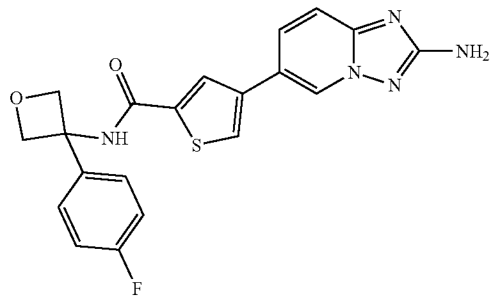 [SMILES: Nc1nc2ccc(-c3csc(C(=O)NC4(c5ccc(F)cc5)COC4)c3)cn2n1] |
| 315 | 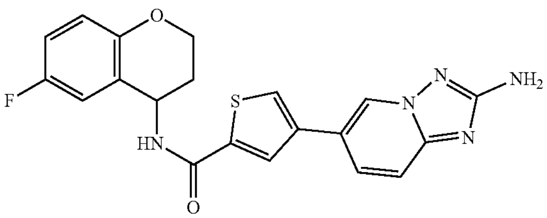 [SMILES: Nc1nc2ccc(-c3csc(C(=O)NC4CCOc5ccc(F)cc54)c3)cn2n1] |
| 316 | 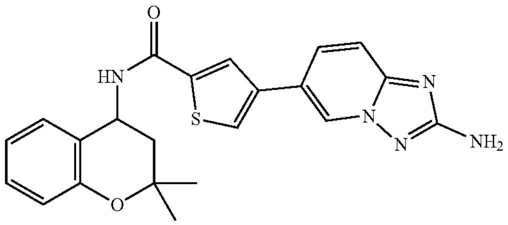 [SMILES: CC1(C)CC(NC(=O)c2cc(-c3ccc4nc(N)nn4c3)cs2)c2ccccc2O1] |
| 317 | 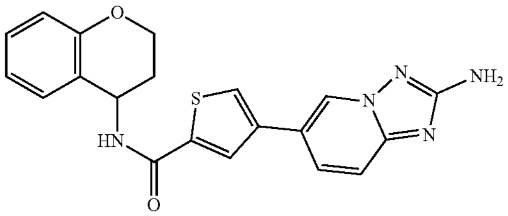 [SMILES: Nc1nc2ccc(-c3csc(C(=O)NC4CCOc5ccccc54)c3)cn2n1] |
| 318 | 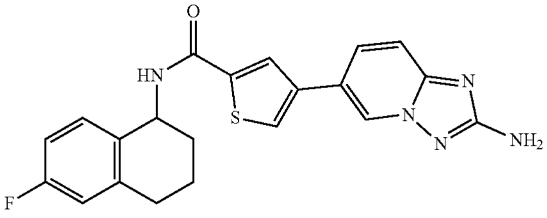 [SMILES: Nc1nc2ccc(-c3csc(C(=O)NC4CCCc5cc(F)ccc54)c3)cn2n1] |
| 319 | 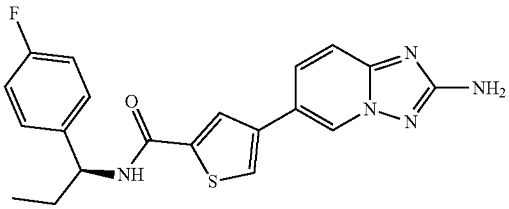 [SMILES: CC[C@H](NC(=O)c1cc(-c2ccc3nc(N)nn3c2)cs1)c1ccc(F)cc1] |

TABLE IC-continued
| Compound Number | Structure |
|---|---|
| 320 | 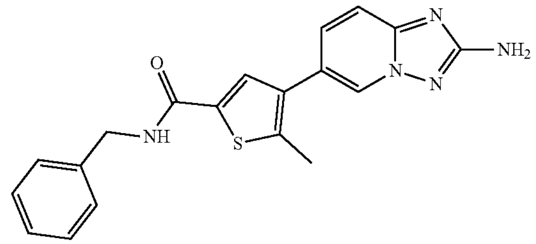 [SMILES: Cc1sc(C(=O)NCc2ccccc2)cc1-c1ccc2nc(N)nn2c1] |
| 321 | 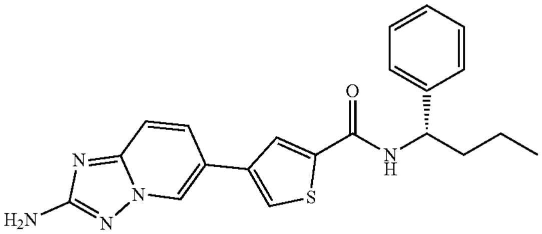 |
| 322 | 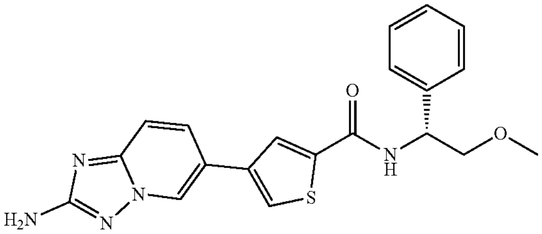 [SMILES: CCC[C@H](NC(=O)c1cc(-c2ccc3nc(N)nn3c2)cs1)c1ccccc1] |
| 323 | 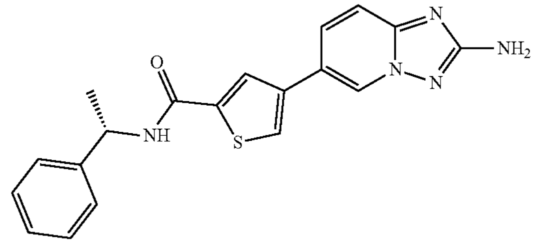 [SMILES: C[C@H](NC(=O)c1cc(-c2ccc3nc(N)nn3c2)cs1)c1ccccc1] |
| 324 | 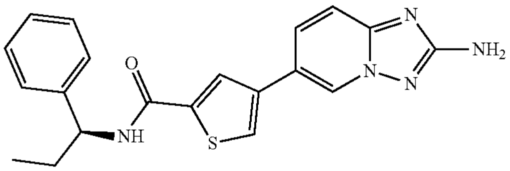 [SMILES: CC[C@H](NC(=O)c1cc(-c2ccc3nc(N)nn3c2)cs1)c1ccccc1] |
| 325 | 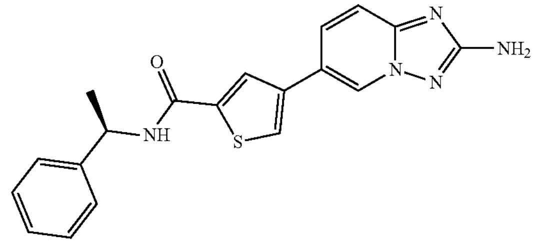 [SMILES: C[C@@H](NC(=O)c1cc(-c2ccc3nc(N)nn3c2)cs1)c1ccccc1] |

TABLE IC-continued
| Compound Number | Structure |
| --- | --- |
| 326 | 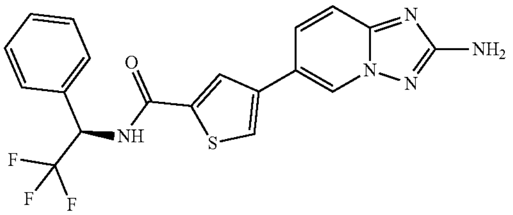 [SMILES: Nc1nc2ccc(-c3csc(C(=O)N[C@H](c4ccccc4)C(F)(F)F)c3)cn2n1] |
| 327 | 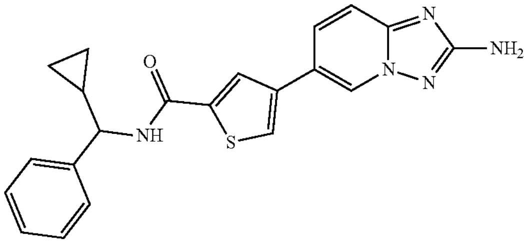 [SMILES: Nc1nc2ccc(-c3csc(C(=O)NC(c4ccccc4)C4CC4)c3)cn2n1] |
| 328 | 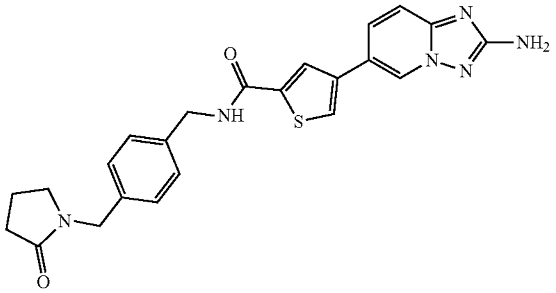 [SMILES: Nc1nc2ccc(-c3csc(C(=O)NCc4ccc(CN5CCCC5=O)cc4)c3)cn2n1] |
| 329 | 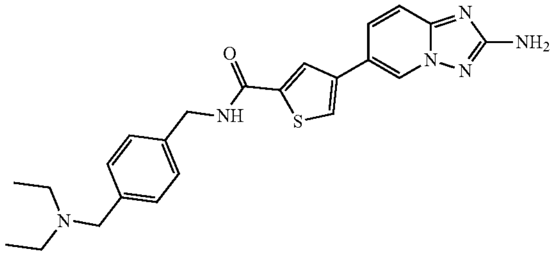 [SMILES: CCN(CC)Cc1ccc(CNC(=O)c2cc(-c3ccc4nc(N)nn4c3)cs2)cc1] |
| 330 | 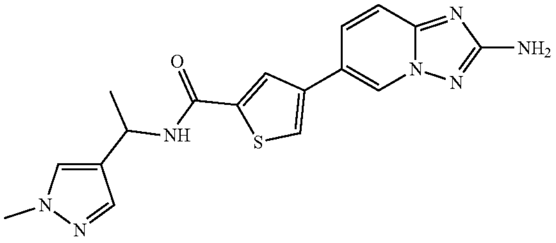 |
| 331 | 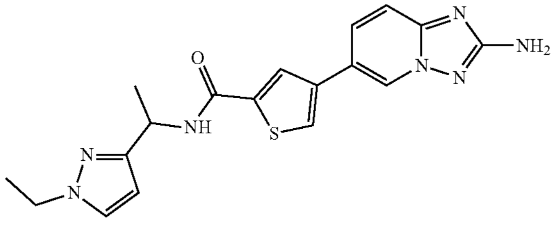 [SMILES: CCn1ccc(C(C)NC(=O)c2cc(-c3ccc4nc(N)nn4c3)cs2)n1] |

TABLE IC-continued
| Compound Number | Structure |
| --- | --- |
| 332 | 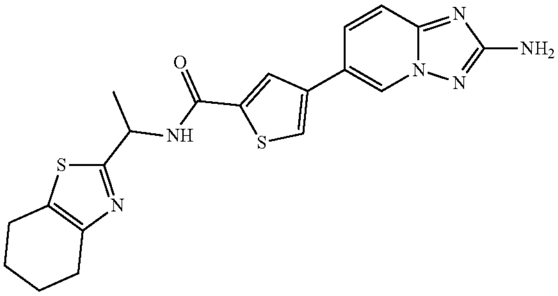 [SMILES: CC(NC(=O)c1cc(-c2ccc3nc(N)nn3c2)cs1)c1nc2c(s1)CCCC2] |
| 333 | 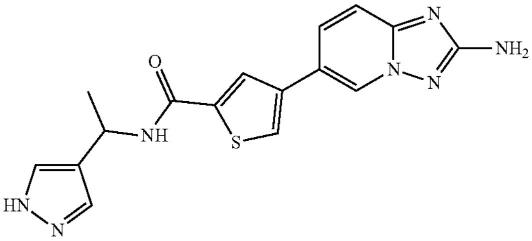 [SMILES: CC(NC(=O)c1cc(-c2ccc3nc(N)nn3c2)cs1)c1cn[nH]c1] |
| 334 | 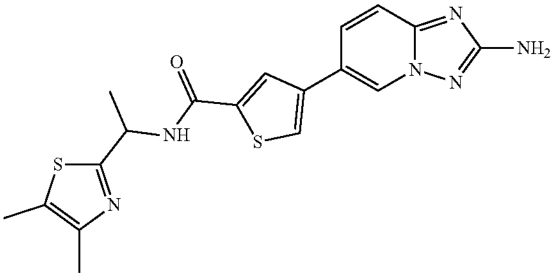 [SMILES: Cc1nc(C(C)NC(=O)c2cc(-c3ccc4nc(N)nn4c3)cs2)sc1C] |
| 335 | 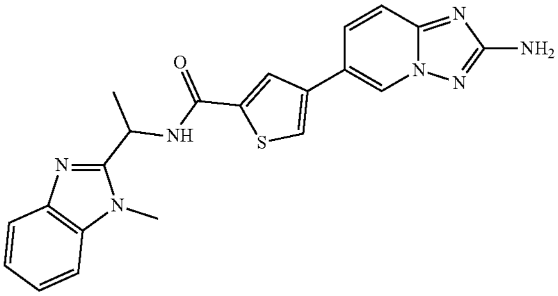 [SMILES: CC(NC(=O)c1cc(-c2ccc3nc(N)nn3c2)cs1)c1nc2ccccc2n1C] |
| 336 | 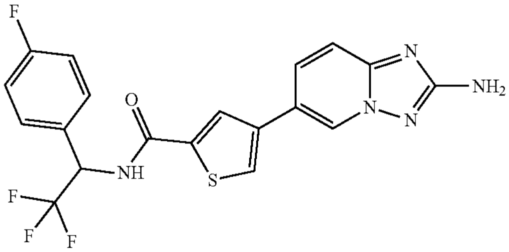 [SMILES: Nc1nc2ccc(-c3csc(C(=O)NC(c4ccc(F)cc4)C(F)(F)F)c3)cn2n1] |

TABLE IC-continued
| Compound Number | Structure |
|---|---|
| 337 | 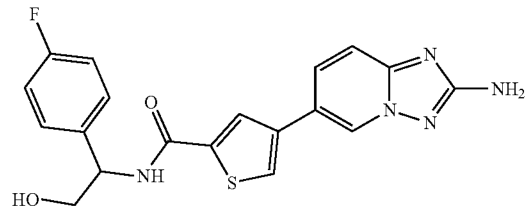 [SMILES: Nc1nc2ccc(-c3csc(C(=O)NC(CO)c4ccc(F)cc4)c3)cn2n1] |
| 338 | 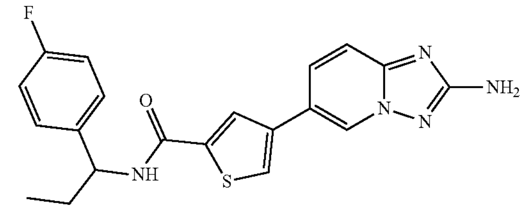 [SMILES: CCC(NC(=O)c1cc(-c2ccc3nc(N)nn3c2)cs1)c1ccc(F)cc1] |
| 339 | 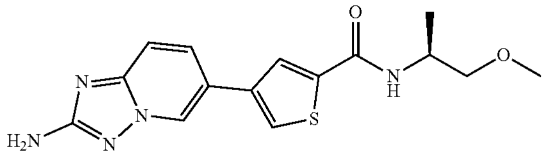 [SMILES: COC[C@H](C)NC(=O)c1cc(-c2ccc3nc(N)nn3c2)cs1] |
| 340 | 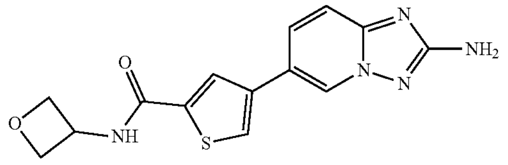 [SMILES: Nc1nc2ccc(-c3csc(C(=O)NC4COC4)c3)cn2n1] |
| 341 | 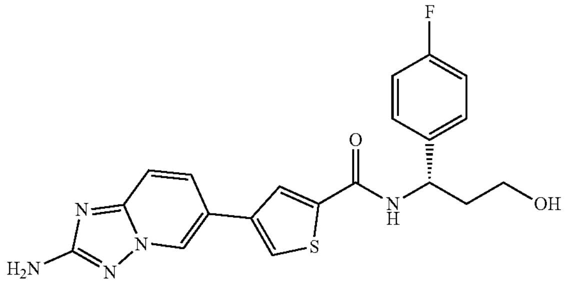 [SMILES: Nc1nc2ccc(-c3csc(C(=O)N[C@@H](CCO)c4ccc(F)cc4)c3)cn2n1] |
| 342 | 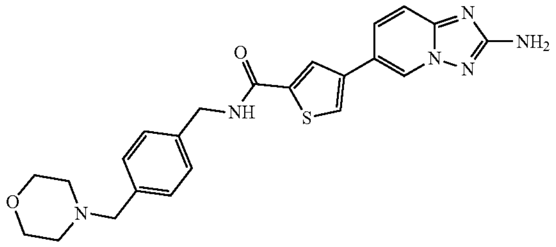 [SMILES: Nc1nc2ccc(-c3csc(C(=O)NCc4ccc(CN5CCOCC5)cc4)c3)cn2n1] |
| 343 | 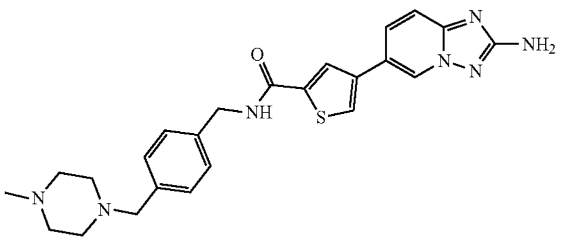 [SMILES: CN1CCN(Cc2ccc(CNC(=O)c3cc(-c4ccc5nc(N)nn5c4)cs3)cc2)CC1] |

TABLE IC-continued
| Compound Number | Structure |
| --- | --- |
| 344 | 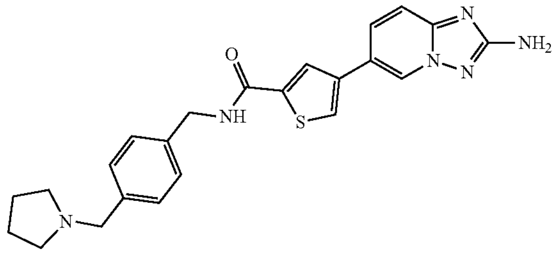 [SMILES: Nc1nc2ccc(-c3csc(C(=O)NCc4ccc(CN5CCCC5)cc4)c3)cn2n1] |
| 345 | 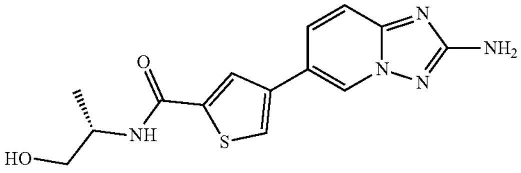 [SMILES: C[C@@H](CO)NC(=O)c1cc(-c2ccc3nc(N)nn3c2)cs1] |
| 346 | 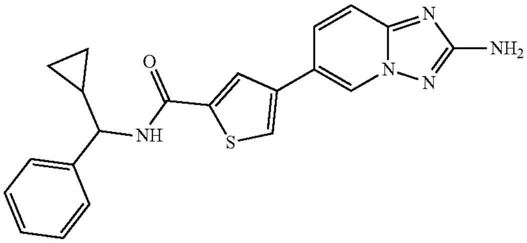 enantiomer 1 |
| 347 | 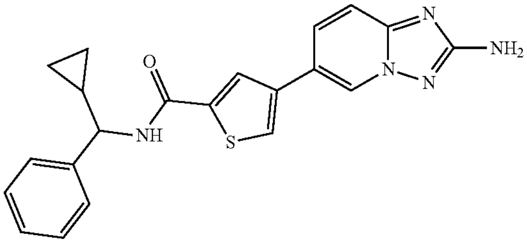 enantiomer 2 |
| 348 | 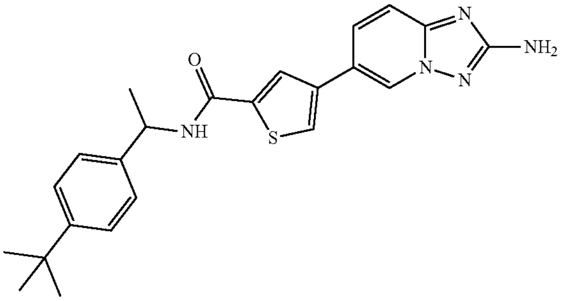 [SMILES: CC(NC(=O)c1cc(-c2ccc3nc(N)nn3c2)cs1)c1ccc(C(C)(C)C)cc1] |

TABLE IC-continued
| Compound Number | Structure |
|---|---|
| 349 | 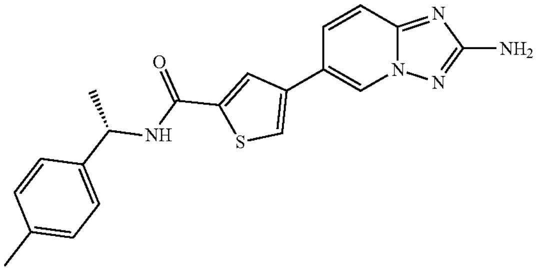 [SMILES: Cc1ccc([C@H](C)NC(=O)c2cc(-c3ccc4nc(N)nn4c3)cs2)cc1] |
| 350 | 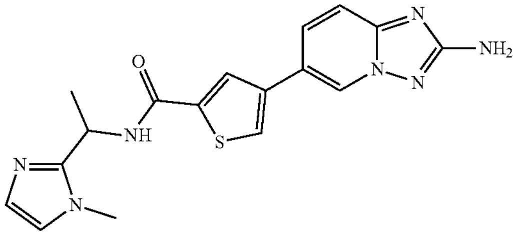 [SMILES: CC(NC(=O)c1cc(-c2ccc3nc(N)nn3c2)cs1)c1nccn1C] |
| 351 | 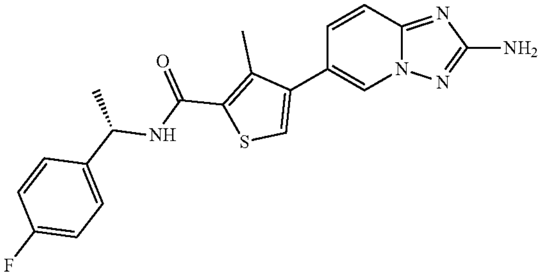 [SMILES: Cc1c(-c2ccc3nc(N)nn3c2)csc1C(=O)N[C@@H](C)c1ccc(F)cc1] |
| 352 | 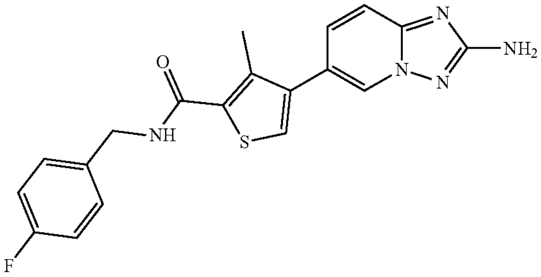 [SMILES: Cc1c(-c2ccc3nc(N)nn3c2)csc1C(=O)NCc1ccc(F)cc1] |
| 353 | 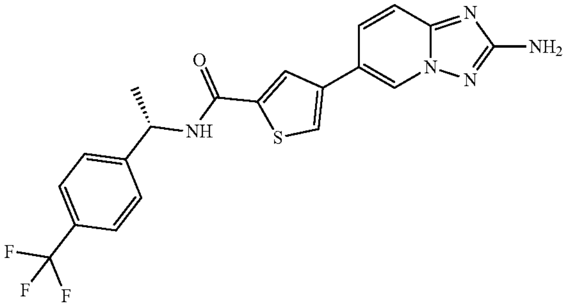 [SMILES: C[C@H](NC(=O)c1cc(-c2ccc3nc(N)nn3c2)cs1)c1ccc(C(F)(F)F)cc1] |

TABLE IC-continued
| Compound Number | Structure |
| --- | --- |
| 354 | 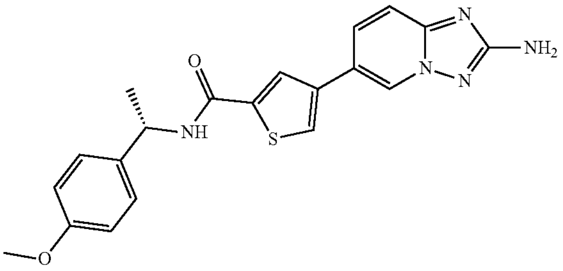 [SMILES: COc1ccc([C@H](C)NC(=O)c2cc(-c3ccc4nc(N)nn4c3)cs2)cc1] |
| 355 | 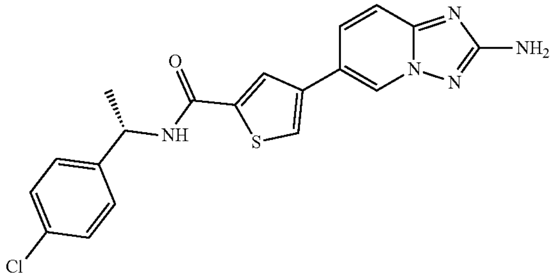 [SMILES: C[C@H](NC(=O)c1cc(-c2ccc3nc(N)nn3c2)cs1)c1ccc(Cl)cc1] |
| 356 | 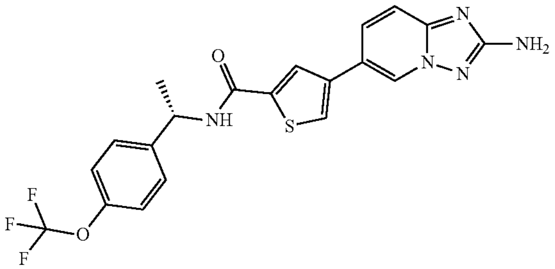 |
| 357 | 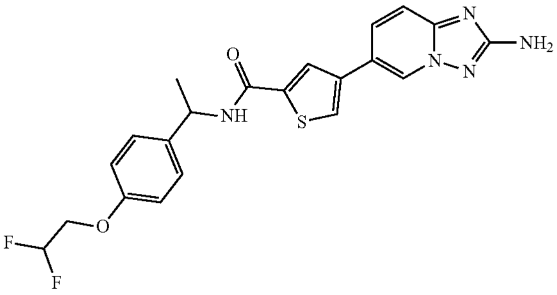 [SMILES: CC(NC(=O)c1cc(-c2ccc3nc(N)nn3c2)cs1)c1ccc(OCC(F)F)cc1] |
| 358 | 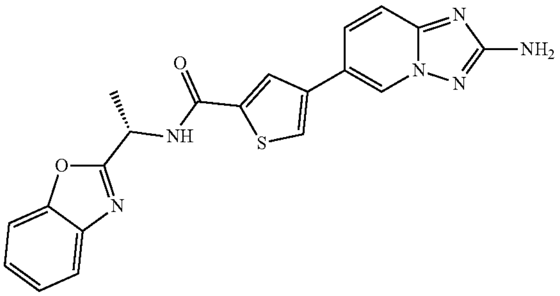 [SMILES: C[C@H](NC(=O)c1cc(-c2ccc3nc(N)nn3c2)cs1)c1nc2ccccc2o1] |

TABLE IC-continued
| Compound Number | Structure |
|---|---|
| 359 | 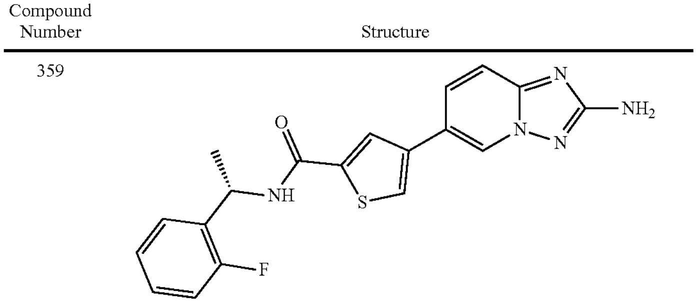 |
| 360 | 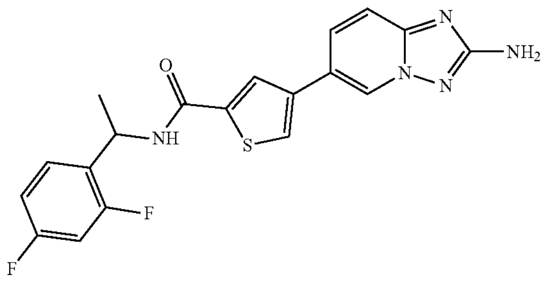 [SMILES: CC(NC(=O)c1cc(-c2ccc3nc(N)nn3c2)cs1)c1ccc(F)cc1F] |
| 361 | 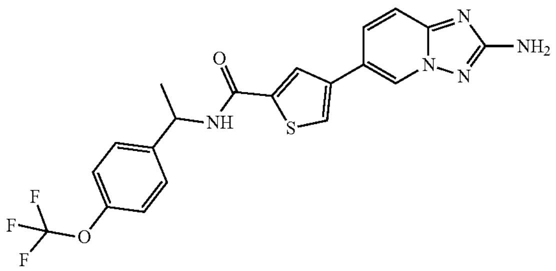 [SMILES: CC(NC(=O)c1cc(-c2ccc3nc(N)nn3c2)cs1)c1ccc(OC(F)(F)F)cc1] |
| 362 | 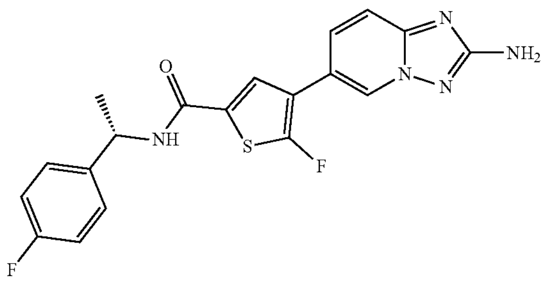 [SMILES: C[C@H](NC(=O)c1cc(-c2ccc3nc(N)nn3c2)c(F)s1)c1ccc(F)cc1] |
and pharmaceutically acceptable salts thereof.

In some embodiments, the compound is selected from the group consisting of the compounds disclosed in Table 1D below:
| Compound Number | Structure |
| --- | --- |
| 363 | 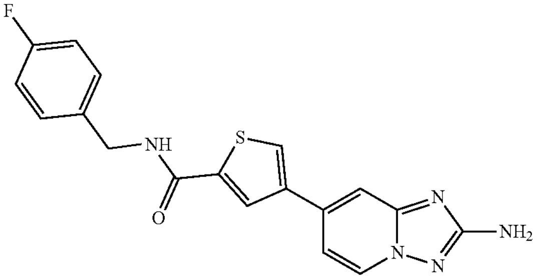 [SMILES: Nc1nc2cc(-c3csc(C(=O)NCc4ccc(F)cc4)c3)ccn2n1] |
| 364 | 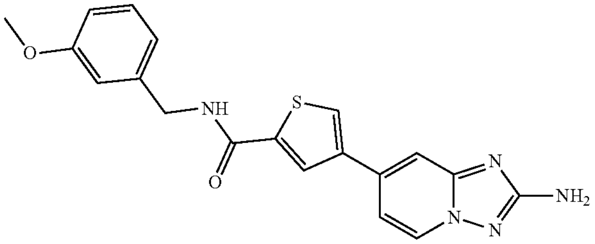 [SMILES: COc1cccc(CNC(=O)c2cc(-c3ccn4nc(N)nc4c3)cs2)c1] |
| 365 | 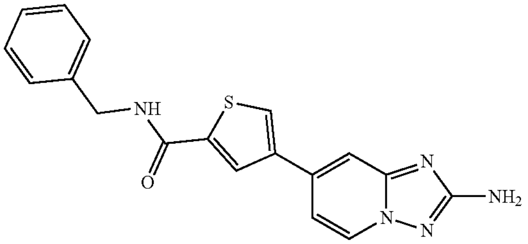 [SMILES: Nc1nc2cc(-c3csc(C(=O)NCc4ccccc4)c3)ccn2n1] |
| 366 | 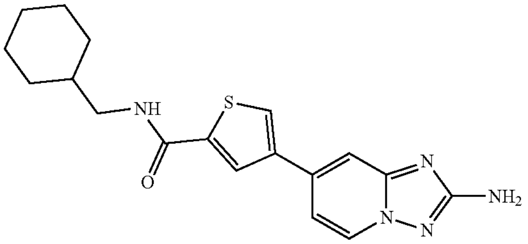 [SMILES: Nc1nc2cc(-c3csc(C(=O)NCC4CCCCC4)c3)ccn2n1] |
| 367 | 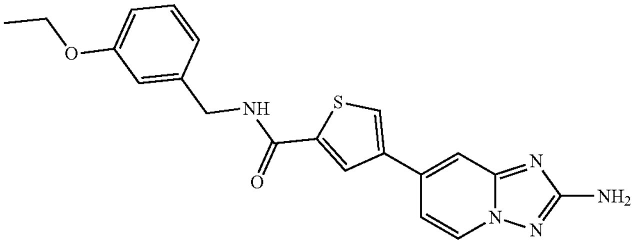 [SMILES: CCOc1cccc(CNC(=O)c2cc(-c3ccn4nc(N)nc4c3)cs2)c1] |
| 368 | 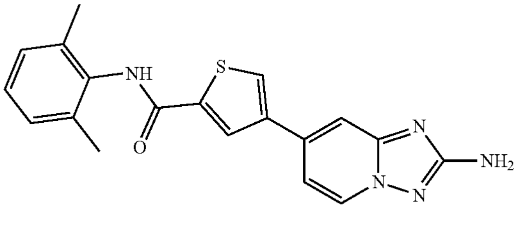 [SMILES: Cc1cccc(C)c1NC(=O)c1cc(-c2ccn3nc(N)nc3c2)cs1] |

-continued
| Compound Number | Structure |
|---|---|
| 369 | 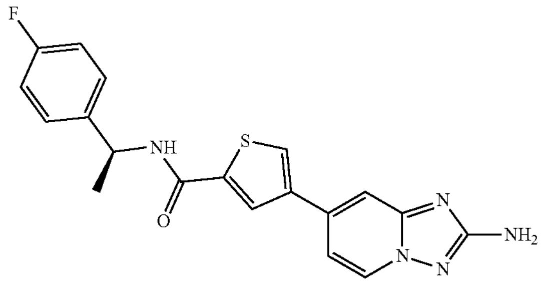 [SMILES: C[C@H](NC(=O)c1cc(-c2ccn3nc(N)nc3c2)cs1)c1ccc(F)cc1] |
and pharmaceutically acceptable salts thereof.
In some embodiments, the compound is selected from the group consisting of the compounds disclosed in Table 1E below:
TABLE 1E
| Compound Number | Structure |
|---|---|
| 370 | 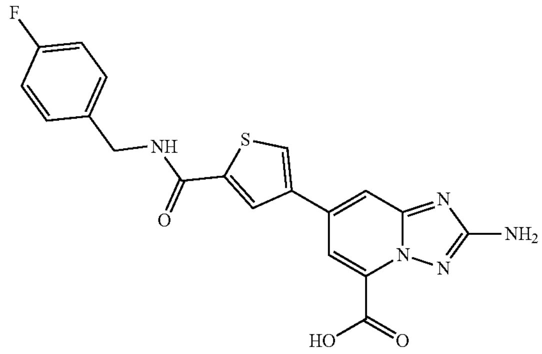 [SMILES: Nc1nc2cc(-c3csc(C(=O)NCc4ccc(F)cc4)c3)cc(C(=O)O)n2n1] |
| 371 | 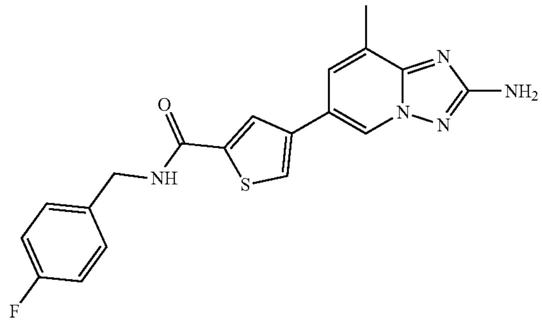 [SMILES: Cc1cc(-c2csc(C(=O)NCc3ccc(F)cc3)c2)cn2nc(N)nc12] |
| 372 | 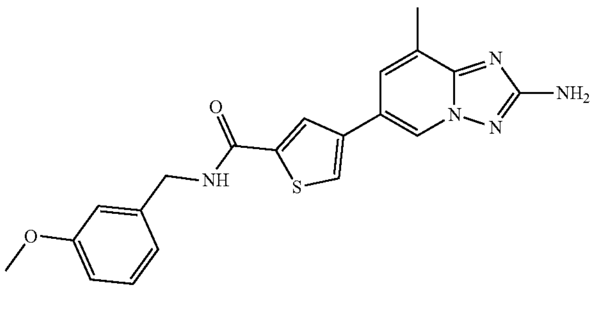 [SMILES: COc1cccc(CNC(=O)c2cc(-c3cc(C)c4nc(N)nn4c3)cs2)c1] |

TABLE 1E-continued
| Compound Number | Structure |
|---|---|
| 373 | 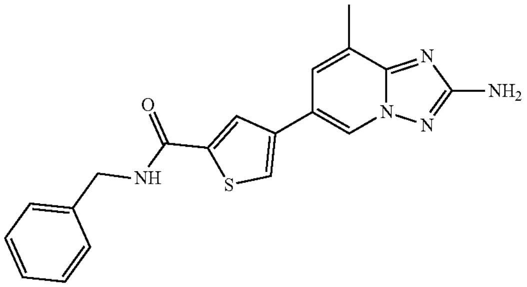 [SMILES: Cc1cc(-c2csc(C(=O)NCc3ccccc3)c2)cn2nc(N)nc12] |
| 374 | 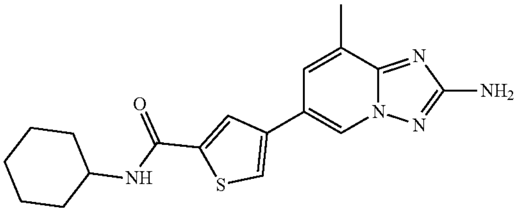 [SMILES: Cc1cc(-c2csc(C(=O)NC3CCCCC3)c2)cn2nc(N)nc12] |
| 375 | 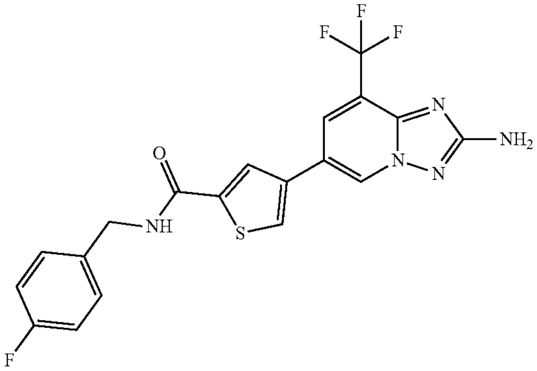 [SMILES: Nc1nc2c(C(F)(F)F)cc(-c3csc(C(=O)NCc4ccc(F)cc4)c3)cn2n1] |
| 376 | 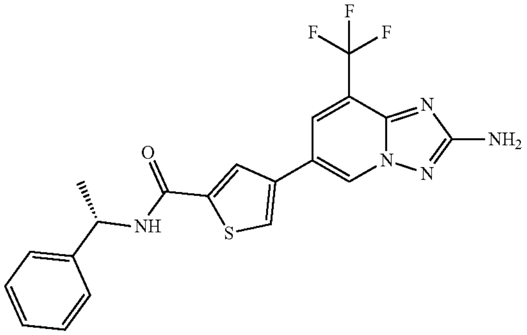 [SMILES: C[C@H](NC(=O)c1cc(-c2cc(C(F)(F)F)c3nc(N)nn3c2)cs1)c1ccccc1] |

TABLE 1E-continued
| Compound Number | Structure |
|---|---|
| 377 | 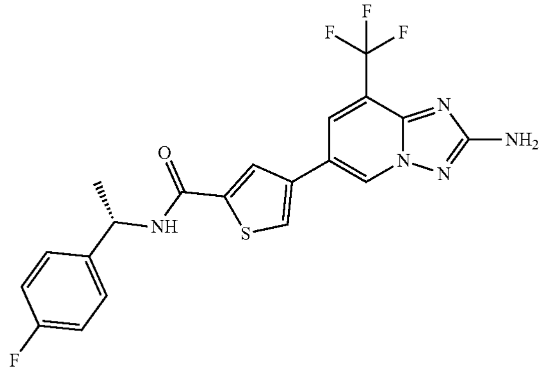 [SMILES: C[C@H](NC(=O)c1cc(-c2cc(C(F)(F)F)c3nc(N)nn3c2)cs1)c1ccc(F)cc1] |
| 378 | 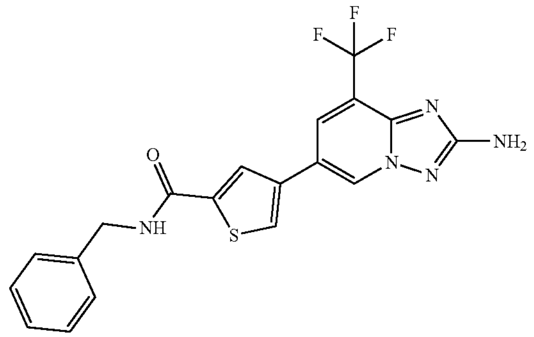 [SMILES: Nc1nc2c(C(F)(F)F)cc(-c3csc(C(=O)NCc4ccccc4)c3)cn2n1] |
| 379 | 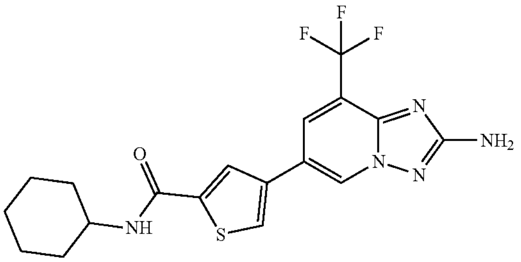 [SMILES: Nc1nc2c(C(F)(F)F)cc(-c3csc(C(=O)NC4CCCCC4)c3)cn2n1] |
| 380 | 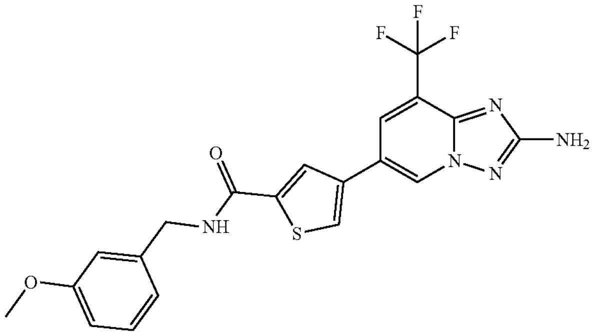 [SMILES: COc1cccc(CNC(=O)c2cc(-c3cc(C(F)(F)F)c4nc(N)nn4c3)cs2)c1] |

TABLE 1E-continued
| Compound Number | Structure |
|---|---|
| 381 | 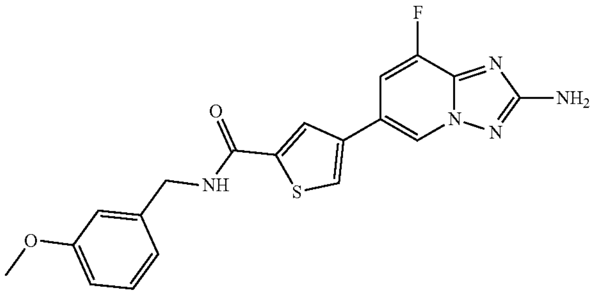 [SMILES: COc1cccc(CNC(=O)c2cc(-c3cc(F)c4nc(N)nn4c3)cs2)c1] |
| 382 | 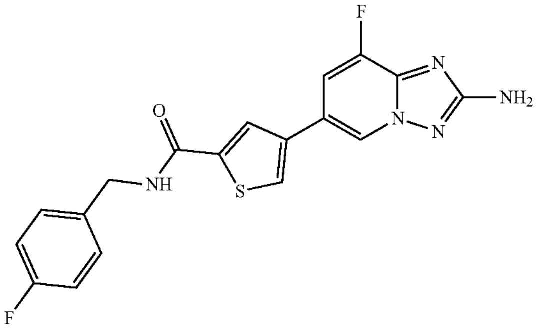 [SMILES: Nc1nc2c(F)cc(-c3csc(C(=O)NCc4ccc(F)cc4)c3)cn2n1] |
| 383 | 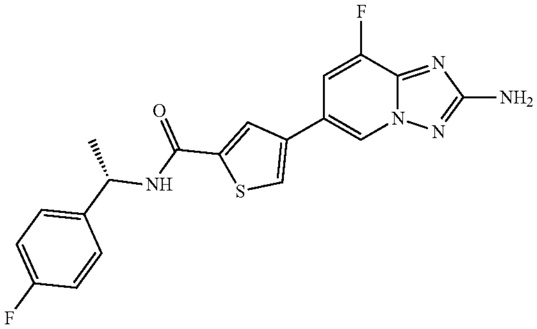 [SMILES: C[C@H](NC(=O)c1cc(-c2cc(F)c3nc(N)nn3c2)cs1)c1ccc(F)cc1] |
| 384 | 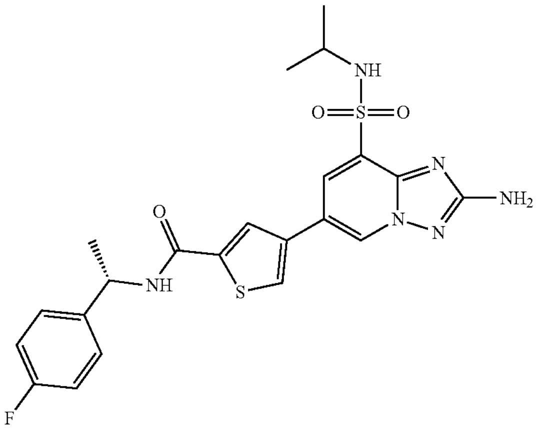 |

TABLE 1E-continued
| Compound Number | Structure |
|---|---|
| 385 | 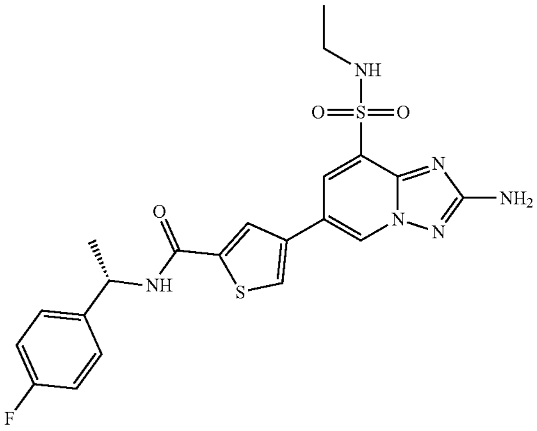 [SMILES: CCNS(=O)(=O)c1cc(-c2csc(C(=O)N[C@@H](C)c3ccc(F)cc3)c2)cn2nc(N)nc12] |
| 386 | 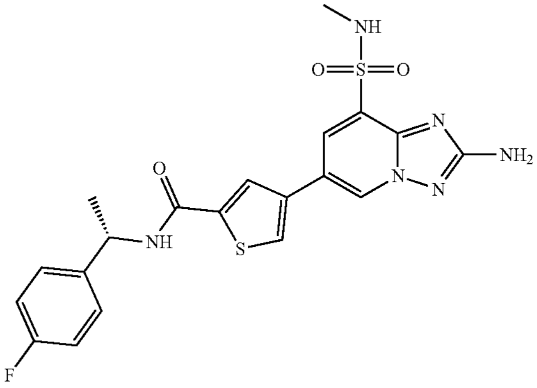 [SMILES: CNS(=O)(=O)c1cc(-c2csc(C(=O)N[C@@H](C)c3ccc(F)cc3)c2)cn2nc(N)nc12] |
| 387 | 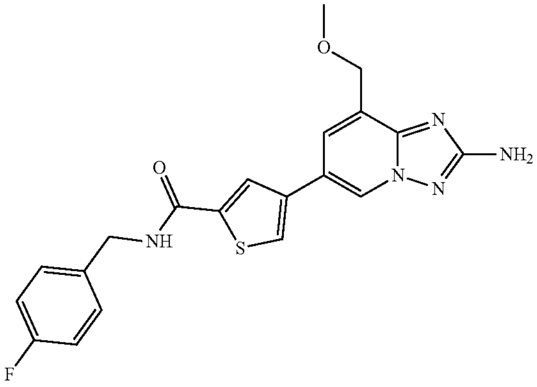 [SMILES: COCc1cc(-c2csc(C(=O)NCc3ccc(F)cc3)c2)cn2nc(N)nc12] |
| 388 | 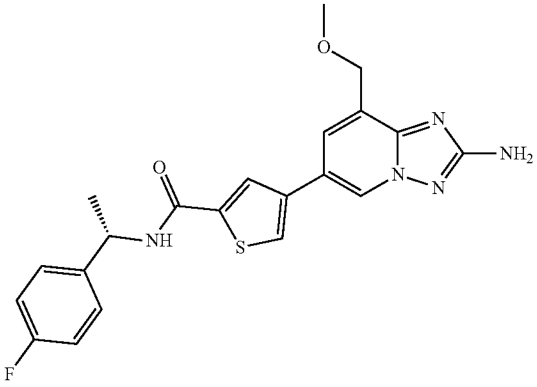 [SMILES: COCc1cc(-c2csc(C(=O)N[C@@H](C)c3ccc(F)cc3)c2)cn2nc(N)nc12] |

TABLE 1E-continued
| Compound Number | Structure |
| --- | --- |
| 389 | 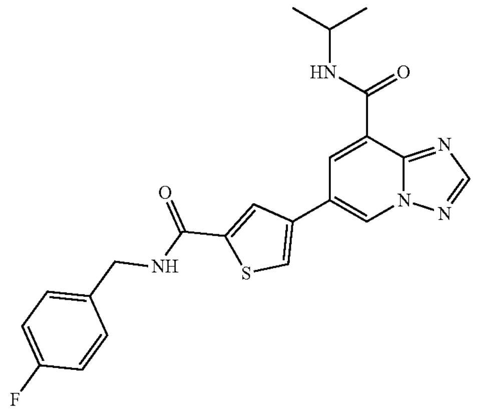 [SMILES: CC(C)NC(=O)c1cc(-c2csc(C(=O)NCc3ccc(F)cc3)c2)cn2ncnc12] |
| 390 | 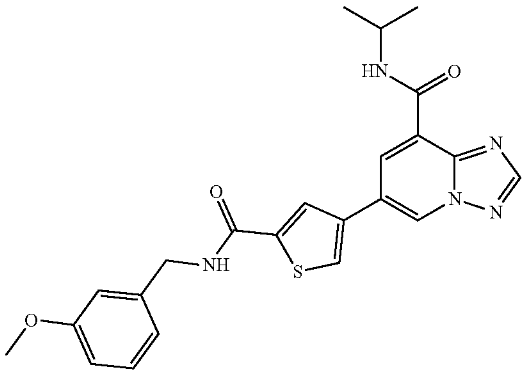 [SMILES: COc1cccc(CNC(=O)c2cc(-c3cc(C(=O)NC(C)C)c4ncnn4c3)cs2)c1] |
| 391 | 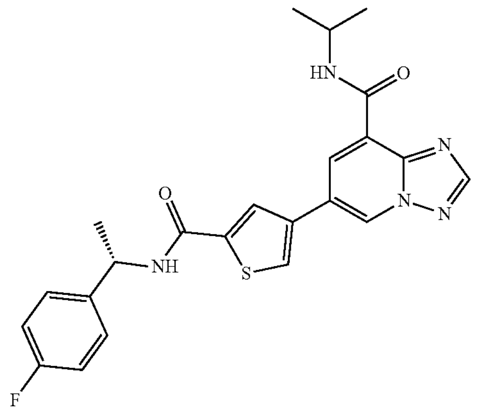 [SMILES: CC(C)NC(=O)c1cc(-c2csc(C(=O)N[C@@H](C)c3ccc(F)cc3)c2)cn2ncnc12] |
and pharmaceutically acceptable salts thereof.

In some embodiments, the compound is selected from the group consisting of the compounds disclosed in Table 1F below:
TABLE IF
| Compound Number | Structure |
|---|---|
| 392 | 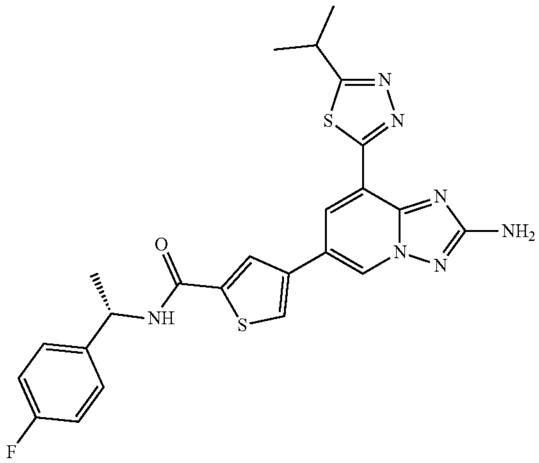 [SMILES: CC(C)c1nnc(-c2cc(-c3csc(C(=O)N[C@@H](C)c4ccc(F)cc4)c3)cn3nc(N)nc23)s1] |
| 393 | 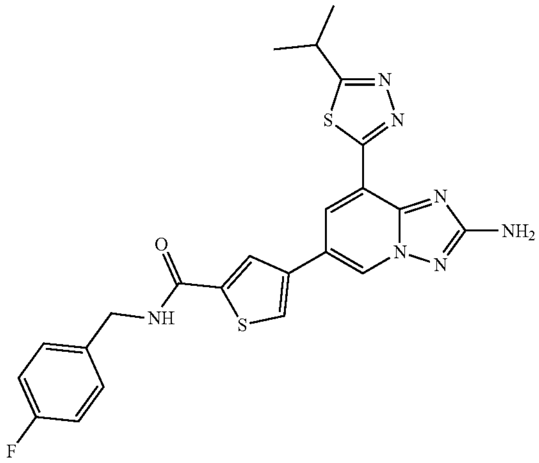 [SMILES: CC(C)c1nnc(-c2cc(-c3csc(C(=O)NCc4ccc(F)cc4)c3)cn3nc(N)nc23)s1] |
| 394 | 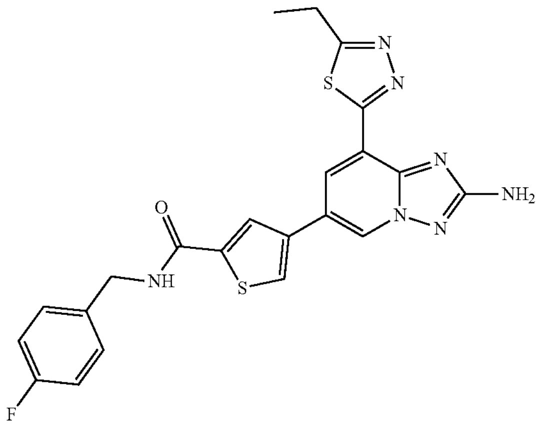 |

TABLE IF-continued
| Compound Number | Structure |
| --- | --- |
| 395 | 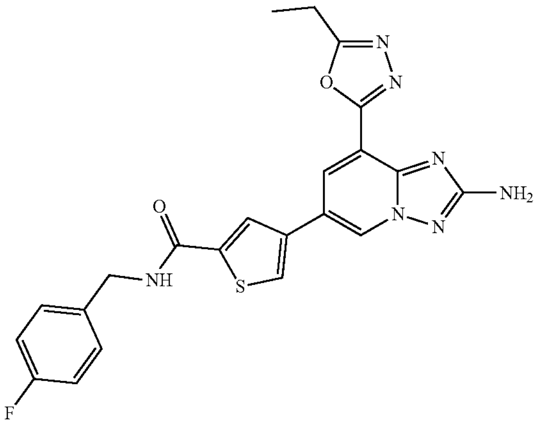 |
| 396 | 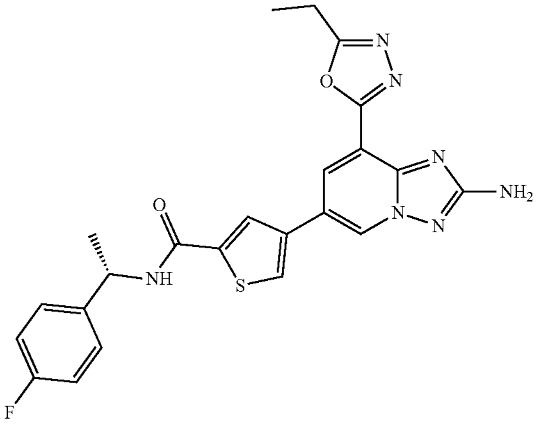 |
| 397 | 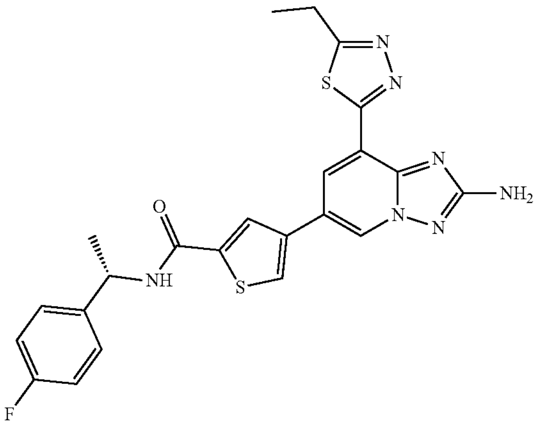 |

TABLE IF-continued
| Compound Number | Structure |
| --- | --- |
| 398 | 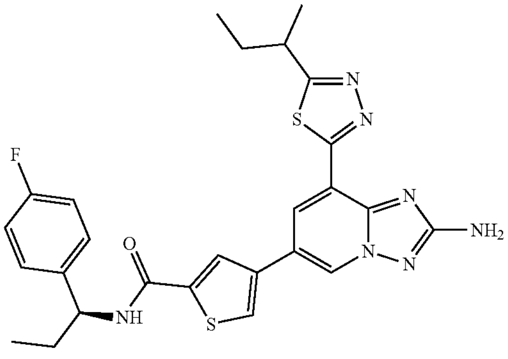 [SMILES: CCC(C)c1nnc(-c2cc(-c3csc(C(=O)N[C@@H](CC)c4ccc(F)cc4)c3)cn3nc(N)nc23)s1] |
| 399 | 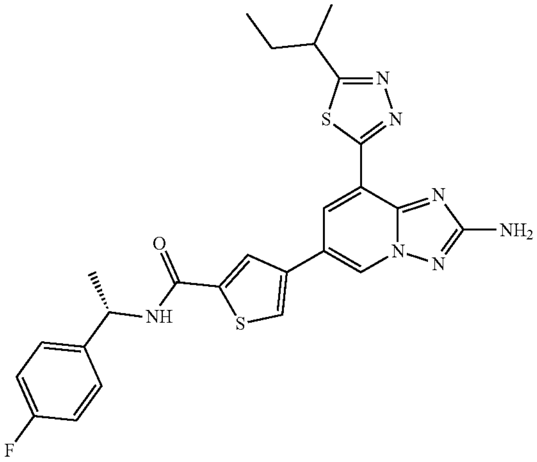 [SMILES: CCC(C)c1nnc(-c2cc(-c3csc(C(=O)N[C@@H](C)c4ccc(F)cc4)c3)cn3nc(N)nc23)s1] |
| 400 | 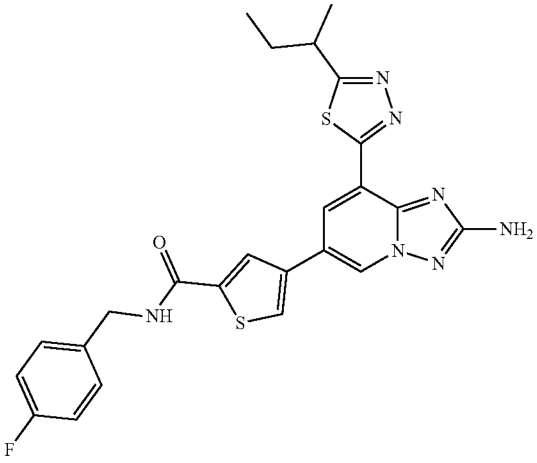 [SMILES: CCC(C)c1nnc(-c2cc(-c3csc(C(=O)NCc4ccc(F)cc4)c3)cn3nc(N)nc23)s1] |

TABLE IF-continued
| Compound Number | Structure |
| --- | --- |
| 401 | 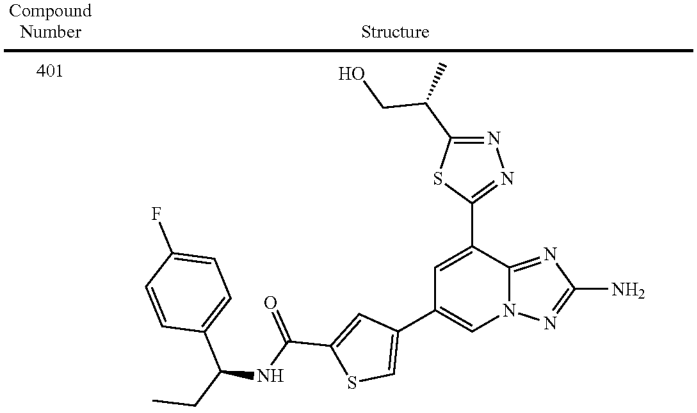 |
| 402 | 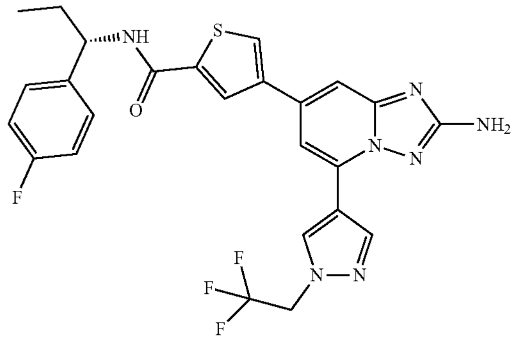 [SMILES: CC[C@H](NC(=O)c1cc(-c2cc(-c3cnn(CC(F)(F)F)c3)n3nc(N)nc3c2)cs1)c1ccc(F)cc1] |
| 403 | 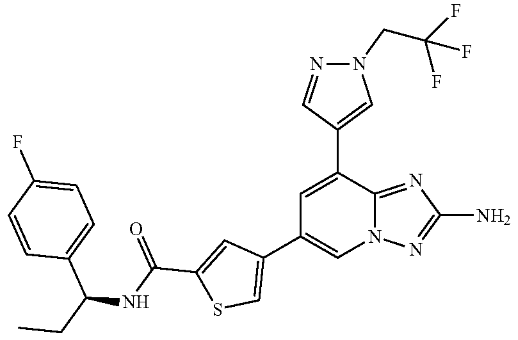 [SMILES: CC[C@H](NC(=O)c1cc(-c2cc(-c3cnn(CC(F)(F)F)c3)c3nc(N)nn3c2)cs1)c1ccc(F)cc1] |
and pharmaceutically acceptable salts thereof.

In some embodiments, the compound is selected from the group consisting of the compounds disclosed in Table 2A below:
TABLE 2A
| Compound Number | Structure |
|---|---|
| 19 | 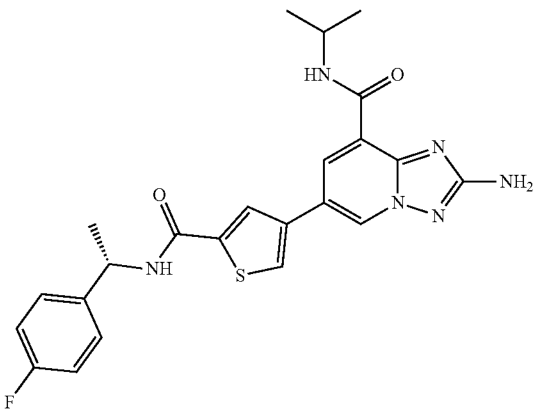 [SMILES: CC(C)NC(=O)c1cc(-c2csc(C(=O)N[C@@H](C)c3ccc(F)cc3)c2)cn2nc(N)nc12] |
| 20 | 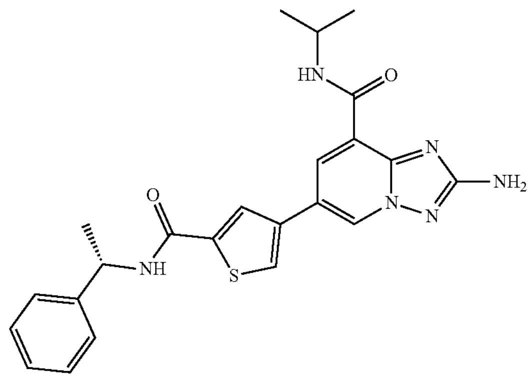 [SMILES: CC(C)NC(=O)c1cc(-c2csc(C(=O)N[C@@H](C)c3ccccc3)c2)cn2nc(N)nc12] |
| 21 | 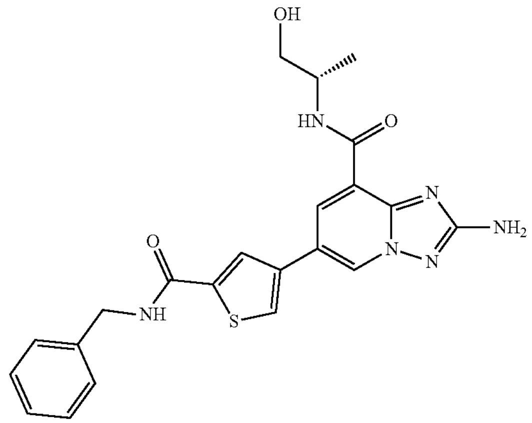 [SMILES: C[C@@H](CO)NC(=O)c1cc(-c2csc(C(=O)NCc3ccccc3)c2)cn2nc(N)nc12] |

TABLE 2A-continued
| Compound Number | Structure |
| --- | --- |
| 25 | 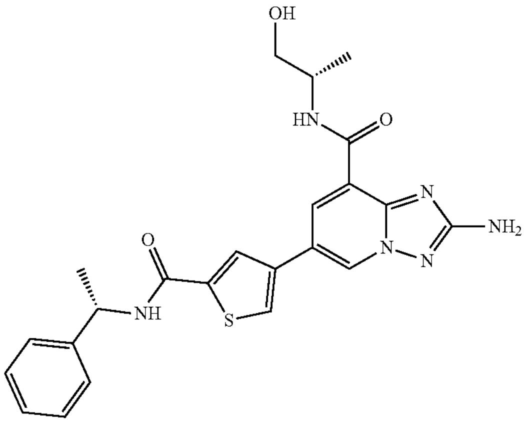 [SMILES: C[C@H](NC(=O)c1cc(-c2cc(C(=O)N[C@@H](C)CO)c3nc(N)nn3c2)cs1)c1ccccc1] |
| 26 | 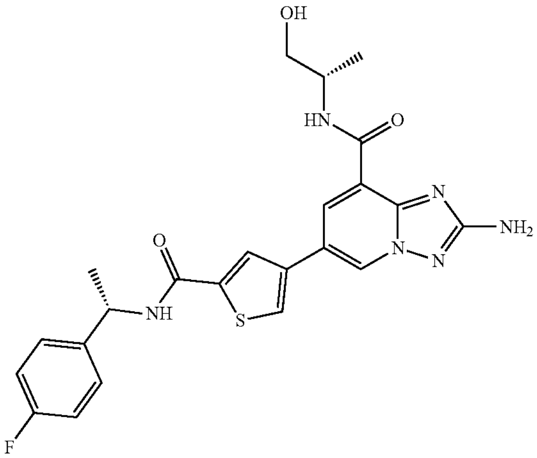 [SMILES: C[C@H](NC(=O)c1cc(-c2cc(C(=O)N[C@@H](C)CO)c3nc(N)nn3c2)cs1)c1ccc(F)cc1] |
| 28 | 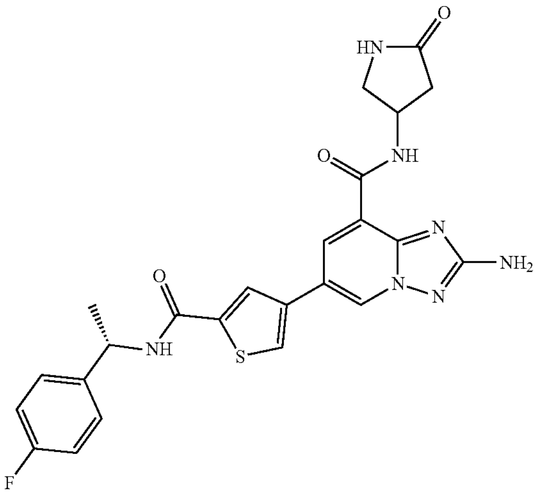 mixture of disastereomers |

TABLE 2A-continued
| Compound Number | Structure |
|---|---|
| 29 | 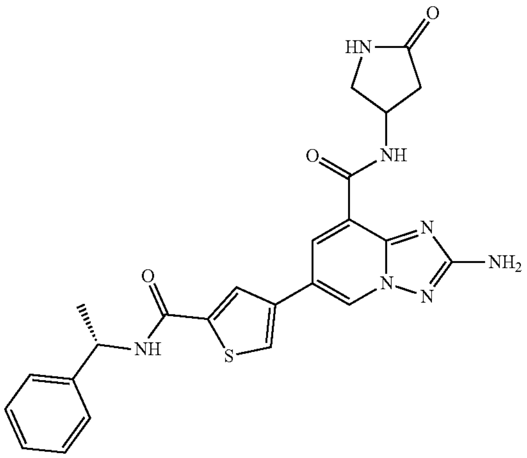<br>mixture of disastereomers |
| 32 | 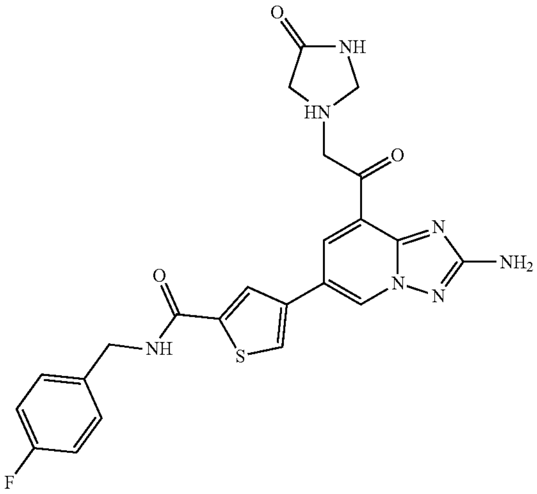 [SMILES: Nc1nc2c(C(=O)CN3CNC(=O)C3)cc(-c3csc(C(=O)NCc4ccc(F)cc4)c3)cn2n1] |
| 41 | 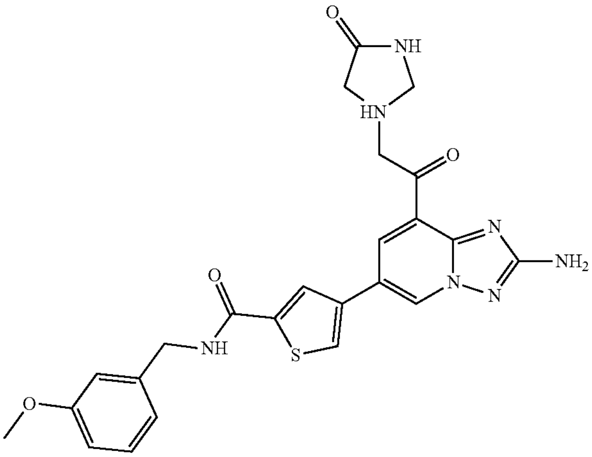 [SMILES: COc1cccc(CNC(=O)c2cc(-c3cc(C(=O)CN4CNC(=O)C4)c4nc(N)nn4c3)cs2)c1] |

TABLE 2A-continued
| Compound Number | Structure |
|---|---|
| 48 | 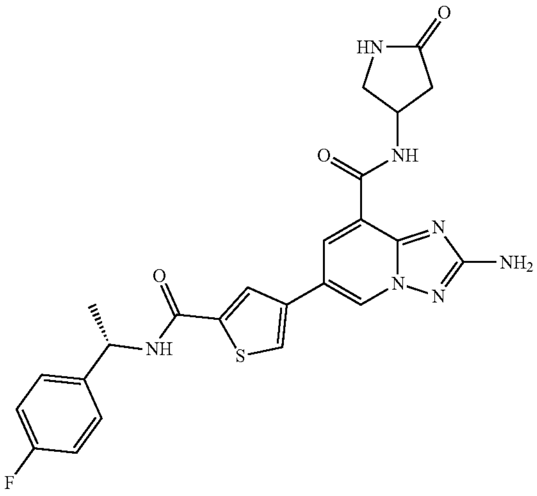 stereoisomer 2 |
| 54 | 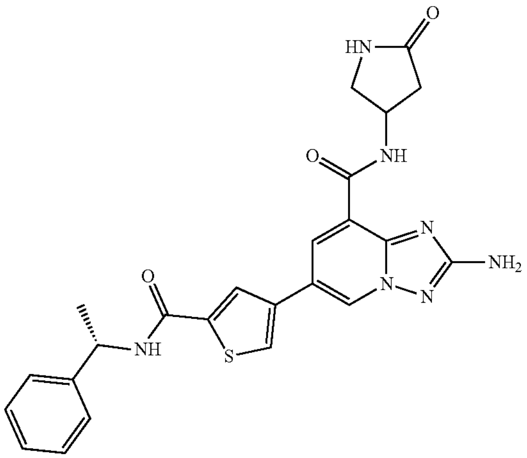 stereoisomer 1 |
| 59 | 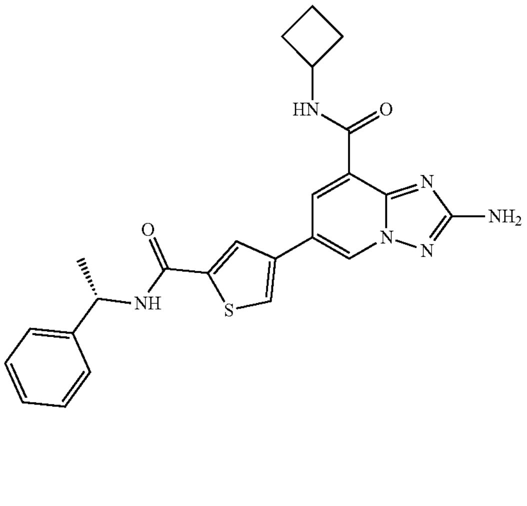 [SMILES: C[C@H](NC(=O)c1cc(-c2cc(C(=O)NC3CCC3)c3nc(N)nn3c2)cs1)c1ccccc1] |

TABLE 2A-continued
| Compound Number | Structure |
|---|---|
| 60 | 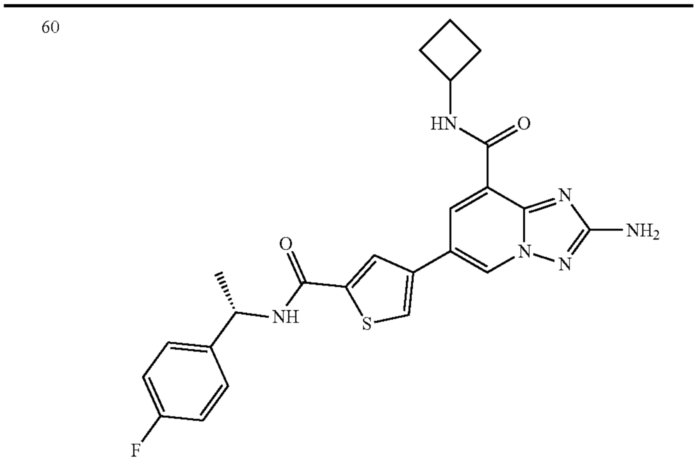 |
| 71 | 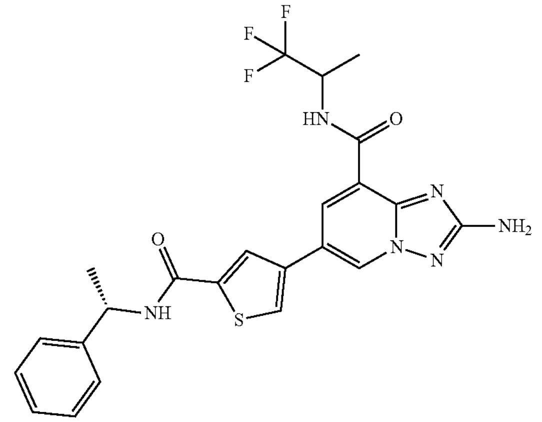 stereoisomer 1 |
| 76 | 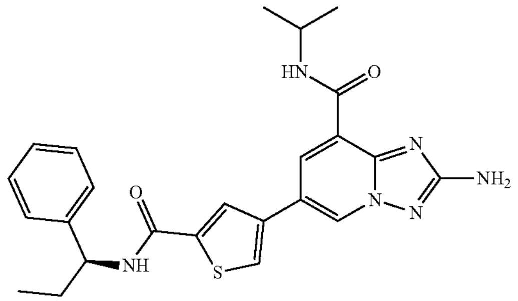 [SMILES: CC[C@H](NC(=O)c1cc(-c2cc(C(=O)NC(C)C)c3nc(N)nn3c2)cs1)c1ccccc1] |
| 77 | 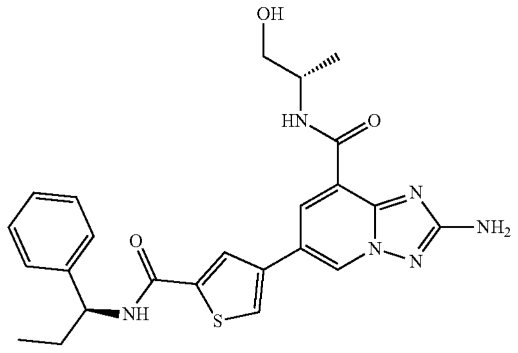 [SMILES: CC[C@H](NC(=O)c1cc(-c2cc(C(=O)N[C@@H](C)CO)c3nc(N)nn3c2)cs1)c1ccccc1] |

TABLE 2A-continued
| Compound Number | Structure |
|---|---|
| 78 | 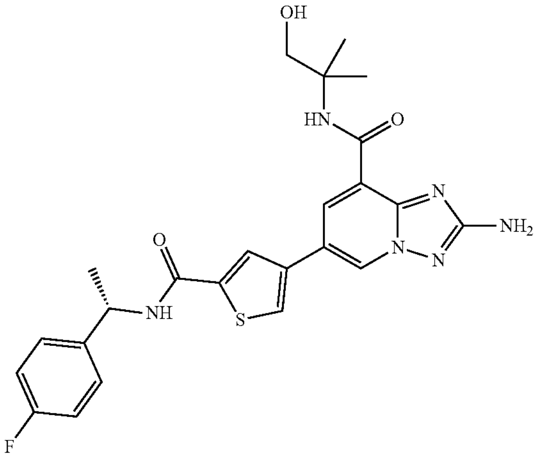 [SMILES: C[C@H](NC(=O)c1cc(-c2cc(C(=O)NC(C)(C)CO)c3nc(N)nn3c2)cs1)c1ccc(F)cc1] |
| 81 | 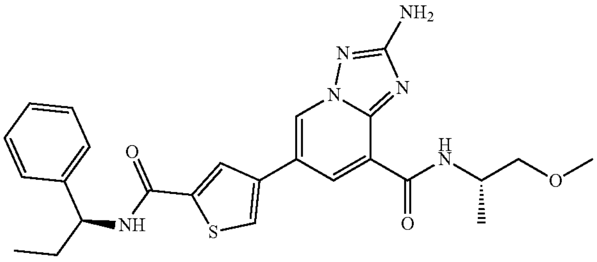 [SMILES: CC[C@H](NC(=O)c1cc(-c2cc(C(=O)N[C@@H](C)COC)c3nc(N)nn3c2)cs1)c1ccccc1] |
| 88 | 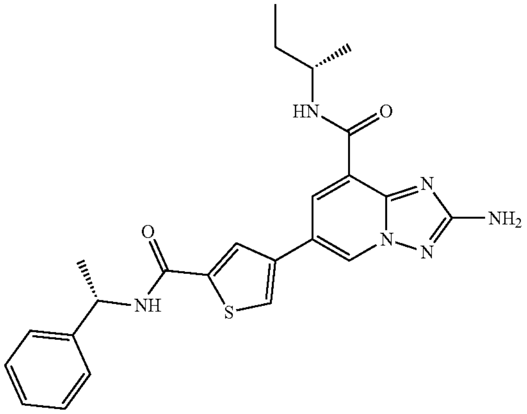 [SMILES: CC[C@H](C)NC(=O)c1cc(-c2csc(C(=O)N[C@@H](C)c3ccccc3)c2)cn2nc(N)nc12] |
| 89 | 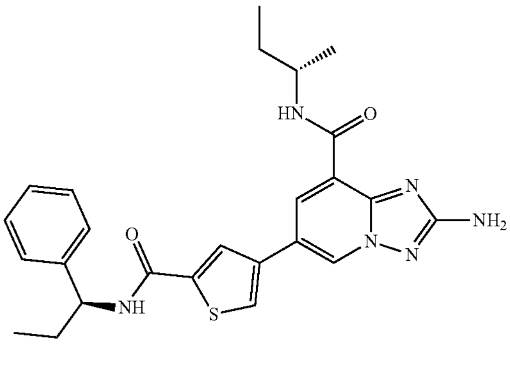 [SMILES: CC[C@H](NC(=O)c1cc(-c2cc(C(=O)N[C@@H](C)CC)c3nc(N)nn3c2)cs1)c1ccccc1] |

TABLE 2A-continued
| Compound Number | Structure |
| --- | --- |
| 91 | 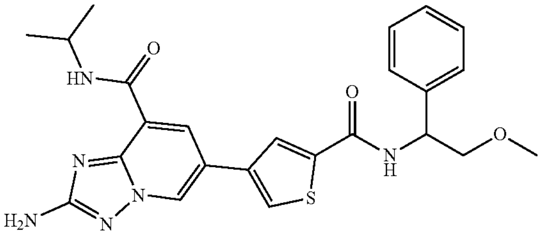 |
| 94 | 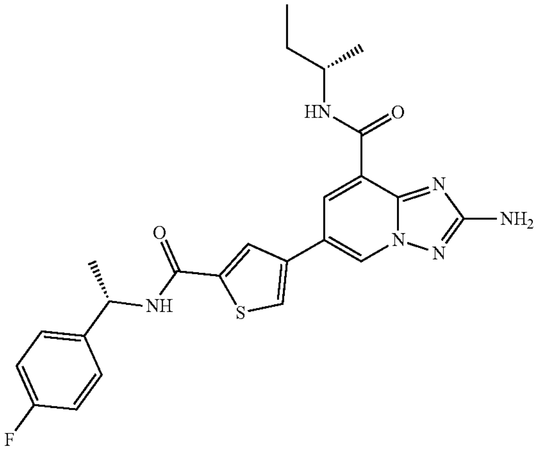 [SMILES: CC[C@H](C)NC(=O)c1cc(-c2csc(C(=O)N[C@@H](C)c3ccc(F)cc3)c2)cn2nc(N)nc12] |
| 98 | 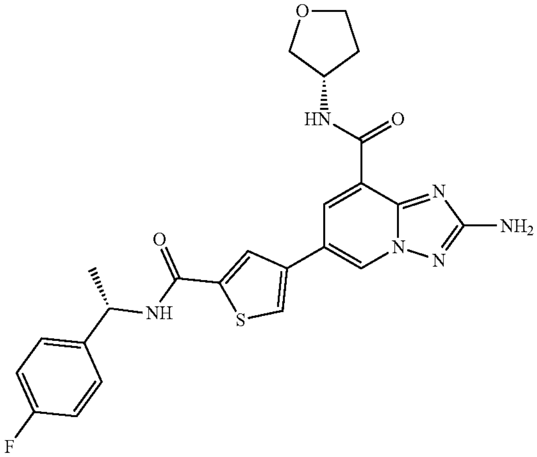 [SMILES: C[C@H](NC(=O)c1cc(-c2cc(C(=O)N[C@H]3CCOC3)c3nc(N)nn3c2)cs1)c1ccc(F)cc1] |

TABLE 2A-continued
| Compound Number | Structure |
| --- | --- |
| 100 | 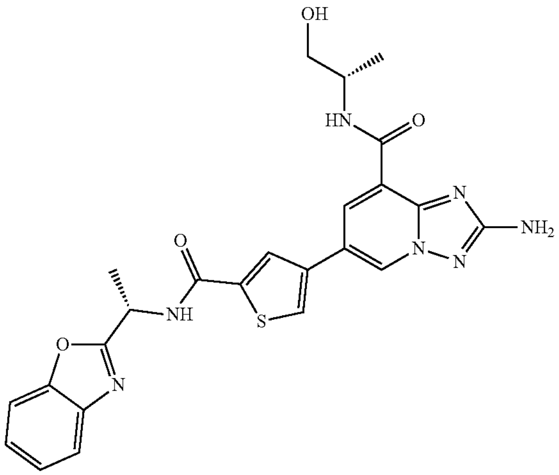 [SMILES: C[C@H](NC(=O)c1cc(-c2cc(C(=O)N[C@@H](C)CO)c3nc(N)nn3c2)cs1)c1nc2ccccc2o1] |
| 102 | 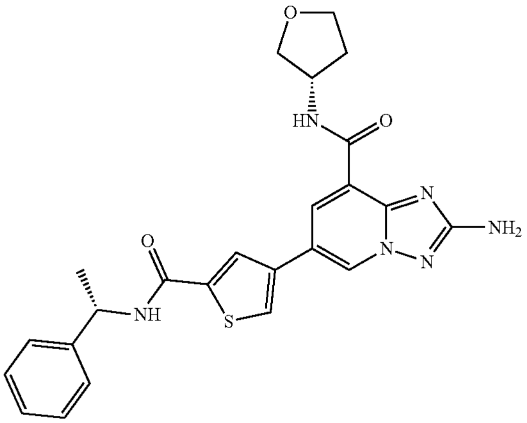 [SMILES: C[C@H](NC(=O)c1cc(-c2cc(C(=O)N[C@H]3CCOC3)c3nc(N)nn3c2)cs1)c1ccccc1] |
| 104 | 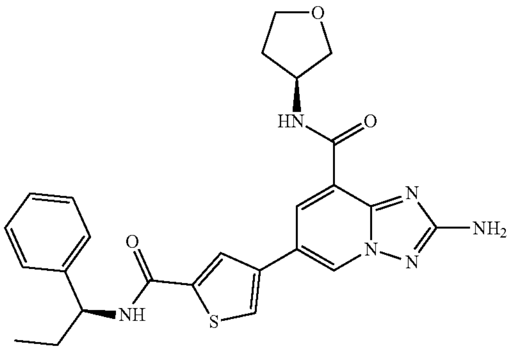 [SMILES: CC[C@H](NC(=O)c1cc(-c2cc(C(=O)N[C@H]3CCOC3)c3nc(N)nn3c2)cs1)c1ccccc1] |
| 107 | 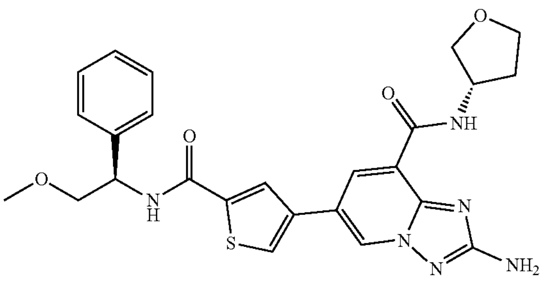 [SMILES: COC[C@H](NC(=O)c1cc(-c2cc(C(=O)N[C@H]3CCOC3)c3nc(N)nn3c2)cs1)c1ccccc1] |

TABLE 2A-continued
| Compound Number | Structure |
|---|---|
| 108 | 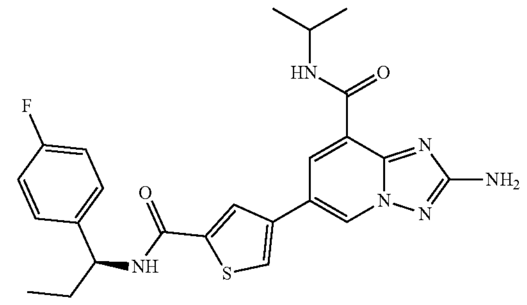 [SMILES: CC[C@H](NC(=O)c1cc(-c2cc(C(=O)NC(C)C)c3nc(N)nn3c2)cs1)c1ccc(F)cc1] |
| 109 | 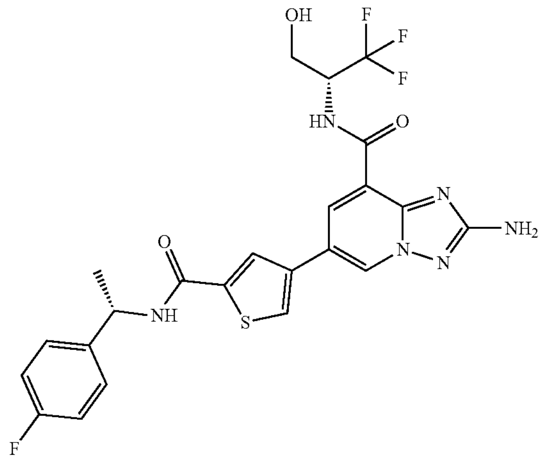 [SMILES: C[C@H](NC(=O)c1cc(-c2cc(C(=O)N[C@H](CO)C(F)(F)F)c3nc(N)nn3c2)cs1)c1ccc(F)cc1] |
| 112 | 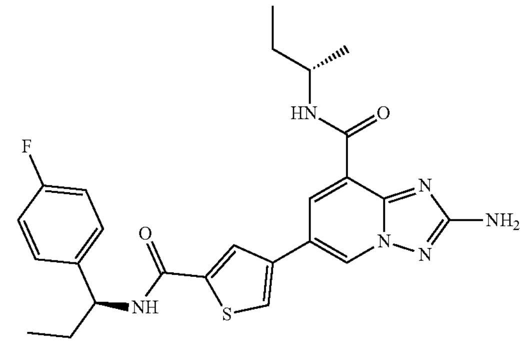 [SMILES: CC[C@H](NC(=O)c1cc(-c2cc(C(=O)N[C@@H](C)CC)c3nc(N)nn3c2)cs1)c1ccc(F)cc1] |
| 115 | 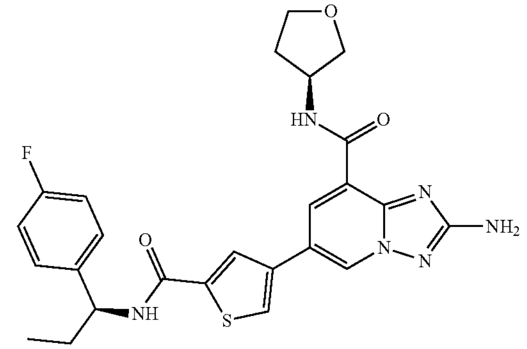 [SMILES: CC[C@H](NC(=O)c1cc(-c2cc(C(=O)N[C@H]3CCOC3)c3nc(N)nn3c2)cs1)c1ccc(F)cc1] |

TABLE 2A-continued
| Compound Number | Structure |
| --- | --- |
| 116 | 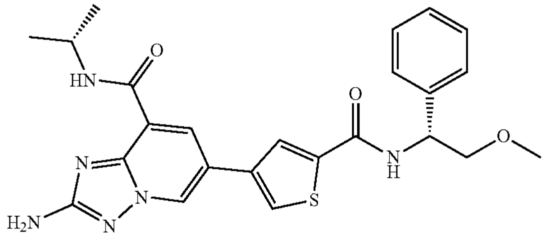 |
| 120 | 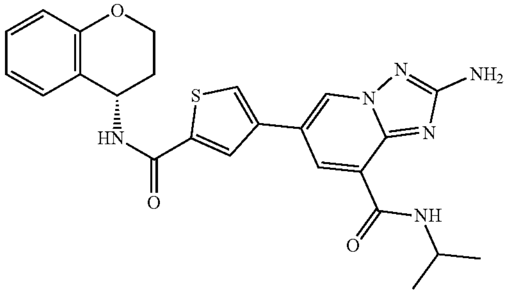 [SMILES: CC(C)NC(=O)c1cc(-c2csc(C(=O)N[C@H]3CCOc4ccccc43)c2)cn2nc(N)nc12] |
| 122 | 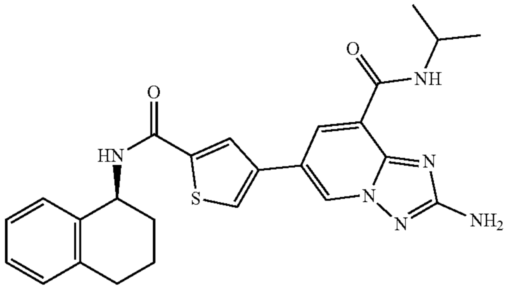 [SMILES: CC(C)NC(=O)c1cc(-c2csc(C(=O)N[C@H]3CCCc4ccccc43)c2)cn2nc(N)nc12] |
| 123 | 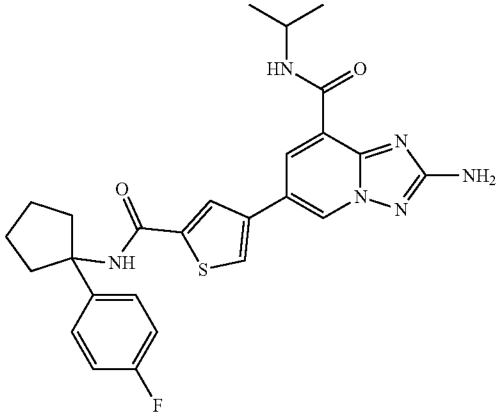 [SMILES: CC(C)NC(=O)c1cc(-c2csc(C(=O)NC3(c4ccc(F)cc4)CCCC3)c2)cn2nc(N)nc12] |

TABLE 2A-continued
| Compound Number | Structure |
|---|---|
| 133 | 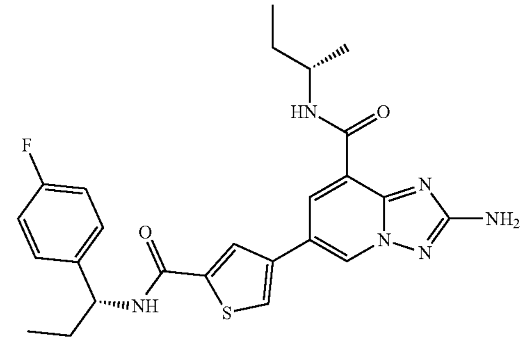 [SMILES: CC[C@H](C)NC(=O)c1cc(-c2csc(C(=O)N[C@H](CC)c3ccc(F)cc3)c2)cn2nc(N)nc12] |
| 135 | 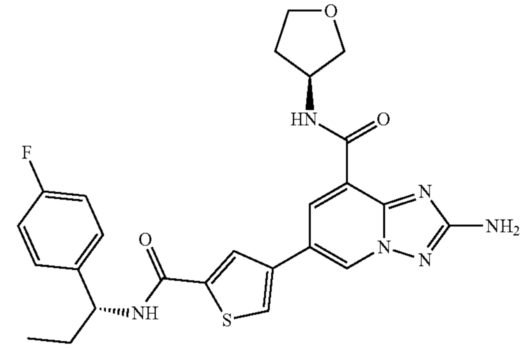 [SMILES: CC[C@@H](NC(=O)c1cc(-c2cc(C(=O)N[C@H]3CCOC3)c3nc(N)nn3c2)cs1)c1ccc(F)cc1] |
| 137 | 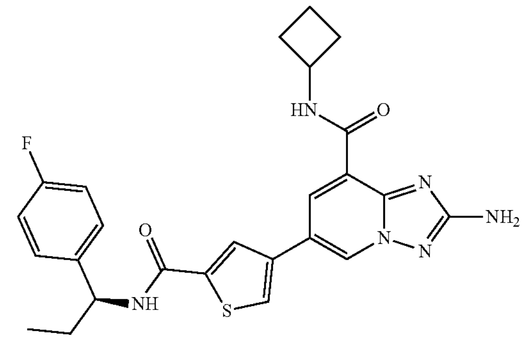 [SMILES: CC[C@H](NC(=O)c1cc(-c2cc(C(=O)NC3CCC3)c3nc(N)nn3c2)cs1)c1ccc(F)cc1] |
| 138 | 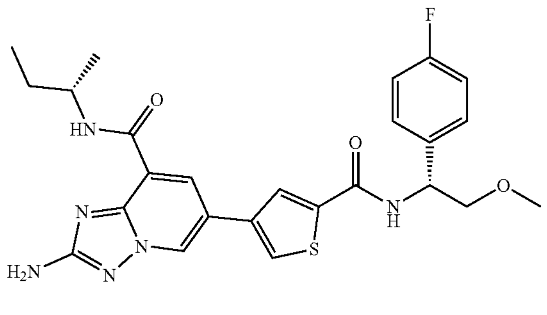 [SMILES: CC[C@H](C)NC(=O)c1cc(-c2csc(C(=O)N[C@@H](COC)c3ccc(F)cc3)c2)cn2nc(N)nc12] |

TABLE 2A-continued
| Compound Number | Structure |
| --- | --- |
| 139 | 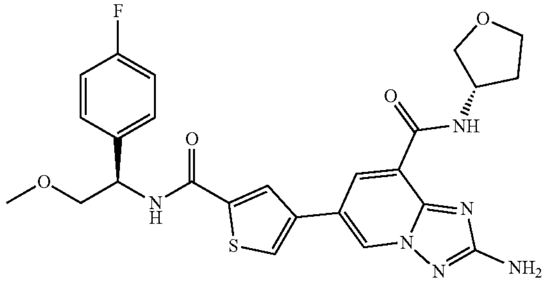 [SMILES: COC[C@H](NC(=O)c1cc(-c2cc(C(=O)N[C@H]3CCOC3)c3nc(N)nn3c2)cs1)c1ccc(F)cc1] |
| 141 | 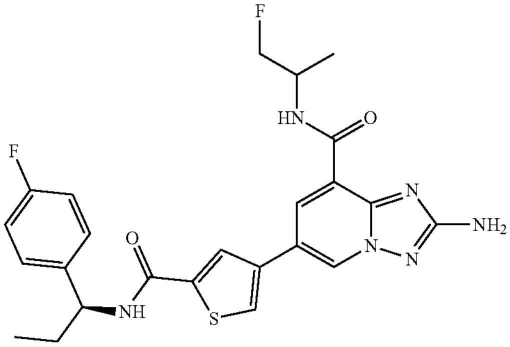 [SMILES: CC[C@H](NC(=O)c1cc(-c2cc(C(=O)NC(C)CF)c3nc(N)nn3c2)cs1)c1ccc(F)cc1] mixture of diastereomers |
| 143 | 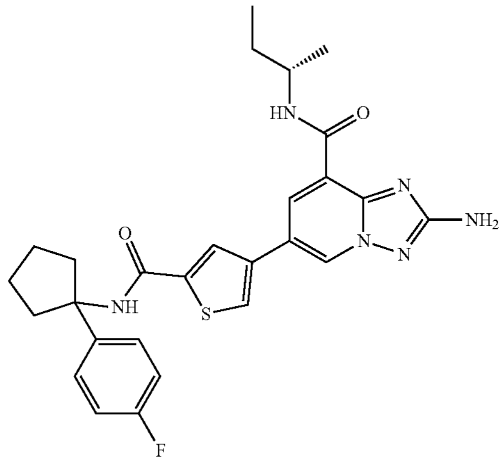 [SMILES: CC[C@H](C)NC(=O)c1cc(-c2csc(C(=O)NC3(c4ccc(F)cc4)CCCC3)c2)cn2nc(N)nc12] |
| 144-1 | 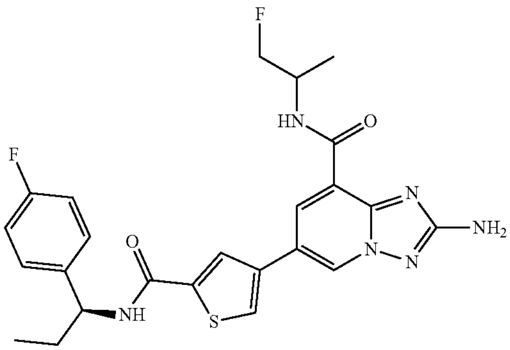 [SMILES: CC[C@H](NC(=O)c1cc(-c2cc(C(=O)NC(C)CF)c3nc(N)nn3c2)cs1)c1ccc(F)cc1] stereoisomer 1 |

TABLE 2A-continued
| Compound Number | Structure |
|---|---|
| 152 | 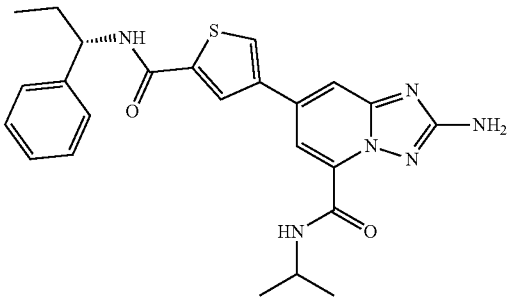 [SMILES: CC[C@H](NC(=O)c1cc(-c2cc(C(=O)NC(C)C)n3nc(N)nc3c2)cs1)c1ccccc1] |
| 154 | 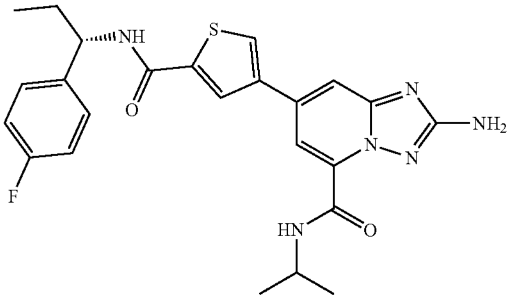 [SMILES: CC[C@H](NC(=O)c1cc(-c2cc(C(=O)NC(C)C)n3nc(N)nc3c2)cs1)c1ccc(F)cc1] |
| 155 | 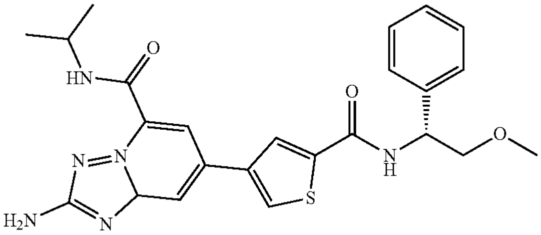 |
| 156 | 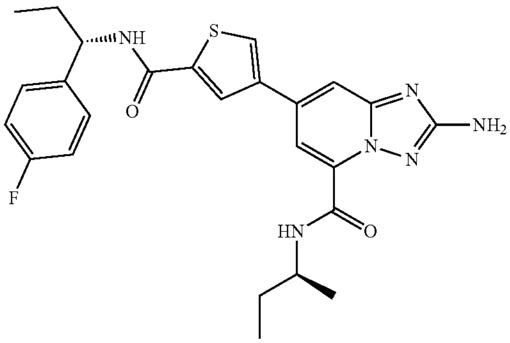 [SMILES: CC[C@H](NC(=O)c1cc(-c2cc(C(=O)N[C@@H](C)CC)n3nc(N)nc3c2)cs1)c1ccc(F)cc1] |
| 159 | 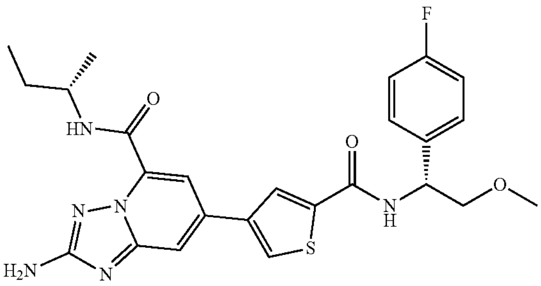 [SMILES: CC[C@H](C)NC(=O)c1cc(-c2csc(C(=O)N[C@@H](COC)c3ccc(F)cc3)c2)cc2nc(N)nn12] |

TABLE 2A-continued

| Compound Number | Structure |
|---|---|
| 160 | 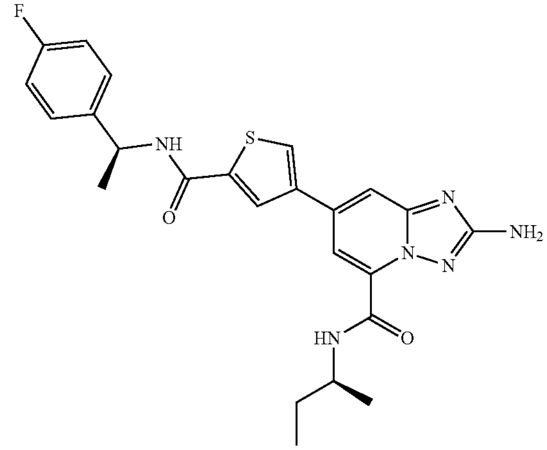 [SMILES: CC[C@H](C)NC(=O)c1cc(-c2csc(C(=O)N[C@@H](C)c3ccc(F)cc3)c2)cc2nc(N)nn12] |
| 162 | 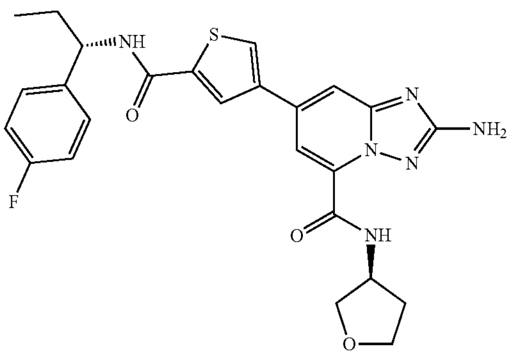 [SMILES: CC[C@H](NC(=O)c1cc(-c2cc(C(=O)N[C@H]3CCOC3)n3nc(N)nc3c2)cs1)c1ccc(F)cc1] |
| 401 | 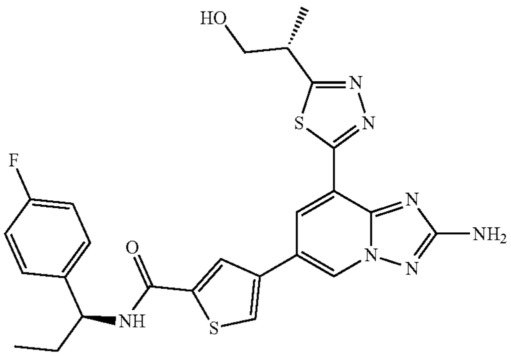 [SMILES: CC[C@H](NC(=O)c1cc(-c2cc(-c3nnc([C@@H](C)CO)s3)c3nc(N)nn3c2)cs1)c1ccc(F)cc1] |

and pharmaceutically acceptable salts thereof.

The compounds provided herein include the compounds of formulae (Z), (Y), (X), (A), and salts, solvates, and solvates of salts thereof, the compounds of the formulae (I), (I-A), (I-B), (I-C), and (I-D) below that are encompassed by formulae (Z), (Y), (X), (A), and salts, solvates, and solvates of salts thereof, and the compounds cited hereinafter as working examples that are encompassed by formulae (Z), (Y), (X), (A), and salts, solvates, and solvates of salts thereof.

Salts in the context of the present disclosure are physiologically acceptable salts of compounds of Formula (Z), (Y), (X), (A), (I), (I-A), (I-B), (I-C), and (I-D). Also encompassed are salts which are not themselves suitable for pharmaceutical applications but can be used, for example, for the isolation, purification or storage of compounds of Formulae (Z), (Y), (X), (A), (I), (I-A), (I-B), (I-C), and (I-D).

Physiologically acceptable salts of compounds of Formulae (Z), (Y), (X), (A), (I), (I-A), (I-B), (I-C), and (I-D) include acid addition salts of mineral acids, carboxylic acids and sulfonic acids, for example, salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, formic acid, acetic acid, trifluoroacetic acid, propionic acid, succinic acid, fumaric acid, maleic acid, lactic acid, tartaric acid, malic acid, citric acid, gluconic acid, benzoic acid and embonic acid.

In addition, physiologically acceptable salts of compounds of Formula (Z), (Y), (X), (A), (I) (I-A), (I-B), (I-C), or (I-D) also include salts derived from conventional bases, by way of example alkali metal salts (e.g. sodium and potassium salts), alkaline earth metal salts (e.g. calcium and magnesium salts), zinc salts and ammonium salts derived from ammonia or organic amines having 1 to 20 carbon atoms, by way of example ethylamine, diethylamine, triethylamine, N,N-ethyldiisopropylamine, monoethanolamine, diethanolamine, triethanolamine, dimethylaminoethanol, diethylaminoethanol, tris(hydroxymethyl)aminomethane, choline, benzalkonium, procaine, dibenzylamine, dicyclohexylamine, N-methylmorpholine, N-methylpiperidine, arginine, lysine and 1,2-ethylenediamine.

Solvates in the context of the disclosure are described as those forms of a compound of Formula (Z), (Y), (X), (A), (I), (I-A), (I-B), (I-C), or (I-D) which form a complex in the solid or liquid state by coordination with solvent molecules. Hydrates are a specific form of the solvates in which the coordination is with water. Solvates exemplified in the context of the present disclosure are hydrates.

A compound of Formula (Z), (Y), (X), (A), (I), (I-A), (I-B), (I-C), or (I-D) may, depending on its structure, exist in different stereoisomeric forms, i.e. in the form of configurational isomers or else, if appropriate, of conformational isomers (enantiomers and/or diastereomers, including those in the case of atropisomers). The present disclosure therefore encompasses the enantiomers and diastereomers, and the respective mixtures thereof. The stereoisomerically homogeneous constituents can be isolated from such mixtures of enantiomers and/or diastereomers in a known manner; chromatography processes can be used for the purpose, especially HPLC chromatography on achiral or chiral separation phases. In the case of carboxylic acids as intermediates or end products, separation is alternatively also possible via diastereomeric salts using chiral amine bases.

If a compound of Formula (Z), (Y), (X), (A), (I), (I-A), (I-B), (I-C), or (I-D) can occur in tautomeric forms, the present disclosure encompasses all the tautomeric forms.

The present disclosure also encompasses all suitable isotopic variants of a compound of Formula (Z), (Y), (X), (A), (I), (I-A), (I-B), (I-C), or (I-D). An isotopic variant of a compound of Formula (Z), (Y'), (X), (A), (I), (I-A), (I-B), (I-C), or (I-D) is understood here to mean a compound in which at least one atom within the compound of Formula (Z), (Y), (X), (A), (I), (I-A), (I-B), (I-C), or (I-D) has been exchanged for another atom of the same atomic number, but with a different atomic mass than the atomic mass which usually or predominantly occurs in nature. Examples of isotopes which can be incorporated into a compound of Formula (Z), (Y), (X), (A), (I), (I-A), (I-B), (I-C), or (I-D) are those of hydrogen, carbon, nitrogen, oxygen, phosphorus, sulfur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{18}F$, $^{36}Cl$, $^{82}Br$, $^{123}I$, $^{124}I$, $^{129}I$ and $^{131}I$. Particular isotopic variants of a compound of Formula (Z), (Y), (X), (A), (I), (I-A), (I-B), (I-C), or (I-D), especially those in which one or more radioactive isotopes have been incorporated, may be beneficial, for example, for the examination of the mechanism of action or of the active ingredient distribution in the body; due to comparatively easy preparability and detectability, particularly compounds labelled with $^{3}H$, $^{14}C$ and/or $^{18}F$ isotopes are suitable for the purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of a compound of Formula (Z), (Y), (X), (A), (I), (I-A), (I-B), (I-C), or (I-D) may therefore possibly also constitute an exemplified embodiment of the present disclosure. Isotopic variants of a compound of Formula (Z), (Y), (X), (A), (I), (I-A), (I-B), (I-C), or (I-D) can be prepared by commonly used processes known to those skilled in the art, for example by the methods described further down and the procedures described in the working examples, by using corresponding isotopic modifications of the respective reagents and/or starting compounds.

In addition, the present disclosure also encompasses prodrugs of a compound of Formula (Z), (Y), (X), (A), (I), (I-A), (I-B), (I-C), or (I-D). The term "prodrugs" refers here to compounds which may themselves be biologically active or inactive, but are converted while present in the body, for example by a metabolic or hydrolytic route, to compounds of Formula (Z), (Y), (X), (A), (I), (I-A), (I-B) (I-C), or (I-D).

For purposes of clarification, when a compound disclosed in any of Tables 1A, 1B, 1C, 1D, 1E, 1F, or 2A includes one chiral center, the configuration at the chiral center may be unspecified (i.e., no bond to the chiral center is expressed using dash or wedge notation). In these instances, the compound is assumed to be a mixture of enantiomers unless it is indicated as "enantiomer 1" or "enantiomer 2", in which case the compound is a single enantiomer wherein the configuration at the unspecified stereocenter is not yet identified, and wherein the opposite enantiomer is disclosed elsewhere herein as "enantiomer 2" or "enantiomer 1", respectively.

For purposes of clarification, when a compound disclosed in any of Tables 1A, 1B, 1C, 1D, 1E, 1F, or 2A includes two chiral centers, the configuration at one of the two chiral centers may be unspecified (i.e., no bond to the chiral center is expressed using dash or wedge notation). In these instances, (1) when the compound has no explicit indication or is indicated as a "mixture of diastereomers", the compound is a mixture of two diastereoners whose configuration at the unspecified stereocenter is (R) and (S); and (2) when the compound is indicated as "stereoisomer 1" (and "stereoisomer 2" is disclosed elsewhere herein) or "stereoisomer 2" (and "stereoisomer 1" is disclosed elsewhere herein), then "stereoisomer 1" and "stereoisomer 2" are a pair of diastereomers wherein the configuration of the unspecified stereocenter in each diastereoner is not yet identified and is the opposite of the other diastereorer. In some instances, the configuration at both chiral centers is unspecified, which is understood to mean that the compound is a mixture of all four possible diastereomers. In the structures of compounds 165 and 200, (1) the configuration at the two stereocenters is expressed in a "cis" configuration, (2) compound 165 is indicated as "stereoisomer 1", and (3) compound 200 is indicated as "stereoisomer 2"; in this context, it is understood that each of compounds 165 and 200 is a "cis" diastereomer of unidentified absolute configuration that is the enantiomer of the other of compound 165 and 200. In the structures of compounds 198 and 199, (1) the configuration at the two stereocenters is expressed in a "trans" configuration, (2) compound 198 is indicated as "stereoisomer 1", and (3) compound 199 is indicated as "stereoisomer 2"; in this context, it is understood that each of compounds 198 and 199 is a "trans" diastereomer of unidentified absolute configuration that is the enantiomer of the other of compound 198 and 199, respectively.

In the context of the present disclosure, unless specified otherwise, the following terms are defined as follows:

As used herein, when a ring is "fused" to another ring, it shares two adjacent ring members with the other ring. For example, a cyclohexyl fused to a cyclopentyl is octahydro- 1H-indene. As another example, a cyclohexyl fused to a phenyl is 1,2,3,4-tetrahydronaphthalene.

"Alkyl" in the context of the disclosure represent a straight-chain or branched alkyl radical having 1 to 10 (e.g., 1 to 6, 1 to 4, or 1 to 3) carbon atoms. Examples include: methyl, ethyl, n-propyl, isopropyl, n-butyl, isobutyl, sec-butyl, tert-butyl, n-pentyl, 2-pentyl, 3-pentyl, neopentyl, 3-methylbutyl, n-hexyl, 2-hexyl, 3-hexyl and 4-methylpentyl. Examples include a straight-chain or branched alkyl radical having 1 to 4 carbon atoms, such as methyl, ethyl, n-propyl, isopropyl, n-butyl, isobutyl, sec-butyl and tert-butyl. Examples include a straight-chain or branched alkyl radical having 1 to 3 carbon atoms, such as methyl, ethyl, n-propyl and isopropyl.

"Alkoxy" in the context of the disclosure represents a straight-chain or branched alkoxy radical having 1 to 8 (e.g., 1 to 6, 1 to 4, or 1 to 2) carbon atoms. Examples include: methoxy, ethoxy, n-propoxy, isopropoxy, n-butoxy, isobutoxy, sec-butoxy and tert-butoxy. Examples include a straight-chain or branched alkoxy radical, such as methoxy, ethoxy, n-propoxy and isopropoxy.

"Aryl" in the context of the disclosure is an aromatic ring containing 1-10 carbon ring members. Examples include phenyl, naphthyl, anthracene, and pyrene.

"Bicyclic ring" includes bicyclic ring systems wherein each ring is independently aromatic or nonarornatic, and wherein the ring system is a fused bicyclic, bridged bicyclic, or spirocyclic ring system. For example, in the context of the disclosure, when $R^C$ and $R^D$ are joined to one another and, taken together with the carbon atom to which they are attached, form a 4- to 10-membered monocyclic or bicyclic ring, the bicyclic ring includes bicyclic ring systems wherein each ring is independently aromatic or nonaromatic, and wherein the ring system is a fused bicyclic, bridged bicyclic, or spirocyclic ring system.

"Cycloalkyl" in the context of the disclosure is a monocyclic saturated cycloalkyl group having 3 to 10 ring carbon atoms. Examples include: cyclopropyl, cyclobutyl, cyclopentyl, cyclohexyl and cycloheptyl.

"Cycloalkoxy" in the context of the disclosure is a monocyclic saturated cycloalkyl group having 3 to 10 ring carbon atoms bound via an oxy linker to the rest of the molecule. Examples include: cyclopropoxy, cyclobutoxy, cyclopentoxy, cyclohexoxy and cycloheptoxy.

"Cycloalkyl-alkyl" in the context of the disclosure is an alkyl substituted by cycloalkyl and bound to the rest of the molecule via the alkyl group. For example, $(C_3-C_7)$-Cycloalkyl-$(C_1-C_3)$-alkyl in is a $(C_1-C_3)$-alkyl substituted by $(C_3-C_7)$-cycloalkyl and bound to the rest of the molecule via the $(C_1-C_3)$-alkyl group.

"Aryl-alkyl" in the context of the disclosure is an alkyl substituted by aryl and bound to the rest of the molecule via the alkyl group. For example, $(C_6-C_{10})$-aryl-$(C_1-C_4)$-alkyl in the context of the disclosure is a $(C_1-C_4$-alkyl substituted by $(C_6-C_{10})$-aryl and bound to the rest of the molecule via the $(C_1-C_4)$-alkyl group.

"Halo" in the context of the disclosure is a fluoro, chloro, bromo, or iodo substituent.

"Heterocyclyl" in the context of the disclosure is a monocyclic or bicyclic saturated heterocycle which has a total of 4 to 10 ring atoms, contains one to four identical or different ring heteroatoms from the group of N, O and S. and is joined to the rest of the molecule via a ring carbon atom or optionally via a ring nitrogen atom. Examples include: azetidinyl, oxetanyl, thietanyl, pyrrolidinyl, pyrazolidinyl, tetrahydrofuranyl, thiolanyl, 1,2-oxazolidinyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, 1,2-oxazinanyl, morpholinyl, thiomorpholinyl, azepanyl, 1,4-diazepanyl, 1,4-oxazepanyl and 7-azabicyclo[2.2.1]heptyl. When the heterocyclyl is a bicyclic ring, it can be a fused bicyclic, bridged bicyclic, or spirocyclic.

"Heteroaryl" in the context of the disclosure is a monocyclic or optionally bicyclic aromatic heterocycle (heteroaromatic) which has a total of 5 to 10 ring atoms, contains up to four identical or different ring heteroatoms from the group of N, O, and S, and is joined via a ring carbon atom or optionally via a ring nitrogen atom to the rest of the molecule. Examples include: furyl, pyrrolyl, thienyl, pyrazolyl, imidazolyl 1,2-oxazolyl (isoxazolyl), 1,3-oxazolyl, 1,2-thiazolyl (isothiazolyl), 1,3-thiazolyl, 1,2,3-triazolyl, 1,2,4-triazolyl, 1,2,4-oxadiazolyl, 1,3,4-oxadiazolyl, 1,2,4-thiadiazolyl, 1,3,4-thiadiazolyl, tetrazolyl, pyridyl, pyrimidinyl, pyridazinyl, pyrazinyl, 1,2,4-triazinyl, 1,3,5-triazinyl, benzofuranyl, benzothienyl, benzimidazolyl, benzoxazolyl, benzothiazolyl, benzotriazolyl, indolyl, indolizinyl, indazolyl, quinolinyl, isoquinolinyl, naphthyridinyl, quinazolinyl, quinoxalinyl, cinnolinyl, phthalazinyl, pyrazolo[3,4-b]pyridinyl, purinyl and pteridinyl.

An "oxo" substituent in the context of the disclosure is an oxygen atom bonded to a carbon atom via a double bond.

Unless otherwise specified, all radicals which occur more than once are defined independently of one another. When radicals in a compounds of Formula (Z), (Y), (X), (A), (I), (I-A), (I-B), (I-C), or (I-D) are substituted, the radicals may be mono- or polysubstituted, unless specified otherwise. Substitution by one or two identical or different substituents (e.g., 1 substituent) is exemplified.

As used herein, the terms "subject," "individual," or "patient," are used interchangeably, refer to any animal, including mammals such as mice, rats, other rodents, rabbits, dogs, cats, swine, cattle, sheep, horses, primates, and humans. In some embodiments, the subject is a human. In some embodiments, the subject has experienced and/or exhibited at least one symptom of the disease or disorder to be treated and/or prevented.

In the context of the present disclosure, the term "treatment" or "treating" includes inhibition, retardation, checking, alleviating, attenuating, restricting, reducing, suppressing, repelling or healing of a disease, a condition, a disorder, an injury or a health problem, the course or the progression of such states and/or the symptoms of such states. The term "therapy" is understood here to be synonymous with the term "treatment".

The terms "prevention", "prophylaxis" and "preclusion" are used synonymously in the context of the present disclosure and refer to the avoidance or reduction of the risk of contracting, experiencing, suffering from or having a disease, a condition, a disorder, an injury or a health problem, or a development or advancement of such states and/or the symptoms of such states.

Methods of Use

Provided herein are methods for modulating the DLK and/or LZK signalling pathway, for example, the compounds provided herein can modulate DLK and/or LZK. Such compounds can be useful for treating diseases and disorders which can be treated with a modulator of DLK and/or LZK. Compounds of Formula (Z), (Y), (X), (A), (I), (I-A), (I-B), (i-C), or (I-D), or pharmaceutically acceptable salts thereof, can have valuable pharmacological properties and can be used for the prevention and/or treatment of diseases in humans and animals. Compounds of Formula (Z), (Y), (X), (A), (I), (I-A), (I-B), (I-C), or (I-D), which are low molecular weight, potent and dual-action inhibitors of the DLK and LZK signalling pathway, can be suitable for treatment and/or prevention of neurodegenerative disorders, such as ophthalmological neurodegenerative disorders.

The neurodegenerative ophthalmological disorders which can be treated and/or prevented using a compound of Formula (Z), (Y), (X), (A), (I), (I-A), (I-B), (I-C) or (I-D), in the context of the disclosure, should be understood, for example, to include the following disorders: age-related macular degeneration (AMD) including dry (non-exudative) and wet (exudative, neovascular) AND, choroidal neovascularization (CNV), choroidal neovascular membranes (CNVM), cystoid macular oedema (CME), epiretinal membranes (ERM) and macular perforations, myopia-associated choroidal neovascularization, angioid and vascular streaks, retinal detachment, diabetic retinopathy, diabetic macular oedema (DME), atrophic and hypertrophic lesions in the retinal pigment epithelium, retinal vein occlusion, choroidal retinal vein occlusion, mnacular oedemna, macular oedema associated with renal vein occlusion, retinitis pigmentosa and other inherited retinal degenerations (e.g. Stargardt disease), retinopathy of prematurity, glaucoma (including open-angle and narrow/closed-angle glaucoma, primary and secondary glaucoma, normal tension and high-IOP glaucoma), other optic neuropathies including toxic optic neuropathy (e.g. methanol, ethambutol), nonarteritic ischemic optic neuropathy, arteritic ischemic optic neuropathy/giant cell arteritis, traumatic optic neuropathy (including traumatic brain injury), idiopathic intracranial hypertension/pseudotumor cerebri, inflammatory optic neuropathies (e.g. optic neuritis), compressive optic neuropathies (e.g. pituitary adenoma), infiltrative optic neuropathies (e.g. sarcoidosis, lymphoma), autoimmune optic neuropathies, lipid storage diseases (e.g. Tay-Sachs), nutritional optic neuropathies, Leber's hereditary optic neuropathy, dominant optic atrophy, Friedrich's ataxia, radiation-induced optic neuropathy, iatrogenic optic neuropathies, space flight-associated neuro-ocular syndrome (SANS), inflammation disorders of the eye, for example uveitis, scleritis, cataract, refraction anomalies, for example myopia, hyperopia, astigmatism or keratoconus, neurotrophic keratopathy, corneal denneratvation and promoting corneal reinnervation and diabetic keratopathy. Neurodegenerative non-ophthalmological disorders which can be treated and prevented using a compound of Formula (Z), (Y), (X), (A), (I), (I-A), (I-B), (I-C), or (I-D), in the context of the disclosure, should be understood, for example, to mean but not limited to the following disorders: Amyotrophic lateral sclerosis (ALS), Alzheimer's disease, Parkinson's disease, Parkinson's-plus disease, Huntington's disease, peripheral neuropathies, ischemia, stroke, intracranial haemorrhage, cerebral haemorrhage, nerve damage caused by exposure to toxic compounds selected from the group consisting of heavy metals, industrial solvents, drugs and chemotherapeutic agents, injury to the nervous system caused by physical, mechanical or chemical trauma trigeminal neuralgia, glossopharyngeal neuralgia, Bell's Palsy, myasthenia gravis, muscular dystrophy, progressive muscular atrophy, primary lateral sclerosis (PLS), spinal muscular atrophy, inherited muscular atrophy, invertebrate disk syndromes, cervical spondylosis, plexus disorders, thoracic outlet destruction syndromes, *porphyria*, pseudobulbar palsy, progressive bulbar palsy, multiple system atrophy, progressive supranuclear palsy, corticobasal degeneration, dementia with Lewy bodies, frontotemporal dementia, demyelinating diseases, Guillain-Barré syndrome, multiple sclerosis, Charcot-Marie-Tooth disease, prion disease, Creutzfeldt-Jakob disease, Gerstmann-Sträussler-Scheinker syndrome (GSS), fatal familial insomnia (FFI), bovine spongiform encephalopathy, Pick's disease, epilepsy, sensorineural hearing loss, traumatic brain injury, and AIDS demential complex. In some embodiments, the disorder is chemotherapy-induced peripheral neuropathy (CIPN), e.g,. nerve damage caused by exposure to chemotherapeutic agents.

Because of their profile of activity, compounds of Formula (Z), (Y), (X), (A), (I), (I-A), (I-B), (I-C), or (I-D) can be suitable for treatment and/or prevention of age-related macular degeneration (AMD), choroidal neovascularization (CMV), myopia-associated choroidal neovascularization, diabetic retinopathy, macular oedema, and retinal vein occlusion.

In some embodiments, a compound of Formula (Z), (Y), (X), (A), (I), (I-A), (I-B), (I-C), or (I-D) can be used to treat and/or prevent optic neuropathies, including glaucoma, inherited retinal degenerations, non-exudative AMD/geographic atrophy, retinal vascular diseases that produce ischemia (diabetes, vein occlusion), retinal detachments and edema-producing diseases (including exudative AMD).

Another aspect of the disclosure are cell transplantation-based regenerative approaches which are being developed for the treatment of ocular and other forms of neurodegeneration. These include photoreceptor and/or RPE transplantation for treatment of macular degeneration and forms of photoreceptor degeneration, and RGC transplantation for the treatment of glaucoma and other forms of optic nerve disease which unfortunately show evidence of significant death of the transplanted cells. Compounds of Formula (Z), (Y), (X), (A), (I), (I-A), (I-B), (I-C), or (I-D) can be suitable to reduce death and dysfunction of the transplanted cells, for regenerative therapies for both ocular degenerative diseases and other forms of neurodegeneration.

The aforementioned well-characterized diseases in humans can also occur with comparable aetiology in other mammals and can likewise be treated therein with the compounds of the present disclosure.

The present disclosure thus further provides for the use of a compound of Formula (Z), (Y), (X), (A), (I), (I-A), (I-B), (I-C), or (I-D), or a pharmaceutically acceptable salt thereof, for the treatment and/or prevention of a disorder, for example, any of the aforementioned disorders, in a subject.

In some embodiments, the compound of Formula (Z), (Y), (X), (A), (I), (I-A), (I-B), (I-C), or (I-D) or pharmaceutical composition thereof is formulated for ocular administration. In some embodiments, the compound of Formula (Z), (Y), (X), (A), (I), (I-A), (I-B), (I-C), or (I-D) or pharmaceutical composition thereof is formulated as an eye drop, an ocular ointment, an ocular gel, an ocular coil, a contact lens, or an opthalmic insert. In some embodiments, the compound of Formula (Z), (Y), (X), (A), (I), (I-A), (I-B), (I-C), or (I-D) or pharmaceutical composition thereof is formulated for intravitreal administration. In some embodiments, the compound of Formula (Z), (Y), (X), (A), (I), (I-A), (I-B), (I-C), or (I-D) or pharmaceutical composition thereof forms a depot at the site of injection.

In some embodiments, the compound of Formula (Z), (Y), (X), (A), (I), (I-A), (I-B), (I-C), or (I-D) or pharmaceutical composition thereof is formulated for systemic delivery (e.g., delivery to the central nervous system).

The treatment or prevention of a disease, a condition, a disorder, an injury or a health problem may be partial or complete.

The present disclosure further provides for the use of a compound of Formula (Z), (Y), (X), (A), (I), (I-A), (I-B), (I-C), or (I-D), or a pharmaceutically acceptable salt thereof, for the production of a medicament for the treatment and/or prevention of a disorder, for example, any of the aforementioned disorders.

The present disclosure further provides a pharmaceutical composition comprising at least one of the compounds of Formula (Z), (Y), (X), (A), (I), (I-A), (I-B), (I-C), or (I-D), or a pharmaceutically acceptable salt thereof, for the treatment and/or prevention of a disorder, for example, any of the aforementioned disorders.

The present disclosure further provides for the use of compounds of Formula (Z), (Y), (X), (A), (I), (I-A), (I-B), (I-C), or (I-D), or a pharmaceutically acceptable salt thereof, in a method for the treatment and/or prevention of a disorder, for example, any of the aforementioned disorders, in a subject.

The present disclosure further provides a process for the treatment and/or prevention of a disorder, for example, any of the aforementioned disorders, in a subject using an effective amount of at least one compound of Formula (Z), (Y), (X), (A), (I), (I-A), (I-B), (I-C), or (I-D), or a pharmaceutically acceptable salt thereof.

The terms "effective amount" or "therapeutically effective amount," as used herein, refer to a sufficient amount of a chemical entity being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

Also provided is a method for modulating DLK and/or LZK activity in a cell, comprising contacting the cell with a compound of Formula (Z), (Y), (X), (A), (I), (I-A), (I-B), (I-C), or (I-D). In some embodiments, the compounds provided herein inhibit DLK and/or LZK in a cell. In some embodiments, the contacting is in vitro. In some embodiments, the contacting is in vivo. In some embodiments, the contacting is in vivo, wherein the method comprises administering an effective amount of a compound of Formula (Z), (Y), (X), (A), (I), (I-A), (I-B), (I-C), or (I-D), or a pharmaceutically acceptable salt thereof, to a subject having a cell having DLK and/or LZK activity. In some embodiments, the cell is a neuronal cell.

As used herein, the term "contacting" refers to the bringing together of indicated moieties in an in vitro system or an in vivo system. For example, "contacting" DLK and/or LZK with a compound provided herein includes the administration of a compound provided herein to an individual or subject, such as a human, having DLK and/or LZK, as well as, for example, introducing a compound provided herein into a sample containing a cellular or purified preparation containing DLK and/or LZK.

In some embodiments, the compound of Formula (Z), (Y), (X). (A), (I), (I-A), (I-B), (I-C), or (I-D) (or a pharmaceutically acceptable salt thereof) is MINT (micronucleus test) negative. MINT positivity can indicate that a compound is genotoxic. In some embodiments, an in vitro micronucleus test, e.g., a test that evaluates the presence of micronuclei after exposure of cells to a compound of Formula (Z), (Y), (X), (A), (I), (I-A), (I-B), (I-C), or (I-D), can be used to determine if a compound of Formula (Z), (Y), (X), (A), (I), (I-A), (I-B), (I-C), or (I-D) is MNT negative.

In some embodiments of any the methods described herein, the compound of Formula (Z), (Y), (X), (A), (I), (I-A), (I-B), (I-C), or (I-D) (or a pharmaceutically acceptable salt thereof) is administered in combination with a therapeutically effective amount of at least one additional therapeutic agent selected from one or more additional therapies or therapeutic agents. In some embodiments, the compound of Formula (Z), (Y), (X), (A), (I), (I-A), (I-B), (I-C), or (I-D), or a pharmaceutically acceptable salt thereof, can be used in combination with one or more other pharmacologically active substances, provided that this combination does not lead to undesirable and unacceptable side effects. The present disclosure therefore further provides medicaments comprising at least one of a compound of Formula (Z), (Y), (X), (A), (I), (A), (PB), (I-C), or (I-D), or a pharmaceutically acceptable salt thereof, and one or more further active ingredients, for example, for the treatment and/or prevention of the aforementioned disorders. In some embodiments, examples of combination active ingredients suitable for the purpose include IOP-lowering/neuroprotective combinations like prostaglandin/neuroprotective (e.g. bimatoprost, tafluprost, latanoprost, travaprost), beta-blocker/neuroprotective (e.g. timolol, levobunolol, carteolol, betaxalol), alpha-agonist/neuroprotective (e.g. brimonidine, apraclonidine), carbonic anhydrase inhibitor/neuroprotective (e.g. dorzolamide, brinzolamide), rho kinase inhibitor/neuroprotective (e.g. netarsudil), cholinergics (e.g. pilocarpine), and anti-inflammatory/neuroprotective combinations like steroid/neuroprotective (e.g. prednisolone, dexamethasone, fluoromethalone, loteprednol, fluocinolone, difluprednate, triamcinolone).

Accordingly, also provided herein is a method for treating a neurodegenerative disorder, comprising administering to a subject in need thereof a pharmaceutical combination for treating a neurodegenerative disorder which comprises (a) a compound of Formula (Z), (Y), (X), (A), (I), (I-A), (I-B), (I-C), or (I-D), or a pharmaceutically acceptable salt thereof, (b) an additional therapeutic agent, and (c) optionally at least one pharmaceutically acceptable carrier for simultaneous, separate or sequential use for the treatment of a neurodegenerative disease, wherein the amounts of the compound of Formula (Z), (Y), (X), (A), (I), (I-A), (I-B), (I-C), or (I-D), or a pharmaceutically acceptable salt thereof, and the additional therapeutic agent are together effective in treating the neurodegenerative disease.

These additional therapeutic agents may be administered with one or more doses of the compound of Formula (Z), (Y), (X), (A), (I), (I-A), (I-B), (I-C), or (I-D), or a pharmaceutically acceptable salt thereof, or pharmaceutical composition thereof, as part of the same or separate dosage forms, via the same or different routes of administration, and/or on the same or different administration schedules according to standard pharmaceutical practice known to one skilled in the art.

Pharmaceutical Compositions and Administration

The present disclosure further provides pharmaceutical compositions which comprise at least one compound of Formula (Z), (Y), (X), (A), (I), (I-A), (I-B), (I-C), or (I-D), or a pharmaceutically acceptable salt thereof, typically together with one or more pharmaceutically acceptable excipients.

Compounds of Formula (Z), (Y), (X), (A), (I), (I-A), (I-B), (I-C), or (I-D), or pharmaceutically acceptable salt thereofs, can act systemically and/or locally. For this purpose, they can be administered in a suitable manner, for example by the oral, parenteral, pulmonal, nasal, sublingual, lingual, buccal, rectal, dermal, transdermal, extraocular, intraocular or otic route, or as an implant or stent.

In some embodiments, a compound of Formula (Z), (Y), (X), (A), (I), (I-A), (I-B), (I-C), or (I-D), or a pharmaceutically acceptable salt thereof, or a pharmaceutical composition thereof, is suitable for local and topical administration to the eye (e.g., eye drops, ocular ointments, ocular gels, ocular coil, contact lenses, and other opthalmic inserts). See, e.g., Dubald et al. Pharmaceutics. 2018; 10(1): 10; Bertens et al Eur J Pharm Biopharm. 2020 Mar. 12. pii: S0939-6411 (20)30074-6; Singh et al. Ther Adv Ophthalmol. 2020 Mar. 13; 12:2515841420905710; and Patel et al. World J Pharmacol. 2013; 2(2): 47-64. In some embodiments, the administration route is local extraocular or intraocular. More specifically, possible routes of administration include: intravitreal injection, intravitreal implant, periocular injection (e.g. subtenon, subconjunctival), periocular reservoir, retrobulbar injection, subconjunctival injection or depot, intracameral injection, intracameral implant, topical (eye drop or gel), suprachoroidal injection, subconjunctival insert, subretinal delivery, punctal plug, and suprachoroidal implant. Compounds of Formula (Z), (Y), (X), (A), (I), (I-A), (I-B), (I-C), or (I-D) can be administered in suitable administration forms for these administration routes.

Suitable administration forms for extraocular (topical) administration can include administration forms that release a compound of Formula (Z), (Y), (X), (A), (i), (I-A), (I-B), (I-C), or (I-D), or a pharmaceutically acceptable salt thereof, rapidly and/or in a modified or controlled manner and which contain a compound of Formula (Z), (Y), (X), (A), (I) (I-A), (B), (I-C), or (1-D), or a pharmaceutically acceptable salt thereof, in crystalline and/or amorphized and/or dissolved form, for example eye drops, sprays or lotions (e.g. solutions, suspensions, vesicular/colloidal systems, emulsions, aerosols), powders for eye drops, sprays or lotions (e.g. ground active ingredient, mixtures, lyophilizates, precipitated active ingredient), semisolid eye preparations (e.g. hydrogels, in-situ hydrogels, creams or ointments) or opthalmic inserts (solid or semisolid preparations, e.g. bioadhesives, films/wafers, tablets, contact lenses).

Intraocular administration includes, for example, intravitreal, subretinal, subscleral, intrachoroidal, subconjunctival, retrobulbar and subtenon administration. Suitable administration forms for intraocular administration include administration forms that release compounds of Formula (Z), (Y), (X), (A), (I), (I-A), (I-B), (I-C), or (I-D) rapidly and/or in a modified or controlled manner and which contain compounds of Formula (Z), (Y), (X), (A), (I), (I-A), (I-B), (I-C), or (I-D) in crystalline and/or amorphized and/or dissolved form such as, for example, preparations for injection and concentrates for preparations for injection (e.g. solutions, suspensions, vesicular/colloidal systems, emulsions), powders for preparations for injection (e.g. ground active ingredient, mixtures, lyophilizates, precipitated active ingredient), gels for injection (semisolid preparations, e.g. hydrogels, in-situ hydrogels) or implants (solid preparations, e.g. biodegradable and nonbiodegradable implants, implantable pumps).

In some embodiments, an injectable composition is implanted at the site of drug release, An injectable composition can include a polymer delivery vehicle. Such polymer delivery vehicles can allow for extended release. In some embodiments, the polymer delivery vehicle can prolong delivery up to a few months in the surrounding tissue. In some embodiments, an injectable composition can form a depot of a compound of Formula (Z), (Y), (X), (A), (I), (I-A), (I-B), (I-C), or (I-D) at the injection site. In some embodiments, the compound of Formula (Z), (Y), (X), (A), (I), (I-A), (I-B), (I-C), or (I-D) is released and/or diffuses from the depot over a period of time. For example, a compound of Formula (Z), (Y), (X), (A), (I), (I-A), (I-B), (I-C), or (I-D) can be released over a few days and up to a few months.

Opthalmic inserts include multi-layered, drug-impregnated devices placed into the eye. In some embodiments, an opthalmic insert is multi-layered. In some embodiments, an opthalmic insert is sterile. In some embodiments, the ophthalmic insert is placed into the cul-de-sac or conjunctival sac or the eye. In some embodiments, the release of the drug from the ophthalmic insert is prolonged. In some embodiments, an opthalmic insert is a soluble ocular drug insert, a poly(vinyl methyl ether-maleic anhydride)anhydride ocular insert, a collagen shield, an ocusert, a minidisc, a new opthalalmic delivery system, or a topical bimatoprost ocular insert. See, e.g., Jervis. *J. Bioequiv. Availab.* 2017, 9:1.

In some embodiments, compositions suitable for ocular delivery include in situ gelling systems, liposomes, nanoparticles (e.g., chitosan-based polymeric nanoparticles, poly (lactic-co-glycolic acid) nanoparticles, gelatin nanoparticles, propoxylated glyceryl triacylate nanoparticles, and PGT-ethylene glycol dimethacrylate nanoparticles), niosomes, nanoemulsions, nanospheres, and microemulsions. In some embodiments, the in situ gelling system is thermosensitive. IN some embodiments, the in situ gelling system comprises triblock polymer PLGA-PEG-PLGA (poly-(DL-lactic acid co-glycolic acid)-polyethylene glycol-poly-(DL-lactic acid co-glycolic acid).

Ocular compositions can include, without limitation, one or more of any of the following: viscogens; stabilizers; preservative; permeation enhancers; and lubricants. Non-limiting examples of viscogens include polyvinylalcohol (PVA), hydroxylmethylcellulose, hydroxylethylcellulose carboxymethylcellulose, glycerin, polyvinylpyrrolidone, and polyethylene glycol. Non-limiting examples of stabilizers include pluronic (triblock copolymers) and cyclodextrins. Non-limiting examples of preservatives include benzalkonium chloride, ETDA, SofZia (boric acid, propylene glycol, sorbitol, and zinc chloride; Alcon Laboratories, Inc.), and purite (stabilized oxychloro complex; Allergan, Inc.)). Non-limiting examples of permeation enhancers include polyoxyethylene glycol ester and ethylenediaminetetra acetic acid sodium salt. In some embodiments, a composition for ocular delivery is isotonic.

In some embodiments, an ocular ointment includes non-aqueous excipients. In some embodiments, an ocular ointment has an oleaginous base, an absorption base, a water-removable base, or a water soluble base. An oleaginous base can be a lipophilic ointment. For example, an oleaginous base can include petrolatum and white ointment. An adsorption base can be used as emollient. For example, an adsorption base can include lanolin, fatty alcohol and petrolatum. A water-soluble base can include only water soluble excipients such as macrogol with high molecular weight. A water removable base includes compositions that are an oil in water emulsion.

In some embodiments, an ocular gel is a hydrogel. For example, a preformed gel or a composition that forms a gel in situ. Hydrogels can include polymers such as methylcellulose, hydroxylethylcellulose, sodium hyaluronate, sodium alginate, povidone, polyvinylalcohol, cellulose acetate and derivatives, carbomer, magrogol, pseudolatex, polymethacrylic acid, alginate sodium, gellan gum (GELRITE®), pluronics, poly(n-isopropyl acrylamide), oly(acrylic acid), polyacrylamide, poloxamer, chitosan, and hydroxyl propyl methyl cellulose.

In some embodiments, a compound of Formula (Z), (Y), (X), (A), (I), (I-A), (I-B), (I-C), or (I-D), or a pharmaceutically acceptable salt thereof, or a pharmaceutical composition thereof, is suitable for systemic administration, e.g., through oral or parenteral administration such as intravenous injection, subcutaneous injection, or intramuscular injection.

Suitable administration forms for oral administration include administration forms that release a compound of Formula (Z), (Y), (X), (A), (I), (I-A), (I-B), (I-C), or (I-D), or a pharmaceutically acceptable salt thereof, rapidly and/or in a modified manner and which contain a compound of Formula (Z), (Y), (X), (A), (I), (I-A), (I-B), (I-C), or (I-D), or a pharmaceutically acceptable salt thereof, in crystalline and/or amorphized and/or dissolved form, for example, tablets (uncoated or coated tablets, for example with gastric juice-resistant or retarded-dissolution or insoluble coatings which control the release of the compound of Formula (Z), (Y), (X), (A), (I), (I-A), (I-B), (I-C), or (I-D)) tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

In some embodiments, a compound of Formula (Z), (Y), (X), (A), (I), (I-A), (I-B), (I-C), or (I-D), or a pharmaceutically acceptable salt thereof, or a pharmaceutical composition thereof, is suitable for administration to the central nervous system (CNS). Compounds of Formula (Z), (Y), (X), (A), (I), (I-A), (I-B), (I-C), or (I-D) can be administered in suitable administration forms for these administration routes. In some embodiments, compositions suitable for CNS delivery include nanoparticles. Non-limiting examples of such nanoparticles include gold nanoparticles, lipid-based nanoparticles (e.g., liposomnes), polymeric nanoparticles, and dendrimers. See, e.g., Spencer et al. Pharmaceutics. 2020 February; 12(2): 192.

Parenteral administration can bypass an absorption step (e.g. intravenously, intraarterially, intracardially, intraspinally or intralumbally) or include an absorption (e.g. inhalatively, intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers, metered aerosols), nasal drops, solutions or sprays, tablets, films/oblates or capsules for lingual, sublingual or buccal administration, suppositores, ear preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

In some embodiments, treatment of ophthalmological disorders includes extraocular topical or intraocular administration of a compound of Formula (Z), (Y), (X), (A), (I), (I-A), (I-B), (I-C), or (I-D). In some embodiments, the treatment of other disorders includes oral or intravenous administration of a compound of Formula (Z), (Y), (X), (A), (I), (I-A), (I-B), (I-C), or (I-D). In some embodiments, the treatment of other disorders includes administration of a compound of Formula (Z), (Y), (X), (A), (I-A), (I-B), (I-C), or (I-D) to the central nervous system of a subject.

Compounds of Formula (Z), (Y), (X), (A), (I), (I-A), (I-B), (I-C), or (I-D) can be converted to the administration forms mentioned. This can be accomplished in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavor and/or odor correctants.

In general, it has been found to be advantageous in the case of parenteral administration to administer amounts of about 0.001 to 1 mg/kg, for example, about 0.01 to 0.5 mg/kg, of body weight to achieve effective results. In the case of oral administration the dosage is about 0.01 to 100 mg/kg, for example, about 0.01 to 20 mg/kg or about 0.1 to 10 mg/kg of body weight. In the case of extraocular administration, the dosage is about 1 to 50 mg/ml with an application volume of 10 to 100 μl.

It may nevertheless be necessary in some cases to deviate from the stated amounts, specifically as a function of the body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

EXAMPLES

The disclosure will be described in greater detail by way of specific examples. The following examples are offered for illustrative purposes, and to exemplify the compositions and methods described herein and are not intended to limit the disclosure in any manner. Many variations will suggest themselves and are within the full-intended scope. Those of skill in the art will readily recognize a variety of non-critical parameters that can be changed or modified to yield essentially the same results.

The following sections include materials, methods, synthetic procedures, and biological data for Compounds of Formula (Z), (Y), (X), (A), (I), (I-A), (I-B), (I-C), or (I-D).

Part I. Materials, Methods, Synthetic Procedures, and Biological Data for Compounds of Formula (I)

The compounds disclosed herein can be prepared in a variety of ways using commercially available starting materials, compounds known in the literature, or from readily prepared intermediates, by employing standard synthetic methods and procedures either known to those skilled in the art, or in light of the teachings herein. The synthesis of the compounds disclosed herein can be achieved by generally following the Schemes and procedures that follow, with modification for specific desired substituents.

Standard synthetic methods and procedures for the preparation of organic molecules and functional group transformations and manipulations can be obtained from the relevant scientific literature or from standard textbooks in the field. Although not limited to any one or several sources, classic texts such as R. Larock, Comprehensive Organic Transformations, VCH Publishers (1989); L Fieser and M. Fieser, Fieser and Fieser's Reagents for Organic Synthesis, John Wiley and Sons (1994); Smith, M. B., March, J., March's Advanced Organic Chemistry: Reactions, Mechanisms, and Structure, 5th edition, John Wiley & Sons: New York, 2001; and Greene, T. W., Wuts, P. G. M., Protective Groups in Organic Synthesis, 3rd edition, John Wiley & Sons: New York, 1999, are useful and recognized reference textbooks of organic synthesis known to those in the art. The following descriptions of synthetic methods are designed to illustrate, but not to limit, general procedures for the preparation of compounds of the present disclosure.

The synthetic processes disclosed herein can tolerate a wide variety of functional groups; therefore, various substituted starting materials can be used. The processes generally provide the desired final compound at or near the end of the overall process, although it may be desirable in certain instances to further convert the compound to a pharmaceutically acceptable salt thereof.

LC-MS Methods

LC-MS method 1: Instrument MS: Thermo Scientific FT-MS: Instrument UHPLC+: Thermo Scientific UltiMate 3000; Column: Waters, HSS T3, C18 1.8 μm, 2.1×75 mm; Eluent A: water+0.01% formic acid; Eluent B: acetonitrile+0.01% formic acid; Gradient: 0.0 min 10% B to 2.5 min 95% B to 3.5 min 95% B; Oven: 50° C.; Flow rate: 0.90 mL/min; UV-Detection: 210 nm/Optimum Integration Path 210-300 nm LC-MS method 2: Instrument: Waters ACQUITY SQD U PLC System; Column: Waters Acquity UPLC HSS T3, 1.8 μm, 50×1 mm; Eluent A: 1 l water+0.25 mL formic acid, Eluent B: 1 l acetonitrile+0.25 ml formic acid; Gradient: 0.0 min 90% A to 1.2 min 5% A to 2.0 min 5% A; Oven: 50° C.; Flow rate: 0.40 mL/min; UV-Detection: 210 nm.

LC-MS method 3: Column: CORTECS C18, 2.7 μm, 2.1×50 mm. A linear gradient was applied, starting at 90% A (A: 0.1% formic acid in water) and ending at 100% B (B: 0.1% formic acid in acetonitrile) over 1.1 min with a total run time of 2.0 min. Oven: 40° C.; Flow rate: 1.0 mL/min.

LC-MS method 4: Column: IntertSustain, 2.1 μm, 3.0×50 mm. A linear gradient was applied, starting at 90% A (A: 0.03% $NH_3 \cdot H_2O$ in water) and ending at 95% B (B: acetonitrile) over 1.3 min with a total run time of 2.0 min. Oven: 40° C.; Flow rate: 1.2 mL/min.

LC-MS method 5: Column: Poroshell MPH-C18, 2.7 μm, 3.0×50 mm. A linear gradient was applied, starting at 90% A (A: 0.03% $NH_3 \cdot H_2O$ in water) and ending at 95% B (B: acetonitrile) over 2.0 min with a total run time of 3.0 min. Oven: 40° C.; Flow rate: 1.2 mL/min.

Scheme 1 depicts formation of thiophenecarboxamide boronic acids (e.g., intermediates 10-12), which were used in the preparation of compounds of Formula (Z).

Scheme 1-Preparation of substituted (5-carbamoylthiophen-3-yl) boronic acids

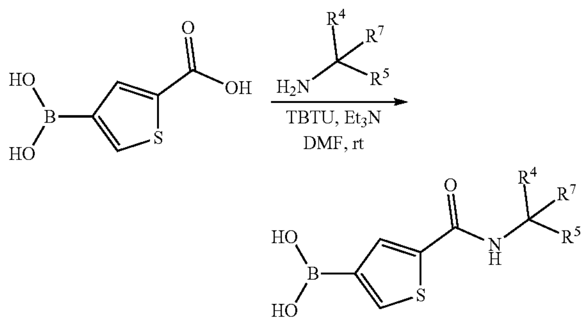

Scheme 2 depicts a preparation of compounds of Formula (Z) wherein $R^E$ is $C(O)NHCR^1R^2R^3$, X is carbon, and Y is nitrogen.

Scheme 2-Preparation of substituted 2-amino-6-(5-carbamoylthiophen-3-yl)-[1,2,4]triazolo[1,5-a]pyridine-8-carboxamides

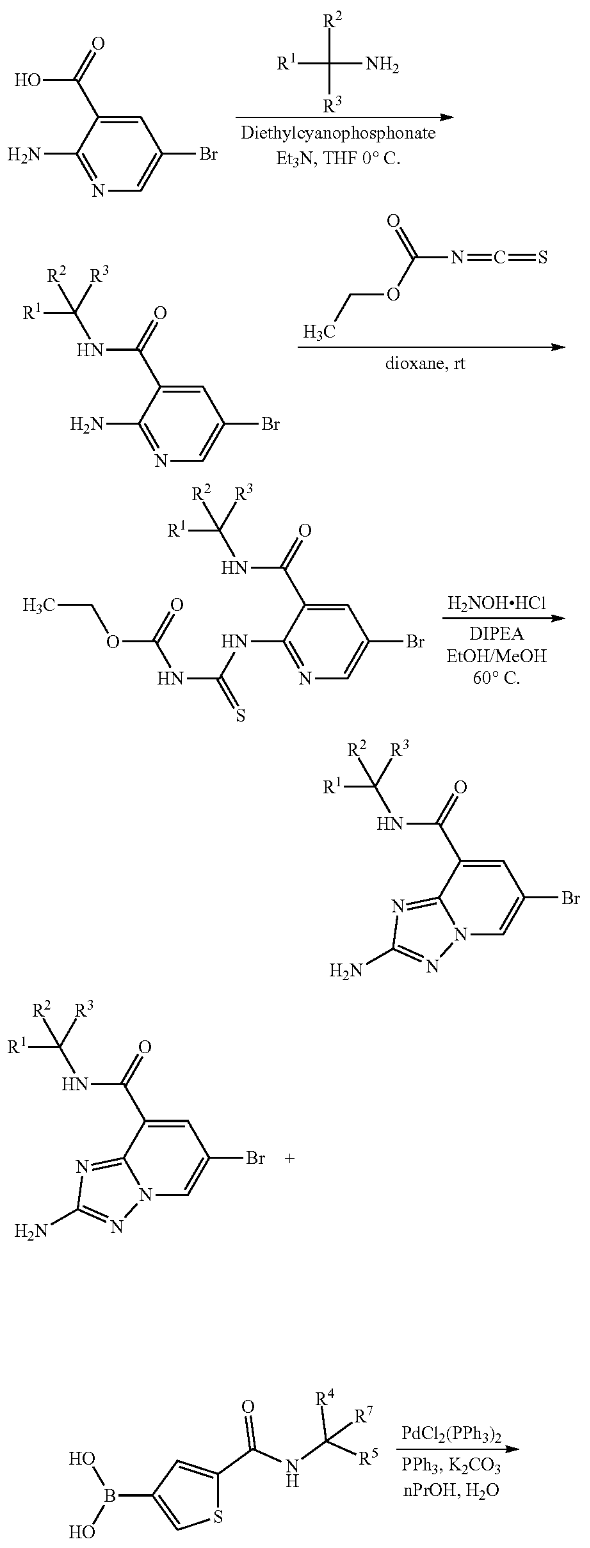

-continued

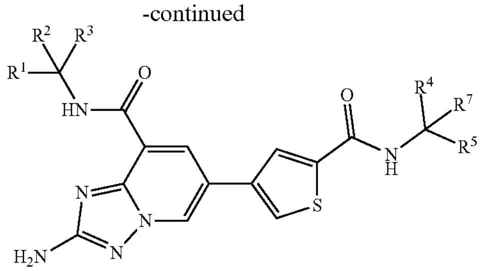

Intermediates

Intermediate 1

2-Amino-5-bromo-N-(propan-2-yl)pyridine-3-carboxamide

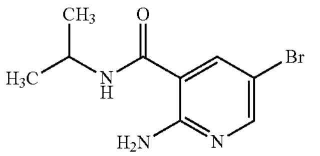

A suspension of 2-amino-5-bromopyridine-3-carboxylic acid (20.0 g, 92.2 mmol) in THF (270 mL) was cooled to 0° C. Propan-2-amine (7.8 mL, 92 mmol) was added followed by diethylcyanophosphonate [CAS-RN 2942-58-7] (17 mL, 93% purity, 100 mmol) and triethylamine (27 mL, 190 mmol). After 15 min the mixture was warmed to rt and stirred for 2 h. Further propan-2-amine (3.1 mL, 37 mmol) and diethylcyanophosphonate (6.0 mL, 93% purity, 37 mmol) was added and stirring was continued for 1.5 h. Subsequently, the reaction mixture was concentrated in vacuo and the residue was triturated with tert-butyl methyl ether:cyclohexane:dichloromethane=2:1:1 (150 mL) and the precipitate was collected by suction filtration and dried in vacuo to yield 18.6 g (100% purity, 78% yield) of the title compound.

LC-MS (method 2): $R_t$=0.67 min; MS (ESIpos): m/z=258/260 $[M+H]^+$ $^1$H-NMR (400 MHz, DMSO-$d_6$) δ [ppm]: 1.14 (d, 6H), 3.98-4.11 (m, 1H), 7.21 (br s, 2H), 8.09 (d, 1H), 8.13 (d, 1H), 8.29 (br d, 1H).

Intermediate 2

Ethyl ({5-bromo-3-[(propan-2-yl)carbamoyl]pyridin-2-yl}carbamothioyl)carbamate

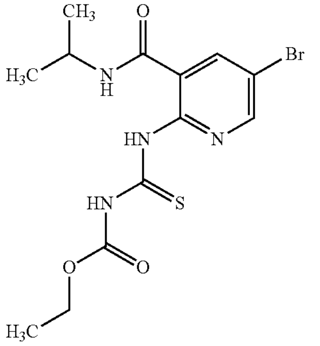 [SMILES: CCOC(=O)NC(=S)Nc1ncc(Br)cc1C(=O)NC(C)C]

2-Amino-5-bromo-N-(propan-2-yl)pyridine-3-carboxamide (18.6 g, 71.9 mmol) was dissolved in 1,4-dioxane (250 mL) and ethyl carbonisothiocyanatidate [CAS-RN 16182-04-0] (8.5 mL, 72 mmol) was added dropwise. The mixture was stirred overnight at rt and then concentrated in vacuo. The residue was triturated with tert-butyl methyl ether (35 mL) and the precipitate was collected by suction filtration and dried in vacuo to yield 27.2 g (100% purity, 97% yield) of the title compound.

LC-MS (method 1): $R_t$=1.71 min; MS (ESIpos): m/z 389/391 $[M+H]^{30}$ $^1$H-NMR (400 MHz, DMSO-$d_6$) δ[ppm]: 1.14 (d, 6H), 1.26 (t, 3H), 3.96-4.09 (m, 1H), 4.21 (q, 2H), 8.33 (d, 1H), 8.57 (br d, 1H), 8.67 (d, 1H), 12.11 (br s, 1H), 12.14 (br s, 1H).

Intermediate 3

2-Amino-6-bromo-N-(propan-2-yl)[1,2,4]triazolo[1,5-a]pyridine-8-carboxamide

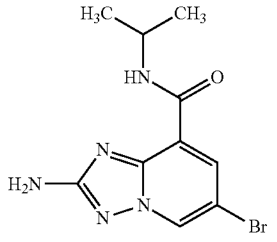 [SMILES: CC(C)NC(=O)c1cc(Br)cn2nc(N)nc12]

Hydroxylamine hydrogenchloride (1:1) (27.1 g, 390 mmol) and N,N-diisopropylethylamine (63 mL, 360 mmol) were dissolved in methanol/ethanol 1:1 (600 mL) and heated to 60° C. Ethyl ({5-bromo-3-[(propan-2-yl)carbamoyl]pyridin-2-yl}carbamothioyl)carbamate (28.1 g, 72.2 mmol) was added and the mixture was stirred at this temperature for 1.5 h. Thereafter, it was cooled to rt and the pH was adjusted to 6-7 by addition of satd. aq. sodium bicarbonate solution (ca. 100 mL). The mixture was poured into water (1.2 L) and stirred for 10 min. The precipitate was collected by suction filtration, washed with water (80 mL) and dried in vacuo to yield 21.1 g (100% purity, 98% yield) of the title compound.

LC-MS (method 2): $R_t$=0.69 min; MS (ESIpos): m/z=298/300 $[M+H]^+$ $^1$H-NMR (400 MHz, DMSO-$d_6$) δ [ppm]: 1.24 (d, 6H), 4.06-4.18 (m, 1H), 6.55 (s, 2H), 8.05 (d, 1H), 9.16 (d, 1H), 9.20 (br d, 1H).

Intermediate 4

2-Amino-5-bromo-N-[(2S)-1-hydroxypropan-2-yl]pyridine-3-carboxamide

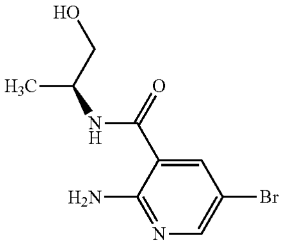

To 2-amino-5-bromopyridine-3-carboxylic acid (20.0 g, 92.2 mmol) and [(1H-benzotriazol-1-yl)oxy](dimethylamino)-N,N-dimethylmethaniminium tetrafluoroborate [CAS-RN 125700-67-6] (38.5 g, 120 mmol) in THF (270 mL) at rt was added (2S)-2-aminopropan-1-ol (8.6 mL, 110 mmol) and the reaction was stirred for 3 h. Subsequently, the mixture was concentrated in vacuo and water was added. It was extracted twice with ethyl acetate and the combined organic layers were washed with brine and dried over sodium sulfate and the solvent was evaporated under reduced pressure. The residue was triturated with tert-butyl methyl ether/acetonitrile and the precipitate was collected by suction filtration to yield 17.7 g (100% purity, 70% yield). The mother liquor was concentrated and purified by column chromatography (Biotage® SNAP Ultra 100 g cartridge, eluent: cyclohexane/ethyl acetate gradient 80:20 to 0:100) to yield another 3.00 g (100% purity, 12% yield) of the title compound.

LC-MS (method 1): $R_t$=0.83 min; MS (ESIpos): m/z=274/276 $[M+H]^+$ $^1$H-NMR (400 MHz, DMSO-$d_6$) δ[ppm]: 1.10 (d, 3H), 3.29-3.37 (m, 1H), 3.38-3.46 (m, 1H), 3.91-4.03 (m, 1H), 4.72 (t, 1H), 7.19 (br s, 2H), 8.08-8.15 (n, 2H), 8.19 (br d, 1H).

Intermediate 5

Ethyl [(5-bromo-3-{[(2S)-1-hydroxypropan-2-yl]carbamoyl}pyridin-2-yl)carbamothioyl]carbamate

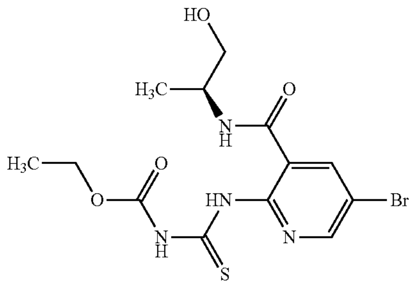 [SMILES: CCOC(=O)NC(=S)Nc1ncc(Br)cc1C(=O)N[C@@H](C)CO]

To 2-amino-5-bromo-N-[(2S)-1-hydroxypropan-2-yl]pyridine-3-carboxamide (20.7 g, 75.5 mmol) in 1,4-dioxane (250 mL) at rt was dropwise added ethyl carbonisothiocyanatidate (9.8 m, 83 mmol) and the reaction was stirred overnight at rt. The solvent was removed tinder reduced pressure and the residue was triturated with tert-butyl methyl ether (200 mL). The precipitate was collected by suction filtration. It was then triturated with tert-butyl methyl ether (150 mL) and dichloromethane (20 mL) and again collected by suction filtration to yield 29.9 g (93% purity, 90% yield) of the title compound.

LC-MS (method 2): $R_t$=0.71 min; MS (ESIpos): m/z=405/407 $[M+H]^+$ $^1$H-NMR (400 MHz, DMSO-$d_6$) δ[ppm]: 1.10 (d, 3H), 1.26 (t, 3H), 3.28-3.36 (in, 1H), 3.43 (dt, 1H), 3.89-4.02 (in, 1H), 4.21 (q, 2H), 4.75 (t, 1H), 8.39 (d, 1H), 8.53 (br d, 1H), 8.67 (d, 1H), 12.10-12.21 (m, 2H).

Intermediate 6

2-Amino-6-bromo-N-[(2S)-1-hydroxypropan-2-yl][1,2,4]triazolo[1,5-a]pyridine-8-carboxamide

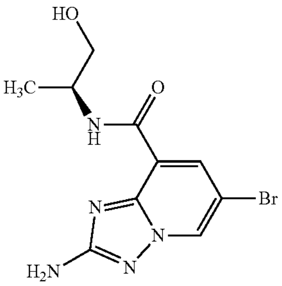 [SMILES: C[C@@H](CO)NC(=O)c1cc(Br)cn2nc(N)nc12]

The reaction was performed in two batches of equal size. To a solution of hydroxylamine hydrogen chloride (25.4 g, 365 mmol) in methanol/ethanol (1:1, 400 mL) was added N,N-diisopropylethylamine (59 mL, 340 mmol) and the mixture was heated to 60° C. Ethyl [(5-bromo-3-{[(2S)-1-hydroxypropan-2-yl]carbamoyl}pyridin-2-yl)carbamothioyl]carbamate (29.8 g, 92% purity, 67.6 mmol) was added and the reaction mixture was stirred at 60° C. for 30 min. The two reactions were cooled to rt and combined. The pH was adjusted to 6-7 by addition of satd. sodium bicarbonate solution (ca. 40 mL) and the mixture was poured into water (600 mL). Ethyl acetate was added and the layers were separated. The aqueous layer was extracted twice with ethyl acetate and the combined organic layers were dried over anhydrous sodium sulfate and the solvent was evaporated under reduced pressure to yield 19.5 g (100% purity, 92% yield) of the title compound.

LC-MS (method 1): $R_t$=0.89 min; MS (ESIpos): m/z=314/316 $[M+H]^+$ $^1$H-NMR (400 MHz DMSO-$d_6$) δ[ppm]: 1.21 (d, 3H), 3.40-3.54 (m, 2H), 4.01-4.14 (m, 1H), 4.90 (t, 1H), 6.54 (s, 2H), 8.07 (d, 1H), 9.16 (d, 1H), 9.24 (d, 1H).

Intermediate 7

2-Amino-5-bromo-N-[(2S)-butan-2-yl]pyridine-3-carboxamide

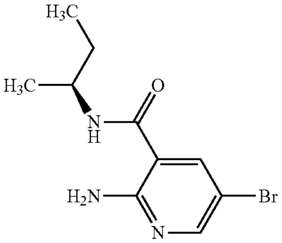

2-Amino-5-bromopyridine-3-carboxylic acid (24.3 g, 112 mmol) was suspended in THF (400 mL) and cooled to 0° C. (2S)-butan-2-amine (9.00 g, 123 mmol) was added leading to a clear solution Diethylcyanophosphonate (21.9 g, 134 mmol) and triethylamine (31 mL, 220 mmol) were added. After 15 min the mixture was warmed to rt and further stirred for 1 h. Subsequently, THF was removed by evaporation under reduced pressure and the residue was triturated with petroleum ether. The precipitate was collected by suction filtration to yield 16.0 g (99% purity, 52% yield) of the title compound.

LC-MS (method 3): $R_t$=0.78 min; MS (ESIpos): m/z=272/274 $[M+H]^+$ $^1$H-NMR (400 MHz, DMSO-$d_6$) δ [PPM]: 0.86 (t, 3H), 1.12 (d, 3H), 1.49-1.56 (m, 2H), 3.84-3.91 (m, 1H), 7.21 (s, 21H), 8.10 (s, 1H), 8.14 (s, 1H) 8.23 (d, 1H).

Intermediate 8

Ethyl [(5-bromo-3-{[(2S)-butan-2-yl]carbamoyl}pyridin-2-yl)carbamothioyl]carbamate

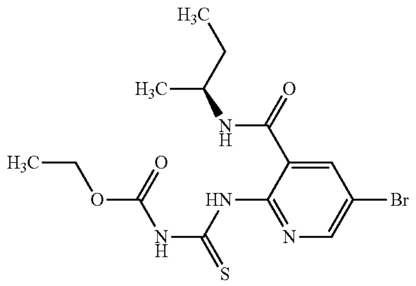 [SMILES: CCOC(=O)NC(=S)Nc1ncc(Br)cc1C(=O)N[C@@H](C)CC]

To a solution of 2-amino-5-bromo-N-[(2S)-butan-2-yl]pyridine-3-carboxamide (16.0 g 58.8 mmol) in 1,4-dioxane (300 ml) was slowly added ethyl carbonisothiocyanatidate (38.6 g, 294 mmol), and the mixture was stirred at rt for 3 h. The solvent was then evaporated under reduced pressure and the residue was triturated with tert-butyl methyl ether. The precipitate was collected by suction filtration to yield 23.0 g (99% purity, 96% yield) of the title compound.

LC-MS (method 4): $R_1$=0.67 min; MS (ESIpos): m/z=403/405 $[M+H]^+$ $^1$H-NMR (300 MHz, DMSO-$d_6$) δ [ppm]: 0.84 (t, 3H), 1.11 (d, 3H), 1.23 (t, 3H), 1.41-1.51 (m, 2H), 3.79-3.88 (m, 1H), 4.19 (q, 2H)), 8.31 (s, 1H), 8.46-8.52 (m, 1H), 8.66 (s, 1H), 12.06-12.13 (m, 2H).

Intermediate 9

2-Amino-6-bromo-N-[(2S)-butan-2-yl][1,2,4]triazolo[1,5-a]pyridine-8-carboxamide

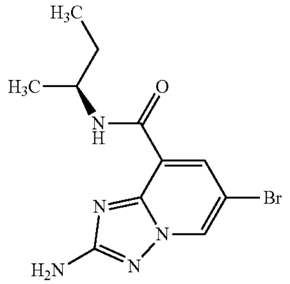 [SMILES: CC[C@H](C)NC(=O)c1cc(Br)cn2nc(N)nc12]

To a solution of hydroxylamine hydrochloride (23.8 g, 342 mmol) in methanol (500 mL) at rt was added N,N-diisopropylethylanine (57 mL, 340 mmol). The mixture was warmed to 60° C. Ethyl [(5-bromo-3-{[(2S)-butan-2-yl]carbamoyl}pyridin-2-yl)carbamothioyl]carbamate (23.0 g, 57.0 mmol) was added and the reaction was further stirred for 1 h at 65° C. After cooling to rt, the solvent was evaporated under reduced pressure. The residue was purified by column chromatography on silica gel (330 g; eluent: petroleum ether/ethyl acetate 1:1) to yield 16.1 g (99% purity, 89% yield) of the title compound.

LC-MS (method 5): $R_t$=1.23 min; MS (ESIpos): m/z=312/314 $[M+H]^+$ $^1$H-NMR (300 MHz, DMSO-$d_6$) δ [ppm]: 0.93 (t, 3H), 1.21 (d, 3H), 1.52-1.62 (m, 2H), 3.94-4.04 (m, 1H), 6.56 (s, 2H), 8.06 (s, 1H), 9.16-9.21 (m, 2H).

Intermediate 10

(5-{[(4-Fluorophenyl)methyl]carbamoyl}thiophen-3-yl)boronic acid

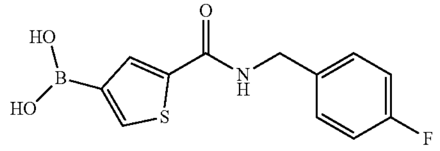 [SMILES: O=C(NCc1ccc(F)cc1)c1cc(B(O)O)cs1]

A mixture of 4-boronothiophene-2-carboxylic acid (8.50 g, 49.4 mmol), 1-(4-fluorophenyl)methanamine (6.2 mL, 54 mmol), [(1H-benzotriazol-1-yl)oxy](dimethylamino)-N,N-dimethylmethaniminium tetrafluoroborate (17.5 g, 54.4 mmol) and triethylamine (8.3 mL, 59 mmol) in DMF (70 mL) was stirred at rt overnight. Water was added to the reaction mixture and it was extracted twice with ethyl acetate. The combined organic layers were washed with satd. aq. sodium bicarbonate solution, dried over sodium sulfate and the solvent was removed in vacuo. The residue was purified by chromatography (in two batches; column: HP-Sphere C18 cartridge, 60 g; eluent A: water, eluent B: acetonitrile; gradient 15% B to 80% in 10 min, 254/280 nm) to yield 12.4 g (95% purity, 85% yield) of the title compound.

LC-MS (method 1): $R_t$=1.19 min; MS (ESIpos): m/z=280 $[M+H]^+$ $^1$H-NMR (400 MHz, DMSO-$d_6$) δ[ppm]: 4.40 (d, 2H), 7.15 (t, 2H), 7.34 (dd, 2H), 7.99 (d, 1H), 8.08-8.14 (m, 3H), 9.02 (t, 1H).

Intermediate 11

(5-{[(1 S)-1-(4-Fluorophenyl)ethyl]carbamoyl}thiophen-3-yl)boronic acid

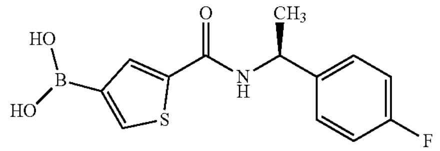 [SMILES: C[C@H](NC(=O)c1cc(B(O)O)cs1)c1ccc(F)cc1]

A mixture of 4-boronothiophene-2-carboxylic acid (10.0 g, 58.2 mmol), (1)-1-(4-fluorophenyl)ethan-1-amine (8.90 g, 64.0 mmol), [(1H-benzotriazol-1-yl)oxy](dimethylamino)-N,N-dimethylmethaniminium tetrafluoroborate (20.5 g, 64.0 mmol) and triethylamine (9.7 mL, 70 mmol) in DMF (70 mL) was stirred at rt overnight. Water was added to the reaction mixture and it was extracted twice with ethyl acetate. The combined organic layers were washed with brine, dried over sodium sulfate and the solvent was removed in vacuo. The residue was purified by chromatography (in two batches; column: HP-Sphere C18 cartridge, 120 g; eluent A: water, eluent B: acetonitrile; 4.4 min 15% B then 3.4 min 30% B then 2.2 min 70% B then 0.8 min 90% B, 254/280 nm) to yield 11.8 g (95% purity, 66% yield) of the title compound.

LC-MS (method 1): $R_t$=1.30 min; MS (ESIpos): n/z=294 $[M+H]^+$ $^1$H-NMR (400 MHz, DMSO-$d_6$) δ[ppm]: 1.45 (d, 3H), 5.06-5.14 (m, 1H), 7.14 (t, 2H), 7.38-7.44 (m, 2H), 8.04-8.15 (m, 4H), 8.84 (d, 1H).

Intermediate 12

(5-{[(1)-1-(4-Fluorophenyl)propyl]carbamoyl}thiophen-35-yl)boronic acid

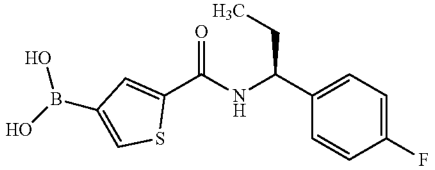 [SMILES: CC[C@H](NC(=O)c1cc(B(O)O)cs1)c1ccc(F)cc1]

A mixture of 4-boronothiophene-2-carboxylic acid (7.81 g, 45.4 mmol), (1S)-1-(4-fluorophenyl)propan-1-amine (7.65 g, 49.9 mmol), [(1H-benzotriazol-1-yl)oxy](dimethylamino)-N,N-dimethylmethaniminium tetrafluoroborate (16.0 g, 49.9 mmol) and triethylamine (7.6 mL, 54 mmol) in DMF (100 mL) was stirred at rt for 4 h. Water was added to the reaction mixture and it was extracted twice with ethyl acetate. The combined organic layers were washed with brine, dried over sodium sulfate and the solvent was removed in vacuo. The residue was purified by chromatography (in two batches; column: HP-Sphere C18 cartridge, 30 g; eluent A: water, eluent B: acetonitrile, 3.5 min 20% B then 2.5 min 30% B then 3.5 min 45% B then 4.8 min 75% B, 254/280 nm) to yield 11.7 g (100% purity, 84% yield) of the title compound.

LC-MS (method 1): $R_t$=1.44 min; MS (ESIpos): m/z=308 $[M+H]^+$ $^1$H-NMR (400 MHz, DMSO-$d_6$) δ [ppm]: 0.86-0.92 (m, 3H), 1.69-1.92 (m, 2H), 4.79-4.93 (m, 1H), 7.14 (t, 2H), 7.38-7.45 (m, 2H), 7.99-8.17 (m, 4H), 8.77 (d, 1H).

Compound 4

2-Amino-6-(5-{[(4-fluorophenyl)methyl]carbamoyl}thiophen-3-yl)-N-(propan-2-yl)[1,2,4]triazolo[1,5-a]pyridine-8-carboxamide

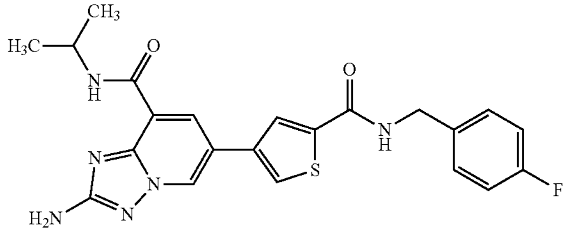 [SMILES: CC(C)NC(=O)c1cc(-c2csc(C(=O)NCc3ccc(F)cc3)c2)cn2nc(N)nc12]

To a mixture of 2-amino-6-bromo-N-(propan-2-yl)[1,2,4]triazolo[1,5-a]pyridine-8-carboxamide (55.0 mug, 184

µmol), (5-{[(4-fluorophenyl)methyl]carbamoyl}thiophen-3-yl)boronic acid (68.6 mg, 221 µmol), potassium carbonate (76.5 mg, 553 µmol), triphenylphosphine (2.42 mg, 9.22 µmol) and bis(triphenylphosphine)palladium(II) dichloride [CAS-RN 13965-03-2] (12.9 mg, 18.4 µmol) was added a degassed mixture of n-propanol (1.4 mL) and water (190 µL). The reaction mixture was heated to 110° C. for 2 h. Water and ethyl acetate were added. The layers were separated and the aqueous layer was extracted twice with ethyl acetate. The combined organic layers were washed with brine and filtered through a hydrophobic phase separation filter. The solvent was removed in vacuo and the residue was purified by column chromatography (Biotage® SNAP KP-NH 11 g cartridge, eluent: dichloromethane/methanol gradient). The product was further puried by preparative HPLC (Chromatorex C18, 10 µm, 125×30 mm; eluent: water (0.1% formic acid)/acetonitrile gradient 90:10 to 5:95) to yield 51.1 mg (100% purity, 61% yield) of the title compound.

LC-MS (method 2): $R_t$=0.89 min; MS (ESIpos): m/z 453 $[M+H]^+$ $^1$H-NMR (400 MHz, DMSO-$d_6$) δ[ppm]: 1.26 (d, 6H), 4.16 (dq, 1H), 4.47 (d, 2H), 6.50 (s, 2H), 7.18 (t, 2H), 7.39 (dd, 2H), 8.27 (d, 1H), 8.38 (t, 2H), 9.10-9.15 (m, 1H), 9.16 (d, 1H), 9.29 (d, 1H).

Compound 19

2-Amino-6-(5-{[(1S)-1-(4-fluorophenyl)ethyl]carbamoyl}thiophen-3-yl)-N-(propan-2-yl)[1,2,4]triazolo[1,5-a]pyridine-8-carboxamide

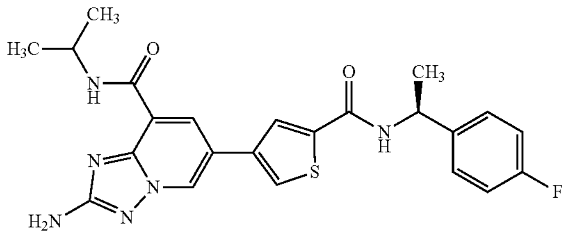 [SMILES: CC(C)NC(=O)c1cc(-c2csc(C(=O)N[C@@H](C)c3ccc(F)cc3)c2)cn2nc(N)nc12]

2-Amino-6-bromo-N-(propan-2-yl)[1,2,4]triazolo[1,5-a]pyridine-8-carboxamide (6.50 g, 21.8 mmol) and (5-{[(1)-1-(4-fluorophenyl)ethyl]carbamoyl}thiophen-3-yl)boronic acid (8.07 g, 26.2 mmol) were reacted in analogy to the previous example to yield 7.97 g (100% purity, 78% yield) of the title compound.

LC-MS (method 1): $R_t$=1.80 min; MS (ESIpos): m/z=467 $[M+H]^+$ $^1$H-NMR (400 MHz, DMSO-$d_6$) δ[ppm]: 1.27 (d, 6H), 1.50 (d, 3H), 4.10-4.24 (m, 1H), 5.09-5.20 (m, 1H), 6.51 (s, 2H), 7.17 (t, 2H), 7.44 (dd, 2H), 8.25 (s, 1H), 8.40 (m, 1H), 8.45 (s, 1H), 8.92 (br d, 1H), 9.17 (s, 1H), 9.30 (d, 1H).

Compound 26

2-Amino-6-(5-{[(1S)-1-(4-fluorophenyl)ethyl]carbamoyl}thiophen-3-yl)-N-[(2S)-1-hydroxypropan-2-yl][1,2,4]triazolo[1,5-a]pyridine-8-carboxamide

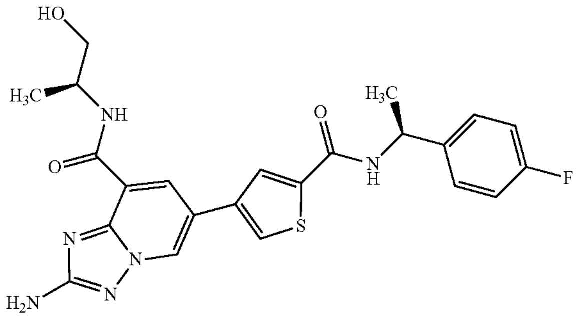 [SMILES: C[C@H](NC(=O)c1cc(-c2cc(C(=O)N[C@@H](C)CO)c3nc(N)nn3c2)cs1)c1ccc(F)cc1]

2-Amino-6-bromo-N-[(2S)-1-hydroxypropan-2-yl][1,2,4]triazolo[1,5-a]pyridine-8-carboxamide (80.0 mg, 255 μmol) and (5-{[(1S)-1-(4-fluorophenyl)ethyl]carbamoyl}thiophen-3-yl)boronic acid (99.5 mg, 306 μmol) were reacted in analogy to example 1 to yield 68.7 mg (100% purity, 56% yield) of the title compound.

LC-MS (method 2): $R_t$=0.82 min; MS (ESIpos): m/z=483 $[M+H]^+$ $^1$H-NMR (400 MHz, DMSO-$d_6$) δ [ppm]: 1.24 (d, 3H), 1.51 (d, 3H), 3.43-3.56 (m, 2H), 4.07-4.18 (m, 1H), 4.91 (t, 1H), 5.10-5.19 (m, 1H), 6.49 (s, 2H), 7.17 (t, 2H), 7.44 (dd, 2H), 8.26 (d, 1H), 8.41 (d, 1H), 8.45 (d, 1H), 8.92 (d, 1H), 9.17 (d, 1H), 9.33 (d, 1H).

Compound 94

2-Amino-N-[(2S)-butan-2-yl]-6-(5-{[(1S)-1-(4-fluorophenyl)ethyl]carbamoyl}thiophen-3-yl)[1,2,4]triazolo[1,5-a]pyridine-8-carboxamide

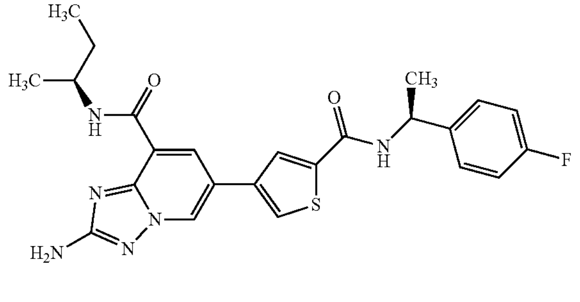 [SMILES: CC[C@H](C)NC(=O)c1cc(-c2csc(C(=O)N[C@@H](C)c3ccc(F)cc3)c2)cn2nc(N)nc12]

2-Amino-6-bromo-N-[(2)-butan-2-yl][1,2,4]triazolo[1,5-a]pyridine-8-carboxamide (75.0 mg, 240 μmol) and (5-{[(1S)-1-(4-fluorophenyl)ethyl]carbamoyl}thiophen-3-yl)boronic acid (84.5 nag, 288 μmol) were reacted in analogy to example 1 to yield 69.0 mg (100% purity, 60% yield) of the title compound.

LC-MS (method 2): $R_t$=0.98 min; MS (ESIpos): m/z=481 $[M+H]^+$ $^1$H-NMR (400 MHz, DMSO-$d_6$) δ[ppm]: 0.95 (t, 3H), 1.23 (d, 3H), 1.50 (d, 3H), 1.53-1.68 (m, 2H), 3.98-4.10 (m, 1H), 5.10-5.19 (m, 1H), 6.50 (s, 2H), 7.17 (t, 2H), 7.44 (dd, 2H), 8.25 (d, 1H), 8.40 (d, 1H), 8.45 (d, 1H), 8.92 (d, 1H)9.17 (d, 1H), 9.28 (d, 1H).

Compound 112

2-Amino-N-[(2S)-butan-2-yl]-6-(5-{[(1S)-1-(4-fluorophenyl)propyl]carbamoyl}thiophen-3-yl)[1,2,4]triazolo[1,5-a]pyridine-8-carboxamide

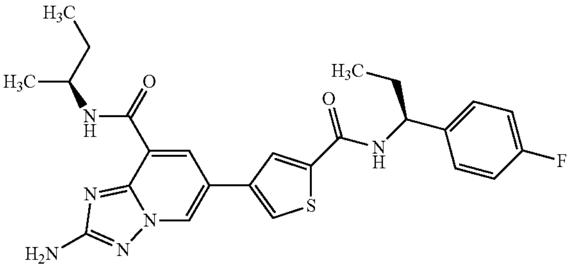 [SMILES: CC[C@H](NC(=O)c1cc(-c2cc(C(=O)N[C@@H](C)CC)c3nc(N)nn3c2)cs1)c1ccc(F)cc1]

To a mixture of 2-amino-6-bromo-N-[(2-butan-2-yl][1,2,4]triazolo[1,5-a]pyridine-8-carboxamide (10.3 g, 32.9 mmol), (5-{[(1)-1-(4-fluorophenyl)propyl]carbamoyl}thiophen-3-yl)boronic acid (11.7 g, 36.2 mmol), sodium carbonate (17.4 g, 164 mmol), [1,1'-bis(diphenylphosphino)ferrocene]dichloropalladium(II) 1:1 complex with dichloromethane [CAS-RN 95464-05-4]) (1.34 g, 1.64 mmol) was added a degassed mixture of 1,4-dioxane (200 mL) and water (66 mL). The mixture was heated to 90° C. for 1 h. Water and ethyl acetate were added and the organic layer was separated. The aqueous layer was extracted twice with ethyl acetate and the combined organic layers were washed with brine and dried over sodium sulfate. The solvent was removed in vacuo and the residue was purified by chromatography (in two batches; column: HP-Sphere 25 μm cartridge, 340 g; eluent cyclohexane/ethyl acetate gradient). The product was further purified by column chromatography (Biotage® SNAP KP-NH 375 g cartridge, eluent: cyclohexane/ethyl acetate gradient) to yield 14.0 g (100% purity, 86% yield) of the title compound.

LC-MS (method 1): $R_t$=1.97 min; MS (ESIpos): m/z=495 $[M+H]^+$ $^1$H-NMR (400 MHz, DMSO-$d_6$) δ[ppm]: 0.90-1.00 (m, 6H), 1.24 (d, 3H), 1.52-1.68 (m, 2H), 1.76-1.93 (m, 2H), 3.98-4.11 (m, 1H), 4.86-4.94 (m, 1H), 6.51 (s, 2H), 7.17 (t, 2H), 7.44 (dd, 2H), 8.25 (s, 1H), 8.41 (d, 1H), 8.46 (s, 1H), 8.85 (br d, 1H), 9.18 (d, 1H), 9.29 (d, 1H).

Similar procedures were used to prepare other compounds of Formula (Z) shown in Table 1A, with appropriate modification for specific desired substituents that are within the purview of one of ordinary skill in the art.

Scheme 3 depicts a preparation of compounds of Formula (Z) wherein $R^E$ is $C(O)NHCR^1R^2R^3$, Y is carbon, and X is nitrogen.

Scheme 3-Preparation of substituted 2-amino-7-(5-carbamoylthiophen-3-yl)-[1,2,4]triazole[1,5-a]pyridine-5-carboxamides

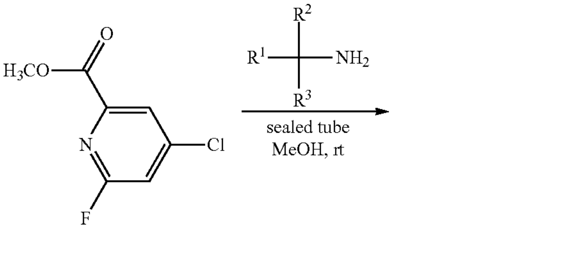

-continued

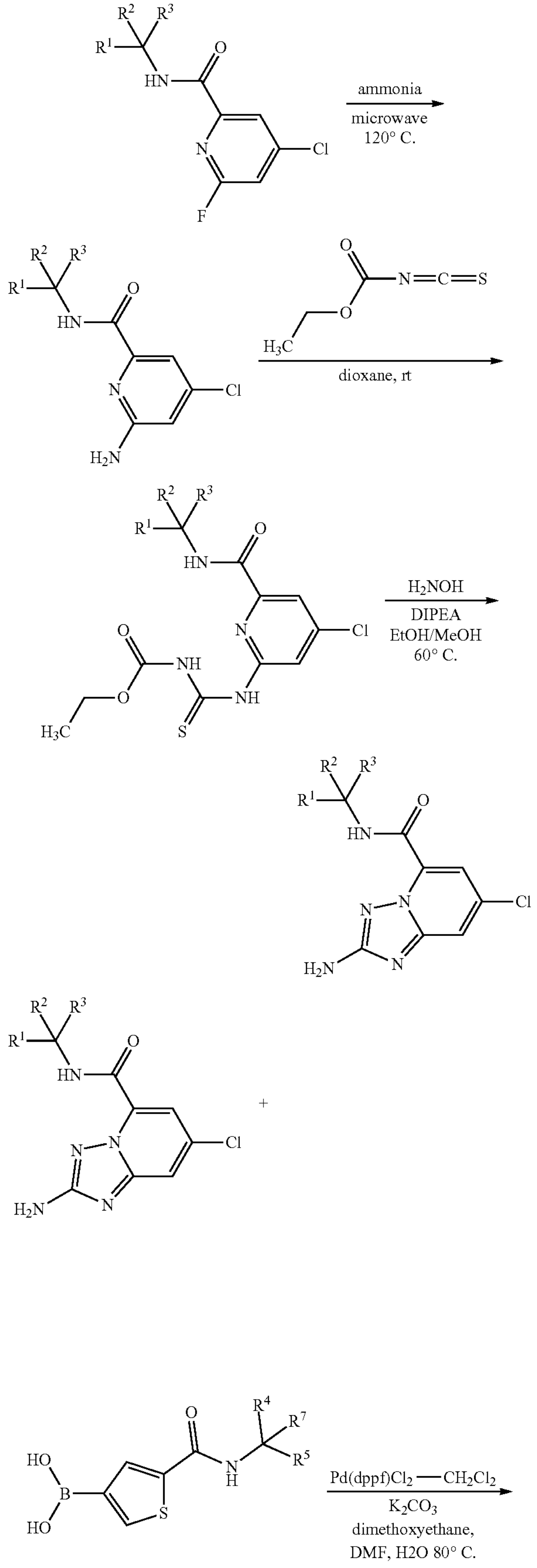

-continued

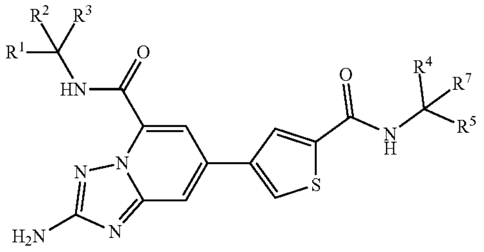

Representative procedures for Intermediates 13-20 related to Scheme 3 are shown below. These procedures, as well as those shown elsewhere herein, were used to prepare other compounds of Formula (Z) shown in Table 1B, with appropriate modification for specific desired substituents that are within the purview of one of ordinary skill in the art.

Intermediate 13

N-[(2S)-Butan-2-yl]-4-chloro-6-fluoropyridine-2-carboxamide

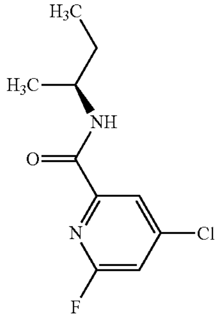

To methyl 4-chloro-6-fluoropyridine-2-carboxylate [CAS-RN 1256810-49-7] (600 mg, 3.16 mmol) in methanol (7.1 ml) was added (2S)-butan-2-amine (1.6 ml, 16 mmol) and the mixture was stirred for 2 h at rt in a sealed vessel. The mixture was then evaporated under reduced pressure and the residue was purified by column chromatography (Biotage® SNAP Ultra 25 g cartridge, eluent: cyclohexane/ethyl acetate gradient) to yield 700 mg (95% purity, 91% yield) of the title compound.

LC-MS (method 1): $R_t$=1.81 min; MS (ESIpos): m/z=231 $[M+H]^+$ $^1$H-NMR (400 MHz, DMSO-$d_6$) δ [ppm]: 0.84 (t, 3H), 1.15 (d, 3H), 1.44-1.65 (m, 2H), 3.85-3.97 (in, 1H), 7.74 (t, 1H), 7.96 (s, 1H), 8.44 (br d, 1H).

Intermediate 14

6-Amino-N-[(2S)-butan-2-yl]-4-chloropyridine-2-carboxamide

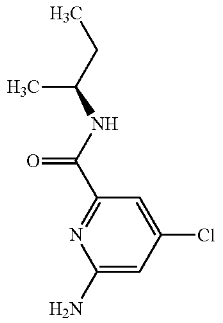

The reaction was performed in four batches of equal size. N-[(2S)-butan-2-yl]-4-chloro-6-fluoropyridine-2-carboxamide (4.50 g, 19.5 mmol) in aq. ammonia (30%, 30 ml) was heated in the microwave oven for 100 min to 120° C. The mixture was then diluted with ethyl acetate and water and the layers were separated. The aqueous phase was extracted twice with ethyl acetate and the combined organic layers were filtered through a hydrophobic phase separation filter. The solvent was removed in vacuo to yield 3.82 g (95% purity, 82% yield) of the title compound.

LC-MS (method 1): $R_t$=1.45 min; MS (ESIpos): m/z=228 $[M+H]^+$ $^1$H-NMR (500 MHz, DMSO-$d_6$) δ[ppm]: 0.86 (t, 3H), 1.14 (d, 3H), 1.51 (quin, 2H), 3.82-3.91 (m, 1H), 6.52 (br s, 2H), 6.68 (d, 1H), 7.11 (d, 1H) 7.91 (br d, 1H).

Intermediate 15

Ethyl [(6-{[(2S)-butan-2-yl]carbamoyl}-4-chloropyridin-2-yl)carbamothioyl]carbamate

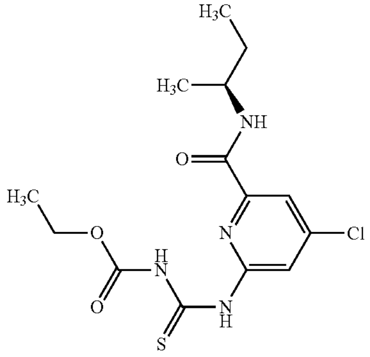 [SMILES: CCOC(=O)NC(=S)Nc1cc(Cl)cc(C(=O)N[C@@H](C)CC)n1]

To 6-amino-N-[(28)-butan-2-yl]-4-chloropyridine-2-carboxamide (4.47 g, 95% purity, 18.6 mmol) in 1,4-dioxane (40 ml) was added dropwise ethyl carbonisothiocyanatidate (2.4 ml, 21 mmol) and the mixture was stirred at rt overnight. The mixture was concentrated under reduced pressure. The residue was triturated with tert-butyl methyl ether (50 ml) and the precipitate was collected by suction filtration and washed twice with tert-butyl methyl ether (5 ml each) to yield 5.39 g (100% purity, 81% yield) of the title compound.

LC-MS (method 1): $R_t$=2.05 min; MS (ESIpos): m/z=359 $[M+H]^+$ $^1$H-NMR (500 MHz, DMSO-$d_6$) δ[ppm]: 0.86 (t, 3H), 1.17 (d, 3H), 1.28 (t, 3H), 1.47-1.63 (n, 2H), 3.86-3.97 (n, 1H), 4.25 (q, 2H), 7.83 (d, 1H), 8.29 (br d, 1H), 8.80 (br s, 1H), 11.76 (br s, 1H), 12.15 (br s, 1H).

Intermediate 16

2-Amino-N-[(2S)-butan-2-yl]-7-chloro[1,2,4]triazolo[1,5-a]pyridine-5-carboxamide

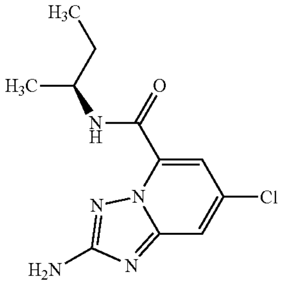 [SMILES: CC[C@H](C)NC(=O)c1cc(Cl)cc2nc(N)nn12]

To hydroxylamine hydrochloride (3.28 g, 47.3 mmol) in methanol/ethanol (1:1, 30 ml) was added N,N-diisopropylethylanine (7.7 ml, 44 mmol), and the mixture was heated to 60° C. Ethyl [(6-{[(2S)-butan-2-yl]carbamoyl}-4-chloropyridin-2-yl)carbamothioyl]carbamate (5.30 g, 14.8 mmol) was added (evolving hydrogen sulfide was led into a sodium hydroxide solution) and heating was continued for 1 h. The mixture was cooled to rt and the pH was adjusted to 6-7 by addition of satd, sodiumbicarbonate solution. The mixture was poured into water (50 ml) and extracted with ethyl acetate. The aqueous layer was extracted twice with ethyl acetate and the combined organic layers filtered through a hydrophobic phase separation filter. The solvent was evaporated and the residue was purified by column chromatography (Biotage® SNAP Ultra 50 g cartridge, eluent: cyclohexane/ethyl acetate gradient) to yield 3.66 g (100% purity, 92% yield) of the title compound.

LC-MS (method 1): $R_t$=1.45 min, MS (ESIpos): m/z=268 $[M+H]^+$ $^1$H-NMR (500 MHz, DMSO-$d_6$) δ [ppm]: 0.94 (t, 3H), 1.22 (d, 3H), 1.59 (quin, 2H), 3.93-4.03 (m, 1H), 6.55 (s, 2H) 7.48 (d, 1H), 7.76 (d, 1H), 9.94 (br d, 1H).

Intermediate 17

4-Chloro-6-fluoro-N-[(3S)-tetrahydrofuran-3-yl]pyridine-2-carboxamide

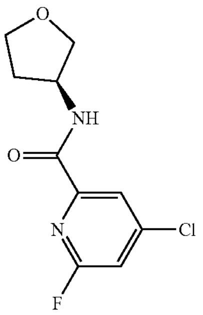 [SMILES: O=C(N[C@H]1CCOC1)c1cc(Cl)cc(F)n1]

Methyl 4-chloro-6-fluoropyridine-2-carboxylate (4.70 g, 24.8 mmol) was dissolved in methanol (10 ml). (3S)-

Tetrahydrofuran-3-amine (6.48 g, 74.4 mmol) was added and the reaction mixture was stirred overnight at rt. Volatiles were removed in vacuo. The crude product was purified by column chromatography (silica gel, 220 g; eluent: petroleum ether/ethyl acetate, 5:1) to yield 4.10 g (99% purity, 67% yield) of the title compound.

LC-MS (method 5): $R_t$=0.81 min; MS (ESIpos): m/z=245 $[M+H]^+$

Intermediate 18

6-Amino-4-chloro-N-[(3S)-tetrahydrofuran-3-yl]pyridine-2-carboxamide

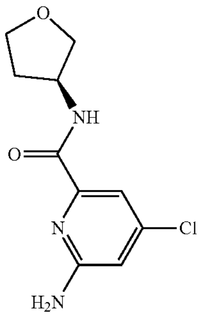 [SMILES: Nc1cc(Cl)cc(C(=O)N[C@H]2CCOC2)n1]

To 4-chloro-6-fluoro-N-[(3S)-tetrahydrofuran-3-yl]pyridine-2-carboxamide (4.00 g, 16.3 mmol) in 1,4-dioxane (30 ml) was added aq. ammonia (30%, 30 ml). The vial was sealed and heated overnight to 120° C. The reaction mixture was then diluted with ethyl acetate (80 ml) and water (80 ml). The layers were separated and the aqueous layer was extracted twice with ethyl acetate (80 ml each). The combined organic layers were dried over anhydrous sodium sulfate and the solvent was evaporated under reduced pressure. The crude product crystallized overnight. It was triturated cyclohexane (20 ml) and tert-butyl methyl ether (1 ml). The precipitate was collected by suction filtration to yield 2.70 g (99% purity, 68% yield) of the title compound.

LC-MS (method 19): $R_t$=0.61 min; MS (ESIpos): m/z=242 $[M+H]^+$

Intermediate 19

Ethyl ({4-chloro-6-[(3S)-tetrahydrofuran-3-ylcarbamoyl]pyridin-2-yl}carbamothioyl)carbamate

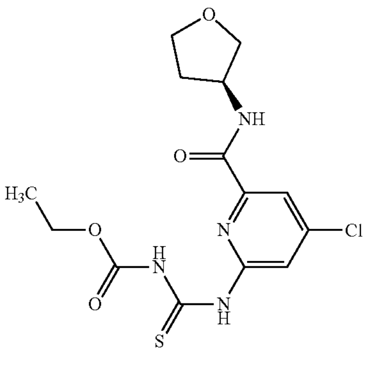 [SMILES: CCOC(=O)NC(=S)Nc1cc(Cl)cc(C(=O)N[C@H]2CCOC2)n1]

To a stirred solution of 6-amino-4-chloro-NV-[(3S)-tetrahydrofuran-3-yl]pyridine-2-carboxamide (3.70 g, 15.3 mmol) in 1,4-dioxane (100 ml) at rt was added dropwise ethyl carbonisothiocyanatidate (4.02 g, 30.6 mmol) and stirring was continued overnight. Hexane (200 ml) was added and the precipitate was collected by suction filtration and washed twice with hexane (20 ml each) to yield 5.45 g (98% purity, 94% yield) of the title compound.

LC-MS (method 12): $R_t$=0.89 min; MS (ESIpos): m/z=373 $[M+H]^+$ $^1$H-NMR (300 MHz, DMSO-$d_4$) δ [ppm]: 1.28 (t, 3H), 1.90-2.03 (m, 1H), 2.12-2.26 (m, 1H), 3.63 (dd, 1H), 3.73 (td, 1H), 3.81-3.93 (m, 2H), 4.26 (q, 2H), 4.43-4.56 (m, 1H), 7.84 (d, 1H), 8.68 (d, 1H), 8.79-8.88 (m, 1H), 11.81 (br s, 1H), 12.18 (br s, 1H).

Intermediate 20

2-Amino-7-chloro-N-[(3S)-tetrahydrofuran-3-yl][1,2,4]triazolo[1,5-a]pyridine-5-carboxamide

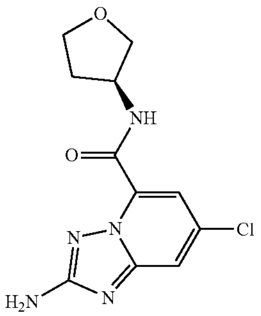 [SMILES: Nc1nc2cc(Cl)cc(C(=O)N[C@H]3CCOC3)n2n1]

To a solution of hydroxylamine hydrochloride (3.65 g, 52.6 mmol) in methanol (80 ml) at rt was added N,N-diisopropylethylamine (11 ml, 66 mmol) The resulting mixture was to warmed to 60° C. Ethyl ({4-chloro-6-[(3S)-tetrahydrofuran-3-ylcarbamoyl]pyridin-2-yl}carbamothioyl)carbamate (4.90 g, 13.1 mmol) was added and the reaction mixture was stirred at 65° C. for 1.5 h. It was then cooled to rt and diluted with water (150 ml). The precipitate was collected by suction filtration. The filter cake was triturated with satd. sodium bicarbonate solution (100 ml) and stirred for 4 h. The precipitate was collected by suction filtration, washed with water (20 ml) and dried in vacuo to yield 3.30 g (98% purity, 87% yield) of the title compound.

LC-MS (method 7): $R_t$=0.88 min; MS (ESIpos): m/z=282 $[M+H]^+$ $^1$H-NMR (300 MHz, DMSO-$d_6$) δ [ppm]: 1.86-1.98 (in, 1H), 2.29 (dq, 1H), 3.69 (dd, 1H), 3.77 (td, 1H), 3.85-3.98 (m, 2H), 4.49-4.61 (m, 1H), 6.59 (s, 2H), 7.47 (d, 1H), 7.78 (d, 1H), 10.23 (br d, 1H).

Scheme 4 depicts an alternative preparation of compounds of Formula (Z) wherein $R^E$ is $C(O)NHCR^1R^2R^3$, Y is carbon, and X is nitrogen.

Scheme 4-Alternative preparation of substituted 2-amino-7-(5-carbamoylthiophen-3-yl)-[1,2,4]triazolo[1,5-a]pyridine-5-carboxamides

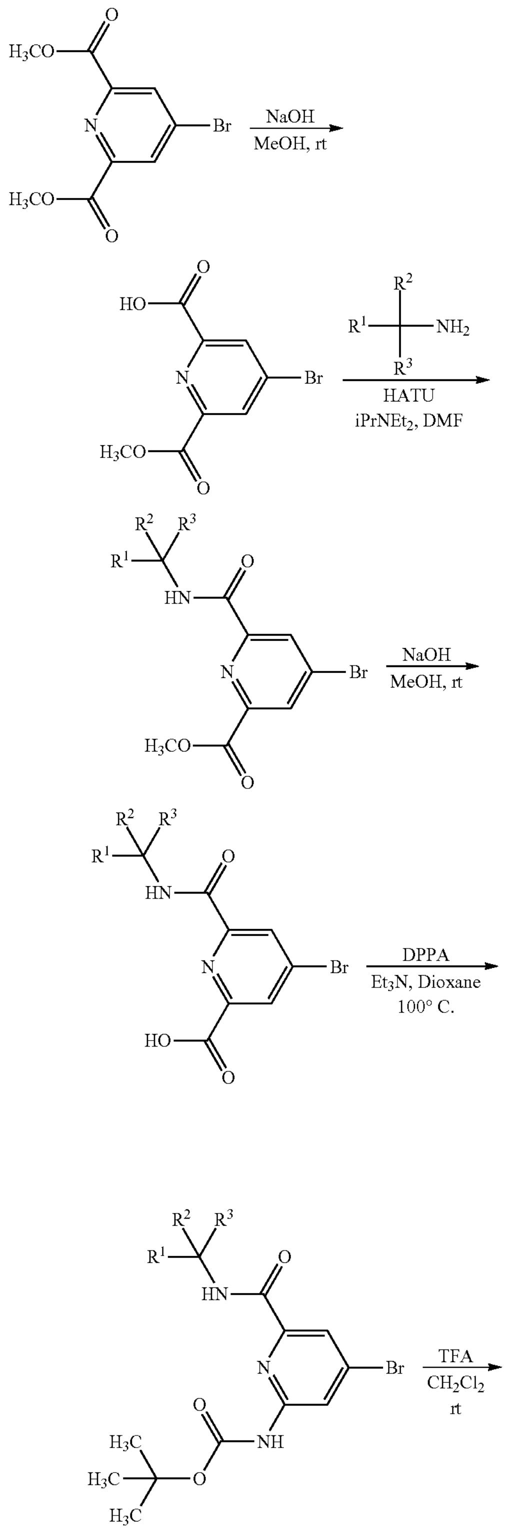

-continued

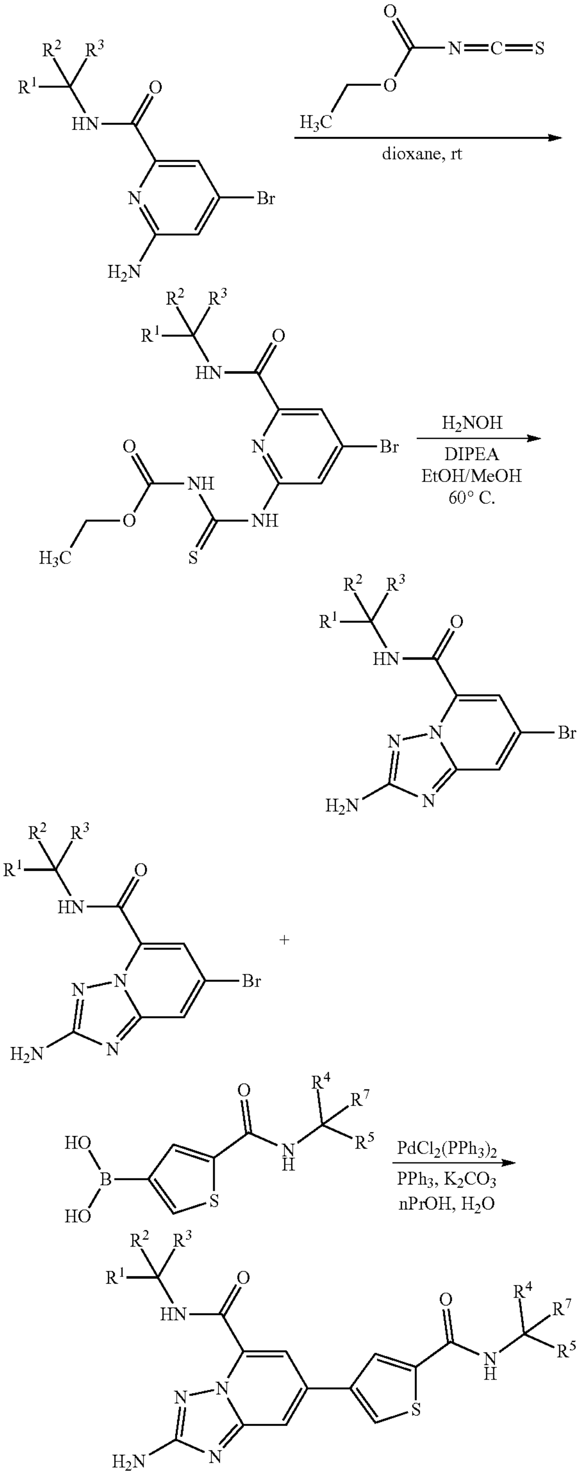

Representative procedures for Intermediates 21-26 related to Scheme 4 are shown below. These procedures, as well as those shown elsewhere herein, were used (or with certain modifications can be used) to prepare other compounds of Formula (Z) shown in Table 1B, with appropriate modification for specific desired substituents that are within the purview of one of ordinary skill in the art.

Intermediate 21

Methyl 4-bromo-6-[(1-fluoropropan-2-yl)carbamoyl]pyridine-2-carboxylate (Mixture of Enantiomers)

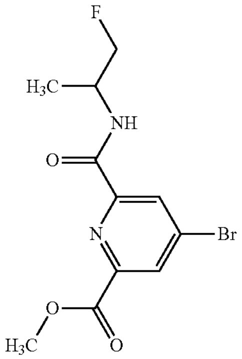 [SMILES: COC(=O)c1cc(Br)cc(C(=O)NC(C)CF)n1]

To a solution of 4-bromo-6-(methoxycarbonyl)pyridine-2-carboxylic acid [CAS-RN 293294-72-1] (4.3 g, 16.54 mmol) in N,N-dimethylformamide (50 ml) were added HATU (9.43 g, 24.8 mmol), N,N-diisopropylethylamine (6.41 g, 49.6 mmol), racemic 1-fluoropropan-2-amine hydrochloride (1:1) [CAS-RN 921602-78-0] (2.25 g, 19.8 mmol). After stirring for 3 h at room temperature, the reaction mixture was diluted with water (150 ml) and extracted three times with ethyl acetate (200 nil each). The combined organic layers were washed three times with brine (200 ml each) and dried over anhydrous sodium sulfate The solvent was evaporated under reduced pressure. The crude product was purified column chromatography (silica gel, 220 g, eluent petroleum ether/ethyl acetate 1:1) to yield 3.80 g (82% purity, 59% yield) of the title compound.

LC-MS (method 16): $R_t$=1.01 min; MS (ESIpos): m/z=319, 321 $[M+H]^+$ $^1$H-NMR (300 MHz, DMSO-$d_6$) δ[ppm]: 1.15-1.23 (m, 3H), 3.94 (s, 3H), 4.31-4.66 (m, 3H), 8.35-8.39 (m, 2H), 8.56 (d, 1H).

Intermediate 22

4-Bromo-6-[(1-fluoropropan-2-yl)carbamoyl]pyridine-2-carboxylic acid

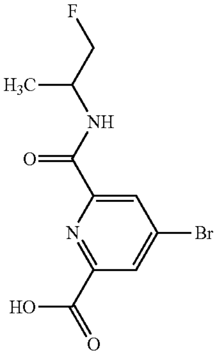 [SMILES: CC(CF)NC(=O)c1cc(Br)cc(C(=O)O)n1]

To a solution of methyl 4-bromo-6-[(1-fluoropropan-2-yl)carbamoyl]pyridine-2 carboxylate (3.8 g, 82% purity, 9.76 mmol) in methanol (50 ml) was added sodium hydroxide (1.56 g, 39.1 mmol). After stirring for 1 h at rt the reaction mixture was concentrated under reduced pressure and diluted with water (40 ml). The pH was adjusted to 5 with 1N hydrochloric acid. The precipitate was collected by suction filtration, washed with water (20 ml) and dried in vacuo to give 2.80 g (99% purity, 93% yield) of the title compound.

LC-MS (method 7): $R_t$=0.77 min; MS (ESIpos): m/z=327, 329 $[M+H]^+$ $^1$H-NMR (300 MHz, DMSO-$d_6$) δ [ppm]: 1.23-1.26 (m, 3H), 4.29-4.42 (m, 2H), 4.56-4.58 (m, 1H), 8.38-8.41 (m, 2H), 9.06 (d, 1H).

Intermediate 23 tert-Butyl {4-bromo-6-[(1-fluoropropan-2-yl)carbamoyl]pyridin-2-yl}carbamate (Mixture of Enantiomers)

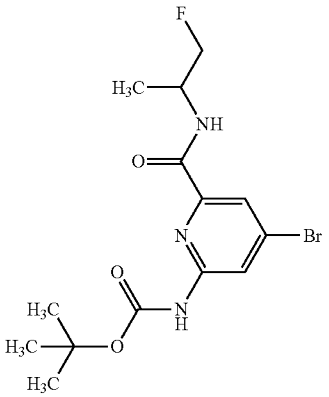 [SMILES: CC(CF)NC(=O)c1cc(Br)cc(NC(=O)OC(C)(C)C)n1]

To a solution of 4-bromo-6-[(1-fluoropropan-2-yl)carbamoyl]pyridine-2-carboxylic acid (2.30 g, 7.54 mmol) in 1,4-dioxane (30 ml) were added triethylamine (1.6 ml, 11 mmol), tert-butanol (12.0 ml, 130 mmol) and diphenyl phosphoroazidate (3.11 g, 11.3 mmol). The resulting mixture was stirred at 100° C. for 4 h. Subsequently, it was cooled to rt and concentrated under reduced pressure. The residue was purified by column chromatography (silica gel 120 g; eluent: petroleum ether/ethyl acetate 5:1) to yield 1.40 g (92% purity, 45% yield) of the title compound.

LC-MS (method 7): $R_t$=1.16 min; MS (ESIpos): m/z=376, 378 $[M+H]^+$

Intermediate 24

6-Amino-4-bromo-N-(1-fluoropropan-2-yl)pyridine-2-carboxamide trifluoroacetate (Mixture of Enantiomers)

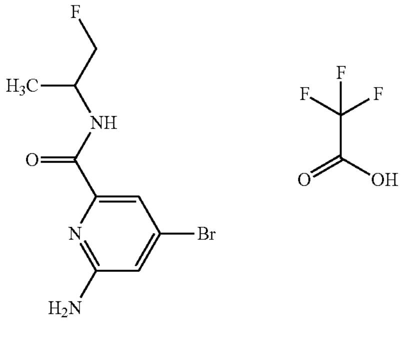

To a solution of tert-butyl {4-bromo-6-[(1-fluoropropan-2-yl)carbamoyl]pyridin-2-yl}carbamate (1.40 g, 92% purity, 3.42 mmol) in dichloromethane (20 ml) was added trifluoroacetic acid (1.3 ml, 17 mmol). After stirring at rt for 3 h, the reaction mixture was concentrated under reduced pressure. The residue was three times coevaporated with dichloromethane (20 ml) to yield 1.00 g (98% purity, 73% yield) of the title compound.

LC-MS (method 16): $R_t$=1.08 min; MS (ESIpos): m/z=276, 278 $[M+H]^+$ $^1$H-NMR (300 MHz, DMSO-$d_6$) δ[ppm]: 1.18 (d, 31), 4.17-4.39 (in, 2H), 4.48-4.53 (m, 1H), 6.52 (br s, 2H), 6.85 (s, 1H), 7.23 (s, 1H), 8.17 (d, 1H).

Intermediate 25

Ethyl ({4-bromo-6-[(1-fluoropropan-2-yl)carbamoyl]pyridin-2-yl}carbamothioyl)carbamate (Mixture of Enantiomers)

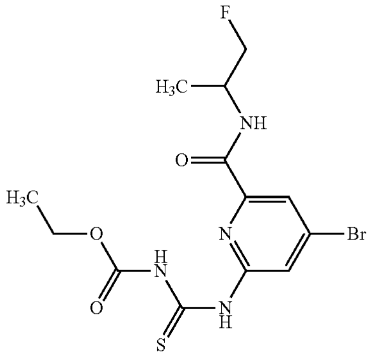 [SMILES: CCOC(=O)NC(=S)Nc1cc(Br)cc(C(=O)NC(C)CF)n1]

To a solution of 6-amino-4-bromo-N-(1-fluoropropan-2-yl)pyridine-2-carboxamide trifluoroacetate (900 mg, 2.31 mmol) in 1,4-dioxane (15 ml) at rt was added dropwise ethyl carbonisothiocyanatidate (908 mg, 6.92 mmol). After stirring overnight at rt, the reaction mixture was diluted with hexane (50 ml). The precipitate was collected by suction filtration, washed with hexane (20 ml) and dried in vacuo to yield 700 mg (96% purity, 71% yield) of the title compound.

LC-MS (method 8): $R_t$=1.47 min; MS (ESIpos): m/z=407, 409 $[M+H]^+$ $^1$H-NMR (300 MHz, DMSO-$d_6$) δ[ppm]. 1.19 (d, 3H), 1.28 (t, 3H), 4.21-4.42 (m, 4H), 4.44-4.60 (m, 1H), 7.98 (s, 1H), 8.58 (d, 1H), 9.00 (s, 1H), 11.79 (s, 1H), 12.18 (s, 1H).

Intermediate 26

2-Amino-7-bromo-N-(1-fluoropropan-2-yl)[1,2,4]triazolo[1,5-a]pyridine-5-carboxamide (Mixture of Enantiomers)

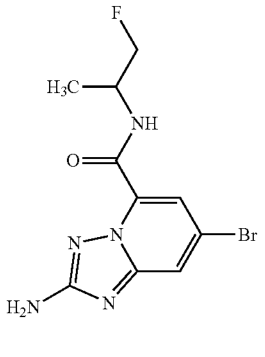 [SMILES: CC(CF)NC(=O)c1cc(Br)cc2nc(N)nn12]

To a solution of hydroxylamine hydrochloride (410 mg, 5.89 mmol) in methanol (15 ml) at rt was added N,N-diisopropylethylamine (1.0 ml, 5.9 mmol). The solution was heated to 65° C. Ethyl ({4-bromo-6-[(1-fluoropropan-2-yl)carbamoyl]pyridin-2-yl}carbamothioyl)carbamate (800 mg, 1.96 mmol) was added. The resulting mixture was stirred at 65° C. for 2 h. Subsequently, it was cooled to rt and concentrated under reduced pressure. The residue was diluted with water (100 ml). The precipitate was collected by suction filtration. It was triturated with satd. sodium bicarbonate solution (100 ml) and stirred for 4 h. The precipitate was collected by suction filtration, washed with water (20 ml) and dried in vacuo to yield 507 mg (96% purity, 78% yield) the title compound.

LC-MS (method 8): $R_t$=1.04 min; MS (ESIpos): m/z=316, 318 $[M+H]^+$ $^1$H-NMR (300 MHz, DMSO-$d_6$) δ[ppm]: 1.30 (d, 3H), 4.25-4.49 (m, 2H), 4.55-4.65 (m, 1H), 6.57 (s, 2H), 7.60 (s, 1H), 7.92 (s, 1H), 10.14 (d, 1H).

Scheme 5 depicts a preparation of compounds of Formula (Z) wherein $R^E$ is H, halo, or ($C_1$-$C_6$)-alkyl; X is carbon; and Y is nitrogen, such as those shown in Table 1C and Table 1E (e.g., compounds 371-383 and 387-388).

Scheme 5-Preparation of substituted 4-(2-amino-[1,2,4]triazolo[1,5-a]pyridin-6-yl)thiophene-2-carboxamides

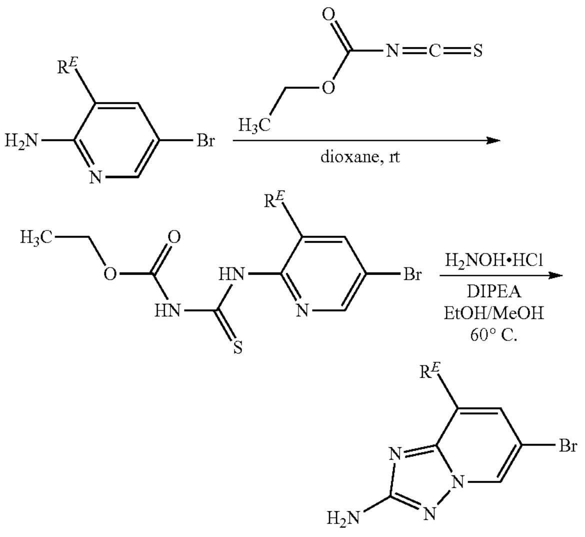

-continued

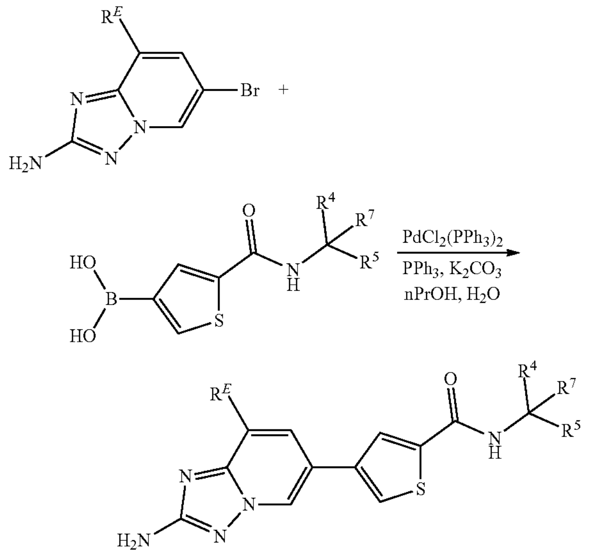

Scheme 6 depicts a preparation of compounds of Formula (Z) wherein $R^E$ is H or C(O)OR$^6$, Y is carbon, and X is nitrogen, such as those shown in Table 1D and certain compounds in Table 1E (e.g., compound 370).

Scheme 6-Preparation of Substituted 4-(2-amino-)[1,2,4]triazolo [1,5-a]pyridin-7-yl)thiophene-2-carboxamides

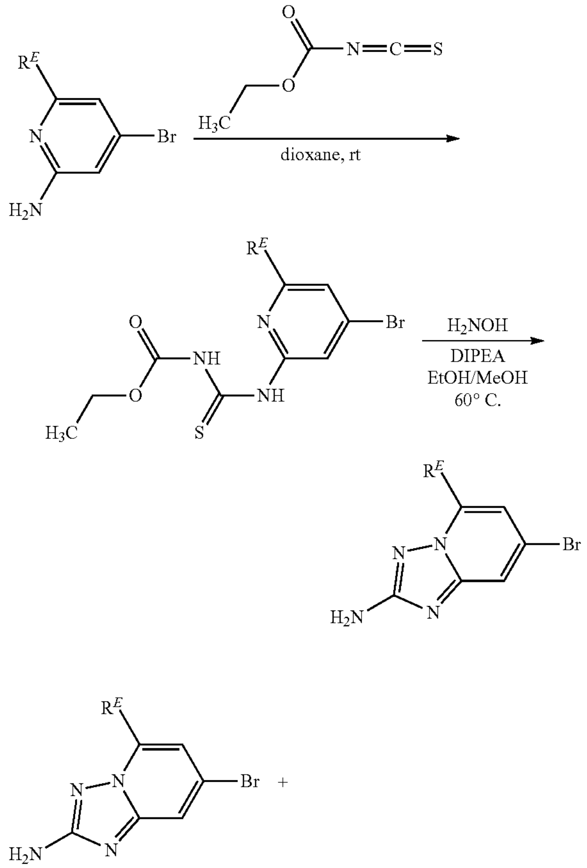

-continued

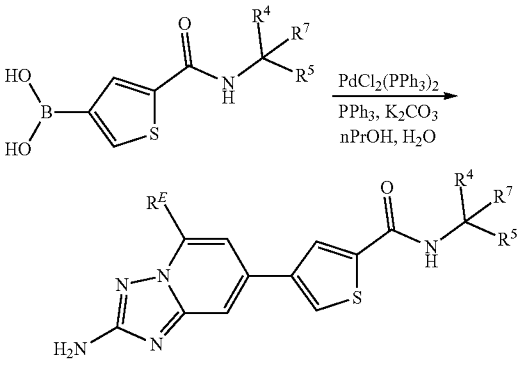

Scheme 7 depicts a preparation of compounds of Formula (Z) wherein $R^E$ is S(O)$_2$NH(C$_1$-C$_6$)-alkyl, X is carbon, and Y is nitrogen, such as certain compounds shown in Table 1E (e.g., compounds 384-386).

Scheme 7- Preparation of substituted 4-(2-amino-8-sulfamoyl-[1,2,4] triazolo[1,5-a]pyridin-6-yl)thiophene-2-carboxamides

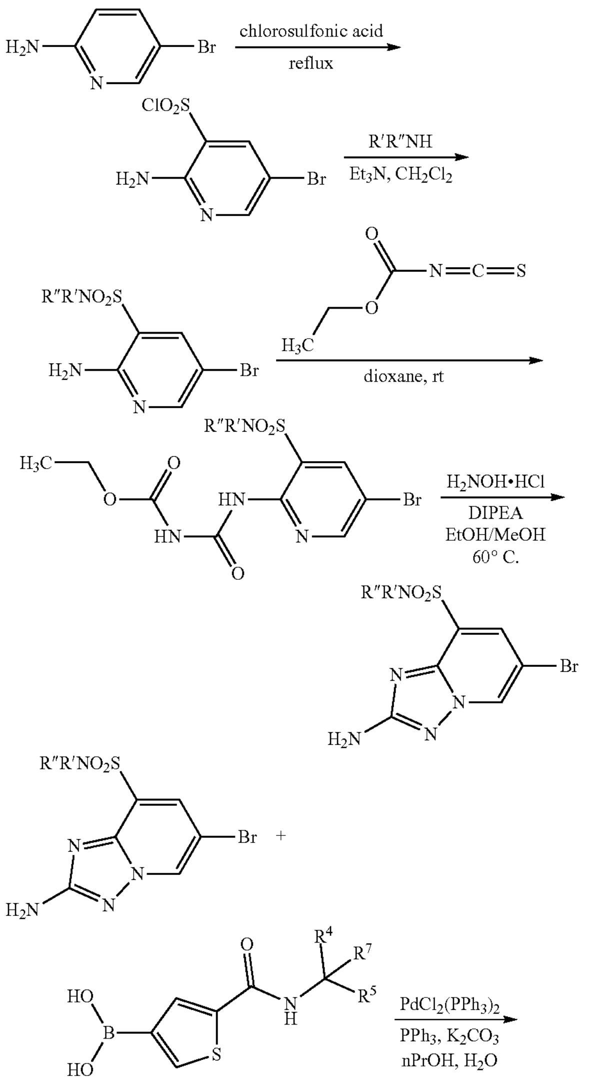

-continued

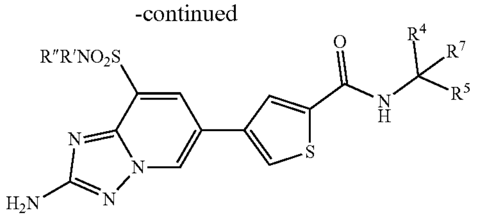

Scheme 8 depicts a preparation of compounds of Formula (Z) wherein $R^E$ is $C(O)NHCR^1R^2R^3$, X is carbon, Y is nitrogen, and Z is H, such as certain compounds shown in Table 1E (e.g., compounds 389-391).

Scheme 8-Preparation of substituted 6-(5-carbamoylthiophen-3-yl)-[1,2,4]triazolo[1,5-a]pyridine-8-carboxamides

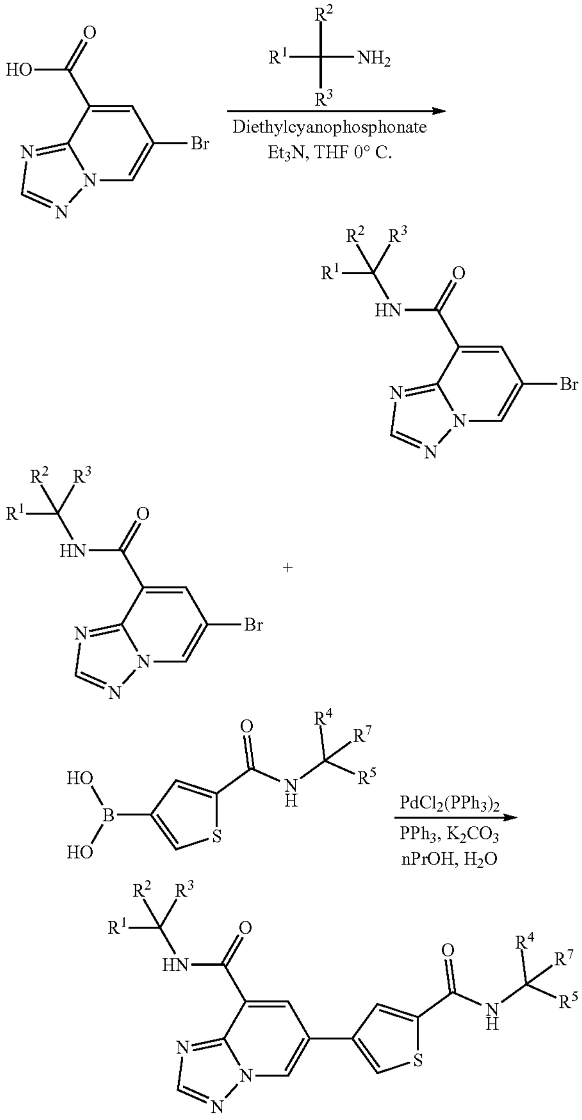

Scheme 9 depicts a preparation of compounds of Formula (Z) wherein $R^E$ is $(C_6\text{-}C_{10})$-aryl or heteroaryl, X is carbon, and Y is nitrogen, such as certain compounds shown in Table 1F (e.g., compounds 395-396).

Scheme 9-Heteroaryl substituted 4-(2-amino[1,2,4]triazolo[1,5-a]pyridin-6-yl)thiophene-2-carboxamides

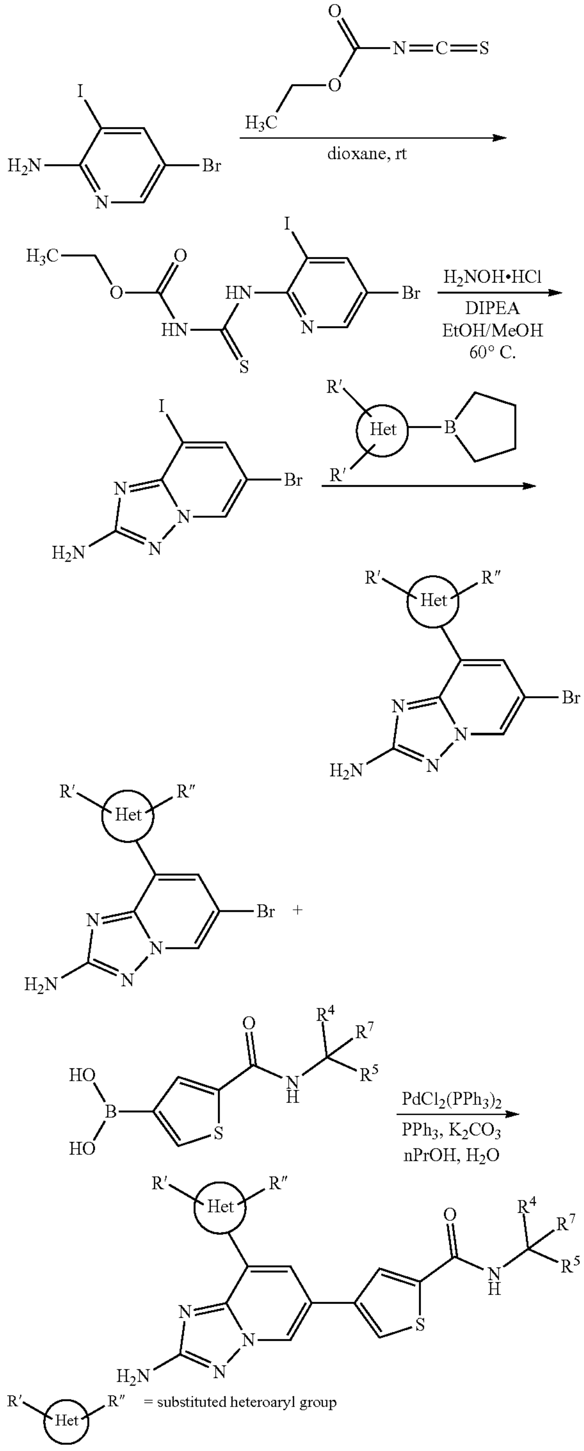

A representative procedure for Intermediate 27 related to Scheme 9 is shown below. This procedure, as well as those shown elsewhere herein were used to prepare compounds of Formula (Z) shown in Table 1F (e.g., compounds 395-396), with appropriate modification for specific desired substituents that are within the purview of one of ordinary skill in the art.

Intermediate 27

6-Bromo-8-[1-(2,2,2-trifluoroethyl)-1H-pyrazol-4-yl][1,2,4]triazolo[1,5-a]pyridin-2-amine

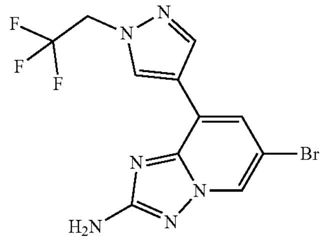 [SMILES: Nc1nc2c(-c3cnn(CC(F)(F)F)c3)cc(Br)cn2n1]

6-Bromo-8-iodo[1,2,4]triazolo[1,5-a]pyridin-2-amine (3.50 g, 10.3 mmol) was reacted with 4-(4,4,5,5-tetramethyl-1,3,2-dioxaborolan-2-yl)-1-(2,2,2-trifluoroethyl)-1H-pyrazole [CAS-RN 1883816-46-3] (3.42 g, 12.4 mmol) for 2 h at 90° C. following general procedure B using 0.06 eq. catalyst. The reaction mixture was diluted with ethyl acetate (400 ml) and water (50 ml). The precipitate was collected by suction filtration and washed with water and acetonitrile to yield 440 mg (100% purity, 12% yield) of the title compound. The organic layer of the filtrate was separated and washed with water and brine and dried over anhydrous anhydrous sodium sulfate. The solvent was concentrated under reduced pressure to a volume of 15 ml and the precipitate was collected by suction filtration and washed with acetonitrile to yield a second batch of 2.70 g (100% purity, 72% yield) of the title compound. The mother liquor was concentrated and purified by column chromatography (Biotage® SNAP Ultra 50 g cartridge, eluent: cyclohexane/ethyl acetate gradient 90:10 to 10:90) which resulted in a third batch of 230 mg (92% purity, 6% yield) of the title compound. The total yield was 90%.

LC-MS (method 2): $R_t$=0.78 min; MS (ESIpos): m/z=361 $[M+H]^+$ $^1$H-NMR. (500 MHz, DMSO-$d_6$) δ[ppm]: 5.28 (q, 2H), 6.21 (s, 2H), 8.02 (d, 1-1), 8.46 (s, 1H), 8.74 (s, 1H), 8.81 (d, 1H).

Scheme 10 depicts a preparation of compounds of Formula (Z) wherein $R^E$ is $(C_6\text{-}C_{10})$-aryl or heteroaryl, Y is carbon, and X is nitrogen, such as certain compounds shown in Table 1F (e.g., compound 402).

Scheme 10-Preparation of substituted 4-(2-amino-5-(1-(2,2,2-trifluoroethyl)-1H-pyrazol-4-yl)-[1,2,4]triazolo[1,5-a]pyridin-7-yl)thiophene-2-carboxamides

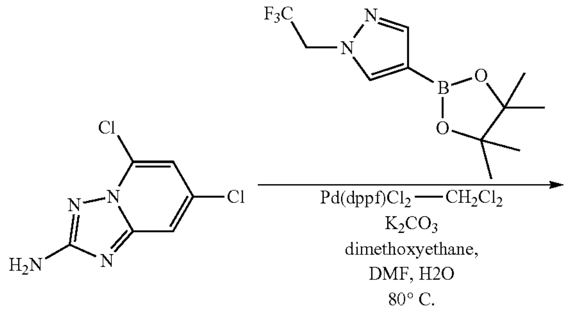

-continued

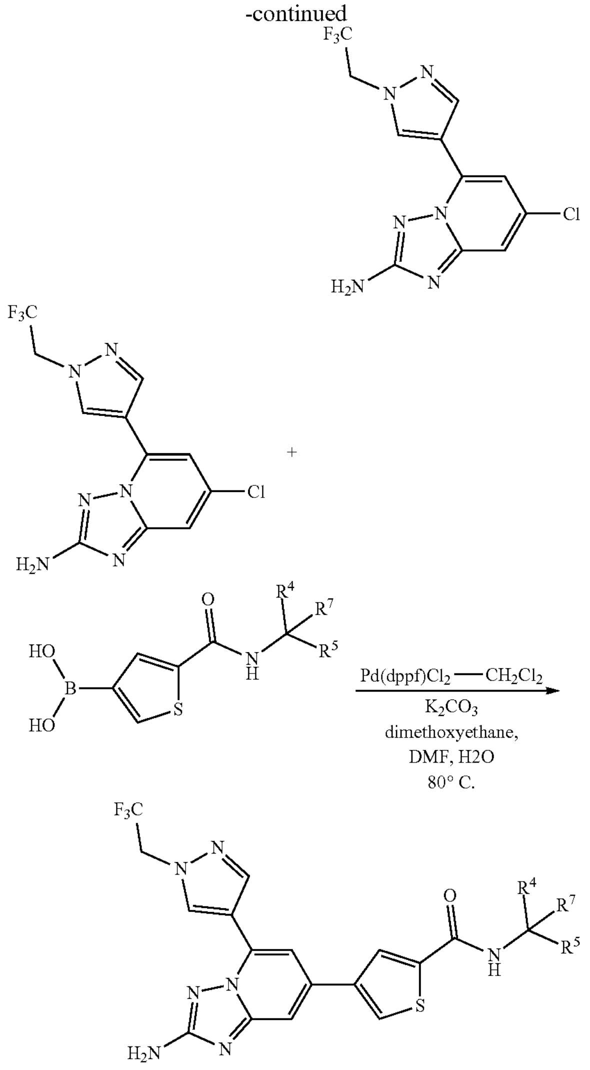

A representative procedure for Intermediate 28 related to Scheme 10 is shown below. This procedure, as well as those shown elsewhere herein, were used to prepare compounds of Formula (Z) shown in Table 1F (e.g., compound 402), with appropriate modification for specific desired substituents that are within the purview of one of ordinary skill in the art.

Intermediate 28

7-Chloro-5-[1-(2,2,2-trifluoroethyl)-1H-pyrazol-4-yl][1,2,4]triazolo[1,5-a]pyridin-2-amine

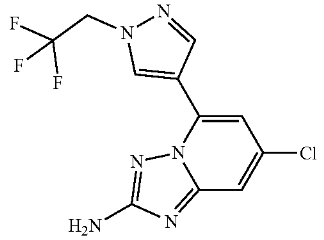 [SMILES: Nc1nc2cc(Cl)cc(-c3cnn(CC(F)(F)F)c3)n2n1]

5,7-Dichloro[1,2,4]triazolo[1,5-a]pyridin-2-amine [CAS-RN 1233526-60-7] (300 mg, 90% purity, 1.33 mmol) was reacted with 4-(4,4,5,5-tetramethyl-1,3,2-dioxaborolan-2-yl)-1-(2,2,2-trifluoroethyl)-1H-pyrazole [CAS-RN 1049730-42-8] (511 mg, 97% purity, 1.80 mmol) for 1.5 h at 90° C. following general procedure C using 0.1 eq. catalyst. The reaction mixture was directly purified by column chromatography (Biotage® SNAP Ultra 50 g cartridge, eluent: dichloromethane/methanol gradient 100:0 to 85:15). The isolated material was triturated with THF (3.0 ml), collected by suction fitration and washed with THF (1.0 ml) to yield 260 mg (97% purity, 60% yield) of the title compound. The mother liquor was purified by column chromatography (Biotage® SNAP KP-NH 28 g cartridge, eluent: cyclohexane/ethyl acetate gradient 100:0 to 10:90) to give a second batch of 40.0 mg (100% purity, 9% yield). The total yield was 69%.

LC-MS (method 2): $R_t$=0.77 min; MS (ESIpos): m/z=317 $[M+H]^+$ $^1$H-NMR (500 MHz, DMSO-$d_4$) δ [ppm]: 5.34 (q 2H), 6.23 (s, 2H), 7.41 (d, 1H), 7.55 (d, 1H), 8.62 (s, 1H), 9.01 (s, 1H).

Scheme 11 depicts a preparation of compounds of Formula (Z) wherein $R^E$ is ($C_6$-$C_{10}$)-aryl or heteroaryl, X is carbon, and Y is nitrogen, such as certain compounds shown in Table 1F (e.g., compounds 392-394 and 397-401).

Scheme 11-Substituted 4-(2-amino-8-(1,3,4-thiadiazol-2-yl)-[1,2,4]triazolo[1,5-a]pyridin-6-yl)thiophene-2-carboxamides

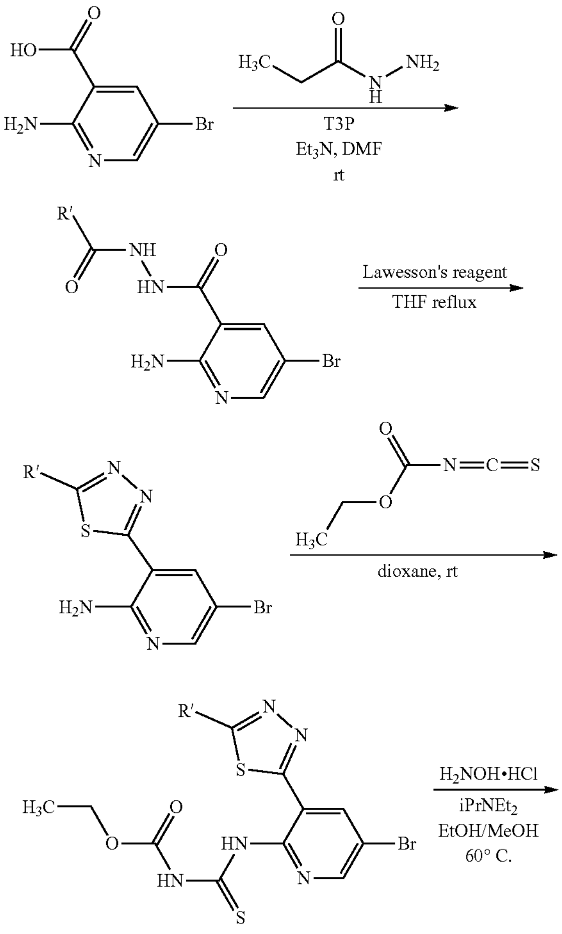

-continued

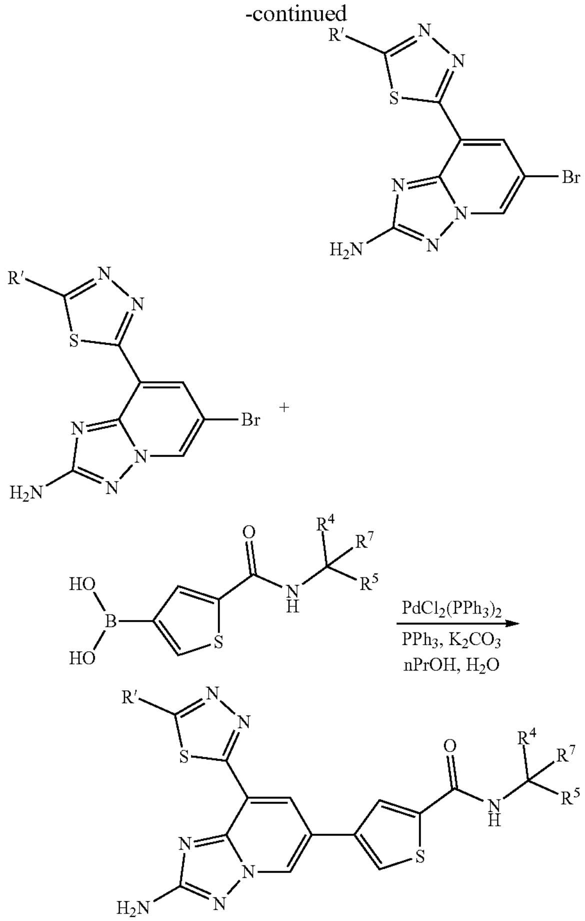

Representative procedures for Intermediates 29-36 related to Scheme 10 are shown below. These procedures, as well as those shown elsewhere herein, were used to prepare compounds of Formula (Z) shown in Table 1F (e.g., compounds 392-394 and 397-401), with appropriate modification for specific desired substituents that are within the purview of one of ordinary skill in the art.

Intermediate 29

2-Amino-5-bromo-N'-propanoylpyridine-3-carbohydrazide

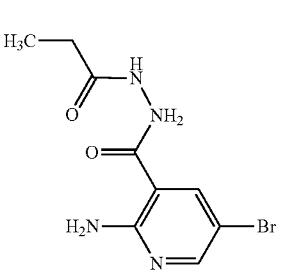 [SMILES: CCC(=O)NNC(=O)c1cc(Br)cnc1N]

To a mixture of 2-amino-5-bromopyridine-3-carboxylic acid (8.21 g, 37.8 mmol), propanehydrazide (4.00 g, 45.4 mmol), and triethylamine (21 ml, 150 mmol) in DMF (28 ml) at rt was added dropwise a solution of T3P (66 ml, 50% in DMF, 113 mmol. The reaction was then stirred at rt for 5 h. Subsequently, it was diluted with water and ethyl acetate and the aqueous layer was separated and extracted twice with ethyl acetate. The combined organic layers were dried over anhydrous anhydrous sodium sulfate and the solvent was evaporated under reduced pressure. The residue was triturated with ethyl acetate/tert-butyl methyl ether and the precipitate was collected by suction filtration to yield 3.90 g (75% purity, 27% yield) of the title compound.

LC-MS (method 2): $R_t$=0.40 min; MS (ESIpos): m/z=287, 289 $[M+H]^+$ $^1$H-NMR (500 MHz, DMSO-$d_6$) δ[ppm]: 1.06 (t, 31H), 2.19 (q, 2H), 7.21 (s, 21H), 8.11 (d, 1H), 8.20 (d, 1H), 9.83 (s, 1H), 10.29 (s, 1H).

Intermediate 30

5-Bromo-3-(5-ethyl-1,3,4-thiadiazol-2-yl)pyridin-2-amine

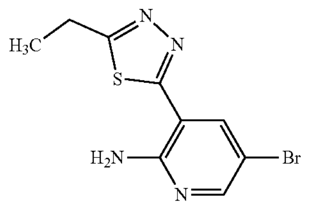

2-Amino-5-bromo-N'-propanoylpyridine-3-carbohydrazide (1.50 g, 75% purity, 3.92 mmol) was dissolved in THF (30 ml) and Lawesson's reagent (1.90 g, 4.70 mmol) was added. The mixture was heated under reflux for 3 h. Solid material was then removed by filtration and the filter was rinsed with ethyl acetate. Water was added to the filtrate and the aqueous layer was separated and extracted twice with ethyl acetate. The combined organic layers were filtered through a hydrophobic phase separation filter and the solvent was removed in vacuo. The residue was purified by column chromatography (Biotage® SNAP KP-NH 110 g cartridge, eluent: cyclohexane/ethyl acetate gradient 90:10 to 15:85) to yield 829 mg (100% purity, 74% yield) of the title compound.

LC-MS (method 1): $R_t$=1.65 min; MS (ESIpos): n/z=285, 287 $[M+H]^+$ $^1$H-NMR (500 MHz, DMSO-$d_6$) δ [ppm]: 1.36 (t, 3H), 3.15 (q, 2H), 7.73 (br s, 2H), 8.06 (d, 1H), 8.21 (d, 1H).

Intermediate 31

Ethyl {[5-bromo-3-(5-ethyl-1,3,4-thiadiazol-2-yl)pyridin-2-yl]carbamothioyl}carbamate

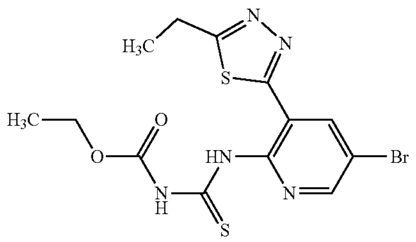 [SMILES: CCOC(=O)NC(=S)Nc1ncc(Br)cc1-c1nnc(CC)s1]

5-Bromo-3-(5-ethyl-1,3,4-thiadiazol-2-yl)pyridin-2-amine (850 mg, 2.98 mmol) was dissolved in 1,4-dioxane (15 ml) and ethyl carbonisothiocyanatidate (390 µl, 3.3 mmol) was added dropwise. The mixture was heated to 50° C. overnight. Subsequently, the mixture was concentrated in vacuo and the residue was triturated with cyclohexane/tert-butyl methyl ether. The precipitate was collected by suction filtration to yield 972 mg (93% purity, 73% yield) of the title compound.

LC-MS (method 1): $R_t$=1.81 min; MS (ESIpos): m/z=416, 418 $[M+H]^+$ $^1$H-NMR (500 MHz, DMSO-$d_6$) δ[ppm]: 1.28 (t, 3H), 1.34 (t, 3H), 3.17 (q, 2H), 4.25 (q, 2H), 8.73 (d, 1H), 8.80 (d, 1H), 11.60-11.74 (m, 2H).

Intermediate 32

6-Bromo-8-(5-ethyl-1,3,4-thiadiazol-2-yl)[1,2,4]triazolo[1,5-a]pyridin-2-amine

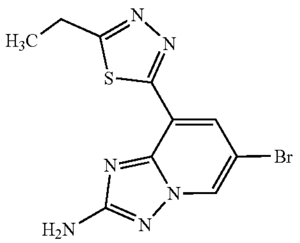 [SMILES: CCc1nnc(-c2cc(Br)cn3nc(N)nc23)s1]

A solution of hydroxylamine hydrochloride (771 mg, 11.1 mmol) and N,N-diisopropylethylamine (1.8 ml, 10 mmol) in methanol/ethanol (1:1, 15 ml) was heated to 60° C. and ethyl {[5-bromo-3-(5-ethyl-1,3,4-thiadiazol-2-yl)pyridin-2-yl]carbamothioyl}carbamate (920 mg, 93% purity, 2.06 mmol) was added. The mixture was stirred at 60° C. for 1 h and then cooled to rt. The pH was adjusted to 6-7 by addition of satd. sodium bicarbonate solution and the mixture was poured into water (100 ml). It was stirred for 10 min and the precipitate was collected by suction filtration and washed with water (5 ml) and dried in vacuo to yield 658 mg (90% purity, 89% yield) of the title compound.

LC-MS (method 1): $R_t$=1.28 min; MS (ESIpos): m/z=325, 327 $[M+H]^+$ $^1$H-NMR (500 MHz, DMSO-$d_6$) δ [ppm]: 1.40 (t, 3H), 3.20 (q, 2H), 6.56 (s, 2H), 8.36 (s, 1H), 9.16 (s, 1H).

Intermediate 33

2-Amino-5-bromo-N-(2-methylpropanoyl)pyridine-3-carbohydrazide

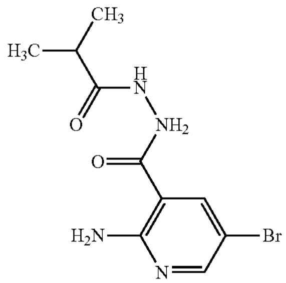 [SMILES: CC(C)C(=O)NNC(=O)c1cc(Br)cnc1N]

To a mixture of 2-amino-5-bromopyridine-3-carboxylic acid (8.85 g, 40.8 mmol), 2-methylpropanehydrazide (5.00 g, 49.0 mmol), and triethylamine (23 ml, 160 mmol) in DMF (30 ml) at rt was added dropwise a solution of T3P (71 ml, 50% purity, 120 mmol). The reaction was then stirred at rt for 5 h. Subsequently, it was diluted with water and ethyl acetate and the aqueous layer was separated and extracted twice with ethyl acetate. The combined organic layers were dried over anhydrous anhydrous sodium sulfate and the solvent was evaporated under reduced pressure. The residue was triturated with ethyl acetate/tert-butyl methyl ether and the precipitate was collected by suction filtration to yield 7.87 g (99% purity, 63% yield) of the title compound.

LC-MS (method 1): $R_t$=0.85 min; MS (ESIpos): n/z=301, 303 $[M+H]^+$ $^1$H-NMR (400 MHz, DMSO-$d_6$) δ[ppm]: 1.07 (d, 6H), 7.21 (s, 2H), 8.12 (d, 1H), 8.20 (d, 1H), 9.84 (s, 1H), 10.29 (br s, 1H).

Intermediate 34

5-Bromo-3-[5-(propan-2-yl)-1,3,4-thiadiazol-2-yl] pyridin-2-amine

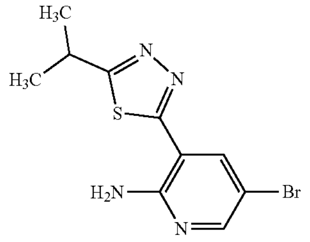 [SMILES: CC(C)c1nnc(-c2cc(Br)cnc2N)s1]

2-Amino-5-bromo-N-(2-methylpropanoyl)pyridine-3-carbohydrazide (3.00 g, 9.96 mmol) was dissolved in THF (60 ml) and Lawesson's reagent (4.84 g, 12.0 mmol) was added. The mixture was heated under reflux for 3 h. The reaction mixture was combined with an experient using 500 mg starting material. Solid material was then removed by filtration and the filter was rinsed with ethyl acetate. The solvent was removed in vacuo. The residue was purified by column chromatography (Biotage® SNAP Ultra C18 60 g cartridge, eluent: acetonitrile/water gradient 25:75 to 77:23, then to 95:5). The product fractions were concentrated in vacuo and the remaining aqueous solution was extracted three times with ethyl acetate. The combined organic layers were washed with brine, filtered through a hydrophobic phase separation filter and the solvent was removed in vacuo to yield 1.86 g (80% purity, 43% yield) of the title compound which was used without further purification.

LC-MS (method 1): $R_t$=1.84 min; MS (ESIpos): m/z=299, 301 $[M+H]^+$ $^1$H-NMR (400 MHz, DMSO-$d_6$) δ [ppm]: 1.41 (d, 6H), 3.49 (spt, 1H), 7.73 (br s, 2H), 8.07 (d, 1H), 8.21 (d, 1H).

Intermediate 35

Ethyl ({5-bromo-3-[5-(propan-2-yl)-1,3,4-thiadiazol-2-yl]pyridin-2-yl}carbamothioyl)carbamate

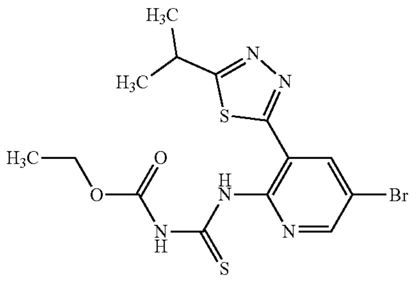 [SMILES: CCOC(=O)NC(=S)Nc1ncc(Br)cc1-c1nnc(C(C)C)s1]

5-Bromo-3-[5-(propan-2-yl)-1,3,4-thiadiazol-2-yl]pyridin-2-amine (1.80 g, 80% purity, 4.81 mmol) was dissolved in 1,4-dioxane (20 ml) and ethyl carbonisothiocyanatidate (620 µl, 5.3 mmol) was added dropwise. The mixture was stirred at rt overnight and then heated to 60° C. for 6 h. Subsequently, the mixture was concentrated in vacuo and the residue was triturated with tert-butyl methyl ether. The precipitate was collected by suction filtration and purified by column chromatography (Biotage® SNAP Ultra 25 g cartridge, eluent: cyclohexane/ethyl acetate gradient 90:10 to 46:54) to yield 1.15 g (80% purity, 44% yield) of the title compound.

LC-MS (method 1): $R_t$=1.98 min; MS (ESIpos): m/z=430, 432 $[M+H]^+$ $^1$H-NMR (400 MHz, DMSO-$d_6$) δ [ppm]: 1.28 (t, 3H), 1.39 (d, 6H), 3.53 (spt, 1H), 4.25 (q, 2H), 8.72 (d, 1H), 8.80 (d, 1H), 11.66 (s, 1H), 11.73 (s, 1H).

Intermediate 36

6-Bromo-8-[5-(propan-2-yl)-1,3,4-thiadiazol-2-yl][1,2,4]triazolo[1,5-c]pyridin-2-amine

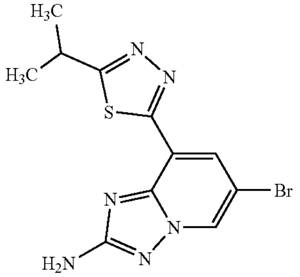 [SMILES: CC(C)c1nnc(-c2cc(Br)cn3nc(N)nc23)s1]

A solution of hydroxylamine hydrochloride (698 mg, 10.0 mmol) and N,N-diisopropylethylamine (1.6 ml, 9.3 mmol) in methanol/ethanol (1:1, 25 ml) was heated to 60° C. and ethyl ({5-bromo-3-[5-(propan-2-yl)-1,3,4-thiadiazol-2-yl] pyridin-2-yl}carbamothioyl)carbamate (1.00 g, 80% purity, 1.86 mmol) was added. The mixture was stirred at 60° C. for 1 h and then cooled to rt. The pH was adjusted to 6-7 by addition of satd. sodium bicarbonate solution and the mixture was poured into water (100 ml). It was stirred for 10 min and the precipitate was collected by suction filtration and washed with water (5 ml) and dried in vacuo to yield 630 mg (98% purity, 97% yield) of the title compound.

LC-MS (method 2): $R_t$=0.78 min; MS (ESIpos): m/z=0.338, 340 $[M+H]^+$ $^1$H-NMR (400 MHz, DMSO-$d_6$) δ[ppm]: 1.43 (d, 6H), 3.55 (spt, 1H), 6.57 (s, 2H), 8.38 (d, 1H), 9.17 (d, 1H).

Part II: Biological Data

The pharmacological activity of Compounds of Formula (Z), (Y) (X), (A), (I), (I-A), (I-B), (I-C), and (I-D) can be demonstrated by in vitro and in vivo studies, as known to the person skilled in the art. The application examples which follow describe the biological action of Compounds of Formula (Z), (Y), (X), (A), (I), (I-A), (I-B), (I-C), and (I-D), without restricting the disclosure to these examples.

Materials and Methods:

DLK Biochemical Assay

DLK assay is a biochemical assay format designed to screen for inhibitors of DLK. Enzymatic activity of DLK was measured by monitoring phosphorylation of the physiological substrate MKK7 (MAP2K7, Dual specificity mitogen-activated protein kinase kinase 7). Phosphorylation was detected by a TR-FRET system whereby His-tagged MKK7 was labeled by a XL665-labeled anti-His antibody (FRET acceptor, emission 665 nm). DLK phosphorylates MKK7 at T275/S277, which was detected by an Eu-labeled anti-phospho-MKK7 (T275/S277) antibody (F RET donor, excitation 340 nm). Phosphorylation of MKK7 results in an increased TR-FRET signal (Ratio XL665-channel/Eu-channel) and inhibition of enzymatic activity of DLK decreases the TR-FRET signal.

Assay Protocol for 1536 MTP format: test compounds were predispensed (60 nl) in test plates; +3 μl DLK solution (10 nM DLK, catalytic domain, Carna Biosiences, 0.6 mM DTT in assay buffer); +2 μl substrate solution (15 nM MKK7, LDB; 60 μM ATP; 0.4 mM DTT in assay buffer); 90 min incubation at RT; +2 μl detection mix (5 nM XL665-labeled anti-His antibody, Cisbio; 0.1 nM Eu-labeled anti-phospho-MKK7 (T275/S277), Cisbio/Millipore in detection buffer); 16 h incubation at 37° C.; endpoint measurement BMG (HTRF).

Assay Protocol for 384 low volume MTP format: 1 μl of test compounds were pipetted into test plate; +5 μl DLK solution (10 nM DLK, catalytic domain, Carna Biosiences in assay buffer); +5 μl substrate solution (15 nM MKK7, LDB; 60 μM ATP, in assay buffer); 90 min incubation at RT; +9 μl detection mix (20 nM XL665-labeled anti-His antibody, Cisbio; 0.4 nM Eu-labeled anti-phospho-MKK7 (T275/S277), Cisbio/Millipore in detection buffer); 16 h incubation at 4° C.; endpoint measurement BMG (HTRF).

All indicated concentrations final concentrations.

Assay buffer (1536 format): 50 mM Hepes pH 7.5, 10 mM $MgCl_2$, 1 mM EGTA, 0.01% Triton X-100, 0.01% BSA, 1:500 Smart Block.

Assay buffer (384 format): 50 mM Hepes pH 7.5, 10 mM $MgCl_2$, 1 mM EGTA, 1 mM DTT, 0,01% Triton X-100, 0.01% BSA, 1:500 Smart Block.

Detection buffer: 25 mM Tris/HCl pH 7.5, 100 mM EDTA, 100 mM NaCl, 200 mM KF, 0.01% Tween 20, 1:500 Smart Block.

LZK Biochemical Assay

LZK assay is a biochemical assay format designed to screen for inhibitors of LZK. Enzymatic activity of LZK was measured by monitoring phosphorylation of the physiological substrate MKK7 (MAP2K7, Dual specificity mitogen-activated protein kinase kinase 7). Phosphorylation was detected by a TR-FRET system whereby His-tagged MKK7 was labeled by a XL665-labeled anti-His antibody (FRET acceptor, emission 665 nm). LZK phosphorylates MKK7 at T275/S277 which were detected by an Eu-labeled anti-phospho-MKK7 (T275/S277) antibody (FRET donor, excitation 340 nm). Phosphorylation of MKK7 results in an increased TR-FRET signal (Ratio XL665-channel/Eu-channel) and inhibition of enzymatic activity of LZK decreases the TR-FRET signal.

Assay Protocol for 384 low volume MTP format: 1 μl of test compound was pipetted into test plate; +5 μl LZK solution (10 nM LZK, catalytic domain, Carna Biosiences in assay buffer); +5 μl substrate solution (15 nM MKK7, LDB; 15 μM ATP, in assay buffer); 90 min incubation at RT; +5 μl detection mix (20 nM XL665-labeled anti-His antibody, Cisbio; 0.4 nM Eu-labeled anti-phospho-MKK7 (T275/S277), Cisbio/Millipore in detection buffer), 16 h incubation at 32° C.; endpoint measurement BMG (HTRF).

All indicated concentrations final concentrations.

Assay buffer (384 format): 50 mM Hepes pH 7.5, 10 mM $MgCl_2$, 1 mM EGTA, 1 mM DTT, 0.01% Triton X-100, 0.01% BSA, 1:500 Smart Block.

Detection buffer: 25 mM Tris/HCl pH 7.5, 100 mM EDTA, 100 mM NaCl, 200 mM KF, 0.01% Tween 20, 1:500 Smart Block.

Metabolic Stability

Metabolic stabilities in rat hepatocytes were determined by incubating the compounds at low concentrations (e.g., below 1 μM) and at low cell numbers (e.g., at $1\times10^6$ cells/ml) to ensure linear kinetics. 7 time-points from the incubation mixture were withdrawn for analysis to define the half-life of the compound. From that half-life the intrinsic clearance in hepatocytes was calculated and used further to extrapolate the blood clearance (using the well-stirred model) and the corresponding $F_{max}$ value (maximum expected bioavailability after first pass of the liver) for the compounds. The CL and $F_{max}$ values reflect Phase I and II metabolism in hepatocytes. To minimize the influence of organic solvents in the incubation mixture their content was limited to max. 1% for ACN or max. 0.2% for DMSO. The values given in row 5 in the table in FIG. 1 are rat hepatocytes $CL_{blood}$ [L/h/kg] and rat hepatocytes $F_{max}$ [%].

Retinal Ganglion Cell (RGC) Viability Assay

The RGC assay detected the viability of primary murine retinal ganglion cells via Cell Titer Glo (Promega), using a previously described assay (*Proc. Natl. Acad. Sci. USA.* 2013, 110(10), 4045-50), which is incorporated herein by reference in its entirety.

RGCs were freshly isolated from approximately P2 murine retinas by immunopanning using mouse anti-CD90 coated plates. Cells are seeded into poly-D-lysine or laminin coated plates in Neurobasal medium supplemented by 1% Pen/Strep (Gibco 15140-122), 0.01 mg/ml insulin, 1 mM sodium pyruvate, 1% of 100× Sato (400 mg transferrin, 400 mg BSA, 0.25 mg progesterone, 64 mg putrescine, 160 μg sodium selenite in 40 mL Neurobasal medium), 0.04 μg/ml triiodo-thyronine, 2 mM L-glutamine, 0.05 mg/ml N-acetyl cysteine, 10 μM forskolin, 2% 50× B27 (Gibco 17504-044).

For the assay 500-2000 cells per well in a volume of 40 μl were used (384 MTP format). After 72 hours 20 μl Cell Titer Glo reagent was added and viability is measured via luminescent quantitation of ATP. The amount of ATP was directly proportional to the number of cells present in culture.

Solubility

Solubility of compounds at pH 6.5 was investigated via precipitation. The dilution of each compound was prepared from DMSO stock solution or from powder. Equilibration time was 24 h. The concentration of the compound in the supernatant after ultracentrifugation or filtrate after filtration was determined via LC-MSMS or HPLC analysis. Solubility data are reported in FIG. 2 in mg/L.

Permeability

To determine the permeability values as an in vitro model for screening compounds for their potential of intestinal absorption in mammalians selected compounds were tested in a Caco-2 drug permeability assay. Caco-2 cells were cultured for 14 days on 24-well plates. Test compounds were dissolved in DMSO and then diluted to a final concentration of 2 μM. The proportion of remaining organic solvent was not higher than 1%. The flux was investigated for both directions by adding the solution to the apical or basal compartment. Cover plates were incubated for 2 h at 37 C. Samples were measured by LC-MS/MS and data reported as Caco-2 permeation $P_{app}$ A-B [nm/s], Caco-2 permeation $P_{app}$ B-A [nm/s] and the quotient Caco-2 permeation efflux ratio. Ratio values bigger than 2 are a hint for active transportation.

Fraction Unbound

For some selected compounds we measured the fraction unbound and reported it in % for mouse, rat, and/or human. Partitioning of a compound between plasma water, plasma proteins, and solid-supported egg-lecithin membranes (Transil) was measured. The test substance was added to the Transil-plasma (water) suspension. After incubation, Transil was separated from the aqueous phase by centrifugation at 1800 g. The drug concentrations before centrifugation and in the aqueous phase were determined. The free fraction was calculated as the ratio of the membrane affinity in plasma (MAplasma) and the membrane affinity in plasma water (MAbuffer).

CYP Inhibition

The CYP inhibition mediated by the respective compound is reported for CYP1A2, CYP2C8, CYP2C9, CYP2D6, and CYP3A4 using pooled human liver microsomes as enzyme source. In addition, the inhibition of CYP3A4 was determined after a 30 min preincubation with the compound. Inhibitory effects were determined at 6 concentrations (0.625, 1.25, 2.5, 5, 10, and 20 μM) of the test compound and compared with the extent of metabolite formation (of phenacetin, amodiaquine, diclofenac, dextromethorphan, midazolam) in the absence of the potential inhibitor, and $IC_{50}$ values were calculated. The values are given in the table in the following format where the last line corresponds to the CYP3A4 inhibition after preincubation.

CYP Induction

CYP induction was measured in the following way: human hepatocyte cultures were treated with medium containing eight different concentrations of the test compound (typical concentration range: 5-10,000 ng/mL), the prototypic inducers omeprazole (CYP1A2) and rifampicin (CYP3A4) and the vehicle alone. Culture media were prepared and changed daily for a typical treatment period of 5 days. Specific enzyme activities were determined by incubating the probe substrates in situ with the intact hepatocyte cultures after the treatment period: (CYP1A2 activity: phenacetin O-deethylation activity; CYP3A4 activity: testosterone 6beta hydroxylation activity). CYP activities were quantified by LC/MS/MS analysis. Reported is the NOEL in μM.

SPR Assay

Surface Plasmon Resonance (SPR)-based biosensor technology was widely used for the characterization of protein/protein and protein/small-molecule interactions in a label-free setup. Here, the interaction of small molecules with the immobilized DLK protein on the biosensor chip surface was characterized in order to determine the equilibrium dissociation constant (KD [M]) as well as kinetic association and dissociation rate constants (kon [1/Ms] and koff [1/s], respectively). The measurements were performed using a Biacore® T200 instrument (GE Healthcare, Uppsala, Sweden). Biotinylated DLK (catalytic domain, amino acid 1-520, Carna-Biosciences 09-411-20N) diluted to a concentration of 10 μg/ml in immobilization buffer (10 mM HEPES, 150 mM NaCl, 3 mM EDTA and 0.05% v/v Surfactant P20, 5 mM $MgCl_2$, 0.5 mM TCEP, pH 7.4) was immobilized on an SA-Chip (GE-Healthcare, #29104992) at 18° C. Compounds were obtained in 100% dimethylsulfoxide (DMSO) at a concentration of 10 mM and diluted in running buffer (10 mM HEPES, 150 mM NaCl, 3 mM EDTA and 0.05% v/v Surfactant P20, 5 mM $MgCl_2$, 0.5 mM TCEP, 1% DMSO). For SPR measurements, serial dilutions of compound (typically eight dilution steps, ranging from 0.5 nM up to 1 μM) were injected over immobilized protein. Binding affinity and kinetics were measured at 18° C. with a flow rate of 100 μl/min. Compounds were injected for 70 s followed by a dissociation time of up to 350 s. The double-referenced sensorgrams were fit to a simple reversible Langmuir 1:1 reaction mechanism as implemented in the Biacore® T200 (T200 evaluation software version 2.0).

In Vivo Pharmokinetics

The in vivo pharmacokinetic parameters were investigated in rats after iv application. The following parameter are reported: Dose applied in [mg/kg] bodyweight; $AUC(0\text{-}24)_{norm}$=Area under the plasma concentration vs. time curve from zero to 24 h divided by dose in [kg*h/L]; $C_{max,norm}$: Maximum drug concentration in plasma divided by dose in [kg/L]; $CL_{matrix}$=Total body clearance of drug from plasma in [L/h/kg]; $CL_{blood}$=Total body clearance of drug from blood in [L/h/kg] ($CL_{matrix}$*$C_p/C_b$) with $C_p/C_b$=blood to plasma partitioning; $V_{ss}$=Apparent volume of distribution at steady state in [L/kg]; $MRT_{iv}$=Mean residence time in [h]; t½=Terminal half-life in [h].

Ischemia/Reperfusion

The animals were placed under anesthesia (Rompun (Xylazin als Xylazinhydrochlorid) 2%, Bayer, PZN-1320422, Ketavet (Ketaminhydrochlorid) 100 mg/mL, Pfizer, PZN-3151811) and the pupil on the right eye dilated (Neosynephrin-POS 5% Augentropfen, URSAPHARM, PZN 0828584).

When anesthetized, local anesthetic eye drops (Alcaine, lokalanästhetische Augentropfen, Alcon, 37516058) were applied to the right eye. The rat is on the left side. After a short exposure time, a 30G cannula was inserted laterally into the anterior chamber of the eye. To do this, the eye was fixed with a cotton swab so that it emerged from the eye socket. Once the cannula was placed, the eye was carefully released. The 30G cannula was connected via infusion set to a bag of isotonic infusion solution. The infusion bag hung in a pressure cuff. The pressure was regulated via the pressure cuff and the manometer. For the model, the intraocular pressure is increased to 120 mm Hg. The duration is 20 min. If the cannula fits correctly, the eye turns white, because the blood circulation was interrupted. During treatment, the rats lied on a warm mat (level 2). It was necessary to observe the anesthetic state of the animal. When necessary, the animal was sprayed as soon as the animal started to move its whiskers, usually after about 15 minutes. A moisture gel was applied to the eye.

Treatment started two days prior to the ischemic event and for two days after the insult. Optokinetic tracking (OKT) measurements are taken within 2-3 days after the final day of treatment.

When the time has elapsed, the cannula was removed and antibiotic eye drops and Bepanthen eye ointment were applied to the treated eye. The animals were then put back in their cage.

For the optometry readout only the spatial resolution is measured (spatial frequency). Both eyes were measured. The cycles/degree [c/d] values were displayed graphically comparing right/left eye.

Device Settings:

Psychophysics: simple staircase

Stimulus: 100% Contrast

Spatial Frequency

Optic Nerve Crush

Approximately three-month-old male C57BL/6 mice were anesthetized with 100/10 mg/kg of Ketamine/Xylazine followed by topical administration of proparacaine. Under the binocular operating scope, optic nerves were surgically exposed and crushed with Dumont N7 self-closing forceps 1-2 mm behind the globe. A small incision was made at the conjunctiva located at lateral orbit of eye globe using spring scissors. To avoid bleeding from the vasculature, minimum incision was continued until the optic nerve was exposed. After clean exposure, the optic nerve was grasped at approximately 1-2 mm from the globe for 3-7 seconds using the fine micro forceps. After careful removal of the micro forceps, the globe was relocated and Tobramycin was administered. Ten days after nerve crush, eyes were enucleated and fixed and surviving RGC was immunostained for SNCG, RBPMS and βIII-tubulin. The retinas were then imaged with a Nikon Eclipse TE2000-5 fluorescence microscope and Plan-fluor 40 Å~/0.6 objective. Images were acquired from the four fields in the superior, inferior, temporal, and nasal quadrants 1 mm from the optic disk. RGCs were counted manually from each image. In a separate cohort of animals, optic nerves and retinas were sectioned and stained for phospho-JUN (an indicator of DLK pathway activation) 24 hours after optic nerve crush. Intravitreal injection, optic nerve crush, immunofluorescence, and RGC counting were performed in a masked fashion.

Light Damage

After two weeks (14 days) acclimation in dim light (under 10-30 lux), female BALBc/J (10-12 weeks) were dark-adapted for 24 hrs. All compound injections were done in darkness with din-red light as needed. All mice were placed in light box after applying dilator (tropicamide or phenylephirine) topically. Then light was left on for 4 h with ~3000 lux followed by dark recovery at the same condition with dark adaptation until any experimental procedure is ready or being placed in dim light condition (under 10-30 lux). Mice were then followed for 3-7 days with OCT, ERG, functional testing, and/or immunohistochemical analysis.

Results

Figure 4:
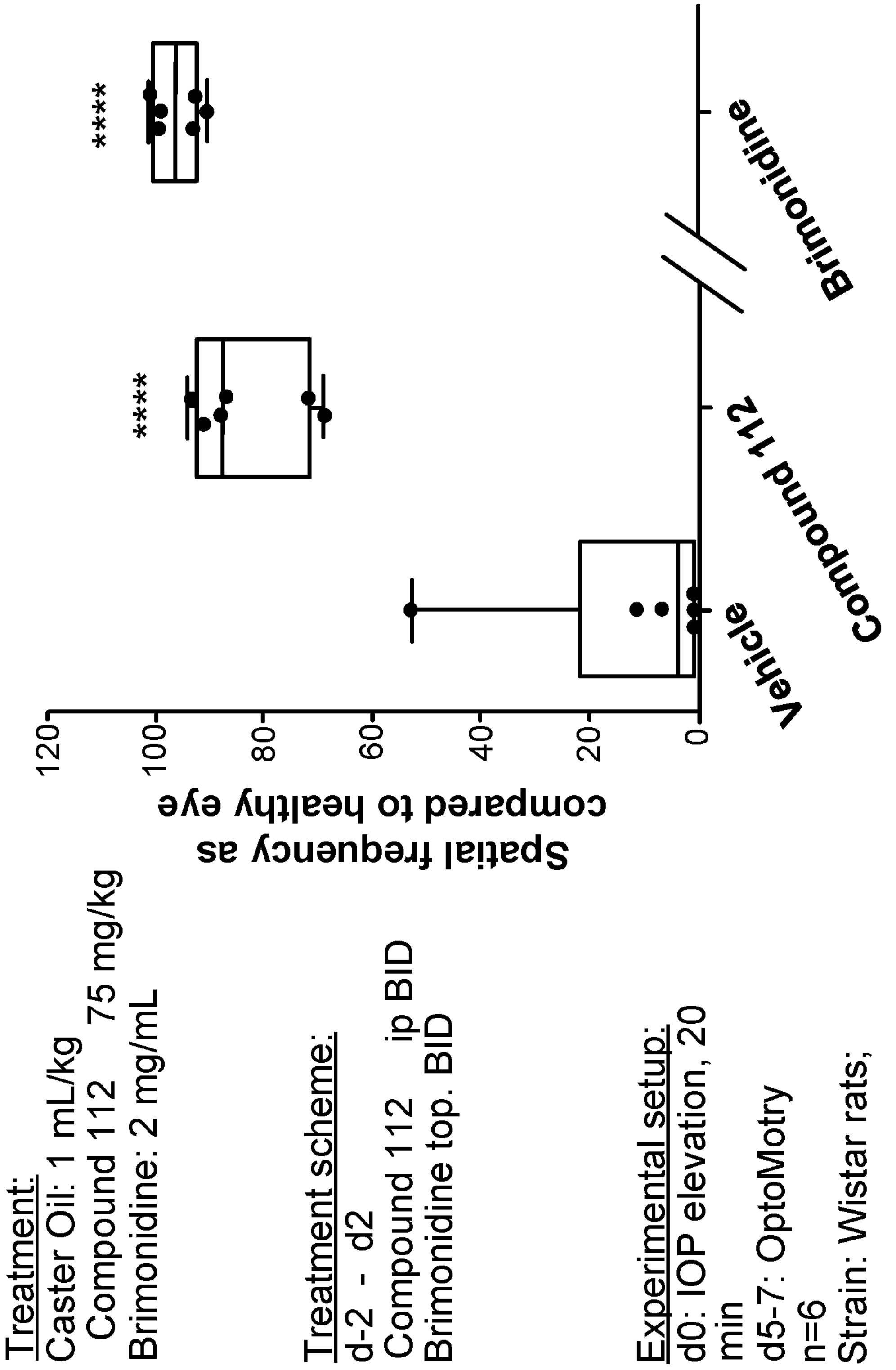
FIG. 4 is a graph depicting percentage retention of mouse vision in a vehicle, compound 112, and brimonidine.
Figure 5:
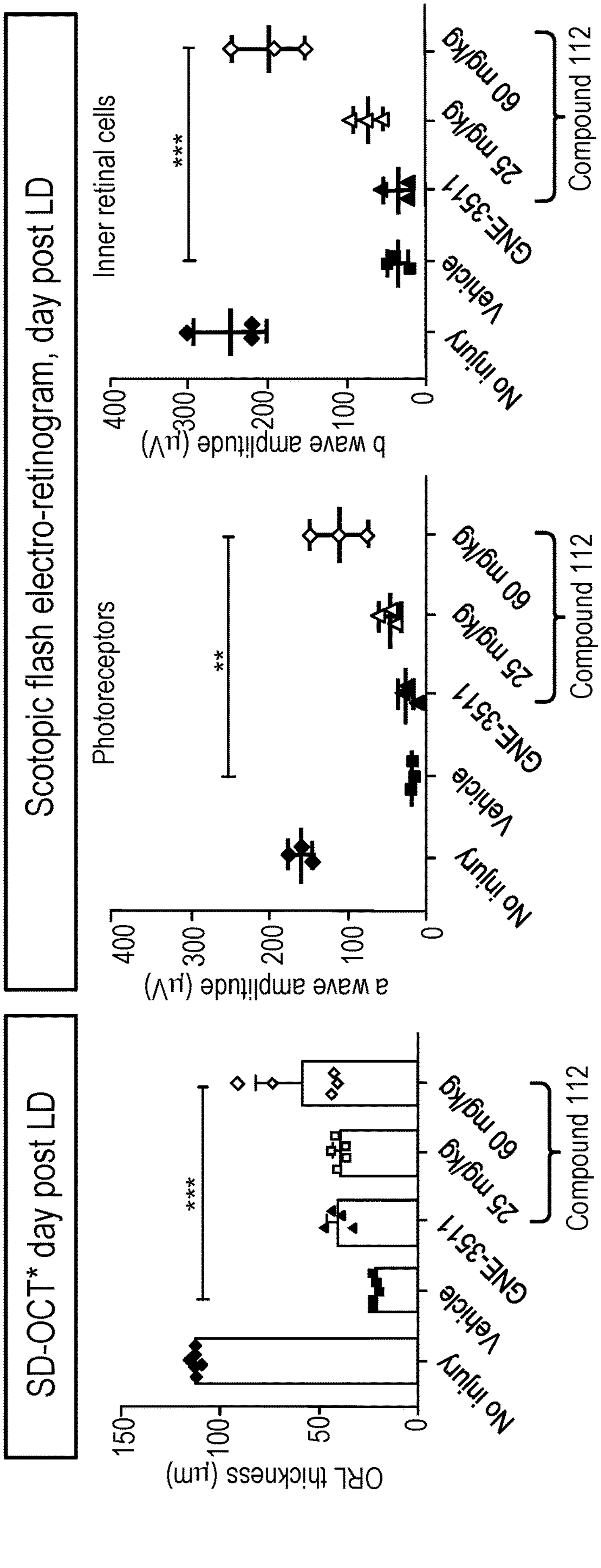
FIG. 5 is a series of graphs depicting ORL thickness, A wave amplitude, and B wave amplitude of compound 112 in a mouse light damage model.

DLK, LZK, retinal ganglion cell viability assay data, permeability data, metabolic data, and clearance data for compounds 4, 19, 94, and 112 are depicted in the table in FIG. 1. Compound 112 was the most active in the DLK, LZK, and RGC assays. In silico absorption, distribution, metabolism, excretion, and toxicology (ADMET) properties, molecular properties, in vitro PhysChem properties, safety data, and in vitro PK properties were obtained for compound 112 and are depicted in FIG. 2. The in vitro PhysChem and PK properties characterized the compound as chemically stable but metabolically labile. In vivo PK data of compound 112 in male Wistar rats is shown in FIG. 6. To demonstrate target engagement in vivo, mouse optic nerve crush experiments were performed (see FIG. 3) and p-JUN immunoreactivity was measured in the retinal ganglion cell (RGC) layer following injury. The decreased p-cJun intensity in the RGCs treated with compound 112 indicated that the DLK pathway activation was inhibited compared to RGCs treated with the vehicle. Compound 112 also showed neuroprotective effects in the Ischemia/Reperfusion (I/R) rat model. In a prophylactic setting after a 20 minute ischemic event animals treated with compound 112 retained ~80% of vision as compared to untreated animals (vehicle) who retained ~5% of vision (see FIG. 4). Compound 112 was also tested in serial optical coherence tomography (OCT) and serial electroretinogram (ERG) (see FIG. 5). In serial OCT, compound 112 demonstrated a higher outer retinal layer (ORL) thickness than the vehicle and exhibited dose-dependence. In serial ERG, compound 112 resulted in higher a wave amplitude in photoreceptors and higher b wave amplitude in inner retinal cells than the vehicle and exhibited dose-dependence. These results indicate that compound 112 showed neuroprotective effects in the mouse light damage model, showing preservation of both photoreceptor morphology (by serial OCT) and function (by serial ERG).

DLK and LZK values for the compounds of Formula Z are disclosed in Table A below.

TABLE A

DLK and LZK values of compounds of Formula Z.

| Compound Number | DLK $IC_{50}$ (mol/L) | LZK $IC_{50}$ (mol/L) |
|---|---|---|
| 1 | 2.00E−05 | >3.00E−5 |
| 2 | 1.80E−05 | >3.00E−5 |
| 3 | 3.40E−08 | 1.95E−07 |
| 4 | 3.50E−08 | 8.75E−08 |
| 5 | 1.60E−07 | 1.20E−06 |
| 6 | 8.40E−08 | 1.10E−06 |
| 7 | 8.70E−08 | 4.80E−07 |
| 8 | 1.40E−07 | 2.20E−06 |
| 9 | 1.30E−07 | 1.20E−06 |
| 10 | 1.20E−07 | 9.90E−07 |
| 11 | 1.70E−08 | 9.00E−08 |
| 12 | 2.10E−08 | 4.00E−07 |
| 13 | 3.40E−08 | 1.40E−07 |
| 14 | 3.40E−08 | 2.70E−07 |
| 15 | 5.80E−08 | 1.50E−07 |
| 16 | 3.70E−08 | 1.30E−07 |
| 17 | 3.10E−08 | 1.50E−07 |
| 18 | 1.20E−08 | 1.10E−07 |
| 19 | 8.65E−09 | 1.09E−07 |
| 20 | 6.32E−09 | 1.22E−07 |
| 21 | 9.30E−09 | 4.00E−08 |
| 22 | 1.85E−07 | 6.50E−07 |
| 23 | 3.00E−07 | 6.30E−07 |
| 24 | 6.90E−08 | 6.30E−07 |
| 25 | 4.61E−09 | 6.10E−08 |
| 26 | 6.40E−09 | 6.80E−08 |
| 27 | 5.80E−08 | 9.90E−08 |
| 28 | 3.40E−09 | 1.10E−07 |
| 29 | 2.80E−09 | 6.00E−08 |
| 30 | 1.60E−08 | 4.50E−08 |
| 31 | 1.30E−08 | 1.70E−07 |
| 32 | 6.50E−09 | 7.80E−08 |
| 33 | 1.20E−08 | 3.60E−07 |
| 34 | 5.50E−08 | 8.80E−07 |
| 35 | 3.20E−08 | 1.20E−07 |
| 36 | 2.30E−07 | 8.40E−07 |
| 37 | 2.20E−07 | 1.25E−06 |
| 38 | 1.70E−08 | 1.30E−07 |
| 39 | 3.75E−08 | 5.90E−07 |
| 40 | 3.90E−08 | 3.80E−07 |
| 41 | 5.50E−09 | 1.90E−07 |
| 42 | 7.00E−08 | 4.80E−07 |
| 43 | 2.20E−08 | 1.30E−07 |
| 44 | 4.70E−08 | 1.40E−06 |
| 45 | 2.40E−08 | 4.30E−07 |
| 46 | 3.60E−07 | 1.20E−06 |
| 47 | 1.30E−07 | 3.60E−06 |
| 48 | 2.40E−09 | 7.70E−08 |
| 49 | 9.40E−08 | 1.10E−06 |
| 50 | 4.20E−08 | 7.30E−07 |

TABLE A-continued

DLK and LZK values of compounds of Formula Z.

| Compound Number | DLK $IC_{50}$ (mol/L) | LZK $IC_{50}$ (mol/L) |
|---|---|---|
| 51 | 2.85E−08 | 2.40E−07 |
| 52 | 2.05E−08 | 2.35E−07 |
| 53 | 2.80E−07 | 6.10E−06 |
| 54 | 2.30E−09 | 3.00E−08 |
| 55 | 8.80E−08 | 6.50E−06 |
| 56 | 1.20E−07 | 2.30E−06 |
| 57 | 9.20E−08 | 2.10E−06 |
| 58 | 2.95E−08 | 3.30E−07 |
| 59 | 4.35E−09 | 2.55E−07 |
| 60 | 5.25E−09 | 2.95E−07 |
| 61 | 5.70E−07 | 3.70E−06 |
| 62 | 1.20E−07 | 1.00E−05 |
| 63 | 1.20E−07 | 4.60E−06 |
| 64 | 2.00E−07 | 7.00E−06 |
| 65 | 1.00E−07 | 1.90E−05 |
| 66 | 8.80E−08 | 3.50E−06 |
| 67 | 2.00E−07 | 1.70E−06 |
| 68 | 3.00E−07 | 1.60E−06 |
| 69 | 6.00E−08 | 1.10E−06 |
| 70 | 7.60E−08 | 1.40E−06 |
| 71 | 4.85E−09 | 5.50E−08 |
| 72 | 8.90E−08 | 6.20E−06 |
| 73 | 1.60E−07 | 9.30E−06 |
| 74 | 3.20E−07 | 5.60E−06 |
| 75 | 6.70E−08 | 4.20E−06 |
| 76 | 5.15E−09 | 8.70E−08 |
| 77 | 1.80E−09 | 3.60E−08 |
| 78 | 6.45E−09 | 1.20E−07 |
| 79 | 1.15E−08 | 2.10E−07 |
| 80 | 5.65E−08 | 1.30E−07 |
| 81 | 1.00E−08 | 1.40E−07 |
| 82 | 1.25E−08 | 4.55E−07 |
| 83 | 7.30E−08 | 4.20E−06 |
| 84 | 1.90E−08 | 3.40E−07 |
| 85 | 3.60E−07 | 9.00E−07 |
| 86 | 3.60E−07 | 1.10E−06 |
| 87 | 1.10E−08 | 4.80E−08 |
| 88 | 3.20E−09 | 3.70E−08 |
| 89 | 3.70E−09 | 5.10E−08 |
| 90 | 2.10E−08 | 4.90E−07 |
| 91 | 3.30E−09 | 4.80E−08 |
| 92 | 5.50E−08 | 2.00E−06 |
| 93 | 1.10E−08 | 4.10E−08 |
| 94 | 4.75E−09 | 3.40E−08 |
| 95 | 1.40E−08 | 1.30E−07 |
| 96 | 1.40E−08 | 7.60E−08 |
| 97 | 1.60E−08 | 1.40E−07 |
| 98 | 7.50E−09 | 6.00E−08 |
| 99 | 3.30E−07 | 2.40E−06 |
| 100 | 5.80E−09 | 2.00E−07 |
| 101 | 1.80E−08 | 2.90E−08 |
| 102 | 4.30E−09 | 7.10E−08 |
| 103 | 2.50E−08 | 1.60E−07 |
| 104 | 1.70E−09 | 3.05E−08 |
| 105 | 2.00E−08 | 5.50E−07 |
| 106 | 1.10E−08 | 1.60E−07 |
| 107 | 5.50E−09 | 4.60E−08 |
| 108 | 4.00E−09 | 2.50E−08 |
| 109 | 7.50E−09 | 1.20E−07 |
| 110 | 8.20E−08 | 4.70E−07 |
| 111 | 4.40E−08 | 2.90E−07 |
| 112 | 3.20E−09 | 2.90E−08 |
| 113 | 2.20E−07 | 6.60E−07 |
| 114 | 4.70E−08 | 7.10E−07 |
| 115 | 1.30E−09 | 4.10E−08 |
| 116 | 2.20E−09 | 1.40E−08 |
| 117 | 2.10E−08 | 2.40E−07 |
| 118 | 2.10E−07 | 5.20E−06 |
| 119 | 2.40E−08 | 5.05E−07 |
| 120 | 6.90E−09 | 1.10E−07 |
| 121 | 1.70E−08 | 5.20E−07 |
| 122 | 6.00E−09 | 3.60E−07 |
| 123 | 2.90E−09 | 8.30E−08 |
| 124 | 1.70E−08 | 3.30E−07 |
| 125 | 1.80E−08 | 2.20E−07 |

TABLE A-continued

DLK and LZK values of compounds of Formula Z.

| Compound Number | DLK $IC_{50}$ (mol/L) | LZK $IC_{50}$ (mol/L) |
|---|---|---|
| 126 | 9.80E−07 | 3.40E−06 |
| 127 | 9.30E−07 | 8.30E−06 |
| 128 | 1.10E−07 | 6.20E−07 |
| 129 | 2.90E−07 | 8.00E−07 |
| 130 | 1.40E−08 | 1.20E−07 |
| 131 | 6.30E−08 | 1.50E−06 |
| 132 | 2.80E−08 | 7.30E−07 |
| 133 | 1.00E−08 | 2.40E−07 |
| 134 | 3.60E−08 | 6.80E−07 |
| 135 | 7.40E−09 | 2.50E−07 |
| 136 | 6.30E−08 | 5.60E−06 |
| 137 | 9.70E−09 | 3.00E−07 |
| 138 | 4.20E−09 | 3.10E−08 |
| 139 | 5.50E−09 | 1.20E−07 |
| 140 | 7.20E−08 | 7.90E−07 |
| 141 | 1.00E−08 | 6.30E−08 |
| 142 | 1.20E−07 | 4.00E−07 |
| 143 | 8.90E−09 | 1.10E−07 |
| 144 | 3.80E−08 | 7.70E−07 |
| 144-1 | 4.60E−09 | 4.20E−08 |
| 144-2 | 2.30E−08 | 2.00E−07 |
| 144-3 | 7.20E−09 | 4.30E−08 |
| 144-4 | 8.00E−07 | 2.50E−06 |
| 144-5 | 6.30E−07 | 2.60E−06 |
| 145 | 3.05E−08 | 1.24E−07 |
| 146 | 1.20E−08 | 7.10E−08 |
| 147 | 2.10E−08 | 1.00E−07 |
| 148 | 6.40E−08 | 2.30E−07 |
| 149 | 2.80E−08 | 1.10E−07 |
| 150 | 4.60E−08 | 4.90E−07 |
| 151 | 3.60E−08 | 1.00E−07 |
| 152 | 4.15E−09 | 5.70E−08 |
| 153 | 3.20E−08 | 2.80E−07 |
| 154 | 4.90E−09 | 8.90E−08 |
| 155 | 4.30E−09 | 4.10E−08 |
| 156 | 7.50E−09 | 7.90E−08 |
| 157 | 1.80E−07 | 8.70E−07 |
| 158 | 3.30E−08 | 5.60E−07 |
| 159 | 2.90E−09 | 1.60E−08 |
| 160 | 6.30E−09 | 5.20E−08 |
| 161 | 2.10E−08 | 4.30E−08 |
| 162 | 3.50E−09 | 7.70E−08 |
| 163 | 1.20E−05 | |
| 164 | 2.80E−05 | |
| 165 | 8.80E−07 | >3.00E−5 |
| 166 | 5.20E−06 | |
| 167 | 1.00E−05 | |
| 168 | 3.80E−07 | 4.60E−06 |
| 169 | 1.10E−06 | >3.00E−5 |
| 170 | 5.20E−07 | >3.00E−5 |
| 171 | 9.70E−07 | >3.00E−5 |
| 172 | 2.60E−06 | >3.00E−5 |
| 173 | 2.15E−06 | 1.90E−05 |
| 174 | 4.40E−07 | >3.00E−5 |
| 175 | 9.55E−06 | >3.00E−5 |
| 176 | 1.00E−06 | >3.00E−5 |
| 177 | 1.60E−06 | >3.00E−5 |
| 178 | 3.50E−06 | |
| 179 | 3.40E−06 | |
| 180 | 2.00E−06 | >3.00E−5 |
| 181 | 3.50E−06 | >3.00E−5 |
| 182 | 1.33E−07 | 2.50E−05 |
| 183 | 4.30E−06 | |
| 184 | 1.95E−06 | 2.40E−05 |
| 185 | 1.70E−06 | 2.60E−05 |
| 186 | 7.60E−06 | |
| 187 | 7.10E−07 | >3.00E−5 |
| 188 | 2.00E−06 | >3.00E−5 |
| 189 | 4.70E−06 | |
| 190 | 5.30E−07 | >3.00E−5 |
| 191 | 3.20E−07 | >3.00E−5 |
| 192 | 4.60E−07 | >3.00E−5 |
| 193 | 6.15E−07 | 5.00E−06 |
| 194 | 6.70E−07 | >3.00E−5 |
| 195 | 4.80E−07 | 8.80E−06 |

TABLE A-continued

DLK and LZK values of compounds of Formula Z.

| Compound Number | DLK $IC_{50}$ (mol/L) | LZK $IC_{50}$ (mol/L) |
|---|---|---|
| 196 | 3.50E−07 | 9.49E−06 |
| 197 | 1.60E−06 | >3.00E−5 |
| 198 | 1.25E−06 | >3.00E−5 |
| 199 | 1.20E−06 | >3.00E−5 |
| 200 | 5.60E−07 | >3.00E−5 |
| 201 | 2.80E−06 | >3.00E−5 |
| 202 | 8.20E−07 | >3.00E−5 |
| 203 | 1.01E−06 | 1.30E−05 |
| 204 | 3.00E−07 | >3.00E−5 |
| 205 | 2.30E−07 | 1.20E−05 |
| 206 | 5.50E−07 | 2.80E−05 |
| 207 | 4.70E−07 | 2.70E−05 |
| 208 | 3.00E−06 | |
| 209 | 2.50E−06 | >3.00E−5 |
| 210 | 2.70E−06 | |
| 211 | 9.70E−07 | 1.80E−05 |
| 212 | 1.07E−06 | 9.60E−06 |
| 213 | 2.45E−06 | 7.60E−06 |
| 214 | 1.75E−06 | 2.50E−05 |
| 215 | 7.20E−07 | 3.00E−5 |
| 216 | 1.14E−06 | 5.90E−06 |
| 217 | 8.60E−06 | |
| 218 | 8.70E−06 | |
| 219 | 5.05E−07 | 3.10E−06 |
| 220 | 5.80E−07 | 2.20E−05 |
| 221 | 1.24E−06 | 9.20E−06 |
| 222 | 1.39E−06 | 5.70E−06 |
| 223 | 6.40E−07 | 2.30E−05 |
| 224 | 1.66E−06 | >3.00E−5 |
| 225 | 7.10E−07 | 6.95E−06 |
| 226 | 6.70E−07 | 5.00E−06 |
| 227 | 8.35E−07 | >3.00E−5 |
| 228 | 4.80E−07 | >3.00E−5 |
| 229 | 7.60E−06 | |
| 230 | 2.50E−06 | 2.80E−05 |
| 231 | 8.60E−07 | 1.10E−05 |
| 232 | 2.00E−07 | 2.50E−05 |
| 233 | 4.40E−07 | 1.70E−05 |
| 234 | 4.70E−07 | 1.80E−05 |
| 235 | 3.70E−07 | 2.30E−05 |
| 236 | 3.15E−07 | >3.00E−5 |
| 237 | 1.20E−05 | |
| 238 | 2.70E−07 | >3.00E−5 |
| 239 | 1.85E−06 | 1.80E−05 |
| 240 | 6.40E−07 | 6.30E−06 |
| 241 | 1.30E−06 | 2.10E−05 |
| 242 | 1.80E−06 | 1.90E−05 |
| 243 | 1.50E−06 | 1.70E−05 |
| 244 | 4.10E−06 | |
| 245 | 1.30E−06 | >3.00E−5 |
| 246 | 1.14E−06 | 4.40E−06 |
| 247 | 8.00E−07 | 3.80E−06 |
| 248 | 3.10E−06 | |
| 249 | 7.45E−07 | 7.60E−06 |
| 250 | 9.35E−07 | 4.50E−06 |
| 251 | 1.96E−06 | 9.10E−06 |
| 252 | 3.90E−06 | |
| 253 | >3.00E−5 | |
| 254 | 1.00E−06 | 1.00E−05 |
| 255 | 1.99E−06 | 4.40E−06 |
| 256 | 1.60E−06 | 1.70E−05 |
| 257 | 1.10E−06 | >3.00E−5 |
| 258 | 7.00E−06 | |
| 259 | 2.90E−06 | |
| 260 | 1.20E−06 | >3.00E−5 |
| 261 | 5.10E−07 | 1.40E−05 |
| 262 | >3.00E−5 | |
| 263 | 3.55E−07 | >3.00E−5 |
| 264 | 5.05E−07 | >3.00E−5 |
| 265 | 1.30E−07 | >3.00E−5 |
| 266 | >3.00E−5 | |
| 267 | 2.60E−07 | >3.00E−5 |
| 268 | 1.80E−07 | 2.20E−05 |
| 269 | 5.90E−07 | >3.00E−5 |
| 270 | 3.50E−06 | >3.00E−5 |

TABLE A-continued

DLK and LZK values of compounds of Formula Z.

| Compound Number | DLK $IC_{50}$ (mol/L) | LZK $IC_{50}$ (mol/L) |
|---|---|---|
| 271 | 3.50E−06 | >3.00E−5 |
| 272 | 1.50E−06 | >3.00E−5 |
| 273 | 5.80E−07 | 1.40E−05 |
| 274 | 2.60E−07 | 1.10E−05 |
| 275 | 6.30E−07 | 1.60E−05 |
| 276 | 4.20E−07 | 1.50E−05 |
| 277 | 4.80E−07 | 1.80E−05 |
| 278 | 4.40E−07 | >3.00E−5 |
| 279 | 2.10E−06 | >3.00E−5 |
| 280 | 2.50E−07 | 2.30E−05 |
| 281 | 1.50E−06 | >3.00E−5 |
| 282 | 7.50E−07 | >3.00E−5 |
| 283 | 5.30E−07 | >3.00E−5 |
| 284 | 2.60E−06 | >3.00E−5 |
| 285 | 1.70E−06 | 2.00E−05 |
| 286 | 6.00E−07 | >3.00E−5 |
| 287 | 5.70E−06 | >3.00E−5 |
| 288 | 2.40E−06 | 2.00E−05 |
| 289 | 2.60E−06 | 2.00E−06 |
| 290 | 6.20E−07 | 7.40E−06 |
| 291 | 7.10E−07 | 1.40E−05 |
| 292 | 1.20E−06 | 1.90E−05 |
| 293 | 2.60E−07 | >3.00E−5 |
| 294 | 7.10E−07 | >3.00E−5 |
| 295 | 3.90E−07 | 1.40E−05 |
| 296 | 7.30E−07 | 1.20E−05 |
| 297 | 7.10E−07 | 1.10E−05 |
| 298 | 3.50E−07 | 4.20E−06 |
| 299 | 1.20E−07 | 2.50E−06 |
| 300 | 1.10E−06 | 3.70E−06 |
| 301 | 1.00E−07 | 1.65E−5 |
| 302 | 7.55E−08 | 1.13E−06 |
| 303 | 1.30E−07 | 1.80E−06 |
| 304 | 2.20E−07 | 4.30E−06 |
| 305 | >3.00E−5 | >3.00E−5 |
| 306 | 1.30E−07 | 2.50E−06 |
| 307 | 1.50E−07 | 4.50E−06 |
| 308 | 3.00E−07 | 3.00E−06 |
| 309 | 1.20E−07 | 6.60E−06 |
| 310 | 5.10E−08 | 1.70E−05 |
| 311 | 1.90E−05 | >3.00E−5 |
| 312 | >3.00E−5 | >3.00E−5 |
| 313 | 2.40E−05 | >3.00E−5 |
| 314 | 5.30E−07 | 7.00E−06 |
| 315 | 1.30E−07 | 4.80E−06 |
| 316 | 1.80E−07 | 4.70E−06 |
| 317 | 9.70E−08 | 3.60E−06 |
| 318 | 1.30E−07 | 1.70E−06 |
| 319 | 1.20E−07 | 1.70E−06 |
| 320 | >3.00E−5 | >3.00E−5 |
| 321 | 6.70E−08 | 3.70E−06 |
| 322 | 1.20E−07 | 1.40E−06 |
| 323 | 1.64E−07 | 2.95E−06 |
| 324 | 6.20E−08 | 1.60E−06 |
| 325 | 2.80E−07 | >3.00E−5 |
| 326 | 2.55E−07 | >3.00E−5 |
| 327 | 4.20E−08 | 6.10E−06 |
| 328 | 4.00E−07 | 8.20E−06 |
| 329 | 7.40E−07 | 2.10E−05 |
| 330 | 6.40E−07 | 1.20E−05 |
| 331 | 9.10E−07 | 1.30E−05 |
| 332 | 1.50E−07 | 3.10E−06 |
| 333 | 4.90E−07 | 6.80E−06 |
| 334 | 4.00E−07 | 5.80E−06 |
| 335 | 1.40E−07 | 3.50E−06 |
| 336 | 2.90E−07 | >3.00E−5 |
| 337 | 4.80E−07 | 1.40E−06 |
| 338 | 1.90E−07 | >3.00E−5 |
| 339 | 2.30E−06 | >3.00E−5 |
| 340 | 4.30E−06 | >3.00E−5 |
| 341 | 2.30E−07 | 5.10E−06 |
| 342 | 5.20E−07 | 1.70E−05 |
| 343 | 8.60E−07 | 2.70E−05 |
| 344 | 4.70E−07 | 2.10E−05 |
| 345 | 2.30E−06 | >3.00E−5 |

TABLE A-continued

DLK and LZK values of compounds of Formula Z.

| Compound Number | DLK $IC_{50}$ (mol/L) | LZK $IC_{50}$ (mol/L) |
|---|---|---|
| 346 | 7.90E−08 | 2.90E−05 |
| 347 | 1.30E−07 | >3.00E−5 |
| 348 | 3.00E−5 | 3.00E−5 |
| 349 | 2.30E−07 | 2.40E−5 |
| 350 | 7.60E−07 | 2.05E−5 |
| 351 | 6.40E−06 | 2.00E−05 |
| 352 | 1.00E−06 | >3.00E−5 |
| 353 | 2.10E−07 | >3.00E−5 |
| 354 | 1.10E−07 | >3.00E−5 |
| 355 | 2.10E−07 | >3.00E−5 |
| 356 | 3.10E−07 | >3.00E−5 |
| 357 | 2.10E−07 | >3.00E−5 |
| 358 | 1.10E−07 | 1.20E−06 |
| 359 | 1.60E−07 | >3.00E−5 |
| 360 | 4.00E−07 | >3.00E−5 |
| 361 | 1.90E−06 | >3.00E−5 |
| 362 | 8.20E−06 | 2.30E−05 |
| 363 | 6.40E−07 | 8.70E−06 |
| 364 | 4.00E−07 | 1.90E−05 |
| 365 | 5.00E−07 | 1.10E−05 |
| 366 | 3.10E−07 | >3.00E−5 |
| 367 | 3.00E−07 | 2.80E−05 |
| 368 | 6.70E−07 | 1.30E−05 |
| 369 | 2.30E−07 | 1.90E−06 |
| 370 | 4.40E−06 | >3.00E−5 |
| 371 | 5.00E−07 | 2.30E−06 |
| 372 | 4.30E−07 | 9.20E−06 |
| 373 | 3.70E−07 | 2.80E−06 |
| 374 | 2.80E−07 | 9.30E−06 |
| 375 | 8.40E−07 | 3.30E−06 |
| 376 | 2.60E−07 | 4.90E−06 |
| 377 | 2.10E−07 | 2.40E−06 |
| 378 | 1.80E−06 | 9.50E−06 |
| 379 | 9.70E−07 | 2.00E−05 |
| 380 | 1.10E−06 | >3.00E−5 |
| 381 | 3.80E−07 | >3.00E−5 |
| 382 | 3.10E−07 | >3.00E−5 |
| 383 | >3.00E−5 | >3.00E−5 |
| 384 | >3.00E−5 | >3.00E−5 |
| 385 | 1.10E−05 | >3.00E−5 |
| 386 | 3.40E−06 | >3.00E−5 |
| 387 | 7.50E−07 | 2.80E−06 |
| 388 | 2.10E−07 | 1.20E−06 |
| 389 | >3.00E−5 | >3.00E−5 |
| 390 | 1.10E−05 | >3.00E−5 |
| 391 | 2.00E−06 | >3.00E−5 |
| 392 | 1.00E−07 | 8.30E−07 |
| 393 | 2.60E−07 | 1.30E−06 |
| 394 | 4.10E−07 | 2.50E−06 |
| 395 | 1.10E−06 | 3.60E−06 |
| 396 | 3.10E−07 | 9.80E−07 |
| 397 | 7.30E−08 | 1.10E−06 |
| 398 | 8.80E−07 | 3.90E−06 |
| 399 | 1.76E−06 | 3.95E−06 |
| 400 | 2.15E−06 | 4.35E−06 |
| 401 | 8.10E−09 | 1.15E−07 |
| 402 | 6.90E−08 | 1.90E−06 |
| 403 | 1.40E−07 | 5.70E−06 |

It is to be understood that while the invention has been described in conjunction with the detailed description thereof, the foregoing description is intended to illustrate and not limit the scope of the invention which is defined by the scope of the appended claims. Other aspects, advantages, and modification are within the scope of the following claims.

What is claimed is:

1. A compound of formula (Z)

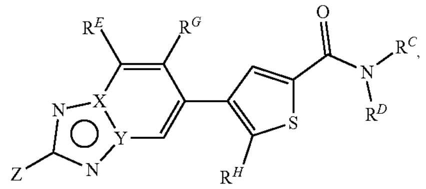

(Z)

wherein

X is carbon and Y is nitrogen, $R^E$ is hydrogen, —C(O)—$NR^AR^B$, C(O)$OR^6$, —$S(O)_2NH$($C_1$-$C_6$)-alkyl, ($C_1$-$C_6$)-alkyl, halo, ($C_6$-$C_{10}$)-aryl, or heteroaryl, wherein the ($C_1$-$C_6$)-alkyl, ($C_6$-$C_{10}$)-aryl, and heteroaryl can be substituted by one or more independently selected ($C_1$-$C_4$)-alkyl, ($C_3$-$C_7$)-cycloalkyl, ($C_3$-$C_7$)-cycloalkyl-($C_1$-$C_3$)-alkyl, 4- to 7-membered heterocyclyl, ($C_1$-$C_4$)-alkoxy, ($C_3$-$C_7$)-cycloalkoxy, —$SO_2R^4$, —$NR^4R^5$, cyano, hydroxyl, or halo, wherein the ($C_1$-$C_4$)-alkyl, ($C_3$-$C_7$)-cycloalkyl, ($C_1$-$C_4$)-alkoxy, ($C_3$-$C_7$)-cycloalkyl-($C_1$-$C_3$)-alkyl, and ($C_3$-$C_7$)-cycloalkoxy can be substituted by one or more independently selected hydroxyl, cyano, or halo, $R^A$ is hydrogen or —$CR^1R^2R^3$, $R^B$ is hydrogen or ($C_1$-$C_6$)-alkyl, $R^1$ and $R^2$ are each independently hydrogen or ($C_1$-$C_3$)-alkyl, wherein the ($C_1$-$C_3$)-alkyl can be substituted by one or more independently selected halo, $R^3$ is hydrogen, ($C_1$-$C_6$)-alkyl, ($C_3$-$C_7$)-cycloalkyl, or ($C_3$-$C_7$)-cycloalkyl-($C_1$-$C_3$)-alkyl, wherein the ($C_1$-$C_6$)-alkyl, ($C_3$-$C_7$)-cycloalkyl, or ($C_3$-$C_7$)-cycloalkyl-($C_1$-$C_3$)-alkyl can be substituted by one or more independently selected hydroxyl, ($C_1$-$C_4$)-alkoxy, oxo, cyano, or halo, and wherein the ($C_1$-$C_4$)-alkoxy can be substituted by one or more independently selected halo, or $R^1$ is hydrogen and $R^2$ and $R^3$ are joined to one another and, taken together with the carbon atom to which they are attached, form a 3- to 7-membered ring containing up to two heteroatoms selected from the group consisting of O or N, wherein the ring can be substituted by one or more independently selected hydroxyl, ($C_1$-$C_4$)-alkoxy, ($C_1$-$C_4$)-alkyl, oxo, cyano, or halo, and wherein the ($C_1$-$C_4$)-alkoxy and ($C_1$-$C_4$)-alkyl can be substituted by one or more independently selected hydroxyl or halo, $R^C$ is hydrogen, ($C_6$-$C_{10}$)-aryl, or $CR^4R^5R^7$, wherein the ($C_6$-$C_{10}$)-aryl is optionally substituted by one or more independently selected ($C_1$-$C_4$)-alkyl, ($C_1$-$C_4$)-alkoxy, or halo, and wherein the ($C_1$-$C_4$)-alkyl and ($C_1$-$C_4$)-alkoxy can be substituted by one or more independently selected hydroxyl or halo, $R^4$ is hydrogen, ($C_1$-$C_6$)-alkyl, ($C_3$-$C_7$)-cycloalkyl, or 4- to 7-membered heterocyclyl, wherein the ($C_1$-$C_6$)-alkyl, ($C_3$-$C_7$)-cycloalkyl, or 4- to 7-membered heterocyclyl can be substituted by one or more independently selected ($C_1$-$C_4$)-alkyl, ($C_1$-$C_4$)-alkoxy, hydroxyl, oxo, cyano, or halo, wherein the ($C_1$-$C_4$)-alkoxy and ($C_1$-$C_4$)-alkyl can be substituted by one or more independently selected halo, and any nitrogen of the 4- to 7-membered heterocyclyl can be substituted by C(O)$OR^6$ or C(O)$R^6$, $R^5$ is ($C_1$-$C_6$)-alkyl, ($C_3$-$C_7$)-cycloalkyl, cyanomethyl, ($C_6$-$C_{10}$)-aryl, ($C_6$-$C_{10}$)-aryl-($C_1$-$C_4$)-alkyl, heteroaryl, or 4- to 7-membered heterocyclyl wherein:

(i) the ($C_1$-$C_6$)-alkyl, ($C_3$-$C_7$)-cycloalkyl, ($C_6$-$C_{10}$)-aryl, ($C_6$-$C_{10}$)-aryl-($C_1$-$C_4$)-alkyl, heteroaryl, or 4- to 7-membered heterocyclyl can be substituted by one or more independently selected ($C_1$-$C_4$)-alkyl, ($C_1$-$C_4$)-alkoxy, C(O)OR$^6$, ($C_3$-$C_7$)-cycloalkoxy, cyano, 4- to 7-membered heterocyclyl, or halo, and wherein the ($C_1$-$C_4$)-alkyl and ($C_1$-$C_4$)-alkoxy can be substituted by one or more independently selected 4- to 7-membered heterocyclyl optionally substituted with oxo or ($C_1$-$C_4$)-alkyl, ($C_1$-$C_4$)-alkoxy, —NR'R", or halo, and (ii) the ($C_3$-$C_7$)-cycloalkyl, ($C_6$-$C_{10}$)-aryl, ($C_6$-$C_{10}$)-aryl-($C_1$-$C_4$)-alkyl, heteroaryl, or 4- to 7-membered heterocyclyl can be fused with a 4- to 7-membered heterocyclyl or ($C_3$-$C_7$)-cycloalkyl, or $R^4$ and $R^5$ are joined to one another and, taken together with the carbon atom to which they are attached, form a 3- to 8-membered monocyclic or bridged bicyclic ring containing up to two heteroatoms selected from the group consisting of O or N, wherein:

(i) the ring can be substituted by one or more independently selected ($C_6$-$C_{10}$)-aryl-($C_1$-$C_4$)-alkyl, ($C_6$-$C_{10}$)-aryl, 4- to 7-membered heterocyclyl, ($C_1$-$C_4$)-alkyl, ($C_1$-$C_4$)-alkoxy, oxo, cyano, or halo, wherein the ($C_1$-$C_4$)-alkyl and ($C_6$-$C_{10}$)-aryl can be substituted by one or more independently selected 4- to 7-membered heterocyclyl, ($C_1$-$C_4$)-alkoxy, or halo, and the nitrogen of each of the 4- to 7-membered heterocyclyl can independently be substituted by C(O)OR$^6$ or C(O)R$^6$, and (ii) the ring can be fused with ($C_6$-$C_{10}$)-aryl, heteroaryl, or 4- to 7-membered heterocyclyl, each of which is optionally substituted with one or more independently selected ($C_1$-$C_4$)-alkoxy or halo, or $R^6$ is hydrogen or ($C_1$-$C_4$)-alkyl, $R^7$ is hydrogen, ($C_1$-$C_6$)-alkyl, ($C_3$-$C_7$)-cycloalkyl, ($C_6$-$C_{10}$)-aryl, or 4- to 7-membered heterocyclyl, wherein the ($C_1$-$C_6$)-alkyl, ($C_3$-$C_7$)-cycloalkyl, ($C_6$-$C_{10}$)-aryl, or 4- to 7-membered heterocyclyl can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more independently selected halo, and the nitrogen of the 4- to 7-membered heterocyclyl can be substituted by C(O)OR$^6$ or C(O)R$^6$, $R^D$ is hydrogen or ($C_1$-$C_6$)-alkyl, or $R^C$ and $R^D$ are joined to one another and, taken together with the nitrogen atom to which they are attached, form a 4- to 10-membered monocyclic or bicyclic ring containing up to three heteroatoms selected from the group consisting of O or N, and wherein the 4- to 10-membered monocyclic or bicyclic ring is optionally substituted with one or more independently selected ($C_1$-$C_6$)-alkyl or ($C_1$-$C_4$)-alkoxy, Z is —NHR$^F$ or H, $R^F$ is hydrogen or ($C_1$-$C_6$)-alkyl, wherein the ($C_1$-$C_6$)-alkyl is optionally substituted with one or more independently selected-NR'R", each occurrence of R' and R" is selected from hydrogen and ($C_1$-$C_4$)-alkyl, or R' and R", joined to one another and, taken together with the nitrogen atom to which they are attached, form a 3-6 membered heterocyclyl, $R^G$ is hydrogen or halo, $R^H$ is hydrogen, halo, or ($C_1$-$C_4$)-alkyl, and salts, solvates, and solvates of salts thereof.

2. The compound of claim 1, wherein the compound is a compound of Formula (I)

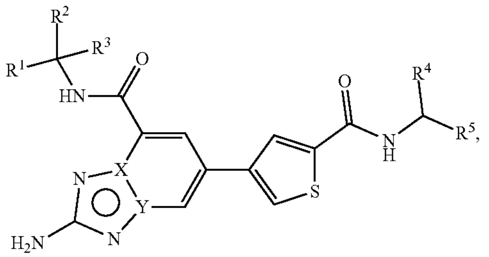

(I)

wherein

X is carbon and Y is nitrogen, $R^1$ and $R^2$ are each independently hydrogen or ($C_1$-$C_3$)-alkyl optionally substituted by one or more fluoro, $R^3$ is ($C_1$-$C_6$)-alkyl, ($C_3$-$C_7$)-cycloalkyl, or ($C_3$-$C_7$)-cycloalkyl-($C_1$-$C_3$)-alkyl wherein the ($C_1$-$C_6$)-alkyl, ($C_3$-$C_7$)-cycloalkyl, or ($C_3$-$C_7$)-cycloalkyl-($C_1$-$C_3$)-alkyl can be substituted by one or more independently selected hydroxyl, ($C_1$-$C_4$)-alkoxy, oxo, cyano, or halo, and wherein the ($C_1$-$C_4$)-alkoxy can be substituted by one or more independently selected halo, or $R^1$ is hydrogen and $R^2$ and $R^3$ are joined to one another and, taken together with the carbon atom to which they are attached, form a 4- to 7-membered ring containing up to two heteroatoms selected from the group consisting of O or N, wherein the ring can be substituted by one or more independently selected hydroxyl, ($C_1$-$C_4$)-alkoxy, ($C_1$-$C_4$)-alkyl, oxo, cyano, or halo, and wherein the ($C_1$-$C_4$)-alkoxy and ($C_1$-$C_4$)-alkyl can be substituted by one or more independently selected halo, $R^4$ is hydrogen, ($C_1$-$C_6$)-alkyl, ($C_3$-$C_7$)-cycloalkyl, or 4- to 7-membered heterocyclyl wherein the ($C_1$-$C_6$)-alkyl, ($C_3$-$C_7$)-cycloalkyl, or 4- to 7-membered heterocyclyl can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more independently selected halo, and any nitrogen of the 4- to 7-membered heterocyclyl can be substituted by C(O)OR$^6$ or C(O)R$^6$, $R^5$ is ($C_3$-$C_7$)-cycloalkyl, ($C_6$-$C_{10}$)-aryl, or heteroaryl, wherein the ($C_3$-$C_7$)-cycloalkyl, ($C_6$-$C_{10}$)-aryl, or heteroaryl can be substituted by one or more independently selected ($C_1$-$C_4$)-alkyl, ($C_1$-$C_4$)-alkoxy, cyano, 4- to 7-membered heterocyclyl, or halo, and wherein the ($C_1$-$C_4$)-alkyl and ($C_1$-$C_4$)-alkoxy can be substituted by one or more fluoro, or $R^4$ and $R^5$ are joined to one another and, taken together with the carbon atom to which they are attached, form a 4- to 7-membered ring containing up to two heteroatoms selected from the group consisting of O or N, wherein:

(i) the ring can be substituted by one or more independently selected ($C_6$-$C_{10}$)-aryl-($C_1$-$C_4$)-alkyl, 4- to 7-membered heterocyclyl, ($C_1$-$C_4$)-alkyl, ($C_1$-$C_4$)-alkoxy, oxo, cyano, or halo, wherein the ($C_1$-$C_4$)-alkyl is optionally substituted by one or more independently selected 4- to 7-membered heterocyclyl or fluoro, and any nitrogen of each of the 4- to 7-membered heterocyclyl can independently be substituted by $C(O)OR^6$ or $C(O)R^6$, and (ii) the ring can be fused with ($C_6$-$C_{10}$)-aryl or heteroaryl, $R^6$ is ($C_1$-$C_4$)-alkyl.

3. The compound of claim 1, wherein $R^1$ is hydrogen.

4. The compound of claim 1, wherein $R^2$ is ($C_1$-$C_3$)-alkyl optionally substituted by one or more fluoro.

5. The compound of claim 4, wherein $R^2$ is methyl.

6. The compound of claim 1, wherein $R^3$ is ($C_1$-$C_6$)-alkyl, wherein the ($C_1$-$C_6$)-alkyl can be substituted by one or more independently selected hydroxyl, ($C_1$-$C_4$)-alkoxy, oxo, cyano, or halo, and wherein the ($C_1$-$C_4$)-alkoxy can be substituted by one or more independently selected halo.

7. The compound of claim 1, wherein $R^4$ is ($C_1$-$C_6$)-alkyl, wherein the ($C_1$-$C_6$)-alkyl can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more independently selected halo.

8. The compound of claim 1, wherein $R^5$ is ($C_6$-$C_{10}$)-aryl, wherein the ($C_6$-$C_{10}$)-aryl can be substituted by one or more independently selected ($C_1$-$C_4$)-alkyl, ($C_1$-$C_4$)-alkoxy, cyano, 4- to 7-membered heterocyclyl, or halo, and wherein the ($C_1$-$C_4$)-alkyl and ($C_1$-$C_4$)-alkoxy can be substituted by one or more fluoro.

9. The compound of claim 1, wherein the compound is a compound of Formula (I-C)

(I-C)

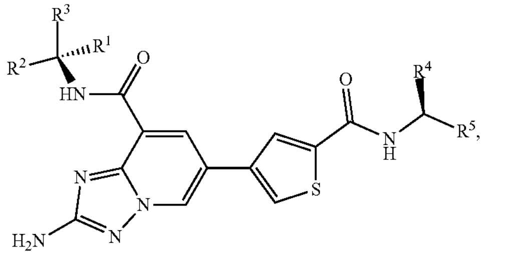

wherein $R^1$ is hydrogen, $R^2$ is methyl optionally substituted by one or more fluoro, $R^3$ is methyl or ethyl which can be substituted by one or more independently selected hydroxyl, ($C_1$-$C_4$)-alkoxy, chloro, or fluoro, wherein the ($C_1$-$C_4$)-alkoxy can be substituted by one or more fluoro, or $R^2$ and $R^3$ are joined to one another and, taken together with the carbon atom to which they are attached, form pyrrolidinone, a cyclobutyl, or a tetrahydrofuranyl, $R^4$ is hydrogen, ($C_1$-$C_6$)-alkyl, cyclopropyl, cyclobutyl, cyclopentyl, or 4- to 7-membered heterocyclyl wherein the ($C_1$-$C_6$)-alkyl, cyclopropyl, cyclobutyl, cyclopentyl, or 4- to 7-membered heterocyclyl can be substituted by one or more independently selected ($C_1$-$C_4$)-alkoxy or halo, and any nitrogen of the 4- to 7-membered heterocyclyl can be substituted by $C(O)OR^6$ or $C(O)R^6$, $R^5$ is phenyl or benzoxazolyl, each of which can be substituted by one or more independently selected ($C_1$-$C_4$)-alkyl, ($C_1$-$C_4$)-alkoxy, cyano, or halo, wherein the ($C_1$-$C_4$)-alkyl and ($C_1$-$C_4$)-alkoxy can be substituted by one or more fluoro, or $R^4$ and $R^5$ are joined to one another and, taken together with the carbon atom to which they are attached, form a 5- to 6-membered ring containing up to one O atom, wherein the ring can be fused with phenyl, $R^6$ is ($C_1$-$C_4$)-alkyl.

10. The compound of claim 1, wherein $R^3$ is ethyl which can be substituted by one or more fluoro.

11. The compound of claim 1, wherein $R^4$ is hydrogen, methyl, ethyl, or methoxymethyl.

12. The compound of claim 1, wherein $R^5$ is phenyl, which can be substituted by one or more independently selected ($C_1$-$C_4$)-alkoxy or halo.

13. The compound of claim 1, wherein:

Z is $NH_2$, $R^E$ is heteroaryl, wherein the heteroaryl can be substituted by one or more independently selected ($C_1$-$C_4$)-alkyl, ($C_3$-$C_7$)-cycloalkyl, ($C_3$-$C_7$)-cycloalkyl-($C_1$-$C_3$)-alkyl, 4- to 7-membered heterocyclyl, ($C_1$-$C_4$)-alkoxy, ($C_3$-$C_7$)-cycloalkoxy, $—SO_2R^4$, $—NR^4R^5$, cyano, hydroxyl, or halo, wherein the ($C_1$-$C_4$)-alkyl, ($C_3$-$C_7$)-cycloalkyl, ($C_1$-$C_4$)-alkoxy, ($C_3$-$C_7$)-cycloalkyl-($C_1$-$C_3$)-alkyl, and ($C_3$-$C_7$)-cycloalkoxy can be substituted by one or more independently selected hydroxyl, cyano, or halo, $R^C$ is $CR^4R^5R^7$, and $R^D$ is hydrogen, $R^4$ is hydrogen, ($C_1$-$C_6$)-alkyl, ($C_3$-$C_7$)-cycloalkyl, or 4- to 7-membered heterocyclyl, each of which can be substituted by one or more independently selected ($C_1$-$C_4$)-alkyl, ($C_1$-$C_4$)-alkoxy, oxo, cyano, or halo, wherein the ($C_1$-$C_4$)-alkoxy and ($C_1$-$C_4$)-alkyl can be substituted by one or more fluoro; and any nitrogen of the 4- to 7-membered heterocyclyl can be substituted by $C(O)OR^6$ or $C(O)R^6$;

$R^5$ is ($C_3$-$C_7$)-cycloalkyl, phenyl, or heteroaryl wherein the ($C_3$-$C_7$)-cycloalkyl, phenyl, or heteroaryl can be substituted by one or more independently selected ($C_1$-$C_4$)-alkyl, ($C_1$-$C_4$)-alkoxy, cyano, 4- to 7-membered heterocyclyl, or halo, wherein the ($C_1$-$C_4$)-alkyl and ($C_1$-$C_4$)-alkoxy can be substituted by one or more fluoro; and $R^6$ is ($C_1$-$C_4$)-alkyl.

14. The compound of claim 1, wherein:

Z is $NH_2$, $R^E$ is thiadiazolyl or oxadiazolyl, each of which can be substituted by one or more independently selected ($C_1$-$C_4$)-alkyl, wherein the ($C_1$-$C_4$)-alkyl, can be substituted by one or more independently selected hydroxyl, cyano, or halo, $R^C$ is $CR^4R^5R^7$, and $R^D$ is hydrogen, $R^4$ is ($C_1$-$C_6$)-alkyl, wherein the ($C_1$-$C_6$)-alkyl can be substituted by one or more fluoro; and $R^5$ is phenyl or heteroaryl wherein the phenyl or heteroaryl can be substituted by one or more independently selected ($C_1$-$C_4$)-alkyl, ($C_1$-$C_4$)-alkoxy, cyano, or fluoro, wherein the ($C_1$-$C_4$)-alkyl and ($C_1$-$C_4$)-alkoxy can be substituted by one or more fluoro.

15. The compound of claim 11, wherein $R^4$ is ethyl.

16. The compound of claim 1, wherein the compound is selected from the compounds disclosed in Table 1A, Table 1C, Table 1E, and Table 1F below, and pharmaceutically acceptable salts thereof
Table 1A,
| Compound Number | Structure |
|---|---|
| 1 | 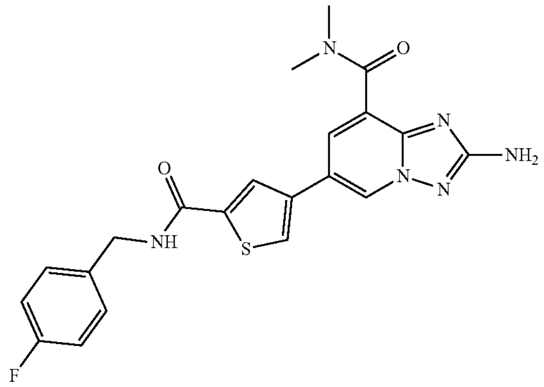 [SMILES: CN(C)C(=O)c1cc(-c2csc(C(=O)NCc3ccc(F)cc3)c2)cn2nc(N)nc12] |
| 2 | 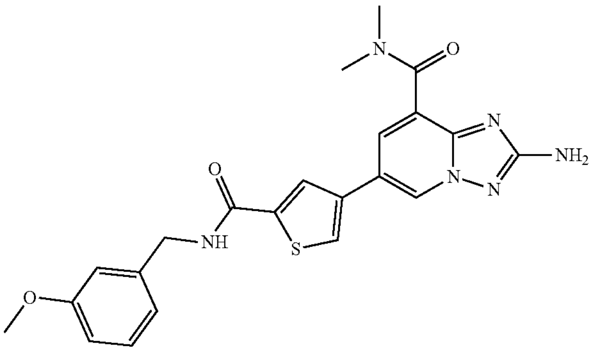 [SMILES: COc1cccc(CNC(=O)c2cc(-c3cc(C(=O)N(C)C)c4nc(N)nn4c3)cs2)c1] |
| 3 | 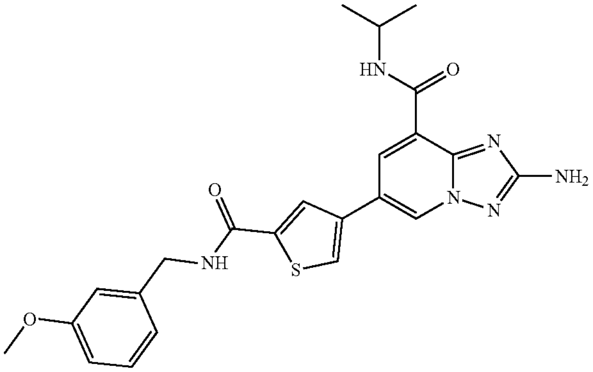 [SMILES: COc1cccc(CNC(=O)c2cc(-c3cc(C(=O)NC(C)C)c4nc(N)nn4c3)cs2)c1] |

-continued
| Compound Number | Structure |
|---|---|
| 4 | 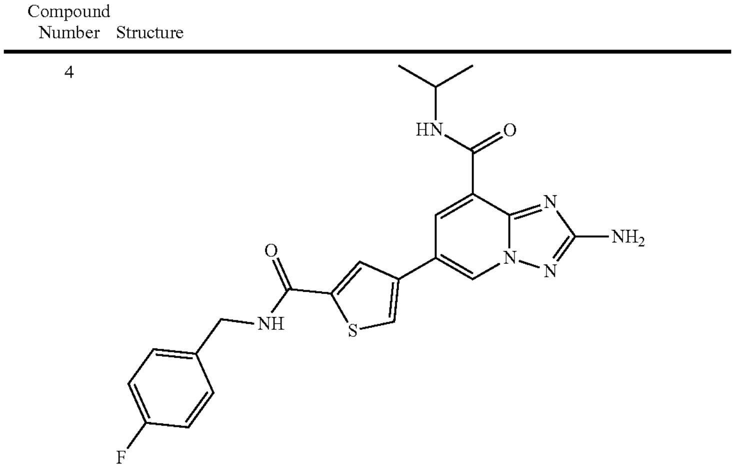 |
| 5 | 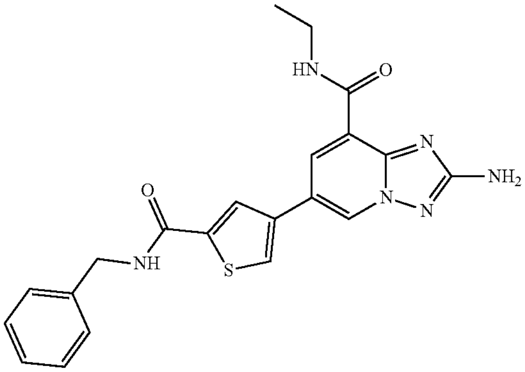 [SMILES: CCNC(=O)c1cc(-c2csc(C(=O)NCc3ccccc3)c2)cn2nc(N)nc12] |
| 6 | 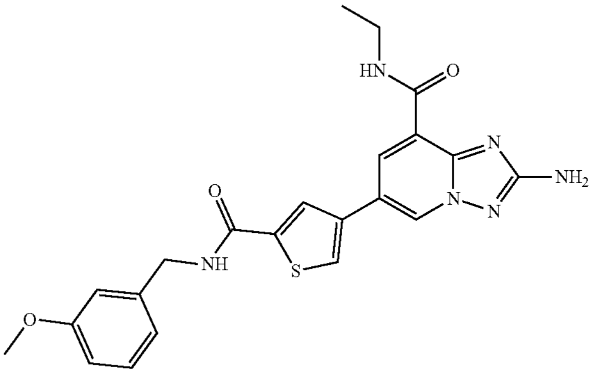 [SMILES: CCNC(=O)c1cc(-c2csc(C(=O)NCc3cccc(OC)c3)c2)cn2nc(N)nc12] |
| 7 | 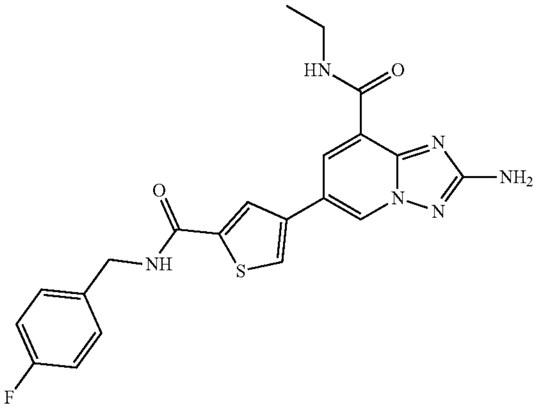 [SMILES: CCNC(=O)c1cc(-c2csc(C(=O)NCc3ccc(F)cc3)c2)cn2nc(N)nc12] |

-continued
| Compound Number | Structure |
|---|---|
| 8 | 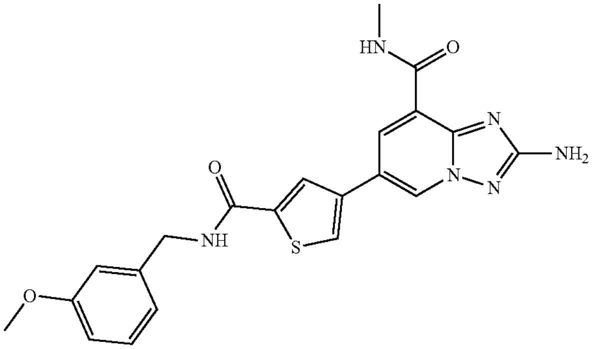 |
| 9 | 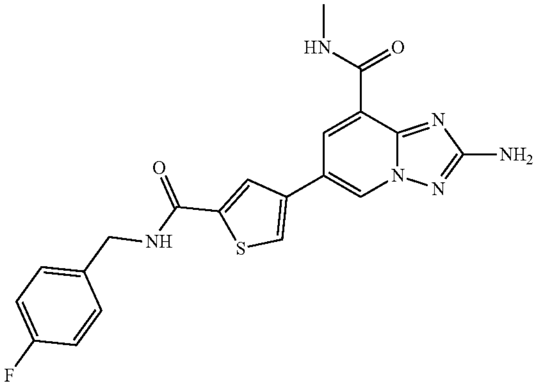 [SMILES: CNC(=O)c1cc(-c2csc(C(=O)NCc3ccc(F)cc3)c2)cn2nc(N)nc12] |
| 10 | 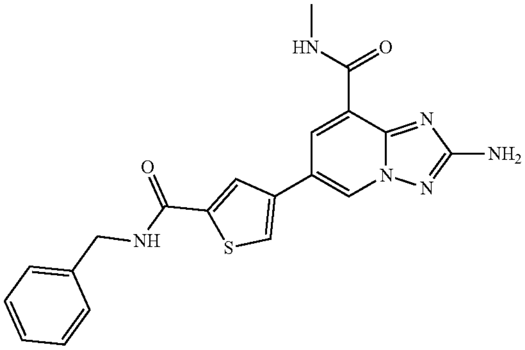 [SMILES: CNC(=O)c1cc(-c2csc(C(=O)NCc3ccccc3)c2)cn2nc(N)nc12] |
| 11 | 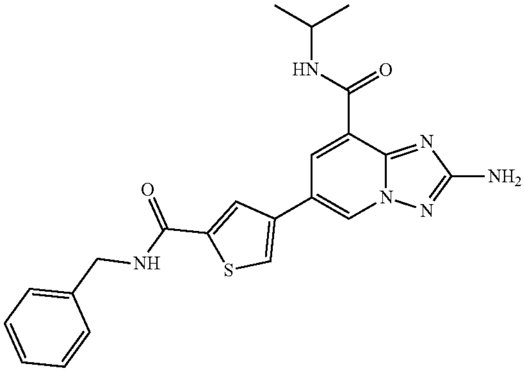 [SMILES: CC(C)NC(=O)c1cc(-c2csc(C(=O)NCc3ccccc3)c2)cn2nc(N)nc12] |

-continued
| Compound Number | Structure |
| --- | --- |
| 12 | 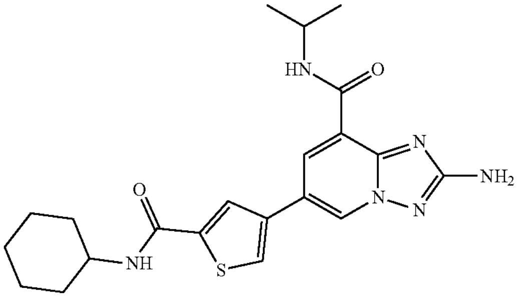 [SMILES: CC(C)NC(=O)c1cc(-c2csc(C(=O)NC3CCCCC3)c2)cn2nc(N)nc12] |
| 13 | 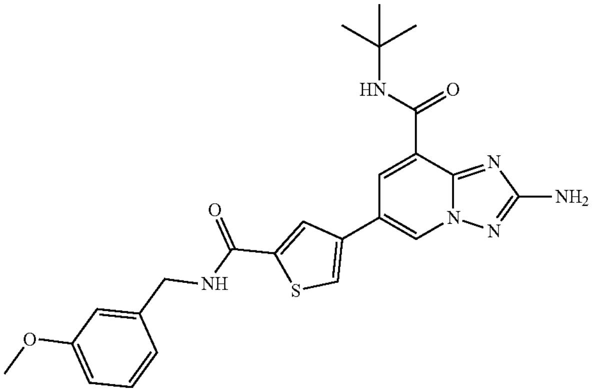 [SMILES: COc1cccc(CNC(=O)c2cc(-c3cc(C(=O)NC(C)(C)C)c4nc(N)nn4c3)cs2)c1] |
| 14 | 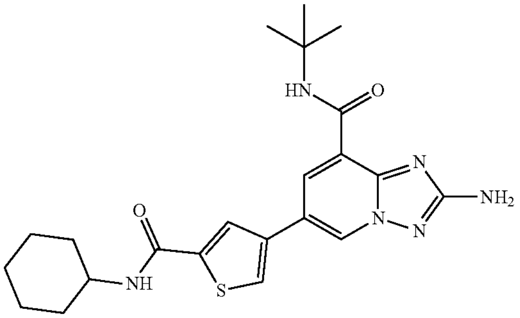 [SMILES: CC(C)(C)NC(=O)c1cc(-c2csc(C(=O)NC3CCCCC3)c2)cn2nc(N)nc12] |
| 15 | 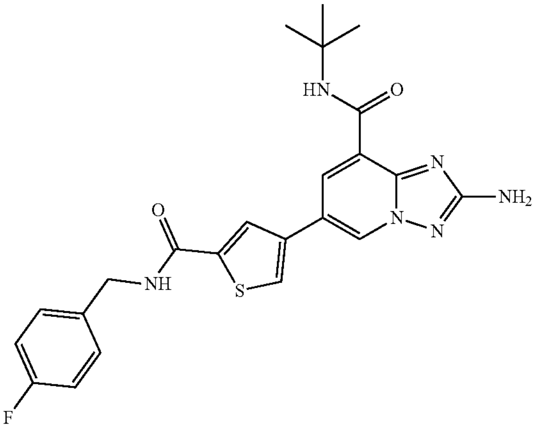 [SMILES: CC(C)(C)NC(=O)c1cc(-c2csc(C(=O)NCc3ccc(F)cc3)c2)cn2nc(N)nc12] |

-continued
| Compound Number | Structure |
|---|---|
| 16 | 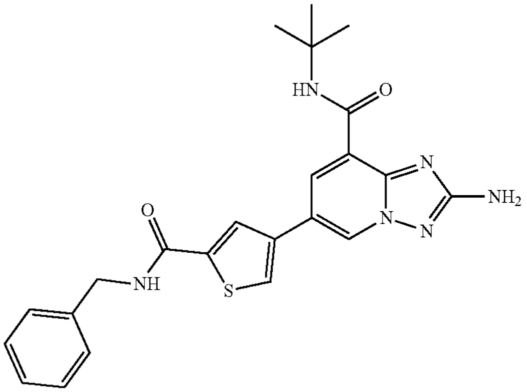 [SMILES: CC(C)(C)NC(=O)c1cc(-c2csc(C(=O)NCc3ccccc3)c2)cn2nc(N)nc12] |
| 17 | 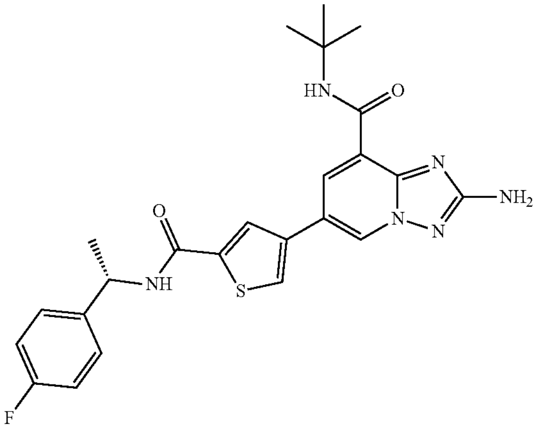 [SMILES: C[C@H](NC(=O)c1cc(-c2cc(C(=O)NC(C)(C)C)c3nc(N)nn3c2)cs1)c1ccc(F)cc1] |
| 18 | 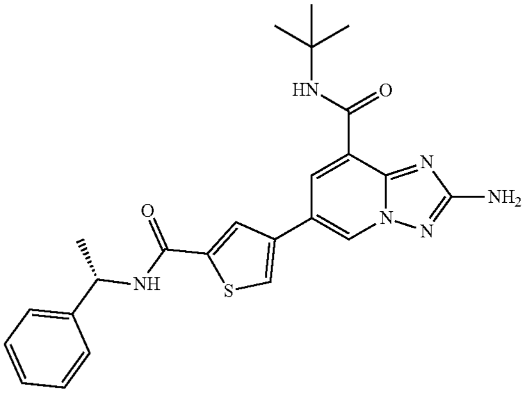 [SMILES: C[C@H](NC(=O)c1cc(-c2cc(C(=O)NC(C)(C)C)c3nc(N)nn3c2)cs1)c1ccccc1] |

-continued
| Compound Number | Structure |
|---|---|
| 19 | 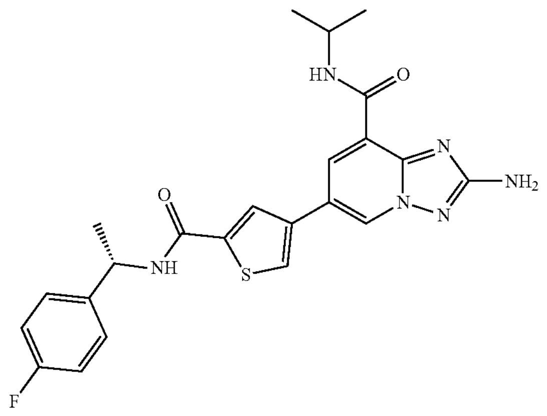 [SMILES: CC(C)NC(=O)c1cc(-c2csc(C(=O)N[C@@H](C)c3ccc(F)cc3)c2)cn2nc(N)nc12] |
| 20 | 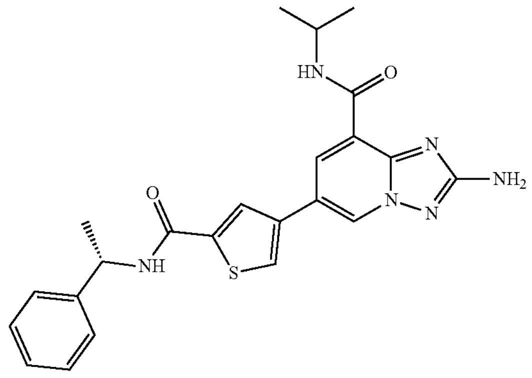 [SMILES: CC(C)NC(=O)c1cc(-c2csc(C(=O)N[C@@H](C)c3ccccc3)c2)cn2nc(N)nc12] |
| 21 | 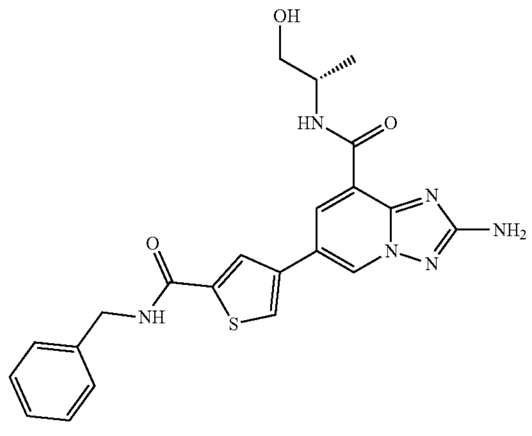 [SMILES: C[C@@H](CO)NC(=O)c1cc(-c2csc(C(=O)NCc3ccccc3)c2)cn2nc(N)nc12] |

-continued
| Compound Number | Structure |
|---|---|
| 22 | 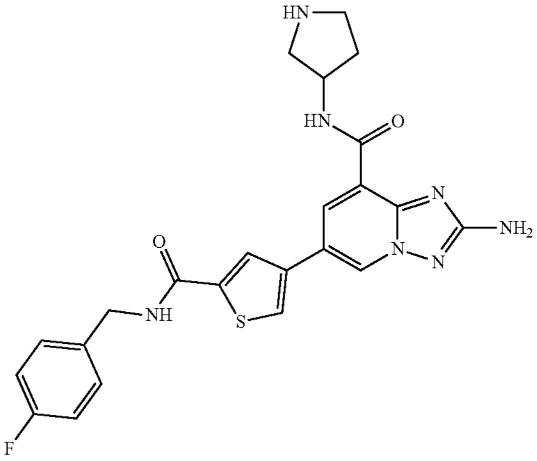 |
| 23 | 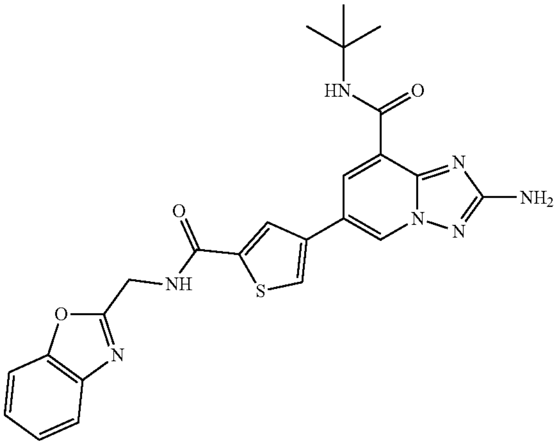 [SMILES: CC(C)(C)NC(=O)c1cc(-c2csc(C(=O)NCc3nc4ccccc4o3)c2)cn2nc(N)nc12] |
| 24 | 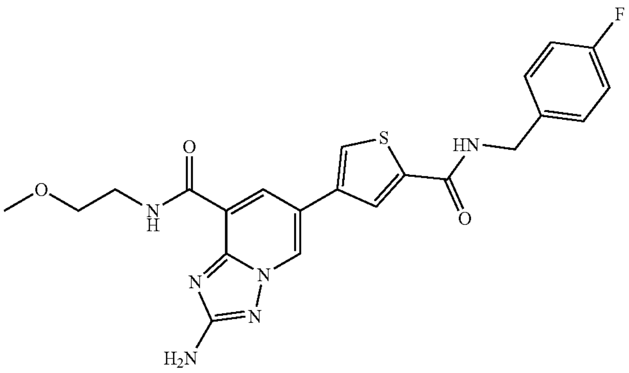 [SMILES: COCCNC(=O)c1cc(-c2csc(C(=O)NCc3ccc(F)cc3)c2)cn2nc(N)nc12] |

-continued
| Compound Number | Structure |
|---|---|
| 25 | 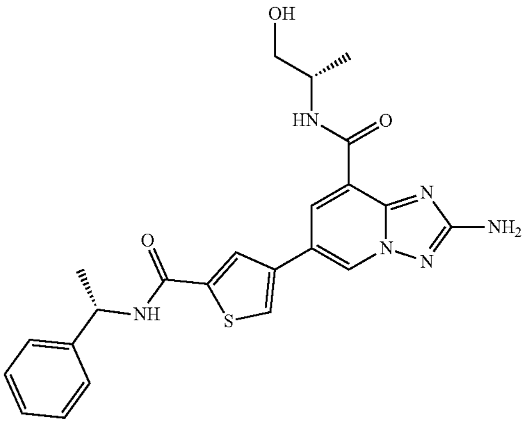 [SMILES: C[C@H](NC(=O)c1cc(-c2cc(C(=O)N[C@@H](C)CO)c3nc(N)nn3c2)cs1)c1ccccc1] |
| 26 | 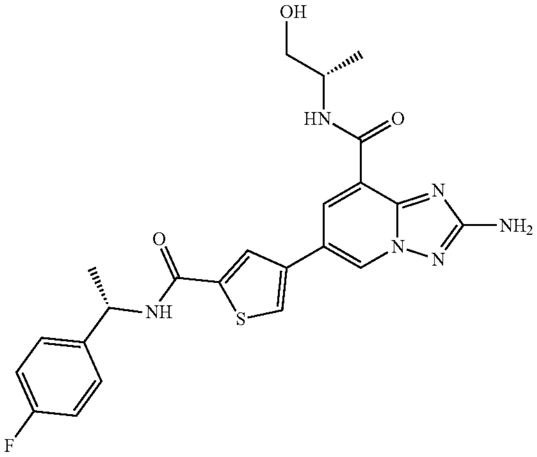 [SMILES: C[C@H](NC(=O)c1cc(-c2cc(C(=O)N[C@@H](C)CO)c3nc(N)nn3c2)cs1)c1ccc(F)cc1] |
| 27 | 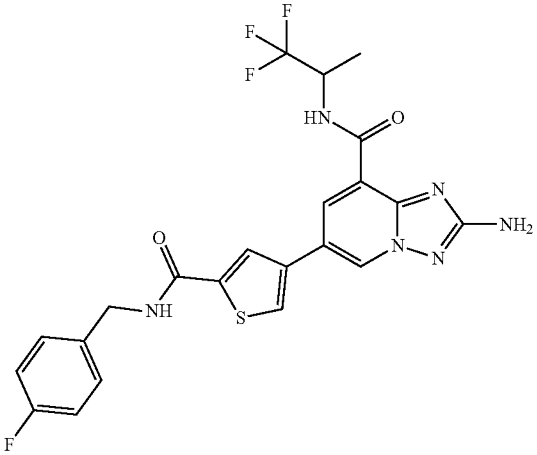 [SMILES: CC(NC(=O)c1cc(-c2csc(C(=O)NCc3ccc(F)cc3)c2)cn2nc(N)nc12)C(F)(F)F] |

-continued
| Compound Number | Structure |
|---|---|
| 28 | 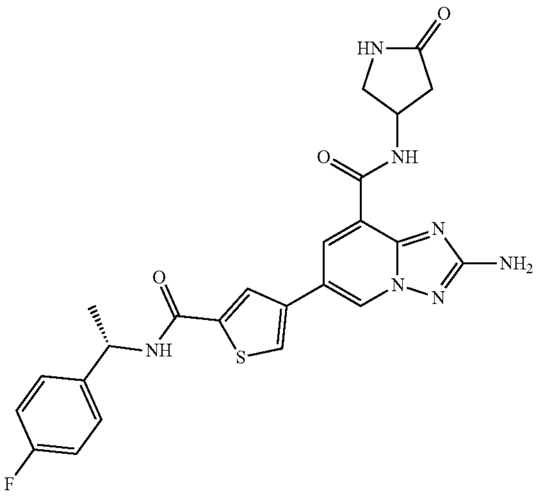 mixture of diastereomers |
| 29 | 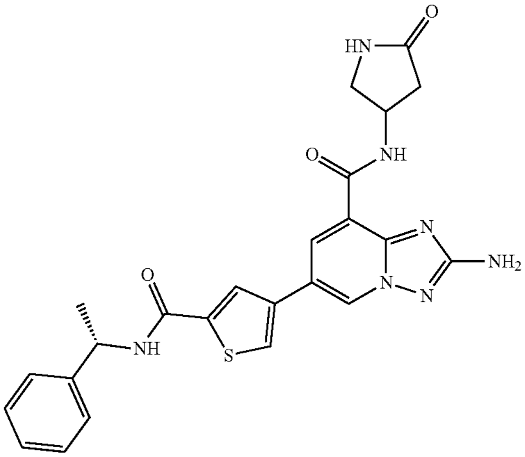 mixture of diastereomers |
| 30 | 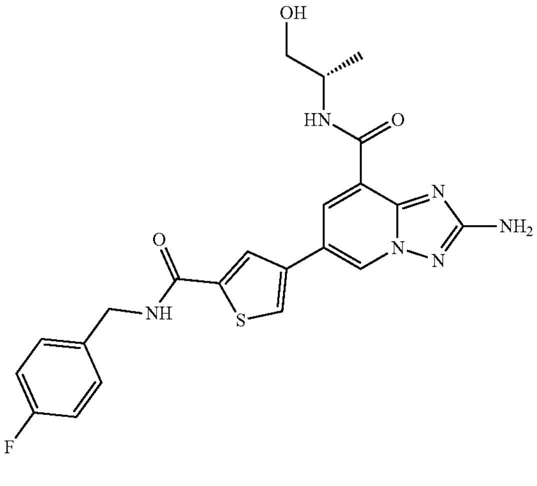 |

-continued
| Compound Number | Structure |
|---|---|
| 31 | 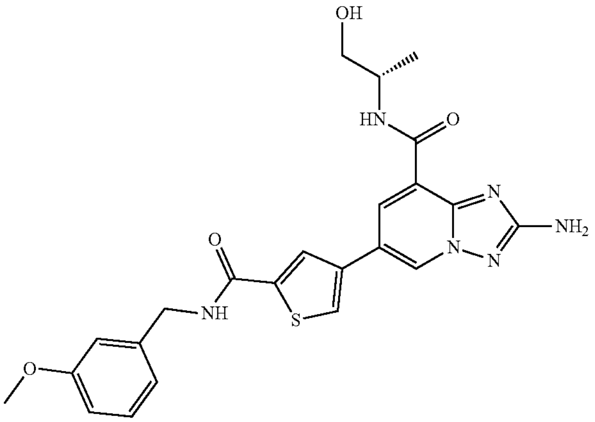 [SMILES: COc1cccc(CNC(=O)c2cc(-c3cc(C(=O)N[C@@H](C)CO)c4nc(N)nn4c3)cs2)c1] |
| 32 | 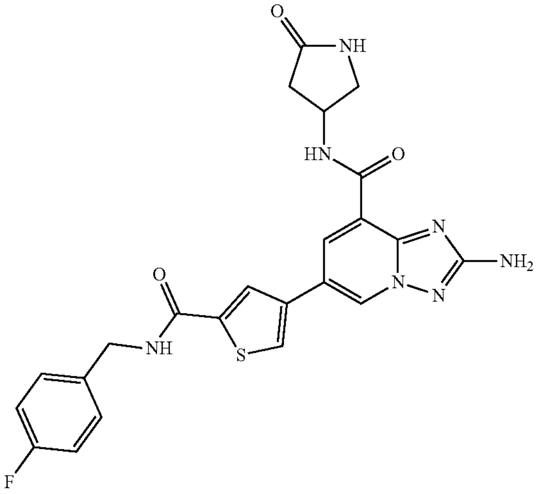 [SMILES: Nc1nc2c(C(=O)NC3CNC(=O)C3)cc(-c3csc(C(=O)NCc4ccc(F)cc4)c3)cn2n1] |
| 33 | 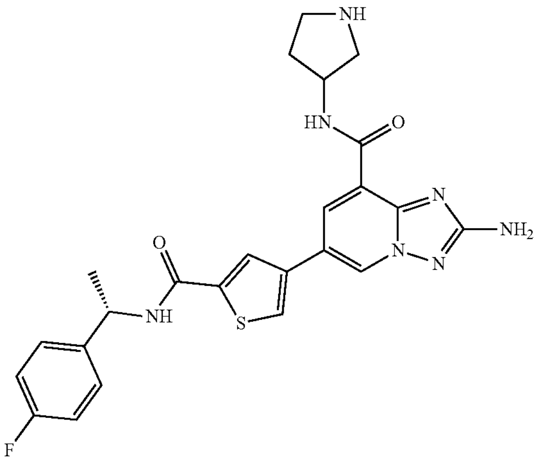<br>mixture of diastereomers |

-continued
| Compound Number | Structure |
|---|---|
| 34 | 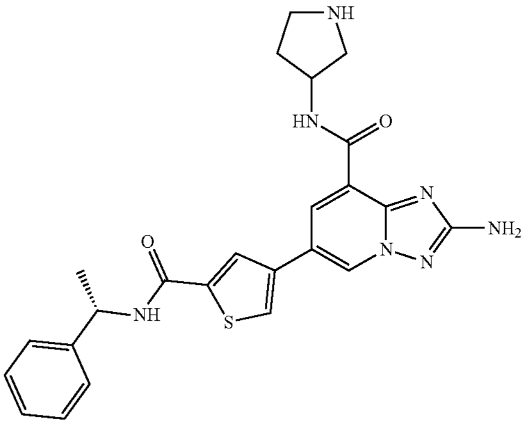 mixture of diastereomers |
| 35 | 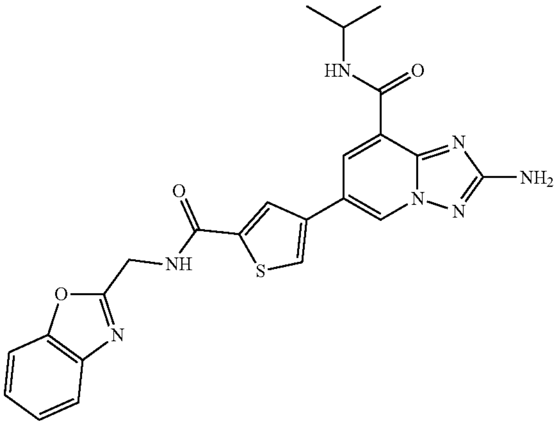 [SMILES: CC(C)NC(=O)c1cc(-c2csc(C(=O)NCc3nc4ccccc4o3)c2)cn2nc(N)nc12] |
| 36 | 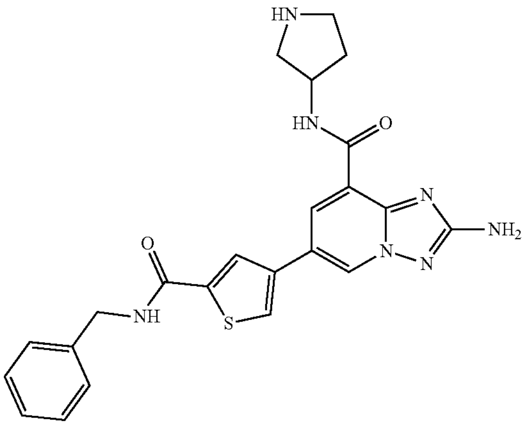 [SMILES: Nc1nc2c(C(=O)NC3CCNC3)cc(-c3csc(C(=O)NCc4ccccc4)c3)cn2n1] |

-continued
| Compound Number | Structure |
|---|---|
| 37 | 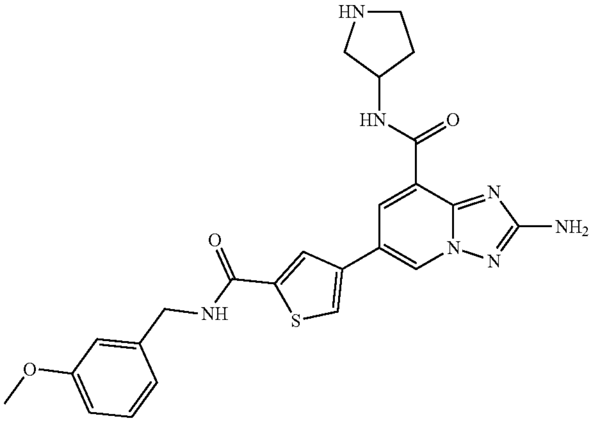 [SMILES: COc1cccc(CNC(=O)c2cc(-c3cc(C(=O)NC4CCNC4)c4nc(N)nn4c3)cs2)c1] |
| 38 | 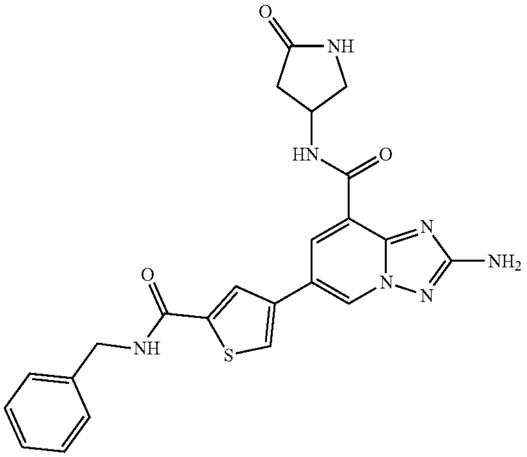 [SMILES: Nc1nc2c(C(=O)NC3CNC(=O)C3)cc(-c3csc(C(=O)NCc4ccccc4)c3)cn2n1] |
| 39 | 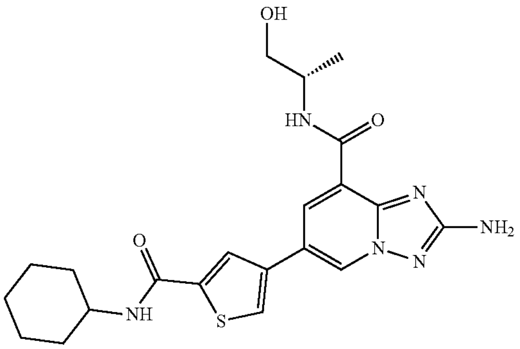 [SMILES: C[C@@H](CO)NC(=O)c1cc(-c2csc(C(=O)NC3CCCCC3)c2)cn2nc(N)nc12] |

-continued
| Compound Number | Structure |
|---|---|
| 40 | 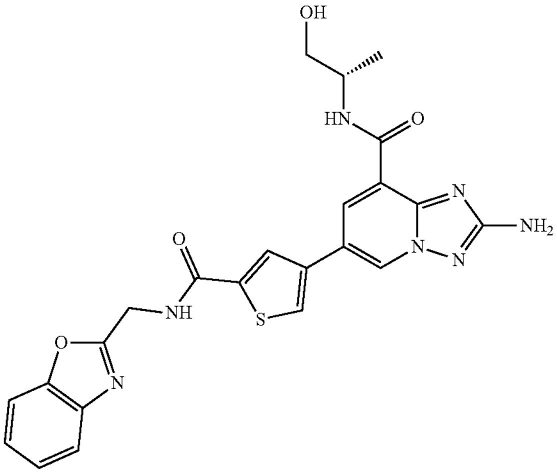 [SMILES: C[C@@H](CO)NC(=O)c1cc(-c2csc(C(=O)NCc3nc4ccccc4o3)c2)cn2nc(N)nc12] |
| 41 | 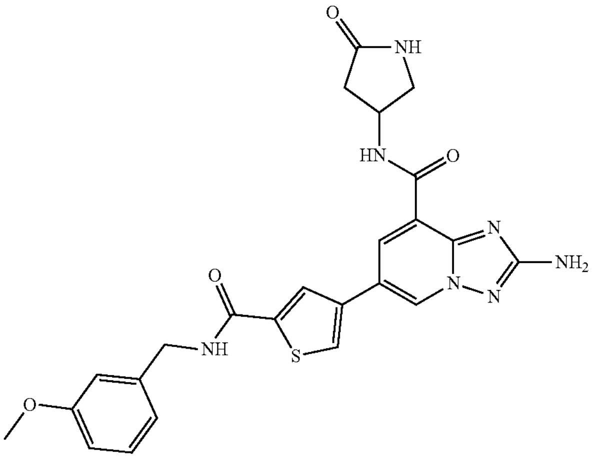 [SMILES: COc1cccc(CNC(=O)c2cc(-c3cc(C(=O)NC4CNC(=O)C4)c4nc(N)nn4c3)cs2)c1] |
| 42 | 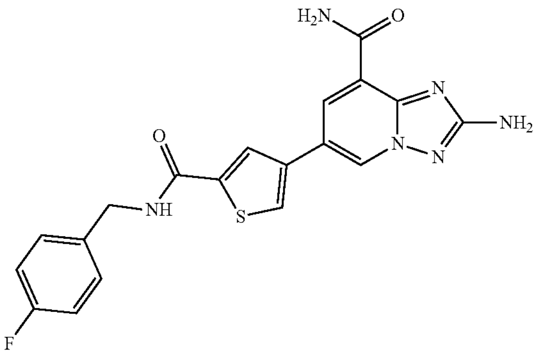 [SMILES: NC(=O)c1cc(-c2csc(C(=O)NCc3ccc(F)cc3)c2)cn2nc(N)nc12] |

-continued
| Compound Number | Structure |
|---|---|
| 43 | 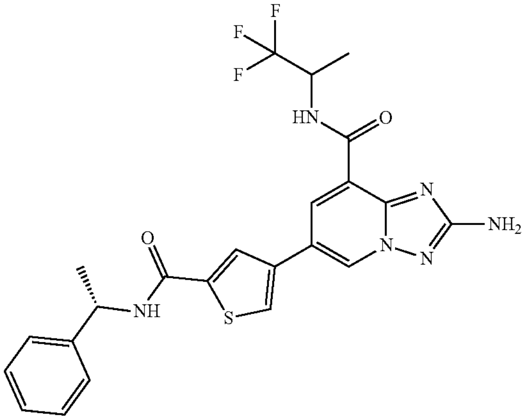 mixture of diastereomers |
| 44 | 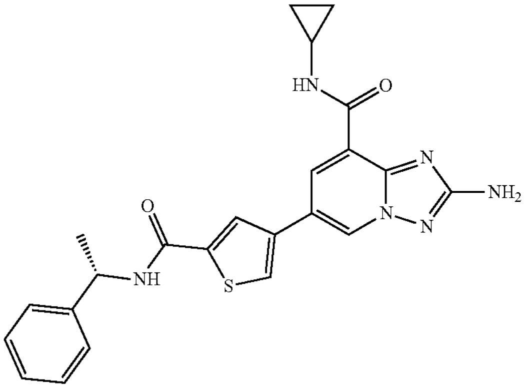 [SMILES: C[C@H](NC(=O)c1cc(-c2cc(C(=O)NC3CC3)c3nc(N)nn3c2)cs1)c1ccccc1] |
| 45 | 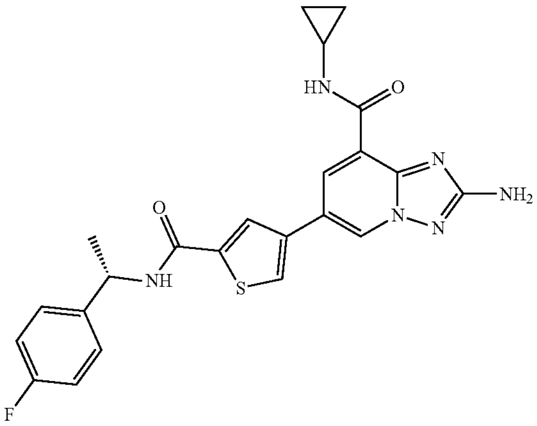 [SMILES: C[C@H](NC(=O)c1cc(-c2cc(C(=O)NC3CC3)c3nc(N)nn3c2)cs1)c1ccc(F)cc1] |

-continued
| Compound Number | Structure |
|---|---|
| 46 | 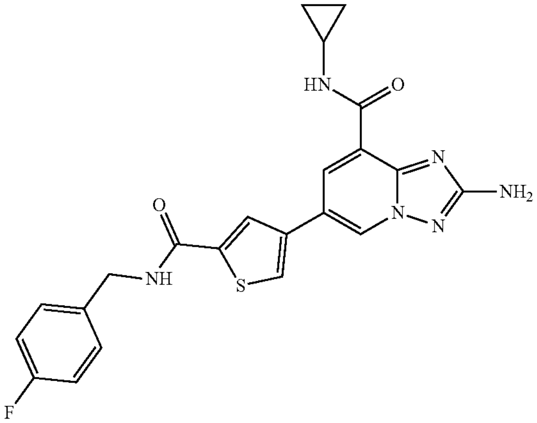 [SMILES: Nc1nc2c(C(=O)NC3CC3)cc(-c3csc(C(=O)NCc4ccc(F)cc4)c3)cn2n1] |
| 47 | 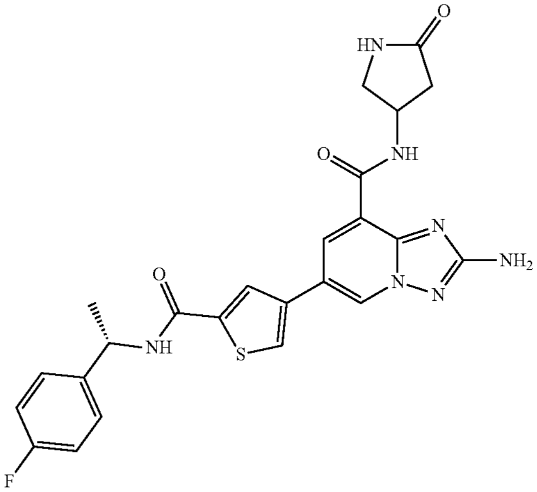 stereoisomer 1 |
| 48 | 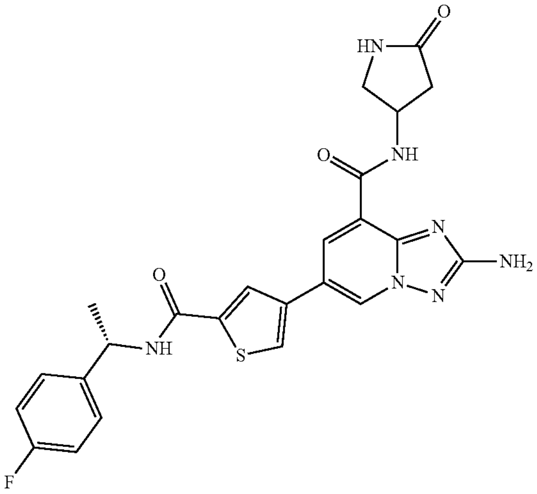 stereoisomer 2 |

-continued
| Compound Number | Structure |
| --- | --- |
| 49 | 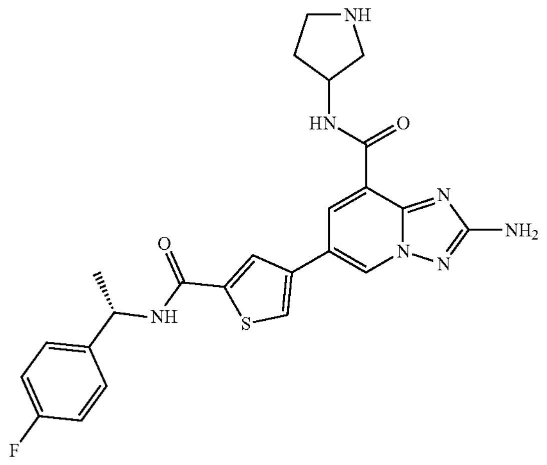 stereoisomer 1 |
| 50 | 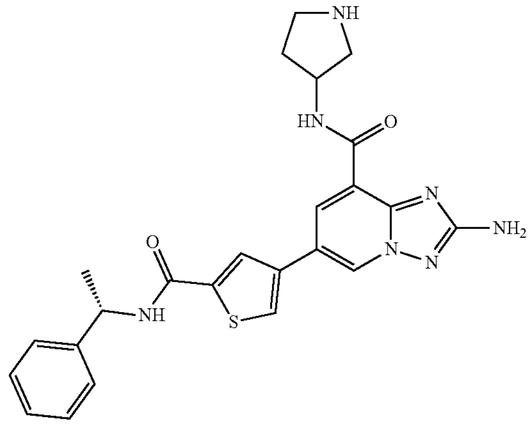 stereoisomer 1 |
| 51 | 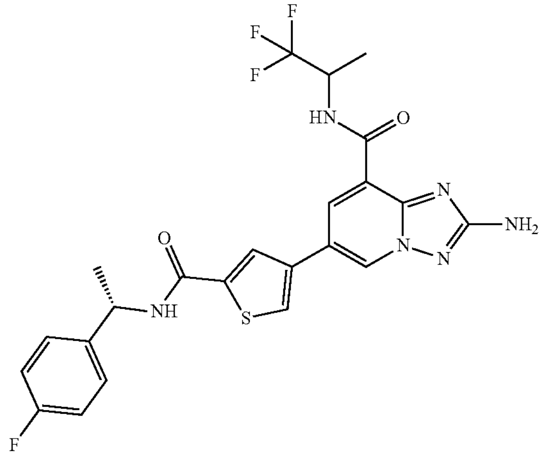 mixture of diastereomers |

-continued
| Compound Number | Structure |
|---|---|
| 52 | 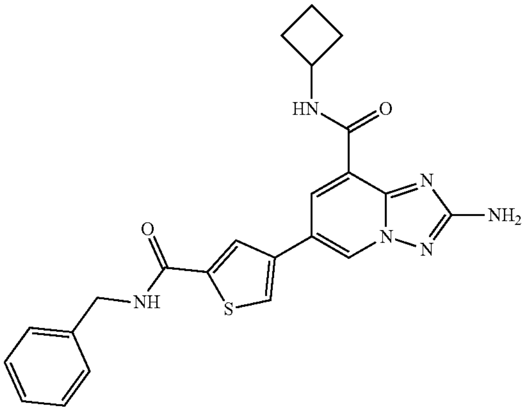 [SMILES: Nc1nc2c(C(=O)NC3CCC3)cc(-c3csc(C(=O)NCc4ccccc4)c3)cn2n1] |
| 53 | 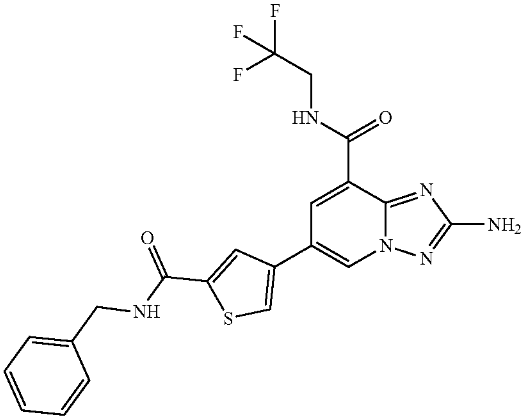 [SMILES: Nc1nc2c(C(=O)NCC(F)(F)F)cc(-c3csc(C(=O)NCc4ccccc4)c3)cn2n1] |
| 54 | 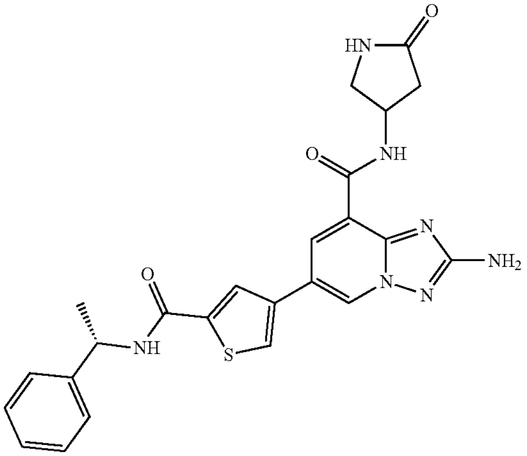 stereoisomer 1 |

-continued
| Compound Number | Structure |
| --- | --- |
| 55 | 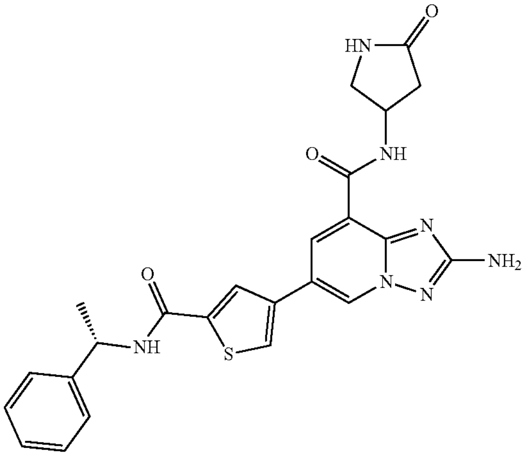 stereoisomer 2 |
| 56 | 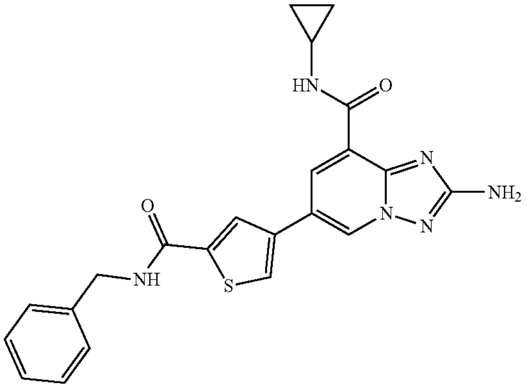 [SMILES: Nc1nc2c(C(=O)NC3CC3)cc(-c3csc(C(=O)NCc4ccccc4)c3)cn2n1] |
| 57 | 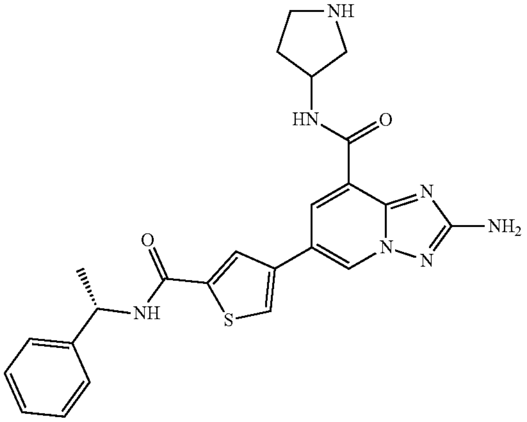 stereoisomer 2 |

-continued
| Compound Number | Structure |
|---|---|
| 58 | 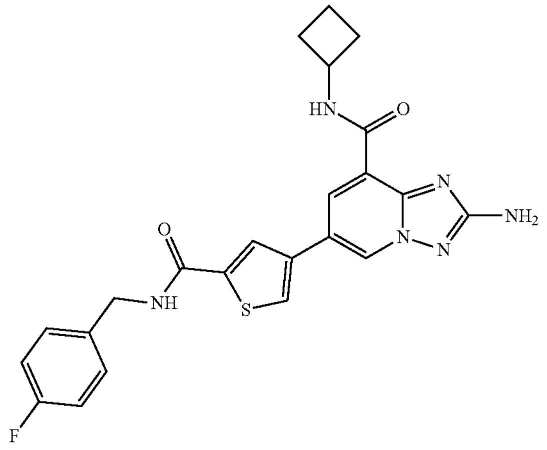 |
| 59 | 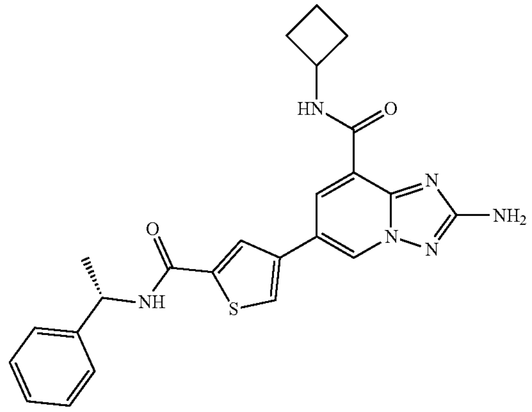 [SMILES: C[C@H](NC(=O)c1cc(-c2cc(C(=O)NC3CCC3)c3nc(N)nn3c2)cs1)c1ccccc1] |
| 60 | 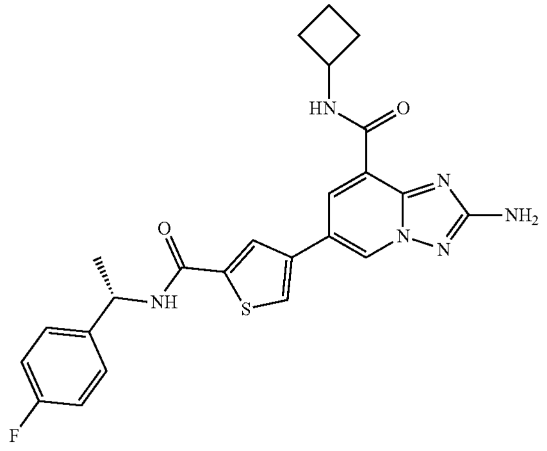 [SMILES: C[C@H](NC(=O)c1cc(-c2cc(C(=O)NC3CCC3)c3nc(N)nn3c2)cs1)c1ccc(F)cc1] |

-continued
| Compound Number | Structure |
|---|---|
| 61 | 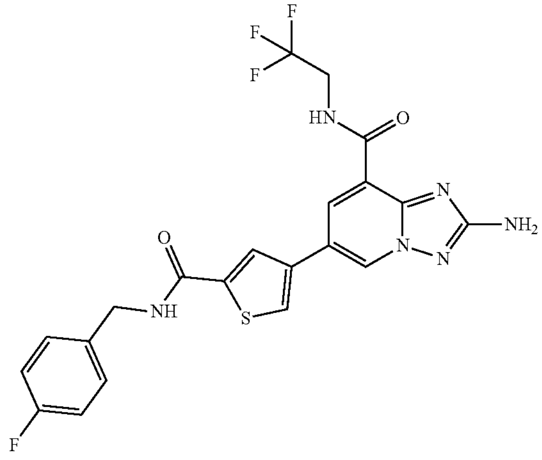 [SMILES: Nc1nc2c(C(=O)NCC(F)(F)F)cc(-c3csc(C(=O)NCc4ccc(F)cc4)c3)cn2n1] |
| 62 | 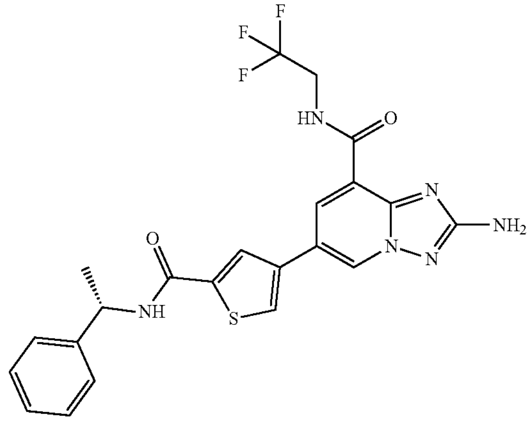 [SMILES: C[C@H](NC(=O)c1cc(-c2cc(C(=O)NCC(F)(F)F)c3nc(N)nn3c2)cs1)c1ccccc1] |
| 63 | 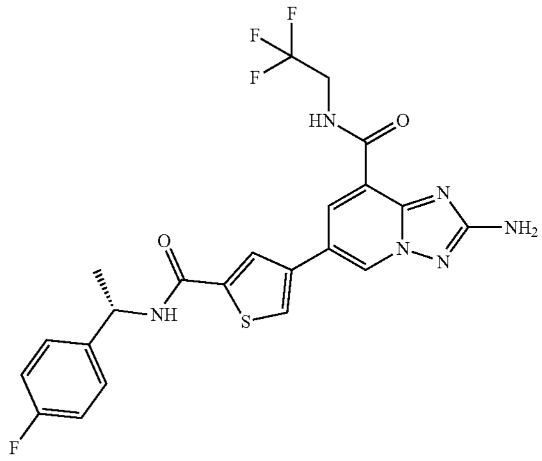 [SMILES: C[C@H](NC(=O)c1cc(-c2cc(C(=O)NCC(F)(F)F)c3nc(N)nn3c2)cs1)c1ccc(F)cc1] |

-continued
| Compound Number | Structure |
| --- | --- |
| 64 | 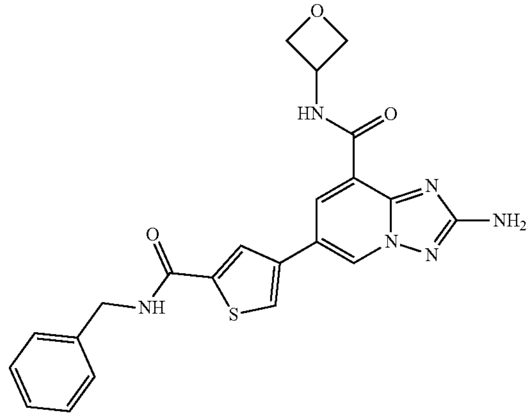 [SMILES: Nc1nc2c(C(=O)NC3COC3)cc(-c3csc(C(=O)NCc4ccccc4)c3)cn2n1] |
| 65 | 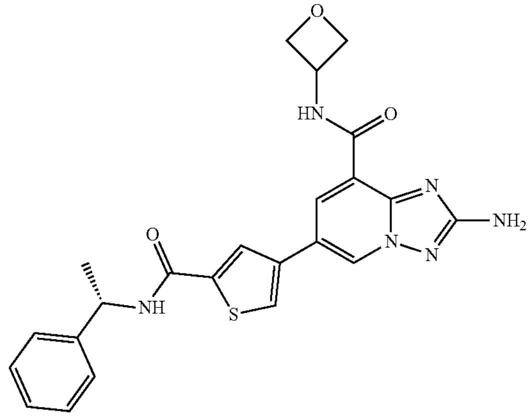 [SMILES: C[C@H](NC(=O)c1cc(-c2cc(C(=O)NC3COC3)c3nc(N)nn3c2)cs1)c1ccccc1] |
| 66 | 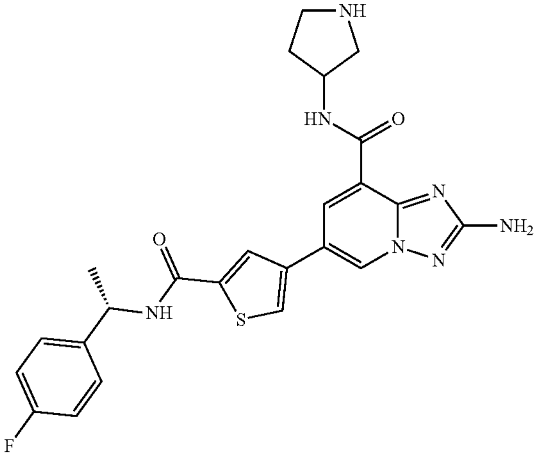 stereoisomer 2 |

-continued
| Compound Number | Structure |
|---|---|
| 67 | 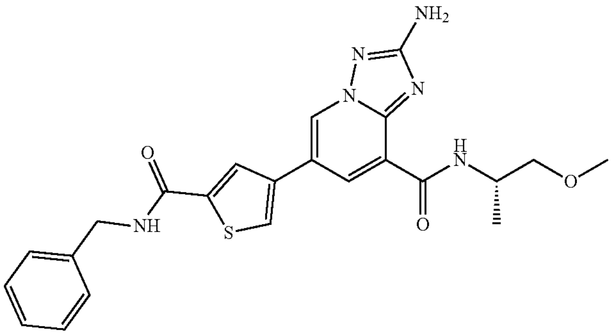 [SMILES: COC[C@H](C)NC(=O)c1cc(-c2csc(C(=O)NCc3ccccc3)c2)cn2nc(N)nc12] |
| 68 | 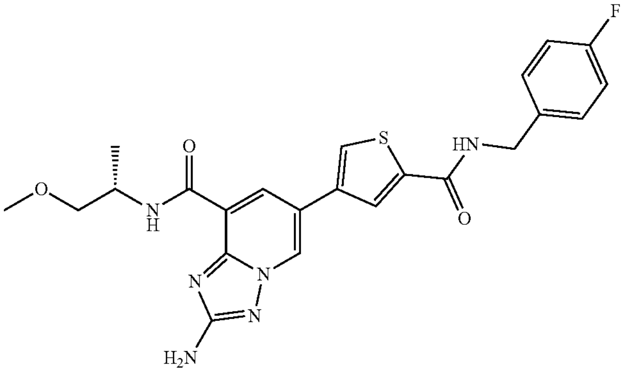 [SMILES: COC[C@H](C)NC(=O)c1cc(-c2csc(C(=O)NCc3ccc(F)cc3)c2)cn2nc(N)nc12] |
| 69 | 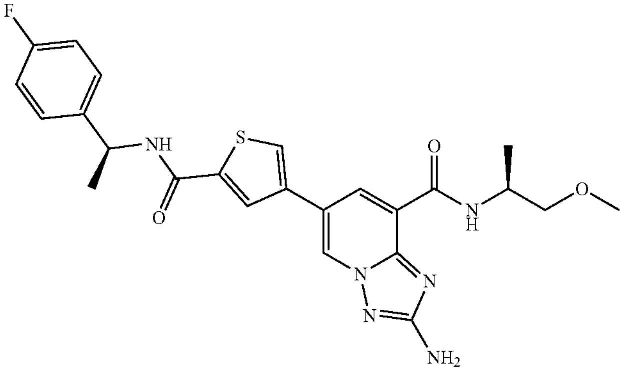 [SMILES: COC[C@H](C)NC(=O)c1cc(-c2csc(C(=O)N[C@@H](C)c3ccc(F)cc3)c2)cn2nc(N)nc12] |
| 70 | 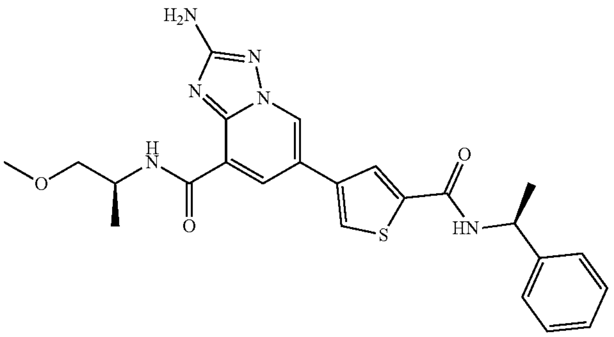 [SMILES: COC[C@H](C)NC(=O)c1cc(-c2csc(C(=O)N[C@@H](C)c3ccccc3)c2)cn2nc(N)nc12] |

-continued
| Compound Number | Structure |
|---|---|
| 71 | 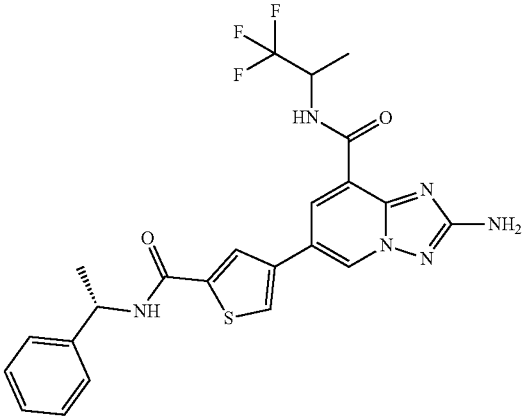<br>stereoisomer 1 |
| 72 | 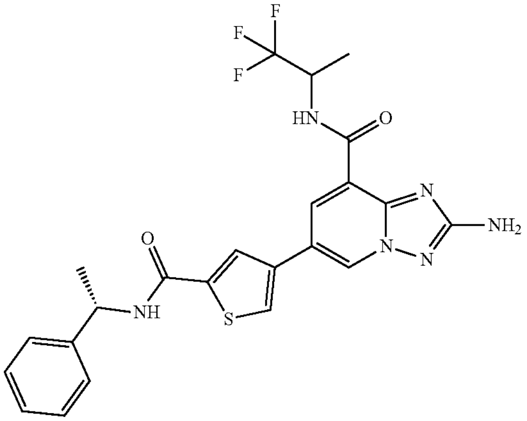<br>stereoisomer 2 |
| 73 | 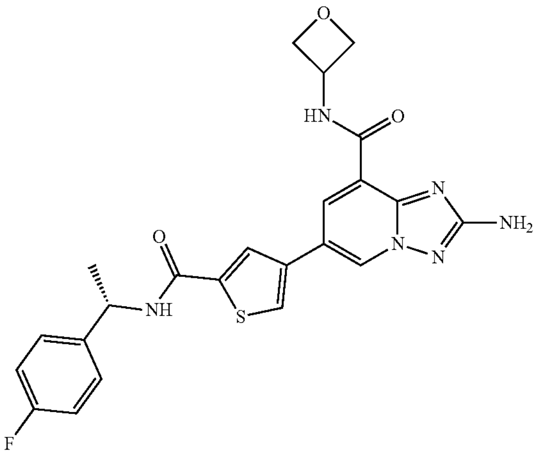 [SMILES: C[C@H](NC(=O)c1cc(-c2cc(C(=O)NC3COC3)c3nc(N)nn3c2)cs1)c1ccc(F)cc1] |

-continued
| Compound Number | Structure |
|---|---|
| 74 | 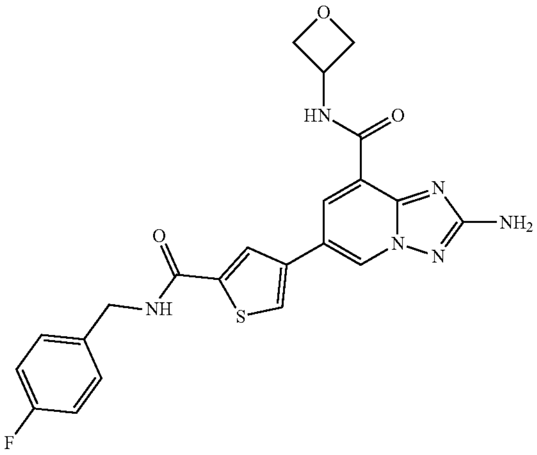 [SMILES: Nc1nc2c(C(=O)NC3COC3)cc(-c3csc(C(=O)NCc4ccc(F)cc4)c3)cn2n1] |
| 75 | 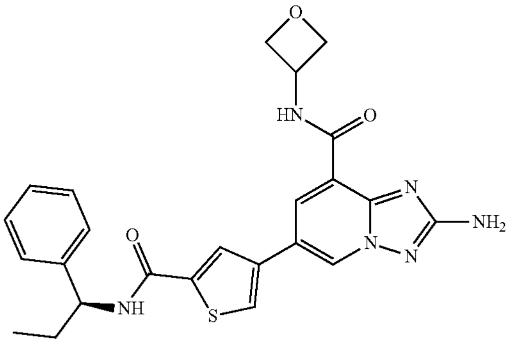 [SMILES: CC[C@H](NC(=O)c1cc(-c2cc(C(=O)NC3COC3)c3nc(N)nn3c2)cs1)c1ccccc1] |
| 76 | 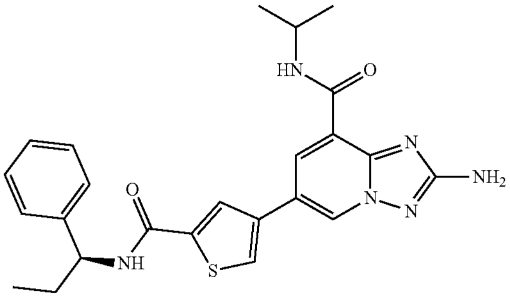 [SMILES: CC[C@H](NC(=O)c1cc(-c2cc(C(=O)NC(C)C)c3nc(N)nn3c2)cs1)c1ccccc1] |
| 77 | 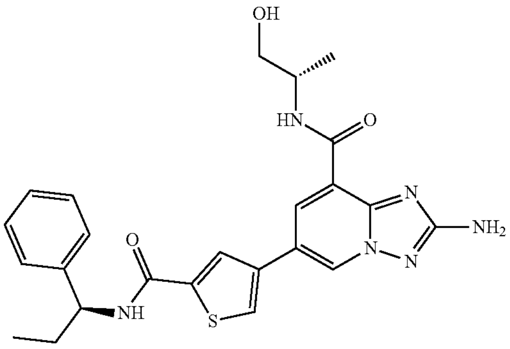 [SMILES: CC[C@H](NC(=O)c1cc(-c2cc(C(=O)N[C@@H](C)CO)c3nc(N)nn3c2)cs1)c1ccccc1] |

-continued
| Compound Number | Structure |
|---|---|
| 78 | 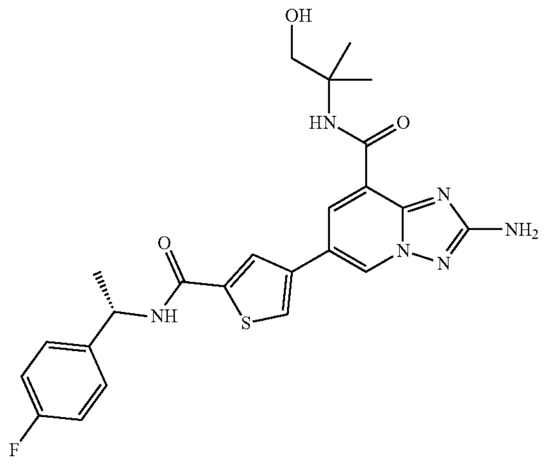 [SMILES: C[C@H](NC(=O)c1cc(-c2cc(C(=O)NC(C)(C)CO)c3nc(N)nn3c2)cs1)c1ccc(F)cc1] |
| 79 | 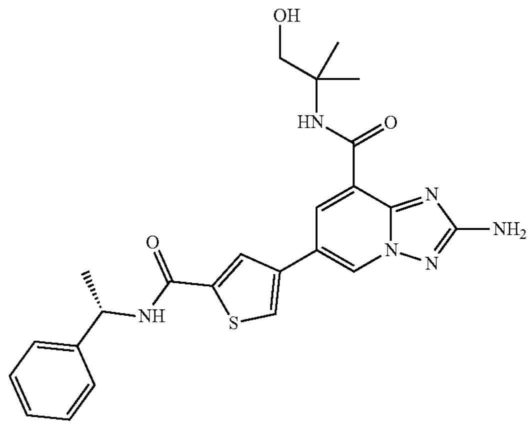 [SMILES: C[C@H](NC(=O)c1cc(-c2cc(C(=O)NC(C)(C)CO)c3nc(N)nn3c2)cs1)c1ccccc1] |
| 80 | 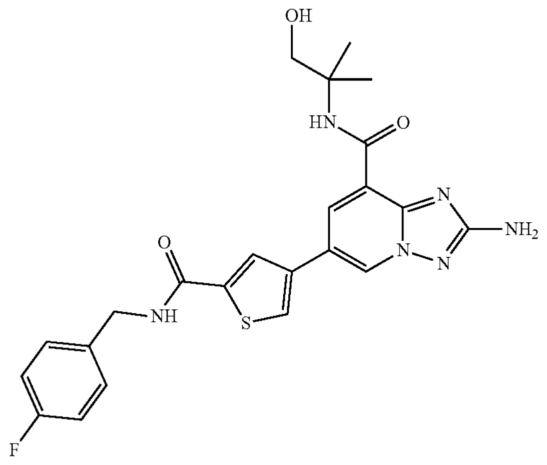 [SMILES: CC(C)(CO)NC(=O)c1cc(-c2csc(C(=O)NCc3ccc(F)cc3)c2)cn2nc(N)nc12] |

-continued
| Compound Number | Structure |
|---|---|
| 81 | 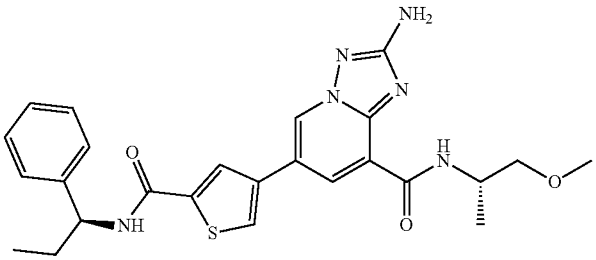 [SMILES: CC[C@H](NC(=O)c1cc(-c2cc(C(=O)N[C@@H](C)COC)c3nc(N)nn3c2)cs1)c1ccccc1] |
| 82 | 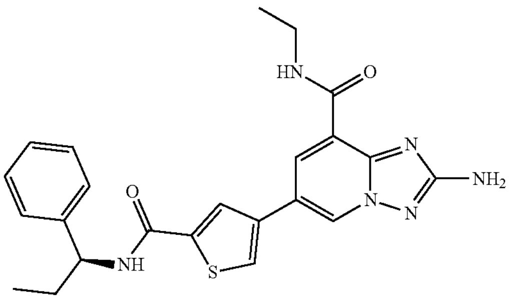 [SMILES: CCNC(=O)c1cc(-c2csc(C(=O)N[C@@H](CC)c3ccccc3)c2)cn2nc(N)nc12] |
| 83 | 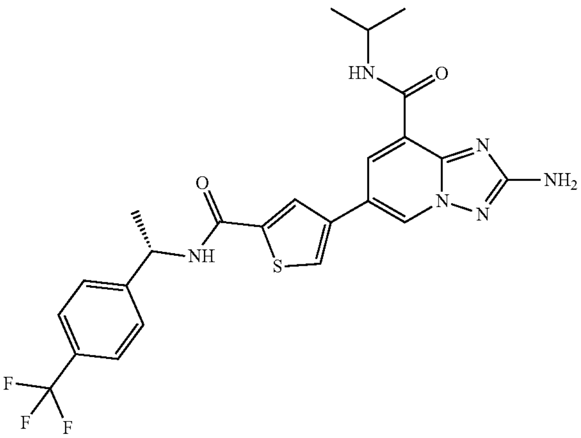 [SMILES: CC(C)NC(=O)c1cc(-c2csc(C(=O)N[C@@H](C)c3ccc(C(F)(F)F)cc3)c2)cn2nc(N)nc12] |
| 84 | 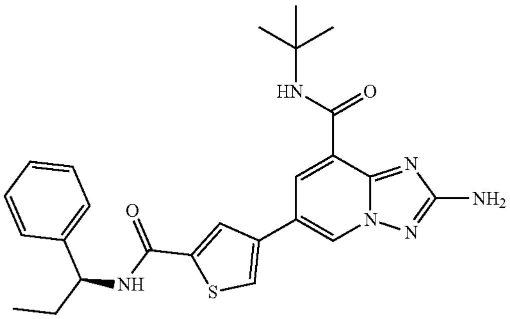 [SMILES: CC[C@H](NC(=O)c1cc(-c2cc(C(=O)NC(C)(C)C)c3nc(N)nn3c2)cs1)c1ccccc1] |

-continued
| Compound Number | Structure |
|---|---|
| 85 | 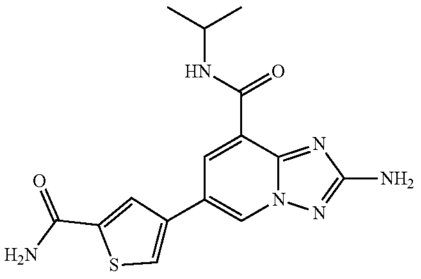 [SMILES: CC(C)NC(=O)c1cc(-c2csc(C(N)=O)c2)cn2nc(N)nc12] |
| 86 | 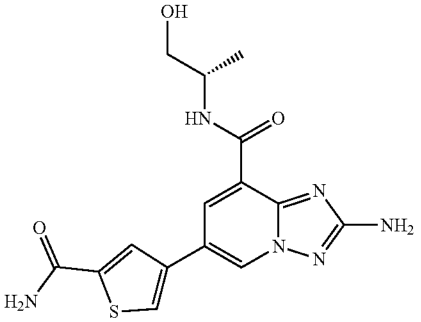 [SMILES: C[C@@H](CO)NC(=O)c1cc(-c2csc(C(N)=O)c2)cn2nc(N)nc12] |
| 87 | 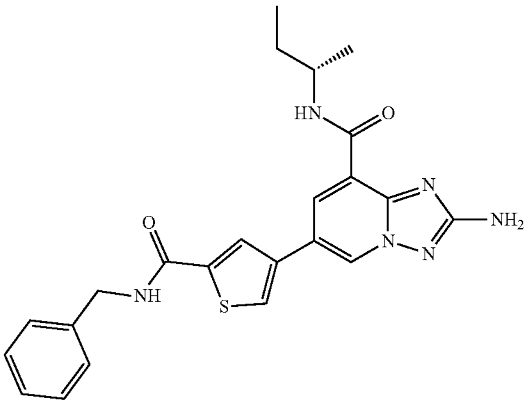 [SMILES: CC[C@H](C)NC(=O)c1cc(-c2csc(C(=O)NCc3ccccc3)c2)cn2nc(N)nc12] |
| 88 | 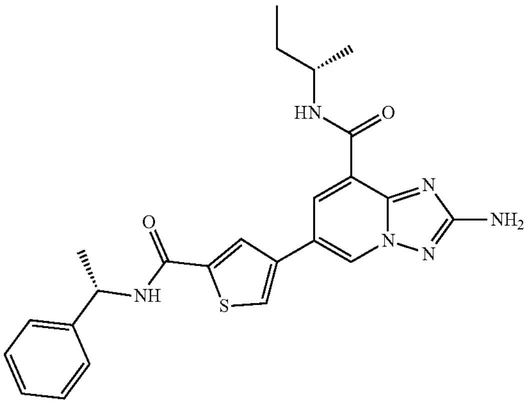 [SMILES: CC[C@H](C)NC(=O)c1cc(-c2csc(C(=O)N[C@@H](C)c3ccccc3)c2)cn2nc(N)nc12] |

-continued
| Compound Number | Structure |
|---|---|
| 89 | 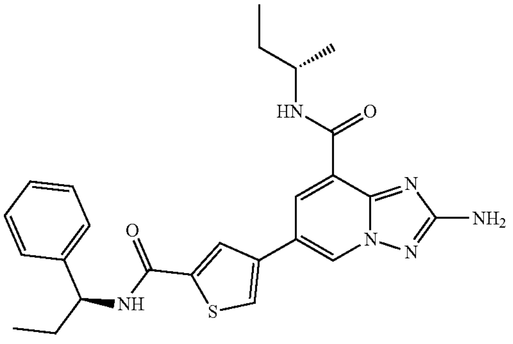 [SMILES: CC[C@H](NC(=O)c1cc(-c2cc(C(=O)N[C@@H](C)CC)c3nc(N)nn3c2)cs1)c1ccccc1] |
| 90 | 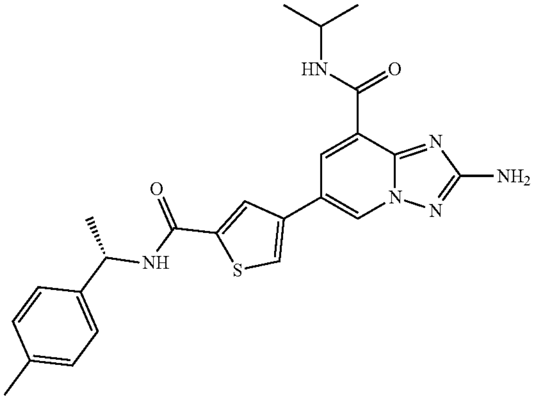 [SMILES: Cc1ccc([C@H](C)NC(=O)c2cc(-c3cc(C(=O)NC(C)C)c4nc(N)nn4c3)cs2)cc1] |
| 91 | 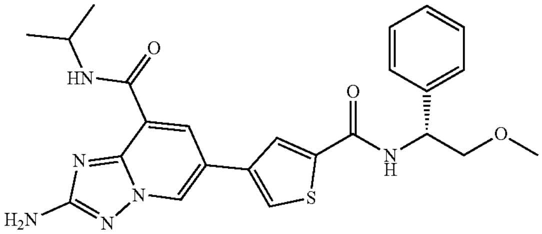 |
| 92 | 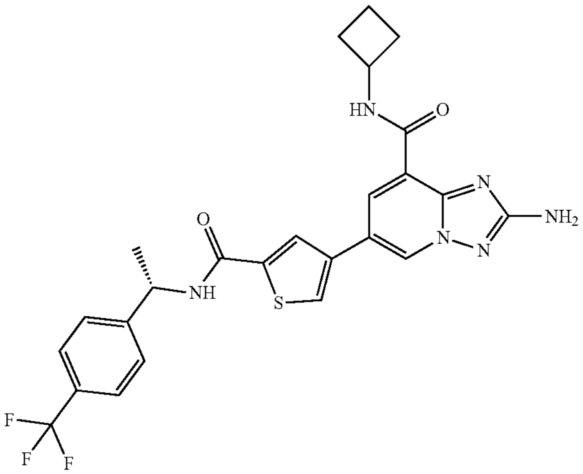 [SMILES: C[C@H](NC(=O)c1cc(-c2cc(C(=O)NC3CCC3)c3nc(N)nn3c2)cs1)c1ccc(C(F)(F)F)cc1] |

-continued
| Compound Number | Structure |
|---|---|
| 93 | 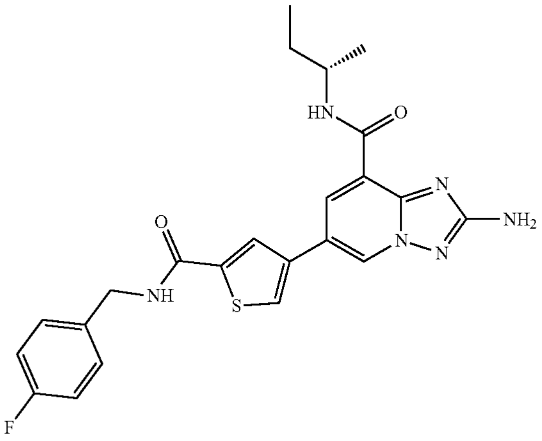 [SMILES: CC[C@H](C)NC(=O)c1cc(-c2csc(C(=O)NCc3ccc(F)cc3)c2)cn2nc(N)nc12] |
| 94 | 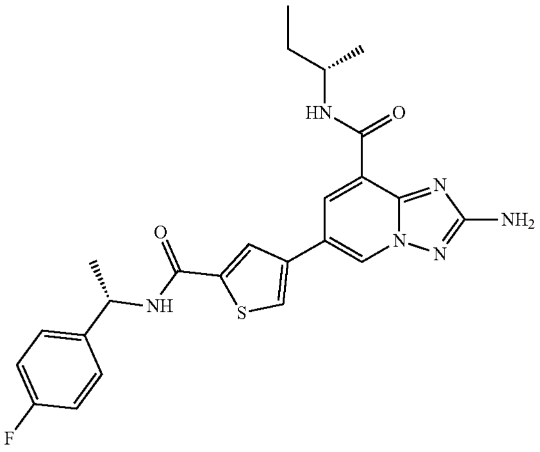 [SMILES: CC[C@H](C)NC(=O)c1cc(-c2csc(C(=O)N[C@@H](C)c3ccc(F)cc3)c2)cn2nc(N)nc12] |
| 95 | 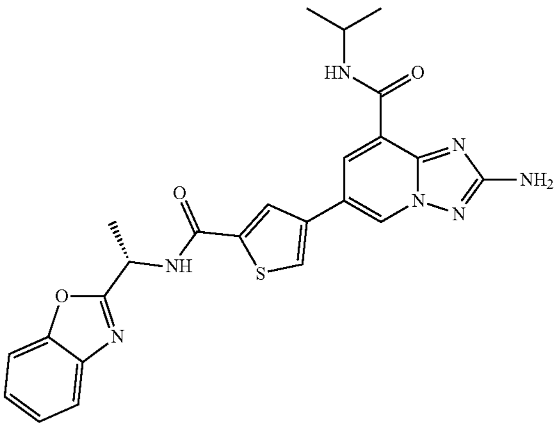 [SMILES: CC(C)NC(=O)c1cc(-c2csc(C(=O)N[C@@H](C)c3nc4ccccc4o3)c2)cn2nc(N)nc12] |

-continued
| Compound Number | Structure |
|---|---|
| 96 | 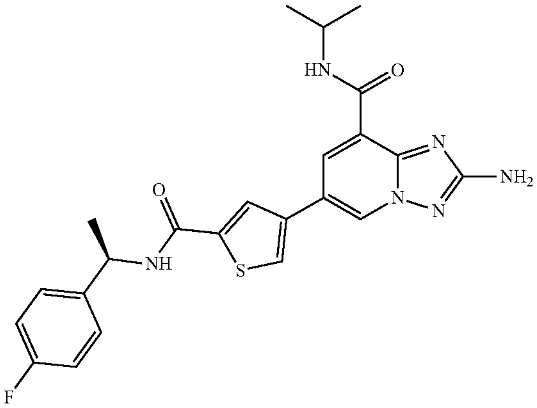 [SMILES: CC(C)NC(=O)c1cc(-c2csc(C(=O)N[C@H](C)c3ccc(F)cc3)c2)cn2nc(N)nc12] |
| 97 | 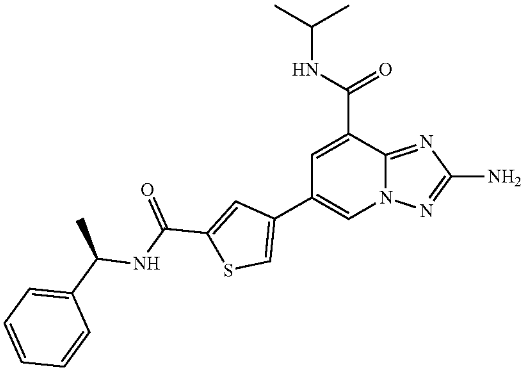 [SMILES: CC(C)NC(=O)c1cc(-c2csc(C(=O)N[C@H](C)c3ccccc3)c2)cn2nc(N)nc12] |
| 98 | 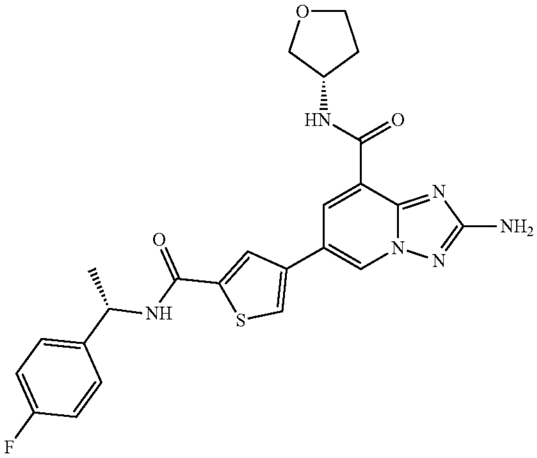 [SMILES: C[C@H](NC(=O)c1cc(-c2cc(C(=O)N[C@H]3CCOC3)c3nc(N)nn3c2)cs1)c1ccc(F)cc1] |

-continued
| Compound Number | Structure |
|---|---|
| 99 | 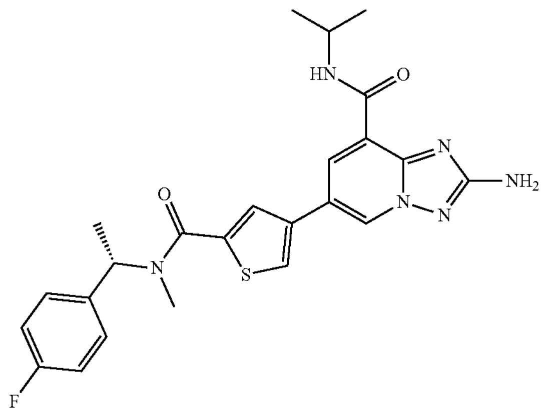 [SMILES: CC(C)NC(=O)c1cc(-c2csc(C(=O)N(C)[C@@H](C)c3ccc(F)cc3)c2)cn2nc(N)nc12] |
| 100 | 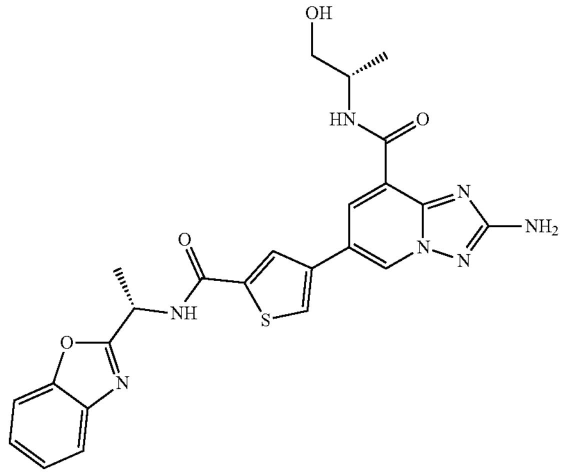 [SMILES: C[C@H](NC(=O)c1cc(-c2cc(C(=O)N[C@@H](C)CO)c3nc(N)nn3c2)cs1)c1nc2ccccc2o1] |
| 101 | 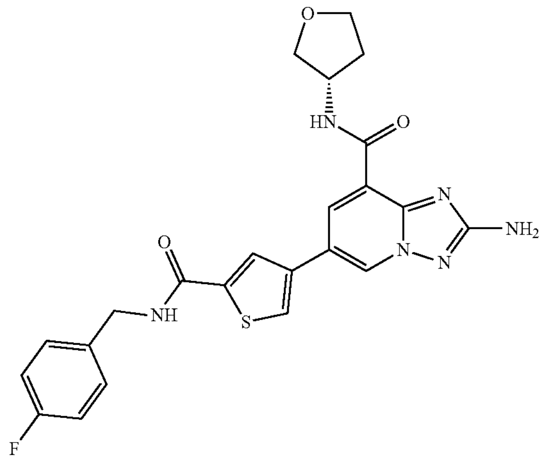 [SMILES: Nc1nc2c(C(=O)N[C@H]3CCOC3)cc(-c3csc(C(=O)NCc4ccc(F)cc4)c3)cn2n1] |

-continued
| Compound Number | Structure |
|---|---|
| 102 | 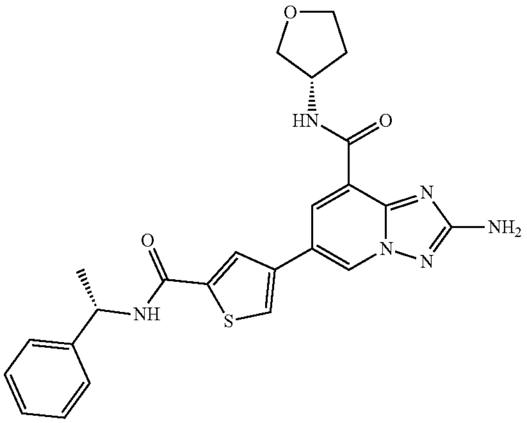 [SMILES: C[C@H](NC(=O)c1cc(-c2cc(C(=O)N[C@H]3CCOC3)c3nc(N)nn3c2)cs1)c1ccccc1] |
| 103 | 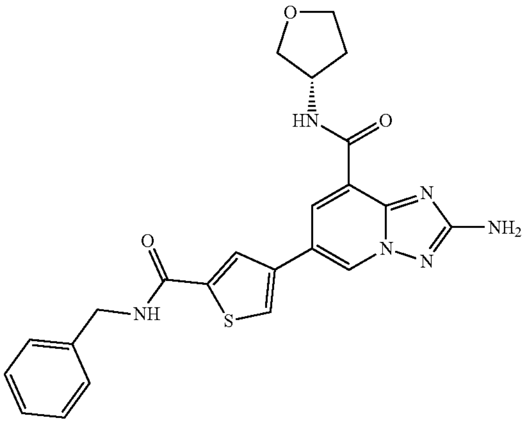 [SMILES: Nc1nc2c(C(=O)N[C@H]3CCOC3)cc(-c3csc(C(=O)NCc4ccccc4)c3)cn2n1] |
| 104 | 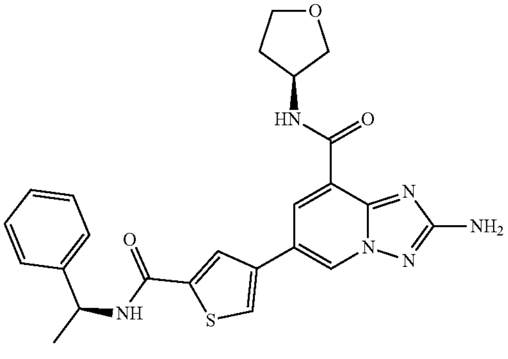 [SMILES: C[C@H](NC(=O)c1cc(-c2cc(C(=O)N[C@H]3CCOC3)c3nc(N)nn3c2)cs1)c1ccccc1] |

-continued
| Compound Number | Structure |
| --- | --- |
| 105 | 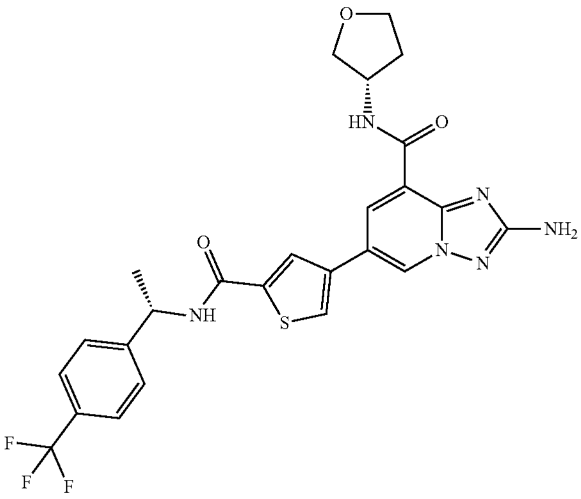 [SMILES: C[C@H](NC(=O)c1cc(-c2cc(C(=O)N[C@H]3CCOC3)c3nc(N)nn3c2)cs1)c1ccc(C(F)(F)F)cc1] |
| 106 | 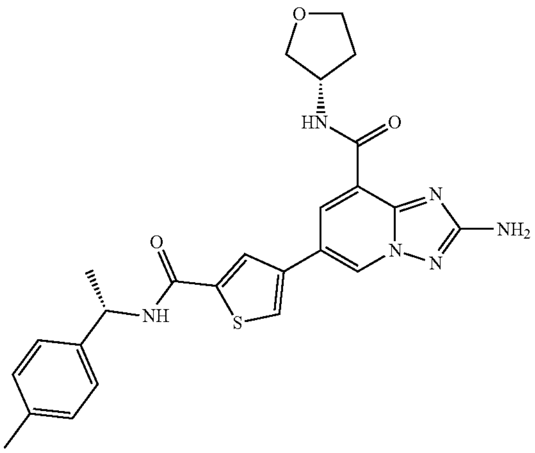 [SMILES: Cc1ccc([C@H](C)NC(=O)c2cc(-c3cc(C(=O)N[C@H]4CCOC4)c4nc(N)nn4c3)cs2)cc1] |
| 107 | 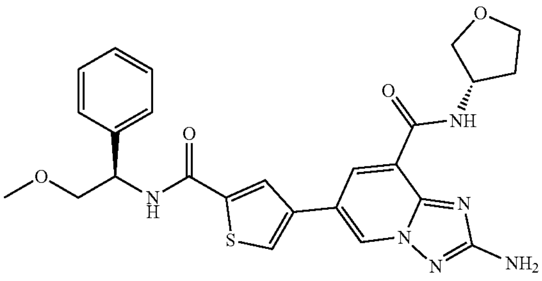 [SMILES: COC[C@H](NC(=O)c1cc(-c2cc(C(=O)N[C@H]3CCOC3)c3nc(N)nn3c2)cs1)c1ccccc1] |
| 108 | 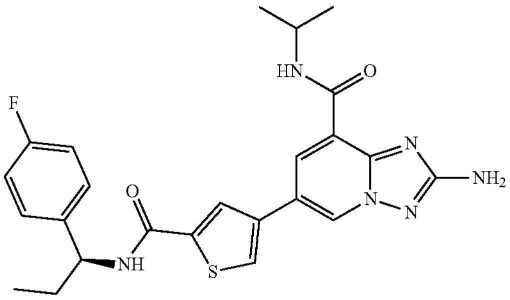 [SMILES: CC[C@H](NC(=O)c1cc(-c2cc(C(=O)NC(C)C)c3nc(N)nn3c2)cs1)c1ccc(F)cc1] |

-continued
| Compound Number | Structure |
|---|---|
| 109 | 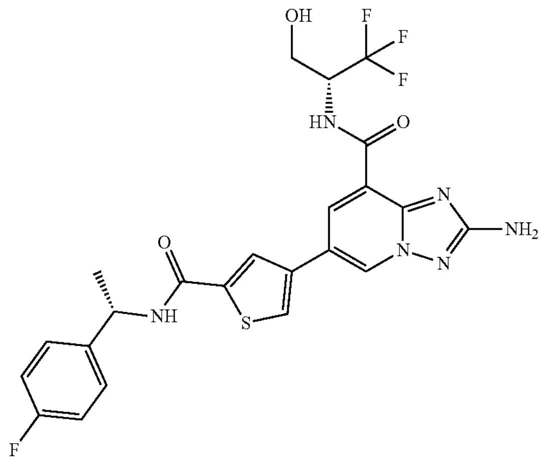 [SMILES: C[C@H](NC(=O)c1cc(-c2cc(C(=O)N[C@H](CO)C(F)(F)F)c3nc(N)nn3c2)cs1)c1ccc(F)cc1] |
| 110 | 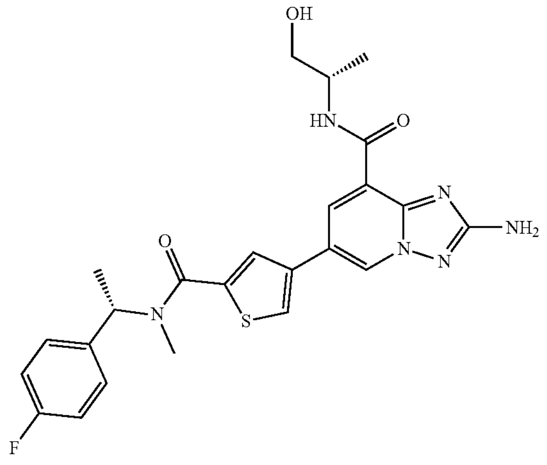 [SMILES: C[C@@H](CO)NC(=O)c1cc(-c2csc(C(=O)N(C)[C@@H](C)c3ccc(F)cc3)c2)cn2nc(N)nc12] |
| 111 | 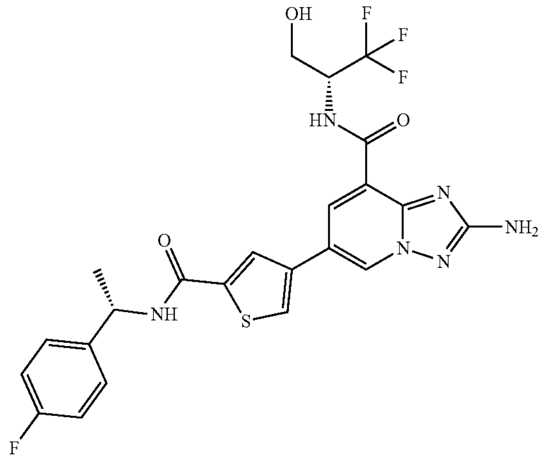 [SMILES: C[C@H](NC(=O)c1cc(-c2cc(C(=O)N[C@H](CO)C(F)(F)F)c3nc(N)nn3c2)cs1)c1ccc(F)cc1] |

-continued
| Compound Number | Structure |
|---|---|
| 112 | 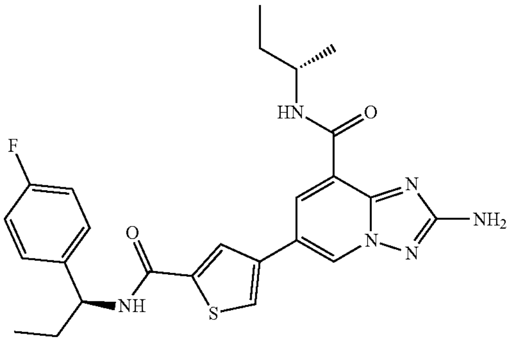 [SMILES: CC[C@H](NC(=O)c1cc(-c2cc(C(=O)N[C@@H](C)CC)c3nc(N)nn3c2)cs1)c1ccc(F)cc1] |
| 113 | 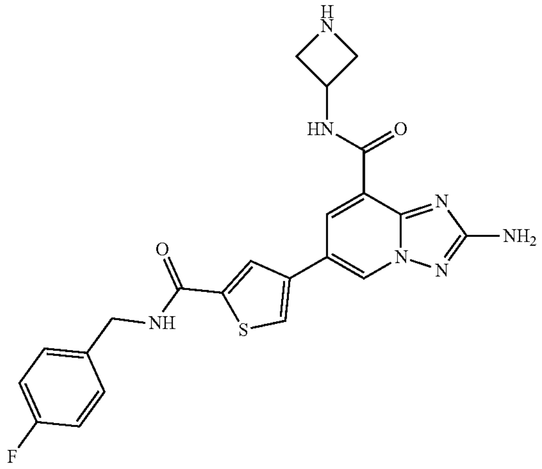 [SMILES: Nc1nc2c(C(=O)NC3CNC3)cc(-c3csc(C(=O)NCc4ccc(F)cc4)c3)cn2n1] |
| 114 | 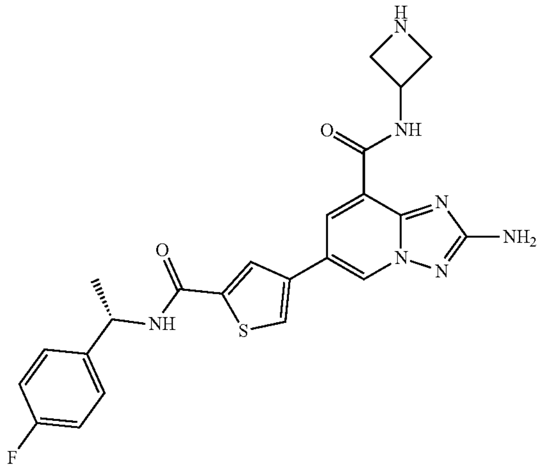 [SMILES: C[C@H](NC(=O)c1cc(-c2cc(C(=O)NC3CNC3)c3nc(N)nn3c2)cs1)c1ccc(F)cc1] |

-continued
| Compound Number | Structure |
|---|---|
| 115 | 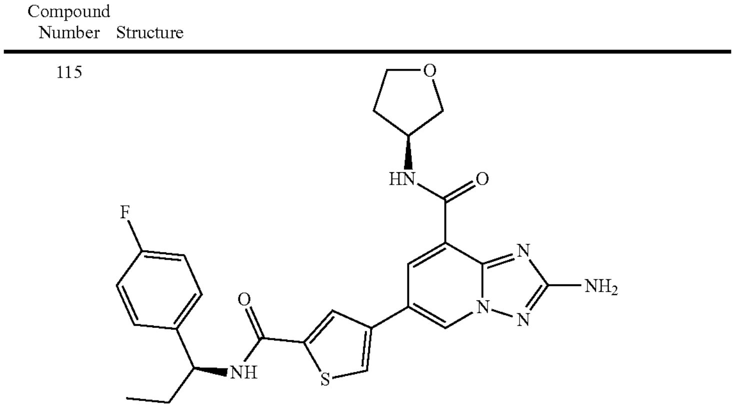 |
| 116 | 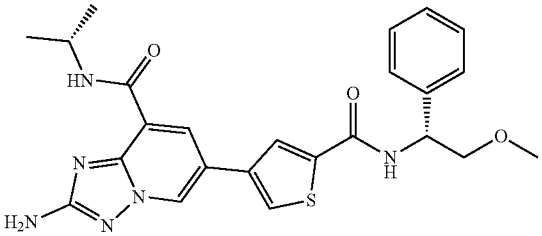 |
| 117 | 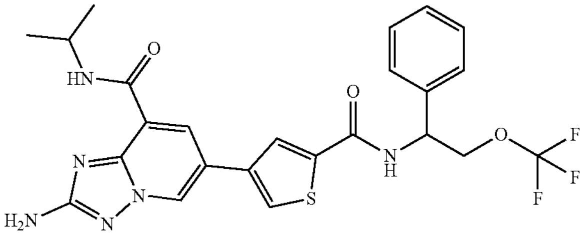 [SMILES: CC(C)NC(=O)c1cc(-c2csc(C(=O)NC(COC(F)(F)F)c3ccccc3)c2)cn2nc(N)nc12] |
| 118 | 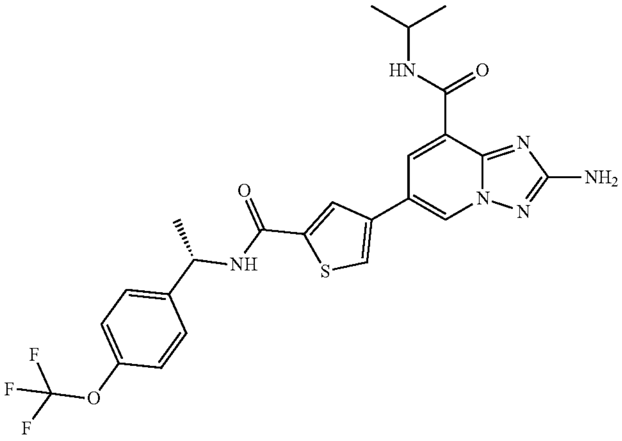 [SMILES: CC(C)NC(=O)c1cc(-c2csc(C(=O)N[C@@H](C)c3ccc(OC(F)(F)F)cc3)c2)cn2nc(N)nc12] |
| 119 | 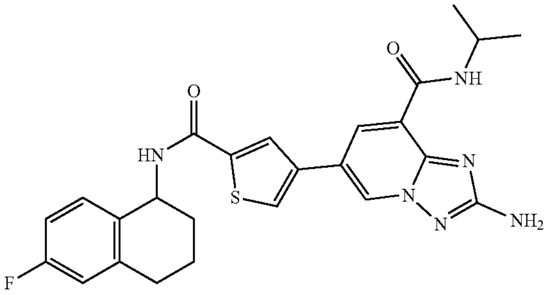 [SMILES: CC(C)NC(=O)c1cc(-c2csc(C(=O)NC3CCCc4cc(F)ccc43)c2)cn2nc(N)nc12] |

-continued
| Compound Number | Structure |
|---|---|
| 120 | 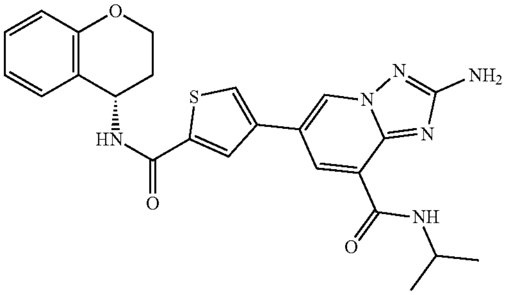 [SMILES: CC(C)NC(=O)c1cc(-c2csc(C(=O)N[C@H]3CCOc4ccccc43)c2)cn2nc(N)nc12] |
| 121 | 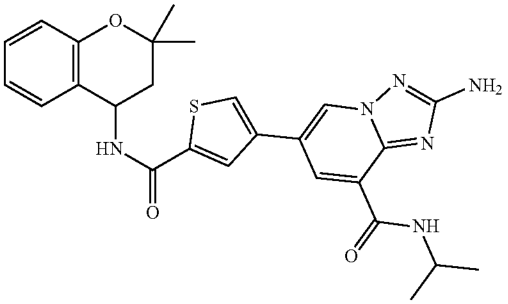 [SMILES: CC(C)NC(=O)c1cc(-c2csc(C(=O)NC3CC(C)(C)Oc4ccccc43)c2)cn2nc(N)nc12] |
| 122 | 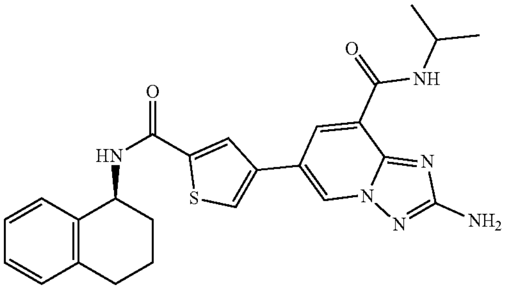 [SMILES: CC(C)NC(=O)c1cc(-c2csc(C(=O)N[C@H]3CCCc4ccccc43)c2)cn2nc(N)nc12] |
| 123 | 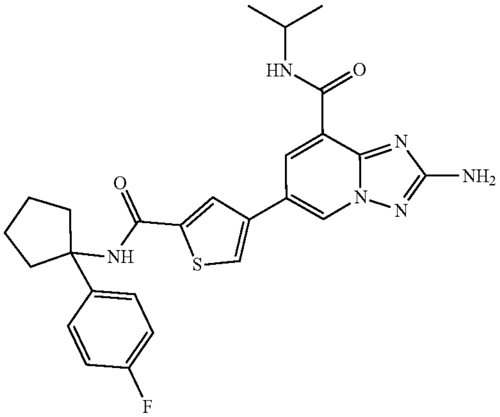 [SMILES: CC(C)NC(=O)c1cc(-c2csc(C(=O)NC3(c4ccc(F)cc4)CCCC3)c2)cn2nc(N)nc12] |

-continued
| Compound Number | Structure |
| --- | --- |
| 124 | 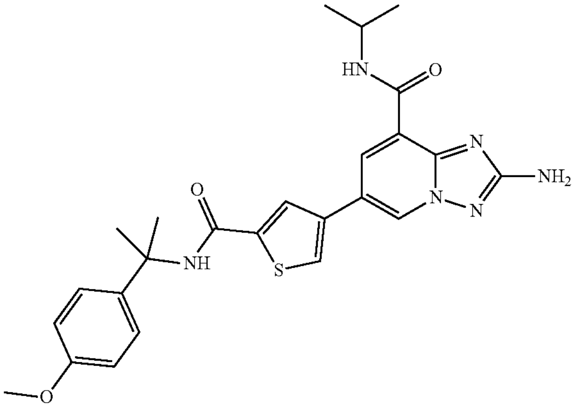 [SMILES: COc1ccc(C(C)(C)NC(=O)c2cc(-c3cc(C(=O)NC(C)C)c4nc(N)nn4c3)cs2)cc1] |
| 125 | 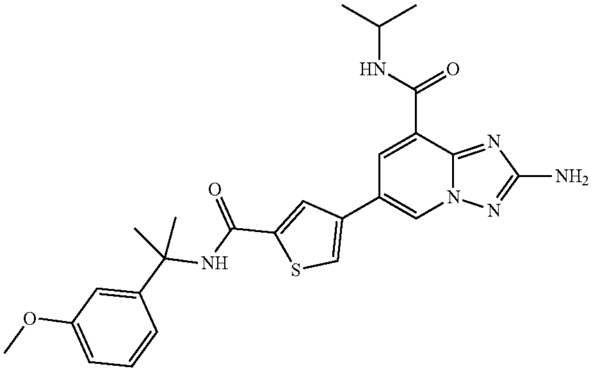 [SMILES: COc1cccc(C(C)(C)NC(=O)c2cc(-c3cc(C(=O)NC(C)C)c4nc(N)nn4c3)cs2)c1] |
| 126 | 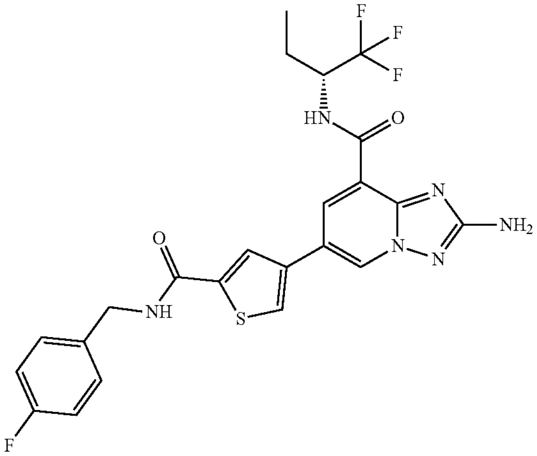 [SMILES: CC[C@@H](NC(=O)c1cc(-c2csc(C(=O)NCc3ccc(F)cc3)c2)cn2nc(N)nc12)C(F)(F)F] |

-continued
| Compound Number | Structure |
|---|---|
| 127 | 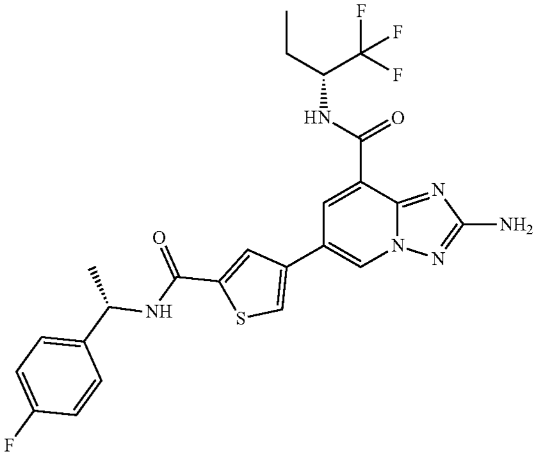 [SMILES: CC[C@@H](NC(=O)c1cc(-c2csc(C(=O)N[C@@H](C)c3ccc(F)cc3)c2)cn2nc(N)nc12)C(F)(F)F] |
| 128 | 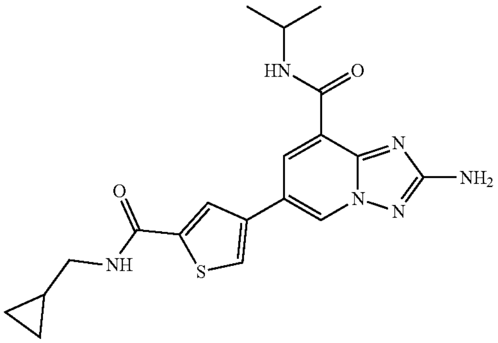 [SMILES: CC(C)NC(=O)c1cc(-c2csc(C(=O)NCC3CC3)c2)cn2nc(N)nc12] |
| 129 | 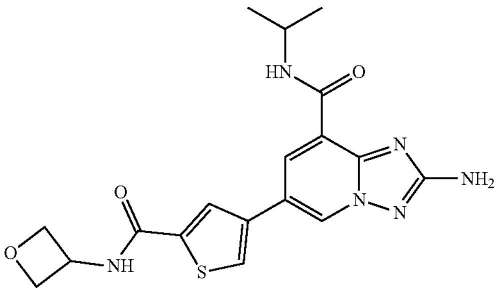 [SMILES: CC(C)NC(=O)c1cc(-c2csc(C(=O)NC3COC3)c2)cn2nc(N)nc12] |
| 130 | 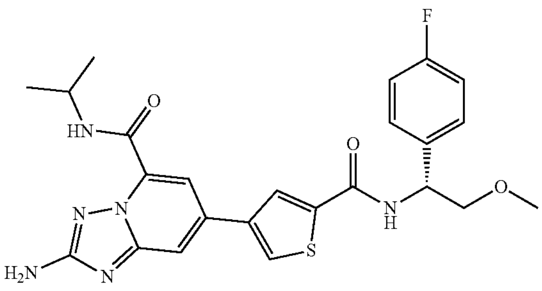 [SMILES: COC[C@H](NC(=O)c1cc(-c2cc(C(=O)NC(C)C)n3nc(N)nc3c2)cs1)c1ccc(F)cc1] |

-continued
| Compound Number | Structure |
|---|---|
| 131 | 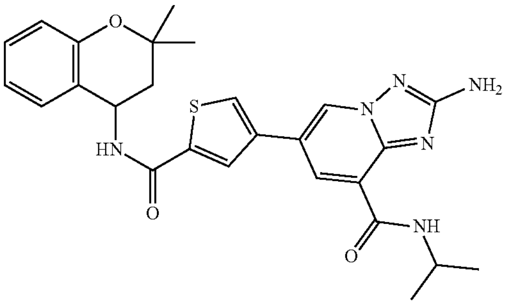 enantiomer 1 |
| 132 | 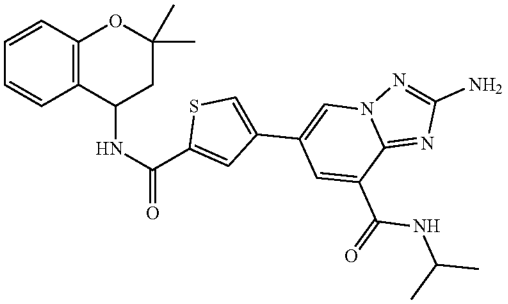 enantiomer 2 |
| 133 | 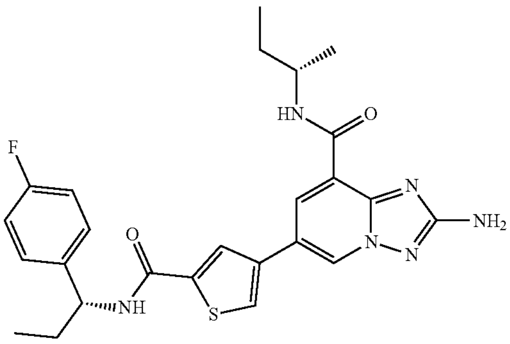 [SMILES: CC[C@H](C)NC(=O)c1cc(-c2csc(C(=O)N[C@H](CC)c3ccc(F)cc3)c2)cn2nc(N)nc12] |
| 134 | 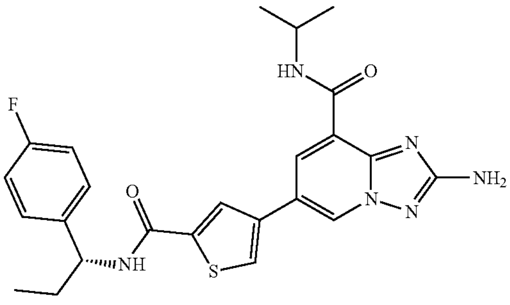 [SMILES: CC[C@@H](NC(=O)c1cc(-c2cc(C(=O)NC(C)C)c3nc(N)nn3c2)cs1)c1ccc(F)cc1] |

-continued
| Compound Number | Structure |
|---|---|
| 135 | 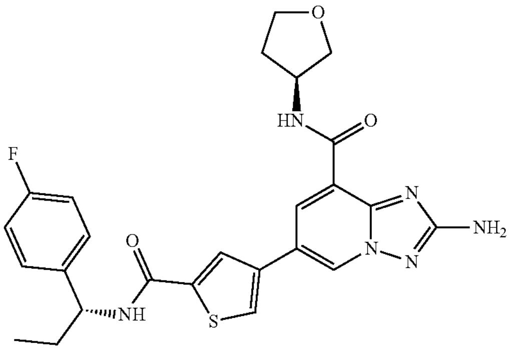 [SMILES: CC[C@@H](NC(=O)c1cc(-c2cc(C(=O)N[C@H]3CCOC3)c3nc(N)nn3c2)cs1)c1ccc(F)cc1] |
| 136 | 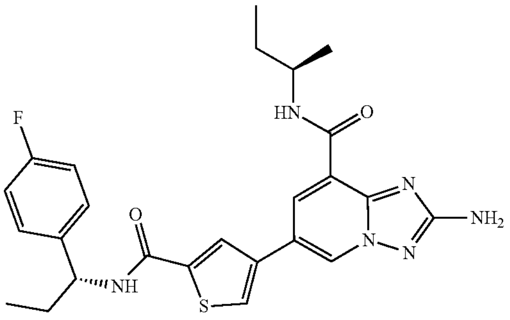 [SMILES: CC[C@@H](C)NC(=O)c1cc(-c2csc(C(=O)N[C@H](CC)c3ccc(F)cc3)c2)cn2nc(N)nc12] |
| 137 | 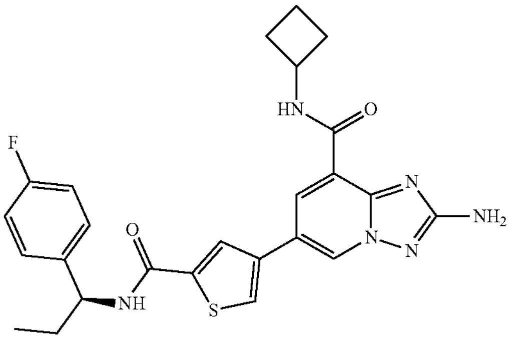 [SMILES: CC[C@H](NC(=O)c1cc(-c2cc(C(=O)NC3CCC3)c3nc(N)nn3c2)cs1)c1ccc(F)cc1] |
| 138 | 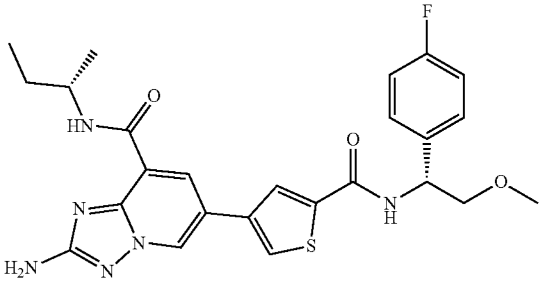 [SMILES: CC[C@H](C)NC(=O)c1cc(-c2csc(C(=O)N[C@@H](COC)c3ccc(F)cc3)c2)cn2nc(N)nc12] |

-continued
| Compound Number | Structure |
|---|---|
| 139 | 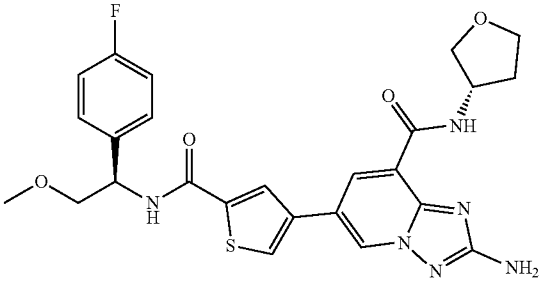 [SMILES: COC[C@H](NC(=O)c1cc(-c2cc(C(=O)N[C@H]3CCOC3)c3nc(N)nn3c2)cs1)c1ccc(F)cc1] |
| 140 | 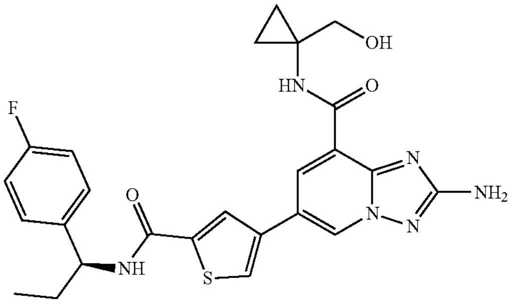 [SMILES: CC[C@H](NC(=O)c1cc(-c2cc(C(=O)NC3(CO)CC3)c3nc(N)nn3c2)cs1)c1ccc(F)cc1] |
| 141 | 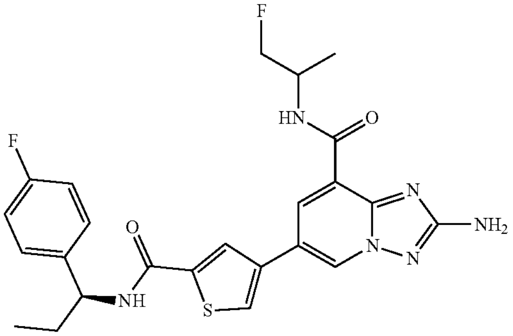 mixture of diastereomers |
| 142 | 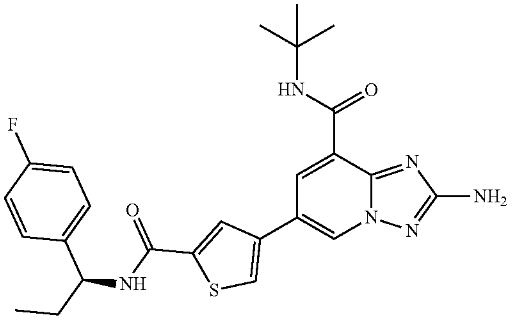 [SMILES: CC[C@H](NC(=O)c1cc(-c2cc(C(=O)NC(C)(C)C)c3nc(N)nn3c2)cs1)c1ccc(F)cc1] |

-continued
| Compound Number | Structure |
|---|---|
| 143 | 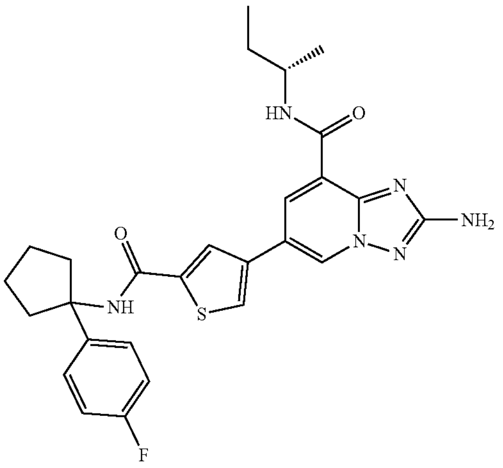 [SMILES: CC[C@H](C)NC(=O)c1cc(-c2csc(C(=O)NC3(c4ccc(F)cc4)CCCC3)c2)cn2nc(N)nc12] |
| 144 | 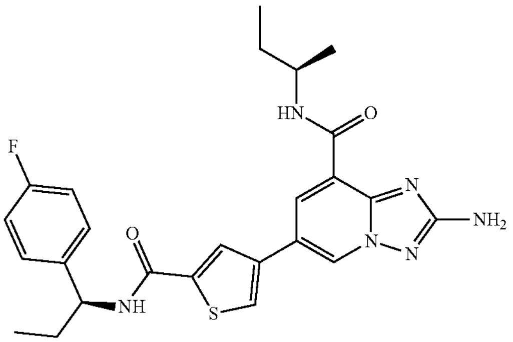 [SMILES: CC[C@@H](C)NC(=O)c1cc(-c2csc(C(=O)N[C@@H](CC)c3ccc(F)cc3)c2)cn2nc(N)nc12] |
| 144-1 | 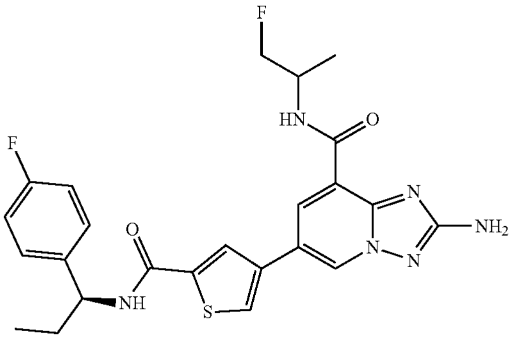<br>stereoisomer 1 |
| 144-2 | 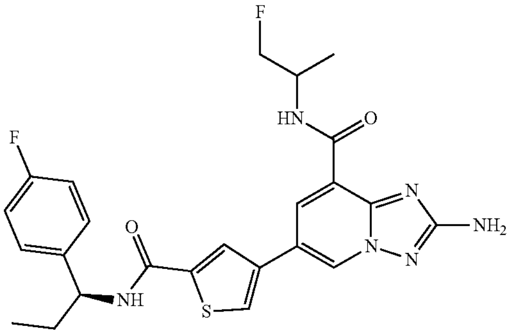<br>stereoisomer 2 |

-continued
| Compound Number | Structure |
|---|---|
| 144-3 | 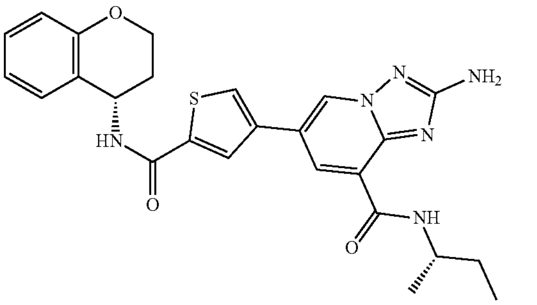 [SMILES: CC[C@H](C)NC(=O)c1cc(-c2csc(C(=O)N[C@H]3CCOc4ccccc43)c2)cn2nc(N)nc12] |
| 144-4 | 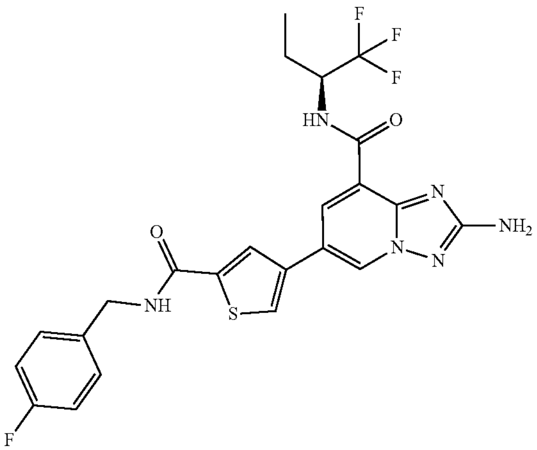 [SMILES: CC[C@H](NC(=O)c1cc(-c2csc(C(=O)NCc3ccc(F)cc3)c2)cn2nc(N)nc12)C(F)(F)F] |
| 144-5 | 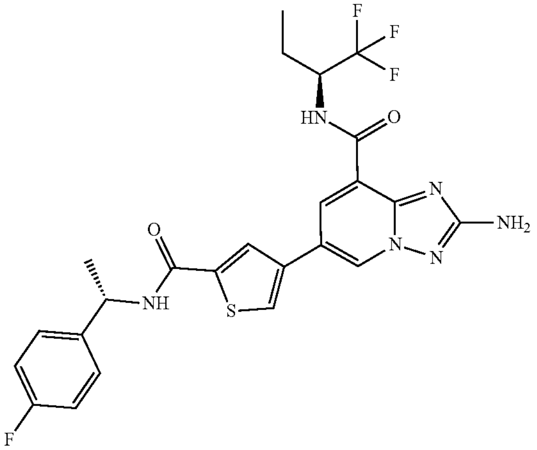 [SMILES: CC[C@H](NC(=O)c1cc(-c2csc(C(=O)N[C@@H](C)c3ccc(F)cc3)c2)cn2nc(N)nc12)C(F)(F)F] |

TABLE 1C
| Compound Number | Structure |
|---|---|
| 163 | 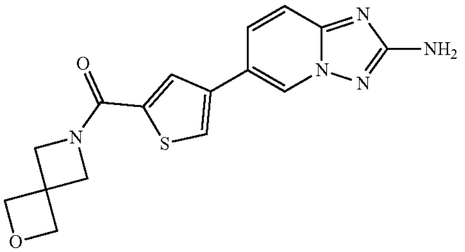 [SMILES: Nc1nc2ccc(-c3csc(C(=O)N4CC5(COC5)C4)c3)cn2n1] |
| 164 | 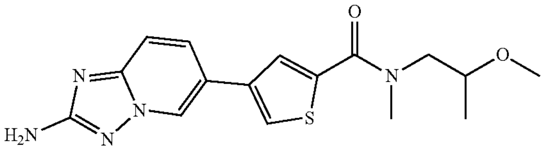 [SMILES: COC(C)CN(C)C(=O)c1cc(-c2ccc3nc(N)nn3c2)cs1] |
| 165 | 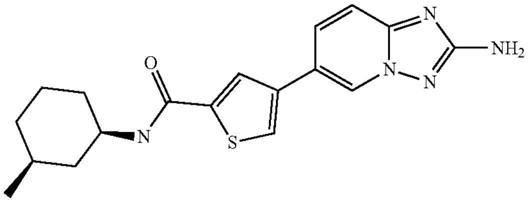<br>stereoisomer 1 |
| 166 | 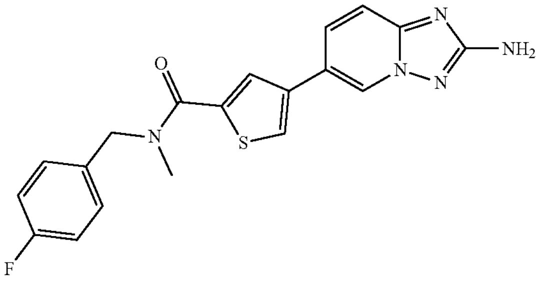 [SMILES: CN(Cc1ccc(F)cc1)C(=O)c1cc(-c2ccc3nc(N)nn3c2)cs1] |
| 167 | 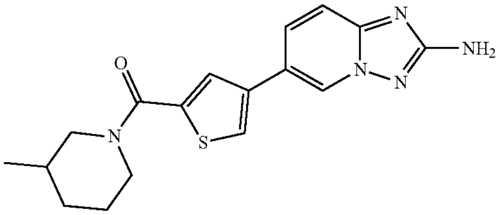 [SMILES: CC1CCCN(C(=O)c2cc(-c3ccc4nc(N)nn4c3)cs2)C1] |
| 168 | 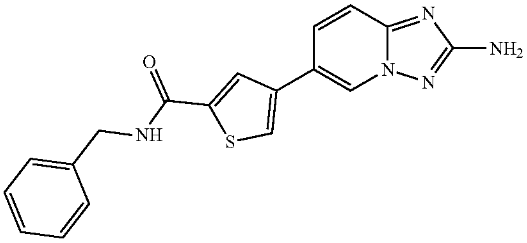 [SMILES: Nc1nc2ccc(-c3csc(C(=O)NCc4ccccc4)c3)cn2n1] |

TABLE 1C-continued
| Compound Number | Structure |
|---|---|
| 169 | 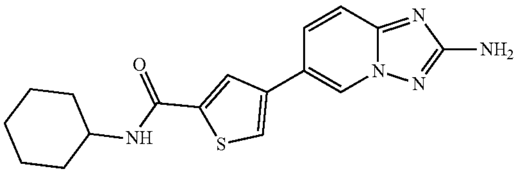 [SMILES: Nc1nc2ccc(-c3csc(C(=O)NC4CCCCC4)c3)cn2n1] |
| 170 | 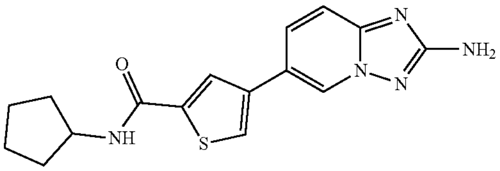 [SMILES: Nc1nc2ccc(-c3csc(C(=O)NC4CCCC4)c3)cn2n1] |
| 171 | 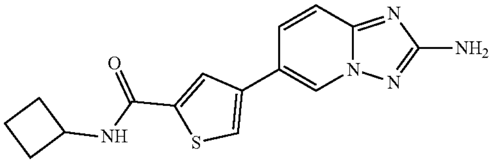 [SMILES: Nc1nc2ccc(-c3csc(C(=O)NC4CCC4)c3)cn2n1] |
| 172 | 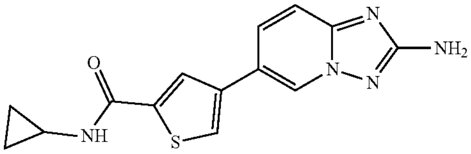 [SMILES: Nc1nc2ccc(-c3csc(C(=O)NC4CC4)c3)cn2n1] |
| 173 | 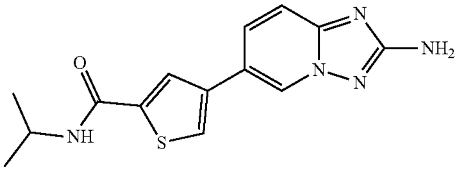 [SMILES: CC(C)NC(=O)c1cc(-c2ccc3nc(N)nn3c2)cs1] |
| 174 | 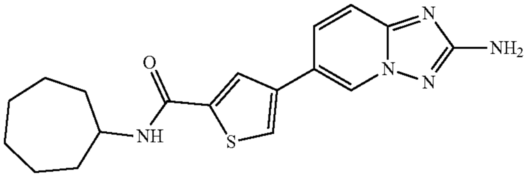 [SMILES: Nc1nc2ccc(-c3csc(C(=O)NC4CCCCCC4)c3)cn2n1] |
| 175 | 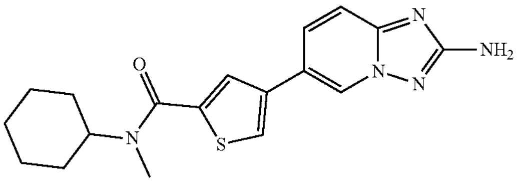 [SMILES: CN(C(=O)c1cc(-c2ccc3nc(N)nn3c2)cs1)C1CCCCC1] |
| 176 | 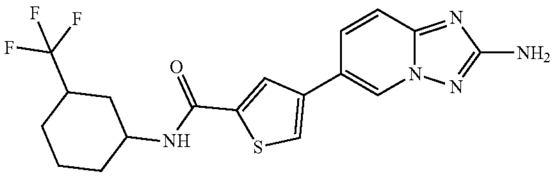 [SMILES: Nc1nc2ccc(-c3csc(C(=O)NC4CCCC(C(F)(F)F)C4)c3)cn2n1] |

TABLE 1C-continued
| Compound Number | Structure |
| --- | --- |
| 177 | 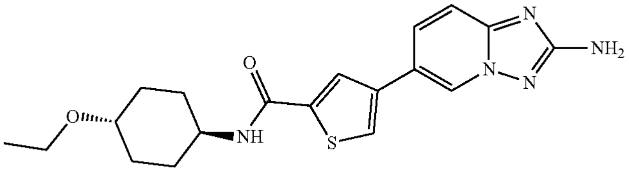 [SMILES: CCO[C@H]1CC[C@H](NC(=O)c2cc(-c3ccc4nc(N)nn4c3)cs2)CC1] |
| 178 | 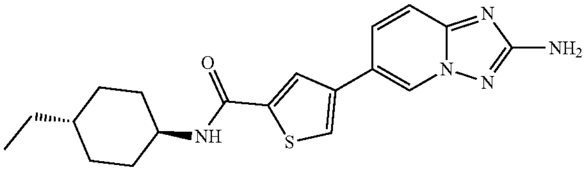 [SMILES: CC[C@H]1CC[C@H](NC(=O)c2cc(-c3ccc4nc(N)nn4c3)cs2)CC1] |
| 179 | 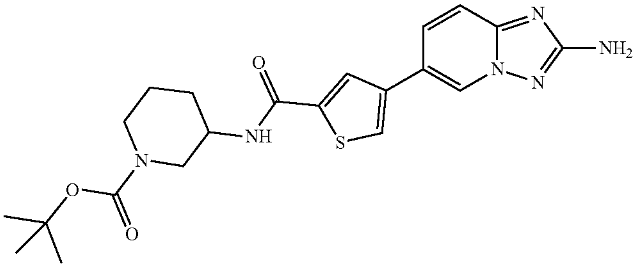 [SMILES: CC(C)(C)OC(=O)N1CCCC(NC(=O)c2cc(-c3ccc4nc(N)nn4c3)cs2)C1] |
| 180 | 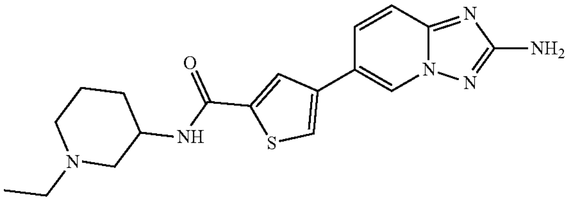 [SMILES: CCN1CCCC(NC(=O)c2cc(-c3ccc4nc(N)nn4c3)cs2)C1] |
| 181 | 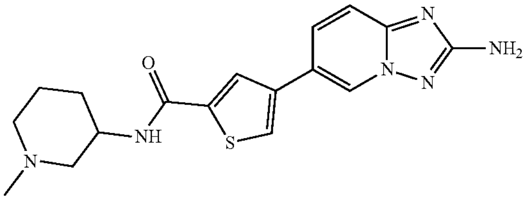 [SMILES: CN1CCCC(NC(=O)c2cc(-c3ccc4nc(N)nn4c3)cs2)C1] |
| 182 | 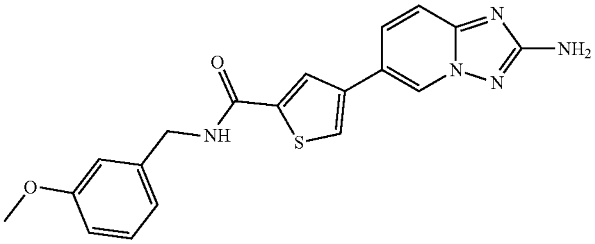 [SMILES: COc1cccc(CNC(=O)c2cc(-c3ccc4nc(N)nn4c3)cs2)c1] |
| 183 | 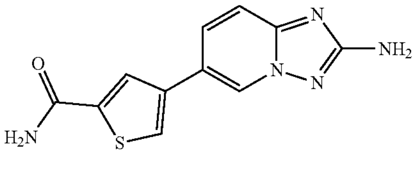 [SMILES: NC(=O)c1cc(-c2ccc3nc(N)nn3c2)cs1] |

TABLE 1C-continued
| Compound Number | Structure |
|---|---|
| 184 | 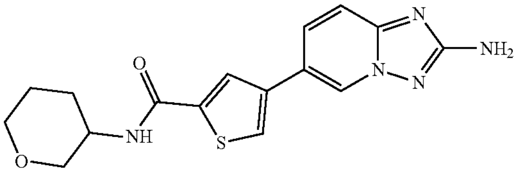 [SMILES: Nc1nc2ccc(-c3csc(C(=O)NC4CCCOC4)c3)cn2n1] |
| 185 | 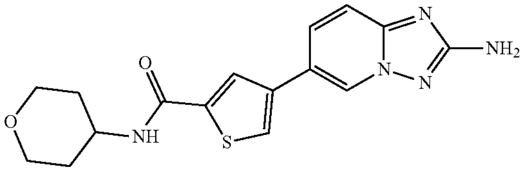 [SMILES: Nc1nc2ccc(-c3csc(C(=O)NC4CCOCC4)c3)cn2n1] |
| 186 | 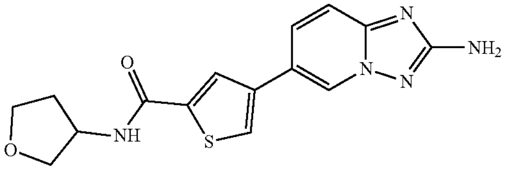 [SMILES: Nc1nc2ccc(-c3csc(C(=O)NC4CCOC4)c3)cn2n1] |
| 187 | 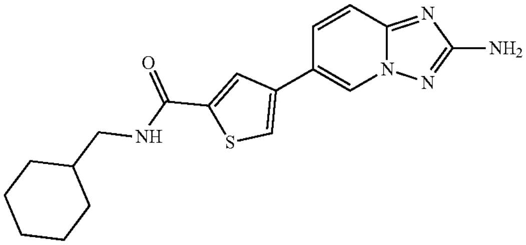 |
| 188 | 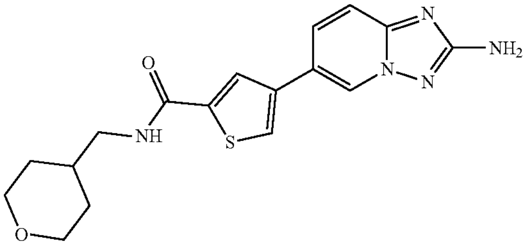 [SMILES: Nc1nc2ccc(-c3csc(C(=O)NCC4CCOCC4)c3)cn2n1] |
| 189 | 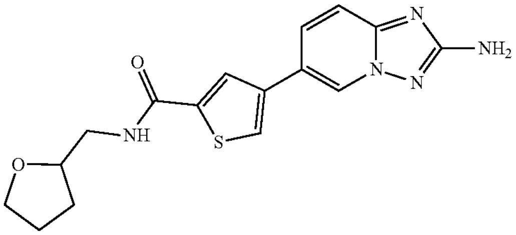 [SMILES: Nc1nc2ccc(-c3csc(C(=O)NCC4CCCO4)c3)cn2n1] |
| 190 | 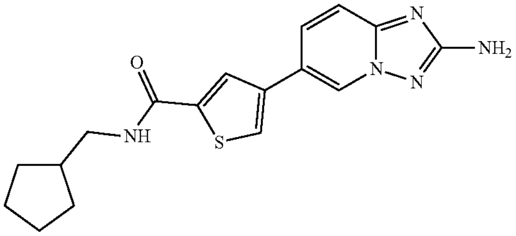 [SMILES: Nc1nc2ccc(-c3csc(C(=O)NCC4CCCC4)c3)cn2n1] |

TABLE 1C-continued
| Compound Number | Structure |
|---|---|
| 191 | 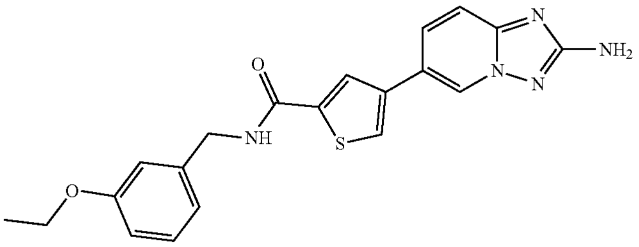 [SMILES: CCOc1cccc(CNC(=O)c2cc(-c3ccc4nc(N)nn4c3)cs2)c1] |
| 192 | 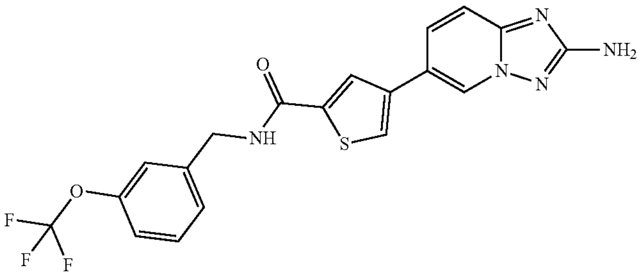 [SMILES: Nc1nc2ccc(-c3csc(C(=O)NCc4cccc(OC(F)(F)F)c4)c3)cn2n1] |
| 193 | 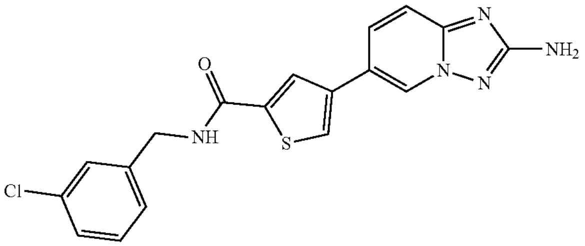 [SMILES: Nc1nc2ccc(-c3csc(C(=O)NCc4cccc(Cl)c4)c3)cn2n1] |
| 194 | 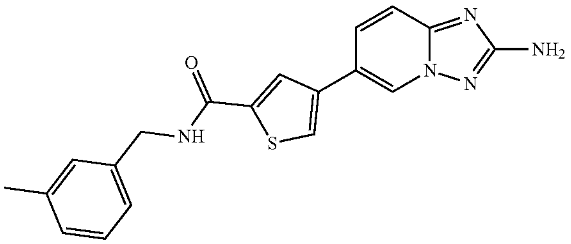 |
| 195 | 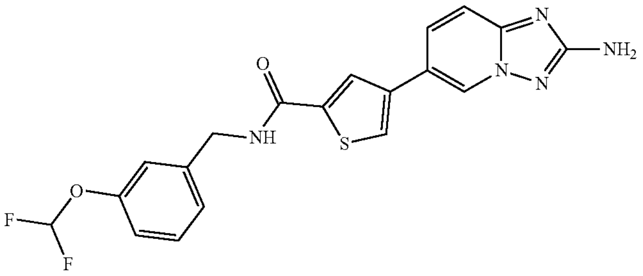 [SMILES: Nc1nc2ccc(-c3csc(C(=O)NCc4cccc(OC(F)F)c4)c3)cn2n1] |

TABLE 1C-continued
| Compound Number | Structure |
|---|---|
| 196 | 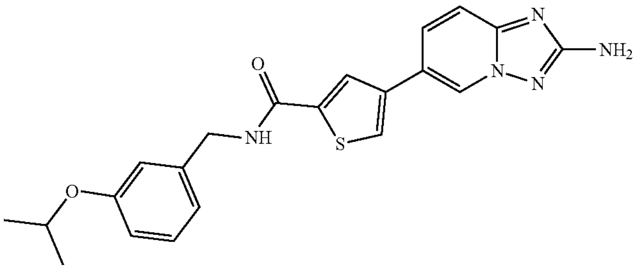 [SMILES: CC(C)Oc1cccc(CNC(=O)c2cc(-c3ccc4nc(N)nn4c3)cs2)c1] |
| 197 | 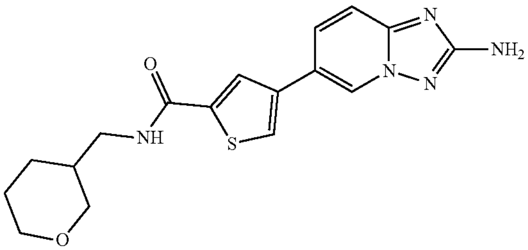 [SMILES: Nc1nc2ccc(-c3csc(C(=O)NCC4CCCOC4)c3)cn2n1] |
| 198 | 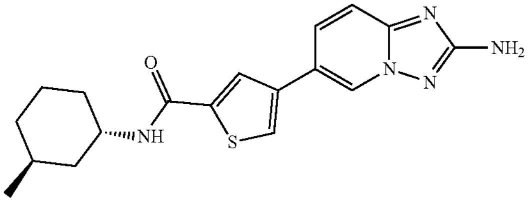 stereoisomer 1 |
| 199 | 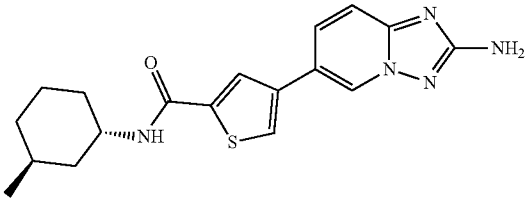 stereoisomer 2 |
| 200 | 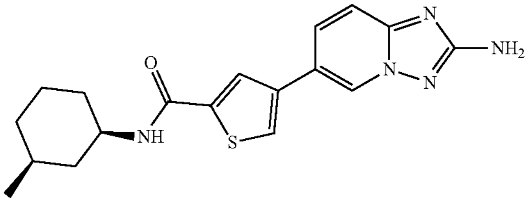 stereoisomer 2 |
| 201 | 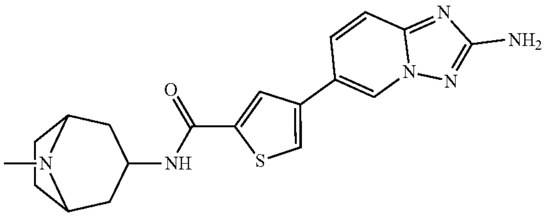 [SMILES: CN1C2CCC1CC(NC(=O)c1cc(-c3ccc4nc(N)nn4c3)cs1)C2] |

TABLE 1C-continued
| Compound Number | Structure |
| --- | --- |
| 202 | 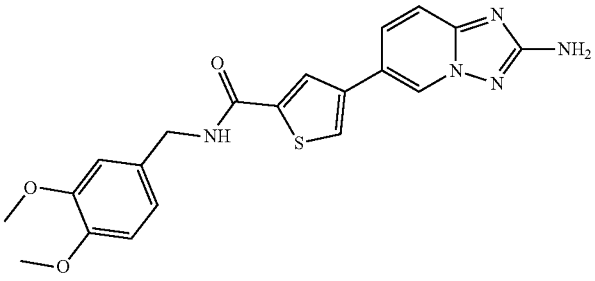 [SMILES: COc1ccc(CNC(=O)c2cc(-c3ccc4nc(N)nn4c3)cs2)cc1OC] |
| 203 | 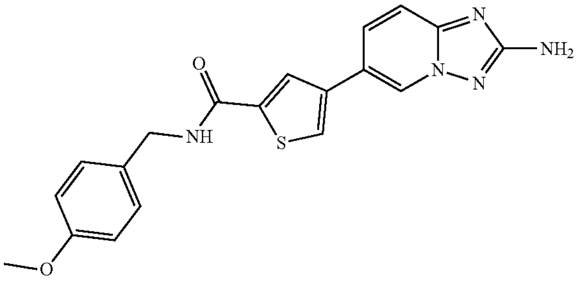 [SMILES: COc1ccc(CNC(=O)c2cc(-c3ccc4nc(N)nn4c3)cs2)cc1] |
| 204 | 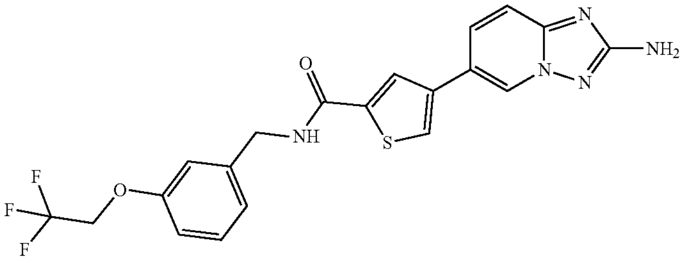 [SMILES: Nc1nc2ccc(-c3csc(C(=O)NCc4cccc(OCC(F)(F)F)c4)c3)cn2n1] |
| 205 | 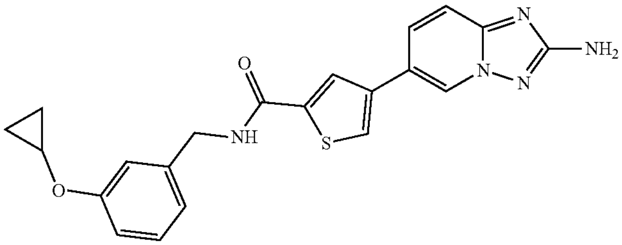 [SMILES: Nc1nc2ccc(-c3csc(C(=O)NCc4cccc(OC5CC5)c4)c3)cn2n1] |
| 206 | 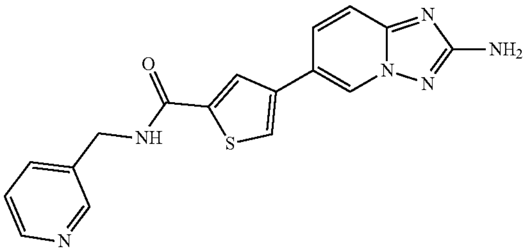 [SMILES: Nc1nc2ccc(-c3csc(C(=O)NCc4cccnc4)c3)cn2n1] |

TABLE 1C-continued
| Compound Number | Structure |
|---|---|
| 207 | 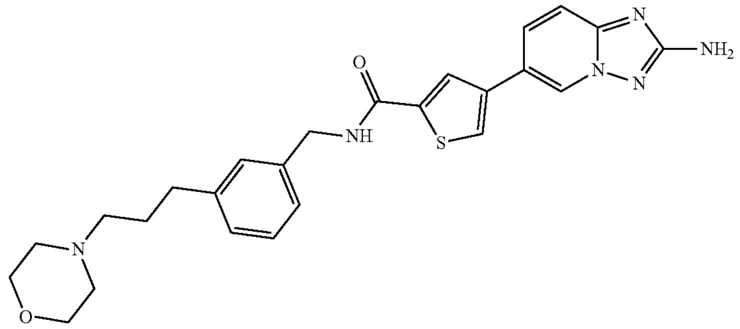 [SMILES: Nc1nc2ccc(-c3csc(C(=O)NCc4cccc(CCCN5CCOCC5)c4)c3)cn2n1] |
| 208 | 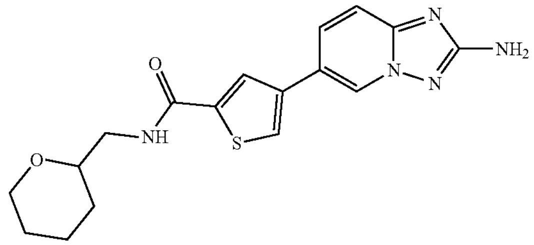 [SMILES: Nc1nc2ccc(-c3csc(C(=O)NCC4CCCCO4)c3)cn2n1] |
| 209 | 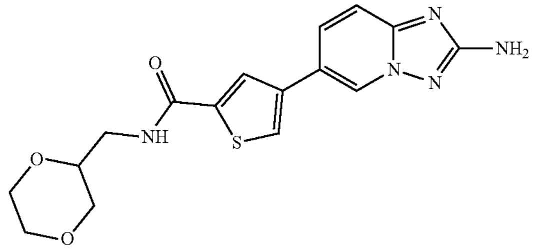 [SMILES: Nc1nc2ccc(-c3csc(C(=O)NCC4COCCO4)c3)cn2n1] |
| 210 | 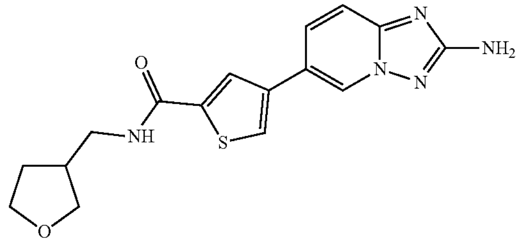 [SMILES: Nc1nc2ccc(-c3csc(C(=O)NCC4CCOC4)c3)cn2n1] |
| 211 | 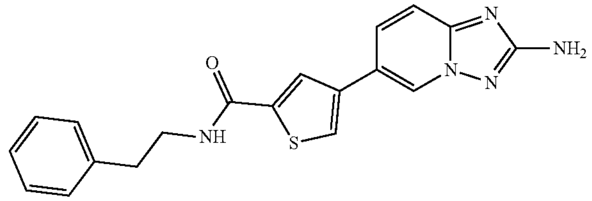 [SMILES: Nc1nc2ccc(-c3csc(C(=O)NCCc4ccccc4)c3)cn2n1] |
| 212 | 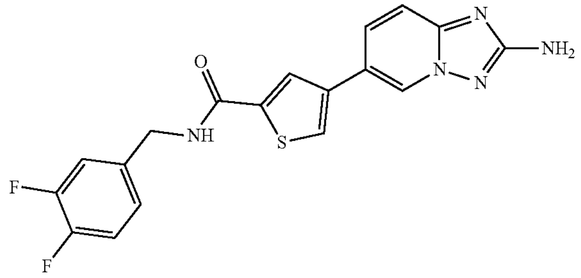 [SMILES: Nc1nc2ccc(-c3csc(C(=O)NCc4ccc(F)c(F)c4)c3)cn2n1] |

TABLE 1C-continued
| Compound Number | Structure |
|---|---|
| 213 | 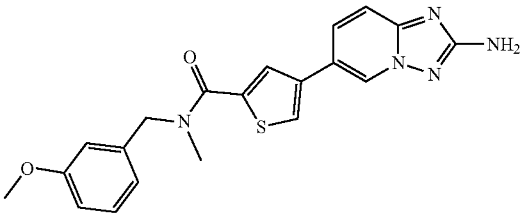 [SMILES: COc1cccc(CN(C)C(=O)c2cc(-c3ccc4nc(N)nn4c3)cs2)c1] |
| 214 | 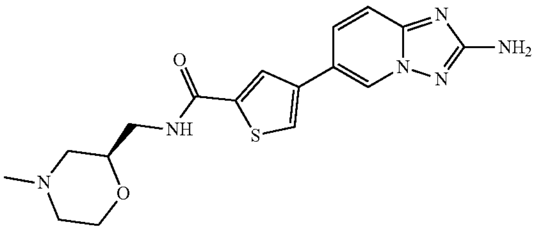 [SMILES: CN1CCO[C@H](CNC(=O)c2cc(-c3ccc4nc(N)nn4c3)cs2)C1] |
| 215 | 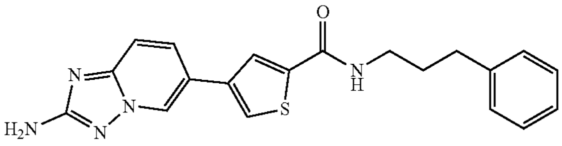 [SMILES: Nc1nc2ccc(-c3csc(C(=O)NCCCc4ccccc4)c3)cn2n1] |
| 216 | 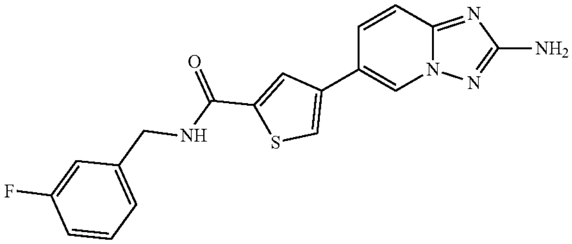 [SMILES: Nc1nc2ccc(-c3csc(C(=O)NCc4cccc(F)c4)c3)cn2n1] |
| 217 | 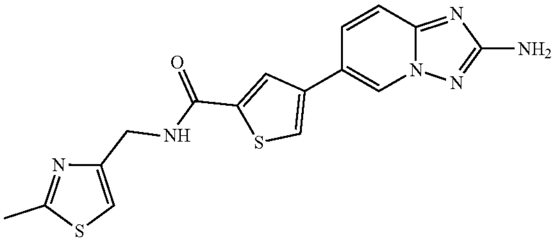 [SMILES: Cc1nc(CNC(=O)c2cc(-c3ccc4nc(N)nn4c3)cs2)cs1] |
| 218 | 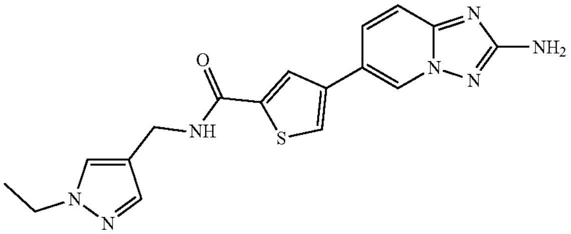 [SMILES: CCn1cc(CNC(=O)c2cc(-c3ccc4nc(N)nn4c3)cs2)cn1] |

TABLE 1C-continued
| Compound Number | Structure |
| --- | --- |
| 219 | 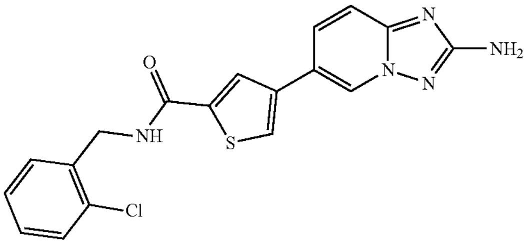 [SMILES: Nc1nc2ccc(-c3csc(C(=O)NCc4ccccc4Cl)c3)cn2n1] |
| 220 | 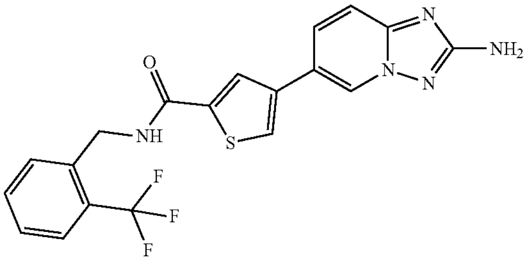 [SMILES: Nc1nc2ccc(-c3csc(C(=O)NCc4ccccc4C(F)(F)F)c3)cn2n1] |
| 221 | 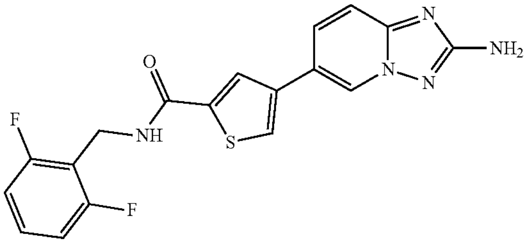 [SMILES: Nc1nc2ccc(-c3csc(C(=O)NCc4c(F)cccc4F)c3)cn2n1] |
| 222 | 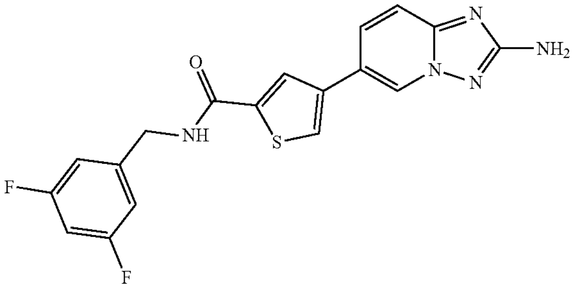 [SMILES: Nc1nc2ccc(-c3csc(C(=O)NCc4cc(F)cc(F)c4)c3)cn2n1] |
| 223 | 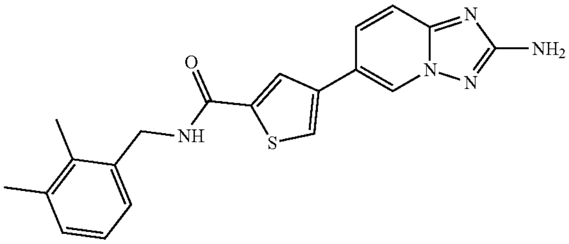 [SMILES: Cc1cccc(CNC(=O)c2cc(-c3ccc4nc(N)nn4c3)cs2)c1C] |
| 224 | 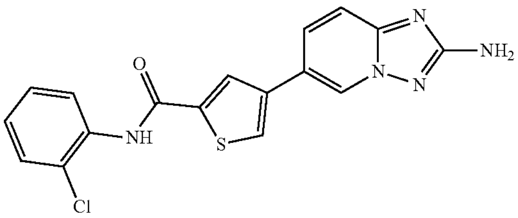 [SMILES: Nc1nc2ccc(-c3csc(C(=O)Nc4ccccc4Cl)c3)cn2n1] |

TABLE 1C-continued
| Compound Number | Structure |
|---|---|
| 225 | 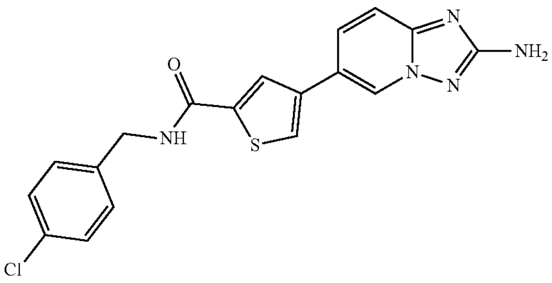 [SMILES: Nc1nc2ccc(-c3csc(C(=O)NCc4ccc(Cl)cc4)c3)cn2n1] |
| 226 | 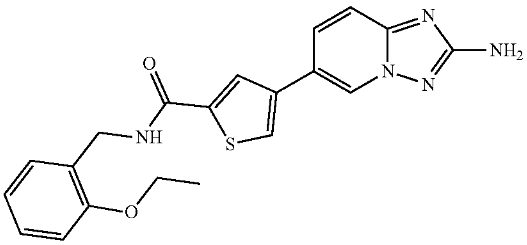 [SMILES: CCOc1ccccc1CNC(=O)c1cc(-c2ccc3nc(N)nn3c2)cs1] |
| 227 | 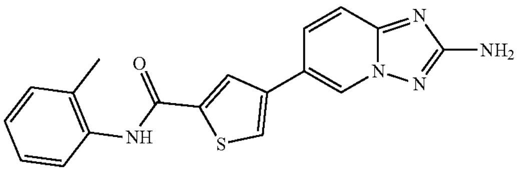 [SMILES: Cc1ccccc1NC(=O)c1cc(-c2ccc3nc(N)nn3c2)cs1] |
| 228 | 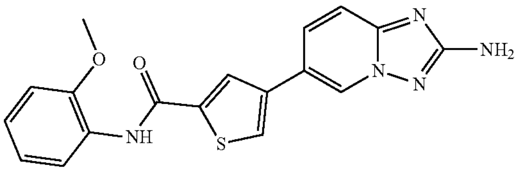 [SMILES: COc1ccccc1NC(=O)c1cc(-c2ccc3nc(N)nn3c2)cs1] |
| 229 | 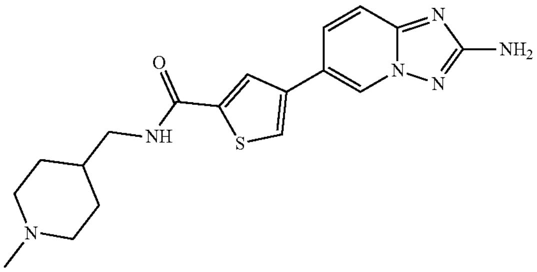 [SMILES: CN1CCC(CNC(=O)c2cc(-c3ccc4nc(N)nn4c3)cs2)CC1] |
| 230 | 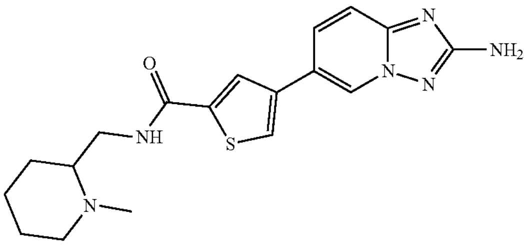 [SMILES: CN1CCCCC1CNC(=O)c1cc(-c2ccc3nc(N)nn3c2)cs1] |

TABLE 1C-continued
| Compound Number | Structure |
|---|---|
| 231 | 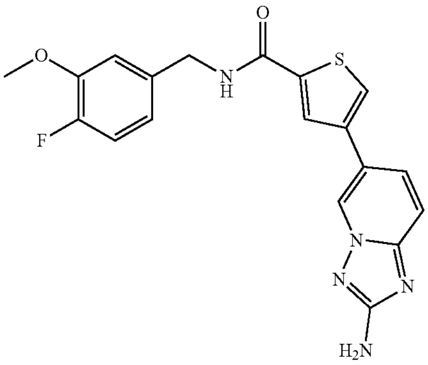 [SMILES: COc1cc(CNC(=O)c2cc(-c3ccc4nc(N)nn4c3)cs2)ccc1F] |
| 232 | 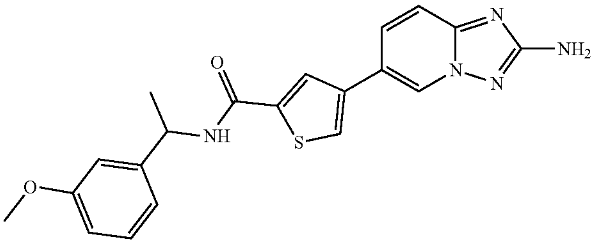 [SMILES: COc1cccc(C(C)NC(=O)c2cc(-c3ccc4nc(N)nn4c3)cs2)c1] |
| 233 | 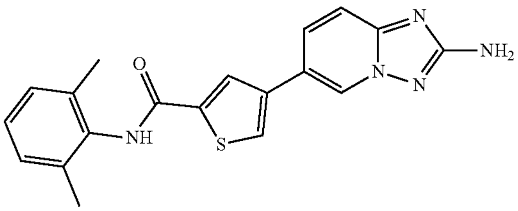 [SMILES: Cc1cccc(C)c1NC(=O)c1cc(-c2ccc3nc(N)nn3c2)cs1] |
| 234 | 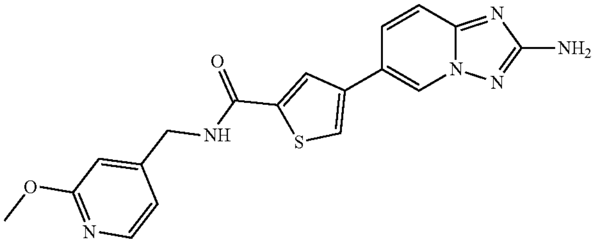 [SMILES: COc1cc(CNC(=O)c2cc(-c3ccc4nc(N)nn4c3)cs2)ccn1] |
| 235 | 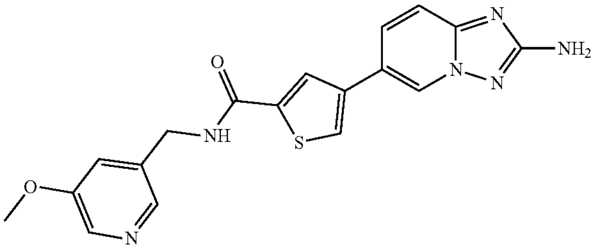 [SMILES: COc1cncc(CNC(=O)c2cc(-c3ccc4nc(N)nn4c3)cs2)c1] |

TABLE 1C-continued
| Compound Number | Structure |
| --- | --- |
| 236 | 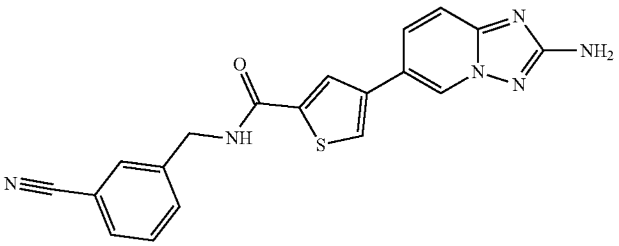 [SMILES: N#Cc1cccc(CNC(=O)c2cc(-c3ccc4nc(N)nn4c3)cs2)c1] |
| 237 | 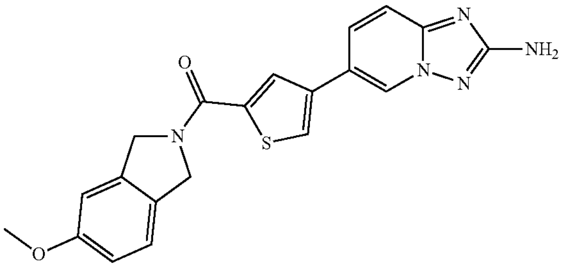 [SMILES: COc1ccc2c(c1)CN(C(=O)c1cc(-c3ccc4nc(N)nn4c3)cs1)C2] |
| 238 | 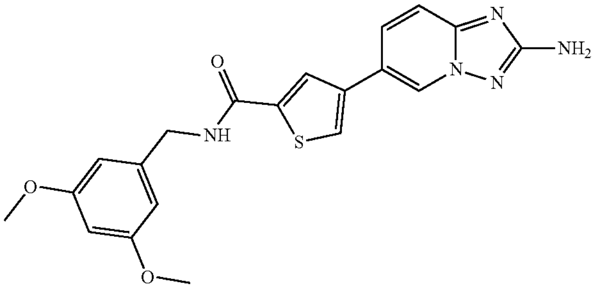 [SMILES: COc1cc(CNC(=O)c2cc(-c3ccc4nc(N)nn4c3)cs2)cc(OC)c1] |
| 239 | 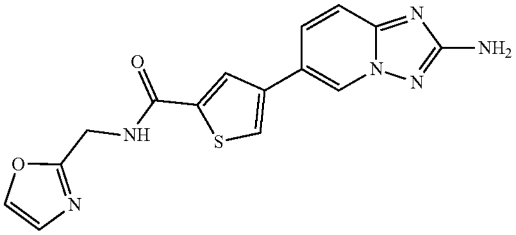 |
| 240 | 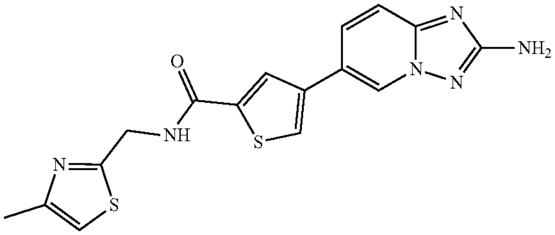 [SMILES: Cc1csc(CNC(=O)c2cc(-c3ccc4nc(N)nn4c3)cs2)n1] |
| 241 | 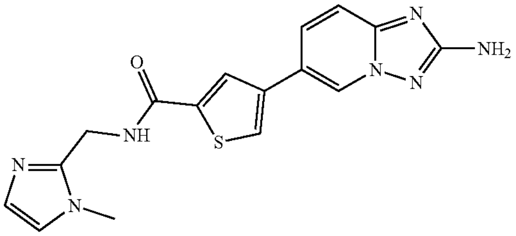 |

TABLE 1C-continued
| Compound Number | Structure |
|---|---|
| 242 | 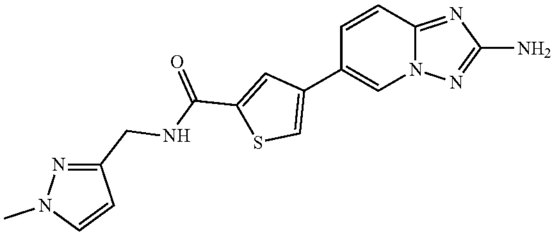 [SMILES: Cn1ccc(CNC(=O)c2cc(-c3ccc4nc(N)nn4c3)cs2)n1] |
| 243 | 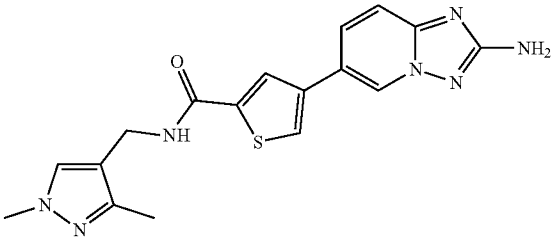 [SMILES: Cc1nn(C)cc1CNC(=O)c1cc(-c2ccc3nc(N)nn3c2)cs1] |
| 244 | 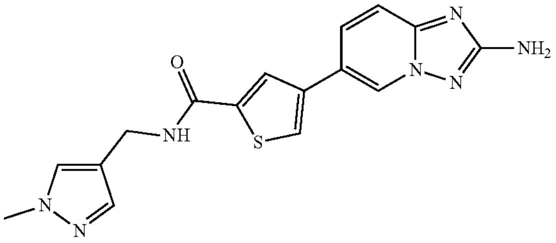 [SMILES: Cn1cc(CNC(=O)c2cc(-c3ccc4nc(N)nn4c3)cs2)cn1] |
| 245 | 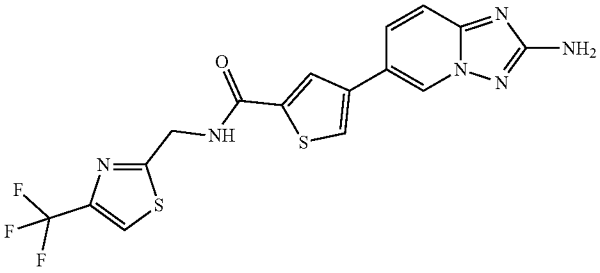 [SMILES: Nc1nc2ccc(-c3csc(C(=O)NCc4nc(C(F)(F)F)cs4)c3)cn2n1] |
| 246 | 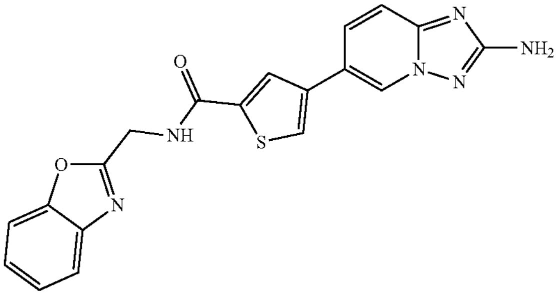 [SMILES: Nc1nc2ccc(-c3csc(C(=O)NCc4nc5ccccc5o4)c3)cn2n1] |

TABLE 1C-continued
| Compound Number | Structure |
|---|---|
| 247 | 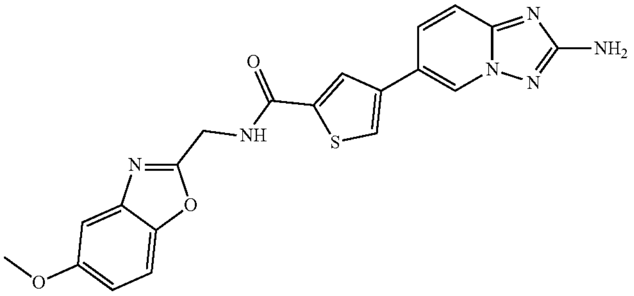 [SMILES: COc1ccc2oc(CNC(=O)c3cc(-c4ccc5nc(N)nn5c4)cs3)nc2c1] |
| 248 | 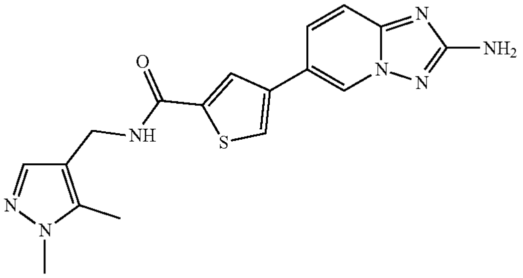 [SMILES: Cc1c(CNC(=O)c2cc(-c3ccc4nc(N)nn4c3)cs2)cnn1C] |
| 249 | 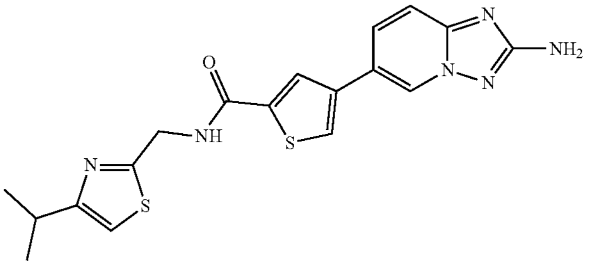 [SMILES: CC(C)c1csc(CNC(=O)c2cc(-c3ccc4nc(N)nn4c3)cs2)n1] |
| 250 | 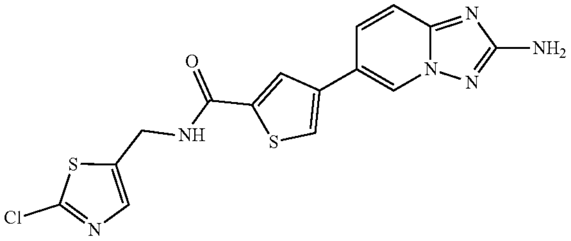 [SMILES: Nc1nc2ccc(-c3csc(C(=O)NCc4cnc(Cl)s4)c3)cn2n1] |
| 251 | 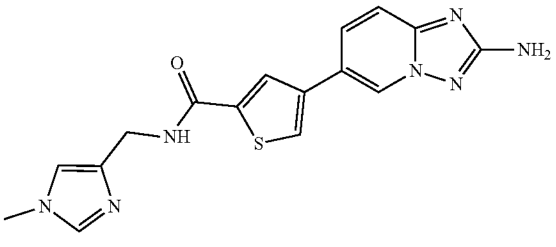 [SMILES: Cn1cnc(CNC(=O)c2cc(-c3ccc4nc(N)nn4c3)cs2)c1] |

TABLE 1C-continued
| Compound Number | Structure |
|---|---|
| 252 | 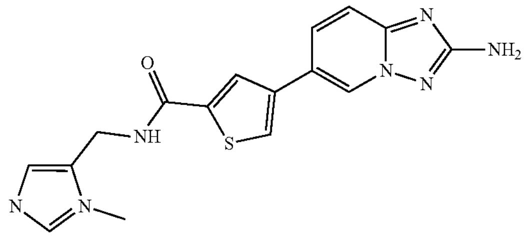 |
| 253 | 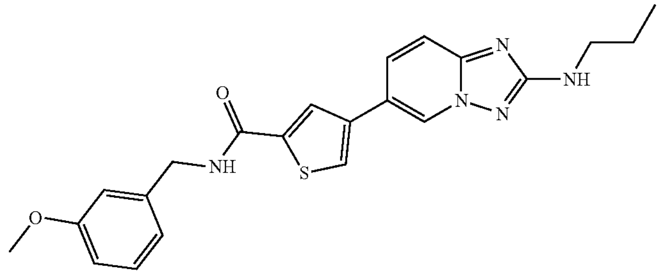 [SMILES: CCCNc1nc2ccc(-c3csc(C(=O)NCc4cccc(OC)c4)c3)cn2n1] |
| 254 | 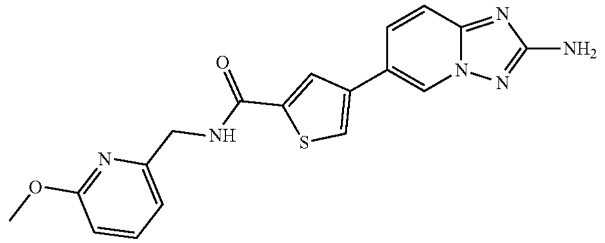 |
| 255 | 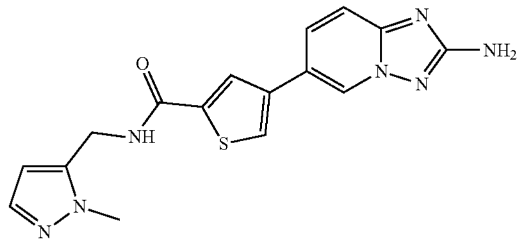 [SMILES: Cn1nccc1CNC(=O)c1cc(-c2ccc3nc(N)nn3c2)cs1] |
| 256 | 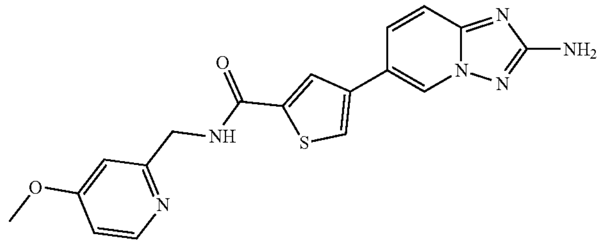 |
| 257 | 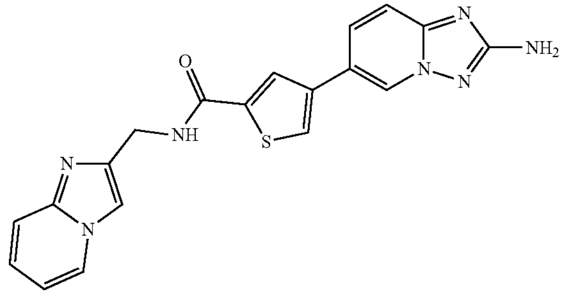 [SMILES: Nc1nc2ccc(-c3csc(C(=O)NCc4cn5ccccc5n4)c3)cn2n1] |

TABLE 1C-continued
| Compound Number | Structure |
|---|---|
| 258 | 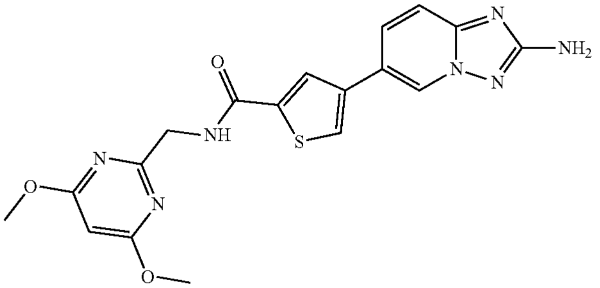 [SMILES: COc1cc(OC)nc(CNC(=O)c2cc(-c3ccc4nc(N)nn4c3)cs2)n1] |
| 259 | 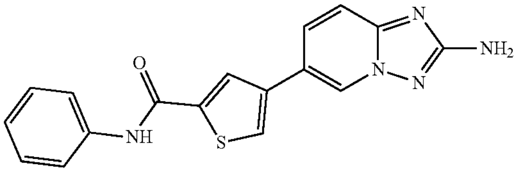 [SMILES: Nc1nc2ccc(-c3csc(C(=O)Nc4ccccc4)c3)cn2n1] |
| 260 | 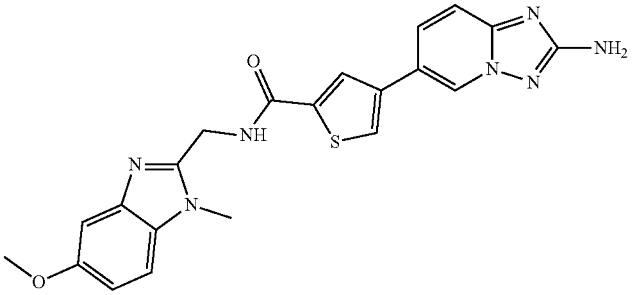 [SMILES: COc1ccc2c(c1)nc(CNC(=O)c1cc(-c3ccc4nc(N)nn4c3)cs1)n2C] |
| 261 | 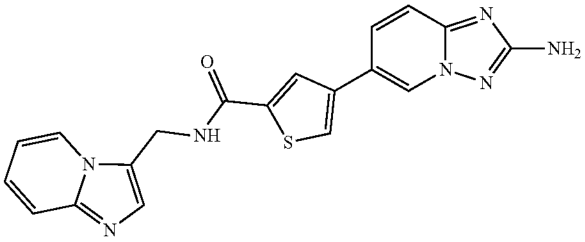 [SMILES: Nc1nc2ccc(-c3csc(C(=O)NCc4cnc5ccccn45)c3)cn2n1] |
| 262 | 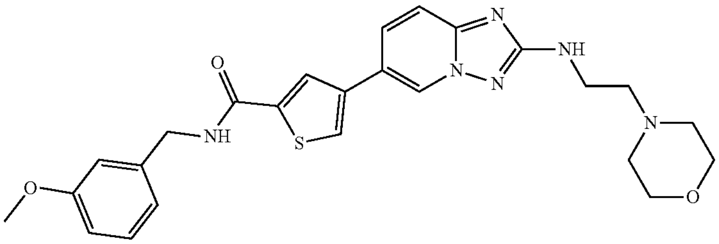 [SMILES: COc1cccc(CNC(=O)c2cc(-c3ccc4nc(NCCN5CCOCC5)nn4c3)cs2)c1] |
| 263 | 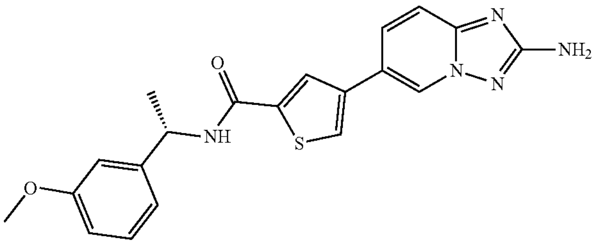 [SMILES: COc1cccc([C@H](C)NC(=O)c2cc(-c3ccc4nc(N)nn4c3)cs2)c1] |

TABLE 1C-continued
| Compound Number | Structure |
| --- | --- |
| 264 | 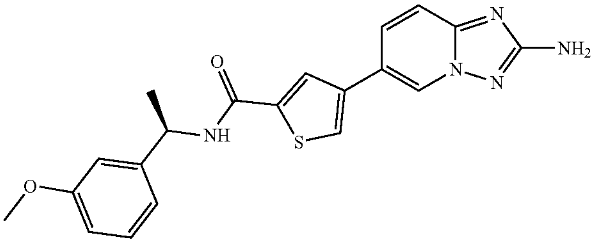 [SMILES: COc1cccc([C@@H](C)NC(=O)c2cc(-c3ccc4nc(N)nn4c3)cs2)c1] |
| 265 | 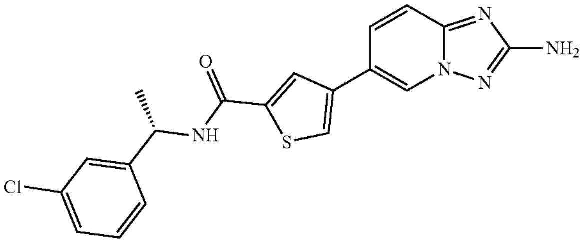 [SMILES: C[C@H](NC(=O)c1cc(-c2ccc3nc(N)nn3c2)cs1)c1cccc(Cl)c1] |
| 266 | 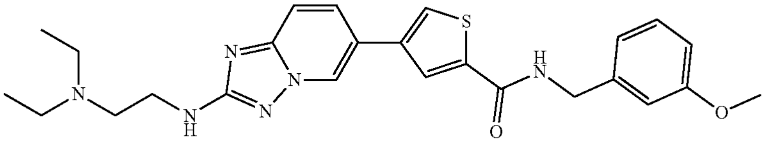 [SMILES: CCN(CC)CCNc1nc2ccc(-c3csc(C(=O)NCc4cccc(OC)c4)c3)cn2n1] |
| 267 | 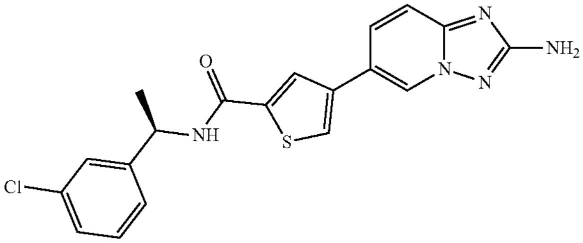 [SMILES: C[C@@H](NC(=O)c1cc(-c2ccc3nc(N)nn3c2)cs1)c1cccc(Cl)c1] |
| 268 | 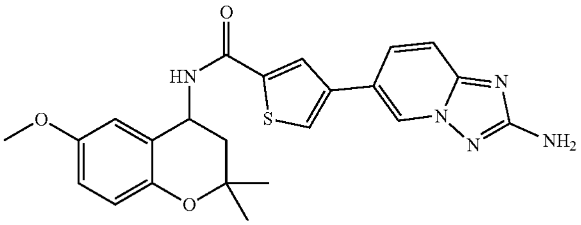 [SMILES: COc1ccc2c(c1)C(NC(=O)c1cc(-c3ccc4nc(N)nn4c3)cs1)CC(C)(C)O2] |
| 269 | 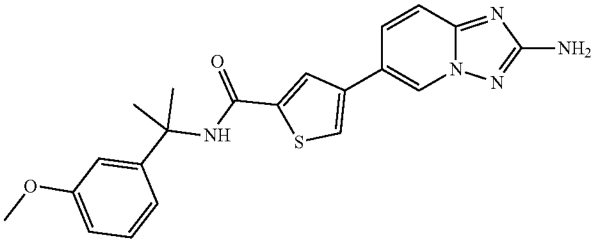 [SMILES: COc1cccc(C(C)(C)NC(=O)c2cc(-c3ccc4nc(N)nn4c3)cs2)c1] |
| 270 | 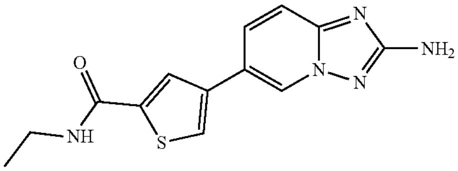 [SMILES: CCNC(=O)c1cc(-c2ccc3nc(N)nn3c2)cs1] |

TABLE 1C-continued
| Compound Number | Structure |
| --- | --- |
| 271 | 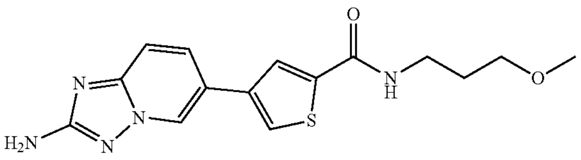 [SMILES: COCCCNC(=O)c1cc(-c2ccc3nc(N)nn3c2)cs1] |
| 272 | 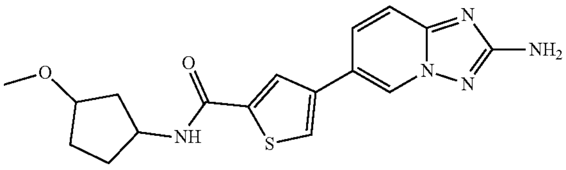 [SMILES: COC1CCC(NC(=O)c2cc(-c3ccc4nc(N)nn4c3)cs2)C1] |
| 273 | 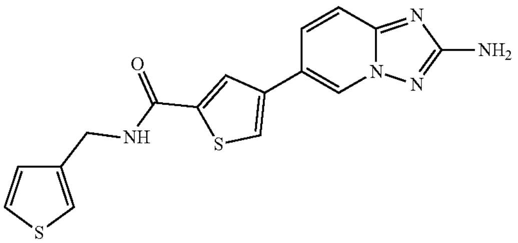 [SMILES: Nc1nc2ccc(-c3csc(C(=O)NCc4ccsc4)c3)cn2n1] |
| 274 | 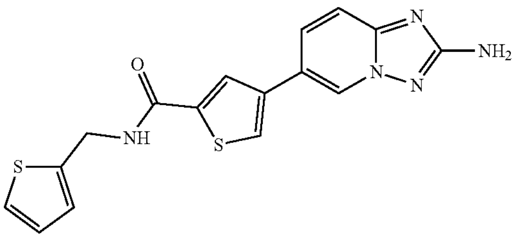 |
| 275 | 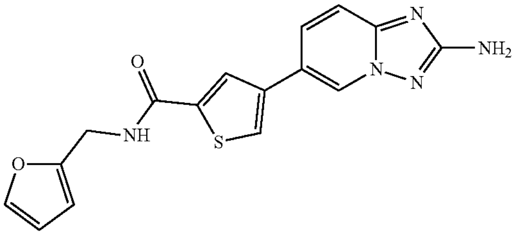 [SMILES: Nc1nc2ccc(-c3csc(C(=O)NCc4ccco4)c3)cn2n1] |
| 276 | 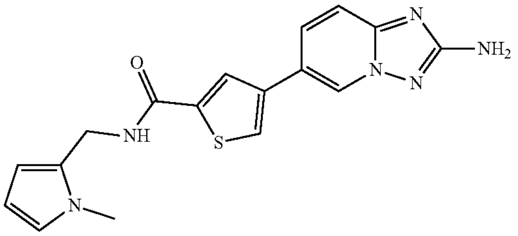 [SMILES: Cn1cccc1CNC(=O)c1cc(-c2ccc3nc(N)nn3c2)cs1] |

TABLE 1C-continued
| Compound Number | Structure |
|---|---|
| 277 | 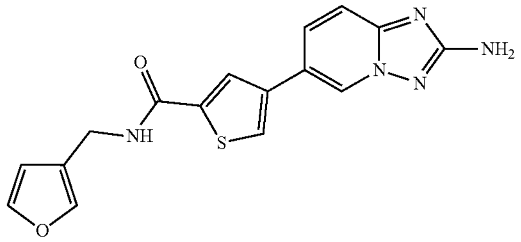 [SMILES: Nc1nc2ccc(-c3csc(C(=O)NCc4ccoc4)c3)cn2n1] |
| 278 | 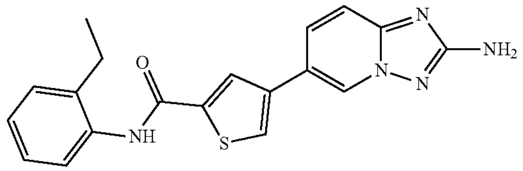 [SMILES: CCc1ccccc1NC(=O)c1cc(-c2ccc3nc(N)nn3c2)cs1] |
| 279 | 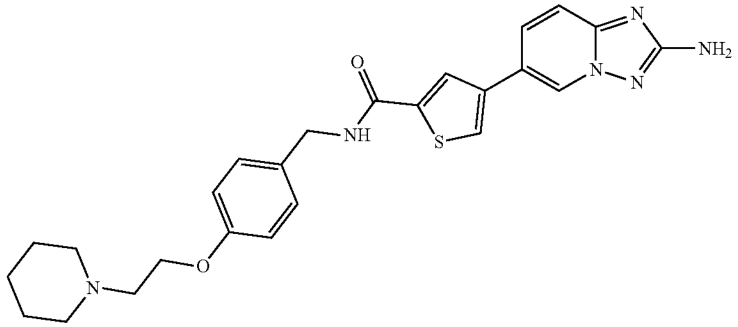 [SMILES: Nc1nc2ccc(-c3csc(C(=O)NCc4ccc(OCCN5CCCCC5)cc4)c3)cn2n1] |
| 280 | 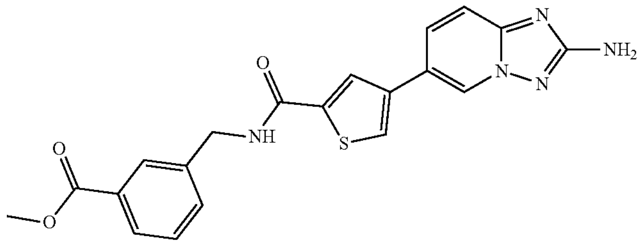 [SMILES: COC(=O)c1cccc(CNC(=O)c2cc(-c3ccc4nc(N)nn4c3)cs2)c1] |
| 281 | 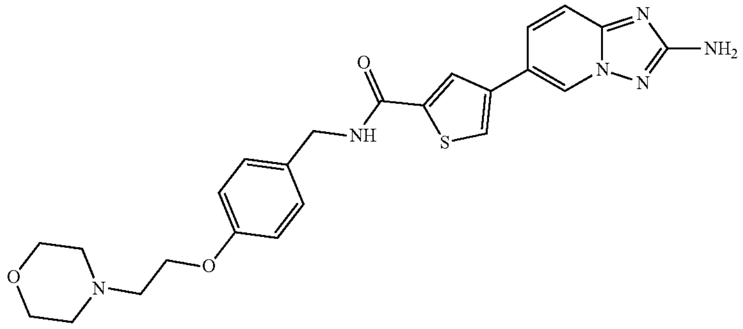 [SMILES: Nc1nc2ccc(-c3csc(C(=O)NCc4ccc(OCCN5CCOCC5)cc4)c3)cn2n1] |
| 282 | 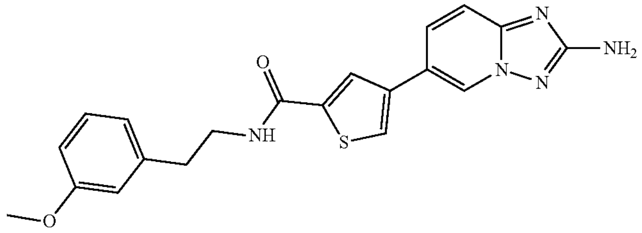 [SMILES: COc1cccc(CCNC(=O)c2cc(-c3ccc4nc(N)nn4c3)cs2)c1] |

TABLE 1C-continued
| Compound Number | Structure |
|---|---|
| 283 | 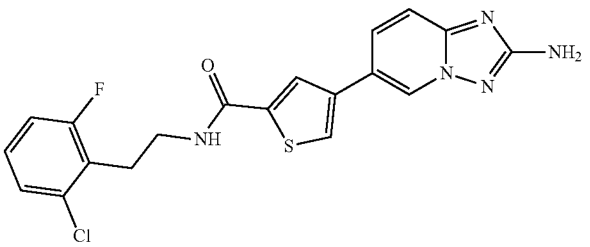 [SMILES: Nc1nc2ccc(-c3csc(C(=O)NCCc4c(F)cccc4Cl)c3)cn2n1] |
| 284 | 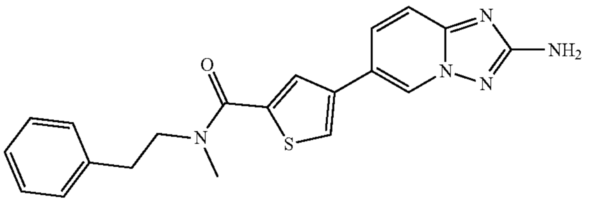 [SMILES: CN(CCc1ccccc1)C(=O)c1cc(-c2ccc3nc(N)nn3c2)cs1] |
| 285 | 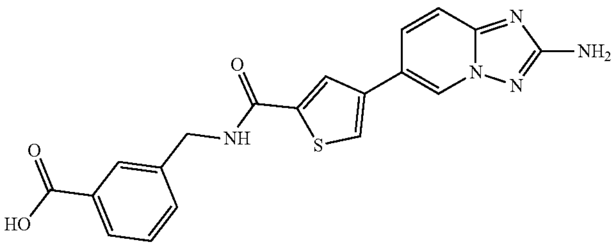 [SMILES: Nc1nc2ccc(-c3csc(C(=O)NCc4cccc(C(=O)O)c4)c3)cn2n1] |
| 286 | 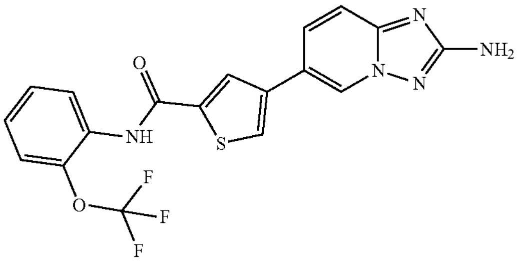 [SMILES: Nc1nc2ccc(-c3csc(C(=O)Nc4ccccc4OC(F)(F)F)c3)cn2n1] |
| 287 | 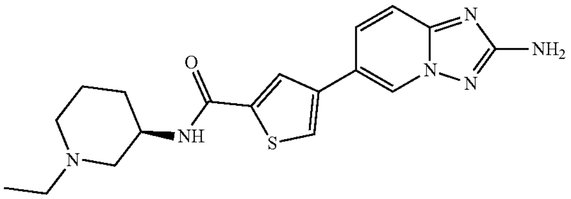 [SMILES: CCN1CCC[C@@H](NC(=O)c2cc(-c3ccc4nc(N)nn4c3)cs2)C1] |
| 288 | 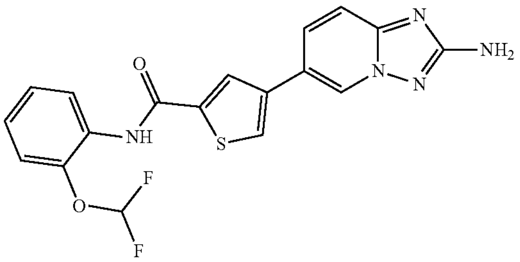 [SMILES: Nc1nc2ccc(-c3csc(C(=O)Nc4ccccc4OC(F)F)c3)cn2n1]

TABLE 1C-continued
| Compound Number | Structure |
| --- | --- |
| 289 | 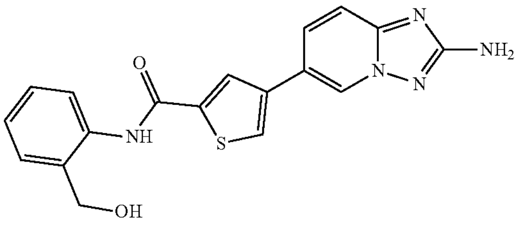 [SMILES: Nc1nc2ccc(-c3csc(C(=O)Nc4ccccc4CO)c3)cn2n1] |
| 290 | 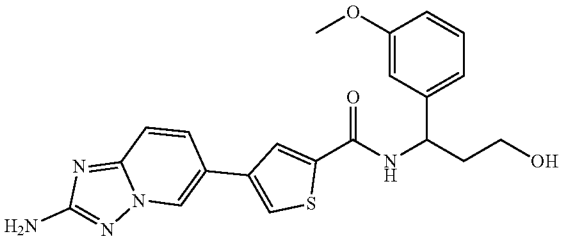 [SMILES: COc1cccc(C(CCO)NC(=O)c2cc(-c3ccc4nc(N)nn4c3)cs2)c1] |
| 291 | 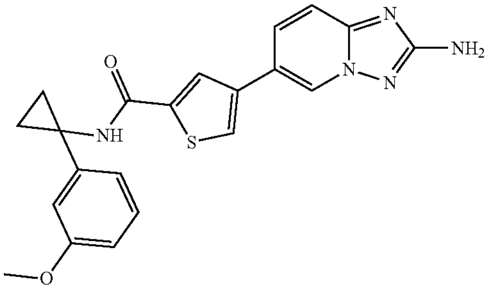 [SMILES: COc1cccc(C2(NC(=O)c3cc(-c4ccc5nc(N)nn5c4)cs3)CC2)c1] |
| 292 | 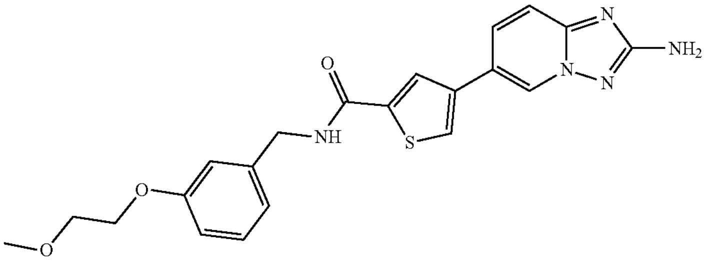 [SMILES: COCCOc1cccc(CNC(=O)c2cc(-c3ccc4nc(N)nn4c3)cs2)c1] |
| 293 | 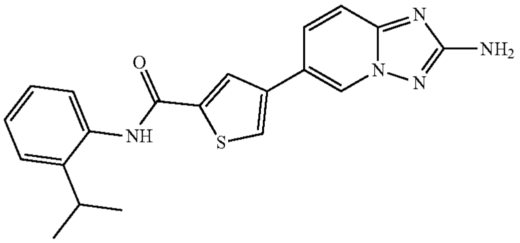 [SMILES: CC(C)c1ccccc1NC(=O)c1cc(-c2ccc3nc(N)nn3c2)cs1] |
| 294 | 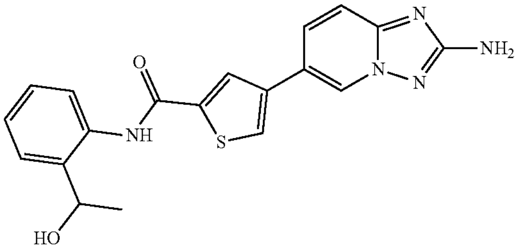 [SMILES: CC(O)c1ccccc1NC(=O)c1cc(-c2ccc3nc(N)nn3c2)cs1] |

TABLE 1C-continued
| Compound Number | Structure |
|---|---|
| 295 | 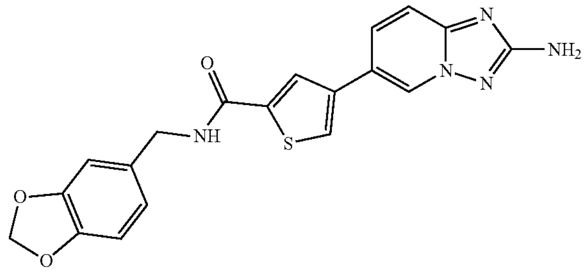 [SMILES: Nc1nc2ccc(-c3csc(C(=O)NCc4ccc5c(c4)OCO5)c3)cn2n1] |
| 296 | 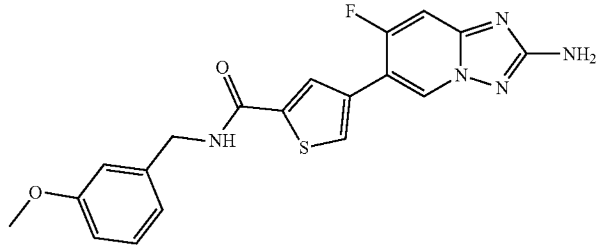 [SMILES: COc1cccc(CNC(=O)c2cc(-c3cn4nc(N)nc4cc3F)cs2)c1] |
| 297 | 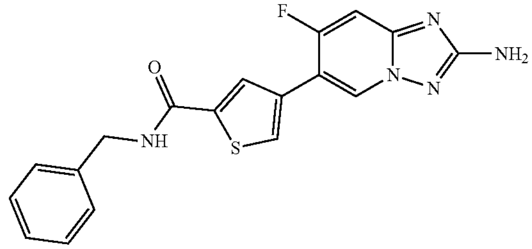 [SMILES: Nc1nc2cc(F)c(-c3csc(C(=O)NCc4ccccc4)c3)cn2n1] |
| 298 | 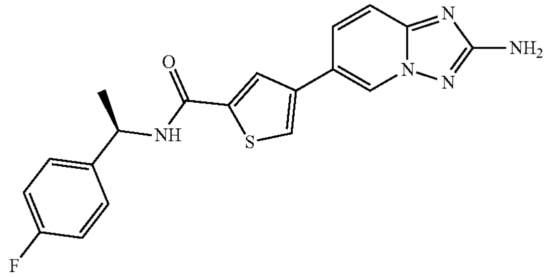 [SMILES: C[C@@H](NC(=O)c1cc(-c2ccc3nc(N)nn3c2)cs1)c1ccc(F)cc1] |
| 299 | 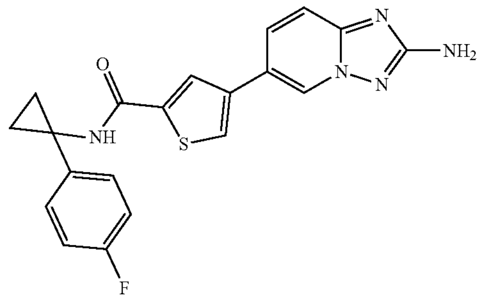 [SMILES: Nc1nc2ccc(-c3csc(C(=O)NC4(c5ccc(F)cc5)CC4)c3)cn2n1] |

TABLE 1C-continued
| Compound Number | Structure |
|---|---|
| 300 | 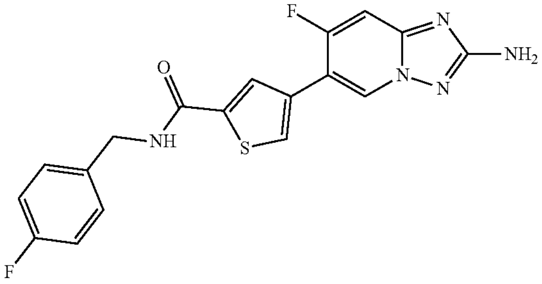 [SMILES: Nc1nc2cc(F)c(-c3csc(C(=O)NCc4ccc(F)cc4)c3)cn2n1] |
| 301 | 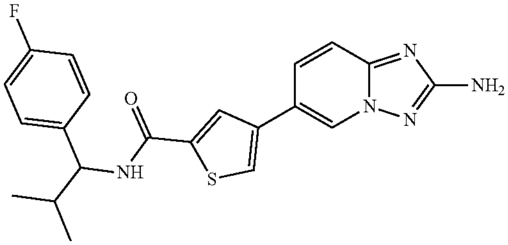 [SMILES: CC(C)C(NC(=O)c1cc(-c2ccc3nc(N)nn3c2)cs1)c1ccc(F)cc1] |
| 302 | 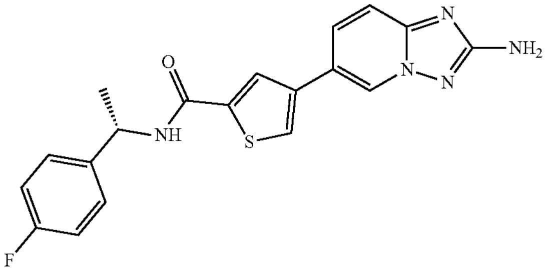 [SMILES: C[C@H](NC(=O)c1cc(-c2ccc3nc(N)nn3c2)cs1)c1ccc(F)cc1] |
| 303 | 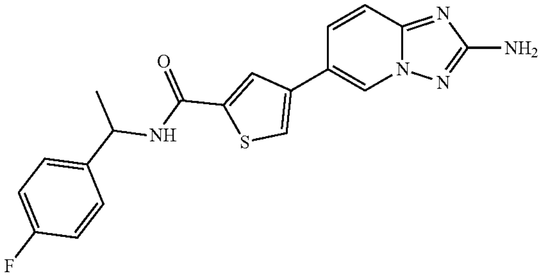 [SMILES: CC(NC(=O)c1cc(-c2ccc3nc(N)nn3c2)cs1)c1ccc(F)cc1] |
| 304 | 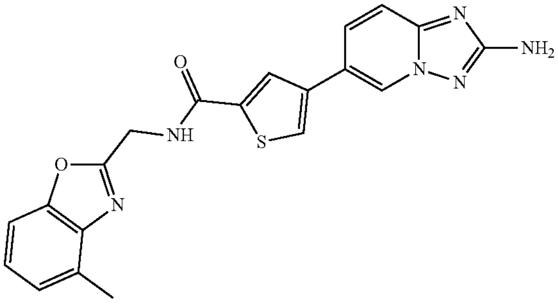 [SMILES: Cc1cccc2oc(CNC(=O)c3cc(-c4ccc5nc(N)nn5c4)cs3)nc12] |

TABLE 1C-continued
| Compound Number | Structure |
|---|---|
| 305 | 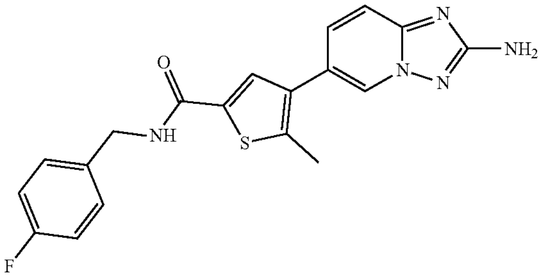 [SMILES: Cc1sc(C(=O)NCc2ccc(F)cc2)cc1-c1ccc2nc(N)nn2c1] |
| 306 | 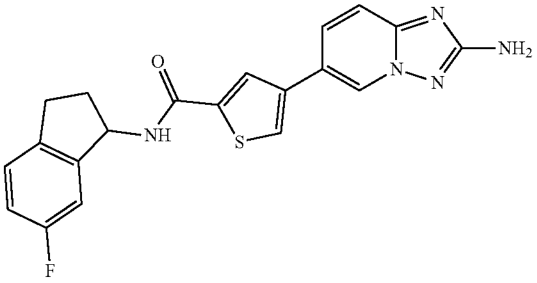 [SMILES: Nc1nc2ccc(-c3csc(C(=O)NC4CCc5ccc(F)cc54)c3)cn2n1] |
| 307 | 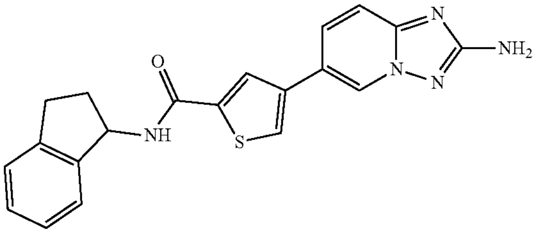 [SMILES: Nc1nc2ccc(-c3csc(C(=O)NC4CCc5ccccc54)c3)cn2n1] |
| 308 | 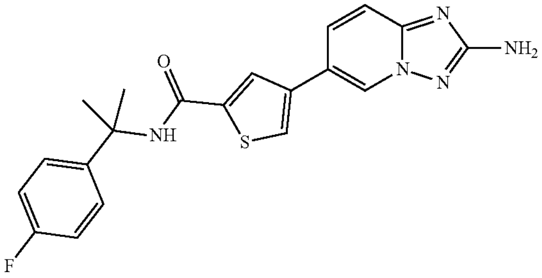 [SMILES: CC(C)(NC(=O)c1cc(-c2ccc3nc(N)nn3c2)cs1)c1ccc(F)cc1] |
| 309 | 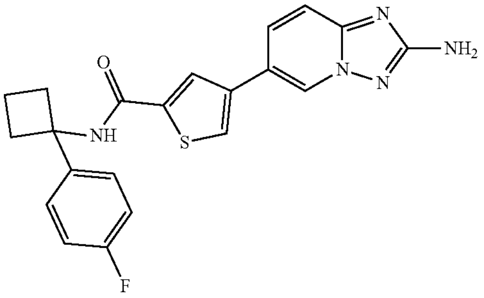 [SMILES: Nc1nc2ccc(-c3csc(C(=O)NC4(c5ccc(F)cc5)CCC4)c3)cn2n1] |

TABLE 1C-continued
| Compound Number | Structure |
|---|---|
| 310 | 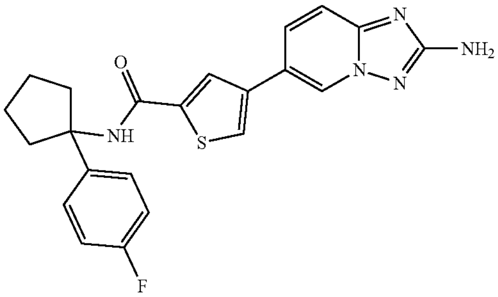 [SMILES: Nc1nc2ccc(-c3csc(C(=O)NC4(c5ccc(F)cc5)CCCC4)c3)cn2n1] |
| 311 | 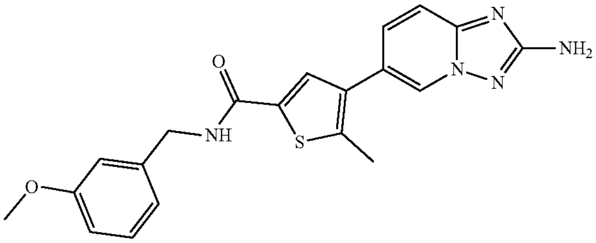 [SMILES: COc1cccc(CNC(=O)c2cc(-c3ccc4nc(N)nn4c3)c(C)s2)c1] |
| 312 | 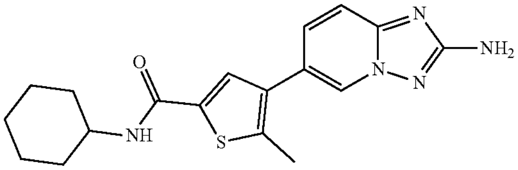 [SMILES: Cc1sc(C(=O)NC2CCCCC2)cc1-c1ccc2nc(N)nn2c1] |
| 313 | 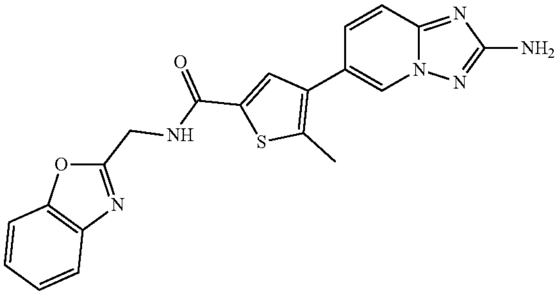 [SMILES: Cc1sc(C(=O)NCc2nc3ccccc3o2)cc1-c1ccc2nc(N)nn2c1] |
| 314 | 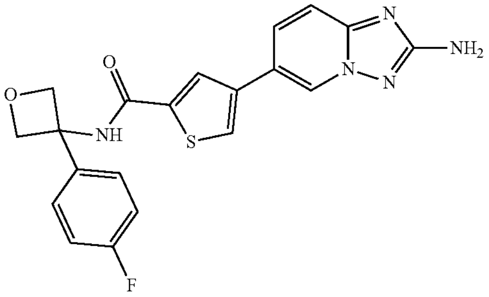 [SMILES: Nc1nc2ccc(-c3csc(C(=O)NC4(c5ccc(F)cc5)COC4)c3)cn2n1] |
| 315 | 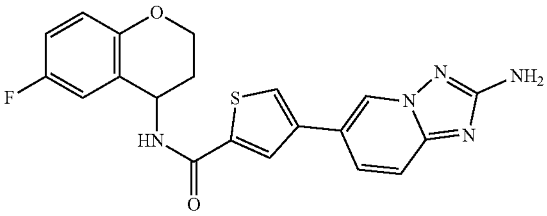 [SMILES: Nc1nc2ccc(-c3csc(C(=O)NC4CCOc5ccc(F)cc54)c3)cn2n1] |

TABLE 1C-continued
| Compound Number | Structure |
|---|---|
| 316 | 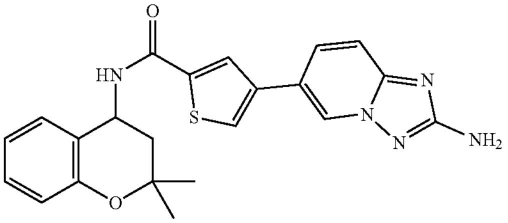 [SMILES: CC1(C)CC(NC(=O)c2cc(-c3ccc4nc(N)nn4c3)cs2)c2ccccc2O1] |
| 317 | 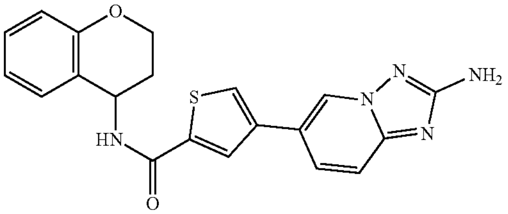 [SMILES: Nc1nc2ccc(-c3csc(C(=O)NC4CCOc5ccccc54)c3)cn2n1] |
| 318 | 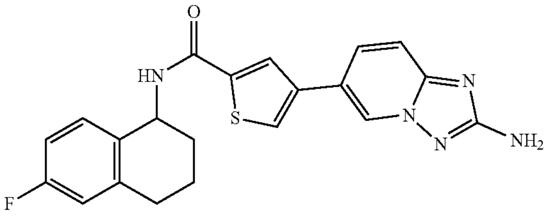 [SMILES: Nc1nc2ccc(-c3csc(C(=O)NC4CCCc5cc(F)ccc54)c3)cn2n1] |
| 319 | 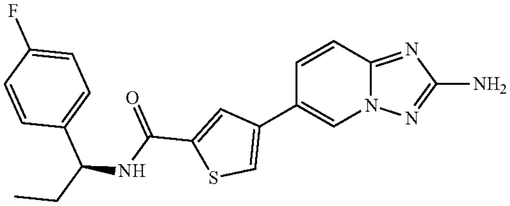 [SMILES: CC[C@H](NC(=O)c1cc(-c2ccc3nc(N)nn3c2)cs1)c1ccc(F)cc1] |
| 320 | 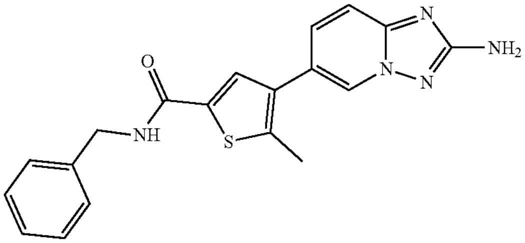 [SMILES: Cc1sc(C(=O)NCc2ccccc2)cc1-c1ccc2nc(N)nn2c1] |
| 321 | 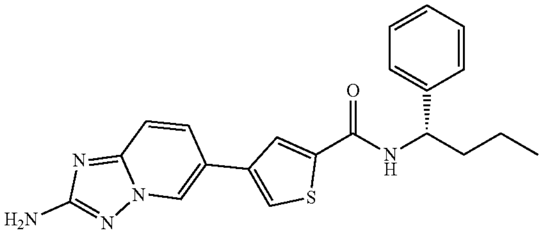 |

TABLE 1C-continued
| Compound Number | Structure |
| --- | --- |
| 322 | 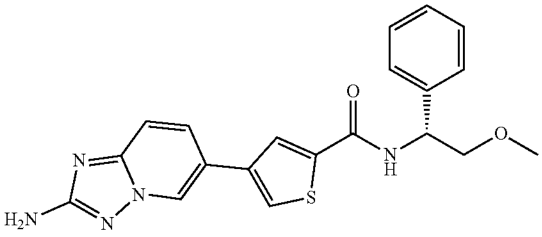 |
| 323 | 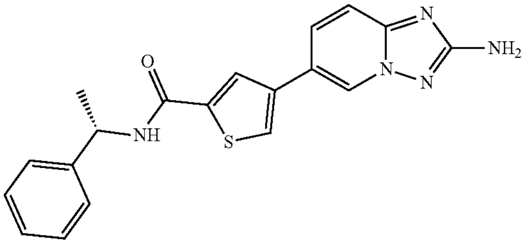 [SMILES: C[C@H](NC(=O)c1cc(-c2ccc3nc(N)nn3c2)cs1)c1ccccc1] |
| 324 | 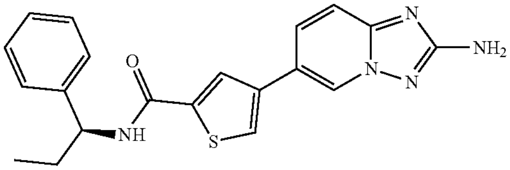 [SMILES: CC[C@H](NC(=O)c1cc(-c2ccc3nc(N)nn3c2)cs1)c1ccccc1] |
| 325 | 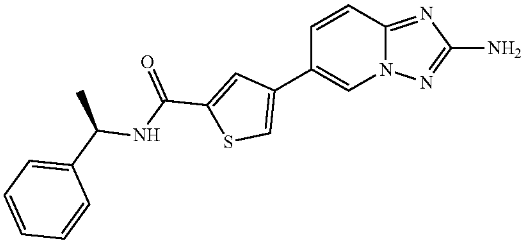 [SMILES: C[C@@H](NC(=O)c1cc(-c2ccc3nc(N)nn3c2)cs1)c1ccccc1] |
| 326 | 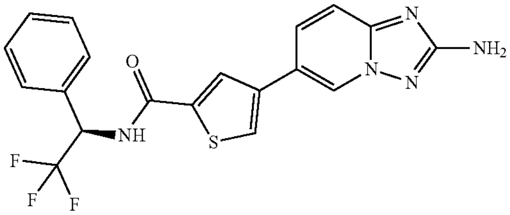 [SMILES: Nc1nc2ccc(-c3csc(C(=O)N[C@H](c4ccccc4)C(F)(F)F)c3)cn2n1] |
| 327 | 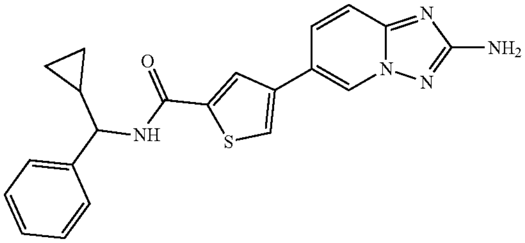 [SMILES: Nc1nc2ccc(-c3csc(C(=O)NC(c4ccccc4)C4CC4)c3)cn2n1] |

TABLE 1C-continued
| Compound Number | Structure |
|---|---|
| 328 | 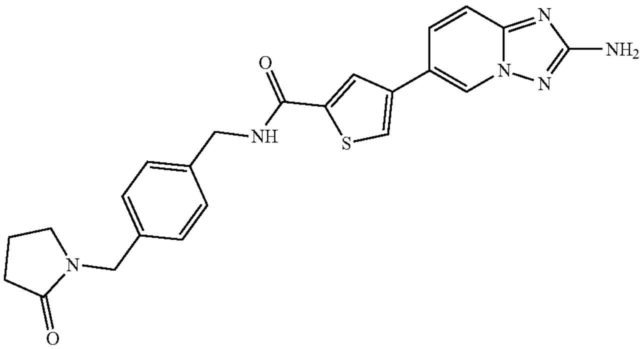 [SMILES: Nc1nc2ccc(-c3csc(C(=O)NCc4ccc(CN5CCCC5=O)cc4)c3)cn2n1] |
| 329 | 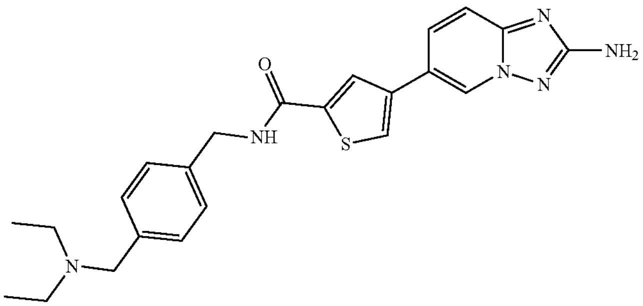 [SMILES: CCN(CC)Cc1ccc(CNC(=O)c2cc(-c3ccc4nc(N)nn4c3)cs2)cc1] |
| 330 | 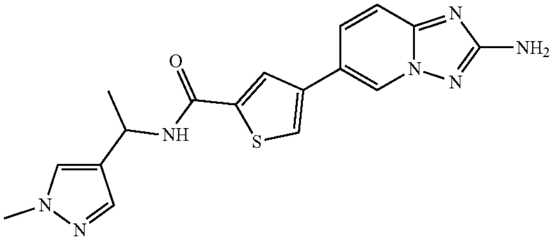 [SMILES: CC(NC(=O)c1cc(-c2ccc3nc(N)nn3c2)cs1)c1cnn(C)c1] |
| 331 | 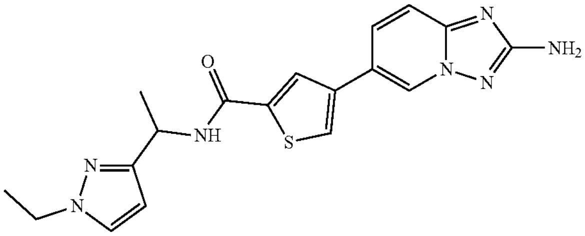 [SMILES: CCn1ccc(C(C)NC(=O)c2cc(-c3ccc4nc(N)nn4c3)cs2)n1] |
| 332 | 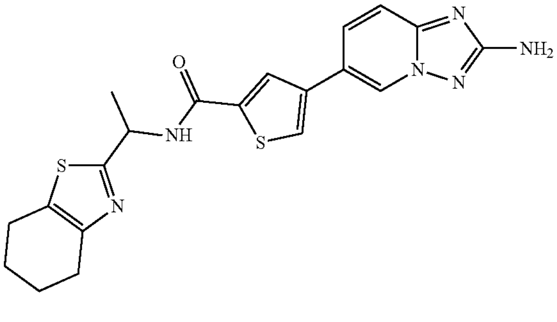 [SMILES: CC(NC(=O)c1cc(-c2ccc3nc(N)nn3c2)cs1)c1nc2c(s1)CCCC2] |

TABLE 1C-continued
| Compound Number | Structure |
|---|---|
| 333 | 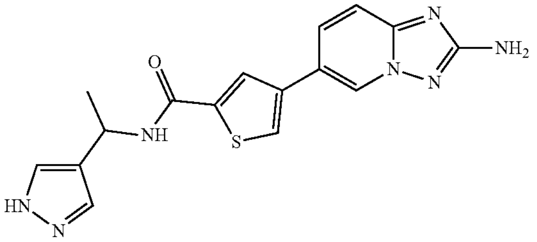 [SMILES: CC(NC(=O)c1cc(-c2ccc3nc(N)nn3c2)cs1)c1cn[nH]c1] |
| 334 | 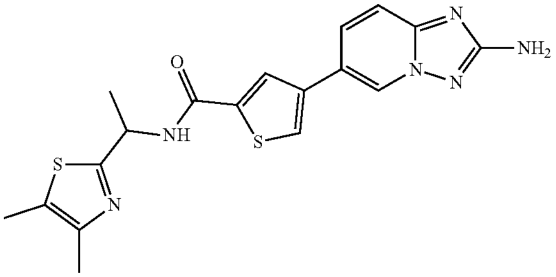 [SMILES: Cc1nc(C(C)NC(=O)c2cc(-c3ccc4nc(N)nn4c3)cs2)sc1C] |
| 335 | 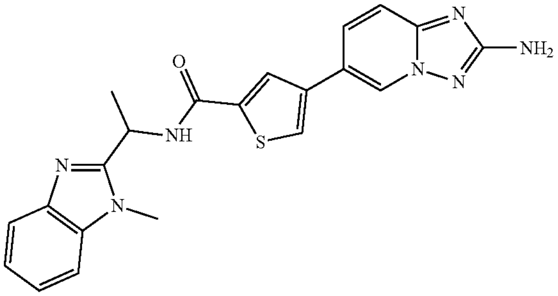 [SMILES: CC(NC(=O)c1cc(-c2ccc3nc(N)nn3c2)cs1)c1nc2ccccc2n1C] |
| 336 | 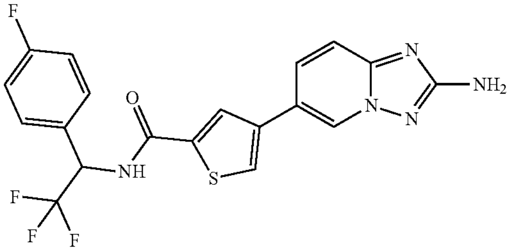 [SMILES: Nc1nc2ccc(-c3csc(C(=O)NC(c4ccc(F)cc4)C(F)(F)F)c3)cn2n1] |
| 337 | 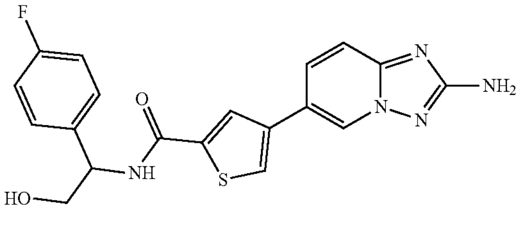 [SMILES: Nc1nc2ccc(-c3csc(C(=O)NC(CO)c4ccc(F)cc4)c3)cn2n1] |
| 338 | 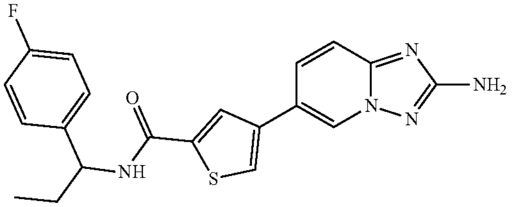 [SMILES: CCC(NC(=O)c1cc(-c2ccc3nc(N)nn3c2)cs1)c1ccc(F)cc1] |

TABLE 1C-continued
| Compound Number | Structure |
|---|---|
| 339 | 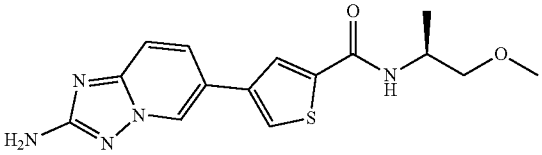 [SMILES: COC[C@H](C)NC(=O)c1cc(-c2ccc3nc(N)nn3c2)cs1] |
| 340 | 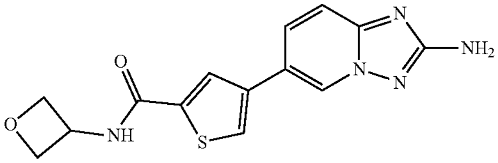 [SMILES: Nc1nc2ccc(-c3csc(C(=O)NC4COC4)c3)cn2n1] |
| 341 | 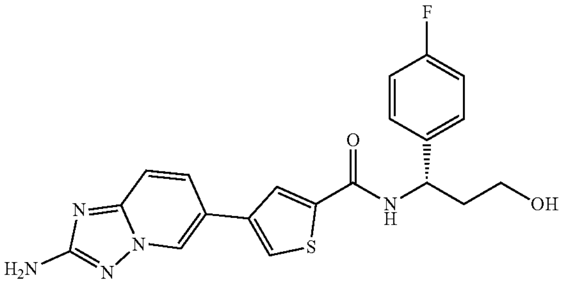 [SMILES: Nc1nc2ccc(-c3csc(C(=O)N[C@@H](CCO)c4ccc(F)cc4)c3)cn2n1] |
| 342 | 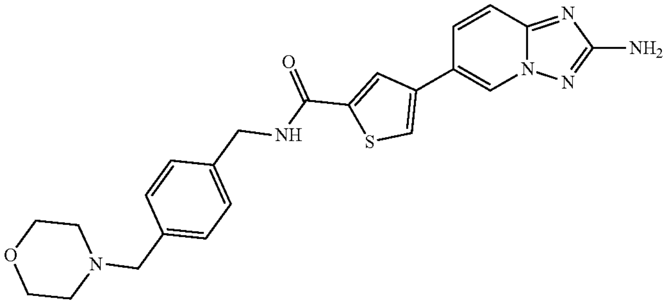 [SMILES: Nc1nc2ccc(-c3csc(C(=O)NCc4ccc(CN5CCOCC5)cc4)c3)cn2n1] |
| 343 | 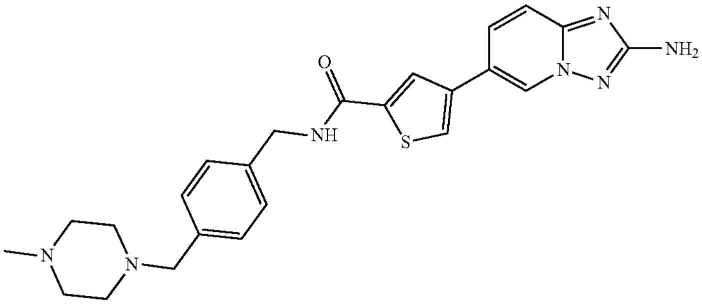 [SMILES: CN1CCN(Cc2ccc(CNC(=O)c3cc(-c4ccc5nc(N)nn5c4)cs3)cc2)CC1] |
| 344 | 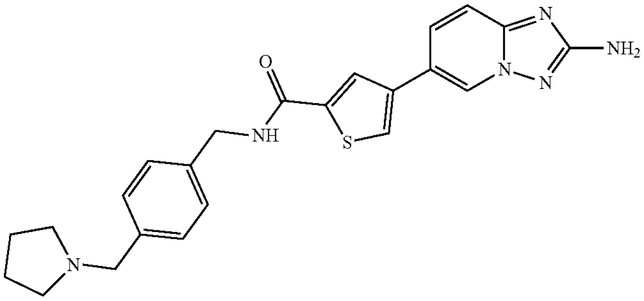 [SMILES: Nc1nc2ccc(-c3csc(C(=O)NCc4ccc(CN5CCCC5)cc4)c3)cn2n1] |

TABLE 1C-continued
| Compound Number | Structure |
| --- | --- |
| 345 | 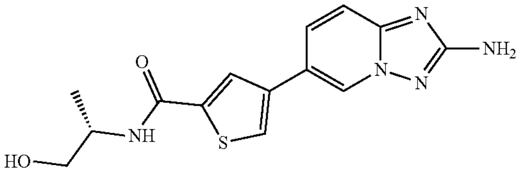 [SMILES: C[C@@H](CO)NC(=O)c1cc(-c2ccc3nc(N)nn3c2)cs1] |
| 346 | 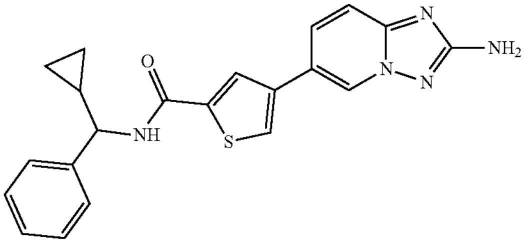 enantiomer 1 |
| 347 | 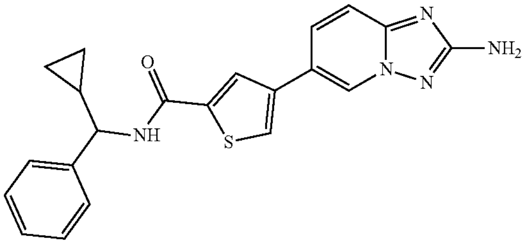 enantiomer 2 |
| 348 | 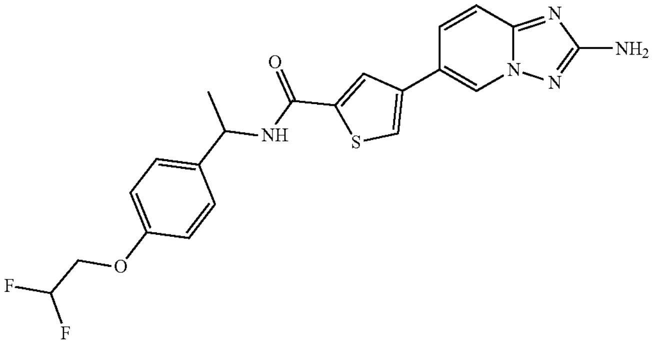 [SMILES: CC(NC(=O)c1cc(-c2ccc3nc(N)nn3c2)cs1)c1ccc(OCC(F)F)cc1] |
| 349 | 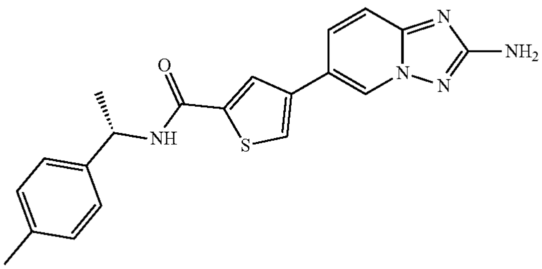 [SMILES: Cc1ccc([C@H](C)NC(=O)c2cc(-c3ccc4nc(N)nn4c3)cs2)cc1] |

TABLE 1C-continued
| Compound Number | Structure |
|---|---|
| 350 | 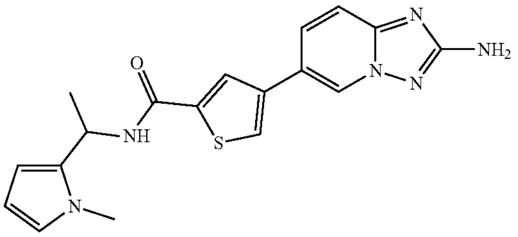 [SMILES: CC(NC(=O)c1cc(-c2ccc3nc(N)nn3c2)cs1)c1cccn1C] |
| 351 | 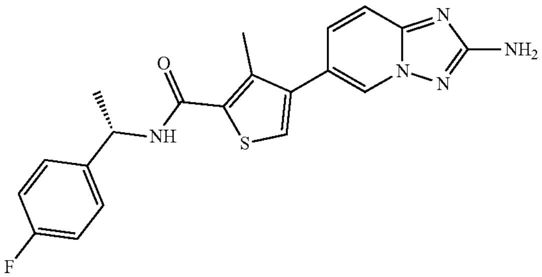 [SMILES: Cc1c(-c2ccc3nc(N)nn3c2)csc1C(=O)N[C@@H](C)c1ccc(F)cc1] |
| 352 | 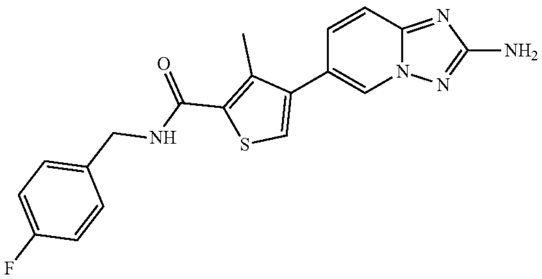 [SMILES: Cc1c(-c2ccc3nc(N)nn3c2)csc1C(=O)NCc1ccc(F)cc1] |
| 353 | 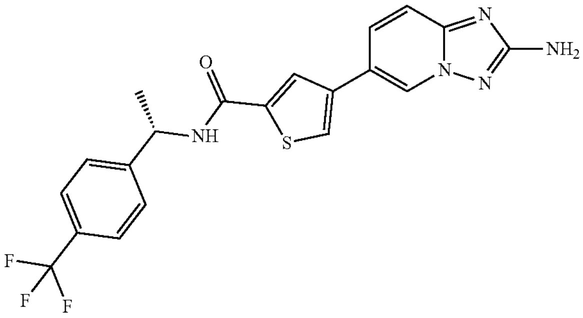 [SMILES: C[C@H](NC(=O)c1cc(-c2ccc3nc(N)nn3c2)cs1)c1ccc(C(F)(F)F)cc1] |
| 354 | 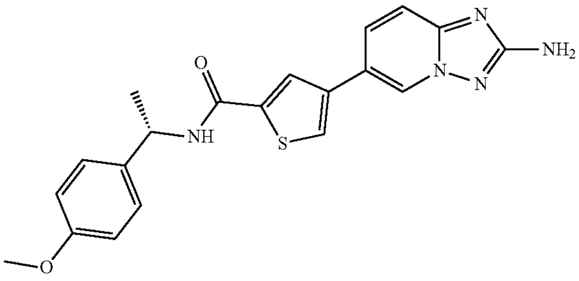 [SMILES: COc1ccc([C@H](C)NC(=O)c2cc(-c3ccc4nc(N)nn4c3)cs2)cc1] |

TABLE 1C-continued
| Compound Number | Structure |
|---|---|
| 355 | 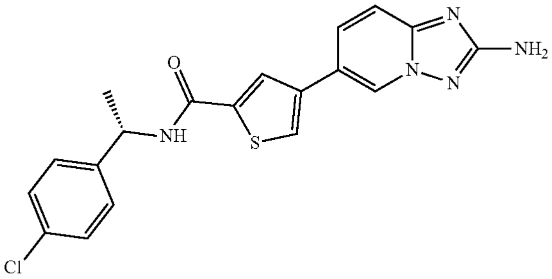 [SMILES: C[C@H](NC(=O)c1cc(-c2ccc3nc(N)nn3c2)cs1)c1ccc(Cl)cc1] |
| 356 | 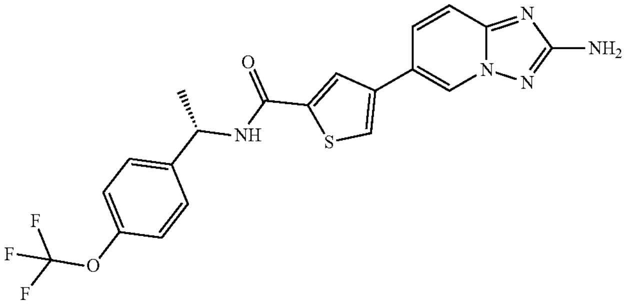 [SMILES: C[C@H](NC(=O)c1cc(-c2ccc3nc(N)nn3c2)cs1)c1ccc(OC(F)(F)F)cc1] |
| 357 | 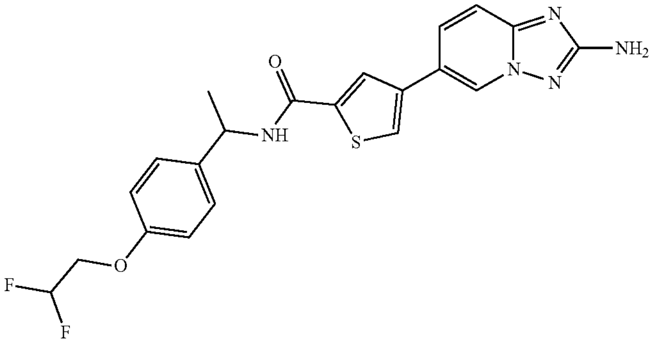 [SMILES: CC(NC(=O)c1cc(-c2ccc3nc(N)nn3c2)cs1)c1ccc(OCC(F)F)cc1] |
| 358 | 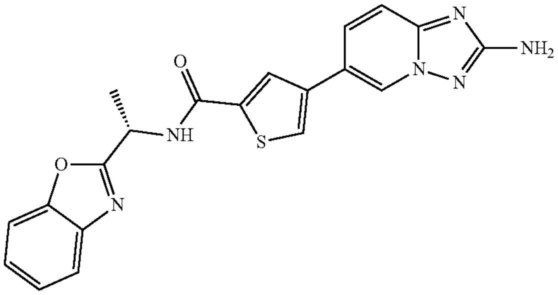 [SMILES: C[C@H](NC(=O)c1cc(-c2ccc3nc(N)nn3c2)cs1)c1nc2ccccc2o1] |
| 359 | 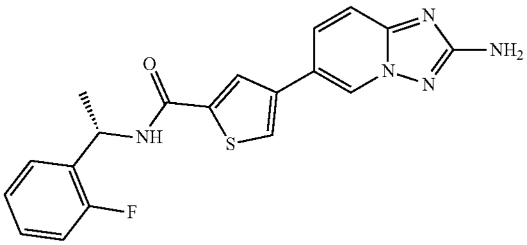 [SMILES: C[C@H](NC(=O)c1cc(-c2ccc3nc(N)nn3c2)cs1)c1ccccc1F] |

TABLE 1C-continued
| Compound Number | Structure |
| --- | --- |
| 360 | 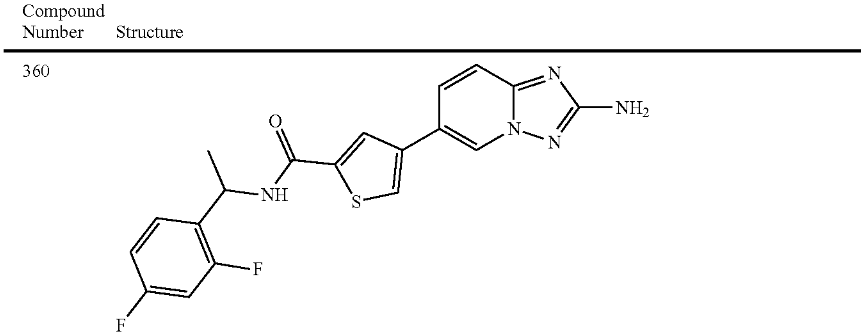 |
| 361 | 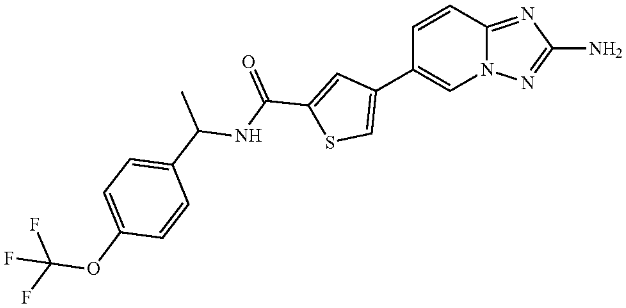 [SMILES: CC(NC(=O)c1cc(-c2ccc3nc(N)nn3c2)cs1)c1ccc(OC(F)(F)F)cc1] |
| 362 | 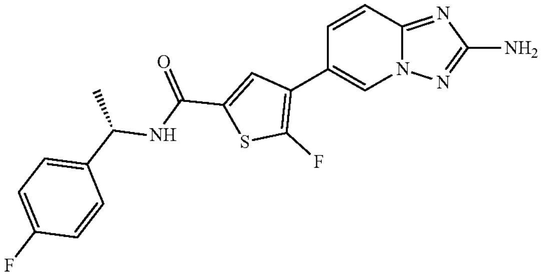 [SMILES: C[C@H](NC(=O)c1cc(-c2ccc3nc(N)nn3c2)c(F)s1)c1ccc(F)cc1] |
TABLE 1E
| Compound Number | Structure |
| --- | --- |
| 372 | 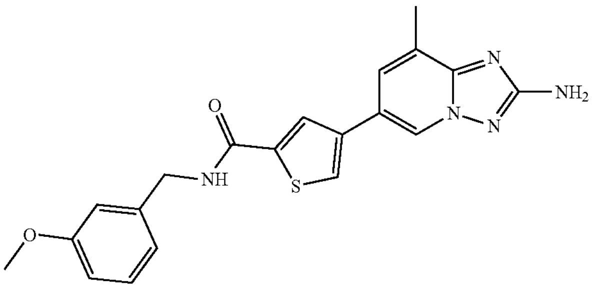 [SMILES: COc1cccc(CNC(=O)c2cc(-c3cc(C)c4nc(N)nn4c3)cs2)c1] |

TABLE 1E-continued
| Compound Number | Structure |
|---|---|
| 373 | 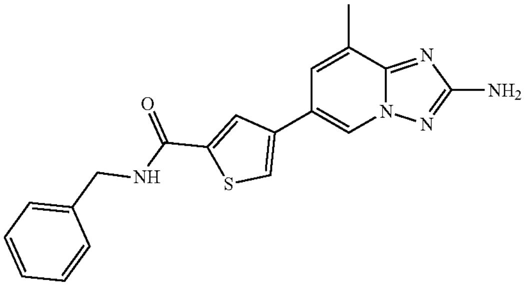 [SMILES: Cc1cc(-c2csc(C(=O)NCc3ccccc3)c2)cn2nc(N)nc12] |
| 374 | 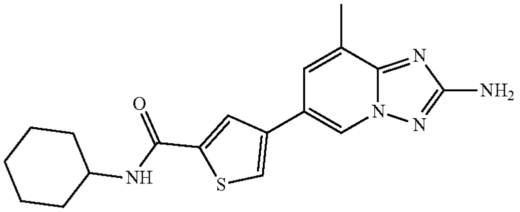 [SMILES: Cc1cc(-c2csc(C(=O)NC3CCCCC3)c2)cn2nc(N)nc12] |
| 375 | 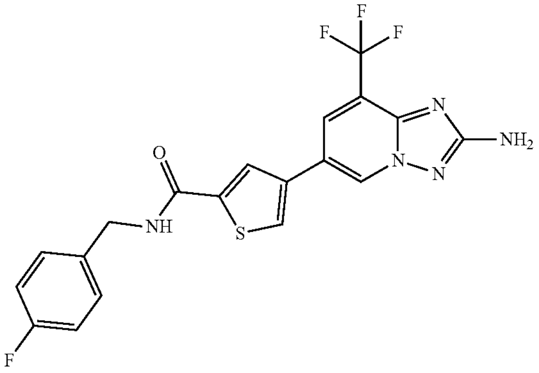 [SMILES: Nc1nc2c(C(F)(F)F)cc(-c3csc(C(=O)NCc4ccc(F)cc4)c3)cn2n1] |
| 376 | 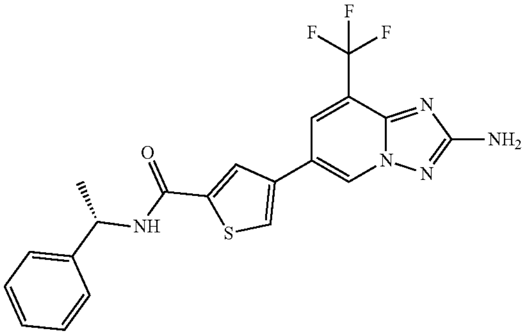 [SMILES: C[C@H](NC(=O)c1cc(-c2cc(C(F)(F)F)c3nc(N)nn3c2)cs1)c1ccccc1] |

TABLE 1E-continued
| Compound Number | Structure |
|---|---|
| 377 | 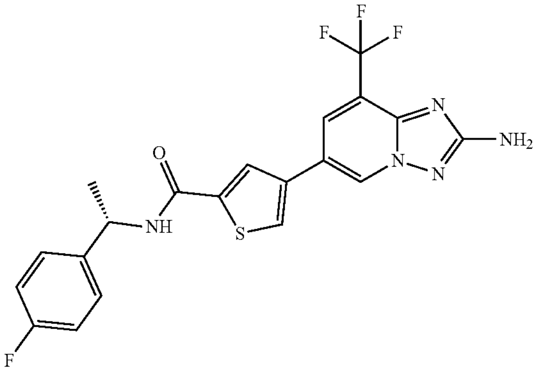 [SMILES: C[C@H](NC(=O)c1cc(-c2cc(C(F)(F)F)c3nc(N)nn3c2)cs1)c1ccc(F)cc1] |
| 378 | 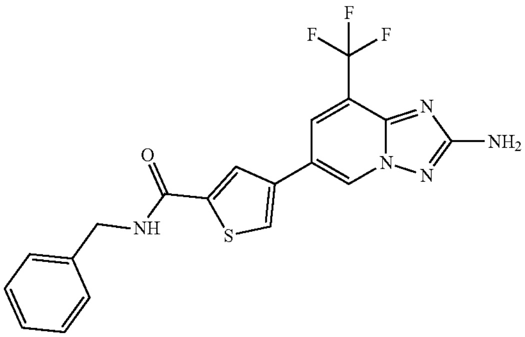 [SMILES: Nc1nc2c(C(F)(F)F)cc(-c3csc(C(=O)NCc4ccccc4)c3)cn2n1] |
| 379 | 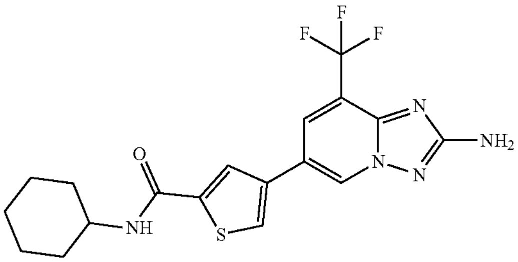 [SMILES: Nc1nc2c(C(F)(F)F)cc(-c3csc(C(=O)NC4CCCCC4)c3)cn2n1] |
| 380 | 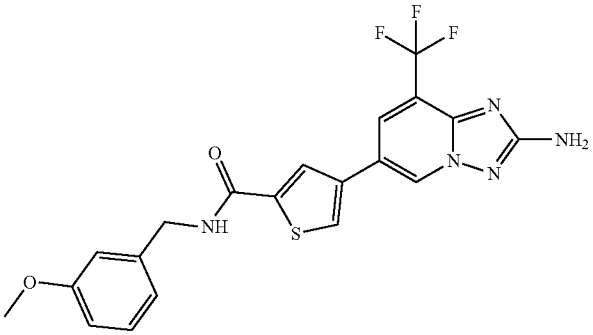 [SMILES: COc1cccc(CNC(=O)c2cc(-c3cc(C(F)(F)F)c4nc(N)nn4c3)cs2)c1] |

TABLE 1E-continued
| Compound Number | Structure |
|---|---|
| 381 | 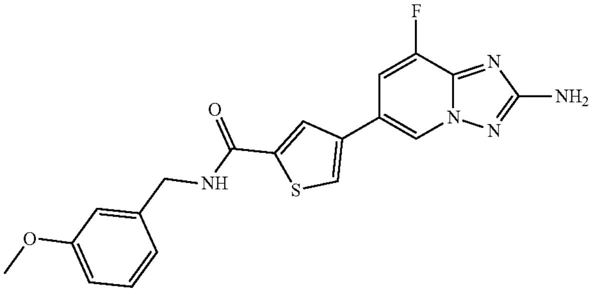 [SMILES: COc1cccc(CNC(=O)c2cc(-c3cc(F)c4nc(N)nn4c3)cs2)c1] |
| 382 | 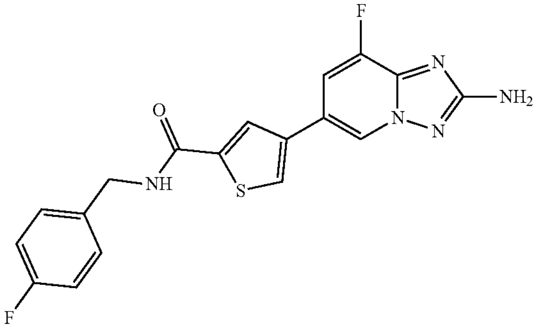 [SMILES: Nc1nc2c(F)cc(-c3csc(C(=O)NCc4ccc(F)cc4)c3)cn2n1] |
| 383 | 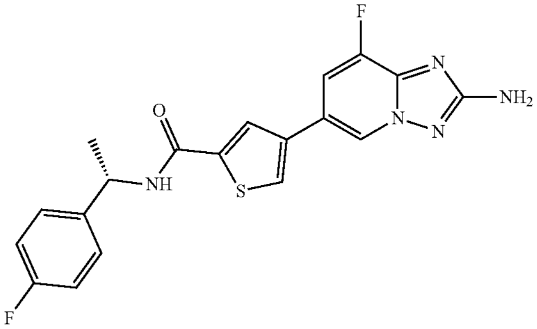 [SMILES: C[C@H](NC(=O)c1cc(-c2cc(F)c3nc(N)nn3c2)cs1)c1ccc(F)cc1] |
| 384 | 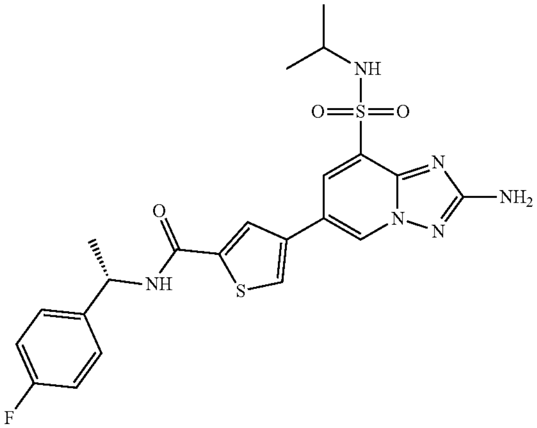 [SMILES: CC(C)NS(=O)(=O)c1cc(-c2csc(C(=O)N[C@@H](C)c3ccc(F)cc3)c2)cn2nc(N)nc12] |

TABLE 1E-continued
| Compound Number | Structure |
|---|---|
| 385 | 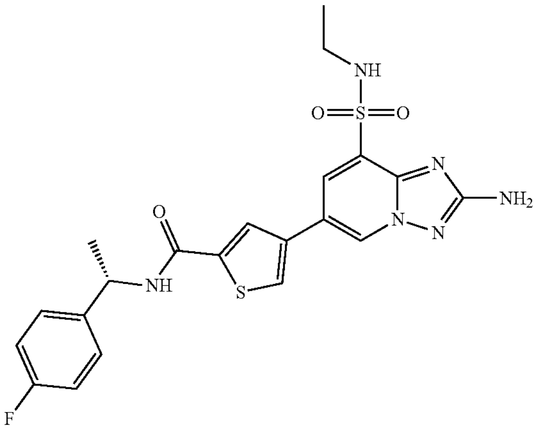 [SMILES: CCNS(=O)(=O)c1cc(-c2csc(C(=O)N[C@@H](C)c3ccc(F)cc3)c2)cn2nc(N)nc12] |
| 386 | 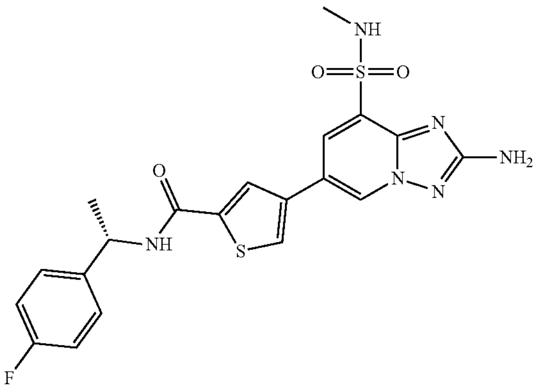 [SMILES: CNS(=O)(=O)c1cc(-c2csc(C(=O)N[C@@H](C)c3ccc(F)cc3)c2)cn2nc(N)nc12] |
| 387 | 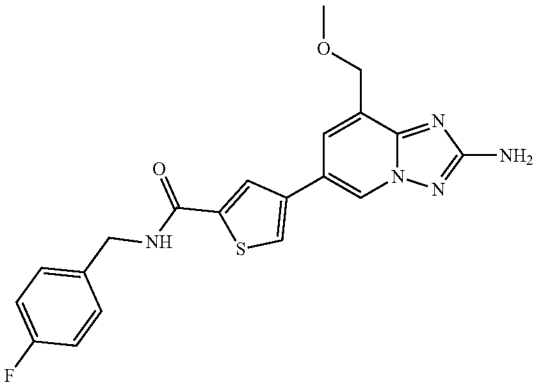 [SMILES: COCc1cc(-c2csc(C(=O)NCc3ccc(F)cc3)c2)cn2nc(N)nc12] |

TABLE 1E-continued
| Compound Number | Structure |
|---|---|
| 388 | 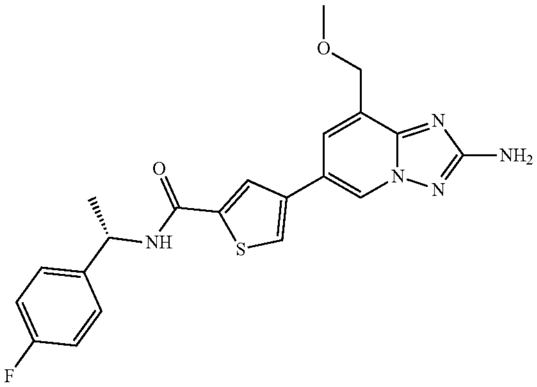 [SMILES: COCc1cc(-c2csc(C(=O)N[C@@H](C)c3ccc(F)cc3)c2)cn2nc(N)nc12] |
| 389 | 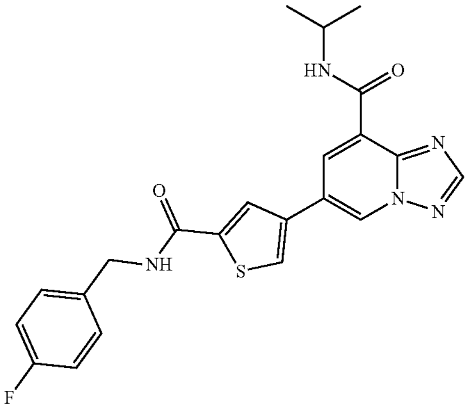 [SMILES: CC(C)NC(=O)c1cc(-c2csc(C(=O)NCc3ccc(F)cc3)c2)cn2ncnc12] |
| 390 | 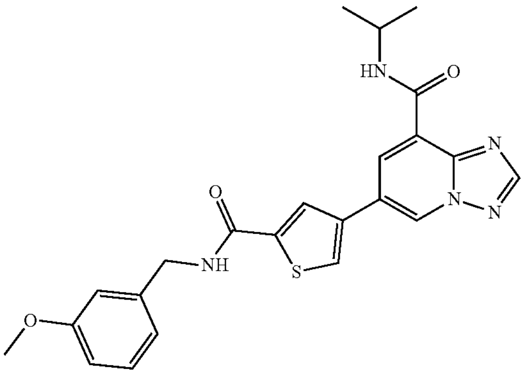 [SMILES: COc1cccc(CNC(=O)c2cc(-c3cc(C(=O)NC(C)C)c4ncnn4c3)cs2)c1] |

TABLE 1E-continued
| Compound Number | Structure |
| --- | --- |
| 391 | 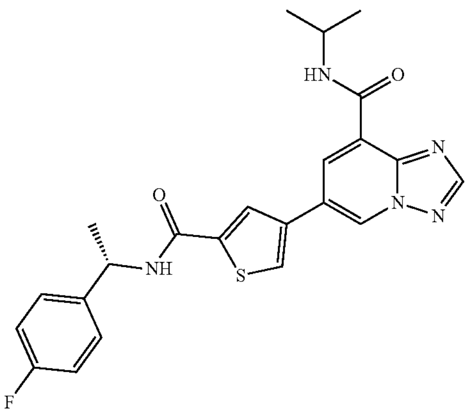 [SMILES: CC(C)NC(=O)c1cc(-c2csc(C(=O)N[C@@H](C)c3ccc(F)cc3)c2)cn2ncnc12] |
TABLE 1F
| Compound Number | Structure |
| --- | --- |
| 392 | 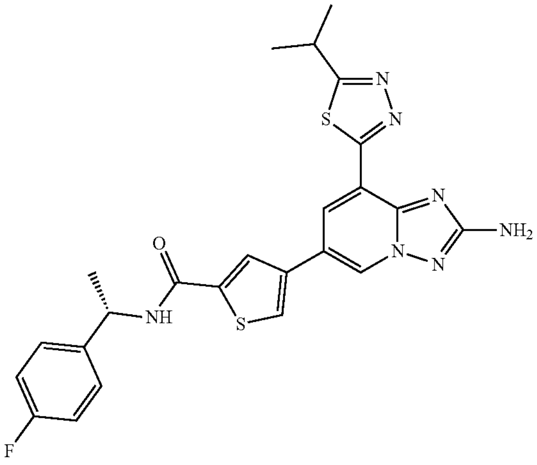 [SMILES: CC(C)c1nnc(-c2cc(-c3csc(C(=O)N[C@@H](C)c4ccc(F)cc4)c3)cn3nc(N)nc23)s1] |
| 393 | 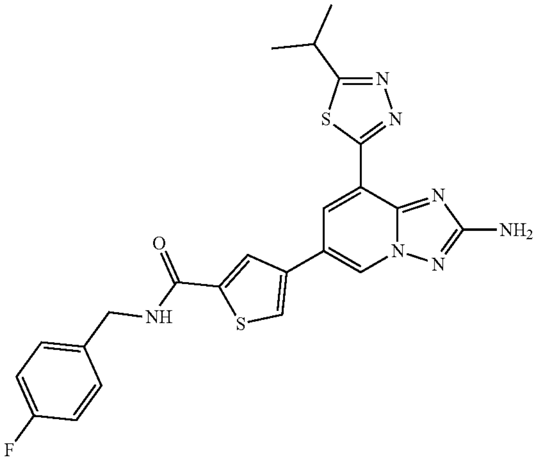 [SMILES: CC(C)c1nnc(-c2cc(-c3csc(C(=O)NCc4ccc(F)cc4)c3)cn3nc(N)nc23)s1] |

TABLE 1F-continued
| Compound Number | Structure |
|---|---|
| 394 | 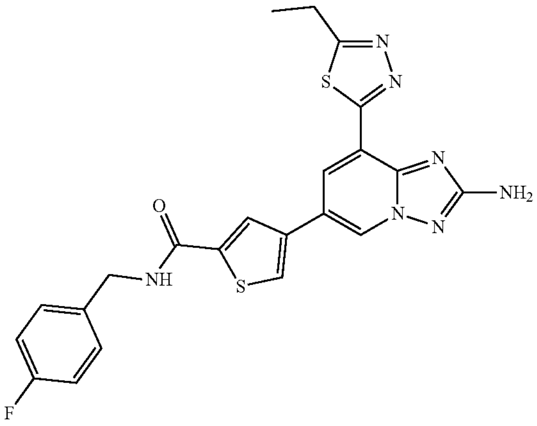 [SMILES: CCc1nnc(-c2cc(-c3csc(C(=O)NCc4ccc(F)cc4)c3)cn3nc(N)nc23)o1] |
| 395 | 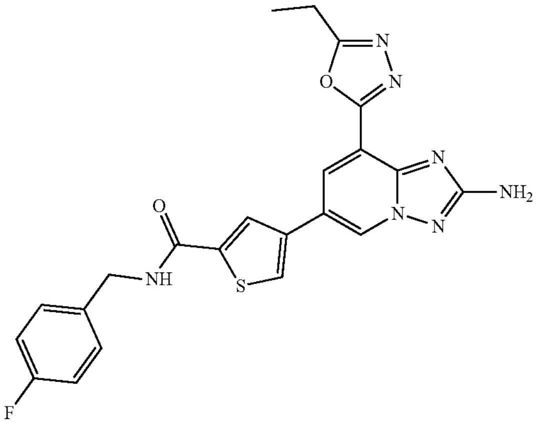 |
| 396 | 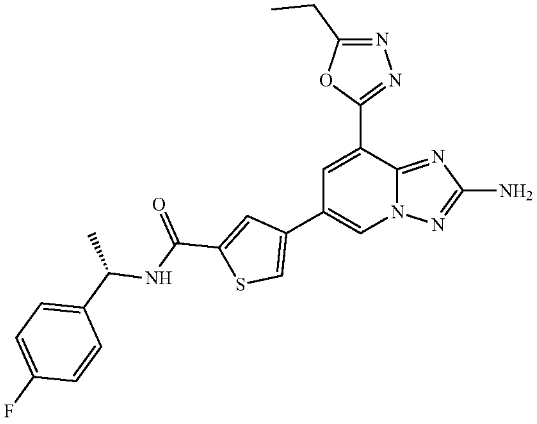 [SMILES: CCc1nnc(-c2cc(-c3csc(C(=O)N[C@@H](C)c4ccc(F)cc4)c3)cn3nc(N)nc23)o1] |

TABLE 1F-continued
| Compound Number | Structure |
| --- | --- |
| 397 | 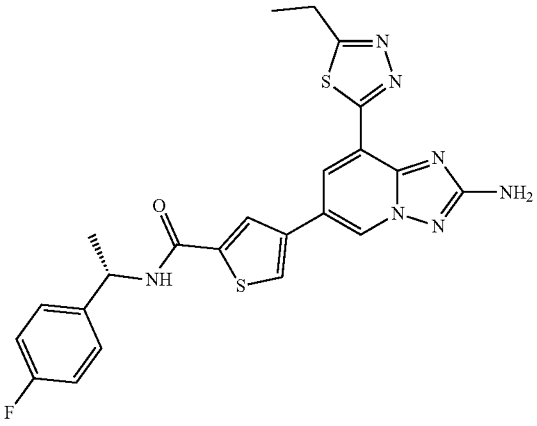 [SMILES: CCc1nnc(-c2cc(-c3csc(C(=O)N[C@@H](C)c4ccc(F)cc4)c3)cn3nc(N)nc23)s1] |
| 398 | 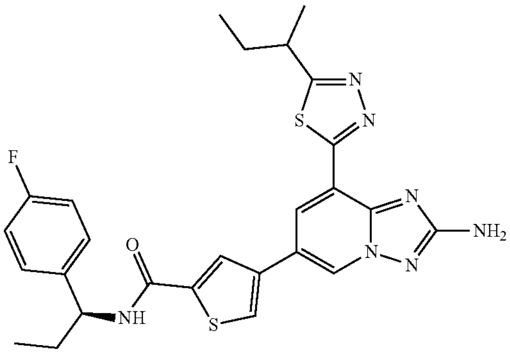 [SMILES: CCC(C)c1nnc(-c2cc(-c3csc(C(=O)N[C@@H](CC)c4ccc(F)cc4)c3)cn3nc(N)nc23)s1] |
| 399 | 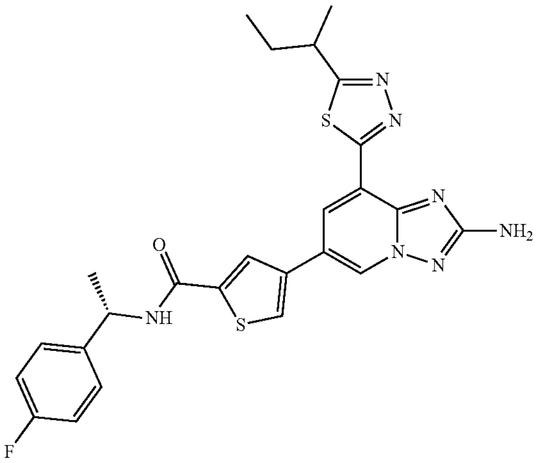 [SMILES: CCC(C)c1nnc(-c2cc(-c3csc(C(=O)N[C@@H](C)c4ccc(F)cc4)c3)cn3nc(N)nc23)s1] |

TABLE 1F-continued

| Compound Number | Structure |
|---|---|
| 400 | 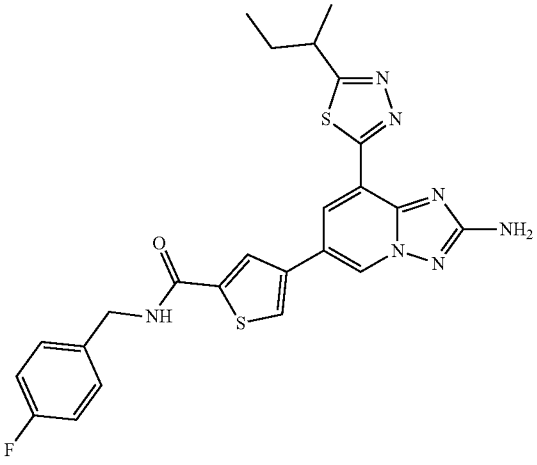 [SMILES: CCC(C)c1nnc(-c2cc(-c3csc(C(=O)NCc4ccc(F)cc4)c3)cn3nc(N)nc23)s1] |
| 401 | 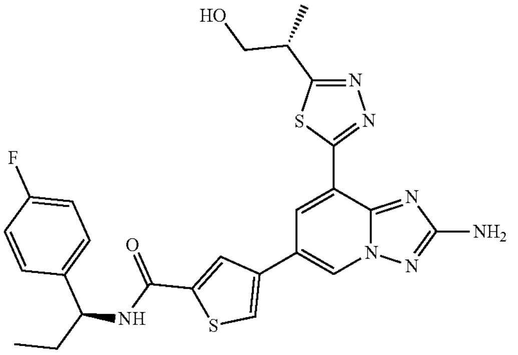 [SMILES: CC[C@H](NC(=O)c1cc(-c2cc(-c3nnc([C@@H](C)CO)s3)c3nc(N)nn3c2)cs1)c1ccc(F)cc1] |
| 403 | 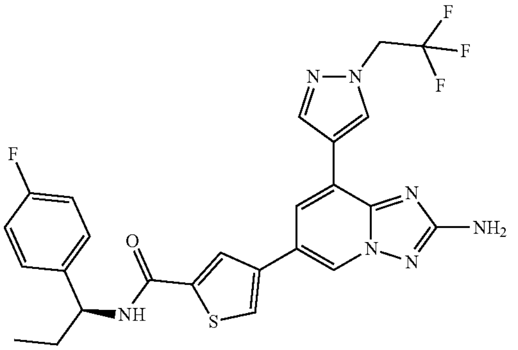 [SMILES: CC[C@H](NC(=O)c1cc(-c2cc(-c3cnn(CC(F)(F)F)c3)c3nc(N)nn3c2)cs1)c1ccc(F)cc1] |

17. A pharmaceutical composition, the pharmaceutical composition comprising a compound of claim 1, or a pharmaceutically acceptable salt thereof, and a pharmaceutically acceptable excipient.

18. The pharmaceutical composition of claim 17, wherein the pharmaceutical composition is formulated for ocular administration.

19. The pharmaceutical composition of claim 1, wherein the pharmaceutical composition is formulated as an eye drop, an ocular ointment, an ocular gel, an ocular coil, a contact lens, or an opthalmic insert.

20. The pharmaceutical composition of claim 1, wherein the pharmaceutical composition is formulated for intravitreal administration.

21. A method for treating a neurodegenerative disease in a subject, the method comprising administering to the subject an effective amount of a compound of claim 1, or a pharmaceutical composition comprising a compound of claim 1 and a pharmaceutically acceptable excipient.

22. The method of claim 21, wherein the neurodegenerative disease is selected from Amyotrophic lateral sclerosis (ALS), Alzheimer's disease, Parkinson's disease, Parkinson's-plus disease, Huntington's disease, peripheral neuropathies, ischemia, stroke, intracranial haemorrhage, cerebral haemorrhage, nerve damage caused by exposure to toxic compounds, injury to the nervous system, trigeminal neuralgia, glossopharyngeal neuralgia, Bell's Palsy, myasthenia gravis, muscular dystrophy, progressive muscular atrophy, primary lateral sclerosis (PLS), spinal muscular atrophy, inherited muscular atrophy, invertebrate disk syndromes, cervical spondylosis, plexus disorders, thoracic outlet destruction syndromes, *porphyria*, pseudobulbar palsy, progressive bulbar palsy, multiple system atrophy, progressive supranuclear palsy, corticobasal degeneration, dementia with Lewy bodies, frontotemporal dementia, demyelinating diseases, Guillain-Barré syndrome, multiple sclerosis, Charcot-Marie-Tooth disease, prion disease, Creutzfeldt-Jakob disease, Gerstmann-Sträussler-Scheinker syndrome (GSS), fatal familial insomnia (FFI), bovine spongiform encephalopathy, Pick's disease, epilepsy, sensorineural hearing loss, traumatic brain injury, and AIDS demential complex.

23. The method of claim 21, wherein the neurodegenerative disease is a neurodegenerative ophthalmological disorder.

24. The method of claim 23, wherein the neurodegenerative ophthalmological disorder is selected from age-related macular degeneration (AMD), choroidal neovascularization (CNV), choroidal neovascular membranes (CNVM), cystoid macular oedema (CME), epiretinal membranes (ERM) and macular perforations, myopia-associated choroidal neovascularization, angioid and vascular streaks, retinal detachment, diabetic retinopathy, diabetic macular oedema (DME), atrophic and hypertrophic lesions in the retinal pigment epithelium, retinal vein occlusion, choroidal retinal vein occlusion, macular oedema, macular oedema associated with renal vein occlusion, retinitis pigmentosa and other inherited retinal degenerations, retinopathy of prematurity, glaucoma, other optic neuropathies including toxic optic neuropathy, nonarteritic ischemic optic neuropathy, arteritic ischemic optic neuropathy/giant cell arteritis, traumatic optic, idiopathic intracranial hypertension/pseudotumor cerebri, inflammatory optic neuropathies, compressive optic neuropathies, infiltrative optic neuropathies, autoimmune optic neuropathies, lipid storage diseases, nutritional optic neuropathies, Leber's hereditary optic neuropathy, dominant optic atrophy, Friedrich's ataxia, radiation-induced optic neuropathy, iatrogenic optic neuropathies, space flight-associated neuro-ocular syndrome (SANS), inflammation disorders of the eye, refraction anomalies, neurotrophic keratopathy, corneal denneratvation, and diabetic keratopathy.

25. The method of claim 24, wherein the inflammatory optic neuropathy is optic neuritis.

26. The method of claim 23, wherein the neurodegenerative ophthalmological disorder is selected from glaucoma, age-related macular degeneration (AMD), choroidal neovascularization (CNV), myopia-associated choroidal neovascularization, diabetic retinopathy, macular oedema, and retinal vein occlusion.

27. A method for treating an optic neuropathy in a subject, the method comprising administering to the subject an effective amount of a compound of claim 1, or a pharmaceutical composition comprising a compound of claim 1 and a pharmaceutically acceptable excipient; wherein the optic neuropathy is selected from glaucoma, inherited retinal degenerations, non-exudative AMD/geographic atrophy, retinal vascular diseases that produce ischemia, retinal detachments, and edema-producing diseases.

28. A method of inhibiting DLK and/or LZK activity in a mammalian cell, the method comprising contacting the mammalian cell with a compound of claim 1, or a pharmaceutically acceptable salt thereof.

29. The method of claim 28, wherein the cell is a neuronal cell.

* * * * *